US011939343B2

(12) United States Patent
Duvall et al.

(10) Patent No.: US 11,939,343 B2
(45) Date of Patent: Mar. 26, 2024

(54) STING AGONIST COMPOUNDS AND METHODS OF USE

(71) Applicant: Mersana Therapeutics, Inc., Cambridge, MA (US)

(72) Inventors: Jeremy R. Duvall, Topsfield, MA (US); Keith W. Bentley, Everett, MA (US); Brian D. Jones, Boston, MA (US); Eugene W. Kelleher, Wellesley, MA (US); Soumya S. Ray, Quincy, MA (US); Joshua D. Thomas, Natick, MA (US); Dorin Toader, Cambridge, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 75 days.

(21) Appl. No.: 17/469,983

(22) Filed: Sep. 9, 2021

(65) Prior Publication Data

US 2022/0064189 A1   Mar. 3, 2022

Related U.S. Application Data

(63) Continuation of application No. 16/944,646, filed on Jul. 31, 2020, now Pat. No. 11,155,567.

(60) Provisional application No. 62/982,935, filed on Feb. 28, 2020, provisional application No. 62/944,643, filed on Dec. 6, 2019, provisional application No. 62/882,081, filed on Aug. 2, 2019.

(51) Int. Cl.

| | | |
|---|---|---|
| C07D 519/00 | (2006.01) |
| A61P 1/16 | (2006.01) |
| A61P 3/04 | (2006.01) |
| A61P 3/06 | (2006.01) |
| A61P 29/00 | (2006.01) |
| A61P 31/00 | (2006.01) |
| A61P 31/12 | (2006.01) |
| A61P 31/14 | (2006.01) |
| A61P 31/16 | (2006.01) |
| A61P 31/18 | (2006.01) |
| A61P 35/02 | (2006.01) |
| A61P 37/00 | (2006.01) |
| A61P 37/02 | (2006.01) |
| A61P 37/04 | (2006.01) |
| A61P 37/06 | (2006.01) |
| A61P 37/08 | (2006.01) |
| C07D 403/14 | (2006.01) |
| C07D 405/14 | (2006.01) |
| C07D 413/14 | (2006.01) |
| C07D 417/14 | (2006.01) |
| C07D 471/04 | (2006.01) |
| C07D 487/04 | (2006.01) |
| C07D 491/04 | (2006.01) |
| C07D 491/048 | (2006.01) |
| C07D 513/04 | (2006.01) |

(52) U.S. Cl.
CPC ......... *C07D 519/00* (2013.01); *C07D 403/14* (2013.01); *C07D 413/14* (2013.01); *C07D 417/14* (2013.01); *C07D 471/04* (2013.01); *C07D 487/04* (2013.01); *C07D 513/04* (2013.01)

(58) Field of Classification Search
CPC .. C07D 519/00; C07D 403/14; C07D 413/14; C07D 417/14; C07D 471/04; C07D 487/04; C07D 513/04; C07D 491/04; C07D 491/048; C07D 405/14; A61P 1/16; A61P 3/04; A61P 3/06; A61P 31/12; A61P 31/4192; A61P 31/4355; A61P 31/437; A61P 31/422; A61P 31/427; A61P 35/00; A61P 37/00; A61P 37/02; A61P 37/04; A61P 37/08; A61P 29/00; A61P 31/00; A61P 31/14; A61P 31/16; A61P 31/18; A61P 35/02; A61P 37/06
See application file for complete search history.

(56) References Cited

U.S. PATENT DOCUMENTS

| | | |
|---|---|---|
| 7,488,802 B2 | 2/2009 | Collins et al. |
| 7,521,051 B2 | 4/2009 | Collins et al. |
| 8,008,449 B2 | 8/2011 | Korman et al. |
| 8,168,757 B2 | 5/2012 | Finnefrock et al. |
| 8,354,509 B2 | 1/2013 | Carven et al. |
| 8,603,474 B2 | 12/2013 | Ritter et al. |
| 10,189,820 B2 | 1/2019 | Mehlmann et al. |
| 11,596,694 B2 | 3/2023 | Mosher et al. |
| 2011/0271358 A1 | 11/2011 | Freeman et al. |
| 2017/0298139 A1 | 10/2017 | Thompson et al. |
| 2018/0105514 A1 | 4/2018 | Mehlmann et al. |

(Continued)

FOREIGN PATENT DOCUMENTS

| | | |
|---|---|---|
| CN | 110016025 A | 7/2019 |
| CN | 110963997 A | 4/2020 |

(Continued)

OTHER PUBLICATIONS

Elemes, Y. and Ragnarsson, U. "Synthesis of enantiopure α-deuteriated Boc-L-amino acids", J. Chem. Soc, Perkin Trans. 1, 1996, vol. 6, p. 537-540.

(Continued)

*Primary Examiner* — Sun Jae Yoo
(74) *Attorney, Agent, or Firm* — COOLEY LLP; Heidi A. Erlacher; Christine E. Dunne

(57) ABSTRACT

The present disclosure relates to STING (Stimulator of Interferon Genes) agonist compounds, methods of making the compounds and their methods of use.

11 Claims, No Drawings

(56) References Cited

U.S. PATENT DOCUMENTS

| | | |
|---|---|---|
| 2019/0336615 A1 | 11/2019 | Thompson et al. |
| 2020/0031825 A1 | 1/2020 | Slassi et al. |
| 2020/0113912 A1 | 4/2020 | Odegard et al. |
| 2021/0032269 A1 | 2/2021 | Duvall et al. |
| 2021/0332080 A1 | 10/2021 | Han |
| 2022/0233707 A1 | 7/2022 | Lowinger et al. |
| 2022/0378749 A1 | 12/2022 | Duvall et al. |
| 2023/0074558 A1 | 3/2023 | Duvall et al. |
| 2023/0172910 A1 | 6/2023 | Duvall et al. |

FOREIGN PATENT DOCUMENTS

| | | |
|---|---|---|
| CN | 111393404 A | 7/2020 |
| CN | 111499617 A | 8/2020 |
| CN | 111848573 A | 10/2020 |
| CN | 112300227 A | 2/2021 |
| CN | 112898286 A | 6/2021 |
| CN | 113248475 A | 8/2021 |
| EP | 2 176 293 B1 | 4/2019 |
| WO | WO-0102369 A2 | 1/2001 |
| WO | WO-0210192 A2 | 2/2002 |
| WO | WO-02068470 A2 | 9/2002 |
| WO | WO-2004004771 A1 | 1/2004 |
| WO | WO-2004056875 A1 | 7/2004 |
| WO | WO-2004072286 A1 | 8/2004 |
| WO | WO-2009097128 A1 | 8/2009 |
| WO | WO-2010027827 A2 | 3/2010 |
| WO | WO-2010077634 A1 | 7/2010 |
| WO | WO-2011066342 A2 | 6/2011 |
| WO | WO-2013019906 A1 | 2/2013 |
| WO | WO-2014093936 A1 | 6/2014 |
| WO | WO-2014189805 A1 | 11/2014 |
| WO | WO-2014189806 A1 | 11/2014 |
| WO | WO-2015185565 A1 | 12/2015 |
| WO | WO-2015195917 A1 | 12/2015 |
| WO | WO-2016096174 A1 | 6/2016 |
| WO | WO-2016096577 A1 | 6/2016 |
| WO | WO-2016120305 A1 | 8/2016 |
| WO | WO-2017027645 A1 | 2/2017 |
| WO | WO-2017027646 A1 | 2/2017 |
| WO | WO-2017075477 A1 | 5/2017 |
| WO | WO 2017/100305 A2 | 6/2017 |
| WO | WO-2017093933 A1 | 6/2017 |
| WO | WO-2017160754 A1 | 9/2017 |
| WO | WO 2017/175147 A1 | 10/2017 |
| WO | WO 2017/175156 A1 | 10/2017 |
| WO | WO-2018009466 A1 | 1/2018 |
| WO | WO 2018/067423 A1 | 4/2018 |
| WO | WO 2018/098269 A2 | 5/2018 |
| WO | WO 2018/160538 A1 | 9/2018 |
| WO | WO 2018/200812 A1 | 11/2018 |
| WO | WO 2018/227023 A1 | 12/2018 |
| WO | WO 2019/027857 A1 | 2/2019 |
| WO | WO 2019/027858 A1 | 2/2019 |
| WO | WO 2019/069269 A1 | 4/2019 |
| WO | WO 2019/069270 A1 | 4/2019 |
| WO | WO 2019/069275 A1 | 4/2019 |
| WO | WO 2019/084060 A1 | 5/2019 |
| WO | WO 2019/134705 A1 | 7/2019 |
| WO | WO 2019/134707 A1 | 7/2019 |
| WO | WO 2019/195063 A1 | 10/2019 |
| WO | WO 2019/195124 A1 | 10/2019 |
| WO | WO 2019/227007 A1 | 11/2019 |
| WO | WO 2019/236567 A2 | 12/2019 |
| WO | WO-2019243825 A1 | 12/2019 |
| WO | WO 2020/006432 A1 | 1/2020 |
| WO | WO 2020/010451 A1 | 1/2020 |
| WO | WO 2020/038387 A1 | 2/2020 |
| WO | WO-2020028566 A1 | 2/2020 |
| WO | WO 2020/042995 A1 | 3/2020 |
| WO | WO 2020/115676 A1 | 6/2020 |
| WO | WO 2020/132549 A1 | 6/2020 |
| WO | WO 2020/132566 A1 | 6/2020 |
| WO | WO 2020/132582 A1 | 6/2020 |
| WO | WO-2020132582 A1 * | 6/2020 |
| WO | WO 2020/146237 A1 | 7/2020 |
| WO | WO 2020/151682 A1 | 7/2020 |
| WO | WO 2020/156363 A1 | 8/2020 |
| WO | WO-2020181050 A1 | 9/2020 |
| WO | WO 2020/194160 A1 | 10/2020 |
| WO | WO 2020/202091 A1 | 10/2020 |
| WO | WO-2020214858 A1 | 10/2020 |
| WO | WO 2020/221038 A1 | 11/2020 |
| WO | WO-2020227159 A2 | 11/2020 |
| WO | WO 2021/000770 A1 | 1/2021 |
| WO | WO 2021/009365 A1 | 1/2021 |
| WO | WO 2021/013250 A1 | 1/2021 |
| WO | WO 2021/014365 A1 | 1/2021 |
| WO | WO-2021026009 A1 | 2/2021 |
| WO | WO-2021113679 A1 | 6/2021 |
| WO | WO-2021202984 A1 | 10/2021 |

OTHER PUBLICATIONS

Leit De Moradei et al. CAPLUS 2020: 1235220, 2020, 5 pages.
Pan et al. "An orally available non-nucleotide STING agonist with antitumor activity", Science, 2020, vol. 369, 13 pages.
Ramanjulu et al. "Design of amidobenzimidazole STING receptor agonists with systemic activity", Nature, 2018, 16 pages.
Slassi et al., CAPLUS 2020:185181, 2020, 3 pages.
Song et al. "Structure-Activity Relationship Study of Amidobenzimidazole Analogues Leading to Potent and Systemically Administrable Stimulator of Interferon Gene (STING) Agonists", Journal of Medicinal Chemistry, 2020, 21 pages.
Francisco et al., "cAC10-vcMMAE, an anti-CD30-monomethyl auristatin E conjugate with potent and selective antitumor activity". Blood. Aug. 15, 2003; 102(4): 1458-65.
CAS Registry No. 2138299-29-1, date entered STN: Nov. 2, 2017; 1H-Benzimidazole-5-carboxamide, 1-[(2E)-4-[5-(aminocarbonyl)-2-[[(1-ethyl-3-methyl-1H-pyrazol-5-yl)carbonyl]amino]-1H-benzimidazol-1-yl]-2-buten-1-yl]-2-[(1-ethyl-3-methyl-1H-pyrazol-5-yl)carbonyl]amino]-7-(3-hydroxypropoxy), 2 pages.
Enomoto et al., "Synthesis of peptide-grafted comb polypeptides via polymerisation of NCA-peptides". Chemical Communications. 2013; 49(4): 409-411.
Hofland et al., "Preclinical Data Supports the Development of XMT-1536 in a Broad Population of Patients with Ovarian Cancer", ADC Review, News, Oct. 30, 2017, pp. 1-3. Available from: https://www.adcreview.com/news/preclinical-data-supports-development-xmt-1536-broad-population-patients-ovarian-cancer/.
Karaman "The Prodrug Naming Dilemma". Drug Des. 2013; 2: e115, pp. 1-4.
Kim et al., "Antibody-assisted delivery of a peptide-drug conjugate for targeted cancer therapy". Molecular pharmaceutics. Dec. 6, 2018; 16(1): 165-172.
Lowe "Prodrugs: How the Pros Do It?", In the Pipeline: Drug Development. Dec. 1, 2008; 2 pages. Available from: https://www.science.org/contenVblog-posVprodrugs-pros-do.
Rautio et al., "The expanding role of prodrugs in contemporary drug design and development". Nature Reviews Drug Discovery. Aug. 2018; 17(8): 559-587.
Stella "Prodrugs: My initial exploration and where it led". Journal of Pharmaceutical Sciences. Dec. 1, 2020; 109(12): 3514-3523.

* cited by examiner

STING AGONIST COMPOUNDS AND METHODS OF USE

RELATED APPLICATIONS

This application is a continuation of U.S. application Ser. No. 16/944,646, filed Jul. 31, 2020, now allowed, which claims priority to, and the benefit of, U.S. Provisional Application No. 62/882,081 filed Aug. 2, 2019, U.S. Provisional Application No. 62/944,643 filed Dec. 6, 2019, and U.S. Provisional Application No. 62/982,935 filed Feb. 28, 2020. The contents of each of these applications are hereby incorporated by reference in their entireties.

BACKGROUND

Stimulator of Interferon Genes (STING) is a receptor in the endoplasmic reticulum that propagates innate immune sensing of cytosolic pathogen derived- and self-DNA. STING is a 378 amino acid protein, which mainly contains three structural domains: (i)N-terminal transmembrane domain (aa 1-154); (ii) central globular domain (aa 155-341); and (iii)C-terminal tail (aa 342-379). STING may form symmetrical dimers combined with its ligands in V-shaped conformation, while not completely covering the bound ligands. A STING agonist can bind into the pocket region of STING. However, the STING activation process is easily inhibited in some severe disease conditions, resulting in the inactivation of the STING pathway. Therefore, screening and designing potent STING agonists is of great importance for cancer immune therapy and other infectious diseases treatments, including, but not limited to, obesity, liver injury, sugar-lipid metabolism, and virus infection. Specific targeting of immune pathways presents opportunities for cancer therapy, potentially offering greater specificity than cell population-based therapeutic approaches.

The compounds of this disclosure modulate the activity of STING, and accordingly, may provide a beneficial therapeutic impact in treatment of diseases, disorders and/or conditions in which modulation of STING (Stimulator of Interferon Genes) is beneficial, including, but not limited to, inflammation, allergic and autoimmune diseases, infectious diseases, cancer, pre-cancerous syndromes, and as vaccine adjuvants.

SUMMARY

In some aspects, the present disclosure provides a compound of Formula (IA')

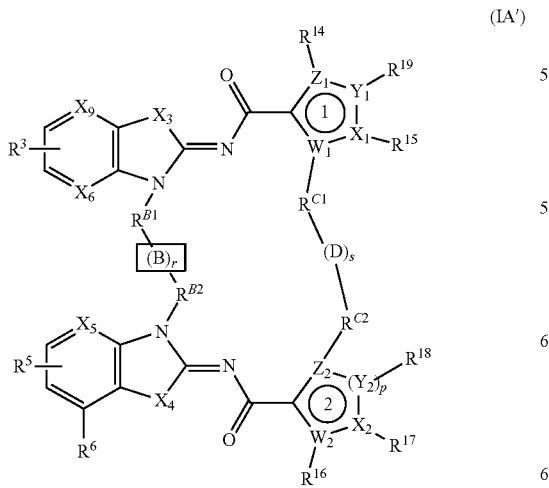

(IA')

or a prodrug, solvate, pharmaceutically acceptable salt, or tautomer thereof, wherein:
$W_1$, $X_1$, $Y_1$, $Z_1$, $W_2$, $X_2$, $Y_2$, and $Z_2$ are each independently O, S, C, or N;
$X_3$ and $X_4$ are each independently S or $NR^f$;
$X_5$ is N or $CR^{A2}$;
$X_6$ is N or $CR^{A1}$;
$X_9$ is N or $CR^4$;
r and s are each independently 0 or 1;
p is 1 or 2;
the total of r and s is 1 or 2;
$R^{A1}$ and $R^{A2}$ are each independently H, halogen, amino, amino($C_{1-4}$ alkyl)-, hydroxy, —O—P(O)(OH)$_2$, —O—P(O)($R^IR^{II}$)$_2$, —N($R^e$)($R^f$), —CO$_2R^f$, —N($R^f$)COR$^b$, —N($R^g$)SO$_2$($C_{1-4}$ alkyl)-N($R^e$)($R^f$), —N($R^g$)CO($C_{1-4}$ alkyl)-N($R^h$)($R^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, $C_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-;
when r is 0, $R^{B1}$ and $R^{B2}$ are each independently H, optionally substituted $C_{1-6}$ alkyl, halo($C_{1-6}$ alkyl), optionally substituted $C_2$-6 alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted $C_{1-6}$ alkyl, optionally substituted $C_2$-6 alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —O—P(O)(OH)$_2$, —O—P(O)($R^IR^{II}$)$_2$ —OR$^c$, —NH$_2$, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;
when s is 0, $R^{C1}$ is absent, H, halogen, or $C_1$-4 alkyl and $R^{C2}$ is absent or optionally substituted $C_{1-4}$ alkyl, wherein said optionally substituted $C_1$-4 alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

when r is 1, $R^{B1}$ and $R^{B2}$ are each independently —$CH_2$—, and B, taken together with $R^{B1}$ and $R^{B2}$, forms a linking group, wherein B is a bond or B is -halo($C_{1-10}$) alkyl)-, optionally substituted —$C_{1-10}$alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-$NR^a$—$C_{1-6}$ alkyl-, optionally substituted $C_{3-6}$ cycloalkyl, optionally substituted phenyl, optionally substituted 4-6 membered heterocycloalkyl, optionally substituted 5-6 membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl)-$C_{1-4}$ alkyl-, wherein the alkyl moiety of said optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-NW—$C_{1-6}$ alkyl-, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl-$C_{1-4}$ alkyl)- is optionally substituted by 1 or 2 substituents each independently selected from halogen, halo($C_{1-4}$ alkyl), —OH, —O—P(O)(OH)$_2$, —O—P(O)($R^I R^{II}$)$_2$, —$OR^c$, —$NH_2$, $NR^c R^d$, —$OCOR^c$, —$CO_2H$, —$CO_2 R^c$, —$SOR^c$, —$SO_2 R^c$, —$CONH_2$, —$CONR^c R^d$, —$SO_2 NH_2$, —$SO_2 NR^c R^d$, —$OCONH_2$, —$OCONR^c R^d$, —$NR^d COR^c$, —$NR^d SOR^c$, —$NR^d CO_2 R^c$, and —$NR^d SO_2 R^c$, and the $C_{3-6}$ cycloalkyl, phenyl, 4-6 membered heterocycloalkyl, or 5-6 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl)-$C_{1-4}$ alkyl- is optionally substituted by 1-4 substituents each independently selected from halogen, hydroxy, —O—P(O)(OH)$_2$, —O—P(O)($OR^I R^{II}$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, and $C_{1-4}$ alkoxy-($C_{1-4}$ alkoxy)-;

when s is 1, $W_1$ and $Z_2$ are each independently C or N, $R^{C1}$ and $R^{C2}$ are each independently —$CH_2$—, and D taken together with $R^{C1}$ and $R^{C2}$, forms a linking group, wherein D is -halo($C_{1-12}$ alkyl)-, optionally substituted —$C_{1-12}$ alkyl-, optionally substituted —$C_{2-12}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NW—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl-, wherein the alkyl moiety of said optionally substituted —$C_{1-12}$ alkyl-, optionally substituted —$C_{1-6}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-$NR^a$—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)$C_{1-6}$ alkyl- is optionally substituted by 1 or 2 substituents each independently selected from halogen, halo ($C_{1-4}$ alkyl), —OH, —O—P(O)(OH)$_2$, —O—P(O)($R^I R^{II}$)$_2$, —$OR^c$, —$NH_2$, —$NR^c R^d$, —$OCOR^c$, —$CO_2H$, —$SOR^c$, —$CONH_2$, —$CONR^c R^d$, —$SO_2 NH_2$, —$SO_2 NR^c R^d$, —$OCONH_2$, —$OCONR^c R^d$, —$NR^d COR^c$, —$NR^d SOR^c$, —$NR^d CO_2 R^c$, and —$NR^d SO_2 R^c$, and the $C_{3-6}$ cycloalkyl, phenyl, 4-6 membered heterocycloalkyl, or 5-6 membered heteroaryl moiety of said optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl- is optionally substituted by 1-4 substituents each independently selected from halogen, hydroxy, —O—P(O)(OH)$_2$, O—P(O)($R^I R^{II}$)$_2$, amino, ($C_{1-4}$ alkyl) amino-, ($C_{1-4}$ alkyl)($C_{1-4}$ alkyl)amino-, $C_{1-4}$ alkyl, halo ($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, and $C_{1-4}$ alkoxy-($C_{1-4}$ alkoxy)-;

$R^3$ and $R^5$ are each independently —CON(R d)($R^f$), —$CH_2$N(R d)($R^f$), —N(R d)($R^f$), —N(R d)CO($R^f$), —$CH_2$N(R d)CO($R^f$), or one of $R^3$ and $R^5$ is —CON(R d)($R^f$), —$CH_2$N(R d)($R^f$), —N(R d)($R^f$), —N(R d)CO($R^f$), or —$CH_2$N(R d)CO ($R^f$), and the other of $R^3$ and $R^5$ is H, COOH, or —$CO_2 R^c$;

$R^4$ and $R^6$ are each independently selected from H, halogen, halo($C_{1-6}$ alkyl), halo($C_{1-6}$ alkoxy)-, hydroxy, —O—P(O)(OH)$_2$, O—P(O)($R^I R^{II}$)$_2$, —$NH_2$, —$NR^c R^c$, —$NR^c R^d$, —$COR^c$, —$N(R^d)COR^c$, —$N(R^d)SO_2 R^c$, —$N(R^g)$ $SO_2(C_{1-2}$ alkyl)-N(R h)($R^f$), —$N(R^g)$ CO($C_{1-2}$ alkyl)-N($R^h$)($R^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-, wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from —OH, —O—P(O)(OH)$_2$, —O—P(O)($R^I R^{II}$)$_2$, —$OR^c$, —$NH_2$, —$NR^c R^c$, —$CO_2H$, —$OCOR^c$, —$CO_2H$, —$SOR^c$, —$SO_2 R^c$, —$CONH_2$, —$CONR^c R^d$, —$SO_2 NH_2$, —$SO_2 NR^c R^d$, —$OCONH_2$, —$OCONR^c R^d$, —$NR^d COR^c$, —$NR^d$- $SOR^c$, —$NR^d CO_2 R^c$, —$NR^d SO_2 R^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or membered heteroaryl is optionally substituted by 1-4 substituents each independently selected from halogen, hydroxy, —O—P(O)(OH)$_2$, —O—P(O)($R^I R^{II}$)$_2$, amino, ($C_{1-4}$ alkyl)amino-, ($C_{1-4}$ alkyl)($C_{1-4}$ alkyl) amino-, $C_{1-4}$ alkyl, halo($C_{1-4}$ alkyl), hydroxy-($C_{1-4}$ alkyl)-, —($C_{1-4}$ alkyl)-O—P(O)(OH)$_2$, —($C_{1-4}$ alkyl)-O—P(O)($R^I R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, $C_{1-4}$ alkoxy-($C_{1-4}$ alkoxy)-, —COR$^d$, —CON(R$^d$)(R$^f$), and —CO$_2$R$^d$, $R^{14}$ is absent, H, halogen, or optionally substituted $C_1$-4 alkyl, wherein said optionally substituted $C_1$-4 alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;

$R^{16}$ is absent, H, halogen, or $C_1$-4 alkyl;

$R^{15}$ and $R^{17}$ are each independently absent, H, cyclopropyl, halogen or optionally substituted $C_1$-4 alkyl, wherein said optionally substituted $C_1$-4 alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$; or $R^{15}$ and $R^{19}$ taken together with the atom or atoms through which they are connected, form a 5-6 membered ring; or $R^{16}$ and $R^{17}$ taken together with the atom or atoms through which they are connected, form a 5-6 membered ring;

$R^{18}$ and $R^{19}$ are each independently absent, H, halogen, optionally substituted $C_1$-4 alkyl, wherein said optionally substituted $C_1$-4 alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$; or $R^{17}$ and $R^{18}$ taken together with the atom or atoms through which they are connected, form a 5-6 membered ring;

$R^a$ is H, —R$^c$, —COR$^c$, —CO$_2$H, —CO$_2$R$^c$, —SORB, —SO$_2$R$^c$, —CONH$_2$, —CONR$^c$R$^d$, —SO$_2$NH$_2$, —CH$_2$—CO$_2$R$^c$, or —SO$_2$NR$^c$R$^d$;

each $R^b$ is independently $C_{1-4}$ alkyl, halo($C_{1-4}$ alkyl), —($C_{1-4}$ alkyl)-OH, —($C_{1-4}$ alkyl)-O—P(O)(OH)$_2$, —($C_{1-4}$ alkyl)-O—P(O)($R^I R^{II}$)$_2$, —($C_{1-4}$ alkyl)-O—($C_{1-4}$ alkyl), —($C_{1-4}$ alkyl)-N(R$^e$)(R$^f$), —($C_1$-4 alkyl)-O—CO($C_{1-4}$ alkyl), or —($C_{1-4}$ alkyl)-CO—O—($C_{1-4}$ alkyl);

each $R^c$ is independently H, $C_{1-4}$ alkyl, halo($C_{1-4}$ alkyl), —($C_{1-4}$ alkyl)-OH, —($C_{1-4}$ alkyl)-O—P(O)(OH)$_2$, —($C_{1-4}$ alkyl)-O—P(O)($R^I R^{II}$)$_2$, —($C_{1-4}$ alkyl)-O—($C_{1-4}$ alkyl), —($C_{1-4}$ alkyl)-N(R$^e$)(R$^f$), —($C_{1-4}$ alkyl)-O—CO($C_{1-4}$ alkyl), —($C_{1-4}$ alkyl)-CO—O—($C_{1-4}$ alkyl), optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl, wherein the $C_{3-6}$ cycloalkyl, phenyl, 4-6 membered heterocycloalkyl, 5-6 membered heteroaryl or 9-10 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, $C_{1-4}$ alkoxy-($C_{1-4}$ alkoxy)-, —COR$^d$, —CON(R$^d$)(R$^f$), and —CO$_2$R$^d$;

each $R^d$ is independently H, hydroxy, or $C_{1-4}$ alkyl;

each $R^e$ is independently H, ($C_{1-4}$ alkyl), —CO($C_{1-4}$ alkyl), —OCO($C_{1-4}$ alkyl), —CO$_2$($C_{1-4}$ alkyl), —($C_{1-4}$ alkyl)amino, —($C_{1-4}$ alkyl)-$C_{1-4}$ alkoxy, —CO-(optionally substituted 5-6 membered heterocycloalkyl), —CO—($C_{1-4}$ alkyl)-(optionally substituted 5-6 membered heterocycloalkyl), —CO-(optionally substituted 5-6 membered heteroaryl), —CO—($C_{1-4}$ alkyl)-(optionally substituted 5-6 membered heteroaryl), wherein the optionally substituted 5-6 membered heterocycloalkyl or optionally substituted 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)O—P(O)(OH)$_2$, —($C_{2-4}$ alkoxy)-O—P(O)($R^I R^{II}$)$_2$, $C_{1-4}$ alkoxy-($C_{1-4}$ alkoxy)-, —COR$^d$, —CON(R$^d$)(R$^f$), and —CO$_2$R$^d$;

each $R^f$ is independently H, hydroxy, or ($C_{1-4}$ alkyl);

$R^g$ and $R^h$ are each independently H or ($C_{1-4}$ alkyl) or $R^g$ and R h, taken together with the atom or atoms through which they are connected, form a 5-6 membered ring; and each $R^I$ and $R^{II}$ are independently ($C_{1-6}$ alkyl)oxy-;

provided that at least one of (i), (ii), or (iii) applies:

(i) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S or $X_9$ is N; or (ii) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —OR$^c$, —NR$^c$R$^d$, —CO$_2$R$^c$, —CONR$^c$R$^d$, —SO$_2$NR$^c$R$^d$, and —OCONR$^c$R$^d$ wherein R$^c$ is H; or (iii) when s is 0, r is 1, (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{41}$ or $R^{42}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^I R^{II}$)$_2$, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy).

In some embodiments, the compound is of Formula (IA'), wherein the compound is Formula (IA):

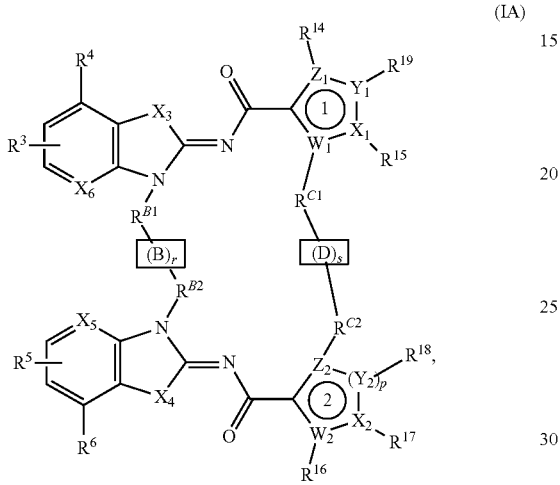

(IA)

or a prodrug, solvate, pharmaceutically acceptable salt, or tautomer thereof.

In some embodiments the compound is of Formula (V'):

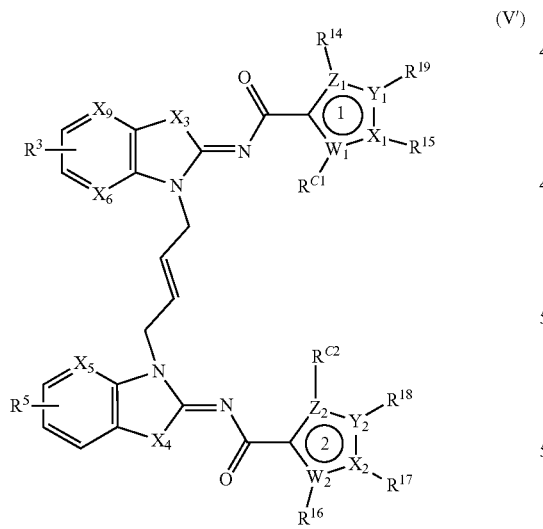

(V')

or a prodrug, solvate, pharmaceutically acceptable salt, or tautomer thereof, wherein:

Y$_1$, Y$_2$, Z$_1$ and Z$_2$ are each independently O, S, C or N;
X$_1$, X$_2$, W$_1$ and W$_2$ are each independently C or N;
X$_3$ and X$_4$ are each independently S or NR$^f$;
X$_5$ is N or CR$^{A2}$;
X$_6$ is N or CR$^{A1}$;
X$_9$ is N or CH;

R$^3$ and R$^5$ are each independently —CON(R$^d$)(R$^f$), —CH$_2$N(R$^d$)(R$^f$), —N(R$^d$)(R$^f$), —N(R$^d$)CO(R$^f$), —CH$_2$N(R$^d$)CO(R$^f$) or one of R$^3$ and R$^5$ is —CON(R$^d$)(R$^f$), —CH$_2$N(R$^d$)(R$^f$), —N(R$^d$)(R$^f$), —N(R$^d$)CO(R$^f$) or —CH$_2$N(R$^d$)CO(R$^f$), and the other of R$^3$ and R$^5$ is H, —COOH, or —CO$_2$R$^c$;

R$^c$ is C$_{1-4}$ alkyl;

R$^{A2}$ and R$^{A1}$ are each independently H, halogen, amino, amino(C$_{1-4}$ alkyl)-, hydroxy, optionally substituted (C$_{1-6}$ alkyl), or optionally substituted (C$_{1-6}$ alkyl)oxy-, wherein C$_{1-6}$ alkyl of said optionally substituted (C$_{1-6}$ alkyl), or optionally substituted (C$_{1-6}$ alkyl)oxy- is optionally substituted with 1-4 substituents each independently selected from the group comprising hydroxy, C$_{1-4}$ alkoxyl, —N(R$^e$)(R$^f$), —CO$_2$(R$^f$), —CON(R$^e$)(R$^f$), and —COOH;

each R$^d$ is independently H, hydroxy, or C$_{1-4}$ alkyl;

R$^e$ is selected from H, (C$_{1-4}$ alkyl), —CO(C$_{1-4}$ alkyl), —OCO(C$_{1-4}$ alkyl), and —CO$_2$(C$_{1-4}$ alkyl);

each R$^f$ is independently H, hydroxy, or (C$_{1-4}$ alkyl);

R$^{14}$ and R$^{C2}$ are each independently absent or C$_{1-4}$ alkyl, wherein C$_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$; R$^{16}$ and R$^{C1}$ are each independently absent, H or C$_{1-4}$ alkyl; and R$^{15}$, R$^{17}$, R$^{18}$, or R$^{19}$ are each independently absent, H, or C$_{1-4}$ alkyl, wherein C$_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;

provided that at least one of (i), (ii), or (iii) applies:

(i) when (a) Z$_1$, Z$_2$, Y$_1$ and Y$_2$ are each N, W$_1$, W$_2$, X$_1$ and X$_2$ are each C; or (b) W$_1$, W$_2$, X$_1$ and X$_2$ are each N, Z$_1$, Z$_2$, Y$_1$ and Y$_2$ are each C; or (c) Z$_1$ and Y$_1$ are each N, W$_1$ and X$_1$ are each C; or (d) Z$_2$ and Y$_2$ are each N, W$_2$ and X$_2$ are each C; or (e) W$_1$ and X$_1$ are each N, Z$_1$ and Y$_1$ are each C; or (f) W$_2$ and X$_2$ are each N, Z$_2$ and Y$_2$ are each C, then at least one of X$_3$ and X$_4$ is S or X$_9$ is N; or (ii) when (a) Z$_1$, Z$_2$, Y$_1$ and Y$_2$ are each N, W$_1$, W$_2$, X$_1$ and X$_2$ are each C; or (b) W$_1$, W$_2$, X$_1$ and X$_2$ are each N, Z$_1$, Z$_2$, Y$_1$ and Y$_2$ are each C, then R$^{14}$ is a C$_{1-4}$ alkyl substituted with halogen, —OR$^c$, —NR$^c$R$^d$, —CO$_2$R$^c$, —CONR$^c$R$^d$, —SO$_2$NR$^c$R$^d$, and —OCONR$^c$R$^d$ wherein R$^e$ is H; or (iii) when (a) Z$_1$ and Y$_1$ are each N, W$_1$ and X$_1$ are each C; or (b) Z$_2$ and Y$_2$ are each N, W$_2$ and X$_2$ are each C; or (c) W$_1$ and X$_1$ are each N, Z$_1$ and Y$_1$ are each C; or (d) W$_2$ and X$_2$ are each N, Z$_2$ and Y$_2$ are each C, then at least one of X$_5$, X$_6$, and X$_9$ is N and R$^{A1}$ or R$^{A2}$ is halogen, hydroxy, optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino-, wherein C$_{1-6}$ alkyl of said optionally substituted (C$_{1-6}$ alkyl), or substituted (C$_{1-6}$ alkyl)oxy is optionally substituted with 1-4 substituents each independently selected from the group comprising hydroxy, C$_{1-4}$ alkoxyl, —N(R$^e$)(R$^f$), —CO$_2$(R$^f$), —CON(R$^e$)(R$^f$), and —COOH.

In some embodiments, the compound is of Formula (V'), wherein the compound is of Formula (V):

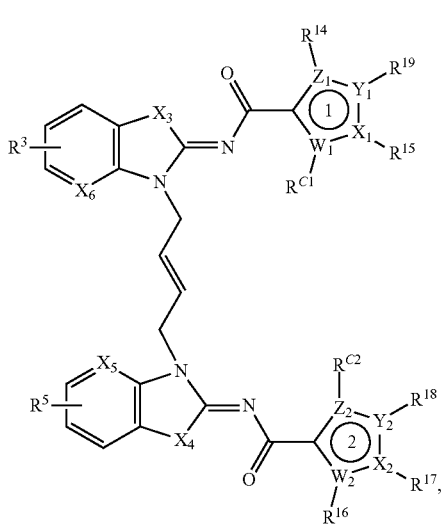

or a prodrug, solvate, pharmaceutically acceptable salt, or tautomer thereof.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

It is to be understood that the references herein to compounds of any one or more of Formula (I'), (IA'), (II'), (III'), (IV'), or (V'), and salts thereof covers the compounds of Formula (I'), (IA'), (II'), (III'), (IV'), or (V'), as free bases, or as salts thereof, for example as pharmaceutically acceptable salts thereof. Thus, In some embodiments, the disclosure is directed to compounds of any one or more of Formula (I'), (IA'), (II'), (III'), (IV'), or (V'), as the free base. In some embodiments, the disclosure is directed to compounds of any one or more of Formula (I'), (IA'), (II'), (III'), (IV'), or (V'), and salts thereof. In some embodiments, the disclosure is directed to compounds of any one or more of Formula (I'), (IA'), (II'), (III'), (IV'), or (V'), and pharmaceutically acceptable salts thereof.

The compounds according to any one or more of Formula (I'), (IA'), (II'), (III'), (IV'), or (V'), or salts, including pharmaceutically acceptable salts, thereof, are modulators of STING. Accordingly, this disclosure provides a compound of any one or more of Formula (I'), (IA'), (II'), (III'), (IV'), or (V'), or a salt thereof, including a pharmaceutically acceptable salt thereof, for use in therapy. This disclosure provides for the use of a compound of any one or more of Formula (I'), (IA'), (II'), (III'), (IV'), or (V'), or a pharmaceutically acceptable salt thereof, as an active therapeutic substance in the treatment of a STING-mediated disease or disorder. In some embodiments, a compound of any one or more of any one or more of Formula (I'), (IA'), (II'), (III'), (IV'), or (V'), or a salt thereof, including a pharmaceutically acceptable salt thereof, for use in the treatment of a disease mediated by agonism or antagonism of STING. The disclosure also provides a compound of any one or more of Formula (I'), (IA'), (II'), (III'), (IV'), or (V'), or a salt thereof, including a pharmaceutically acceptable salt thereof, for use in the manufacture of a medicament for the treatment of a STING-mediated disease or disorder.

The disclosure is further directed to a method of modulating STING, which method comprises contacting a cell with a compound according to any one or more of Formula (I'), (IA'), (II'), (III'), (IV'), or (V'), or a salt, including a pharmaceutically acceptable salt, thereof. The disclosure is further directed to a method of treating a STING-mediated disease or disorder which comprises administering a therapeutically effective amount of a compound according to any one or more of Formula (I'), (IA'), (II'), (III'), (IV'), or (V'), or a salt, including a pharmaceutically acceptable salt thereof, to a patient (a human or other mammal) in need thereof. Such STING-mediated diseases or disorders include inflammation, allergic and autoimmune diseases, infectious diseases, cancer, and pre-cancerous syndromes. In addition, modulators of STING may be useful as immunogenic composition or vaccine adjuvants.

The present disclosure is further directed to a pharmaceutical composition comprising a compound according to any one or more of Formula (I'), (IA'), (II'), (III'), (IV'), or (V'), or a salt, including a pharmaceutically acceptable salt, thereof and a pharmaceutically acceptable excipient. The disclosure is directed to a pharmaceutical composition for the treatment of a STING-mediated disease or disorder, where the composition comprises a compound according to any one or more of Formula (I'), (IA'), (II'), (III'), (IV'), or (V'), or a salt, including a pharmaceutically acceptable salt, thereof and a pharmaceutically acceptable excipient.

Definitions

The chemical names provided for the intermediate compounds and/or the compounds of this disclosure described herein may refer to any one of the tautomeric representations of such compounds (in some instances, such alternate names are provided with the experimental). It is to be understood that any reference to a named compound (an intermediate compound or a compound of the disclosure) or a structurally depicted compound (an intermediate compound or a compound of the disclosure) is intended to encompass all tautomeric forms including zwitterionic forms of such compounds and any mixture thereof.

It is understood that in any one or more of Formula (I'), (IA'), (II'), (III'), (IV'), or (V'), ① when present, denotes Ring 1 which may be specified according to various embodiments described herein; and ②, when present, denotes Ring 2 which may be specified according to various embodiments described herein.

It is to be understood that the embodiments for a compound of Formula (I'), (IA'), (II'), (III'), (IV'), or (V'), is intended to encompass Formula (I'), (IA'), (II'), (III'), (IV'), and (V') where applicable.

It is to be understood that the terms "In some embodiments", "In some embodiments of the present disclosure", and "In some embodiments of a compound of the present disclosure" may be used interchangeably where appropriate.

The term "alkyl", as used herein, represents a saturated, straight or branched hydrocarbon group having the specified number of carbon atoms. The term "$C_{1-4}$ alkyl" refers to a straight or branched alkyl moiety comprising from 1 to 4 carbon atoms. Exemplary alkyls include, but are not limited to methyl, ethyl, n-propyl, isopropyl, n-butyl, isobutyl, s-butyl, t-butyl, pentyl and hexyl.

When a substituent term such as "alkyl" is used in combination with another substituent term, for example as in "hydroxy($C_{1-4}$ alkyl)", the linking substituent term (e.g., alkyl) is intended to encompass a divalent moiety, wherein the point of attachment is through that linking substituent. Examples of "hydroxy($C_{1-4}$ alkyl)" groups include, but are not limited to, hydroxy methyl, hydroxyethyl, and hydroxyisopropyl.

The term "halo(alkyl)", as used herein, represents a saturated, straight or branched hydrocarbon group having the specified number (n) of carbon atoms and one or more (up to 2n+1) halogen atoms. For example, the term "halo ($C_{1-4}$ alkyl)" represents a group having one or more halogen atoms, which may be the same or different, at one or more carbon atoms of an alkyl moiety comprising from 1 to 4 carbon atoms. Examples of "halo($C_{1-4}$ alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

The term "Alkenyl", as used herein, refers to straight or branched hydrocarbon group having the specified number of carbon atoms and at least 1 and up to 3 carbon-carbon double bonds. Examples include ethenyl and propenyl.

The term "Alkynyl", as used herein, refers to straight or branched hydrocarbon group having the specified number of carbon atoms and at least 1 and up to 3 carbon-carbon triple bonds. Examples include ethynyl and propynyl.

The term "Alkoxy-" or "(alkyl)oxy-", as used herein, refers to an "alkyl-oxy-" group, comprising an alkyl moiety, having the specified number of carbon atoms, attached through an oxygen linking atom. For example, the term "$C_{1-4}$ alkoxy-" represents a saturated, straight or branched hydrocarbon moiety having at least 1 and up to 4 carbon atoms attached through an oxygen linking atom. Exemplary "$C_{1-4}$ alkoxy-" or "($C_{1-4}$ alkyl)oxy-" groups include, but are not limited to, methoxy, ethoxy, n-propoxy, isopropoxy, n-butoxy, s-butoxy, and t-butoxy.

The term "halo(alkoxy)-", as used herein, represents a saturated, straight or branched hydrocarbon group having the specified number (n) of carbon atoms and one or more (up to 2n+1) halogen atoms, attached through an oxygen linking atom. For example, the term "halo($C_{1-4}$ alkoxy)-" refers to a "haloalkyl-oxy-" group, comprising a "halo($C_{1-4}$ alkyl)" moiety attached through an oxygen linking atom. Exemplary "halo($C_{1-4}$ alkoxy)-" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

The term "amino" as used herein refers to a substituent comprising at least one nitrogen atom. Specifically, —$NH_2$, —NH($C_{1-4}$ alkyl), alkylamino, or ($C_{1-4}$ alkyl)amino- or ($C_{1-4}$ alkyl)($C_{1-4}$ alkyl)amino- or dialkylamino, amide-, carbamide-, urea, and sulfamide substituents are included in the term "amino".

The term "carbocyclic group or moiety" as used herein, refers to a cyclic group or moiety in which the ring members are carbon atoms, which may be saturated, partially unsaturated (non-aromatic) or fully unsaturated (aromatic).

The term "cycloalkyl", as used herein, refers to a non-aromatic, saturated, hydrocarbon ring group comprising the specified number of carbon atoms in the ring. For example, the term "$C_{3-6}$ cycloalkyl" refers to a cyclic group having from three to six ring carbon atoms. Exemplary "$C_{3-6}$ cycloalkyl" groups include cyclopropyl, cyclobutyl, cyclopentyl, and cyclohexyl.

The term "heterocyclic group or moiety", as used herein, refers to a cyclic group or moiety having, as ring members, atoms of at least two different elements, which cyclic group or moiety may be saturated, partially unsaturated (non-aromatic) or fully unsaturated (aromatic).

The term "heteroatom", as used herein, refers to a nitrogen, sulfur, or oxygen atom, for example a nitrogen atom or an oxygen atom.

The term "heterocycloalkyl", as used herein, refers to a non-aromatic, monocyclic or bicyclic group comprising 3-10 ring atoms and comprising one or more (generally one or two) heteroatom ring members independently selected from oxygen, sulfur, and nitrogen. The point of attachment of a heterocycloalkyl group may be by any suitable carbon or nitrogen atom.

Examples of "heterocycloalkyl" groups include, but are not limited to, aziridinyl, thiiranyl, oxiranyl, azetidinyl, oxetanyl, thietanyl, pyrrolidinyl, tetrahydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, and hexahydro-11,4-diazepinyl.

Examples of "4-membered heterocycloalkyl" groups include oxetanyl, thietanyl and azetidinyl.

The term "5-6 membered heterocycloalkyl", as used herein, refers to a saturated, monocyclic group, comprising 5 or 6 ring atoms, which includes one or two heteroatoms selected independently from oxygen, sulfur, and nitrogen. Illustrative examples of 5-6 membered heterocycloalkyl groups include, but are not limited to pyrrolidinyl, tetrahydrofuranyl, tetrahydrothienyl, tetrahydropyranyl, tetrahydrothiopyranyl, piperidinyl, piperazinyl, morpholinyl, and thiomorpholinyl.

The term "heteroaryl", as used herein, refers to an aromatic monocyclic or bicyclic group comprising 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups comprising either a phenyl ring fused to a heterocyclic moiety or a heteroaryl ring moiety fused to a carbocyclic moiety. The point of attachment of a heteroaryl group may be by any suitable carbon or nitrogen atom.

The term "5-6 membered heteroaryl", as used herein refers to an aromatic monocyclic group comprising 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, and oxadiazolyl. Selected 6-membered heteroaryl groups include pyridinyl (pyridyl), pyrazinyl, pyrimidinyl, pyridazinyl and triazinyl.

The term "9-10 membered heteroaryl", as used herein, refers to an aromatic bicyclic group comprising 9 or 10 ring atoms, including 1 to 4 heteroatoms independently selected from nitrogen, oxygen and sulfur. Examples of 9-membered heteroaryl (6,5-fused heteroaryl) groups include benzothienyl, benzofuranyl, indolyl, indolinyl (dihydroindolyl), isoindolyl, isoindolinyl, indazolyl, isobenzofuryl, 2,3-dihydrobenzofuryl, benzoxazolyl, benzoisoxazolyl, benzothiazolyl, benzoisothiazolyl, benzimidazolyl, benzoxadiazolyl, benzothiadiazolyl, benzotriazolyl, purinyl, imidazopyridinyl, pyrazolopyridinyl, triazolopyridinyl and 1,3-benzodioxolyl.

Examples of 10-membered heteroaryl (6,6-fused heteroaryl) groups include, but are not limited to, quinolinyl (quinolyl), isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, 1,2,3,4-tetrahydroquinolinyl (tetrahydroquinolinyl), 1,2,3,4-tetrahydroisoquinolinyl (tetrahydroisoquinolinyl), cinnolinyl, pteridinyl, and 2,3-dihydrobenzo[b][1,4]dioxinyl.

The terms "halogen" and "halo", as used herein, refers to a halogen radical, for example, a fluoro, chloro, bromo, or iodo substituent.

The term "oxo", as used herein, refers to a double-bonded oxygen moiety; for example, if attached directly to a carbon atom forms a carbonyl moiety (C=O).

The term "hydroxy" or "hydroxyl", as used herein, is intended to mean the radical —OH.

The term "cyano", as used herein, refers to a nitrile group, —C≡N.

The term "optionally substituted", as used herein, indicates that a group (such as an alkyl, cycloalkyl, alkoxy, heterocycloalkyl, aryl, or heteroaryl group) or ring or moiety may be unsubstituted, or the group, ring or moiety may be substituted with one or more substituent(s) as defined in the substituent definitions (A, $R^3$, etc,) provided herein. In the case where groups may be selected from a number of alternative groups, the selected groups may be the same or different.

The term "independently", as used herein, means that where more than one substituent is selected from a number of possible substituents, those substituents may be the same or different.

The term "pharmaceutically acceptable", as used herein, refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The length of the linking groups defined herein represents the lowest number of atoms in a direct chain composed of —$R^{B1}$—B—$R^{B2}$— and/or —$R^{C1}$-D-$R^{C2}$—. For example, when B is an optionally substituted phenyl, the linking group —$R^{B1}$—B—$R^{B2}$— may be represented as —(CH$_2$)-phenyl-(CH$_2$)—. This linking group is characterized as a 4-membered linking group when the 2 —(CH$_2$)— moieties are located on adjacent carbon atoms of the phenyl ring (1,2 substituted phenyl).

In some embodiments, this linking group is characterized as a 6-membered linking group when the 2—(CH$_2$)— moieties are substituted at para positions on the phenyl ring (1,4 substituted phenyl). It will be understood that any alkyl, alkenyl, or alkynyl group or moiety of B or D is a straight or branched-alkyl, alkenyl, or alkynyl group or moiety. For example, a —$R^{B1}$—B—$R^{B2}$-linking group, wherein B is alkyl- may contain an 8-membered linking group having a (C$_{1-4}$ alkyl) branching group or 2-4 (C$_{1-3}$ alkyl) branching groups, for example, 4 branching methyl groups (2 gem-dimethyl groups) or 2 branching methyl groups.

The terms "compound(s) of the disclosure" or "compound(s) of this disclosure", as used herein, mean a compound of Formula (I'), Formula (IA'), Formula (II'), Formula (III'), Formula (IV'), and Formula (V') as defined herein, in any form, i.e., any tautomeric form, any isomeric form, any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present disclosure are the compounds of any one or more of Formula (I'), (IA'), (II'), (III'), (IV'), or (V'), as defined herein, in any salt or non-salt form and any physical form thereof, and mixtures of various forms. While such are included within the present disclosure, it will be understood that the compounds of any one or more of Formula (I'), (IA'), (II'), (III'), (IV'), or (V'), as defined herein, in any salt or non-salt form, and in any physical form thereof, may have varying levels of activity, different bioavailabilities and different handling properties for formulation purposes.

Compound of the Present Disclosure

In some aspects, the present disclosure provides a compound of Formula (IA')

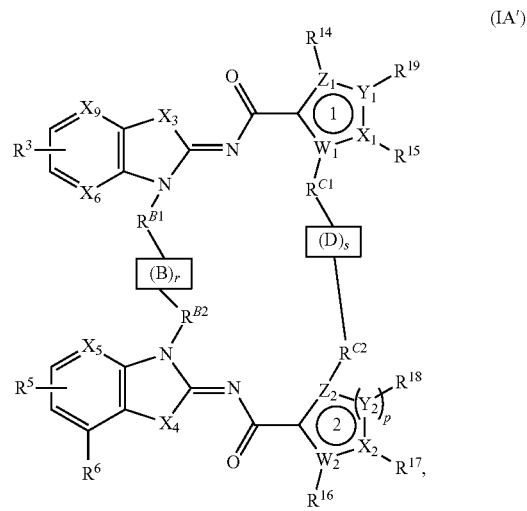

(IA')

or a prodrug, solvate, pharmaceutically acceptable salt, or tautomer thereof, wherein:

$W_1$, $X_1$, $Y_1$, $Z_1$, $W_2$, $X_2$, $Y_2$, and $Z_2$ are each independently O, S, C, or N;

$X_3$ and $X_4$ are each independently S or NR C;

$X_5$ is N or $CR^{A2}$;

$X_6$ is N or $CR^{A1}$;

$X_9$ is N or $CR^4$;

r and s are each independently 0 or 1;

p is 1 or 2;

the total of r and s is 1 or 2;

$R^{A1}$ and $R^{A2}$ are each independently H, halogen, amino, amino(C$_{1-4}$ alkyl)-, hydroxy, —O—P(O)(OH)$_2$, —O—

P(O)(R$^I$R$^{II}$)$_2$, —N(R$^e$)(R$^f$), —CO$_2$R$^f$, —N(R$^f$)COR$^b$, —N(R$^g$)SO$_2$(C$_{1-4}$ alkyl)-N(R$^e$)(R$^f$), —N(R$^g$)CO(C$_{1-4}$ alkyl)-N(10(R$^f$), optionally substituted (C$_{1-6}$ alkyl), optionally substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-, wherein the (C$_{1-6}$ alkyl) of said optionally substituted (C$_{1-6}$ alkyl), optionally substituted (C$_{1-6}$ alkyl)oxy-, optionally substituted (C$_{1-6}$ alkyl)amino- and optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)(R$^I$R$^{II}$)$_2$, C$_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-;

when r is 0, R$^{B1}$ and R$^{B2}$ are each independently H, optionally substituted C$_{1-6}$ alkyl, halo(C$_{1-6}$ alkyl), optionally substituted C$_{2-6}$ alkenyl, optionally substituted C$_{2-6}$ alkynyl, optionally substituted C$_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl, wherein said optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —O—P(O)(OH)$_2$, —O—P(O)(R$^I$R$^{II}$)$_2$ —OR$^c$, —NH$_2$, —NR$^c$R$^c$, —NR$^c$R$^d$, OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;

when s is 0, R$^{C1}$ is absent, H, halogen, or C$_{1-4}$ alkyl and R$^{C2}$ is absent or optionally substituted C$_{1-4}$ alkyl, wherein said optionally substituted C$_{1-4}$ alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

when r is 1, R$^{B1}$ and R$^{B2}$ are each independently —CH$_2$—, and B, taken together with R$^{B1}$ and R$^{B2}$, forms a linking group, wherein B is a bond or B is -halo(C$_{1-10}$ alkyl)-, optionally substituted —C$_{1-10}$ alkyl-, optionally substituted —C$_{2-11}$) alkenyl-, optionally substituted —C$_{2-11}$) alkynyl-, optionally substituted —C$_{1-6}$ alkyl-O—C$_{1-6}$ alkyl-, optionally substituted —C$_{1-6}$ alkyl-NR$^a$—C$_{1-6}$ alkyl-, optionally substituted C$_{3-6}$ cycloalkyl, optionally substituted phenyl, optionally substituted 4-6 membered heterocycloalkyl, optionally substituted 5-6 membered heteroaryl, optionally substituted —C$_{1-4}$ alkyl-(C$_{3-6}$ cycloalkyl)-C$_{1-4}$ alkyl-, optionally substituted —C$_{1-4}$ alkyl-phenyl-C$_{1-4}$ alkyl-, optionally substituted —C$_{1-4}$ alkyl-(4-6 membered heterocycloalkyl)-C$_{1-4}$ alkyl-, or optionally substituted —C$_{1-4}$ alkyl-(5-6 membered heteroaryl)-C$_{1-4}$ alkyl-, wherein the alkyl moiety of said optionally substituted —C$_{1-10}$ alkyl-, optionally substituted —C$_{2-10}$ alkenyl-, optionally substituted —C$_{2-10}$ alkynyl-, optionally substituted —C$_{1-6}$ alkyl-O—C$_{1-6}$ alkyl-, optionally substituted —C$_{1-6}$ alkyl-NR$^a$—C$_{1-6}$ alkyl-, optionally substituted —C$_{1-4}$ alkyl-(C$_{3-6}$ cycloalkyl)-C$_{1-4}$ alkyl-, optionally substituted —C$_{1-4}$ alkyl-phenyl-C$_{1-4}$ alkyl-, optionally substituted —C$_{1-4}$ alkyl-(4-6 membered heterocycloalkyl)-C$_{1-4}$ alkyl-, or optionally substituted —C$_{1-4}$ alkyl-(5-6 membered heteroaryl-C$_{1-4}$ alkyl)- is optionally substituted by 1 or 2 substituents each independently selected from halogen, halo(C$_{1-4}$ alkyl), —OH, —O—P(O)(OH)$_2$, —O—P(O)(R$^I$R$^{II}$)$_2$, —OR$^c$, —NH$_2$, —NR$^c$R$^d$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_{3-6}$ cycloalkyl, phenyl, 4-6 membered heterocycloalkyl, or 5-6 membered heteroaryl moiety of said optionally substituted C$_{3-6}$ cycloalkyl, optionally substituted phenyl, optionally substituted 4-6 membered heterocycloalkyl, optionally substituted 5-6 membered heteroaryl, optionally substituted —C$_{1-4}$ alkyl-(C$_{3-6}$ cycloalkyl)-C$_{1-4}$ alkyl-, optionally substituted —C$_{1-4}$ alkyl-phenyl-C$_{1-4}$ alkyl-, optionally substituted —C$_{1-4}$ alkyl-(4-6 membered heterocycloalkyl)-C$_{1-4}$ alkyl-, or optionally substituted —C$_{1-4}$ alkyl-(5-6 membered heteroaryl)-C$_{1-4}$ alkyl- is optionally substituted by 1-4 substituents each independently selected from halogen, hydroxy, —O—P(O)(OH)$_2$, —O—P(O)(OR$^I$R$^{II}$)$_2$, amino, (C$_{1-4}$ alkyl)amino-, (C$_{1-4}$ alkyl)(C$_{1-4}$ alkyl)amino-, C$_{1-4}$ alkyl, halo(C$_{1-4}$ alkyl), halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$$_2$, and C$_{1-4}$ alkoxy-(C$_{1-4}$ alkoxy)-;

when s is 1, W$_1$ and Z$_2$ are each independently C or N, R$^{C1}$ and R$^{C2}$ are each independently —CH$_2$—, and D taken together with R d and R$^{C2}$, forms a linking group, wherein D is -halo(C$_{1-12}$ alkyl)-, optionally substituted —C$_{1-12}$ alkyl-, optionally substituted —C$_{2-12}$ alkenyl-, optionally substituted —C$_{2-12}$ alkynyl-, optionally substituted —C$_{1-6}$ alkyl-O—C$_{1-6}$ alkyl-, optionally substituted —C$_{1-6}$ alkyl-NW—C$_{1-6}$ alkyl-, optionally substituted —C$_{1-6}$ alkyl-(C$_{3-6}$ cycloalkyl)-C$_{1-6}$ alkyl-, optionally substituted —C$_{1-6}$ alkyl-phenyl-C$_{1-6}$ alkyl-, optionally substituted —C$_{1-6}$ alkyl-(4-6 membered heterocycloalkyl)-C$_{1-6}$ alkyl-, or optionally substituted —C$_{1-6}$ alkyl-(5-6 membered heteroaryl)-C$_{1-6}$ alkyl-, wherein the alkyl moiety of said optionally substituted —C$_{1-12}$ alkyl-, optionally substituted —C$_{1-6}$ alkenyl-, optionally substituted —C$_{2-12}$ alkynyl-, optionally substituted —C$_{1-6}$ alkyl-O—C$_{1-6}$ alkyl-, optionally substituted —C$_{1-6}$ alkyl-NW—C$_{1-6}$ alkyl-, optionally substituted —C$_{1-6}$ alkyl-(C$_{3-6}$ cycloalkyl)-C$_{1-6}$ alkyl-, optionally substituted —C$_{1-6}$ alkyl-phenyl-C$_{1-6}$ alkyl-, optionally substituted —C$_{1-6}$ alkyl-(4-6 membered heterocycloalkyl)-C$_{1-6}$ alkyl-, or optionally substituted —C$_{1-6}$ alkyl-(5-6 membered heteroaryl)C$_{1-6}$ alkyl- is optionally substituted by 1 or 2 substituents each independently selected from halogen, halo(C$_{1-4}$ alkyl), —OH, —O—P(O)(OH)$_2$, —O—P(O)(R$^I$R$^{II}$$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_{3-6}$ cycloalkyl, phenyl, 4-6 membered heterocycloalkyl, or 5-6 membered heteroaryl moiety of said optionally substituted —C$_{1-6}$ alkyl-(C$_{3-6}$ cycloalkyl)-C$_{1-6}$ alkyl-, optionally substituted —C$_{1-6}$ alkyl-phenyl-C$_{1-6}$ alkyl-, optionally substituted —C$_{1-6}$ alkyl-(4-6 membered heterocycloalkyl)-C$_{1-6}$ alkyl-, or optionally substituted —C$_{1-6}$ alkyl-(5-6 membered heteroaryl)-C$_{1-6}$ alkyl- is optionally substituted by 1-4 substituents each independently selected from halogen, hydroxy, —O—P(O)(OH)$_2$, O—P—(O)(R$^I$R$^{II}$)$_2$, amino, (C$_{1-4}$ alkyl)amino-, (C$_{1-4}$ alkyl)(C$_{1-4}$ alkyl)amino-, C$_{1-4}$ alkyl, halo(C$_{1-4}$ alkyl), halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, and C$_{1-4}$ alkoxy-(C$_{1-4}$ alkoxy)-;

R$^3$ and R$^5$ are each independently —CON(R$^d$)(R$^f$), —CH$_2$N(R$^d$)(R$^f$), —N(R$^d$)(R$^f$), —N(R$^d$)CO(R$^f$), —CH$_2$N(R$^d$)CO(R$^f$), or one of R$^3$ and R$^5$ is —CON(R$^d$)(R$^f$), —CH$_2$N(R$^d$)(R$^f$), —N(R$^d$)(R$^f$), —N(R$^d$)CO(R$^f$), or —CH$_2$N(R$^d$)CO(R$^f$), and the other of R$^3$ and R$^5$ is H, COOH, or —CO$_2$R$^c$;

R$^4$ and R$^6$ are each independently selected from H, halogen, halo(C$_{1-6}$ alkyl), halo(C$_{1-6}$ alkoxy)-, hydroxy, —O—O—P(O)(OH)$_2$, O—P(O)a(R$^I$R$^{II}$)$_2$, —NH$_2$, —NR$^c$R$^c$, —NR$^c$R$^d$, —COR$^c$, —CO$_2$R$^c$, —N(R$^d$)COR$^c$, —N(R$^d$)SO$_2$R$^c$, —N(R$^g$)SO$_2$(C$_{1-2}$ alkyl)-N(R$^h$)(R$^f$), —N(R$^g$)CO(C$_{1-2}$ alkyl)-N(R$^h$)(R$^f$), optionally substituted (C$_{1-6}$ alkyl), optionally substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-, wherein the (C$_{1-6}$ alkyl) of said optionally substituted (C$_{1-6}$ alkyl), optionally substituted (C$_{1-6}$ alkyl)oxy-, optionally substituted (C$_{1-6}$ alkyl)amino- and optionally substituted (C$_{1-6}$ alkyl)(C$_{1-4}$ alkyl)amino- is optionally substituted by 1-4 substituents each independently selected from —OH, —O—P(O)(OH)$_2$, —O—P(O)(R$^I$R$^{II}$)$_2$, —OR$^c$, —NH$_2$, —NR$^c$R$^c$, —NR$^c$R$^d$, —CO$_2$H, —CO$_2$R$^c$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, —NR$^d$SO$_2$R$^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-4}$ alkyl)amino-, (C$_{1-4}$ alkyl)(C$_{1-4}$ alkyl)amino-, C$_{1-4}$ alkyl, halo(C$_{1-4}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, C$_{1-4}$ alkoxy-(C$_{1-4}$ alkoxy)-, —COR$^d$, —CON(R$^d$)(R$^f$), and —CO$_2$R$^d$, R$^{14}$ is absent, H, halogen, or optionally substituted C$_{1-4}$ alkyl, wherein said optionally substituted C$_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;

R$^{16}$ is absent, H, halogen, or C$_{1-4}$ alkyl;

R$^{15}$ and R$^{17}$ are each independently absent, H, cyclopropyl, halogen or optionally substituted C$_{1-4}$ alkyl, wherein said optionally substituted C$_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$; or R$^{15}$ and R$^{19}$ taken together with the atom or atoms through which they are connected, form a 5-6 membered ring; or R$^{16}$ and R$^{17}$ taken together with the atom or atoms through which they are connected, form a 5-6 membered ring;

R$^{18}$ and R$^{19}$ are each independently absent, H, halogen, optionally substituted C$_{1-4}$ alkyl, wherein said optionally substituted C$_{1-4}$ alkyl is optionally substituted by a substituent selected from halogen, —OR$^c$, —NR$^c$R$^d$, —CONR$^c$R$^d$, —SO$_2$NR$^c$R$^d$, and —OCONR$^c$R$^d$; or R$^{17}$ and R$^{18}$ taken together with the atom or atoms through which they are connected, form a 5-6 membered ring;

R$^a$ is H, —COR$^c$, —CO$_2$H, —CO$_2$R$^c$, —SO$_2$R$^c$, —CONH$_2$, —CONR$^c$R$^d$, —SO$_2$NH$_2$, —CH$_2$—CO$_2$R$^c$, or —SO$_2$NR$^c$R$^d$;

each R$^b$ is independently C$_{1-4}$ alkyl, halo(C$_{1-4}$ alkyl), —(C$_{1-4}$ alkyl)-OH, —(C$_{1-4}$ alkyl)-O—P(O)(OH)$_2$, —(C$_{1-4}$ alkyl)-O—P(O)(R$^I$R$^{II}$)$_2$, —(C$_{1-4}$ alkyl)-O—(C$_{1-4}$ alkyl), —(C$_{1-4}$ alkyl)-N(R$^e$)(R$^f$), —(C$_{1-4}$ alkyl)-O—CO(C$_{1-4}$ alkyl), or —(C$_{1-4}$ alkyl)-CO—O—(C$_{1-4}$ alkyl);

each R$^c$ is independently H, C$_{1-4}$ alkyl, halo(C$_{1-4}$ alkyl), —(C$_{1-4}$ alkyl)-OH, —(C$_{1-4}$ alkyl)-O—P(O)(OH)$_2$, —(C$_{1-4}$ alkyl)-O—P(O)(R$^I$R$^{II}$)$_2$, —(C$_{1-4}$ alkyl)-O—(C$_{1-4}$ alkyl), —(C$_{1-4}$ alkyl)-N(R$^e$)(R$^f$), —(C$_{1-4}$ alkyl)-O—CO(C$_{1-4}$ alkyl), —(C$_{1-4}$ alkyl)-CO—O—(C$_{1-4}$ alkyl), optionally substituted C$_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C$_{1-4}$ alkyl-C$_{3-6}$ cycloalkyl, optionally substituted —C$_{1-4}$ alkyl-phenyl, optionally substituted —C$_{1-4}$ alkyl-4-6 membered heterocycloalkyl, optionally substituted —C$_{1-4}$ alkyl-5-6 membered heteroaryl, or optionally substituted —C$_{1-4}$ alkyl-9-10 membered heteroaryl, wherein the C$_{3-6}$ cycloalkyl, phenyl, 4-6 membered heterocycloalkyl, 5-6 membered heteroaryl or 9-10 membered heteroaryl moiety of said optionally substituted C$_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C$_{1-4}$ alkyl-C$_{3-6}$ cycloalkyl, optionally substituted —C$_{1-4}$ alkyl-phenyl, optionally substituted —C$_{1-4}$ alkyl-4-6 membered heterocycloalkyl, optionally substituted —C$_{1-4}$ alkyl-5-6 membered heteroaryl, or optionally substituted —C$_{1-4}$ alkyl-9-10 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-4}$ alkyl)amino-, (C$_{1-4}$ alkyl)(C$_{1-4}$ alkyl)amino-, C$_{1-4}$ alkyl, halo(C$_{1-4}$ alkyl), halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, C$_{1-4}$ alkoxy-(C$_{1-4}$ alkoxy)-, —COR$^d$, —CON(R$^d$)(R$^f$), and —CO$_2$R$^d$;

each R$^d$ is independently H, hydroxy, or C$_{1-4}$ alkyl;

each R$^e$ is independently H, (C$_{1-4}$ alkyl), —CO(C$_{1-4}$ alkyl), —OCO(C$_{1-4}$ alkyl), —CO$_2$(C$_{1-4}$ alkyl), —(C$_{1-4}$ alkyl)amino, —(C$_{1-4}$ alkyl)-C$_{1-4}$ alkoxy, —CO-(optionally substituted 5-6 membered heterocycloalkyl), —CO—($C_{1-4}$ alkyl)-(optionally substituted 5-6 membered heterocycloalkyl), —CO-(optionally substituted 5-6 membered heteroaryl), —CO—($C_{1-4}$ alkyl)-(optionally substituted 5-6 membered heteroaryl), wherein the optionally substituted 5-6 membered heterocycloalkyl or optionally substituted 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)O—P(O)(OH)$_2$, —($C_{2-4}$ alkoxy)-O—P(O)(R$^I$R$^{II}$)$_2$, $C_{1-4}$ alkoxy-($C_{1-4}$ alkoxy)-, —COR$^d$, —CON(R$^d$)(R$^f$), and —CO$_2$R$^d$;

each R$^f$ is independently H, hydroxy, or ($C_{1-4}$ alkyl);

R$^g$ and R$^h$ are each independently H or ($C_{1-4}$ alkyl) or R$^g$ and R h, taken together with the atom or atoms through which they are connected, form a 5-6 membered ring; and each R$^I$ and R$^{II}$ are independently ($C_{1-6}$ alkyl)oxy-;

provided that at least one of (i), (ii), or (iii), applies:

(i) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and Yi are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S or $X_9$ is N; or (ii) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then R" is a $C_{1-4}$ alkyl substituted with halogen, —OR$^c$, —NR$^c$R$^d$, —CO$_2$R$^c$, —CONR$^c$R$^d$, —SO$_2$NR$^c$R$^d$, and —OCONR$^c$R$^d$ wherein R$^c$ is H; or (iii) when s is 0, r is 1, (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and Yi are each C; or (d) $W_2$ and $X_2$ are each N, $Z_2$ and $Y_2$ are each C, then at least one of $X_5$, $X_6$, and $X_9$ is N and R$^{41}$ or R$^{42}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)(R$^I$R$^{II}$)$_2$, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-$C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, the compound is of Formula (IA'), wherein the compound is Formula (IA):

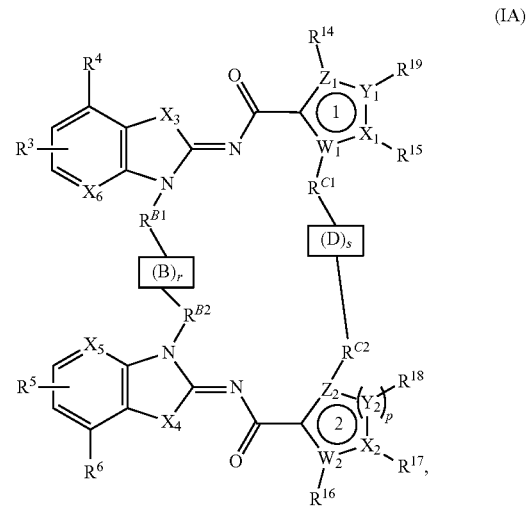

(IA)

or a prodrug, solvate, pharmaceutically acceptable salt, or tautomer thereof.

In some aspects, the present disclosure provides a compound of Formula (I')

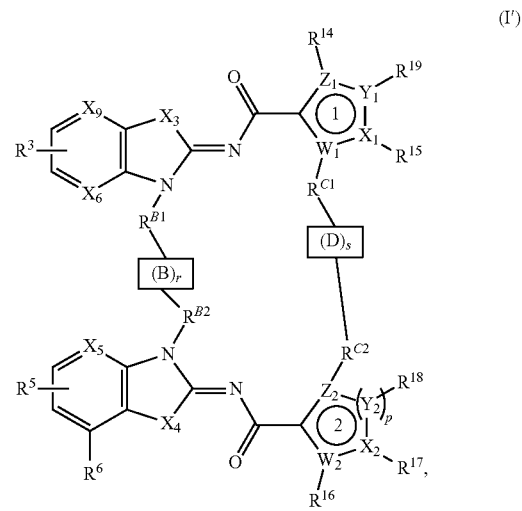

(I')

or a prodrug, solvate, pharmaceutically acceptable salt, or tautomer thereof, wherein:

$W_1$, $X_1$, $Y_1$, $Z_1$, $W_2$, $X_2$, $Y_2$, $Z_2$, r, s, $X_3$, $X_4$, $X_5$, $X_6$, $X_9$, $R^3$, $R^5$, $R^{14}$, $R^a$, $R^b$, $R^c$, $R^d$, $R^e$, $R^f$, $R^I$ and $R^{II}$ are each independently as defined for Formula (IA');

when r is 0, $R^{B1}$ and $R^{B2}$ are each independently as defined for Formula (IA');

when s is 0, $R^{C1}$ is as defined for Formula (IA');

when r is 1, $R^{B1}$ and $R^{B2}$ are each independently —CH$_2$—, and B, taken together with $R^{B1}$ and $R^{B2}$, forms a linking group, wherein B is a bond or B is as defined for Formula (IA');

when s is 1, $W_1$ and $Z_2$ are each independently C or N, $R^{C1}$ and $R^{C2}$ are each independently —CH$_2$—, and D taken together with IC and $R^{C2}$, forms a linking group, wherein D is as defined for Formula (IA');

$R^{16}$ is absent, H, halogen, or $C_{1-4}$ alkyl;

$R^{15}$ and $R^{17}$ are each independently absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring;

$R^{18}$ and $R^{19}$ are each independently as defined for Formula (IA'); or $R^{17}$ and $R^{18}$ taken together with the atom or atoms through which they are connected, form a 5-6 membered ring;

$R^g$ and $R^h$ are each independently as defined for Formula (IA')or $R^g$ and R h, taken together with the atom or atoms through which they are connected, form a 5-6 membered ring; and provided that at least one of (i), (ii), or (iii) of Formula (IA') applies.

In some aspects, the present disclosure provides a compound of Formula (I') or a prodrug, solvate, pharmaceutically acceptable salt, or tautomer thereof, provided that at least one of (i), (ii), or (iii) applies:

(i) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then R" is a $C_{1-4}$ alkyl substituted with halogen, —$OR^c$, —$NR^cR^d$, —$CO_2R^c$, —$CONR^cR^d$, —$SO_2NR^cR^d$, and —$OCONR^cR^d$ wherein $R^c$ is H; or (iii) when s is 0, r is 1, (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or R A2 is hydroxy, substituted ($C_{1-6}$ alkyl), substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-, wherein the ($C_{1-6}$ alkyl) of said substituted ($C_{1-6}$ alkyl) and substituted ($C_{1-6}$ alkyl)oxy- is substituted by 1-4 substituents each independently selected from —O—P(O)(OH)$_2$, —O—P(O)($R^IR^{II}$)$_2$, -optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-;

and the ($C_{1-6}$ alkyl) of said optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, —N($R^e$)($R^f$), —$CO_2(R^f)$, —$CON(R^e)(R^f)$, optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, the compound is of Formula (I'), wherein the compound is Formula (I):

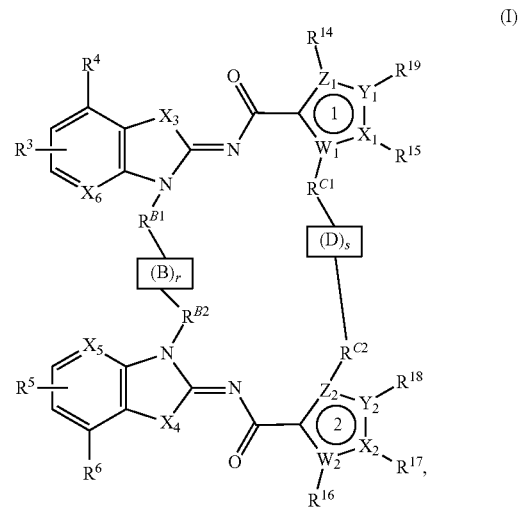

(I)

or a prodrug, solvate, pharmaceutically acceptable salt, or tautomer thereof

In some aspects, the present disclosure provides a compound of Formula (II')

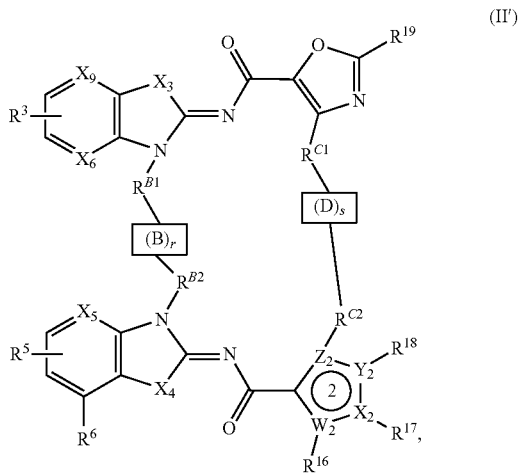

(II')

or a prodrug, solvate, pharmaceutically acceptable salt, or tautomer thereof, wherein:

$W_2$, $X_2$, $Y_2$, $Z_2$, r, s, $X_3$, $X_4$, $X_5$, $X_6$, $X_9R^3$, $R^4$, $R^5$, $R^6$, $R^a$, $R^c$, $R^b$, $R^d$, $R^e$, $R^f$, $R^I$ and $R^{II}$ are each independently as defined in Formula (IA');

when r is 0, $R^{B1}$ and $R^{B2}$ are each independently as defined in Formula (IA');

when s is 0, $R^{C1}$ is as defined in Formula (IA');

when r is 1, $R^{B1}$ and $R^{B2}$ are each independently —$CH_2$—, and B, taken together with $R^{B1}$ and $R^{B2}$, forms a linking group, wherein B is a bond or B is as defined in Formula (IA');

when s is 1, $Z_2$ is C or N, $R^{C1}$ and $R^{C2}$ are each independently —$CH_2$—, and D taken together with $R^{C1}$ and $R^{C2}$, forms a linking group, wherein D is as defined in Formula (IA');

$R^{16}$ is absent, H, halogen, or $C_{1-4}$ alkyl;

$R^{17}$ is absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;

$R^{18}$ is absent, H, halogen, optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{17}$ and $R^{18}$ taken together with the atom or atoms through which they are connected, form a 5-6 membered ring;

$R^{19}$ is absent, H, halogen, optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; and $R^g$ and $R^h$ are each independently as defined in Formula (IA') or $R^g$ and $R^h$, taken together with the atom or atoms through which they are connected, form a 5-6 membered ring.

In some aspects, the present disclosure provides a compound of Formula (II'), or a prodrug, solvate, pharmaceutically acceptable salt, or tautomer thereof, provided that when s is 0, r is 1, (a) $Z_2$ and $Y_2$ are each N, $W_2$ and $X_2$ are each C; or (b) $W_2$ and $X_2$ are each N, $Z_2$ and $Y_2$ are each C, then at least one of $X_5$, $X_6$, and $X_9$ is N and $R^{A1}$ or $R^{A2}$ is hydroxy, substituted ($C_{1-6}$ alkyl), substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-, wherein the ($C_{1-6}$ alkyl) of said substituted ($C_{1-6}$ alkyl) and substituted ($C_{1-6}$ alkyl)oxy-, is optionally substituted by 1-4 substituents each independently selected from —O—P(O)(OH)$_2$, —O—P(O)($R^IR^{II}$)$_2$, —optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo ($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-;

and the ($C_{1-6}$ alkyl) of said optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, —N($R^e$)($R^f$), —$CO_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O) ($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, the compound is of Formula (II'), wherein the compound is Formula (II):

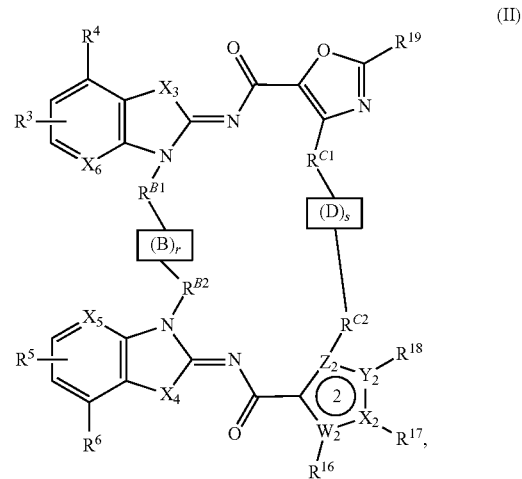

(II)

or a prodrug, solvate, pharmaceutically acceptable salt, or tautomer thereof.

In some aspects, the present disclosure provides a compound of Formula (III')

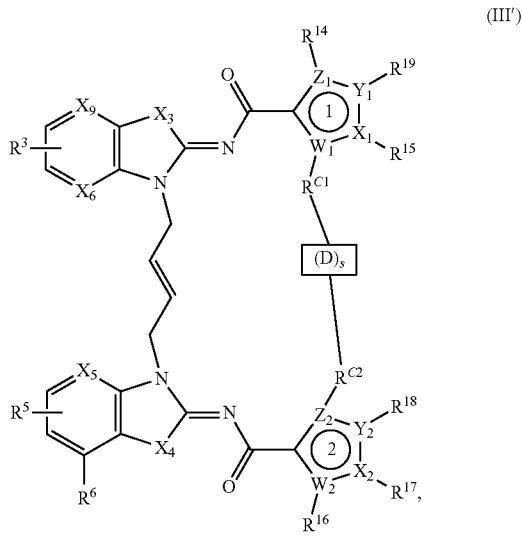

(III')

or a prodrug, solvate, pharmaceutically acceptable salt, or tautomer thereof, wherein:

$W_1$, $X_1$, $Y_1$, $Z_1$, $W_2$, $X_2$, $Y_2$, $Z_2$, s, $X_3$, $X_4$, $X_5$, $X_6$, $X_9$, $R^3$, $R^4$, $R^5$, $R^6$, $R^{14}$, $R^a$, $R^b$, $R^c$, $R^d$, $R^e$, $R^f$, $R^I$, and $R^{II}$ are each independently as defined in Formula (IA');

when s is 0, $R^{C1}$ is as defined in Formula (IA');

when s is 1, $W_1$ and $Z_2$ are each independently C or N, $R^{C1}$ and $R^{C2}$ are each independently —$CH_2$—, and D taken together with $R^{C1}$ and $R^{C2}$, forms a linking group, wherein D is as defined in Formula (IA');

$R^{16}$ is absent, H, halogen, or $C_{1-4}$ alkyl;

$R^{15}$ and $R^{17}$ are each independently absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring;

$R^{18}$ and $R^{19}$ are each independently as defined herein; or $R^{17}$ and $R^{18}$ taken together with the atom or atoms through which they are connected, form a 5-6 membered ring; and $R^g$ and $R^h$ are each independently as defined in Formula (IA')or $R^g$ and R h, taken together with the atom or atoms through which they are connected, form a 5-6 membered ring; and provided that at least one of (i), (ii), or (iii) applies:

(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when s is 0, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —$OR^c$, —$NR^cR^d$, —$CO_2R^c$, —$CONR^cR^d$, —$SO_2NR^cR^d$, and —$OCONR^cR^d$ wherein $R^c$ is H; or (iii) when s is 0, (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{41}$ or $R^{42}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl) amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^H$)$_2$, —N($R^e$)($R^f$), —$CO_2$($R^f$), —CON($R^e$)($R^f$), optionally substituted phenyl, and optionally substituted 5-6 membered heteroaryl group, wherein said optionally substituted phenyl, or 5-6 membered heteroaryl is optionally substituted by 1-4 substituents each independently selected from halogen, hydroxy, —O—P(O)(OH)$_2$, —O—P(O)($R^IR^H$)$_2$, amino, ($C_{1-6}$ alkyl)amino-, ($C_{1-6}$ alkyl)($C_{1-6}$ alkyl) amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^H$)$_2$, halo($C_{1-4}$ alkyl)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^H$)$_2$, —$C_{1-4}$ alkyl-($C_{1-4}$ alkoxy), and $C_{1-4}$ alkoxy-($C_{1-4}$ alkoxy)-.

In some embodiments, the compound is of Formula (III'), wherein the compound is Formula (III):

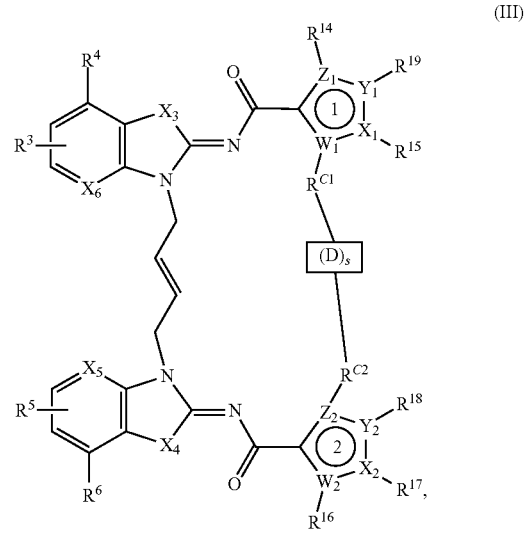

(III)

or a prodrug, solvate, pharmaceutically acceptable salt, or tautomer thereof.

In some aspects, the present disclosure provides a compound of Formula (IV')

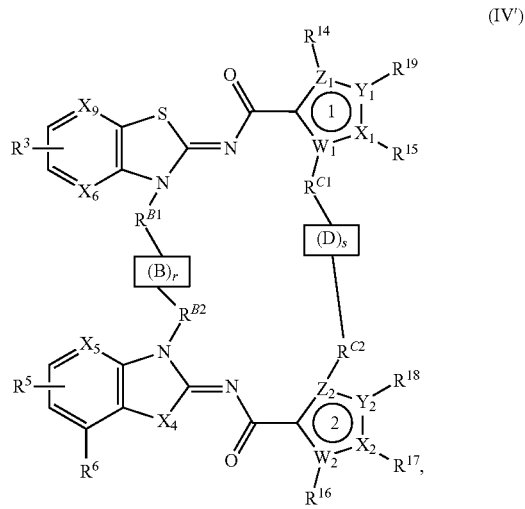

(IV')

or a prodrug, solvate, pharmaceutically acceptable salt, or tautomer thereof, wherein:

$W_1$, $X_1$, $Y_1$, $Z_1$, $W_2$, $X_2$, $Y_2$, $Z_2$, r, s, $X_3$, $X_4$, $X_5$, $X_6$, $X_9$. $R^3$, $R^4$ $R^5$, $R^6$, $R^{14}$, $R^{18}$, $R^{19}$, $R^a$, $R^b$, $R^c$, $R^d$, $R^e$, $R^f$, $R^I$, and $R^H$ are each independently when r is 0, $R^{B1}$ and $R^{B2}$ are each independently as defined in Formula (IA');

when s is 0, $R^{C1}$ is as defined in Formula (IA');

when r is 1, $R^{B1}$ and $R^{B2}$ are each independently —$CH_2$—, and B, taken together with $R^{B1}$ and $R^{B2}$, forms a linking group, wherein B is a bond or B is as defined in Formula (IA');

when s is 1, $W_1$ and $Z_2$ are each independently C or N, $R^{C1}$ and $R^{C2}$ are each independently —$CH_2$—, and D taken together with $R^{C1}$ and $R^{C2}$, forms a linking group, wherein D is as defined in Formula (IA');

$R^{16}$ is absent, H, halogen, or $C_{1-4}$ alkyl;

$R^{15}$ and $R^{17}$ are each independently absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring; and $R^g$ and $R^h$ are each independently as defined in Formula (IA') or $R^g$ and R h, taken together with the atom or atoms through which they are connected, form a 5-6 membered ring.

In some embodiments, the compound is of Formula (IV'), wherein the compound is Formula (IV):

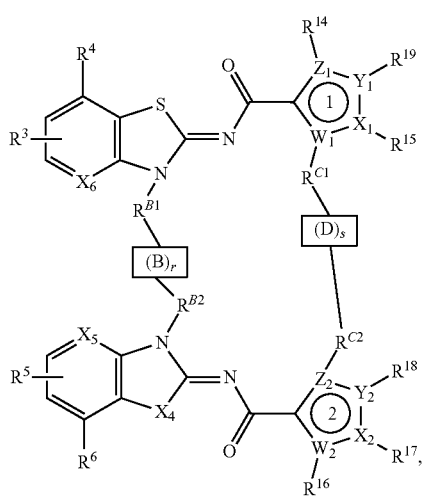

(IV)

or a prodrug, solvate, pharmaceutically acceptable salt, or tautomer thereof.

In some embodiments, the compound is of Formula (V'):

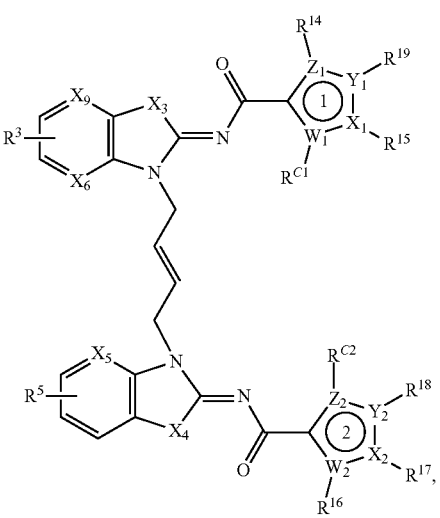

(V')

or a prodrug, solvate, pharmaceutically acceptable salt, or tautomer thereof, wherein:

$Y_1$, $Y_2$, $Z_1$ and $Z_2$ are each independently O, S, C or N;

$X_1$, $X_2$, $W_1$ and $W_2$ are each independently C or N;

$X_3$ and $X_4$ are each independently S or $NR^f$;

$X_5$ is N or $CR^{A2}$;

$X_6$ is N or $CR^{A1}$;

$X_9$ is N or CH;

$R^3$ and $R^5$ are each independently —$CON(R^d)(R^f)$, —$CH_2N(R^d)(R^f)$, —$N(R^d)(R^f)$, —$N(R^d)CO(R^f)$, —$CH_2N(R^d)CO(R^f)$ or one of $R^3$ and $R^5$ is —$CON(R^d)$ $(R^f)$, —$CH_2N(R^d)(R^f)$, —$N(R^d)(R^f)$, —$N(R^d)CO(R^f)$ or —$CH_2N(R^d)CO(R^f)$, and the other of $R^3$ and $R^5$ is H, —COOH, or —$CO_2R^c$;

$R^c$ is $C_{1-4}$ alkyl;

$R^{A2}$ and $R^{A1}$ are each independently H, halogen, amino, amino($C_{1-4}$ alkyl)-, hydroxy, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxy, $C_{1-4}$ alkoxyl, —$N(R^e)(R^f)$, —$CO_2(R^f)$, —$CON(R^e)(R^f)$, and —COOH;

each $R^d$ is independently H, hydroxy, or $C_{1-4}$ alkyl;

$R^e$ is selected from H, ($C_{1-4}$ alkyl), —$CO(C_{1-4}$ alkyl), —$OCO(C_{1-4}$ alkyl), and —$CO_2(C_{1-4}$ alkyl);

each $R^f$ is independently H, hydroxy, or ($C_{1-4}$ alkyl);

$R^{14}$ and $R^{C2}$ are each independently absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;

$R^{16}$ and IC are each independently absent, H or $C_{1-4}$ alkyl; and $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$;

provided that at least one of (i), (ii), or (iii) applies:

(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —$NR^cR^d$, —$CO_2R^c$, —$CONR^cR^d$, —$SO_2NR^cR^d$, and —$OCONR^cR^d$ wherein $R^c$ is H; or (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein $C_{1-6}$ alkyl of said optionally substituted ($C_{1-6}$ alkyl) or substituted ($C_{1-6}$ alkyl)oxy is optionally substituted with 1-4 substituents each independently selected from the group comprising hydroxy, $C_{1-4}$ alkoxyl, —N($R^e$)($R^f$), —CO$_2$($R^f$), —CON($R^e$)($R^f$), and —COOH.

In some embodiments, the compound is of Formula (V'), wherein the compound is of Formula (V):

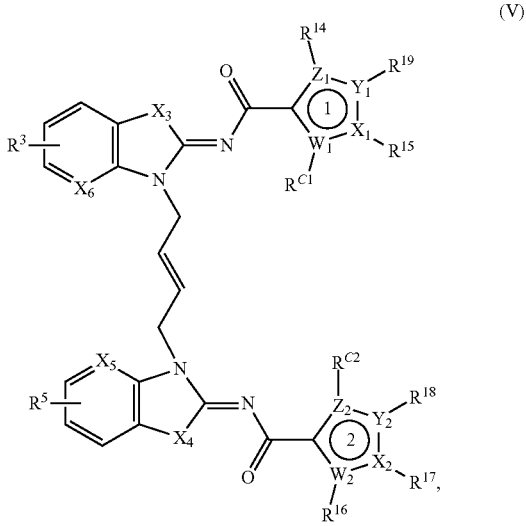

(V)

or a prodrug, solvate, pharmaceutically acceptable salt, or tautomer thereof.

In some aspects, the present disclosure provides a compound of Formula (I'), or a prodrug, solvate, pharmaceutically acceptable salt, or tautomer thereof, wherein:

$Y_1$, $Y_2$, $Z_1$, and $Z_2$ are each independently O, S, C, or N; $X_1$, $X_2$, $W_1$, and $W_2$ are each independently C or N;

$R^{A1}$ and $R^{A2}$ are each independently H, halogen, hydroxy, —O—P(O)(OH)$_2$, —O—P(O)($R^I R^{II}$)$_2$, —N($R^e$)($R^f$), CO$_2 R^f$, —N($R^f$)COR$^b$, —N($R^g$)SO$_2$(C$_{1-4}$ alkyl)-N($R^e$)($R^f$), —N($R^g$)CO(C$_{1-4}$ alkyl)-N($R^h$)($R^f$), optionally substituted (C$_{1-6}$ alkyl), optionally substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-, wherein the (C$_{1-6}$ alkyl) of said optionally substituted (C$_{1-6}$ alkyl), optionally substituted (C$_{1-6}$ alkyl)oxy-, optionally substituted (C$_{1-6}$ alkyl)amino- and optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)($R^I R^{II}$)$_2$, C$_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$—(C$_{1-4}$ alkyl)-O—P(O)(OH)$_2$, —(C$_{1-4}$ alkyl)-O—P(O)($R^I R^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)($R^I R^{II}$)$_2$, and C$_{1-4}$ alkoxy-(C$_{1-4}$ alkoxy)-;

and provided that at least one of (i), (ii), or (iii) applies:
(i) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a C$_{1-4}$ alkyl substituted with halogen, —OR$^c$, —NR$^c R^d$, —CO$_2 R^c$, —CONR$^c R^d$, —SO$_2$NR$^c R^d$, and —OCONR$^c R^d$ wherein R$^c$ is H; or (iii) when s is 0, r is 1, (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino-, wherein the (C$_{1-6}$ alkyl) of said optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)($R^I R^{II}$)$_2$, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo (C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)($R^I R^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)($R^I R^{II}$)$_2$, —C$_{1-4}$ alkyl-(C$_{1-4}$ alkoxy), and C$_{1-4}$ alkoxy-(C$_{1-4}$ alkoxy)-.

In some aspects, the present disclosure provides a compound of Formula (I'), or a prodrug, solvate, pharmaceutically acceptable salt, or tautomer thereof, wherein:

$R^{A1}$ and $R^{A2}$ are each independently H, halogen, hydroxy, —N($R^e$)($R^f$), —CO$_2 R^f$, —N($R^f$)COR$^b$, —N($R^g$)SO$_2$(C$_{1-4}$ alkyl)-N($R^e$)($R^f$), —N($R^g$)CO(C$_{1-4}$ alkyl)-N($R^h$)($R^f$), optionally substituted (C$_{1-6}$ alkyl), optionally substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-, wherein the (C$_{1-6}$ alkyl) of said optionally substituted (C$_{1-6}$ alkyl), optionally substituted (C$_{1-6}$ alkyl)oxy-, optionally substituted (C$_{1-6}$ alkyl)amino- and optionally substituted (C$_{1-6}$ alkyl)(C$_{1-4}$ alkyl)amino- is optionally substituted by 1-4 substituents each independently selected from hydroxy, C$_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, amino, (C$_{1-6}$ alkyl) amino-, (C$_{1-6}$ alkyl)(C$_{1-6}$ alkyl)amino-, halo(C$_{1-6}$ alkyl), hydroxy-(C$_{1-4}$ alkyl)-, halo(C$_{1-4}$ alkoxy)-, C$_{1-4}$ alkoxy-, hydroxy-(C$_{2-4}$ alkoxy)-, and C$_{1-4}$ alkoxy-(C$_{1-4}$ alkoxy)-;

when r is 0, $R^{B1}$ and $R^{B2}$ are each independently H, optionally substituted C$_{1-6}$ alkyl, halo(C$_{1-6}$ alkyl), optionally substituted C$_{2-6}$ alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl, wherein said optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —$OR^c$, —$NH_2$, —$NR^cR^c$, —$NR^cR^d$, —$OCOR^c$, —$CO_2H$, —$CO_2R^c$, —SORB, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$;

when r is 1, $R^{B1}$ and $R^{B2}$ are each independently —$CH_2$—, and B, taken together with $R^{B1}$ and $R^{B2}$, forms a linking group, wherein B is a bond or B is -halo($C_{1-10}$ alkyl)-, optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-$NR^a$—$C_{1-6}$ alkyl-, optionally substituted $C_{3-6}$ cycloalkyl, optionally substituted phenyl, optionally substituted 4-6 membered heterocycloalkyl, optionally substituted 5-6 membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl)-$C_{1-4}$ alkyl-, wherein the alkyl moiety of said optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-NR—$C_{1-6}$ alkyl-, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl-$C_{1-4}$ alkyl)- is optionally substituted by 1 or 2 substituents each independently selected from halogen, halo($C_{1-4}$ alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —NR d $SO_2R^c$, and the $C_{3-6}$ cycloalkyl, phenyl, 4-6 membered heterocycloalkyl, or 5-6 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl)-$C_{1-4}$ alkyl- is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, and $C_{1-4}$ alkoxy-($C_{1-4}$ alkoxy)-;

when s is 1, $W_1$ and $Z_2$ are each independently C or N, $R^{C1}$ and $R^{C2}$ are each independently —$CH_2$—, and D taken together with $R^{C1}$ and $R^{C2}$, forms a linking group, wherein D is -halo($C_{1-12}$ alkyl)-, optionally substituted —$C_{1-12}$ alkyl-, optionally substituted —$C_{2-12}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NR—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl-, wherein the alkyl moiety of said optionally substituted —$C_{1-12}$ alkyl-, optionally substituted —$C_{1-6}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NR—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)$C_{1-6}$ alkyl- is optionally substituted by 1 or 2 substituents each independently selected from halogen, halo($C_{1-4}$ alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, and the $C_{3-6}$ cycloalkyl, phenyl, 4-6 membered heterocycloalkyl, or 5-6 membered heteroaryl moiety of said optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl- is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, and $C_{1-4}$ alkoxy-($C_{1-4}$ alkoxy)-;

$R^4$ and $R^6$ are each independently selected from H, halogen, halo($C_{1-6}$ alkyl), halo($C_{1-6}$ alkoxy)-, hydroxy, —$NH_2$, —$NR^cR^c$, —$NR^cR^d$, —$COR^c$, —$CO_2R^c$, —$N(R^d)COR^c$, —$N(R^d)SO_2R^c$, —$N(R^g)$ $SO_2(C_{1-2}$ alkyl)-$N(R^h)(R^f)$, —$N(R^g)CO(C_{1-2}$ alkyl)-$N(R^h)(R^f)$, optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-, wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —SORB, —$SO_2R^c$—$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —$NR^dSO_2R^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or 5-6 membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), hydroxy-($C_{1-4}$ alkyl)-, halo($C_{1-4}$ alkoxy)-, $C_{1-4}$ alkoxy-, hydroxy-($C_{2-4}$ alkoxy)-, $C_{1-4}$ alkoxy-($C_{1-4}$ alkoxy)-, —$COR^d$, —$CON(R^d)(R^f)$, and —$CO_2R^d$;

each $R^b$ is independently $C_{1-4}$ alkyl, halo($C_{1-4}$ alkyl), —($C_{1-4}$ alkyl)-OH, —($C_{1-4}$ alkyl)-O—($C_{1-4}$ alkyl), —($C_{1-4}$ alkyl)-N($R^e$)($R^f$), —($C_{1-4}$ alkyl)-O—CO($C_{1-4}$ alkyl), or —($C_{1-4}$ alkyl)-CO—O—($C_{1-4}$ alkyl);

each $R^c$ is independently H, $C_{1-4}$ alkyl, halo($C_{1-4}$ alkyl), —($C_{1-4}$ alkyl)-OH, —($C_{1-4}$ alkyl)-O—($C_{1-4}$ alkyl), —($C_{1-4}$ alkyl)-N($R^e$)($R^f$), —($C_{1-4}$ alkyl)-O—CO($C_{1-4}$ alkyl), —($C_{1-4}$ alkyl)-CO—O—($C_{1-4}$ alkyl), optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-membered heteroaryl, wherein the $C_{3-6}$ cycloalkyl, phenyl, 4-6 membered heterocycloalkyl, 5-6 membered heteroaryl or 9-10 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl is optionally substituted by 1-4 substituents each independently selected from halogen, hydroxy, amino, —($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, $C_{1-4}$ alkoxy-($C_{1-4}$ alkoxy)-, —$COR^d$, —$CON(R^d)(R^f)$, and —$CO_2R^d$; and each $R^e$ is independently H, ($C_{1-4}$ alkyl), —$CO(C_{1-4}$ alkyl), —$OCO(C_{1-4}$ alkyl), —$CO_2(C_{1-4}$ alkyl), —CO-(optionally substituted 5-6 membered heterocycloalkyl), —CO—($C_{1-4}$ alkyl)-(optionally substituted 5-6 membered heterocycloalkyl), —CO-(optionally substituted 5-6 membered heteroaryl), —CO—($C_{1-4}$ alkyl)-(optionally substituted 5-6 membered heteroaryl), wherein the optionally substituted 5-6 membered heterocycloalkyl or optionally substituted 5-6 membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, $C_{1-4}$ alkoxy-($C_{1-4}$ alkoxy)-, —$COR^d$, —$CON(R^d)(R^f)$, and —$CO_2R^d$; provided that at least one of (i), (ii), or (iii) applies:

(i) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when s is 0, r is 1, (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —$OR^c$, —$NR^cR^d$, —$CO_2R^c$, —$CONR^cR^d$, —$SO_2NR^cR^d$, and —$OCONR^cR^d$ wherein $R^c$ is H; or (iii) when s is 0, r is 1, (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino- or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, —N($R^e$)($R^f$), —$CO_2(R^f)$, —$CON(R^e)(R^f)$, optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

The alternative definitions for the various groups and substituent groups of Formula (I'), Formula (IA'), Formula (II'), Formula (III'), Formula (IV'), or Formula (V') provided throughout the specification are intended to describe each compound species disclosed herein, individually, as well as groups of one or more compound species. The scope of this disclosure includes any combination of these group and substituent group definitions. The compounds of the disclosure are only those which are contemplated to be "chemically stable" as will be appreciated by those skilled in the art.

It will be appreciated by those skilled in the art that the compounds of this disclosure may exist in other tautomeric forms including zwitterionic forms, or isomeric forms. All tautomeric (including zwitterionic forms) and isomeric forms of the formulas and compounds described herein are intended to be encompassed within the scope of the present disclosure.

It will also be appreciated by those skilled in the art that the compounds of this disclosure may exist in tautomeric forms including, but not limited to, Formula (A), Formula (B), Formula (C), Formula (D) and/or Formula (E) or zwitterionic forms including, but not limited to, Formula (F), Formula (G) or Formula (H):

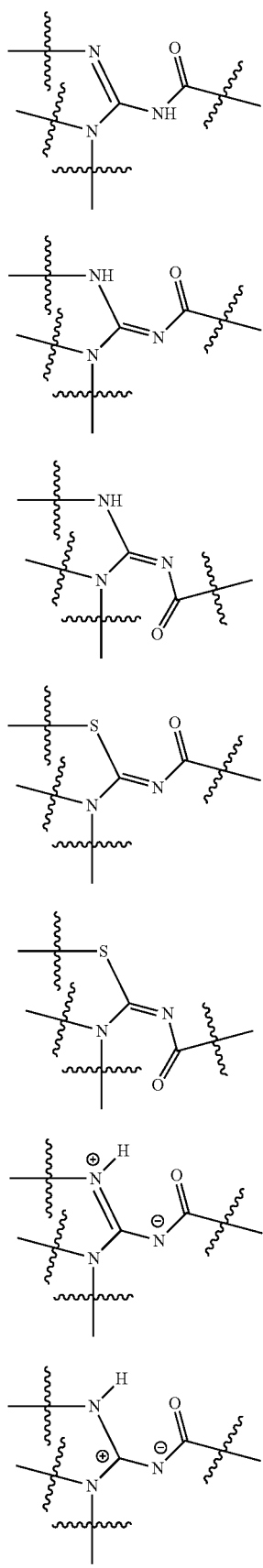

In some embodiments, when r is 1 and s is 0 (the total of r and s is 1), the compound of the disclosure is a compound of Formula (I-B') or Formula (I-b'):

(I-B')

(I-b')

wherein $X_7$ and $X_8$ are each independently C=O or $CH_2$.

In some embodiments, the compound of the disclosure is a compound of Formula (I-B') or Formula (I-b') wherein $X_9$ is $CR^4$.

In some embodiments, when r is 0 and s is 1 (the total of r and s is 1), $W_1$ and $Z_2$ are each independently C or N, the compound of the disclosure is a compound of Formula (I-D') or Formula (I-d'):

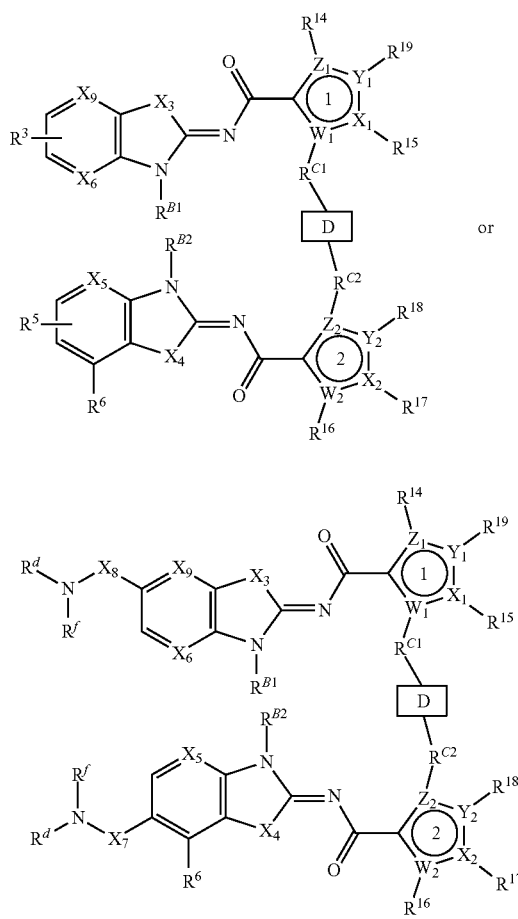

(I-D')

(I-d')

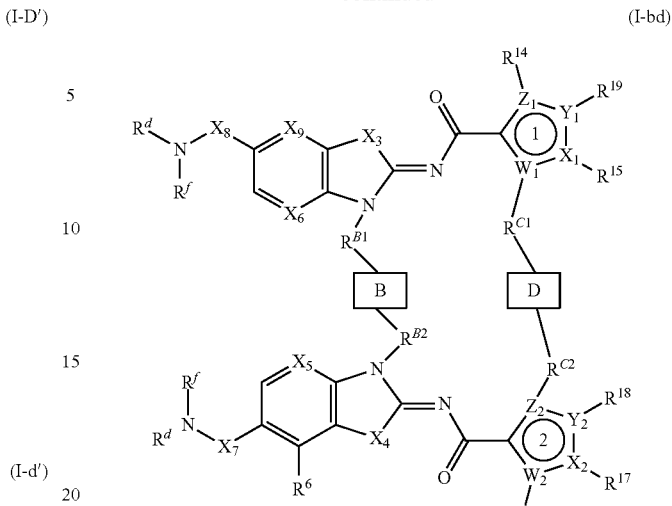

(I-bd)

wherein $X_7$ and $X_8$ are each independently C=O or $CH_2$.

In some embodiments, the compound of the disclosure is a compound of Formula (I-BD') or Formula (I-bd') wherein $X_9$ is $CR^4$.

It is to be understood that for a compound of Formula (I'), Formula (IA'), Formula (II'), Formula (III'), Formula (IV'), or Formula (V'), where applicable:

In some embodiments, $W_1$, $X_1$, $Y_1$, $Z_1$, $W_2$, $X_2$, $Y_2$, and $Z_2$ are each independently O, S, C, or N.

In some embodiments, $W_1$, $X_1$, $Y_1$, and $Z_1$ are each independently O, S, C, or N.

In some embodiments, $W_1$, $X_1$, $Y_1$, and $Z_1$ are each independently 0, C, or N. In some embodiments, $W_1$, $X_1$, $Y_1$, and $Z_1$ are each independently S, C, or N. In some embodiments, $W_1$, $X_1$, $Y_1$, and $Z_1$ are each independently 0, S, or C. In some embodiments, $W_1$, $X_1$, $Y_1$, and $Z_1$ are each independently O, S, or N.

In some embodiments, $W_1$ is O, S, C, or N. In some embodiments, $W_1$ is 0. In some embodiments, $W_1$ is S. In some embodiments, $W_1$ is C. In some embodiments, $W_1$ is N.

In some embodiments, $X_1$ is O, S, C, or N. In some embodiments, $X_1$ is 0. In some embodiments, $X_1$ is S. In some embodiments, $X_1$ is C. In some embodiments, $X_1$ is N.

In some embodiments, $Y_1$ is O, S, C, or N. In some embodiments, $Y_1$ is 0. In some embodiments, $Y_1$ is S. In some embodiments, $Y_1$ is C. In some embodiments, $Y_1$, is N.

In some embodiments, $Z_1$ is O, S, C, or N. In some embodiments, $Z_1$ is 0. In some embodiments, $Z_1$ is S. In some embodiments, $Z_1$ is C. In some embodiments, $Z_1$ is N.

In some embodiments, $W_2$, $X_2$, $Y_2$, and $Z_2$ are each independently O, S, C, or N.

In some embodiments, $W_2$, $X_2$, $Y_2$, and $Z_2$ are each independently 0, C, or N. In some embodiments, $W_2$, $X_2$, $Y_2$, and $Z_2$ are each independently S, C, or N. In some embodiments, $W_2$, $X_2$, $Y_2$, and $Z_2$ are each independently 0, S, or C. In some embodiments, $W_2$, $X_2$, $Y_2$, and $Z_2$ are each independently O, S, or N.

In some embodiments, $W_2$ is O, S, C, or N. In some embodiments, $W_2$ is 0. In some embodiments, $W_2$ is S. In some embodiments, $W_2$ is C. In some embodiments, $W_2$ is N.

In some embodiments, $X_2$ is O, S, C, or N. In some embodiments, $X_2$ is 0. In some embodiments, $X_2$ is S. In some embodiments, $X_2$ is C. In some embodiments, $X_2$ is N.

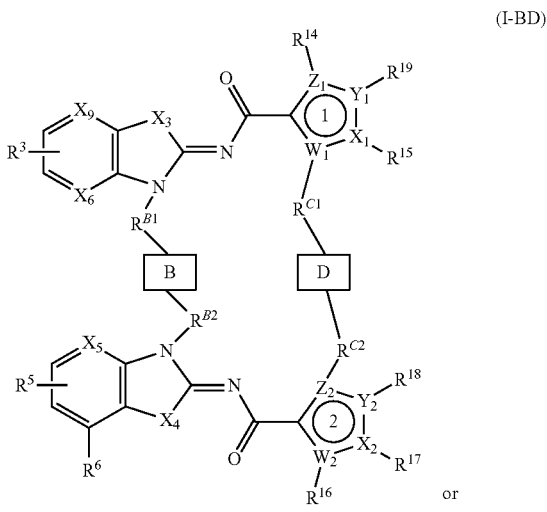

(I-BD)

wherein $X_7$ and $X_8$ are each independently C=O or $CH_2$.

In some embodiments, the compound of the disclosure is a compound of Formula (I-D') or Formula (I-d') wherein $X_9$ is $CR^4$.

In some embodiments, when r is 1 and s is 1 (the total of r and s is 2), $W_1$ and $Z_2$ are each independently C or N, the compound of the disclosure is a compound of Formula (I-BD') or Formula (I-bd').

or

In some embodiments, $Y_2$ is O, S, C, or N. In some embodiments, $Y_2$ is O. In some embodiments, $Y_2$ is S. In some embodiments, $Y_2$ is C. In some embodiments, $Y_2$ is N.

In some embodiments, $Z_2$ is O, S, C, or N. In some embodiments, $Z_2$ is O. In some embodiments, $Z_2$ is S. In some embodiments, $Z_2$ is C. In some embodiments, $Z_2$ is N.

In some embodiments, $X_3$ and $X_4$ are each independently S or NR C.

In some embodiments, $X_3$ and $X_4$ are each independently S. In some embodiments, $X_3$ and $X_4$ are each independently NR C.

In some embodiments, $X_3$ is S or NR C. In some embodiments, $X_3$ is S. In some embodiments, $X_3$ is NR C.

In some embodiments, $X_4$ is S or NR C. In some embodiments, $X_4$ is S. In some embodiments, $X_4$ is NR C.

In some embodiments, r is 0 or 1. In some embodiments, r is 0. In some embodiments, r is 1.

In some embodiments, s is 0 or 1. In some embodiments, s is 0. In some embodiments, s is 1.

In some embodiments, p is 1 or 2. In some embodiments, p is 1. In some embodiments, p is 2.

In some embodiments, when r is 0, B is absent and $R^{B1}$ and $R^{B2}$ are not connected.

In some embodiments, when s is 0, D is absent and $R^{C1}$ and $R^{C2}$ are not connected.

In some embodiments of the compounds of the present disclosure, $R^{A1}$ and $R^{A2}$ are each independently H, halogen, hydroxy, —N($R^e$)($R^f$), —CO$_2R^f$, —N($R^f$)COR$^b$, —N($R^g$)SO$_2$(C$_{1-4}$ alkyl)-N($R^e$)($R^f$), —N($R^g$)CO(C$_{1-4}$ alkyl)-N($R^h$)($R^f$), optionally substituted (C$_{1-6}$ alkyl), optionally substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-,
  wherein the (C$_{1-6}$ alkyl) of said optionally substituted (C$_{1-6}$ alkyl), optionally substituted (C$_{1-6}$ alkyl)oxy-, optionally substituted (C$_{1-6}$ alkyl)amino- and optionally substituted (C$_{1-6}$ alkyl)(C$_{1-4}$ alkyl)amino- is optionally substituted by 1-4 substituents each independently selected from hydroxy, C$_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, amino, (C$_{1-6}$ alkyl)amino-, (C$_{1-6}$ alkyl)(C$_{1-6}$ alkyl)amino-, halo(C$_{1-6}$ alkyl), hydroxy-(C$_{1-4}$ alkyl)-, halo-(C$_{1-4}$ alkoxy)-, C$_{1-4}$ alkoxy-, hydroxy-(C$_{2-4}$ alkoxy)-, and C$_{1-4}$ alkoxy-(C$_{1-4}$ alkoxy)-.

In some embodiments of the compounds of the present disclosure, $R^{A1}$ and $R^{A2}$ are each independently hydroxy, substituted (C$_{1-6}$ alkyl), substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-,
  wherein the (C$_{1-6}$ alkyl) of said substituted (C$_{1-6}$ alkyl) and substituted (C$_{1-6}$ alkyl)oxy-, is optionally substituted by 1-4 substituents each independently selected from —O—P(O)(OH)$_2$, —O—P(O)(R$^I$R$^{II}$)$_2$, —optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo (C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-;
and the (C$_{1-6}$ alkyl) of said optionally substituted (C$_{1-6}$ alkyl)amino- and optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)(R$^I$R$^{II}$)$_2$, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-.

In some embodiments of the compounds of this present disclosure, $R^{A1}$ and $R^{A2}$ are each independently H, halogen, hydroxy, —O—P(O)(OH)$_2$, —O—P(O)(R$^I$R$^{II}$)$_2$, —N($R^e$)($R^f$), —CO$_2R^f$, —N($R^f$)COR$^b$, —N($R^g$)SO$_2$(C$_{1-4}$ alkyl)-N($R^e$)($R^f$), —N($R^g$)CO(C$_{1-4}$ alkyl)-N($R^h$)($R^f$), optionally substituted (C$_{1-6}$ alkyl), optionally substituted (C$_{1-6}$ alkyl)oxy-, optionally substituted (C$_{1-6}$ alkyl)amino-, and optionally substituted (C$_{1-6}$ alkyl)(C$_{1-4}$ alkyl)amino-,
  wherein the (C$_{1-6}$ alkyl) of said optionally substituted (C$_{1-6}$ alkyl), optionally substituted (C$_{1-6}$ alkyl)oxy-, optionally substituted (C$_{1-6}$ alkyl)amino- and optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)(R$^I$R$^{II}$)$_2$, C$_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, and C$_{1-4}$ alkoxy-(C$_{1-4}$ alkoxy).

In some embodiments of the compounds of the present disclosure, $R^{A1}$ and $R^{A2}$ are each independently H, halogen, hydroxy, amino, (C$_{1-4}$ alkyl)amino-, (C$_{1-4}$ alkyl)(C$_{1-4}$ alkyl)amino-, (C$_{1-4}$ alkyl), hydroxy(C$_{1-4}$ alkyl)-, amino(C$_{1-4}$ alkyl)-, (C$_{1-4}$ alkyl)amino(C$_{1-4}$ alkyl)-, (C$_{1-4}$ alkyl)(C$_{1-4}$ alkyl)amino(C$_{1-4}$ alkyl)-, C$_{1-4}$ alkoxyl, hydroxy(C$_{2-4}$ alkoxyl)-, amino(C$_{2-4}$ alkoxyl)-, (C$_{1-4}$ alkyl)amino(C$_{2-4}$ alkoxyl)-, (C$_{1-4}$ alkyl)(C$_{1-4}$ alkyl)amino(C$_{2-4}$ alkoxyl)-, 6-membered heterocycloalkyl-(C$_{1-4}$alkyl)-, phenyl(C$_{1-4}$ alkoxy)-, (C$_{1-4}$ alkyl)OCONH(C$_{1-4}$ alkyl)-, hydroxy(C$_{1-4}$ alkyl)amino-, (C$_{1-4}$ alkyl)CONH—, (C$_{1-4}$ alkyl)CON(C$_{1-4}$ alkyl)-, —CO$_2$H, —CO$_2$(C$_{1-4}$ alkyl), amino(C$_{1-4}$ alkyl) CONH—, (C$_{1-4}$ alkyl)amino(C$_{1-4}$ alkyl)CONH—, (C$_{1-4}$ alkyl)(C$_{1-4}$ alkyl)amino(C$_{1-4}$ alkyl)CONH—, amino(C$_{1-4}$ alkyl)CON(C$_{1-4}$ alkyl)-, (C$_{1-4}$ alkyl)amino(C$_{1-4}$ alkyl)CON (C$_{1-4}$ alkyl)-, hydroxy(C$_{1-4}$alkyl)CONH—, (C$_{1-4}$alkyl)(C$_{1-}$ 4alkyl)amino($C_{1-4}$alkyl)CON($C_{1-4}$alkyl)-, hydroxy($C_{1-4}$ alkyl)CON($C_{1-4}$ alkyl)-, HO$_2$C($C_{1-4}$ alkoxy)-, ($C_{1-4}$ alkyl) OCO($C_{1-4}$ alkoxy)-, H$_2$NCO($C_{1-4}$ alkoxy)-, ($C_{1-4}$ alkyl) HNCO($C_{1-4}$ alkoxy)-, ($C_{1-4}$ alkyl)($C_{1-4}$ alkyl)NCO($C_{1-4}$ alkoxy)-, and —NHSO$_2$($C_{1-4}$ alkyl)-.

In some embodiments of the compounds of the present disclosure, $R^{41}$ and $R^{42}$ are each independently H, halogen, hydroxy, —O—P(O)(OH)$_2$, —O—P(O)($R^I R^{II}$)$_2$, amino, ($C_{1-4}$ alkyl)amino-, ($C_{1-4}$ alkyl)($C_{1-4}$ alkyl)amino-, ($C_{1-4}$ alkyl), hydroxy($C_{1-4}$ alkyl)-, amino($C_{1-4}$ alkyl)-, ($C_{1-4}$ alkyl) amino($C_{1-4}$ alkyl)-, ($C_{1-4}$ alkyl)($C_{1-4}$ alkyl)amino($C_{1-4}$ alkyl)-, $C_{1-4}$ alkoxy-, hydroxy($C_{2-4}$ alkoxy)-, —($C_{2-4}$ alkoxy)-O—P(O)(OH)$_2$, —($C_{2-4}$ alkoxy-O—P(O)($R^I R^{II}$)$_2$, amino($C_{2-4}$ alkoxy)-, ($C_{1-4}$ alkyl)amino($C_{2-4}$ alkoxy)-, ($C_{1-4}$ alkyl)($C_{1-4}$ alkyl)amino($C_{2-4}$ alkoxy)-, 6-membered heterocycloalkyl-($C_{1-4}$ alkyl)-, phenyl($C_{1-4}$ alkoxy)-, ($C_{1-4}$ alkyl) OCONH($C_{1-4}$ alkyl)-, hydroxy($C_{1-4}$ alkyl)amino-, -amino ($C_{1-4}$ alkyl)-O—P(O)(OH)$_2$, -amino($C_{1-4}$ alkyl)-O—P(O) ($R^I R^{II}$)$_2$, ($C_{1-4}$ alkyl)CONH—, ($C_{1-4}$ alkyl)CON($C_{1-4}$ alkyl)-, —CO$_2$H, —CO$_2$($C_{1-4}$ alkyl), amino($C_{1-4}$ alkyl) CONH—, ($C_{1-4}$ alkyl)amino($C_{1-4}$ alkyl)CONH—, ($C_{1-4}$ alkyl)($C_{1-4}$ alkyl)amino($C_{1-4}$ alkyl)CONH—, amino($C_{1-4}$ alkyl)CON($C_{1-4}$ alkyl)-, ($C_{1-4}$ alkyl)amino($C_{1-4}$ alkyl)CON ($C_{1-4}$ alkyl)-, hydroxy($C_{1-4}$ alkyl)CONH—, —NHCO($C_{1-4}$ alkyl)-O—P(O)(OH)$_2$, —NHCO($C_{1-4}$ alkyl)-O— P(O) ($R^I R^{II}$)$_2$, ($C_{1-4}$ alkyl)($C_{1-4}$ alkyl)amino($C_{1-4}$ alkyl)CON($C_{1-4}$ alkyl)-, hydroxy($C_{1-4}$ alkyl)CON($C_{1-4}$ alkyl)-, —($C_{1-4}$ alkyl) NCO($C_{1-4}$ alkyl)-O—P(O)(OH)$_2$, —($C_{1-4}$ alkyl)NCO($C_{1-4}$ alkyl)-O—P(O)($R^I R^{II}$)$_2$, HO$_2$C($C_{1-4}$ alkoxy)-, ($C_{1-4}$ alkyl) OCO($C_{1-4}$ alkoxy)-, H$_2$NCO($C_{1-4}$ alkoxy)-, ($C_{1-4}$ alkyl) HNCO($C_{1-4}$ alkoxy)-, ($C_{1-4}$ alkyl)($C_{1-4}$ alkyl)NCO($C_{1-4}$ alkoxy)-, and —NHSO$_2$($C_{1-4}$ alkyl)-.

In some embodiments, $R^{41}$ and $R^{42}$ are each independently H, halogen, ($C_{1-6}$ alkyl)oxy-, hydroxy($C_{2-6}$ alkyl) oxy-, HO(O)C—($C_{2-6}$ alkyl)oxy-, amino($C_{2-6}$ alkyl)oxy-, hydroxy, amino, or amino($C_{1-4}$ alkyl)-.

In some embodiments, $R^{41}$ and $R^{42}$ each independently H, halogen, hydroxy, ($C_{1-6}$ alkyl)oxy-, hydroxy($C_{2-6}$ alkyl) oxy-, —($C_{2-4}$ alkoxy)-O—P(O)(OH)$_2$, or —($C_{2-4}$ alkoxy)-O—P(O)($R^I R^{II}$)$_2$.

In some embodiments, $R^{41}$ and $R^{42}$ are each independently H. In some embodiments, $R^{41}$ and $R^{42}$ are each H.

In some embodiments, $R^{41}$ and $R^{42}$ are each independently halogen. In some embodiments, $R^{41}$ and $R^{42}$ are each halogen.

In some embodiments, $R^{41}$ and $R^{42}$ are each —OCH$_2$CH$_2$CH$_2$NH$_2$.

In some embodiments, $R^{41}$ and $R^{42}$ are independently H, halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$, or —N(R$^e$)(R$^f$).

In some embodiments of $R^{41}$ and $R^{42}$ is —OCH$_3$ and the other of $R^{41}$ and $R^{42}$ is halogen, —OH, —OCH$_2$CH$_2$CH$_2$OH, —OCH$_2$CH$_2$CH$_2$COOH, —OCH$_2$CH$_2$CH$_2$NH$_2$, —OCH$_3$, or —N(R$^e$)(R$^f$).

In some embodiments of $R^{41}$ and $R^{42}$ is H and the other of $R^{41}$ and $R^{42}$ is halogen, —OH, —OCH$_2$CH$_2$CH$_2$OH, —OCH$_2$CH$_2$CH$_2$COOH, —OCH$_2$CH$_2$CH$_2$NH$_2$, —OCH$_3$, or —N(R$^e$)(R$^f$).

In some embodiments of $R^{41}$ and $R^{42}$ is —OCH$_3$ and the other of $R^{41}$ and $R^{42}$ is —OCH$_2$CH$_2$CH$_2$OH.

In some embodiments of $R^{41}$ and $R^{42}$ is —OCH$_3$ and the other of $R^{41}$ and $R^{42}$ is —OCH$_2$CH$_2$CH$_2$COOH.

In some embodiments of $R^{41}$ and $R^{42}$ is H and the other of $R^{41}$ and $R^{42}$ is —OCH$_2$CH$_2$CH$_2$OH.

In some embodiments of $R^{41}$ and $R^{42}$ is —OCH$_3$ and the other of $R^{41}$ and $R^{42}$ is —OCH$_2$CH$_2$CH$_2$NH$_2$.

In some embodiments of $R^{41}$ and $R^{42}$ is —OH and the other of $R^{41}$ and $R^{42}$ is —OCH$_2$CH$_2$CH$_2$OH.

In some embodiments of $R^{41}$ and $R^{42}$ is —OH and the other of $R^{41}$ and $R^{42}$ is —OCH$_2$CH$_2$CH$_2$COOH.

In some embodiments of $R^{41}$ and $R^{42}$ is —OH and the other of $R^{41}$ and $R^{42}$ is —OCH$_2$CH$_2$CH$_2$NH$_2$.

In some embodiments, $R^{41}$ is H, halogen, amino, amino ($C_{1-4}$ alkyl)-, hydroxy, —O—P(O)(OH)$_2$, —O—P(O) ($R^I R^{II}$)$_2$, —N(R$^e$)(R$^f$), —CO$_2$R$^f$, —N(R$^f$)COR$^b$, —N(R$^g$) SO$_2$($C_{1-4}$ alkyl)-N(R$^e$)(R$^f$), —N(R$^g$)CO($C_{1-4}$ alkyl)-N(R$^h$) (R$^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^I R^{II}$)$_2$, $C_{1-4}$ alkoxy-, —N(R$^e$)(R$^f$), —CO$_2$(R$^f$), —CON(R$^e$)(R$^f$), optionally substituted phenyl and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-6}$ alkyl)amino-, ($C_{1-6}$ alkyl)($C_{1-6}$ alkyl) amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^I R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{41}$ is H.

In some embodiments, $R^{41}$ is halogen, amino, amino($C_{1-4}$ alkyl)-, hydroxy, —O—P(O)(OH)$_2$, —O—P(O)($R^I R^{II}$)$_2$, —N(R$^e$)(R$^f$), —CO$_2$R$^f$, —N(R$^f$)COR$^b$, —N(R$^g$)SO$_2$($C_{1-4}$ alkyl)-N(R$^e$)(R$^f$), —N(R$^g$)CO($C_{1-4}$ alkyl)-N(R$^h$)(R$^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^I R^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-6}$ alkyl)amino-, ($C_{1-6}$ alkyl)($C_{1-6}$ alkyl) amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^I R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{41}$ is halogen. In some embodiments, $R^{41}$ is F, Cl, Br, or I. In some embodiments, $R^{41}$ is F, C$_1$, or Br. In some embodiments, $R^{41}$ is F. In some embodiments, $R^{41}$ is C$_1$. In some embodiments, $R^{41}$ is Br.

In some embodiments, $R^{A1}$ is amino, amino($C_{1-4}$ alkyl)-, hydroxy, —O—P(O)(OH)$_2$, —O—P(O)($R^IR^{II}$)$_2$, —N($R^e$)($R^f$), —CO$_2R^f$, —N($R^f$)COR$^b$, —N($R^g$)SO$_2$($C_{1-4}$ alkyl)-N($R^e$)($R^f$), —N($R^g$)CO($C_{1-4}$ alkyl)-N($R^h$)($R^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
  wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, $C_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A1}$ is amino or amino($C_{1-4}$ alkyl)-, wherein the ($C_{1-6}$ alkyl) of said optionally substituted ($C_{1-6}$ alkyl)amino- is optionally substituted by 1-4 substituents each independently selected from hydroxy, —O—P(O)(OH)$_2$, —O—P(O)($R^IR^{II}$)$_2$, $C_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A1}$ is hydroxy, —O—P(O)(OH)$_2$, —O—P(O)($R^IR^{II}$)$_2$, —N($R^e$)($R^f$), —CO$_2R^f$, —N($R^f$)COR$^b$, —N($R^g$)SO$_2$($C_{1-4}$ alkyl)-N($R^e$)($R^f$), —N($R^g$)CO($C_{1-4}$ alkyl)-N($R^h$)($R^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
  wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, $C_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A1}$ is optionally substituted ($C_{1-6}$ alkyl)oxy-, wherein the ($C_{1-6}$ alkyl) of said optionally substituted ($C_{1-6}$ alkyl)oxy- is optionally substituted by 1-4 substituents each independently selected from hydroxy, —O—P(O)(OH)$_2$, —O—P(O)($R^IR^{II}$)$_2$, $C_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A1}$ is substituted ($C_{1-6}$ alkyl)oxy-, wherein the ($C_{1-6}$ alkyl) of said substituted ($C_{1-6}$ alkyl)oxy- is substituted by 1-4 substituents each independently selected from hydroxy, —O—P(O)(OH)$_2$, —O—P(O)($R^IR^{II}$)$_2$, $C_{1-4}$ alkoxy-, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A1}$ is substituted ($C_{1-6}$ alkyl)oxy-, wherein the ($C_{1-6}$ alkyl) of said substituted ($C_{1-6}$ alkyl)oxy- is substituted by hydroxy. In some embodiments, $R^{A1}$ is —OCH$_2$CH$_2$CH$_2$OH.

In some embodiments, $R^{A1}$ is hydroxy($C_{2-6}$ alkyl)oxy-. In some embodiments, $R^{A1}$ is HO(O)C—($C_{2-6}$ alkyl)oxy-. In some embodiments, $R^{A1}$ is —OCH$_2$CH$_2$CH$_2$COOH.

In some embodiments, $R^{A1}$ is amino($C_{2-6}$ alkyl)oxy-. In some embodiments, $R^{A1}$ is —OCH$_2$CH$_2$CH$_2$NH$_2$.

In some embodiments, $R^{A1}$ is ($C_{1-6}$ alkyl)oxy-. In some embodiments, $R^{A1}$ is (methyl)oxy-(i.e. methoxy).

In some embodiments, $R^{A1}$ is —OH. In some embodiments, $R^{A1}$ is amino.

In some embodiments, $R^{A1}$ is amino($C_{1-4}$ alkyl)-.

In some embodiments, $R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxy, —O—P(O)(OH)$_2$, $C_{1-4}$ alkoxyl, —N($R^e$)($R^f$), —COOH, and optionally substituted phenyl, and each $R^e$ is independently selected from H, $C_{1-4}$ alkyl, —CO($C_{1-4}$ alkyl), —OCO($C_{1-4}$ alkyl), —($C_{1-4}$ alkyl)NH$_2$, —($C_{1-4}$ alkyl)($C_{1-4}$ alkoxy), and —CO$_2$($C_{1-4}$ alkyl).

In some embodiments, $R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from the group comprising hydroxy, —O—P(O)(OH)$_2$, —O—P(O)(R$^I$R$^{II}$)$_2$, —N(R$^e$)(R$^f$), $C_{1-4}$ alkoxyl, phenyl, and optionally substituted 5-6 membered heteroaryl comprising at least one nitrogen or oxygen as a member of the ring, and each R$^e$ is each independently selected from H, $C_{1-4}$ alkyl, —($C_{1-4}$ alkyl)NH$_2$, and —($C_{1-4}$ alkyl)$C_{1-4}$ alkoxy.

In some embodiments, at least one of $R^{A2}$ or $R^{A1}$ are each independently H, hydroxy, halogen, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from —N(R$^e$)(R$^f$), tetrahydropyran, pyrrolidinyl, piperazinyl, piperidyl and morpholinyl and each R$^e$ is each independently selected from H, $C_{1-4}$ alkyl, —($C_{1-4}$ alkyl)NH$_2$, and —($C_{1-4}$ alkyl)$C_{1-4}$alkoxy.

In some embodiments, at least one of $R^{A2}$ or $R^{A1}$ are each independently H, hydroxy, halogen, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from tetrahydropyran, pyrrolidinyl, piperazinyl, piperidyl and morpholinyl, and each R$^e$ is each independently selected from H and $C_{1-4}$ alkyl.

In some embodiments, $R^{A2}$ is H, halogen, amino, amino($C_{1-4}$ alkyl)-, hydroxy, —O—P(O)(OH)$_2$, —O—P(O)(R$^I$R$^{II}$)$_2$, —N(R$^e$)(R$^f$), —CO$_2$R$^f$, —N(R$^f$)COR$^b$, —N(R$^g$)SO$_2$($C_{1-4}$ alkyl)-N(R$^e$)(R$^f$), —N(R$^g$)CO($C_{1-4}$ alkyl)-N(R$^h$)(R$^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)(R$^I$R$^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A2}$ is H.

In some embodiments, $R^{A2}$ is halogen, amino, amino($C_{1-4}$ alkyl)-, hydroxy, —O—P(O)(OH)$_2$, —O—P(O)(R$^I$R$^{II}$)$_2$, —N(R$^e$)(R$^f$), —CO$_2$R$^f$, —N(R$^f$)COR$^b$, —N(R$^g$)SO$_2$($C_{1-4}$ alkyl)-N(R$^e$)(R$^f$), —N(R$^g$)CO($C_{1-4}$ alkyl)-N(10)(R$^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)(R$^I$R$^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A2}$ is halogen. In some embodiments, $R^{A2}$ is F, Cl, Br, or I. In some embodiments, $R^{A2}$ is F, C$_1$, or Br. In some embodiments, $R^{A2}$ is F. In some embodiments, $R^{A2}$ is C$_1$. In some embodiments, $R^{A2}$ is Br.

In some embodiments, $R^{A2}$ is amino, amino($C_{1-4}$ alkyl)-, hydroxy, —O—P(O)(OH)$_2$, —O—P(O)(R$^I$R$^{II}$)$_2$, —N(R$^e$)(R$^f$), —CO$_2$R$^f$, —N(R$^f$)COR$^b$, —N(R$^g$)SO$_2$($C_{1-4}$ alkyl)-N(R$^e$)(R$^f$), —N(R$^g$)CO($C_{1-4}$ alkyl)-N(R$^h$)(R$^f$), optionally substituted ($C_{1-6}$ alkyl), optionally substituted ($C_{1-6}$ alkyl)oxy-, optionally substituted ($C_{1-6}$ alkyl)amino-, and optionally substituted ($C_{1-6}$ alkyl)($C_{1-4}$ alkyl)amino-,
wherein the ($C_{1-6}$ alkyl) of said optionally substituted ($C_{1-6}$ alkyl), optionally substituted ($C_{1-6}$ alkyl)oxy-, optionally substituted ($C_{1-6}$ alkyl)amino- and optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)(R$^I$R$^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A2}$ is amino or amino($C_{1-4}$ alkyl)-, wherein the ($C_{1-6}$ alkyl) of said optionally substituted ($C_{1-6}$ alkyl)amino- is optionally substituted by 1-4 substituents each independently selected from hydroxy, —O—P(O)(OH)$_2$, —O—P(O)(R$^I$R$^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A2}$ is optionally substituted ($C_{1-6}$ alkyl)oxy-, wherein the ($C_{1-6}$ alkyl) of said optionally substituted ($C_{1-6}$ alkyl)oxy- is optionally substituted by 1-4 substituents each independently selected from hydroxy, —O—P(O)(OH)$_2$, —O—P(O)(R$^I$R$^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A2}$ is substituted ($C_{1-6}$ alkyl)oxy-, wherein the ($C_{1-6}$ alkyl) of said substituted ($C_{1-6}$ alkyl)oxy- is substituted by 1-4 substituents each independently selected from hydroxy, —O—P(O)(OH)$_2$, —O—P(O)(R$^I$R$^{II}$)$_2$, $C_{1-4}$ alkoxy-, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —$C_{1-4}$ alkyl-($C_{1-4}$ alkoxy), and $C_{1-4}$ alkoxy-($C_{1-4}$ alkoxy)-.

In some embodiments, $R^{A2}$ is substituted ($C_{1-6}$ alkyl)oxy-, wherein the ($C_{1-6}$ alkyl) of said substituted ($C_{1-6}$ alkyl)oxy- is substituted by hydroxy. In some embodiments, $R^{A2}$ is —OCH$_2$CH$_2$CH$_2$OH.

In some embodiments, $R^{A2}$ is hydroxy($C_{2-6}$ alkyl)oxy-. In some embodiments, $R^{A2}$ is H$_0$(O)C—($C_{2-6}$ alkyl)oxy-. In some embodiments, $R^{A2}$ is —OCH$_2$CH$_2$CH$_2$COOH.

In some embodiments, $R^{A2}$ is amino($C_{2-6}$ alkyl)oxy-. In some embodiments, $R^{A2}$ is —OCH$_2$CH$_2$CH$_2$NH$_2$.

In some embodiments, $R^{A2}$ is ($C_{1-6}$ alkyl)oxy-. In some embodiments, $R^{A2}$ is (methyl)oxy-(i.e. methoxy).

In some embodiments, $R^{A2}$ is —OH. In some embodiments, $R^{A2}$ is amino.

In some embodiments, $R^{A2}$ is amino($C_{1-4}$ alkyl)-.

In some embodiments, r is 0 and $R^{B1}$ and $R^{B2}$ are each independently H, optionally substituted $C_{1-6}$ alkyl, halo($C_{1-6}$ alkyl), optionally substituted $C_{2-6}$ alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted $C_{1-6}$ alkyl, optionally substituted $C_{2-6}$ alkenyl, optionally substituted $C_{2-6}$ alkynyl, optionally substituted $C_{3-6}$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —OR$^c$, NH$_2$, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$.

In some embodiments, r is 0 and $R^{B1}$ and $R^{B2}$ are each H.

In some embodiments, r is 0 and $R^{B1}$ and $R^{B2}$ are each independently H, optionally substituted $C_{1-6}$ alkyl, halo($C_{1-6}$ alkyl), optionally substituted $C_{2-6}$ alkenyl, optionally substituted $C_{2-6}$ alkynyl, optionally substituted $C_{3-6}$ cycloalkyl, optionally substituted 4-6 membered heterocycloalkyl, optionally substituted 5-6 membered heteroaryl or optionally substituted 9 membered heteroaryl.

In some embodiments, s is 0, $W_1$ and $Z_2$ are each independently C or N, and $R^{C1}$ is absent, H, halogen, or $C_{1-4}$ alkyl and $R^{C2}$ is absent or an optionally substituted $C_{1-4}$ alkyl, wherein said optionally substituted $C_{1-4}$ alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$.

In some embodiments of the compounds of this disclosure, when s is 0, $W_1$ and $Z_2$ are each independently C or N, and $R^{C1}$ and $R^{C2}$ are each independently absent, H or $C_{1-4}$ alkyl. In some embodiments, when s is 0, $W_1$ is C, $R^{C1}$ is $C_{1-3}$ alkyl, specifically methyl. In some embodiments, when s is 0, $Z_2$ is C or N, $R^{C2}$ is $C_{1-3}$ alkyl, specifically methyl or ethyl. In some embodiments, when s is 0, $Z_2$ is C or N, $R^{C2}$ is ethyl.

In some embodiments of the compounds of this disclosure, s is 0, $W_1$ is C, $Z_2$ is O or S, and $R^{C1}$ is absent, H, halogen, or $C_{1-4}$ alkyl and $R^{C2}$ is absent.

In some embodiments of the compounds of this disclosure, when s is 0, $W_1$ is C, $Z_2$ is O or S, and $R^{C1}$ is absent, H or $C_{1-4}$ alkyl and $R^{C2}$ is absent. In some embodiments, when s is 0, $W_1$ is C, $R^{C1}$ is $C_{1-3}$ alkyl, specifically methyl. In some embodiments, when s is 0, $Z_2$ is O or S, $R^{C2}$ is $C_{1-3}$ alkyl, specifically methyl or ethyl. In some embodiments, when s is 0, $Z_2$ is O or S, $R^{C2}$ is ethyl.

In some embodiments of the compounds of this disclosure, r is 1 and $R^{B1}$ and $R^{B2}$ are each independently —CH$_2$—, and B, taken together with $R^{B1}$ and $R^{B2}$, forms a linking group, wherein B is a bond or B is -halo($C_{1-10}$ alkyl)-, optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-NR$^a$—$C_{1-6}$ alkyl-, optionally substituted $C_{3-6}$ cycloalkyl, optionally substituted phenyl, optionally substituted 4-6 membered heterocycloalkyl, optionally substituted membered heteroaryl, optionally substituted —$C_{1-4}$ alkyl-($C_{3-6}$cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl)-$C_{1-4}$ alkyl-,
wherein the alkyl moiety of said optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-NR$^a$—$C_{1-6}$ alkyl-, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl-$C_{1-4}$ alkyl)- is optionally substituted by 1 or 2 substituents each independently selected from halogen, halo($C_{1-4}$ alkyl), —OH, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR d SO$_2$R$^c$, and the $C_{3-6}$ cycloalkyl, phenyl, 4-6 membered heterocycloalkyl, or 5-6 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl)-$C_{1-4}$ alkyl- is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, —$C_{1-4}$ alkyl, halo($C_{1-4}$ alkyl), halo($C_{1-4}$ alkoxy)-, —$C_{1-4}$ alkoxy-, hydroxy-($C_{2-4}$ alkoxy)-, and $C_{1-4}$ alkoxy-($C_{1-4}$ alkoxy)-.

In some embodiments of the compounds of this disclosure, r is 1 and R$^{B1}$ and R$^{B2}$ are each independently —CH$_2$—, and B, taken together with R$^{B1}$ and R$^{B2}$, forms a linking group, wherein B is a bond or B is -halo($C_{1-10}$alkyl)-, optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-NR$^a$—$C_{1-6}$ alkyl-, optionally substituted $C_{3-6}$ cycloalkyl, optionally substituted phenyl, optionally substituted 4-6 membered heterocycloalkyl, optionally substituted membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl) $C_{1-4}$ alkyl-, wherein the alkyl moiety of said optionally substituted —$C_{1-10}$ alkyl-, optionally substituted —$C_{2-10}$ alkenyl-, optionally substituted —$C_{2-10}$ alkynyl-, optionally substituted —$C_{1-6}$ alkyl-O—$C_{1-6}$ alkyl-, optionally substituted —$C_{1-6}$ alkyl-NR$^a$—$C_{1-6}$ alkyl-, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl-$C_{1-4}$ alkyl)- is optionally substituted by 1 or 2 substituents each independently selected from halogen, halo($C_{1-4}$alkyl), —OH, —O—P(O)(OH)$_2$, —O—P(O)(R$^I$R$^H$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR d, and NR d SO$_2$R$^c$, and the $C_3$-6 cycloalkyl, phenyl, 4-6 membered heterocycloalkyl, or 5-6 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted —$C_{1-4}$ alkyl-($C_{3-6}$ cycloalkyl)-$C_{1-4}$ alkyl-, optionally substituted —$C_{1-4}$ alkyl-phenyl-$C_{1-4}$ alkyl-, optionally substituted —$C_{1-4}$ alkyl-(4-6 membered heterocycloalkyl)-$C_{1-4}$ alkyl-, or optionally substituted —$C_{1-4}$ alkyl-(5-6 membered heteroaryl) $C_{1-4}$ alkyl- is optionally substituted by 1-4 substituents each independently selected from halogen, hydroxy, —O—P(O)(OH)$_2$, —O—P(O)(R$^I$R$^H$)$_2$, amino, ($C_{1-4}$ alkyl)amino-, ($C_{1-4}$ alkyl)($C_{1-4}$ alkyl)amino-, —$C_{1-4}$ alkyl, halo($C_{1-4}$ alkyl), halo($C_{1-4}$ alkoxy)-, —$C_{1-4}$ alkoxy-, hydroxy-($C_{2-4}$ alkoxy)-, and —$C_{1-4}$ alkoxy-($C_{1-4}$ alkoxy)-.

In some embodiments of the compounds of this disclosure, r is 1, R$^{B1}$ and R$^{B2}$ are each independently —CH$_2$—, and B, taken together with R$^{B1}$ and R$^{B2}$, forms a 2-6 membered linking group. In a further embodiment, r is 1, R$^{B1}$ and R$^{B2}$ are each independently —CH$_2$—, and B, taken together with R$^{B1}$ and R$^{B2}$, forms a 3-6 membered linking group. In a still further embodiment, r is 1, R$^{B1}$ and R$^{B2}$ are each independently —CH$_2$—, and B, taken together with R$^{B1}$ and R$^{B2}$, forms a 4-5 membered linking group.

In some embodiments, B is a bond.

In some embodiments, r is 1, R$^{B1}$ and R$^{B2}$ are each independently —CH$_2$—, and B is a substituted —$C_{1-10}$ alkyl- group or is an unsubstituted —$C_{1-10}$ alkyl-, —$C_{2-10}$ alkenyl-, —$C_{2-10}$ alkynyl-, —$C_{1-6}$ alkyl-O—$C_{1-6}$ alkyl-, or —$C_{1-6}$ alkyl-NR$^a$—$C_{1-6}$ alkyl- group, wherein said substituted —$C_{1-10}$ alkyl-group is substituted by 1-4 substituents each independently selected from halogen, hydroxy, amino, ($C_{1-6}$ alkyl)amino-, ($C_{1-6}$ alkyl)($C_{1-6}$ alkyl)amino-, halo($C_{1-6}$ alkyl), halo($C_{1-4}$ alkoxy)-, —$C_{1-4}$ alkoxy-, hydroxy-($C_{2-4}$ alkoxy)-, —$C_{1-4}$ alkoxy-($C_{1-4}$ alkoxy)-, —NHCO($C_{1-4}$ alkyl), optionally substituted phenyl, optionally substituted 5-6 membered heterocycloalkyl, and optionally substituted 5-6 membered heteroaryl, wherein said optionally substituted phenyl, 5-6 membered heterocycloalkyl, or 5-6 membered heteroaryl is optionally substituted by 1-4 substituents each independently selected from halogen, hydroxy, amino, ($C_{1-6}$ alkyl)amino-, ($C_{1-6}$ alkyl)($C_{1-6}$ alkyl)amino-, halo($C_{1-6}$ alkyl), halo($C_{1-4}$ alkoxy)-, —$C_{1-4}$ alkoxy-, hydroxy-($C_{2-4}$ alkoxy)-, and $C_{1-4}$ alkoxy-($C_{1-4}$ alkoxy)-.

In some embodiments, r is 1, R$^{B1}$ and R$^{B2}$ are each independently —CH$_2$—, and B is a substituted —$C_{1-10}$ alkyl- group or is an unsubstituted —$C_{1-10}$ alkyl-, —$C_{2-10}$ alkenyl-, —$C_{2-10}$ alkynyl-, —$C_{1-6}$ alkyl-O—$C_{1-6}$ alkyl-, or —$C_{1-6}$ alkyl-NR$^a$—$C_{1-6}$ alkyl- group, wherein said substituted —$C_{1-10}$ alkyl-group is substituted by 1-4 substituents each independently selected from halogen, hydroxy, —O—P(O)(OH)$_2$, —O—P(O)(R$^I$R$^H$)$_2$, amino, ($C_{1-6}$ alkyl)amino-, ($C_{1-6}$ alkyl)($C_{1-6}$ alkyl)amino-, halo($C_{1-6}$ alkyl), halo($C_{1-4}$ alkoxy)-, —$C_{1-4}$ alkoxy-, hydroxy-($C_{2-4}$ alkoxy)-, $C_{1-4}$ alkoxy-($C_{1-4}$ alkoxy)-, —NHCO($C_{1-4}$ alkyl), optionally substituted phenyl, optionally substituted 5-6 membered heterocycloalkyl, and optionally substituted 5-6 membered heteroaryl, wherein said optionally substituted phenyl, 5-6 membered heterocycloalkyl, or 5-6 membered heteroaryl is optionally substituted by 1-4 substituents each independently selected from halogen, hydroxy, —O—P(O)(OH)$_2$, —O—P(O)(R$^I$R$^H$)$_2$, amino, ($C_{1-6}$ alkyl)amino-, ($C_{1-6}$ alkyl)($C_{1-6}$ alkyl)amino-, halo($C_{1-6}$ alkyl), halo($C_{1-4}$ alkoxy)-, $C_{1-4}$ alkoxy-, hydroxy-($C_{2-4}$ alkoxy)-, and $C_{1-4}$ alkoxy-($C_{1-4}$ alkoxy)-.

In some embodiments, r is 1, R$^{B1}$ and R$^{B2}$ are each independently —CH$_2$—, and B is a substituted —$C_{1-10}$ alkyl- group or is an unsubstituted —$C_{1-10}$ alkyl-, —$C_{2-10}$ alkenyl-, —$C_{2-10}$ alkynyl-, —$C_{1-6}$ alkyl-O—$C_{1-6}$ alkyl-, or —$C_{1-6}$ alkyl-NR$^a$—$C_{1-6}$ alkyl- group, wherein said substituted —$C_{1-10}$ alkyl-group is substituted by 1-4 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, R$^{B1}$ and R$^{B2}$ are each independently —CH$_2$—, and B is a substituted —$C_{1-10}$ alkyl- group or is an unsubstituted —$C_{1-10}$ alkyl-, —$C_{2-10}$ alkenyl-, —$C_{2-10}$ alkynyl-, —$C_{1-6}$ alkyl-O—$C_{1-6}$ alkyl-, or —$C_{1-6}$ alkyl-NW—$C_{1-6}$ alkyl- group, wherein said substituted —$C_{1-10}$ alkyl- group is substituted by 1-4 substituents each independently selected from halogen, hydroxy, —O—P(O)(OH)$_2$, —O—P(O)($R^IR^H$)$_2$, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, $R^{B1}$ and $R^{B2}$ are each independently —CH$_2$—, and B is a substituted —$C_{1-8}$ alkyl- group or is an unsubstituted —$C_{1-8}$ alkyl-, —$C_{2-8}$ alkenyl-, —$C_{2-8}$ alkynyl-, —$C_{1-4}$ alkyl-O—$C_{1-4}$ alkyl-, or —$C_{1-4}$ alkyl-NW—$C_{1-4}$ alkyl- group, wherein said substituted —$C_{1-8}$ alkyl-group is substituted by 1-4 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, $R^{B1}$ and $R^{B2}$ are each independently —CH$_2$—, and B is a substituted —$C_{1-8}$ alkyl- group or is an unsubstituted —$C_{1-8}$alkyl-, —$C_{2-8}$ alkenyl-, —$C_{2-8}$ alkynyl-, —$C_{1-4}$ alkyl-O—$C_{1-4}$ alkyl-, or —$C_{1-4}$ alkyl-NW—$C_{1-4}$ alkyl- group, wherein said substituted —$C_{1-8}$ alkyl- group is substituted by 1-4 substituents each independently selected from halogen, hydroxy, —O—P(O)(OH)$_2$, —O—P(O)($R^IR^H$)$_2$, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, $R^{B1}$ and $R^{B2}$ are each independently —CH$_2$—, and B is a substituted —$C_{1-6}$ alkyl- group or is an unsubstituted —$C_{1-6}$ alkyl-, —$C_{2-6}$ alkenyl-, —$C_{2-6}$ alkynyl-, —$C_{1-2}$ alkyl-O—$C_{1-2}$ alkyl-, or —$C_{1-2}$ alkyl-NW—$C_{1-2}$ alkyl- group, wherein said substituted —$C_{1-6}$ alkyl- group is substituted by 1-2 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$alkoxy)-, and $C_{1-4}$ alkoxy-.

In some embodiments, r is 1, $R^{B1}$ and $R^{B2}$ are each independently —CH$_2$—, and B is a substituted —$C_{1-6}$ alkyl- group or is an unsubstituted —$C_{1-6}$ alkyl-, —$C_{2-6}$ alkenyl-, —$C_{2-6}$ alkynyl-, —$C_{1-2}$ alkyl-O—$C_{1-2}$ alkyl-, or —$C_{1-2}$ alkyl-NW—$C_{1-2}$ alkyl- group, wherein said substituted —$C_{1-6}$ alkyl- group is substituted by 1-2 substituents each independently selected from halogen, hydroxy, —O—P(O)(OH)$_2$, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, $R^{B1}$ and $R^{B2}$ are each independently —CH$_2$—, and B is a substituted —$C_{2-4}$ alkyl- group or is an unsubstituted —$C_{2-4}$ alkyl-, —$C_{2-4}$ alkenyl-, —$C_{2-4}$ alkynyl-, —$C_{1-4}$ alkyl-O—$C_{1-4}$ alkyl-, or —$C_{1-4}$ alkyl-NW—$C_{1-4}$ alkyl- group, wherein said substituted —$C_{1-4}$ alkyl- group is substituted by 1-2 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, $R^{B1}$ and $R^{B2}$ are each independently —CH$_2$—, and B is a substituted —$C_{2-4}$ alkyl- group or is an unsubstituted —$C_{2-4}$ alkyl-, —$C_{2-4}$ alkenyl-, —$C_{2-4}$ alkynyl-, —$C_1$ alkyl-O—$C_1$ alkyl-, or —$C_1$ alkyl-NR$^a$—$C_1$ alkyl- group, wherein said substituted —$C_{2-4}$ alkyl- group is substituted by 1-2 substituents each independently selected from halogen, hydroxy, —O—P(O)(OH)$_2$, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, r is 1, $R^{B1}$ and $R^{B2}$ are each independently —CH$_2$—, and B is —CH═CH—, —CH$_2$CH$_2$—, —CH(OH)CH(OH)-, or —CH$_2$N(CH$_3$)CH$_2$—. In some embodiments, r is 1, B, taken together with $R^{B1}$ and $R^{B2}$, form a —CH$_2$CH═CHCH$_2$—, —CH$_2$CH$_2$CH$_2$CH$_2$—, —CH$_2$CH(OH)CH(OH)CH$_2$—, or —CH$_2$CH$_2$N(CH$_3$)CH$_2$CH$_2$— group. In some embodiments, r is 1, B, taken together with $R^{B1}$ and $R^{B2}$, form a —CH$_2$CH═CHCH$_2$—.

In some embodiments of the compounds of this disclosure, when s is 1, $W_1$ and $Z_2$ are each independently C or N, $R^{C1}$ and $R^{C2}$ are each independently —CH$_2$—, and D, taken together with $R^{C1}$ and $R^{C2}$, forms a linking group, wherein D is -halo($C_{1-12}$alkyl)-, optionally substituted —$C_{1-12}$ alkyl-, optionally substituted —$C_{2-12}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NR$^a$—$C_{1-6}$ alkyl-, optionally substituted —$C_{1-6}$ alkyl-($C_{3-6}$ cycloalkyl)-$C_{1-6}$ alkyl -, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl-,
wherein the alkyl moiety of said optionally substituted —$C_{1-12}$ alkyl-, optionally substituted —$C_{2-12}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NR$^a$—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl- is optionally substituted by 1 or 2 substituents each independently selected from halogen, halo($C_{1-4}$ alkyl), —OH, —OR$^c$, —NH$_2$, —NR$^cR^d$, —OCOR$^c$, —CO$_2$H, —CO$_2$R$^c$, —SOR$^c$, —SO$_2$R$^c$, CONH$_2$, —CONR$^cR^d$, —SO$_2$NH 2, —SO$_2$NR$^cR^d$, —OCONH$_2$, —OCONR$^cR^d$, —NR$^d$COR$^c$, —NR$^d$SOR$^c$, —NR$^d$CO$_2$R$^c$, and —NR d SO$_2$R$^c$, and the $C_{3-6}$ cycloalkyl, phenyl, 4-6 membered heterocycloalkyl, or 5-6 membered heteroaryl moiety of said optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl- is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, and $C_{1-4}$ alkoxy-($C_{1-4}$ alkoxy)-.

In some embodiments of the compounds of this disclosure, when s is 1, $W_1$ and $Z_2$ are each independently C or N, $R^{C1}$ and $R^{C2}$ are each independently —CH$_2$—, and D, taken together with $R^{C1}$ and $R^{C2}$, forms a linking group, wherein D is -halo($C_{1-12}$ alkyl)-, optionally substituted —$C_{1-12}$ alkyl-, optionally substituted —$C_{2-12}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NR—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl-,
wherein the alkyl moiety of said optionally substituted —$C_{1-12}$ alkyl-, optionally substituted —$C_{2-12}$ alkenyl-, optionally substituted —$C_{2-12}$ alkynyl-, optionally substituted —$C_{1-6}$ alkyl-O—$C_{1-6}$ alkyl-, optionally substituted —$C_{1-6}$ alkyl-NR—$C_{1-6}$ alkyl-, optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl- is optionally substituted by 1 or 2 substituents each independently selected from halogen, halo($C_{1-4}$ alkyl), —OH, —O—P(O)(OH)$_2$, —O—P(O)($R^IR^H$)$_2$, —OR$^c$, —NH$_2$, —NR$^cR^d$, —OCOR$^c$, —CO$_2$H, —CO$_2$R$^c$, —SOR$^c$, —SO$_2$R$^c$, —CONH$_2$, —CONR$^cR^d$, —SO$_2$NH$_2$, —SO$_2$NR$^cR^d$, —OCONH$_2$, —OCONR$^cR^d$, —NR$^d$COR$^c$, —NR$^d$SOR$^c$, —NR$^d$CO$_2$R$^c$, and —NR d SO$_2$R$^c$, and the $C_{3-6}$ cycloalkyl, phenyl, 4-6 membered heterocycloalkyl, or 5-6 membered heteroaryl moiety of said optionally substituted —$C_{1-6}$ alkyl-($C_{3-6}$ cycloalkyl)-$C_{1-6}$ alkyl-, optionally substituted —$C_{1-6}$ alkyl-phenyl-$C_{1-6}$ alkyl-, optionally substituted —$C_{1-6}$ alkyl-(4-6 membered heterocycloalkyl)-$C_{1-6}$ alkyl-, or optionally substituted —$C_{1-6}$ alkyl-(5-6 membered heteroaryl)-$C_{1-6}$ alkyl- is optionally substituted by 1-4 substituents each independently selected from halogen, hydroxy, —O—P(O)(OH)$_2$, —O—P(O)($R^IR^H$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^H$)$_2$, and $C_{1-4}$ alkoxy-($C_{1-4}$ alkoxy)-.

In some embodiments of the compounds of this disclosure, s is 1, $W_1$ and $Z_2$ are each independently C or N, $R^{C1}$ and $R^{C2}$ are each independently —CH$_2$—, and D, taken together with $R^{C1}$ and $R^{C2}$, forms a 4-8 membered linking group. In a further embodiment, s is 1, $W_1$ and $Z_2$ are each independently C or N, and D, taken together with $R^{C1}$ and $R^{C2}$, forms a 4-6 membered linking group. In a still further embodiment, s is 1 and D, taken together with $R^{C1}$ and $R^{C2}$, forms a 5 membered linking group.

In some embodiments, when s is 1, $W_1$ and $Z_2$ are each independently C or N, $R^{C1}$ and $R^{C2}$ are each independently —CH$_2$—, and D is a substituted —$C_{2-10}$ alkyl- group or is an unsubstituted —$C_{2-10}$ alkyl-, —$C_{2-10}$ alkenyl-, —$C_{2-10}$ alkynyl-, —$C_{1-4}$ alkyl-O—$C_{1-4}$ alkyl-, or —$C_{1-4}$ alkyl-NW—$C_{1-4}$ alkyl-group, wherein said substituted —$C_{2-10}$ alkyl- group is substituted by 1-4 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, s is 1, $W_1$ and $Z_2$ are each independently C or N, $R^{C1}$ and $R^{C2}$ are each independently —CH$_2$—, and D is a substituted —$C_{2-10}$ alkyl- group or is an unsubstituted —$C_{2-10}$ alkyl-, —$C_{2-10}$ alkenyl-, —$C_{2-10}$ alkynyl-, —$C_{1-4}$ alkyl-O—$C_{1-4}$ alkyl-, or —$C_{1-4}$ alkyl-NW—$C_{1-4}$ alkyl-group, wherein said substituted —$C_{2-10}$ alkyl- group is substituted by 1-4 substituents each independently selected from halogen, hydroxy, —O—P(O)(OH)$_2$, —O—P(O)($R^IR^H$)$_2$, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, s is 1, $W_1$ and $Z_2$ are each independently C or N, $R^{C1}$ and $R^{C2}$ are each independently —CH$_2$—, and D is a substituted —$C_{2-8}$ alkyl- group or is an unsubstituted —$C_{2-8}$ alkyl-, —$C_{2-8}$ alkenyl-, —$C_{2-8}$ alkynyl-, —$C_{1-2}$ alkyl-O—$C_{1-2}$ alkyl-, or —$C_{1-2}$ alkyl-NW—$C_{1-2}$ alkyl- group, wherein said substituted —$C_{2-8}$ alkyl- group is substituted by 1-2 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, s is 1, $W_1$ and $Z_2$ are each independently C or N, $R^{C1}$ and $R^{C2}$ are each independently —CH$_2$—, and D is a substituted —$C_{2-8}$ alkyl- group or is an unsubstituted —$C_{2-8}$ alkyl-, —$C_{2-8}$ alkenyl-, —$C_{2-8}$ alkynyl-, —$C_{1-2}$ alkyl-O—$C_{1-2}$ alkyl-, or —$C_{1-2}$ alkyl-NW—$C_{1-2}$ alkyl- group, wherein said substituted —$C_{2-8}$ alkyl- group is substituted by 1-2 substituents each independently selected from halogen, hydroxy, —O—P(O)(OH)$_2$, —O—P(O)($R^IR^H$)$_2$, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, s is 1, $W_1$ and $Z_2$ are each independently C or N, $R^{C1}$ and $R^{C2}$ are each independently —CH$_2$—, and D is a substituted —$C_{2-6}$ alkyl- group or is an unsubstituted —$C_{2-6}$ alkyl-, —$C_{2-6}$ alkenyl-, —$C_{2-6}$ alkynyl-, —$C_{1-2}$ alkyl-O—$C_{1-2}$ alkyl -, or —$C_{1-2}$ alkyl-NW—$C_{1-2}$ alkyl- group, wherein said substituted —$C_{2-6}$ alkyl- group is substituted by 1-2 substituents each independently selected from halogen, hydroxy, amino, ($C_{1-4}$ alkyl)amino-, ($C_{1-4}$ alkyl)($C_{1-4}$ alkyl)amino-, halo($C_{1-4}$ alkyl), halo($C_{1-4}$ alkoxy)-, and $C_{1-4}$ alkoxy-.

In some embodiments, s is 1, $W_1$ and $Z_2$ are each independently C or N, $R^{C1}$ and $R^{C2}$ are each independently —CH$_2$—, and D is a substituted —$C_{2-6}$ alkyl- group or is an unsubstituted —$C_{2-6}$ alkyl-, —$C_{2-6}$ alkenyl-, —$C_{2-6}$ alkynyl-, $C_{1-2}$ alkyl-O—$C_{1-2}$ alkyl -, or —$C_{1-2}$ alkyl-NW—$C_{1-2}$ alkyl- group, wherein said substituted —$C_{2-6}$ alkyl- group is substituted by 1-2 substituents each independently selected from halogen, hydroxy, —O—P(O)(OH)$_2$, —O—P(O)($R^IR^H$)$_2$, amino, ($C_{1-4}$ alkyl)amino-, ($C_{1-4}$ alkyl)($C_{1-4}$ alkyl) amino-, halo($C_{1-4}$ alkyl), halo($C_{1-4}$ alkoxy)-, and $C_{1-4}$ alkoxy-.

In some embodiments, s is 1, $W_1$ and $Z_2$ are each independently C or N, $R^{C1}$ and $R^{C2}$ are each independently —CH$_2$—, and D is a —$C_{2-4}$ alkyl-, —$C_{2-4}$ alkenyl-, or —$C_{2-4}$ alkynyl- group.

In some embodiments, s is 1, $W_1$ and $Z_2$ are each independently C or N, $R^{C1}$ and $R^{C2}$ are each independently —CH$_2$—, and D is —CH$_2$CH$_2$CH$_2$—, wherein D, taken together with $R^{C1}$ and $R^{C2}$, form a —CH$_2$CH$_2$CH$_2$CH$_2$CH$_2$— group.

In some embodiments, $R^3$ and $R^5$ are each independently —CON($R^d$)($R^f$), —CH$_2$N($R^d$)($R^f$), —N($R^d$)($R^f$), —N($R^d$)CO($R^f$), or —CH$_2$N($R^d$)CO($R^f$).

In some embodiments, one of $R^3$ and $R^5$ is —CON($R^d$)($R^f$), —CH$_2$N($R^d$)($R^f$), —N($R^d$)($R^f$), —N($R^d$)CO($R^f$) or —CH$_2$N($R^d$)CO($R^f$), and the other of $R^3$ and $R^5$ is H, COOH or —CO$_2$R$^C$. In some embodiments, $R^3$ and $R^5$ are each independently —CON($R^d$)($R^f$), or one of $R^3$ and $R^5$ is —CON($R^d$)($R^f$), and the other of $R^3$ and $R^5$ is H, COOH, or —CO$_2$R$^c$. In some embodiments, $R^3$ and $R^5$ are each independently —CON($R^d$)($R^f$), or one of $R^3$ and $R^5$ is —CON($R^d$)($R^f$), and the other of $R^3$ and $R^5$ is H or —CO$_2$R$^c$. In some embodiments, $R^3$ and $R^5$ are each independently —CON($R^d$)($R^f$). In some embodiments, one of $R^3$ and $R^5$ is —CON($R^d$)($R^f$) and the other of $R^3$ and $R^5$ is H. In some embodiments, one of $R^3$ and $R^5$ is —CON($R^d$)($R^f$) and the other of $R^3$ and $R^5$ is —CO$_2$R$^c$. In some embodiments, one of $R^3$ and $R^5$ is —CON($R^d$)($R^f$) and the other of $R^3$ and $R^5$ is —CON($R^d$)($R^f$).

In some embodiments, $R^3$ and $R^5$ are each independently —CH$_2$N($R^d$)($R^f$) or one of $R^3$ and $R^5$ is —CH$_2$N($R^d$)($R^f$), and the other of $R^3$ and $R^5$ is H, COOH, or —CO$_2$R$^c$. In some embodiments, $R^3$ and $R^5$ are each independently —CH$_2$N($R^d$)($R^f$) or one of $R^3$ and $R^5$ is —CH$_2$N($R^d$)($R^f$), and the other of $R^3$ and $R^5$ is H or —CO$_2$R$^c$. In some embodiments, $R^3$ and $R^5$ are each independently —CH$_2$N($R^d$)($R^f$). In some embodiments, one of $R^3$ and $R^5$ is —CH$_2$N($R^d$)($R^f$) and the other of $R^3$ and $R^5$ is H. In some embodiments, one of $R^3$ and $R^5$ is —$CH_2N(R^d)(R^f)$ and the other of $R^3$ and $R^5$ is —$CO_2(10$. In some embodiments, one of $R^3$ and $R^5$ is —$CH_2N(R^d)(R^f)$ and the other of $R^3$ and $R^5$ is —$CON(R^d)(R^f)$.

In some embodiments, $R^3$ and $R^5$ are each independently —$N(R^d)(R^f)$ or one of $R^3$ and $R^5$ is —$N(R^d)(R^f)$, and the other of $R^3$ and $R^5$ is H, COOH, or —$CO_2(R^C)$. In some embodiments, $R^3$ and $R^5$ are each independently —$N(R^d)(R^f)$ or one of $R^3$ and $R^5$ is —$N(R^d)(R^f)$, and the other of $R^3$ and $R^5$ is H or —$CO_2R^c$. In some embodiments, $R^3$ and $R^5$ are each independently —$N(R^d)(R^f)$. In some embodiments, one of $R^3$ and $R^5$ is —$N(R^d)(R^f)$ and the other of $R^3$ and $R^5$ is H. In some embodiments, one of $R^3$ and $R^5$ is —$N(R^d)(R^f)$ and the other of $R^3$ and $R^5$ is —$CO_2R^c$. In some embodiments, one of $R^3$ and $R^5$ is —$N(R^d)(R^f)$ and the other of $R^3$ and $R^5$ is —$CON(R^d)(R^f)$.

In some embodiments, $R^3$ and $R^5$ are each independently —$N(R^d)CO(R^f)$ or one of $R^3$ and $R^5$ is —$N(R^d)CO(R^f)$, and the other of $R^3$ and $R^5$ is H, COOH, —$CO_2R^c$ or —$CON(R^d)(R^f)$. In some embodiments, $R^3$ and $R^5$ are each independently —$N(R^d)CO(R^f)$ or one of $R^3$ and $R^5$ is —$N(R^d)CO(R^f)$, and the other of $R^3$ and $R^5$ is H or —$CO_2R^c$. In some embodiments, $R^3$ and $R^5$ are each independently —$N(R^d)CO(R^f)$. In some embodiments, one of $R^3$ and $R^5$ is —$N(R^d)CO(R^f)$ and the other of $R^3$ and $R^5$ is H. In some embodiments, one of $R^3$ and $R^5$ is —$N(R^d)CO(R^f)$ and the other of $R^3$ and $R^5$ is —$CO_2R^c$. In some embodiments, one of $R^3$ and $R^5$ is —$N(R^d)CO(R^f)$ and the other of $R^3$ and $R^5$ is —$CON(R^d)(R^f)$.

In some embodiments, $R^3$ and $R^5$ are each independently —$CH_2N(R^d)CO(R^f)$ or one of $R^3$ and $R^5$ is —$CH_2N(R^d)CO(R^f)$, and the other of $R^3$ and $R^5$ is H, COOH, —$CO_2R^c$ or —$CON(R^d)(R^f)$. In some embodiments, $R^3$ and $R^5$ are each independently —$CH_2N(R^d)CO(R^f)$ or one of $R^3$ and $R^5$ is —$CH_2N(R^d)CO(R^f)$, and the other of $R^3$ and $R^5$ is H or —$CO_2R^c$. In some embodiments, $R^3$ and $R^5$ are each independently —$CH_2N(R^d)CO(R^f)$. In some embodiments, one of $R^3$ and $R^5$ is —$CH_2N(R^d)CO(R^f)$, and the other of $R^3$ and $R^5$ is H. In some embodiments, one of $R^3$ and $R^5$ is —$CH_2N(R^d)CO(R^f)$, and the other of $R^3$ and $R^5$ is —$CO_2R^c$. In some embodiments, one of $R^3$ and $R^5$ is —$CH_2N(R^d)CO(R^f)$ and the other of $R^3$ and $R^5$ is —$CON(R^d)(R^f)$.

In some embodiments, $R^3$ and $R^5$ are each —$CONH_2$.

In some embodiments, one of $R^3$ and $R^5$ is —$CH_2NH_2$, and the other of $R^3$ and $R^5$ is —$CONH_2$. In some embodiments, one of $R^3$ and $R^5$ is —$CONH_2$, and the other of $R^3$ and $R^5$ is —$COOCH_3$. In some embodiments, one of $R^3$ and $R^5$ is —$CH_2N(CH_3)_2$, and the other of $R^3$ and $R^5$ is —$CONH_2$. In some embodiments, one of $R^3$ and $R^5$ is —$CH_2NHC(O)CH_3$, and the other of $R^3$ and $R^5$ is —$CONH_2$. In some embodiments, one of $R^3$ and $R^5$ is —$NHC(O)CH_3$, and the other of $R^3$ and $R^5$ is —$CONH_2$. In some embodiments, one of $R^3$ and $R^5$ is —$NH_2$, and the other of $R^3$ and $R^5$ is —$CONH_2$.

In some embodiments, $R^4$ and $R^6$ are each independently H, halogen, halo $C_{1-4}$ alkyl), halo($C_{1-6}$ alkoxy)-, hydroxy, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_{1-2}$ alkyl)-$N(R^h)(R^f)$, —$N(R^g)CO_2(C_{1-2}$ alkyl)-$N(R^h)(R^f)$, optionally substituted ($C_{1-4}$ alkyl), optionally substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), optionally substituted ($C_{1-6}$ alkyl)oxy-, optionally substituted —$C_{1-6}$ alkyl)amino- and optionally substituted ($C_{1-6}$ alkyl)($C_{1-4}$ alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2R^d$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —NR d $SO_2R^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or 5-6 membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), hydroxy-($C_{1-4}$ alkyl)-, halo($C_{1-4}$ alkoxy)-, $C_{1-4}$ alkoxy-, hydroxy-($C_{2-4}$ alkoxy)-, $C_{1-4}$ alkoxy-$C_{1-4}$ alkoxy)-, —$COR^d$, —$CON(R^d)(R^f)$, and —$CO_2R^d$.

In some embodiments, $R^4$ and $R^6$ are each independently H, halogen, halo($C_{1-4}$ alkyl), halo($C_{1-6}$ alkoxy)-, hydroxy, —O—$P(O)(OH)_2$, —O—$P(O)(R^IR^{II})_2$, $NH_2$, —$NR^cR^c$, $NR^cR^d$, —$COR^c$, —$CO_2R^c$, —$N(R^d)COR^c$, —$N(R^d)SO_2R^c$, —$N(R^g)SO_2(C_{1-2}$ alkyl)-$N(R^h)(R$, —$N(R^g)CO(C_{1-2}$ alkyl)-$N(R^h)(R^f)$, optionally substituted ($C_{1-6}$ alkyl), optionally substituted ($C_{2-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), optionally substituted ($C_{1-6}$ alkyl)oxy-, optionally substituted —$C_{1-6}$ alkyl)amino- and optionally substituted ($C_{1-6}$ alkyl)($C_{1-4}$ alkyl)amino- is optionally substituted by 1-4 substituents each independently selected from —OH, —O—$P(O)(OH)_2$, —O—$P(O)(R^IR^{II})_2$, —$OR^c$, —$NH_2$—$NR^cR^c$, $NR^cR^d$, $CO_2H$, —$CO_2R^c$, $OCOR^c$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^d$-$COR^c$, —$NR^dSOR^c$, —$NR^dCO_2R^c$, —NR d $SO_2R^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), hydroxy-($C_{1-4}$ alkyl)-, —($C_{1-4}$ alkyl)-O—$P(O)(OH)_2$, —($C_{1-4}$ alkyl)-O—$P(O)(R^IR^{II})_2$, halo($C_{1-4}$ alkoxy)-, $C_{1-4}$ alkoxy-, hydroxy-($C_{2-4}$ alkoxy)-, —($C_{2-4}$ alkoxy)-O—$P(O)(OH)_2$, —($C_{2-4}$ alkoxy)-O—$P(O)(R^IR^{II})_2$, $C_{1-4}$ alkoxy-($C_{1-4}$ alkoxy)-, —$COR^d$, —$CON(R^d)(R^f)$, and —$CO_2R^d$.

In some embodiments, $R^4$ and $R^6$ are each H.

In some embodiments, $R^4$ and $R^6$ are each independently halogen, halo($C_{1-4}$ alkyl), halo($C_{1-6}$ alkoxy)-, hydroxy, —O—$P(O)(OH)_2$, —O—$P(O)(R^IR^{II})_2$, $NH_2$, —$NR^cR^c$, $NR^cR^d$, —$CO_2R^c$, —$N(R^d)COR^c$, —$N(R^d)SO_2R^c$, —$N(R^g)$ $SO_2(C_{1-2}$ alkyl)-$N(R^h)(R$, —$N(R^g)CO(C_{1-2}$ alkyl)-$N(R^h)$ $(R^f)$, optionally substituted ($C_{1-6}$ alkyl), optionally substituted ($C_{2-6}$ alkyl)oxy-, optionally substituted ($C_{1-6}$ alkyl)amino-, or optionally substituted ($C_{1-6}$ alkyl)($C_{1-4}$ alkyl) amino-, wherein the ($C_{1-6}$ alkyl) of said optionally substituted ($C_{1-6}$ alkyl), optionally substituted ($C_{1-6}$ alkyl)oxy-, optionally substituted —$C_{1-6}$ alkyl)amino- and optionally substituted ($C_{1-6}$ alkyl)($C_{1-4}$ alkyl)amino- is optionally substituted by 1-4 substituents each independently selected from —OH, —O—$P(O)(OH)_2$, —O—$P(O)(R^IR^{II})_2$, —$OR^c$, —$NH_2NR^cR^c$, $NR^cR^d$, $CO_2H$, —$CO_2R^c$, $OCOR^c$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —NR d $SO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl, or membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^H$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^H$)$_2$, $C_{1-4}$ alkoxy-($C_{1-4}$ alkoxy)-, —$COR^d$, —CON($R^d$)($R^f$), and —$CO_2R^d$.

In some embodiments, $R^4$ is H.

In some embodiments, $R^4$ is halogen, halo($C_{1-4}$ alkyl), halo($C_{1-6}$ alkoxy)-, hydroxy, —O—P(O)(OH)$_2$, —O—P(O)($R^IR^H$)$_2$, $NH_2$, —$NR^cR^c$, —$NR^cR^d$, —$COR^c$, —$CO_2R^c$, —N($R^d$)$COR^c$, —N($R^d$)$SO_2R^c$, —N($R^g$)$SO_2$($C_{1-2}$ alkyl)-N($R^h$)(R, —N($R^g$)CO($C_{1-2}$ alkyl)-N($R^h$)($R^f$), optionally substituted ($C_{1-6}$ alkyl), optionally substituted ($C_{2-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), optionally substituted ($C_{1-6}$ alkyl)oxy-, optionally substituted —$C_{1-6}$ alkyl)amino- and optionally substituted ($C_{1-6}$ alkyl)($C_{1-4}$ alkyl)amino- is optionally substituted by 1-4 substituents each independently selected from —OH, —O—P(O)(OH)$_2$, —O—P(O)($R^IR^H$)$_2$, —$NH_2$, —$NR^cR^c$, —$NR^cR^d$, —$CO_2H$, —$CO_2R^c$, $OCOR^c$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —NR d $SO_2R^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^H$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^H$)$_2$, $C_{1-4}$ alkoxy-($C_{1-4}$ alkoxy)-, —$COR^d$, —CON($R^d$)($R^f$), and —$CO_2R^d$.

In some embodiments, $R^6$ is H.

In some embodiments, $R^6$ is halogen, halo($C_{1-4}$ alkyl), halo($C_{1-6}$ alkoxy)-, hydroxy, —O—P(O)(OH)$_2$, —O—P(O)($R^IR^H$)$_2$, —$NH_2$, —$NR^cR^c$, —$NCOR^c$, —$CO_2R^c$, —N($R^d$)$COR^c$, —N($R^d$)$SO_2R^c$, —N($R^g$)$SO_2$($C_{1-2}$ alkyl)-N($R^h$)(R, —N($R^g$)CO($C_{1-2}$ alkyl)-N($R^h$)($R^f$), optionally substituted ($C_{1-6}$ alkyl), optionally substituted ($C_{2-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), optionally substituted ($C_{1-6}$ alkyl)oxy-, optionally substituted —$C_{1-6}$ alkyl)amino- and optionally substituted ($C_{1-6}$ alkyl)($C_{1-4}$ alkyl)amino- is optionally substituted by 1-4 substituents each independently selected from —OH, —O—P(O)(OH)$_2$, —O—P(O)($R^IR^H$)$_2$, —$OR^c$, —$NH_2$, —$NR^cR^c$, —$NR^cR^d$, —$CO_2H$, —$CO_2R^c$, $OCOR^c$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —NR d $SO_2R^c$, optionally substituted phenyl, optionally substituted 5-6 membered heterocycloalkyl, and optionally substituted 5-6 membered heteroaryl group, wherein said optionally substituted phenyl, 5-6 membered heterocycloalkyl, or membered heteroaryl is optionally substituted by 1-4 substituents each independently selected from halogen, hydroxy, amino, ($C_{1-4}$ alkyl)amino-, ($C_{1-4}$ alkyl)($C_{1-4}$ alkyl)amino-, $C_{1-4}$ alkyl, halo ($C_{1-4}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^H$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^H$)$_2$, $C_{1-4}$ alkoxy-($C_{1-4}$ alkoxy)-, —$COR^d$, —CON($R^d$)($R^f$), and —$CO_2R^d$.

In some embodiments, $R^{14}$ is absent, H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{14}$ is absent.

In some embodiments, $R^{14}$ is H, halogen, or optionally substituted $C_{1-4}$ alkyl, wherein said optionally substituted $C_{1-4}$ alkyl is optionally substituted by a substituent selected from halogen, —OW, —$NR^cR^d$, —$CO_2R^c$, —$CONR^cR^d$, —$SO_2NR^cR^d$, and —$OCONR^cR^d$.

In some embodiments, $R^{14}$ is H.

In some embodiments, $R^{14}$ is halogen or optionally substituted $C_{1-4}$ alkyl, wherein said optionally substituted $C_{1-4}$ alkyl is optionally substituted by a substituent selected from halogen, —OW, —$NR^cR^d$, —$CO_2R^c$, —$CONR^cR^d$, —$SO_2NR^cR^d$, and —$OCONR^cR^d$.

In some embodiments, $R^{14}$ is halogen.

In some embodiments, $R^{14}$ is optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{14}$ is optionally substituted $C_{1-4}$ alkyl, wherein said optionally substituted $C_{1-4}$ alkyl is optionally substituted by a halogen.

In some embodiments, $R^{14}$ is optionally substituted $C_{1-4}$ alkyl, wherein said optionally substituted $C_{1-4}$ alkyl is optionally substituted by a substituent selected from —$OR^c$, —$NR^cR^d$, —$CO_2R^c$, —$CONR^cR^d$, —$SO_2NR^cR^d$, and —$OCONR^cR^d$.

In some embodiments, $R^{14}$ is substituted $C_{1-4}$ alkyl, wherein said substituted $C_{1-4}$ alkyl is substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{14}$ is $C_{1-4}$ alkyl. In some embodiments, $R^{14}$ is methyl or ethyl. In some embodiments, $R^{14}$ is methyl. In some embodiments, $R^{14}$ is ethyl. In some embodiments, $R^{14}$ is substituted $C_{1-4}$ alkyl, wherein said substituted $C_{1-4}$ alkyl is substituted by a halogen.

In some embodiments, $R^{14}$ is substituted $C_{1-4}$ alkyl, wherein said substituted $C_{1-4}$ alkyl is substituted by a substituent selected from —$OR^c$, —$NR^cR^d$, —$CO_2R^c$, —$CONR^cR^d$, —$SO_2NR^cR^d$, and —$OCONR^cR^d$.

In some embodiments, $R^{14}$ is —$CH_2COOH$.

In some embodiments, $R^{16}$ is H or absent. In some embodiments, $R^{16}$ is H. In some embodiments, $R^{16}$ is absent.

In some embodiments, $R^{16}$ is H, halogen, or $C_{1-4}$ alkyl. In some embodiments, $R^{16}$ halogen.

In some embodiments, $R^{16}$ is $C_{1-4}$ alkyl. In some embodiments, $R^{16}$ is methyl or ethyl. In some embodiments, $R^{16}$ is methyl. In some embodiments, $R^{16}$ is ethyl.

In some embodiments, $R^{15}$ and $R^{17}$ are each independently absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring; or $R^{16}$ and $R^{17}$ taken together with the atom or atoms through which they are connected, form a 5-6 membered ring.

In some embodiments, $R^{15}$ and $R^{17}$ are each independently absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring.

In some embodiments, $R^{15}$ and $R^{17}$ are each independently absent.

In some embodiments, $R^{15}$ and $R^{17}$ are each independently H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring.

In some embodiments, $R^{15}$ and $R^{17}$ are each independently H.

In some embodiments, $R^{15}$ and $R^{17}$ are each independently halo($C_{1-4}$ alkyl).

In some embodiments, $R^{15}$ and $R^{17}$ are each independently cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{15}$ and $R^{19}$ taken together with the atom or atoms through which they are connected, form a 5-6 membered ring.

In some embodiments, $R^{15}$ and $R^{17}$ are each independently cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{15}$ and $R^{19}$ taken together with the atom or atoms through which they are connected, form a 5-6 membered ring.

In some embodiments, $R^{16}$ and $R^{17}$ taken together with the atom or atoms through which they are connected, form a 5-6 membered ring.

In some embodiments, $R^{15}$ and $R^{17}$ are each independently absent, H, cyclopropyl, or $C_{1-4}$ alkyl.

In some embodiments, $R^{15}$ and $R^{17}$ are each methyl.

In some embodiments, $R^{15}$ is absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{15}$ is absent.

In some embodiments, $R^{15}$ is H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{15}$ is H.

In some embodiments, $R^{15}$ is halo($C_{1-4}$ alkyl).

In some embodiments, $R^{15}$ is cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{15}$ is absent, H, cyclopropyl, or $C_{1-4}$ alkyl. In some embodiments, $R^{15}$ is cyclopropyl or $C_{1-4}$ alkyl. In some embodiments, $R^{15}$ is absent, H, cyclopropyl, or $C_{1-4}$ alkyl.

In some embodiments, $R^{15}$ is cyclopropyl. In some embodiments, $R^{15}$ is absent, H, cyclopropyl, or $C_{1-4}$ alkyl. In some embodiments, $R^{15}$ is $C_{1-4}$ alkyl.

In some embodiments, $R^{15}$ is each methyl.

In some embodiments, $R^{17}$ is absent, H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{17}$ is absent.

In some embodiments, $R^{17}$ is H, cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{17}$ is H.

In some embodiments, $R^{17}$ is halo($C_{1-4}$ alkyl).

In some embodiments, $R^{17}$ is cyclopropyl, halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{17}$ is absent, H, cyclopropyl, or $C_{1-4}$ alkyl. In some embodiments, $R^{17}$ is cyclopropyl or $C_{1-4}$ alkyl. In some embodiments, $R^{17}$ is absent, H, cyclopropyl, or $C_{1-4}$ alkyl. In some embodiments, $R^{17}$ is cyclopropyl. In some embodiments, $R^{17}$ is absent, H, cyclopropyl, or $C_{1-4}$ alkyl. In some embodiments, $R^{17}$ is $C_{1-4}$ alkyl.

In some embodiments, $R^{17}$ is each methyl.

In some embodiments, $R^{18}$ and $R^{19}$ are each independently absent, H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{17}$ and $R^{19}$ taken together with the atom or atoms through which they are connected, form a 5-6 membered ring.

In some embodiments, $R^{18}$ and $R^{19}$ are each independently absent.

In some embodiments, $R^{18}$ and $R^{19}$ are each independently H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{17}$ and $R^{18}$ taken together with the atom or atoms through which they are connected, form a 5-6 membered ring.

In some embodiments, $R^{18}$ and $R^{19}$ are each independently H.

In some embodiments, $R^{18}$ and $R^{19}$ are each independently halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; or $R^{17}$ and $R^{18}$ taken together with the atom or atoms through which they are connected, form a 5-6 membered ring.

In some embodiments, $R^{18}$ and $R^{19}$ are each independently halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, —$CH_2$—$CO_2R^c$, and —$OCONR^cR^d$.

In some embodiments, $R^{17}$ and $R^{18}$ taken together with the atom or atoms through which they are connected, form a 5-6 membered ring.

In some embodiments, $R^{18}$ is absent, H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{18}$ is absent.

In some embodiments, $R^{18}$ is H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{18}$ is H.

In some embodiments, $R^{18}$ is halo($C_{1-4}$ alkyl).

In some embodiments, $R^{18}$ is halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, and —$SO_2NR^cR^d$.

In some embodiments, $R^{18}$ is halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{19}$ is absent, H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{19}$ is absent.

In some embodiments, $R^{19}$ is H, halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{19}$ is H.

In some embodiments, $R^{19}$ is halo($C_{1-4}$ alkyl).

In some embodiments, $R^{19}$ is halogen or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, and —$SO_2NR^cR^d$.

In some embodiments, $R^{19}$ is halogen, or optionally substituted $C_{1-4}$ alkyl, wherein said optionally substituted $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$.

In some embodiments, $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen. In some embodiments, $R^{15}$, $R^{17}$, $R^{18}$, or $R^{19}$ are each independently —$OR^c$, —$NR^cR^d$, —$CONR^cR^d$, —$SO_2NR^cR^d$, and —$OCONR^cR^d$.

In some embodiments, $R^{15}$ is absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{15}$ is absent, H, or $C_{1-4}$ alkyl, wherein $C_{1-4}$ alkyl is optionally substituted by a substituent selected from halogen.

In some embodiments, $R^{15}$ is —$OR^c$, —$NR^cR^d$, —$CO_2R^c$, —$CONR^cR^d$, —$SO_2NR^cR^d$, and —$OCONR^cR^d$.

In some embodiments, $R^{17}$ is absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{17}$ is absent, H, or $C_{1-4}$ alkyl, wherein $C_{1-4}$ alkyl is optionally substituted by a substituent selected from halogen.

In some embodiments, $R^{17}$ is —$OR^c$, —$NR^cR^d$, —$CO_2R^c$, —$CONR^cR^d$, —$SO_2NR^cR^d$, and —$OCONR^cR^d$.

In some embodiments, $R^{18}$ is absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{18}$ is absent, H, or $C_{1-4}$ alkyl, wherein $C_{1-4}$ alkyl is optionally substituted by a substituent selected from halogen.

In some embodiments, $R^{18}$ is —$OR^c$, —$NR^cR^d$, —$CO_2R^c$, —$CONR^cR^d$, —$SO_2NR^cR^d$, and —$OCONR^cR^d$.

In some embodiments, $R^{19}$ is absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, $R^{19}$ is absent, H, or $C_{1-4}$ alkyl, wherein $C_{1-4}$ alkyl is optionally substituted by a substituent selected from halogen.

In some embodiments, $R^{19}$ is —$OR^c$, —$NR^cR^d$, —$CO_2R^c$, —$CONR^cR^d$, —$SO_2NR^cR^d$, and —$OCONR^cR^d$.

In some embodiments, when $Z_1$, $Y_1$ and $Y_2$ are each independently C or N, R", $R^{18}$ and $R^{19}$ are each independently absent or optionally substituted $C_{1-4}$ alkyl, wherein said optionally substituted $C_{1-4}$ alkyl is optionally substituted by a substituent selected from halogen —$OR^c$, —$NR^cR^d$, —$CO_2R^c$, —$CONR^cR^d$, —$SO_2NR^cR^d$, and —$OCONR^cR^d$.

In some embodiments, $R^{14}$, $R^{15}$, $R^{16}$, $R^{17}$, $R^{18}$ and $R^{19}$ are each independently absent, H or $C_{1-4}$ alkyl.

In some embodiments, $R^{14}$, $R^{15}$, $R^{16}$, $R^{17}$, $R^{18}$ and $R^{19}$ are each independently $C_{1-4}$ alkyl.

In some embodiments, $R^{14}$, $R^{15}$, $R^{16}$, $R^{17}$, $R^{18}$ and $R^{19}$ are each independently $C_{1-3}$ alkyl, (i.e., methyl or ethyl).

In some embodiments, $R^{14}$ is ethyl.

In some embodiments, $R^{14}$ is absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$. In some embodiments, $R^{14}$ is absent or $C_{1-4}$ alkyl, wherein $C_{1-4}$ alkyl is optionally substituted by a substituent selected from halogen.

In some embodiments, $R^{14}$ is absent or $C_{1-4}$ alkyl, wherein $C_{1-4}$ alkyl is optionally substituted by a substituent selected from —$OR^c$, —$NR^cR^d$, —$CO_2R^c$, —$CONR^cR^d$, —$SO_2NR^cR^d$, and —$OCONR^cR^d$.

In some embodiments, $R^{14}$ is absent or $C_{1-4}$ alkyl, wherein $C_{1-4}$ alkyl is optionally substituted by a substituent selected from —OW and —$NR^cR^d$.

In some embodiments, $R^{14}$ is absent or $C_{1-4}$ alkyl, wherein $C_{1-4}$ alkyl is optionally substituted by a substituent selected from —$CO_2R^c$, —$CONR^cR^d$, —$SO_2NR^cR^d$, and —$OCONR^cR^d$.

In some embodiments, $R^{14}$ is absent or $C_{1-4}$ alkyl, wherein $C_{1-4}$ alkyl is optionally substituted by a substituent selected from —$CO_2H$.

In some embodiments, $R^{14}$ is absent, $C_{1-4}$ alkyl, or —$CH_2$—$CO_2H$.

In some embodiments, $R^{C2}$ is absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

some embodiments, $R^{C2}$ is absent or $C_{1-4}$ alkyl, wherein $C_{1-4}$ alkyl is optionally substituted by a substituent selected from halogen.

In some embodiments, $R^{C2}$ is absent or $C_{1-4}$ alkyl, wherein $C_{1-4}$ alkyl is optionally substituted by a substituent selected from —$OR^c$, —$NR^cR^d$, —$CO_2R^c$, —$CONR^cR^d$, —$SO_2NR^cR^d$, and —$CONR^cR^d$.

In some embodiments, $R^{C2}$ is absent or $C_{1-4}$ alkyl, wherein $C_{1-4}$ alkyl is optionally substituted by a substituent selected from —$OR^c$ and —$NR^cR^d$.

In some embodiments, $R^{C2}$ is absent or $C_{1-4}$ alkyl, wherein $C_{1-4}$ alkyl is optionally substituted by a substituent selected from —$CO_2R^c$, —$CONR^cR^d$, —$SO_2NR^cR^d$, and —$OCONR^cR^d$.

In some embodiments, $R^{C2}$ is absent or $C_{1-4}$ alkyl, wherein $C_{1-4}$ alkyl is optionally substituted by a substituent selected from —$CO_2H$.

In some embodiments, $R^{C2}$ is absent, $C_{1-4}$ alkyl, or —$CH_2$—$CO_2H$.

In some embodiments, $R^{19}$ is methyl.

In some embodiments, $R^{16}$ is ethyl.

In some embodiments, $R^{18}$ is methyl.

In some embodiments, $R^a$ is H, —$COR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, or —$CH_2CO_2R^c$.

In some embodiments, $R^a$ is H, $C_{1-4}$ alkyl, —$CO(C_{1-4}$ alkyl), —$CO(C_{1-4}$alkyl)-OH, —$CO(C_{1-4}$ alkyl)-O—$(C_{1-4}$ alkyl), —$CO(C_{1-4}$ alkyl)-$NH_2$, —$CO(C_{1-4}$ alkyl)-$NH(C_{1-4}$ alkyl), or —$CO(C_{1-4}$ alkyl)-$N(C_{1-4}$ alkyl)$(C_{1-4}$ alkyl).

In some embodiments, $R^a$ is H.

In some embodiments, $R^a$ is —$R^c$, —$COR^c$, —$CO_2H$, —$CO_2R^c$, —$SOR^c$, -$SO_2R^c$, —$CONH_2$, —$CONR^cR^d$, —$SO_2NH_2$, —$SO_2NR^cR^d$, or —$CH_2$—$CO_2R^c$.

In some embodiments, $R^a$ is —$R^c$. In some embodiments, $R^a$ is —$COR^c$. In some embodiments, $R^a$ is —$CO_2H$. In some embodiments, $R^a$ is —$CO_2R^c$. In some embodiments, $R^a$ is —$SOR^c$. In some embodiments, $R^a$ is -$SO_2R^c$. In some embodiments, $R^a$ is —$CONH_2$. In some embodiments, $R^a$ is —$CONR^cR^d$. In some embodiments, $R^a$ is —$SO_2NH_2$. In some embodiments, $R^a$ is—$SO_2NR^cR^d$.

In some embodiments, $R^a$ is —$CH_2$—$CO_2R^c$. In some embodiments, $R^a$ is —$CH_2$—$CO_2H$.

In some embodiments, each $R^b$ is independently $C_{1-4}$ alkyl, halo($C_{1-4}$ alkyl), —$(C_{1-4}$ alkyl)-OH, —$(C_{1-4}$ alkyl)-O—P(O)(OH)$_2$, —$(C_{1-4}$ alkyl)-O—P(O)$(R^IR^{II})_2$, —$(C_{1-4}$ alkyl)-O—$(C_{1-4}$ alkyl), —$(C_{1-4}$ alkyl)-$N(R^e)(R^f)$, —$(C_{1-4}$ alkyl)-O—$CO(C_{1-4}$ alkyl), or —$(C_{1-4}$ alkyl)-CO—O—$(C_{1-4}$ alkyl).

In some embodiments, each $R^b$ is independently $C_{1-4}$ alkyl.

In some embodiments, each $R^b$ is independently halo($C_{1-4}$ alkyl), —$(C_{1-4}$ alkyl)-OH, —$(C_{1-4}$ alkyl)-O—P(O)(OH)$_2$, —$(C_{1-4}$ alkyl)-O—P(O)$(R^IR^{II})_2$, —$(C_{1-4}$ alkyl)-O—$(C_{1-4}$ alkyl), —$(C_{1-4}$ alkyl)-$N(R^e)(R^f)$, —$(C_{1-4}$ alkyl)-O—CO $(C_{1-4}$ alkyl), or —$(C_{1-4}$ alkyl)-CO—O—$(C_{1-4}$ alkyl).

In some embodiments, each $R^c$ is independently H, $C_{1-4}$ alkyl, halo($C_{1-4}$ alkyl), —$(C_{1-4}$ alkyl)-OH, —$(C_{1-4}$ alkyl)-O—P(O)(OH)$_2$, —$(C_{1-4}$ alkyl)-O—P(O)$(R^IR^{II})_2$, —$(C_{1-4}$ alkyl)-O—$(C_{1-4}$ alkyl), —$(C_{1-4}$ alkyl)-$N(R^e)(R^f)$, —$(C_{1-4}$ alkyl)-O—$CO(C_{1-4}$ alkyl), —$(C_{1-4}$ alkyl)-CO—O—$(C_{1-4}$ alkyl), optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl, wherein the $C_{3-6}$ cycloalkyl, phenyl, 4-6 membered heterocycloalkyl, 5-6 membered heteroaryl or 9-10 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl is optionally substituted by 1-4 substituents each independently selected from halogen, hydroxy, —O—P(O)(OH)$_2$, —O—P(O)$(R^IR^{II})_2$, amino, $(C_{1-4}$ alkyl)amino-, $(C_{1-4}$ alkyl)$(C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-$(C_{2-4}$ alkoxy)-, —$(C_{2-4}$ alkoxy)-O—P(O)(OH)$_2$, —$(C_{2-4}$ alkoxy)-O—P(O)$(R^IR^{II})_2$, $C_{1-4}$ alkoxy-$(C_{1-4}$ alkoxy)-, —$COR^d$, —$CON(R^d)(R^f)$, and —$CO_2R^d$.

In some embodiments, each $R^c$ is independently H.

In some embodiments, each $R^c$ is independently $C_{1-4}$ alkyl, halo($C_{1-4}$ alkyl), —$(C_{1-4}$ alkyl)-OH, —$(C_{1-4}$ alkyl)-O—P(O)(OH)$_2$, —$(C_{1-4}$ alkyl)-O—P(O)$(R^IR^{II})_2$, —$(C_{1-4}$ alkyl)-O—$(C_{1-4}$ alkyl), —$(C_{1-4}$ alkyl)-$N(R^e)(R^f)$, —$(C_{1-4}$ alkyl)-O—$CO(C_{1-4}$ alkyl), —$(C_{1-4}$ alkyl)-CO—O—$(C_{1-4}$ alkyl), optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl, wherein the $C_{3-6}$ cycloalkyl, phenyl, 4-6 membered heterocycloalkyl, 5-6 membered heteroaryl or 9-10 membered heteroaryl moiety of said optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_{1-4}$ alkyl-$C_{3-6}$ cycloalkyl, optionally substituted —$C_{1-4}$ alkyl-phenyl, optionally substituted —$C_{1-4}$ alkyl-4-6 membered heterocycloalkyl, optionally substituted —$C_{1-4}$ alkyl-5-6 membered heteroaryl, or optionally substituted —$C_{1-4}$ alkyl-9-10 membered heteroaryl is optionally substituted by 1-4 substituents each independently selected from halogen, hydroxy, —O—P(O)(OH)$_2$, —O—P(O)$(R^IR^{II})_2$, amino, $(C_{1-4}$ alkyl)amino-, $(C_{1-4}$ alkyl)$(C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-$(C_{2-4}$ alkoxy)-, —$(C_{2-4}$ alkoxy)-O—P(O)(OH)$_2$, —$(C_{2-4}$ alkoxy)-O—P(O)$(R^IR^{II})_2$, $C_{1-4}$ alkoxy-$(C_{1-4}$ alkoxy)-, —$COR^d$, —$CON(R^d)(R^f)$, and —$CO_2R^d$.

In some embodiments, each $R^d$ is independently H, hydroxy, or $C_{1-4}$ alkyl. In some embodiments, each $R^d$ is independently H or $C_{1-4}$ alkyl. In some embodiments, each $R^d$ is independently H or hydroxy. In some embodiments, each $R^d$ is independently hydroxy or $C_{1-4}$ alkyl. In some embodiments, each $R^d$ is independently H. In some embodiments, each $R^d$ is independently $C_{1-4}$ alkyl. In some embodiments, each $R^d$ is independently hydroxy.

In some embodiments, each $R^e$ is independently H, ($C_{1-4}$ alkyl), —CO($C_{1-4}$ alkyl), —OCO($C_{1-4}$ alkyl), —CO$_2$($C_{1-4}$ alkyl), —($C_{1-4}$ alkyl)amino, —($C_{1-4}$ alkyl)-$C_{1-4}$ alkoxy, —CO-(optionally substituted membered heterocycloalkyl), —CO—($C_{1-4}$ alkyl)-(optionally substituted 5-6 membered heterocycloalkyl), —CO-(optionally substituted 5-6 membered heteroaryl), —CO—($C_{1-4}$ alkyl)-(optionally substituted 5-6 membered heteroaryl),
wherein the optionally substituted 5-6 membered heterocycloalkyl or optionally substituted membered heteroaryl is optionally substituted by 1-4 substituents each independently selected from halogen, hydroxy, —O—P(O)(OH)$_2$, —O—P(O)($R^I R^{II}$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)O—P(O)(OH)$_2$, —($C_{2-4}$ alkoxy)-O—P(O)($R^I R^{II}$)$_2$, $C_{1-4}$ alkoxy-($C_{1-4}$ alkoxy)-, —COR$^d$, —CON(R$^d$)(R$^f$), and —CO$_2$R$^d$.

In some embodiments, each $R^e$ is independently H.

In some embodiments, each $R^e$ is independently ($C_{1-4}$ alkyl), —CO($C_{1-4}$ alkyl), —OCO($C_{1-4}$ alkyl), —CO$_2$($C_{1-4}$ alkyl), —($C_{1-4}$ alkyl)amino, —($C_{1-4}$ alkyl)-$C_{1-4}$ alkoxy, —CO-(optionally substituted membered heterocycloalkyl), —CO—($C_{1-4}$ alkyl)-(optionally substituted 5-6 membered heterocycloalkyl), —CO-(optionally substituted 5-6 membered heteroaryl), —CO—($C_{1-4}$ alkyl)-(optionally substituted 5-6 membered heteroaryl), wherein the optionally substituted 5-6 membered heterocycloalkyl or optionally substituted 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-4}$ alkyl)amino-, ($C_{1-4}$ alkyl)($C_{1-4}$ alkyl)amino-, $C_{1-4}$ alkyl, halo($C_{1-4}$ alkyl), halo($C_{1-4}$ alkoxy)-, $C_{1-4}$ alkoxy-, hydroxy-($C_{2-4}$ alkoxy)-, —($C_{2-4}$ alkoxy)O—P(O)(OH)$_2$, —($C_{2-4}$ alkoxy)-O—P(O)($R^I R^{II}$)$_2$, $C_{1-4}$ alkoxy-($C_{1-4}$ alkoxy)-, —COR$^d$, —CON(R$^d$)(R$^f$), and —CO$_2$R$^d$.

In some embodiments, each $R^f$ is independently H, hydroxy, or ($C_{1-4}$ alkyl). In some embodiments, each $R^f$ is independently H or ($C_{1-4}$ alkyl). In some embodiments, each $R^f$ is independently H or hydroxy. In some embodiments, each $R^f$ is independently hydroxy or ($C_{1-4}$ alkyl). In some embodiments, each $R^f$ is independently H. In some embodiments, each $R^f$ is independently ($C_{1-4}$ alkyl). In some embodiments, each $R^f$ is independently hydroxy.

In some embodiments, each of $R^I$ and $R^{II}$ are independently ($C_{1-6}$ alkyl)oxy-. In some embodiments, each $R^I$ is independently ($C_{1-6}$ alkyl)oxy-. In some embodiments, each $R^{II}$ is independently ($C_{1-6}$ alkyl)oxy-.

In some embodiments, $X_5$ is N.

In some embodiments, $X_5$ is $CR^{A2}$, wherein $R^{A2}$ is selected from H, halogen, —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_5$ is $CR^{A2}$, wherein $R^{A2}$ is selected from halogen, —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_5$ is $CR^{A2}$, wherein $R^{A2}$ is selected from —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_5$ is $CR^{A2}$, wherein $R^{A2}$ is selected from H, halogen, —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_5$ is $CR^{A2}$, wherein $R^{A2}$ is selected from halogen, —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_5$ is $CR^{A2}$, wherein $R^{A2}$ is selected from —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_6$ is N.

In some embodiments, $X_6$ is $CR^{A1}$, wherein $R^{A1}$ is selected from H, halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_6$ is $CR^{A1}$, wherein $R^{A1}$ is selected from halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_6$ is $CR^{A1}$, wherein $R^{A1}$ is selected from hydroxy, —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_6$ is $CR^{A1}$, wherein $R^{A1}$ is selected from —OCH$_2$CH$_2$CH$_2$OH, —OCH$_2$CH$_2$CH$_2$COOH, —OCH$_2$CH$_2$CH$_2$NH$_2$, —OCH$_3$, and —N(R$^e$)(R$^f$).

In some embodiments, $X_6$ is $CR^{A1}$, wherein $R^{A1}$ is selected from H, halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_6$ is $CR^{A1}$, wherein $R^{A1}$ is selected from halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_6$ is $CR^{A1}$, wherein $R^{A1}$ is selected from hydroxy, —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_6$ is $CR^{A1}$, wherein $R^{A1}$ is selected from —OCH$_2$CH$_2$CH$_2$OH, —OCH$_2$CH$_2$CH$_2$COOH, —OCH$_2$CH$_2$CH$_2$NH$_2$, —OCH$_3$, and —NH$_2$.

In some embodiments, $X_5$ is N and $X_6$ is N.

In some embodiments, $X_5$ is $CR^{A2}$ and $X_6$ is $CR^{A1}$. In some embodiments, $X_5$ is $CR^{A2}$ and $X_6$ is N. In some embodiments, $X_5$ is N and $X_6$ is $CR^{A1}$.

In some embodiments, $X_5$ is $CR^{A2}$ and $X_6$ is $CR^{A1}$, wherein $R^{A1}$ is —OCH$_3$ and $R^{A2}$ is —OCH$_2$CH$_2$CH$_2$OH.

In some embodiments, $X_5$ is $CR^{A2}$ and $X_6$ is $CR^{A1}$, wherein $R^{A1}$ is H and $R^{A2}$ is —OCH$_2$CH$_2$CH$_2$OH.

In some embodiments, $X_5$ is $CR^{A2}$ and $X_6$ is $CR^{A1}$, wherein $R^{A1}$ is —OH and $R^{A2}$ is —OCH$_2$CH$_2$CH$_2$OH.

In some embodiments, $X_5$ is $CR^{A2}$ and $X_6$ is $CR^{A1}$, wherein $R^{A1}$ is —OCH$_3$ and $R^{A2}$ is —OCH$_2$CH$_2$CH$_2$COOH.

In some embodiments, $X_5$ is $CR^{A2}$ and $X_6$ is $CR^{A1}$, wherein $R^{A1}$ is —OH and $R^{A2}$ is —OCH$_2$CH$_2$CH$_2$COOH.

In some embodiments, $X_5$ is $CR^{A2}$ and $X_6$ is $CR^{A1}$, wherein $R^{A1}$ is —OCH$_3$ and $R^{A2}$ is —OCH$_2$CH$_2$CH$_2$NH$_2$.

In some embodiments, $X_5$ is $CR^{A2}$ and $X_6$ is $CR^{A1}$, wherein $R^{A1}$ is —OH and $R^{A2}$ is —OCH$_2$CH$_2$CH$_2$NH$_2$.

In some embodiments, $X_6$ is N and $X_5$ is $CR^{A1}$, wherein $R^{A1}$ is —OCH$_2$CH$_2$CH$_2$OH.

In some embodiments, $X_6$ is N and $X_5$ is $CR^{A1}$, wherein $R^{A1}$ is —OCH$_2$CH$_2$CH$_2$COOH.

In some embodiments, $X_6$ is N and $X_5$ is $CR^{A1}$, wherein $R^{A1}$ is —OCH$_2$CH$_2$CH$_2$NH$_2$.

In some embodiments, $X_6$ is N and $X_5$ is $CR^{A1}$, wherein $R^{A1}$ is halogen.

In some embodiments, $X_6$ is N and $X_5$ is $CR^{A1}$, wherein $R^{A1}$ is —OCH$_3$.

In some embodiments, $X_6$ is N and $X_5$ is $CR^{A1}$, wherein $R^{A1}$ is —OH.

In some embodiments, $X_5$ is $CR^{A2}$ and $X_6$ is $CR^{A1}$, wherein $R^{A1}$ is OCH$_2$CH$_2$CH$_2$NH$_2$ and $R^{A2}$ is —OCH$_2$CH$_2$CH$_2$NH$_2$.

In some embodiments, $R^{A1}$ and $R^{A2}$ are independently H, halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$, or —N(R$^e$)(R$^f$).

In some embodiments, $X_3$ and $X_4$ are each independently S or NR f, wherein R$^f$ is H In some embodiments, $X_3$ is S and $X_4$ is NR f, wherein R$^f$ is H In some embodiments, $X_9$ is N or $CR^4$. In some embodiments, $X_9$ is N. In some embodiments, $X_9$ is $CR^4$. In some embodiments, $X_9$ is CH.

In some embodiments, the disclosure is directed to a compound Formula (I'), Formula (IA'), Formula (II'), Formula (III'), Formula (IV'), or Formula (V') wherein:

the total of r and s is 1 or 2;

$X_3$ and $X_4$ are each independently S or NR$^f$;

$X_5$ is N or $CR^{A2}$; $X_6$ is N or $CR^{A1}$; $X_9$ is N or CH;

$R^{A1}$ and $R^{A2}$ are independently selected from H, halogen, hydroxy, —OCH$_2$CH$_2$CH$_2$OH, —OCH$_2$CH$_2$CH$_2$COOH, —OCH$_2$CH$_2$CH$_2$NH$_2$, —OCH$_3$ and —NR$^e$R$^f$.

r is 0 and $R^{B1}$ and $R^{B2}$ are each H; or r is 1, $R^{B1}$ and $R^{B2}$ are each independently —CH$_2$—, and B is —CH═CH—, —CH$_2$CH$_2$—, —CH(OH)CH(OH)-, or —CH$_2$N(CH$_3$)CH$_2$—;

s is 0, $Y_1$, $Y_2$, $Z_1$ and $Z_2$ are each independently O or S;

s is 0, $W_1$ is C, $R^{C1}$ is methyl;

s is 0, $Z_2$ is C, $R^{C2}$ is ethyl;

s is 0, $W_1$ is N, $R^{C1}$ is absent;

s is 0, $Z_2$ is N, $R^{C2}$ is absent or ethyl;

s is 1, $W_1$ and $Z_2$ are each independently C or N, $R^{C1}$ and $R^{C2}$ are each independently —CH$_2$—, and D is —CH$_2$CH$_2$CH$_2$—;

$R^3$ and $R^5$ are each independently —CONH$_2$, —CH$_2$NH$_2$, —NH$_2$, —CH$_2$N(CH$_3$)$_2$, —CH$_2$NHC(O)CH$_3$ or —NHC(O)CH$_3$;

$R^4$ and $R^6$ are each H;

$R^{14}$ is absent, methyl or ethyl;

$R^{15}$ is absent, H or methyl;

$R^{16}$ is absent, H, methyl or ethyl; and $R^{17}$ is absent or methyl, or a prodrug, solvate, pharmaceutically acceptable salt, or tautomer thereof.

In some embodiments, the compound is of Formula (I-B'):

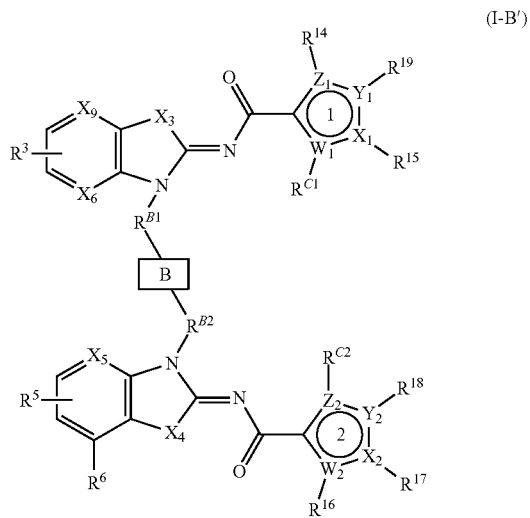

(I-B')

or a prodrug, solvate, pharmaceutically acceptable salt, or tautomer thereof, wherein:

$Y_1$, $Y_2$, $Z_1$, and $Z_2$ are each independently O, S, C, or N;

$X_1$, $X_2$, $W_1$, and $W_2$ are each independently C or N;

$X_3$, $X_4$, $X_5$, $X_6$, $X_9$, $R^3$, $R^5$, $R^d$ and $R^f$ are each independently as defined in Formula (IA');

$R^c$ is $C_{1-4}$ alkyl;

$R^{B1}$ and $R^{B2}$ are each independently —CH$_2$—;

B is -halo($C_{1-5}$ alkyl), unsubstituted —$C_{1-5}$ alkyl, or unsubstituted —$C_{2-5}$ alkenyl-;

$R^{A2}$ and $R^{A1}$ are each independently H, halogen, hydroxy, amino, amino($C_{1-4}$ alkyl)-, P(O)(OH)$_2$, —O—P(O)(R$^I$R$^{II}$)$_2$, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxy, —O—P(O)(OH)$_2$, —O—P(O)(R$^I$R$^{II}$)$_2$, $C_{1-4}$ alkoxyl, —N(R$^e$)(R$^f$), —CO$_2$(R$^f$), optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, —O—PO)(OH)$_2$, —O—P(O)(R$^I$R$^{II}$)$_2$, amino, ($C_{1-6}$ alkyl)amino-, ($C_{1-6}$ alkyl)($C_{1-6}$ alkyl)amino-, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)(R$^I$R$^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)(R$^I$R$^{II}$)$_2$, —($C_{1-6}$ alkyl)-NH$_2$, —$C_{1-4}$ alkyl-($C_{1-4}$ alkoxy), and $C_{1-4}$ alkoxy-($C_{1-4}$ alkoxy)-;

$R^e$ is selected from H, ($C_{1-4}$ alkyl), —CO($C_{1-4}$ alkyl), —OCO($C_{1-4}$ alkyl), —($C_{1-4}$ alkyl)-NH$_2$, —($C_{1-4}$ alkyl)-$C_{1-4}$ alkoxy, and —CO$_2$($C_{1-4}$ alkyl);

$R^4$ and $R^6$ are H;

$R^{14}$ and $R^{C2}$ are each independently absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; $R^{16}$ and $R^{C1}$ are each independently absent, H or $C_{1-4}$ alkyl; and $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; and each $R^I$ and $R^{II}$ are independently ($C_{1-6}$ alkyl)oxy-;

provided that at least one of (i), (ii), or (iii) applies:

(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —$OR^c$, —$NR^cR^d$, —$CO_2R^c$, —$CONR^cR^d$, —$SO_2NR^cR^d$, and —$OCONR^cR^d$ wherein $R^c$ is H; or (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{41}$ or $R^{42}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, —N($R^e$)($R^f$), —$CO_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo ($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

In some embodiments, the compound is of Formula (I-B'), wherein $X_9$, is $CR^4$.

In some embodiments, the compound is of Formula (II-B'):

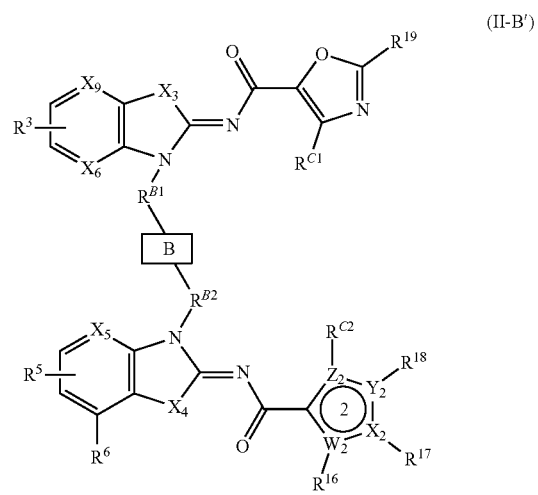

(II-B')

or a prodrug, solvate, pharmaceutically acceptable salt, or tautomer thereof, wherein:

$Y_2$ and $Z_2$ are each independently O, S, C, or N;

$X_2$ and $W_2$ are each independently C or N;

$X_3$, $X_4$, $X_5$, $X_6$, $X_9$, $R^3$, $R^5$, $R^d$ and $R^f$ are each independently as defined in Formula (IA');

$R^c$ is $C_{1-4}$ alkyl;

$R^{B1}$ and $R^{B2}$ are each independently —CH$_2$—;

B is -halo($C_{1-5}$ alkyl), unsubstituted —$C_{1-5}$ alkyl, or unsubstituted —$C_{1-5}$ alkenyl-;

$R^{42}$ and $R^{41}$ are each independently H, halogen, amino, amino($C_{1-4}$ alkyl)-, hydroxy, —O—P(O)(OH)$_2$, —O—P(O)($R^IR^{II}$)$_2$, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxy, —O—P(O)(OH)$_2$, —O—P(O)($R^IR^{II}$)$_2$, $C_{1-4}$ alkoxyl, —N($R^e$)($R^f$), —$CO_2$($R^f$), optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —($C_{1-6}$ alkyl)-NH$_2$, and $C_{1-4}$ alkoxy-($C_{1-4}$ alkoxy)-;

$R^e$ is selected from H, ($C_{1-4}$ alkyl), —CO($C_{1-4}$ alkyl), —OCO($C_{1-4}$ alkyl), —($C_{1-4}$ alkyl)-NH$_2$, —($C_{1-4}$ alkyl)-$C_{1-4}$ alkoxy, and —$CO_2$($C_{1-4}$ alkyl), $R^4$ and $R^6$ are H;

$R^{C2}$ is absent, $C_{1-4}$ alkyl or —CH$_2$COOH;

$R^{16}$ and $R^{C1}$ are each independently absent, H or $C_{1-4}$ alkyl; and $R^{17}$, $R^{18}$, or $R^{19}$ are each independently absent, H, $C_{1-4}$ alkyl or halo($C_{1-4}$ alkyl); and each $R^I$ and $R^{II}$ are independently ($C_{1-6}$ alkyl)oxy-.

In some embodiments, the compound is of Formula (II-B'), wherein $X_9$, is $CR^4$. In some embodiments, the compound is of Formula (I-B'), or a prodrug, solvate, pharmaceutically acceptable salt, or tautomer thereof, wherein:

$R^{A2}$ and $R^{A1}$ are each independently H, halogen, amino, amino($C_{1-4}$ alkyl)-, hydroxy, —O—P(O)(OH)$_2$, —O—P(O)($R^I R^{II}$)$_2$, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxy, —O—P(O)(OH)$_2$, —O—P(O)($R^I R^{II}$)$_2$, $C_{1-4}$ alkoxyl, —N($R^e$)($R^f$), —CO$_2$($R^f$), optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-6}$ alkyl)amino-, ($C_{1-6}$ alkyl)($C_{1-6}$ alkyl)amino-, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^I R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, —($C_{1-6}$ alkyl)-NH$_2$, and $C_{1-4}$ alkoxy-($C_{1-4}$ alkoxy)-;

provided that at least one of (i), (ii), or (iii) applies:
(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or
(ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —NR$^c$R$^d$, —CO$_2$R$^c$, —CONR$^c$R$^d$, —SO$_2$NR$^c$R$^d$, and —OCONR$^c$R$^d$ wherein R$^c$ is H; or
(iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^I R^{II}$)$_2$, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo ($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^I R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^I R^{II}$)$_2$, —$C_{1-4}$ alkyl-($C_{1-4}$ alkoxy), and $C_{1-4}$ alkoxy-($C_{1-4}$ alkoxy)-.

In some embodiments, the compound is of Formula (I-B'), or a prodrug, solvate, pharmaceutically acceptable salt, or tautomer thereof, wherein:

$R^{A2}$ and $R^{A1}$ are each independently H, halogen, amino, amino($C_{1-4}$ alkyl)-, hydroxy, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, $C_{1-4}$ alkoxyl, —N($R^e$)($R^f$), —CO$_2$($R^f$), optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-6}$ alkyl)amino-, ($C_{1-6}$ alkyl)($C_{1-6}$ alkyl)amino-, halo($C_{1-6}$ alkyl), hydroxy-($C_{1-4}$ alkyl)-, halo($C_{1-4}$ alkoxy)-, $C_{1-4}$ alkoxy-, hydroxy-($C_{2-4}$ alkoxy)-, and $C_{1-4}$ alkoxy-($C_{1-4}$ alkoxy)-; and $R^e$ is selected from H, ($C_{1-4}$ alkyl), —CO($C_{1-4}$ alkyl), —OCO($C_{1-4}$ alkyl), and —CO$_2$($C_{1-4}$ alkyl); provided that at least one of (i), (ii), or (iii) applies:
(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or
(ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —NR$^c$R$^d$, —CO$_2$R$^c$, —CONR$^c$R$^d$, —SO$_2$NR$^c$R$^d$, and —OCONR$^c$R$^d$ wherein R$^e$ is H; or
(iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, and $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^I R^{II}$)$_2$, —N($R^e$)($R^f$), —CO$_2$($R^f$), —CON(R e)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo ($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^I R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-.

In some embodiments, the compound is of Formula (I-b'):

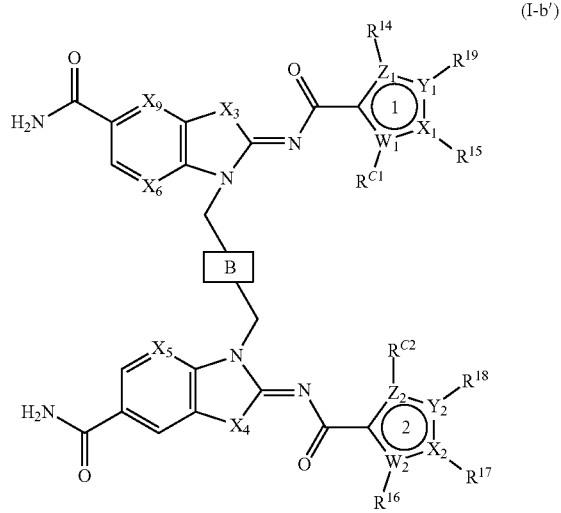

(I-b')

or a prodrug, solvate, pharmaceutically acceptable salt, or tautomer thereof, wherein:

Y$_1$, Y$_2$, Z$_1$, and Z$_2$ are each independently O, S, C, or N;
X$_1$, X$_2$, W$_1$, and W$_2$ are each independently C or N;
X$_3$, X$_4$, X$_5$, X$_6$, and X$_9$ are each independently as defined in Formula (IA');
B is -halo(C$_{1-5}$ alkyl), unsubstituted C$_{1-5}$ alkyl, or unsubstituted —C$_{2-5}$ alkenyl-;
R$^{A2}$ and R$^{A1}$ are each independently H, halogen, amino, amino(C$_{1-4}$ alkyl)-, hydroxy, —O—P(O)(OH)$_2$, —O—P(O)(R$^I$R$^{II}$)$_2$, optionally substituted (C$_{1-6}$ alkyl), or optionally substituted (C$_{1-6}$ alkyl)oxy-,
wherein C$_{1-6}$ alkyl of said optionally substituted (C$_{1-6}$ alkyl) or optionally substituted (C$_{1-6}$ alkyl)oxy- is optionally substituted with 1-4 substituents each independently selected from the group comprising hydroxyl, C$_{1-4}$ alkoxyl, —N(R$^e$)(R$^f$), —CO$_2$(R$^f$), optionally substituted phenyl, and optionally substituted 5-6 membered heteroaryl, and wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —(C$_{1-6}$ alkyl)-NH$_2$, —C$_{1-4}$ alkyl-(C$_{1-4}$ alkoxy), and C$_{1-4}$ alkoxy-(C$_{1-4}$ alkoxy)-;
R$^e$ is selected from H, (C$_{1-4}$ alkyl), —CO(C$_{1-4}$ alkyl), —OCO(C$_{1-4}$ alkyl), —(C$_{1-4}$ alkyl)-NH$_2$, —(C$_{1-4}$ alkyl)-C$_{1-4}$ alkoxy, and —CO$_2$(C$_{1-4}$ alkyl),
each R$^f$ is independently H, hydroxy, or (C$_{1-4}$ alkyl);

R$^4$ and R$^6$ are H;
R$^{14}$ and R$^{C2}$ are each independently absent or C$_{1-4}$ alkyl, wherein C$_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$; R$^{16}$ and R$^{C1}$ are each independently absent, H or C$_{1-4}$ alkyl;
R$^{15}$, R$^{17}$, R$^{18}$, or R$^{19}$ are each independently absent, H, or C$_{1-4}$ alkyl, wherein C$_{1-4}$ alkyl is optionally substituted by a substituent selected from halogen, —OR$^c$, —NR$^c$R$^d$, —CONR$^c$R$^d$, —SO$_2$NR$^c$R$^d$, and —OCONR$^c$R$^d$; and
each R$^I$ and R$^{II}$ are independently (C$_{1-6}$ alkyl)oxy-, provided that at least one of (i), (ii), or (iii) applies:
(i) when (a) Z$_1$, Z$_2$, Y$_1$ and Y$_2$ are each N, W$_1$, W$_2$, X$_1$ and X$_2$ are each C; or (b) W$_1$, W$_2$, X$_1$ and X$_2$ are each N, Z$_1$, Z$_2$, Y$_1$ and Y$_2$ are each C; or (c) Z$_1$ and Y$_1$ are each N, W$_1$ and X$_1$ are each C; or (d) Z$_2$ and Y$_2$ are each N, W$_2$ and X$_2$ are each C; or (e) W$_1$ and X$_1$ are each N, Z$_1$ and Y$_1$ are each C; or (f) W$_2$ and X$_2$ are each N, Z$_2$ and Y$_2$ are each C, then at least one of X$_3$ and X$_4$ is S; or X$_9$ is N; or
(ii) when (a) Z$_1$, Z$_2$, Y$_1$ and Y$_2$ are each N, W$_1$, W$_2$, X$_1$ and X$_2$ are each C; or (b) W$_1$, W$_2$, X$_1$ and X$_2$ are each N, Z$_1$, Z$_2$, Y$_1$ and Y$_2$ are each C, then R$^{14}$ is a C$_{1-4}$ alkyl substituted with halogen, —NR$^c$R$^d$, —CO$_2$R$^c$, —CONR$^c$R$^d$, —SO$_2$NR$^c$R$^d$, and —OCONR$^c$R$^d$ wherein R$^c$ is H; or
(iii) when (a) Z$_1$ and Y$_1$ are each N, W$_1$ and X$_1$ are each C; or (b) Z$_2$ and Y$_2$ are each N, W$_2$ and X$_2$ are each C; or (c) W$_1$ and X$_1$ are each N, Z$_1$ and Y$_1$ are each C; or (d) W$_2$ and X$_2$ are each N, Z$_2$ and Y$_2$ are each C, then at least one of X$_5$, X$_6$, and X$_9$ is N and R$^{A1}$ or R$^{A2}$ is halogen, hydroxy, optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino-,
wherein the (C$_{1-6}$ alkyl) of said optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)(R$^I$R$^{II}$)$_2$, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-.

In some embodiments, the compound is of Formula (I-b'), or a prodrug, solvate, pharmaceutically acceptable salt, or tautomer thereof, wherein X$_9$ is CR$^4$.

In some embodiments, the compound is of Formula

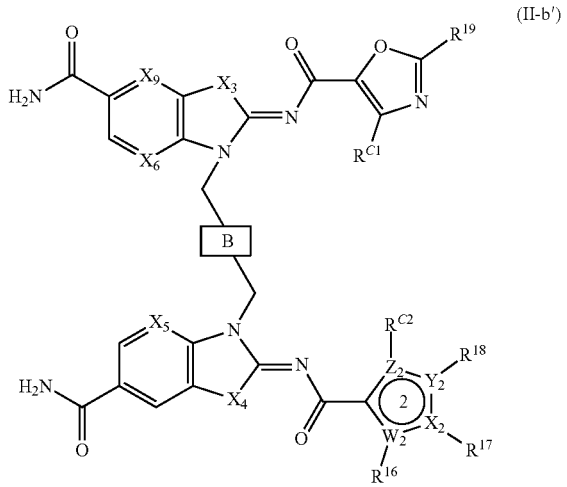

(II-b')

or a prodrug, solvate, pharmaceutically acceptable salt, or tautomer thereof, wherein:

$Y_2$ and $Z_2$ are each independently O, S, C or N;

$X_2$ and $W_2$ are each independently C or N;

$X_3$, $X_4$, $X_5$, $X_6$, and $X_9$ are each independently as defined herein;

B is -halo($C_{1-5}$ alkyl), unsubstituted —$C_{1-5}$ alkyl, or unsubstituted —$C_{2-5}$ alkenyl-;

$R^{42}$ and $R^{41}$ are each independently H, halogen, amino, amino($C_{1-4}$ alkyl)-, hydroxy, —O—P(O)(OH)$_2$, —O—P(O)($R^{I}R^{II}$)$_2$, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, $C_{1-4}$ alkoxyl, —N($R^e$)($R^f$), —CO$_2$($R^f$), optionally substituted phenyl, and optionally substituted 5 6 membered heteroaryl, and wherein said optionally substituted phenyl or membered heteroaryl is optionally substituted by 1-4 substituents each independently selected from halogen, hydroxy, —O—P(O)(OH)$_2$, —O—P(O)($R^{I}R^{II}$)$_2$, amino, ($C_{1-6}$alkyl)amino-, ($C_{1-6}$alkyl)($C_{1-6}$ alkyl)amino-, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^{I}R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^{I}R^{II}$)$_2$, —($C_{1-6}$ alkyl)-NH$_2$, and $C_{1-4}$ alkoxy-($C_{1-4}$ alkoxy)-;

$R^e$ is selected from H, ($C_{1-4}$ alkyl), —CO($C_{1-4}$ alkyl), —OCO($C_{1-4}$ alkyl), —($C_{1-4}$ alkyl)-NH$_2$, —($C_{1-4}$ alkyl)-$C_{1-4}$ alkoxy, and —CO$_2$($C_{1-4}$ alkyl), each $R^f$ is independently H, hydroxy, or ($C_{1-4}$ alkyl);

$R^4$ and $R^6$ are H;

$R^{C2}$ is absent, $C_{1-4}$ alkyl or —CH$_2$COOH;

$R^{16}$ and $R^{C1}$ are each independently absent, H or $C_{1-4}$ alkyl;

$R^{17}$, $R^{18}$, or $R^{19}$ are each independently absent, H, $C_{1-4}$ alkyl or halo($C_{1-4}$ alkyl); and each $R^I$ and $R^{II}$ are independently ($C_{1-6}$ alkyl)oxy-.

In some embodiments, the compound is of Formula or a prodrug, solvate, pharmaceutically acceptable salt, or tautomer thereof, wherein $X_9$ is $CR^4$.

In some embodiments, the compound is of Formula (I-b'), or a prodrug, solvate, pharmaceutically acceptable salt, or tautomer thereof, wherein:

$R^{42}$ and $R^{41}$ are each independently H, halogen, amino, amino($C_{1-4}$ hydroxy, P(O)(OH)$_2$, —O—P(O)($R^{I}R^{II}$)$_2$, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, $C_{1-4}$ alkoxyl, —N($R^e$)($R^f$), —CO$_2$($R^f$), optionally substituted phenyl, and optionally substituted 5 6 membered heteroaryl, and wherein said optionally substituted phenyl or membered heteroaryl is optionally substituted by 1-4 substituents each independently selected from halogen, hydroxy, —O—P(O)(OH)$_2$, —O—P(O)($R^{I}R^{II}$)$_2$, amino, ($C_{1-6}$alkyl)amino-, ($C_{1-6}$alkyl)($C_{1-6}$ alkyl)amino-, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^{I}R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^{I}R^{II}$)$_2$, —($C_{1-6}$ alkyl)-NH$_2$, and $C_{1-4}$ alkoxy-($C_{1-4}$ alkoxy)-;

provided that at least one of (i), (ii), or (iii) applies:

(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —NR$^c$R$^d$, —CO$_2$R$^c$, —CONR$^c$R$^d$, —SO$_2$NR$^c$R$^d$, and —OCONR$^c$R$^d$ wherein R$^c$ is H; or (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{41}$ or $R^{42}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^{I}R^{II}$)$_2$, —N($R^e$)($R^f$), —CO$_2$($R^f$), —CON($R^e$)($R^f$), optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^{I}R^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo ($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^{I}R^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-.

In some embodiments, the compound of disclosure has Formula (I-b'), or a prodrug, solvate, pharmaceutically acceptable salt, or tautomer thereof, wherein:

R$^{42}$ and R$^{41}$ are each independently H, halogen, hydroxy, amino, amino(C$_{1-4}$ alkyl)-, optionally substituted (C$_{1-6}$ alkyl), or optionally substituted (C$_{1-6}$ alkyl)oxy-, wherein C$_{1-6}$ alkyl of said optionally substituted (C$_{1-6}$ alkyl), or optionally substituted (C$_{1-6}$ alkyl)oxy- is optionally substituted with 1-4 substituents each independently selected from the group comprising hydroxyl, C$_{1-4}$ alkoxyl, —N(R$^e$)(R$^f$), —CO$_2$(R$^f$), optionally substituted phenyl, and optionally substituted 5-6 membered heteroaryl, and wherein said optionally substituted phenyl or 5-6 membered heteroaryl is optionally substituted by 1-4 substituents each independently selected from halogen, hydroxy, amino, (C$_{1-6}$ alkyl)amino-, (C$_{1-6}$ alkyl)(C$_{1-6}$ alkyl)amino-, halo(C$_{1-6}$ alkyl), hydroxy-(C$_{1-4}$ alkyl)-, halo(C$_{1-4}$ alkoxy)-, C$_{1-4}$ alkoxy-, hydroxy-(C$_{2-4}$ alkoxy)-, and C$_{1-4}$ alkoxy-(C$_{1-4}$ alkoxy)-; and R$^e$ is H, (C$_{1-4}$ alkyl), —CO(C$_{1-4}$ alkyl), —OCO(C$_{1-4}$ alkyl), or —CO$_2$(C$_{1-4}$ alkyl);

provided that at least one of (i), (ii), or (iii) applies:

(i) when (a) Z$_1$, Z$_2$, Y$_1$ and Y$_2$ are each N, W$_1$, W$_2$, X$_1$ and X$_2$ are each C; or (b) W$_1$, W$_2$, X$_1$ and X$_2$ are each N, Z$_1$, Z$_2$, Y$_1$ and Y$_2$ are each C; or (c) Z$_1$ and Y$_1$ are each N, W$_1$ and X$_1$ are each C; or (d) Z$_2$ and Y$_2$ are each N, W$_2$ and X$_2$ are each C; or (e) W$_1$ and X$_1$ are each N, Z$_1$ and Y$_1$ are each C; or (f) W$_2$ and X$_2$ are each N, Z$_2$ and Y$_2$ are each C, then at least one of X$_3$ and X$_4$ is S; or X$_9$ is N; or (ii) when (a) Z$_1$, Z$_2$, Y$_1$ and Y$_2$ are each N, W$_1$, W$_2$, X$_1$ and X$_2$ are each C; or (b) W$_1$, W$_2$, X$_1$ and X$_2$ are each N, Z$_1$, Z$_2$, Y$_1$ and Y$_2$ are each C, then R$^{14}$ is a C$_{1-4}$ alkyl substituted with halogen, NR$^c$R$^d$, —CO$_2$R$^c$, —CONR$^c$R$^d$, —SO$_2$NR$^c$R$^d$, and —OCONR$^c$R$^d$ wherein R$^c$ is H; or (iii) when (a) Z$_1$ and Y$_1$ are each N, W$_1$ and X$_1$ are each C; or (b) Z$_2$ and Y$_2$ are each N, W$_2$ and X$_2$ are each C; or (c) W$_1$ and X$_1$ are each N, Z$_1$ and Y$_1$ are each C; or (d) W$_2$ and X$_2$ are each N, Z$_2$ and Y$_2$ are each C, then at least one of X$_5$, X$_6$, and X$_9$ is N and R$^{41}$ or R$^{42}$ is halogen, hydroxy, optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino-, wherein the (C$_{1-6}$ alkyl) of said optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino- is optionally substituted by 1-4 substituents each independently selected from hydroxy, —O—P(O)(OH)$_2$, —O—P(O)(R$^I$R$^{II}$)$_2$, —N(R$^e$)(R$^f$), —CO$_2$(R$^f$), —CON(R$^e$)(R$^f$), optionally substituted phenyl, and optionally substituted 5-6 membered heteroaryl group, wherein said optionally substituted phenyl, or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_{1-6}$ alkyl)amino-, (C$_{1-6}$ alkyl)(C$_{1-6}$ alkyl)amino-, —(C$_{1-6}$ alkyl)-NH$_2$, halo(C$_{1-6}$ alkyl), hydroxy-(C$_{1-4}$ alkyl)-, —(C$_{1-4}$ alkyl)-O—P(O)(OH)$_2$, —(C$_{1-4}$ alkyl)-O—P(O)(R$^I$R$^{II}$)$_2$, halo(C$_{1-4}$ alkoxy)-, C$_{1-4}$ alkoxy-, hydroxy-(C$_{2-4}$ alkoxy)-, —(C$_{2-4}$ alkoxy)-O—P(O)(OH)$_2$, —(C$_{2-4}$ alkoxy)-O—P(O)(R$^I$R$^{II}$)$_2$, —C$_{1-4}$ alkyl-(C$_{1-4}$ alkoxy), and C$_{1-4}$ alkoxy-(C$_{1-4}$ alkoxy)-.

In some embodiments, the compound is of Formula (I-B'), (II-B'), (I-b'), or (II-b'), or a prodrug, solvate, pharmaceutically acceptable salt, or tautomer thereof, wherein R$^{42}$ and R$^{41}$ are each independently H, halogen, hydroxy, amino, amino(C$_{1-4}$ alkyl)-, optionally substituted (C$_{1-6}$ alkyl), or optionally substituted (C$_{1-6}$ alkyl)oxy-, and the C$_{1-6}$ alkyl of said optionally substituted (C$_{1-6}$ alkyl), optionally substituted (C$_{1-6}$ alkyl)oxy- is optionally substituted with 1-4 substituents each independently selected from the group comprising hydroxyl, —O—P(O)(OH)$_2$, —O—P(O)(R$^I$R$^{II}$)$_2$, —N(R$^e$)(R$^f$), C$_{1-4}$ alkoxyl, phenyl, and optionally substituted 5-6 membered heteroaryl comprising at least one nitrogen or oxygen as a member of the ring; each R$^e$ is independently selected from H, (C$_{1-4}$ alkyl), —(C$_{1-4}$ alkyl)-NH$_2$, and —(C$_{1-4}$ alkyl)-C$_{1-4}$ alkoxy; and each R$^f$ is independently H, hydroxy, or (C$_{1-4}$ alkyl).

In some embodiments, the compound is of Formula (I-B'), (II-B'), (I-b'), or (II-b'), or a prodrug, solvate, pharmaceutically acceptable salt, or tautomer thereof, wherein R$^{42}$ and R$^{41}$ are each independently H, halogen, hydroxy, amino, amino(C$_{1-4}$ alkyl)-, optionally substituted (C$_{1-6}$ alkyl), or optionally substituted (C$_{1-6}$ alkyl)oxy-, and the C$_{1-6}$ alkyl of said optionally substituted (C$_{1-6}$ alkyl), optionally substituted (C$_{1-6}$ alkyl)oxy- is optionally substituted with 1-4 substituents each independently selected from the group comprising hydroxyl, —N(R$^e$)(R$^f$), C$_{1-4}$ alkoxyl, phenyl, and optionally substituted 5-6 membered heteroaryl comprising at least one nitrogen or oxygen as a member of the ring; each R$^e$ is independently H or (C$_{1-4}$ alkyl); and each R$^f$ is independently H, hydroxy, or (C$_{1-4}$ alkyl).

In some embodiments, the compound is of Formula (I-B'), (II-B'), (I-b'), or (II-b'), or a prodrug, solvate, pharmaceutically acceptable salt, or tautomer thereof, wherein R$^{42}$ and R$^{41}$ are each independently H, halogen, hydroxy, amino, amino(C$_{1-4}$ alkyl)-, optionally substituted (C$_{1-6}$ alkyl), or optionally substituted (C$_{1-6}$ alkyl)oxy-, and the C$_{1-6}$ alkyl of said optionally substituted (C$_{1-6}$ alkyl), optionally substituted (C$_{1-6}$ alkyl)oxy- is optionally substituted with 1-4 substituents each independently selected from the group comprising hydroxyl, —N(R$^e$)(R$^f$), C$_{1-4}$ alkoxyl, phenyl, and optionally substituted 5-6 membered heteroaryl comprising at least one nitrogen or oxygen as a member of the ring; and R$^e$ and R$^f$ are each independently H or (C$_{1-4}$ alkyl).

In some embodiments, the compound is of Formula (I-B'), (II-B'), (I-b'), or (II-b'), or a prodrug, solvate, pharmaceutically acceptable salt, or tautomer thereof, wherein at least one of R$^{42}$ or R$^{41}$ is independently H, halogen, hydroxy, amino, amino(C$_{1-4}$ alkyl)-, optionally substituted (C$_{1-6}$ alkyl), or optionally substituted (C$_{1-6}$ alkyl)oxy-, and the C$_{1-6}$ alkyl of said optionally substituted (C$_{1-6}$ alkyl), optionally substituted (C$_{1-6}$ alkyl)oxy- is optionally substituted with 1-4 substituents each independently selected from —N(R$^e$)(R$^f$), tetrahydropyran, pyrrolidinyl, piperazinyl, piperidyl, and morpholinyl; each R$^e$ is independently selected from H, (C$_{1-4}$ alkyl), —(C$_{1-4}$ alkyl)-NH$_2$, and —(C$_{1-4}$ alkyl)-C$_{1-4}$ alkoxy; and each R$^f$ is independently H, hydroxy, or (C$_{1-4}$ alkyl).

In some embodiments, the compound is of Formula (I-B'), (II-B'), (I-b'), or (II-b'), or a prodrug, solvate, pharmaceutically acceptable salt, or tautomer thereof, wherein at least one of R$^{42}$ or R$^{41}$ is independently H, halogen, hydroxy, amino, amino(C$_{1-4}$ alkyl)-, optionally substituted (C$_{1-6}$ alkyl), or optionally substituted (C$_{1-6}$ alkyl)oxy-, and the C$_{1-6}$ alkyl of said optionally substituted (C$_{1-6}$ alkyl), optionally substituted ($C_{1-6}$ alkyl)oxy- is optionally substituted with 1-4 substituents each independently selected from —N($R^e$)($R^f$), tetrahydropyran, pyrrolidinyl, piperazinyl, piperidyl, and morpholinyl; each $R^e$ is independently H or ($C_{1-4}$ alkyl); and each $R^f$ is independently H, hydroxy, or ($C_{1-4}$ alkyl).

In some embodiments, the compound is of Formula (I-B'), (II-B'), (I-b'), or (II-b'), or a prodrug, solvate, pharmaceutically acceptable salt, or tautomer thereof, wherein at least one of $R^{A2}$ or $R^{A1}$ is independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from —N($R^e$)($R^f$), tetrahydropyran, pyrrolidinyl, piperazinyl, piperidyl, and morpholinyl; and $R^e$ and $R^f$ are each independently H or ($C_{1-4}$ alkyl).

In some embodiments, the compound is of Formula (I-B'), (II-B'), (I-b'), or (II-b'), or a prodrug, solvate, pharmaceutically acceptable salt, or tautomer thereof, wherein
  $Y_1$, $Y_2$, $Z_1$ and $Z_2$ are each independently O, S, C or N;
  $X_1$, $X_2$, $W_1$ and $W_2$ are each independently C or N;
  $X_3$ and $X_4$ are each independently S or N$R^f$;
  $X_5$ is N or C$R^{A2}$;
  $X_6$ is N or C$R^{A1}$;
  B is unsubstituted —$C_{1-6}$ alkyl, or unsubstituted —$C_{2-5}$ alkenyl-;
  $R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-,
  wherein $C_{1-6}$ alkyl of said optionally substituted ($C_{1-6}$ alkyl), or optionally substituted ($C_{1-6}$ alkyl)oxy- is optionally substituted with 1-2 substituents each independently selected from the group comprising hydroxyl, $C_{1-4}$ alkoxyl, —N($R^e$)($R^f$), —CO$_2$($R^f$), unsubstituted phenyl, and unsubstituted 5-6 membered heteroaryl;
  $R^e$ is H, ($C_{1-4}$ alkyl), —CO($C_{1-4}$ alkyl), —OCO($C_{1-4}$ alkyl), or —CO$_2$($C_{1-4}$ alkyl);
  each occurrence of $R^f$ is H, hydroxy, or ($C_{1-4}$ alkyl);
  $R^{14}$ and $R^{C2}$ are each independently absent or $C_{1-4}$ alkyl, wherein $C_{1-4}$ alkyl is optionally substituted by a substituent selected from halogen, —OR$^c$, —NR$^c$R$^d$, —CONR$^c$R$^d$, —SO$_2$NR$^c$R$^d$, and —OCONR$^c$R$^d$; $R^{16}$ and $R^{C1}$ are each independently absent, H or $C_{1-4}$ alkyl; and
  $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —OR$^c$, —NR$^c$R$^d$, —CONR$^c$R$^d$, —SO$_2$NR$^c$R$^d$, and —OCONR$^c$R$^d$;
provided that at least one of (i), (ii), or (iii) applies:
  (i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or
  (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —NR$^c$R$^d$, —CO$_2$R$^c$, —CONR$^c$R$^d$, —SO$_2$NR$^c$R$^d$, and —OCONR$^c$R$^d$ wherein $R^c$ is H; or
  (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-,
  wherein $C_{1-6}$ alkyl of said optionally substituted ($C_{1-6}$ alkyl) or substituted ($C_{1-6}$ alkyl)oxy- is optionally substituted with 1-2 substituents each independently selected from the group comprising hydroxyl, $C_{1-4}$ alkoxyl, —N($R^e$)($R^f$), —CO$_2$($R^f$), unsubstituted phenyl, and unsubstituted membered heterocycloalkyl.

In some embodiments, the compound is of Formula (I-b'), or a prodrug, solvate, pharmaceutically acceptable salt, or tautomer thereof, wherein
  $Y_1$, $Y_2$, $Z_1$ and $Z_2$ are each independently O, S, C or N;
  $X_1$, $X_2$, $W_1$ and $W_2$ are each independently C or N;
  $X_3$, $X_4$, $X_5$, $X_6$, and $X_9$ are each independently as defined in Formula (IA');
  B is unsubstituted —$C_{2-5}$ alkenyl-;
  $R^{A2}$ and $R^{A1}$ are each independently H, hydroxy, optionally substituted ($C_{1-6}$ alkyl), optionally substituted ($C_{1-6}$ alkyl)oxy-, amino or amino($C_{1-4}$ alkyl)-,
  wherein $C_{1-6}$ alkyl of said optionally substituted ($C_{1-6}$ alkyl), or optionally substituted ($C_{1-6}$ alkyl)oxy- is optionally substituted with 1 substituents each independently selected from the group comprising hydroxyl, $C_{1-4}$ alkoxyl, and unsubstituted 5-6 membered heteroaryl,
  $R^{14}$ and $R^{C2}$ are each independently absent or $C_{1-4}$ alkyl, wherein $C_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;
  $R^{16}$ and $R^{C1}$ are each independently absent, H or $C_{1-4}$ alkyl;
  $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;
provided that at least one of (i), (ii), or (iii) applies:
  (i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or
  (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —NR$^c$R$^d$, —CO$_2$R$^c$, —CONR$^c$R$^d$, —SO$_2$NR$^c$R$^d$, and —OCONR$^c$R$^d$ wherein $R^c$ is H; or
  (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein $C_{1-6}$ alkyl of said optionally substituted ($C_{1-6}$ alkyl) or substituted ($C_{1-6}$ alkyl)oxy- is optionally substituted with 1 substituents each independently selected from the group comprising hydroxyl, $C_{1-4}$ alkoxyl, and unsubstituted 5-6 membered heteroaryl.

In some embodiments, the compound is of Formula (I-b'), or a prodrug, solvate, pharmaceutically acceptable salt, or tautomer thereof, wherein $Y_1$, $Y_2$, $Z_1$ and $Z_2$ are each independently O, S, C or N;

$X_1$, $X_2$, $W_1$ and $W_2$ are each independently C or N;

$X_3$, $X_4$, $X_5$, $X_6$, and $X_9$ are each independently as defined in Formula (IA');

B is unsubstituted ethenyl;

$R^{A2}$ and $R^{A1}$ are each independently H, hydroxy, amino, amino($C_{1-4}$ alkyl)-, or optionally substituted ($C_{1-6}$ alkyl)oxy-, wherein $C_{1-6}$ alkyl of said optionally substituted ($C_{1-6}$ alkyl)oxy- is optionally substituted with hydroxyl;

$R^{14}$ and $R^{C2}$ are each independently absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$; $R^{16}$ and $R^{C1}$ are each independently absent, H or $C_{1-4}$ alkyl; and $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;

provided that at least one of (i), (ii), or (iii) applies:

(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —$NR^cR^d$, —$CO_2R^c$, —$CONR^cR^d$, —$SO_2NR^cR^d$, and —$OCONR^cR^d$ wherein $R^c$ is H; or (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A2}$ and $R^{A1}$ are each independently H, hydroxy, amino, amino($C_{1-4}$ alkyl)-, or optionally substituted ($C_{1-6}$ alkyl)oxy-, wherein $C_{1-6}$ alkyl of said optionally substituted ($C_{1-6}$ alkyl)oxy- is optionally substituted with hydroxyl.

In some embodiments, the compound is of Formula (I-bd'):

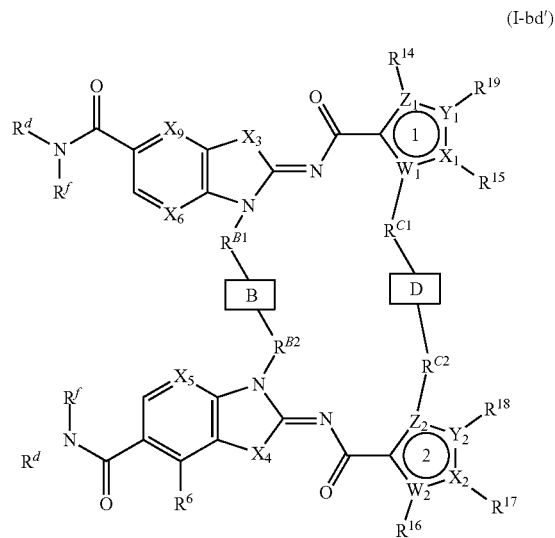

(I-bd')

or a prodrug, solvate, pharmaceutically acceptable salt, or tautomer thereof, wherein:

$Y_1$, $Y_2$, $Z_1$ and $Z_2$ are each independently O, S, C or N;

$X_1$, $X_2$, $W_1$ and $W_2$ are each independently C or N;

$X_6$ is N or $CR^{A1}$;

$X_9$ is N or $CR^4$;

$X_3$, $X_4$, $X_9$, $R^d$, and $R^f$ are each independently as defined herein;

$R^{C1}$ and $R^{C2}$ are each independently —$CH_2$—,

D is -halo($C_{1-5}$ alkyl), unsubstituted —$C_{1-5}$ alkyl, or unsubstituted —$C_{1-5}$ alkenyl-;

$R^{B1}$ and $R^{B2}$ are each independently —$CH_2$—;

B is -halo($C_{1-5}$ alkyl), unsubstituted —$C_{1-5}$ alkyl, or unsubstituted —$C_{1-5}$ alkenyl-;

$R^{A2}$ and $R^{A1}$ are each independently H, halogen, amino, amino($C_{1-4}$ hydroxy, —O—P(O)(OH)$_2$, —O—P(O)($R^IR^{II}$)$_2$, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, —O—P(O)(OH)$_2$, —O—P(O)($R^IR^{II}$)$_2$, $C_{1-4}$ alkoxyl, —N($R^e$)($R^f$), —$CO_2(R^f)$, optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alky)amino-, ($C_{1-6}$ alkyl)($C_{1-6}$ alkyl)amino-, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{1-4}$ alkoxy)-O—P(O)($R^IR^{II}$)$_2$, —($C_{1-6}$ alkyl)-NH$_2$, and $C_{1-4}$ alkoxy-($C_{1-4}$ alkoxy)-;

$R^e$ is selected from H, ($C_{1-4}$ alkyl), —CO($C_{1-4}$ alkyl), —OCO($C_{1-4}$ alkyl), —($C_{1-4}$ alkyl)-NH$_2$, —($C_{1-4}$ alkyl)-$C_{1-4}$ alkoxy, and —$CO_2(C_{1-4}$ alkyl);

$R^4$ and $R^6$ is H;

83

$R^{14}$ is absent or $C_{1-4}$ alkyl, wherein $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$;

$R^{16}$ is absent, H or $C_{1-4}$ alkyl;

$R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CONR^cR^d$, —$SO_2NR^cR^d$, and —$OCONR^cR^d$; and each $R^I$ and $R^{II}$ are independently ($C_{1-6}$ alkyl)oxy-, provided that at least one of (i), (ii), or (iii) applies:

(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or (ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then $R^{14}$ is a $C_{1-4}$ alkyl substituted with halogen, —$NR^cR^d$, —$CO_2R^c$, —$CONR^cR^d$, —$SO_2NR^cR^d$, and —$OCONR^cR^d$ wherein $R^c$ is H; or (iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein the ($C_{1-6}$ alkyl) of said optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino- is optionally substituted by 1-4 substituents each independently selected from hydroxy, —O—P(O)(OH)$_2$, —O—P(O)($R^IR^{II}$)$_2$, —N($R^e$)($R^f$), —$CO_2(R^f)$, —$CON(R^e)(R^f)$, optionally substituted phenyl, and optionally substituted 5-6 membered heteroaryl group, wherein said optionally substituted phenyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, ($C_{1-6}$ alkyl)amino-, ($C_{1-6}$ alkyl)($C_{1-6}$ alkyl)amino-, —($C_{1-6}$ alkyl)-NH$_2$, halo($C_{1-6}$ alkyl), hydroxy-($C_{1-4}$ alkyl)-, —($C_{1-4}$ alkyl)-O—P(O)(OH)$_2$, —($C_{1-4}$ alkyl)-O—P(O)($R^IR^{II}$)$_2$, halo($C_{1-4}$ alkoxy)-, $C_{1-4}$ alkoxy-, hydroxy-($C_{2-4}$ alkoxy)-, —($C_{2-4}$ alkoxy)-O—P(O)(OH)$_2$, —($C_{2-4}$ alkoxy)-O—P(O)($R^IR^{II}$)$_2$, —$C_{1-4}$ alkyl-($C_{1-4}$ alkoxy), and $C_{1-4}$ alkoxy-($C_{1-4}$ alkoxy)-.

84

In some embodiments, the compound is of Formula (I-bd')

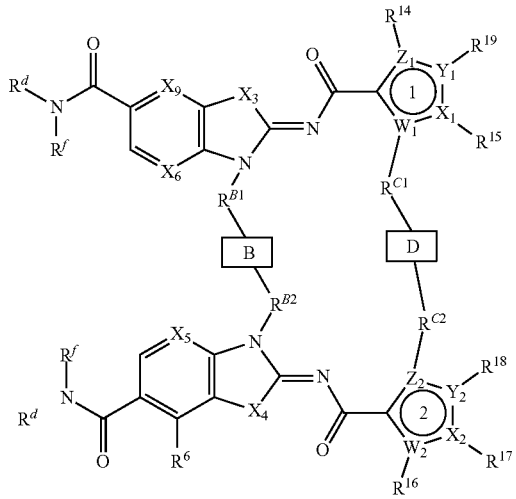

(I-bd')

or a prodrug, solvate, pharmaceutically acceptable salt, or tautomer thereof, wherein:

$Y_1$, $Y_2$, $Z_1$ and $Z_2$ are each independently O, S, C or N;
$X_1$, $X_2$, $W_1$ and $W_2$ are each independently C or N;
$X_5$ is N or $CR^{A2}$;
$X_6$ is N or $CR^{A1}$;
$X_3$, $X_4$, $X_9$, $R^d$, and $R^f$ are each independently as defined in Formula (IA);
$R^{C1}$ and $R^{C2}$ are each independently —$CH_2$—;
D is -halo($C_{1-5}$ alkyl), unsubstituted —$C_{1-5}$ alkyl, or unsubstituted —$C_{2-5}$ alkenyl-;
$R^{B1}$ and $R^{B2}$ are each independently —$CH_2$—;
B is -halo($C_{1-5}$ alkyl), unsubstituted —$C_{1-5}$ alkyl, or unsubstituted —$C_{2-5}$ alkenyl-;
$R^{A2}$ and $R^{A1}$ are each independently H, halogen, amino, amino($C_{1-4}$ alkyl)-, hydroxyl, optionally substituted ($C_{1-6}$ alkyl), or optionally substituted ($C_{1-6}$ alkyl)oxy-,
wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, $C_{1-4}$ alkoxyl, —N($R^e$)($R^f$), —$CO_2(R^f)$, optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, amino, ($C_{1-6}$ alkyl)amino-, ($C_{1-6}$ alkyl)($C_{1-6}$ alkyl)amino-, halo ($C_{1-6}$ alkyl), hydroxy-($C_{1-4}$ alkyl)-, halo($C_{1-4}$ alkoxy)-, $C_{1-4}$ alkoxy-, hydroxy-($C_{2-4}$ alkoxy) and $C_{1-4}$ alkoxy-($C_{1-4}$ alkoxy)-;
$R^e$ is selected from H, ($C_{1-4}$ alkyl), —$CO(C_{1-4}$ alkyl), —$OCO(C_{1-4}$ alkyl), and —$CO_2(C_{1-4}$ alkyl);
$R^4$ and $R^6$ are H;
$R^{14}$ is absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;
$R^{16}$ is independently absent, H or $C_{1-4}$ alkyl; and
$R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;

provided that at least one of (i), (ii), or (iii) applies:
(i) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C; or (c) $Z_1$ and $Y_1$ are each N, $W_1$ and $X_1$ are each C; or (d) $Z_2$ and $Y_2$ are each N, $W_2$ and $X_2$ are each C; or (e) $W_1$ and $X_1$ are each N, $Z_1$ and $Y_1$ are each C; or (f) $W_2$ and $X_2$ are each N, $Z_2$ and $Y_2$ are each C, then at least one of $X_3$ and $X_4$ is S; or $X_9$ is N; or
(ii) when (a) $Z_1$, $Z_2$, $Y_1$ and $Y_2$ are each N, $W_1$, $W_2$, $X_1$ and $X_2$ are each C; or (b) $W_1$, $W_2$, $X_1$ and $X_2$ are each N, $Z_1$, $Z_2$, $Y_1$ and $Y_2$ are each C, then R" is a $C_{1-4}$ alkyl substituted with halogen, —$NR^cR^d$, —$CO_2R^c$, —$CONR^cR^d$, —$SO_2NR^cR^d$, and —$OCONR^cR^d$ wherein $R^c$ is H; or
(iii) when (a) $Z_1$ and $Y_1$ are each N, $W_1$ and $X_1$ are each C; or (b) $Z_2$ and $Y_2$ are each N, $W_2$ and $X_2$ are each C; or (c) $W_1$ and $X_1$ are each N, $Z_1$ and $Y_1$ are each C; or (d) $W_2$ and $X_2$ are each N, $Z_2$ and $Y_2$ are each C, then at least one of $X_5$, $X_6$, and $X_9$ is N and $R^{A1}$ or $R^{A2}$ is halogen, hydroxy, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-,
wherein $C_{1-6}$ alkyl of said optionally substituted ($C_{1-6}$ alkyl) or substituted ($C_{1-6}$ alkyl)oxy- is optionally substituted with 1-4 substituents each independently selected from the group comprising hydroxyl, $C_{1-4}$ alkoxyl, —$N(R^e)(R^f)$, —$CO_2(R^f)$, optionally substituted phenyl, and optionally substituted 5-6 membered heteroaryl; wherein said optionally substituted phenyl, or 5-6 membered heteroaryl is optionally substituted by 1-4 substituents each independently selected from halogen, hydroxy, amino, ($C_{1-6}$ alkyl)amino-, ($C_{1-6}$ alkyl)($C_{1-6}$ alkyl)amino-, halo($C_{1-6}$ alkyl), hydroxy-($C_{1-4}$ alkyl)-, halo($C_{1-4}$ alkoxy)-, $C_{1-4}$ alkoxy-, hydroxy-($C_{2-4}$ alkoxy) and $C_{1-4}$ alkoxy-($C_{1-4}$ alkoxy)-.

In some embodiments, the compound is of Formula (I-bd'), or a prodrug, solvate, pharmaceutically acceptable salt, or tautomer thereof, wherein $X_9$ is $CR^4$.

In some embodiments, the compound is of Formula (I-bd'), or a prodrug, solvate, pharmaceutically acceptable salt, or tautomer thereof, wherein $R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from the group comprising hydroxyl, —O—$P(O)(OH)_2$, —O—$P(O)(R^IR^H)_2$, —$N(R^e)$ ($R^f$), $C_{1-4}$ alkoxyl, phenyl, and optionally substituted 5-6 membered heteroaryl comprising at least one nitrogen or oxygen as a member of the ring;

each $R^e$ is independently selected from H, —($C_{1-4}$ alkyl)-$NH_2$, and —($C_{1-4}$ alkyl)-$C_{1-4}$ alkoxy; and
each $R^f$ is independently H, hydroxy, or $C_{1-4}$ alkyl.

In some embodiments, the compound is of Formula (I-bd'), or a prodrug, solvate, pharmaceutically acceptable salt, or tautomer thereof, wherein $R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from the group comprising hydroxyl, —$N(R^e)(R^f)$, $C_{1-4}$ alkoxyl, phenyl, and optionally substituted 5-6 membered heteroaryl comprising at least one nitrogen or oxygen as a member of the ring; each $R^e$ is independently H or ($C_{1-4}$ alkyl); and each $R^f$ is independently H, hydroxy, or ($C_{1-4}$ alkyl).

In some embodiments, the compound is of Formula (I-bd'), or a prodrug, solvate, pharmaceutically acceptable salt, or tautomer thereof, wherein $R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from the group comprising hydroxyl, —$N(R^e)(R^f)$, $C_{1-4}$ alkoxyl, phenyl, and optionally substituted 5-6 membered heteroaryl comprising at least one nitrogen or oxygen as a member of the ring; and $R^e$ and $R^f$ are each independently H or ($C_{1-4}$ alkyl).

In some embodiments, the compound is of Formula (I-bd'), or a prodrug, solvate, pharmaceutically acceptable salt, or tautomer thereof, wherein at least one of $R^{A2}$ or $R^{A1}$ is independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from —$N(R^e)(R^f)$, tetrahydropyran, pyrrolidinyl, piperazinyl, piperidyl, and morpholinyl; each $R^e$ is independently selected from H, ($C_{1-4}$ alkyl), —($C_{1-4}$ alkyl)-$NH_2$, and —($C_{1-4}$ alkyl)$C_{1-4}$ alkoxy; and each $R^f$ is independently H, hydroxy, or ($C_{1-4}$ alkyl).

In some embodiments, the compound is of Formula (I-bd'), or a prodrug, solvate, pharmaceutically acceptable salt, or tautomer thereof, wherein at least one of $R^{A2}$ or $R^{A1}$ is independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from —$N(R^e)(R^f)$, tetrahydropyran, pyrrolidinyl, piperazinyl, piperidyl, and morpholinyl; each $R^e$ is independently H or ($C_{1-4}$ alkyl); and each $R^f$ is independently H, hydroxy, or ($C_{1-4}$ alkyl).

In some embodiments, the compound is of Formula (I-bd'), or a prodrug, solvate, pharmaceutically acceptable salt, or tautomer thereof, wherein at least one of $R^{A2}$ or $R^{A1}$ is independently H, halogen, hydroxy, amino, amino($C_{1-4}$ alkyl)-, optionally substituted ($C_{1-6}$ alkyl), or optionally substituted ($C_{1-6}$ alkyl)oxy-, and the $C_{1-6}$ alkyl of said optionally substituted ($C_{1-6}$ alkyl), optionally substituted ($C_{1-6}$ alkyl)oxy- is optionally substituted with 1-4 substituents each independently selected from —$N(R^e)(R^f)$, tetrahydropyran, pyrrolidinyl, piperazinyl, piperidyl, and morpholinyl; and $R^e$ and $R^f$ are each independently H or ($C_{1-4}$ alkyl).

In some embodiments, the compound of Formula (V') is a compound of Formula (V-a), (V-b), (V-c), (V-d), (V-e), (V-e1), (V-e2), (V-f), (V-f1), (V-f2), (V-f3), (V-f4), (V-f5), (V-f6), (V-f7), (V-g), (V-g1), (V-g2), (V-g3), (V-g4), (V-g5), (V-g6), (V-g7), (V-h), (V-h1), (V-h2), (V-h3), (V-h4), (V-h5), (V-h6), (V-h7), (V-i), (V-i1), (V-i2), (V-i3), (V-i4), (V-i5), (V-i6), or (V-i7).

In some embodiments, the compound is of Formula (V'), wherein the compound is Formula (V-a), Formula (V-b), Formula (V-c), Formula (V-d), Formula (V-e), Formula (V-e1), or Formula (V-e2):

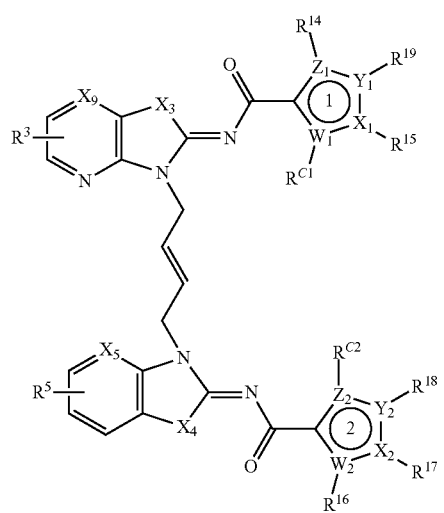
(V-a)
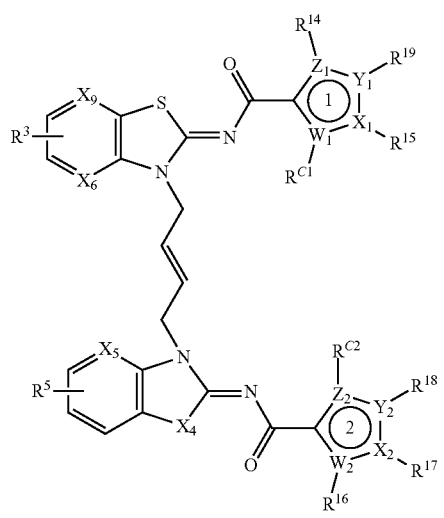
(V-b)
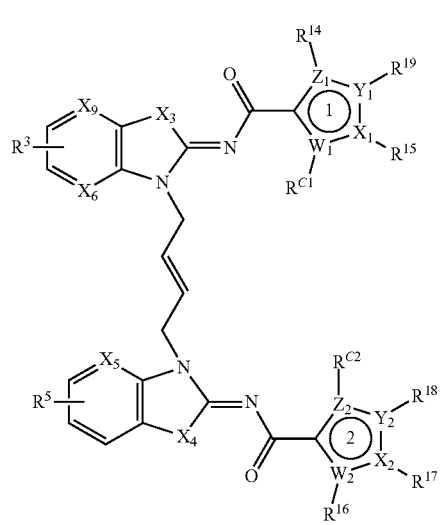
(V-c)
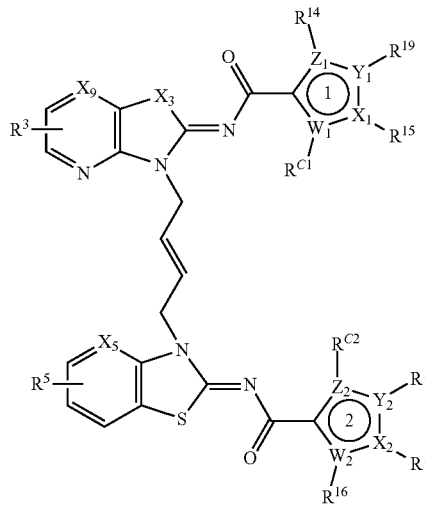
(V-d)
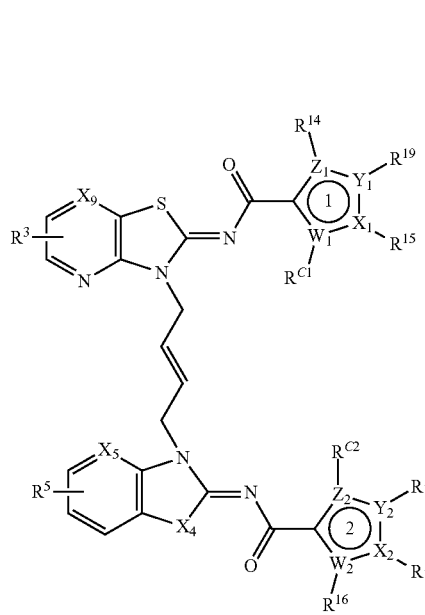
(V-e)
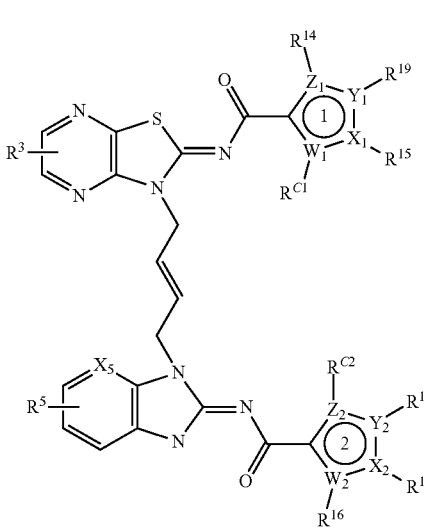
(V-e1)

(V-e2)

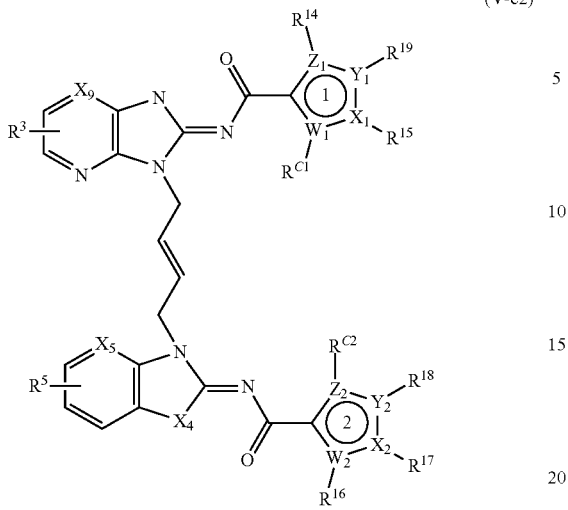

(V-f1)

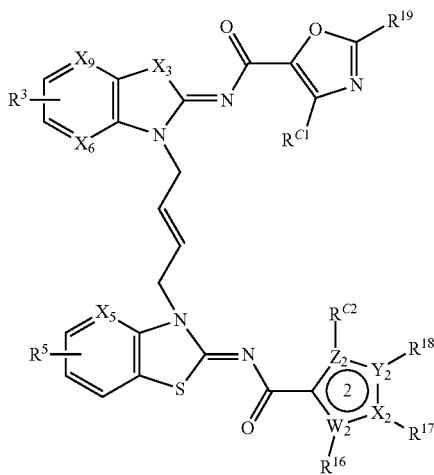

or a prodrug, solvate, pharmaceutically acceptable salt, or tautomer thereof, wherein:

$Y_1$, $Y_2$, $Z_1$, $Z_2$, $X_1$, $X_2$, $W_1$, $W_2$, $X_5$, $X_6$, $X_9$, $X_3$, $X_4$, $R^{C1}$, $R^{C2}$, $R^3$, $R^5$, $R^{14}$, $R^{16}$, $R^{15}$, $R^{17}$, $R^{18}$, $R^{19}$, $R^e$, and $R^f$ are each independently as defined in Formula (V'); and $R^{42}$ and $R^{41}$ when present, are each independently halogen, hydroxyl, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein $C_{1-6}$ alkyl of said optionally substituted ($C_{1-6}$ alkyl) or substituted ($C_{1-6}$ alkyl)oxy- is optionally substituted with 1-4 substituents each independently selected from the group comprising hydroxyl, $C_{1-4}$ alkoxyl, —N($R^e$)($R^f$), —$CO_2$($R^f$), —CON($R^e$)($R^f$), and —COOH.

In some embodiments, the compound is of Formula (V-a), Formula (V-b), Formula (V-c), Formula (V-d), Formula (V-e), or Formula (V-e2), wherein $X_9$ is CH.

In some embodiments, the compound is of Formula (V'), wherein the compound is Formula (V-f), Formula (V-f1), Formula (V-f2), Formula (V-f3), Formula (V-f4), Formula (V-f5), Formula (V-f6), or Formula (V-f7):

(V-f)

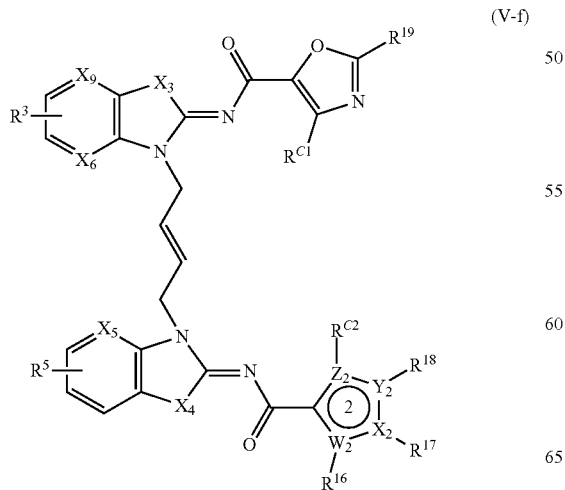

(V-f3)

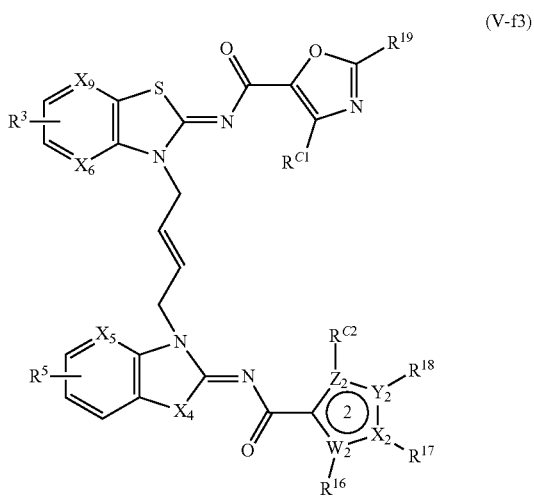

-continued

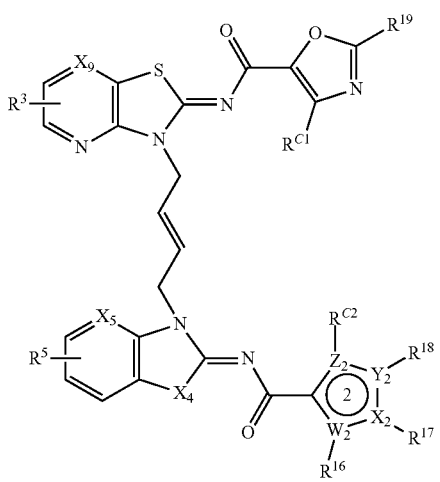

(V-f4)

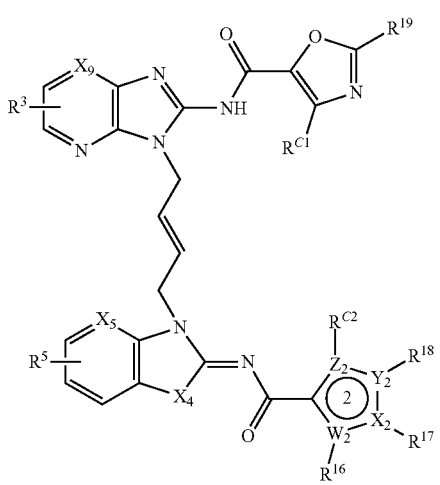

(V-f5)

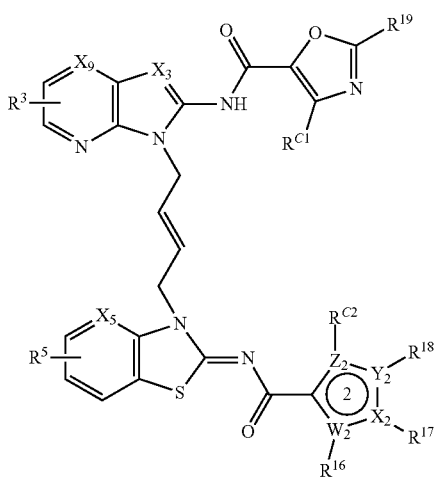

(V-f6)

-continued

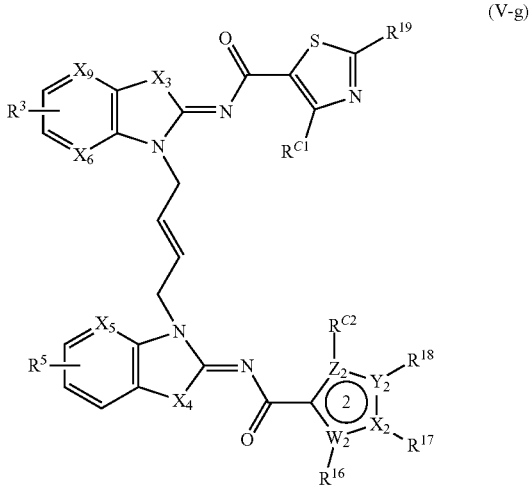

(V-f7)

or a prodrug, solvate, pharmaceutically acceptable salt, or tautomer thereof, wherein:

$Y_2$ and $Z_2$ are each independently O, S, C or N;

$X_2$ and $W_2$ are each independently C or N;

$X_3$, $X_4$, $X_5$, $X_6$, $X_9$, $R^{16}$, $R^{C1}$, $R^c$, $R^3$, $R^5$, $R^{17}$, $R^{18}$, $R^{19}$, and $R^d$, are each independently as defined in Formula (V'); and $R^{C2}$ are each independently absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$CONR^cR^d$.

In some embodiments, the compound is of Formula (V-f), Formula (V-f1), Formula (V-f2), Formula (V-f3), Formula (V-f4), Formula (V-f5), or Formula (V-f6), wherein $X_9$ is CH.

In some embodiments, the compound is of Formula (V'), wherein the compound is Formula (V-g), Formula (V-g1), Formula (V-g2), Formula (V-g3), Formula (V-g4), Formula (V-g5), Formula (V-g6), or Formula (V-f7):

(V-g)

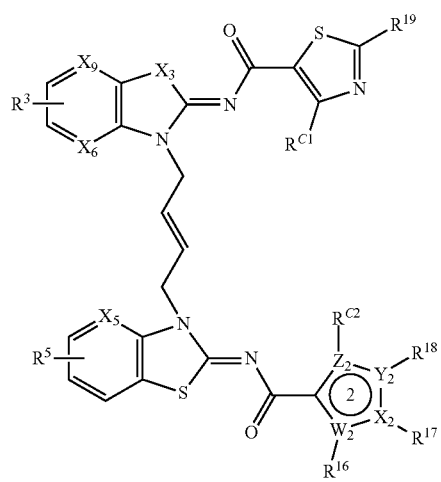
(V-g1)
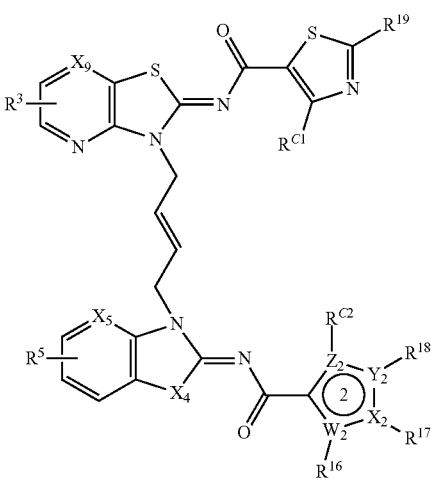
(V-g4)
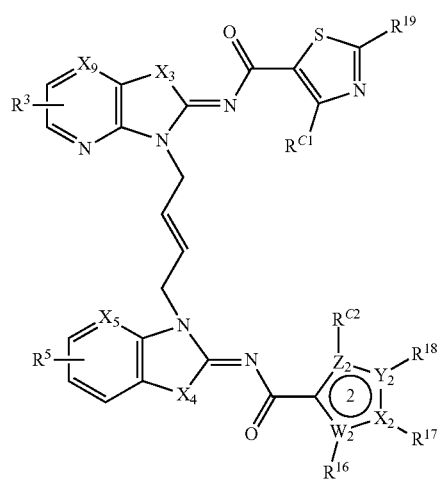
(V-g2)
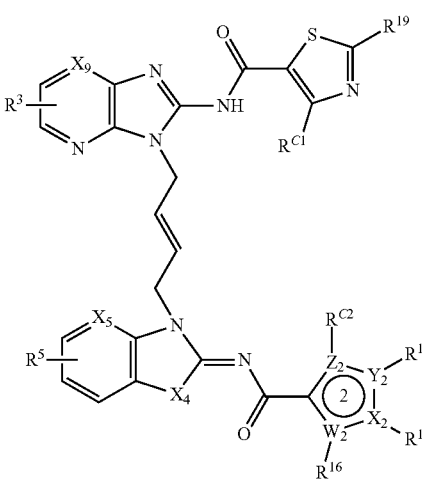
(V-g5)
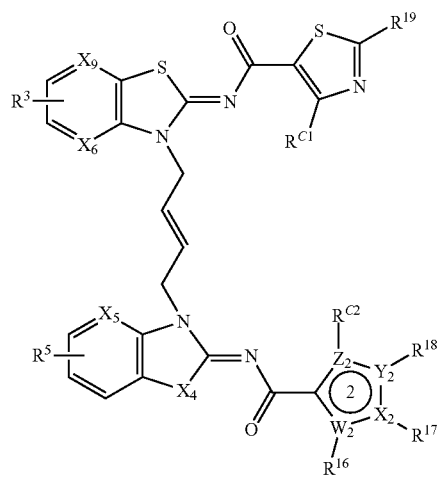
(V-g3)
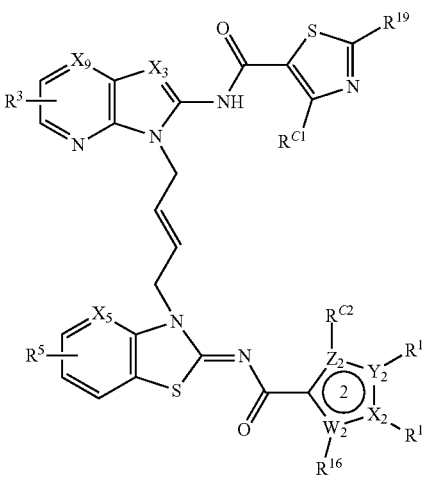
(V-g6)

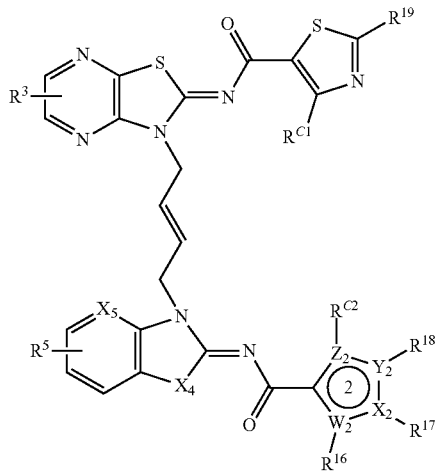

(V-g7)

or a prodrug, solvate, pharmaceutically acceptable salt, or tautomer thereof, wherein:

$Y_2$ and $Z_2$ are each independently O, S, C or N;

$X_2$ and $W_2$ are each independently C or N;

$X_3$, $X_4$, $X_5$, $X_6$, $X_9$, $R^c$, $R^{C1}$, $R^3$, $R^5$, $R^{16}$, $R^{17}$, $R^{18}$, $R^{19}$, and $R^d$, are each independently as defined in Formula (V'); and $R^{C2}$ is absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, the compound is of Formula (V-g), Formula (V-g1), Formula (V-g2), Formula (V-g3), Formula (V-g4), Formula (V-g5), or Formula (V-g6), wherein $X_9$ is CH.

In some embodiments, the compound is of Formula (V'), wherein the compound is Formula (V-h), Formula (V-h1), Formula (V-h2), Formula (V-h3), Formula (V-h4), Formula (V-h5). (Formula (V-h6), or Formula (V-h7):

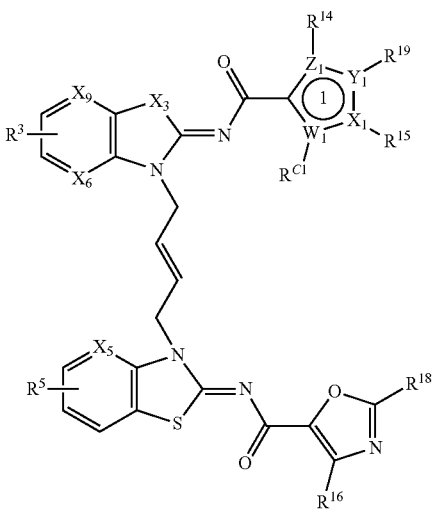

-continued

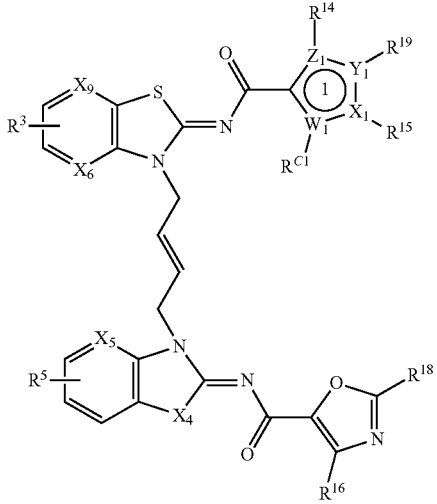
(V-h4)

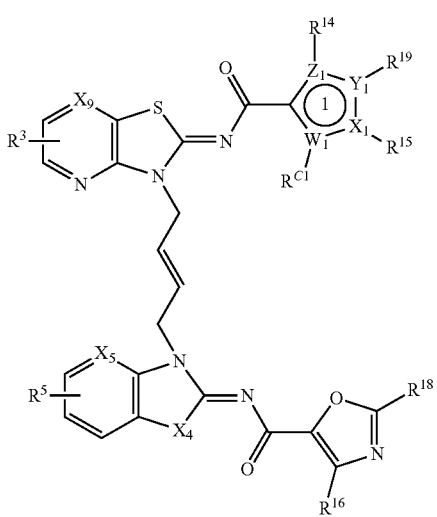
(V-h5)

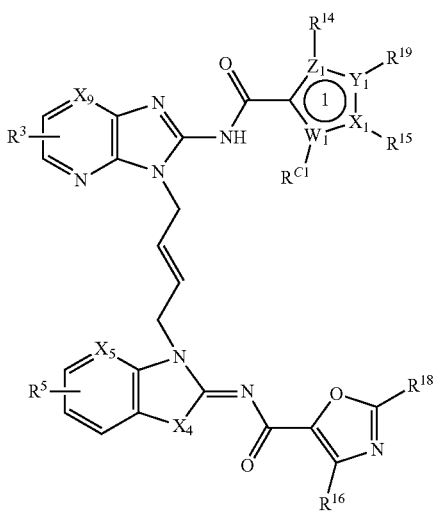
(V-h6)

-continued

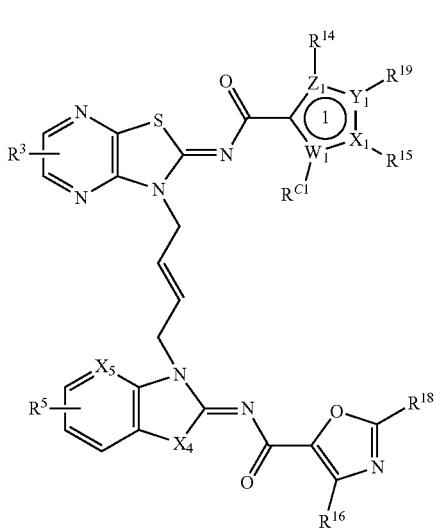
(V-h7)

or a prodrug, solvate, pharmaceutically acceptable salt, or tautomer thereof, wherein:

$Y_1$ and $Z_1$ are each independently O, S, C or N;

$X_1$ and $W_1$ are each independently C or N;

$X_5$, $X_6$, $X_9$, $X_3$, $X_4$, $R^c$, $R^3$, $R^5$, $R^{16}$, $R^{15}$, $R^{18}$, $R^{19}$, $R^{C1}$ and $R^d$ are each independently as defined in Formula (V'); and $R^{14}$ is absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$.

In some embodiments, the compound is of Formula (V-h), Formula (V-h1), Formula (V-h2), Formula (V-h3), Formula (V-h4), Formula (V-h5), or (Formula (V-h6), wherein $X_9$ is CH.

In some embodiments, the compound is of Formula (V'), wherein the compound is Formula (V-i), Formula (V-i1), Formula (V-i2), Formula (V-i3), Formula (V-i4), Formula (V-i5), (Formula (V-i6), or Formula (V-i7):

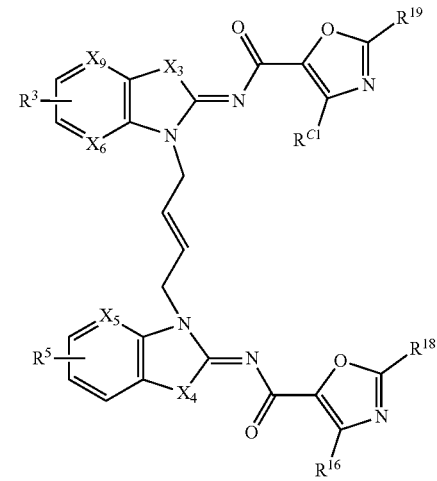
(V-i)

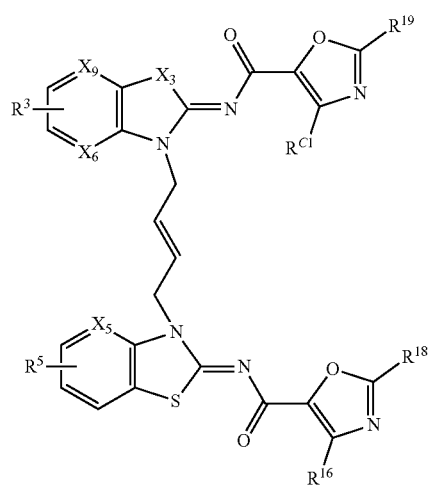
(V-i1)
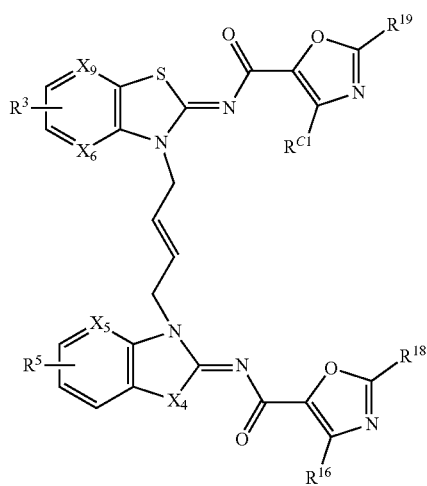
(V-i4)
(V-i2)
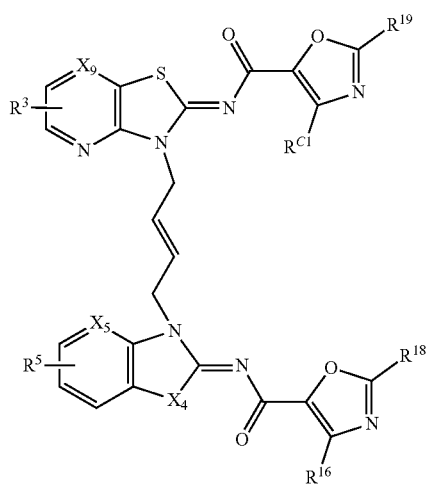
(V-i5)
(V-i3)
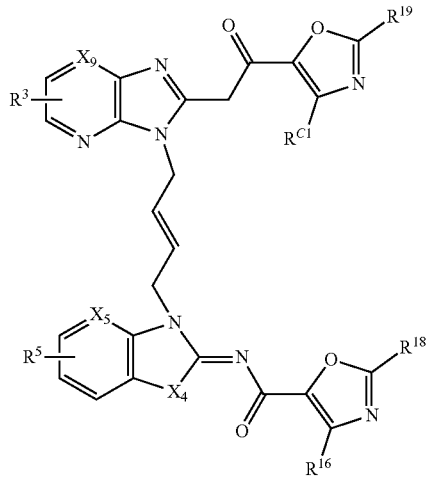
(V-i6)

-continued

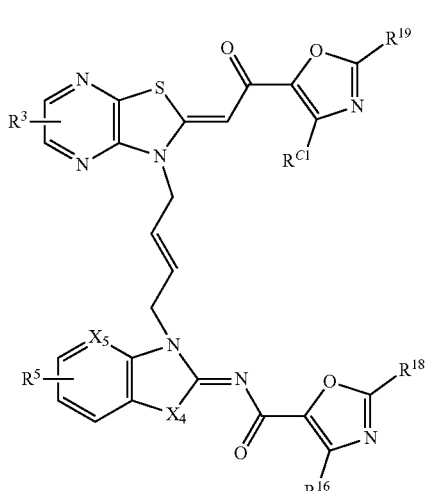

(V-i7)

or a prodrug, solvate, pharmaceutically acceptable salt, or tautomer thereof, wherein:

$X_9$, $X_3$, $X_4$, $X_5$, $X_6$, $R^3$, $R^5$, $R^{16}$, $R^{18}$, $R^{19}$, and $R^{C1}$ are each independently as defined in Formula (V').

In some embodiments, the compound is of Formula (V-i), Formula (V-i1), Formula (V-i2), Formula (V-i3), Formula (V-i4), Formula (V-i5), or Formula (V-i6), wherein $X_9$ is CH.

In some embodiments, when the compound of Formula (V') is Formula (V-c), Formula (V-f), Formula (V-g), Formula (V-h), Formula or (V-i), at least one of $X_3$ and $X_4$ is S or at least one of $X_5$, $X_6$ and $X_9$ is N.

In some embodiments, when s is 0 and r is 1, then at least one of $X_3$ and $X_4$ is S or at least one of $X_5$, $X_6$ and $X_9$ is N.

In some embodiments, at least one of $X_3$ and $X_4$ is S or at least one of $X_5$, $X_6$ and $X_9$ is N.

In some embodiments, at least one of $X_3$ and $X_4$ is S.

In some embodiments, at least one of $X_5$, $X_6$ and $X_9$ is N.

In some embodiments, $X_5$, $X_6$, and $X_9$ are each CH and $X_3$ and $X_4$ are each N.

In some embodiments, $X_5$, $X_6$, and $X_9$ are each CH; $X_3$ is S; and $X_4$ is N.

In some embodiments $X_5$ and $X_9$ are each CH and $X_6$, $X_3$, and $X_4$ are each N.

In some embodiments, $X_5$ and $X_9$ are each CH; $X_6$ and $X_4$ are each N; and $X_3$ is S.

In some embodiments, $X_5$ and $X_9$ are each CH; $X_6$ and $X_3$ are each N; and $X_4$ is S.

In some embodiments, $X_5$ is CH; $X_6$, $X_4$, and $X_9$ are each N; and $X_3$ is S.

In some embodiments, the compound of the disclosure is not selected from:

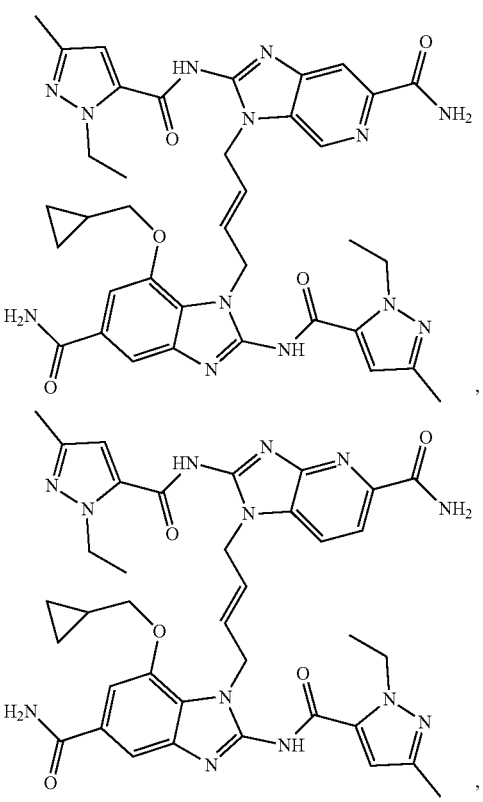

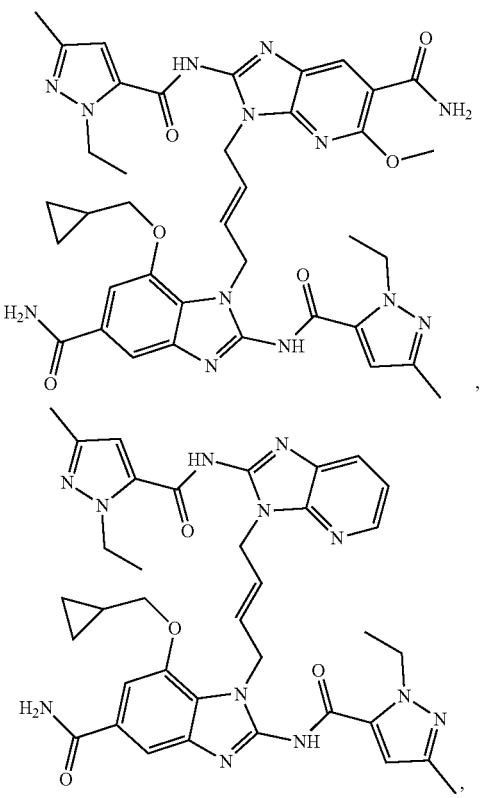

103
-continued
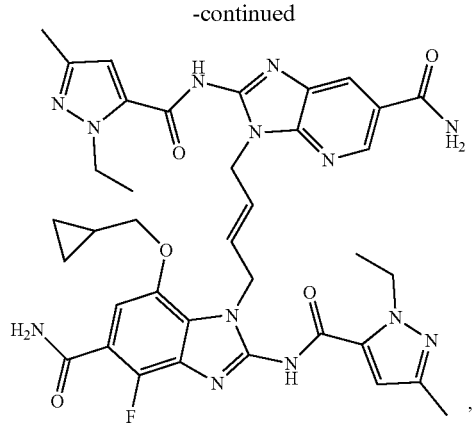
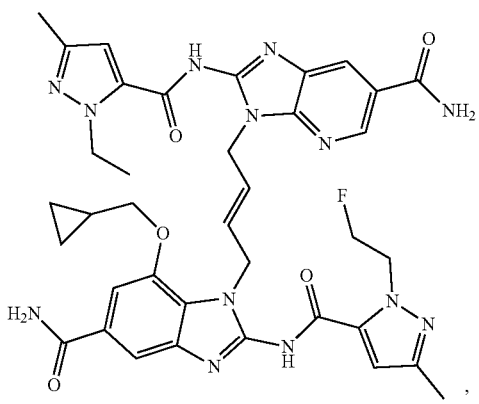
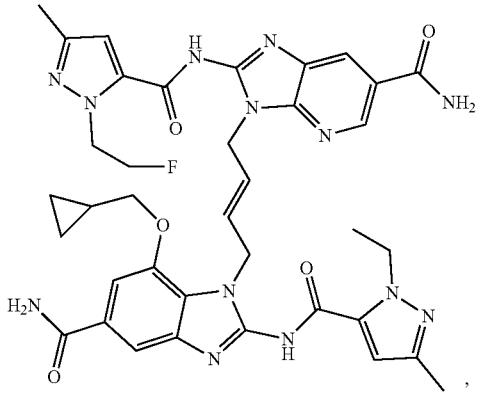
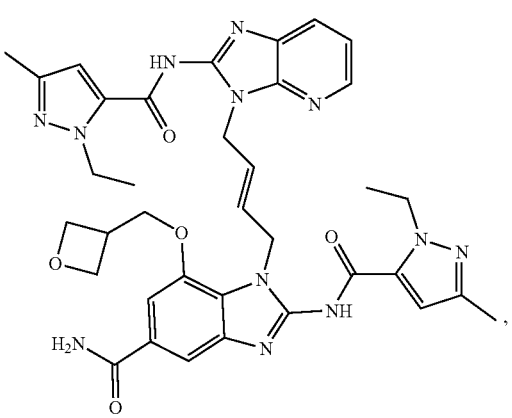
104
-continued
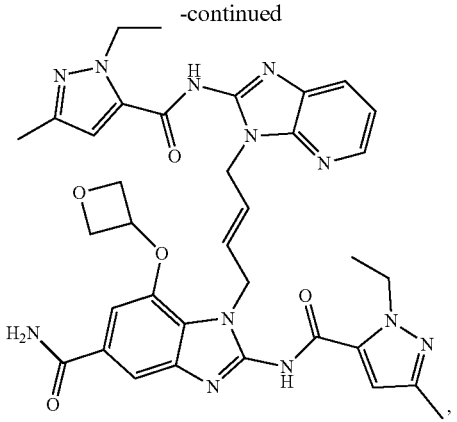
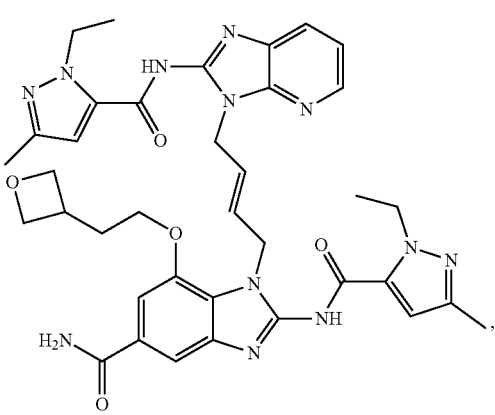
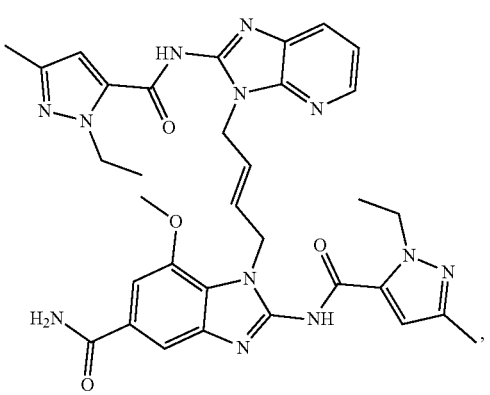
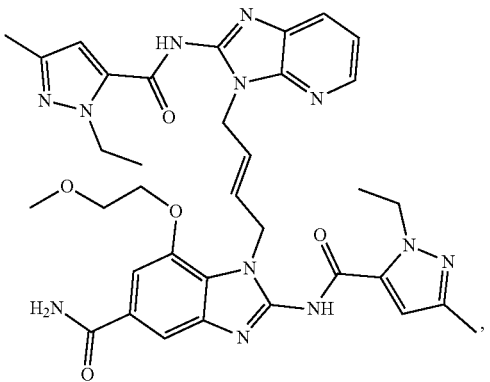

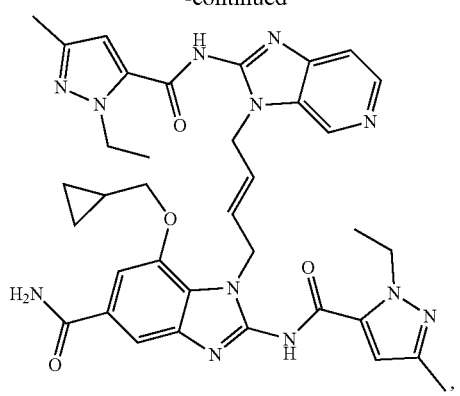
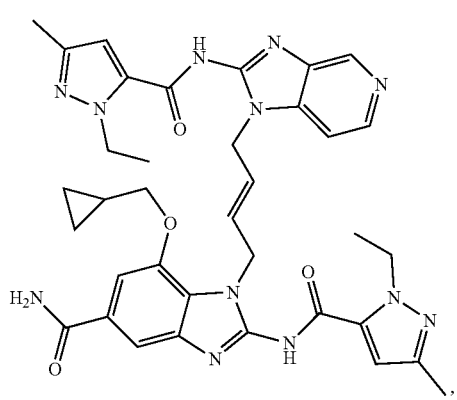
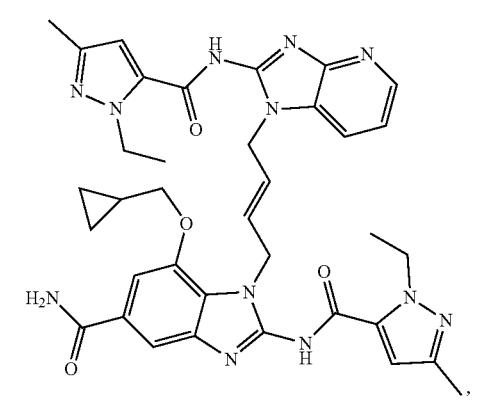
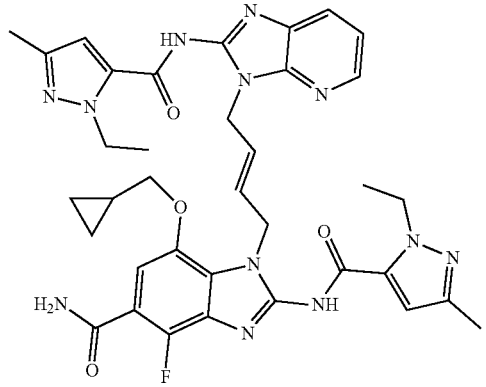
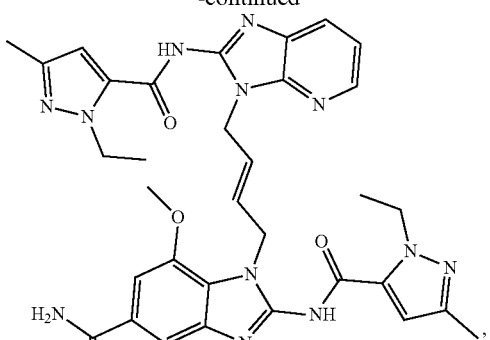
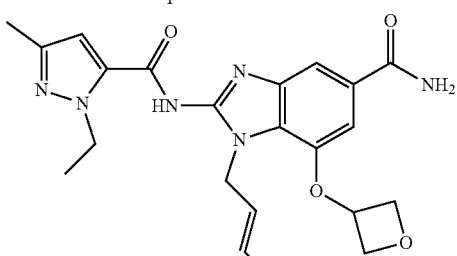
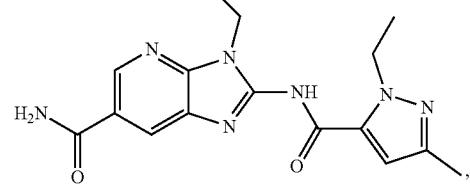
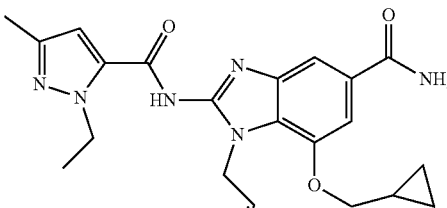
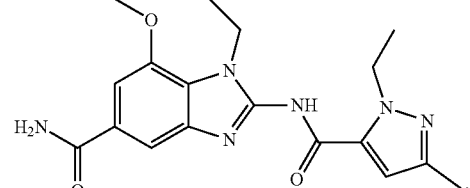
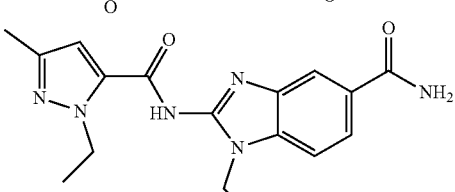
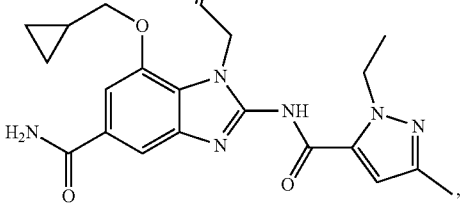

107
-continued
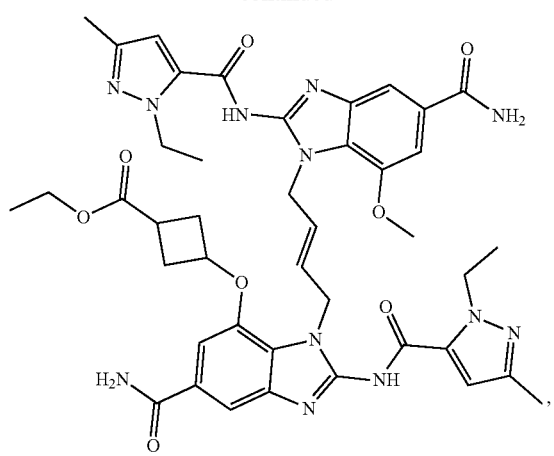
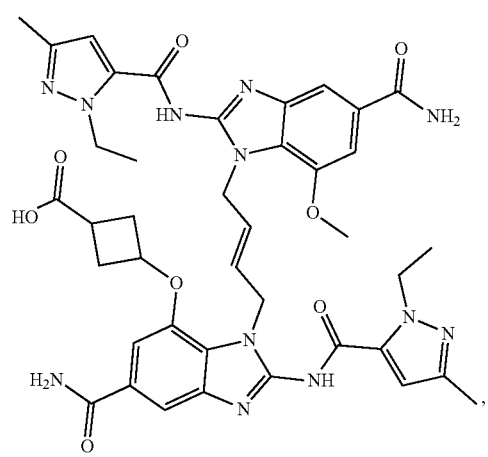
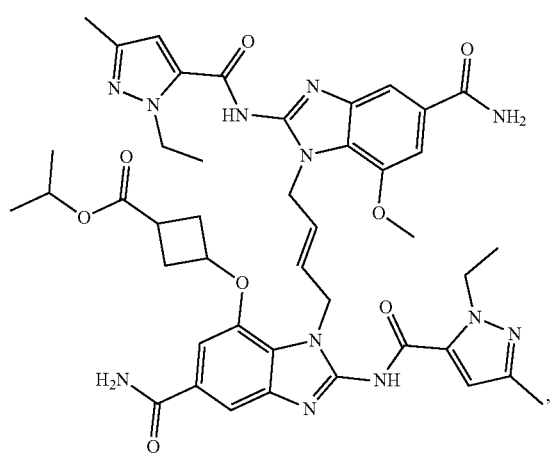
108
-continued
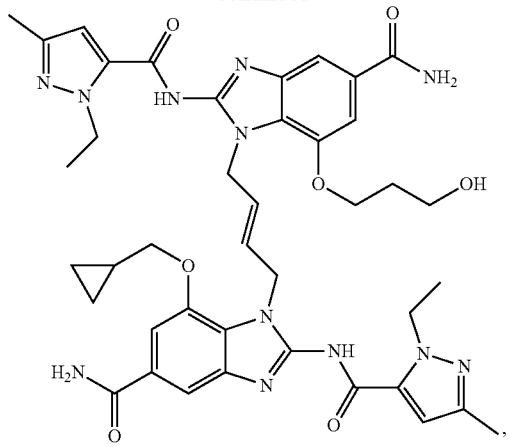
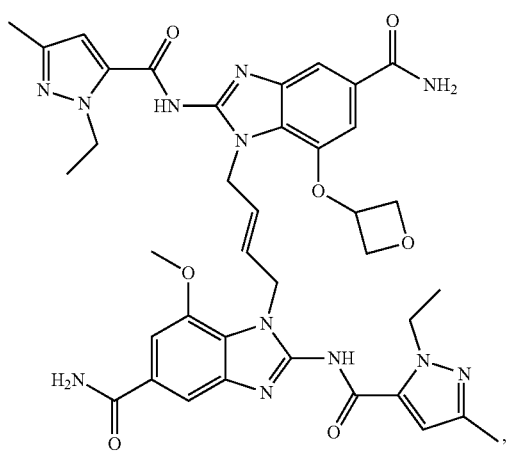
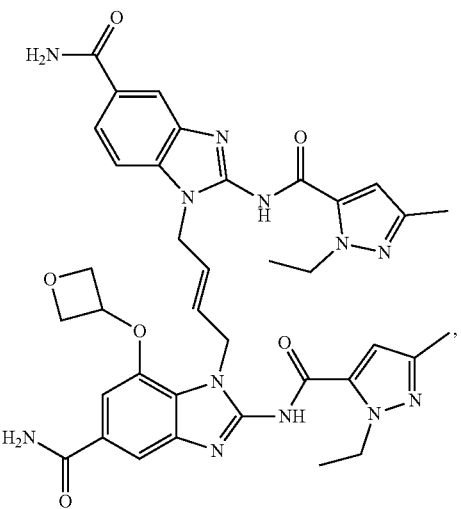

109
-continued
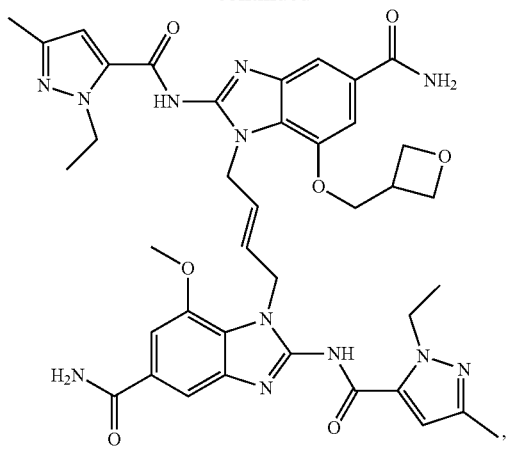
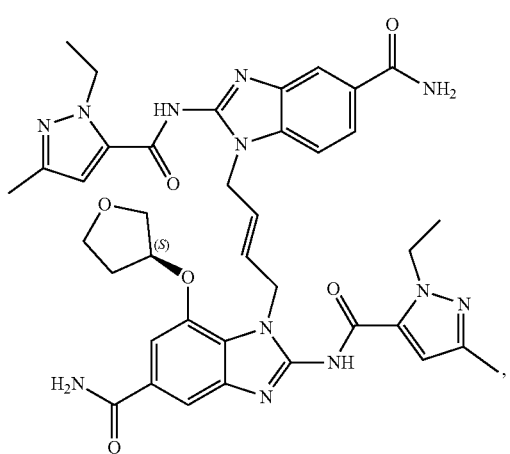
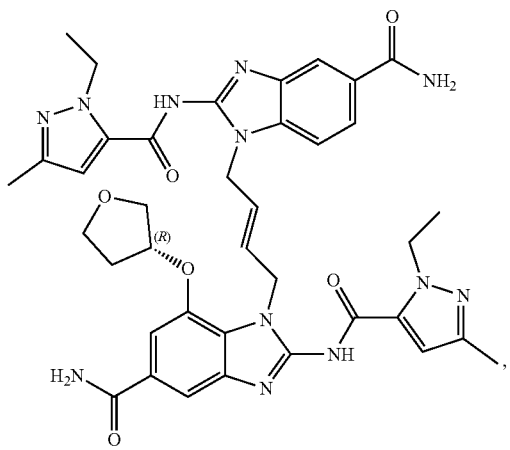
110
-continued
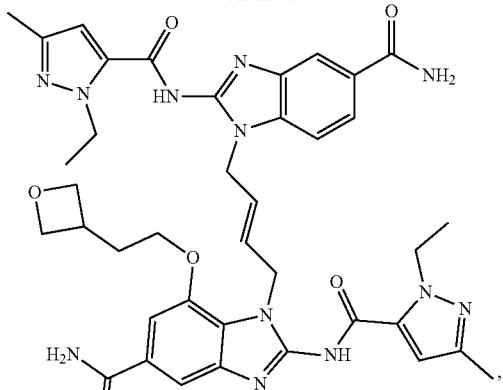
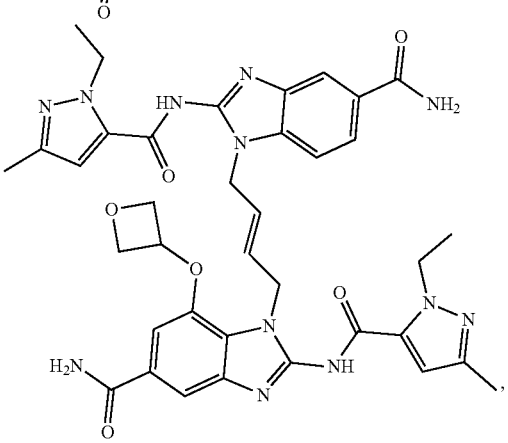
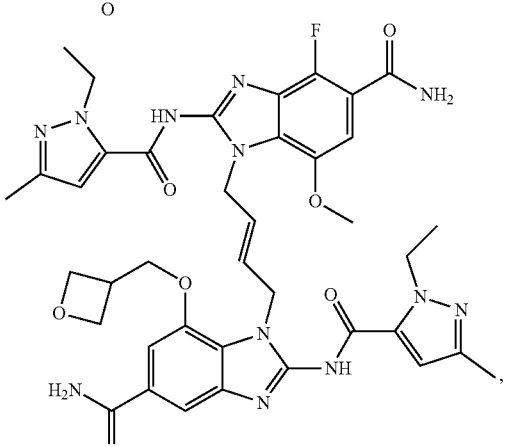
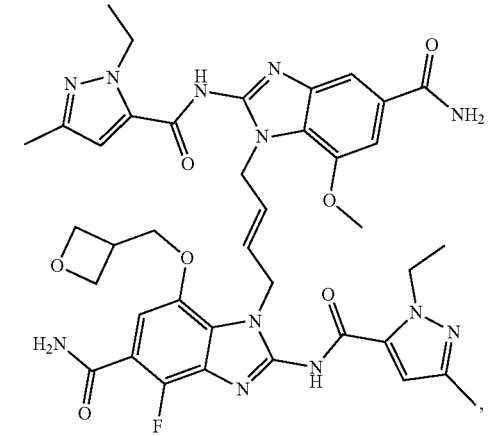

-continued

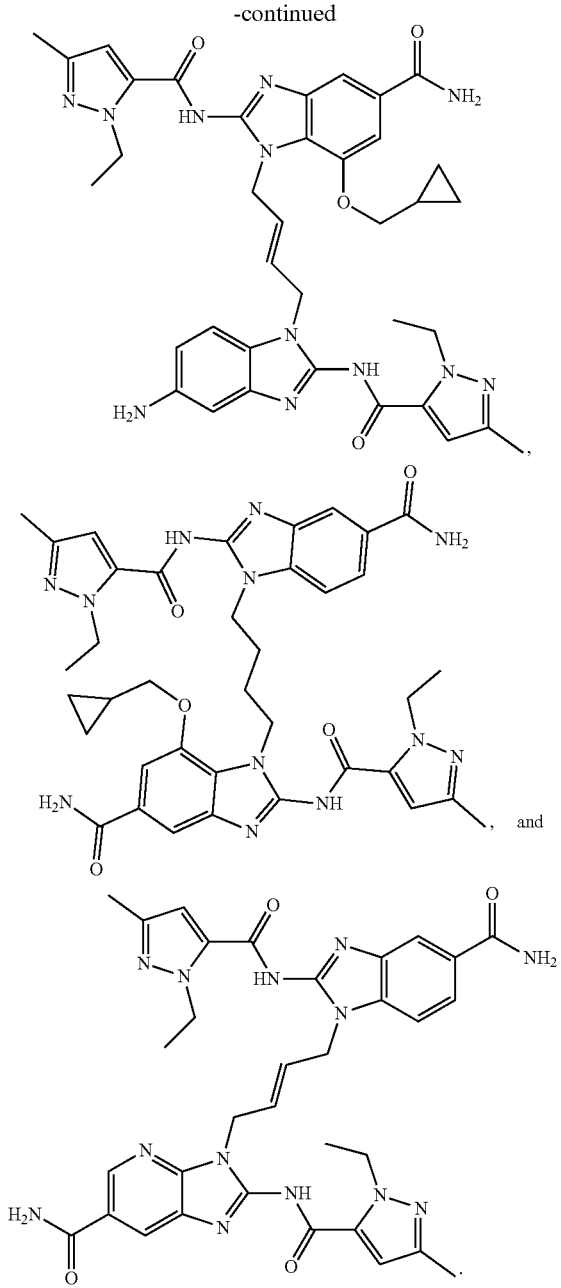

In some embodiments, the compound of the disclosure is not:

(E)-N,N'-(but-2-ene-1,4-diylbis(5-carbamoyl-7-(2-hydroxyethoxy)-1H-benzo[d]imidazole-1,2-diyl))bis(4-ethyl-2-methyloxazole-5-carboxamide);

(E)-N,N'-(but-2-ene-1,4-diylbis(5-carbamoyl-7-hydroxy-1H-benzo[d]imidazole-1,2-diyl))bis(4-ethyl-2-methyloxazole-5-carboxamide);

(E)-N-(5-carbamoyl-1-(4-(5-carbamoyl-2-(4-ethyl-2-methyloxazole-5-carboxamido)-7-hydroxy-1H-benzo[d]imidazol-1-yl)but-2-en-1-yl)-7-methoxy-1H-benzo[d]imidazol-2-yl)-4-ethyl-2-methyloxazole-5-carboxamide;

N,N'-(((((1S,2S)-cyclopropane-1,2-diyl)bis(methylene))bis(5-carbamoyl-1H-benzo[d]imidazole-1,2-diyl))bis(4-ethyl-2-methyloxazole-5-carboxamide);

(E)-1,1'-(but-2-ene-1,4-diyl)bis(2-(2,5-dimethylfuran-3-carboxamido)-7-methoxy-1H-benzo[d]imidazole-5-carboxamide);

(E)-N,N'-(hex-3-ene-1,6-diylbis(5-carbamoyl-1H-benzo[d]imidazole-1,2-diyl))bis(4-ethyl-2-methyloxazole-5-carboxamide);

(E)-N-(5-carbamoyl-1-(4-(5-carbamoyl-2-(4-ethyl-2-methyloxazole-5-carboxamido)-1H-benzo[d]imidazol-1-yl)but-2-en-1-yl)-7-methyl-1H-benzo[d]imidazol-2-yl)-4-ethyl-2-methyloxazole-5-carboxamide;

(E)-N-(5-carbamoyl-1-(4-(5-carbamoyl-2-(2,4-dimethyloxazole-5-carboxamido)-1H-benzo[d]imidazol-1-yl)but-2-en-1-yl)-7-methyl-1H-benzo[d]imidazol-2-yl)-2,4-dimethyloxazole-5-carboxamide;

(E)-N,N'-(but-2-ene-1,4-diylbis(5-carbamoyl-7-methoxy-1H-benzo[d]imidazole-1,2-diyl))bis(2,4-dimethyloxazole-5-carboxamide);

(E)-N,N'-(but-2-ene-1,4-diylbis(5-carbamoyl-7-methoxy-1H-benzo[d]imidazole-1,2-diyl))bis(4-ethyl-2-methyloxazole-5-carboxamide);

(E)-1,1'-(but-2-ene-1,4-diyl)bis(2-(1-ethyl-1H-imidazole-5-carboxamido)-7-methoxy-1H-benzo[d]imidazole-5-carboxamide);

(E)-1,1'-(but-2-ene-1,4-diyl)bis(2-(1-ethyl-1H-imidazole-2-carboxamido)-7-methoxy-1H-benzo[d]imidazole-5-carboxamide);

(Z)-4-carbamoyl-1,15-bis(4-ethyl-2-methyloxazole-5-carboxamido)-8,9,16,19-tetrahydro-7H-6,10-dioxa-2,14,15a,19a-tetraazacyclopentadeca[3,2,1-cd:8,9,10-c'd]diindene-12-carboxylic acid;

(E)-1-(4-(5-carbamoyl-2-(furan-2-carboxamido)-1H-benzo[d]imidazol-1-yl)but-2-en-1-yl)-2-(furan-2-carboxamido)-7-methyl-1H-benzo[d]imidazole-5-carboxamide;

(E)-1-(4-(5-carbamoyl-2-(pyrazolo[1,5-a]pyridine-2-carboxamido)-1H-benzo[d]imidazol-1-yl)but-2-en-1-yl)-7-methyl-2-(pyrazolo[1,5-a]pyridine-2-carboxamido)-1H-benzo[d]imidazole-5-carboxamide;

(E)-1-(4-(5-carbamoyl-2-(1-methyl-1H-pyrrole-2-carboxamido)-1H-benzo[d]imidazol-1-yl)but-2-en-1-yl)-7-methyl-2-(1-methyl-1H-pyrrole-2-carboxamido)-1H-benzo[d]imidazole-5-carboxamide;

(E)-1-(4-(5-carbamoyl-2-(1H-pyrrole-2-carboxamido)-1H-benzo[d]imidazol-1-yl)but-2-en-1-yl)-7-methyl-2-(1H-pyrrole-2-carboxamido)-1H-benzo[d]imidazole-5-carboxamide;

(E)-1-(4-(5-carbamoyl-2-(1-methyl-1H-indole-2-carboxamido)-1H-benzo[d]imidazol-1-yl)but-2-en-1-yl)-7-methyl-2-(1-methyl-1H-indole-2-carboxamido)-1H-benzo[d]imidazole-5-carboxamide;

(E)-N-(5-carbamoyl-1-(4-(5-carbamoyl-2-(4-ethyl-2-methyloxazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide;

(Z)-1,15-bis(4-ethyl-2-methyloxazole-5-carboxamido)-8,9,16,19-tetrahydro-7H-6,10-dioxa-2,14,15a,19a-tetraazacyclopentadeca[3,2,1-cd:8,9,10-c'd]diindene-4,12-dicarboxamide;

N-(5-carbamoyl-1-(2-((1R,2R)-2-(2-(5-carbamoyl-2-(4-ethyl-2-methyloxazole-5-carboxamido)-1H-benzo[d]imidazol-1-yl)ethyl)cyclopropyl)ethyl)-7-methyl-1H-benzo[d]imidazol-2-yl)-4-ethyl-2-methyloxazole-5-carboxamide;

(E)-N-(5-carbamoyl-1-(4-(5-carbamoyl-2-(4-ethyl-2-methyloxazole-5-carboxamido)-7-(2-hydroxyethoxy)-1H- benzo[d]imidazol-1-yl)but-2-en-1-yl)-7-methoxy-1H-benzo[d]imidazol-2-yl)-4-ethyl-2-methyloxazole-5-carboxamide;

(E)-2-((5-carbamoyl-1-(4-(5-carbamoyl-2-(4-ethyl-2-methyl oxazol e-5-carboxamido)-7-methoxy-1H-benzo[d]imidazol-1-yl)but-2-en-1-yl)-2-(4-ethyl-2-methyl oxazol e-5-carboxamido)-1H-benzo[d]imidazol-7-yl)oxy) acetic acid;

(E)-2-((5-carbamoyl-1-(4-(5-carbamoyl-2-(4-ethyl-2-methyl oxazol e-5-carboxamido)-7-(2-hydroxyethoxy)-1H-benzo[d]imidazol-1-yl)but-2-en-1-yl)-2-(4-ethyl-2-methyl oxazol e-5-carboxamido)-1H-benzo[d]imidazol-7-yl)oxy)acetic acid;

(E)-1,15-bis(4-ethyl-2-methyl oxazol e-5-carboxamido)-N-(2-hydroxyethyl)-8,9,16,19-tetrahydro-7H-6,10-di oxa-2,14,15a,19a-tetraazacyclopentadeca[3,2, 1-cd:8,9,10-c'd] diindene-4,12-dicarboxamide;

(E)-N-(5-carbamoyl-1-(4-(5-carbamoyl-2-(4-ethyl-2-methyl oxazol e-5-carboxamido)-7-methoxy-1H-benzo[d]imidazol-1-yl)but-2-en-1-yl)-7-(2-(dimethylamino) ethoxy)-1H-benzo[d]imidazol-2-yl)-4-ethyl-2-methyloxazole-5-carboxamide; or (E)-1-(4-(5-carbamoyl-2-(1-(2-hydroxyethyl)-3-methyl-1H-pyrazol e-5-carboxamido)-1H-benzo[d]imidazol-1-yl) but-2-en-1-yl)-2-(1-ethyl-3-methyl-1H-pyrazol e-5-carboxamido)-1H-benzo[d]imidazol e-5-carboxamide.

Representative compounds of this disclosure include the compounds of the Examples. It will be appreciated that the present disclosure encompasses compounds of Formula (I'), Formula (IA'), Formula (II'), Formula (III'), Formula (IV'), and Formula (V') as the free base and as salts thereof, for example as a pharmaceutically acceptable salt thereof. In some embodiments the disclosure relates to compounds of Formula (I'), Formula (IA'), Formula (II'), Formula (III'), Formula (IV'), and Formula (V') in the form of a free base. In some embodiments, the disclosure relates to compounds of Formula (I'), Formula (IA'), Formula (II'), Formula (III'), Formula (IV'), and Formula (V') in the form of a salt, particularly, a pharmaceutically acceptable salt. It will be further appreciated that, In some embodiments, the disclosure relates to compounds of the Examples in the form of a free base. In some embodiments, the disclosure relates to compounds of the Examples in the form of a salt, particularly, a pharmaceutically acceptable salt.

In some embodiments, in the compound of Formula (I'), (IA'), (III'), (IV'), (V'), (I-B'), (I-b'), (II-B'), (II-b'), (V-a), (V-b), (V-c), (V-d), (V-e), (V-e1), (V-e2), (V-h), (V-h1), (V-h2), (V-h3), (V-h4), (V-h5), (V-h6), or (V-h7), Ring 1 is selected from any one of the following:

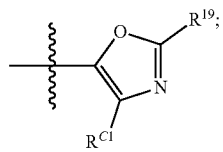
(1)

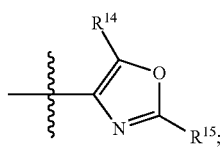
(2)

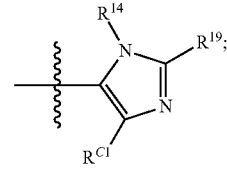
(3)

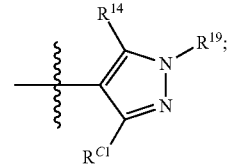
(4)

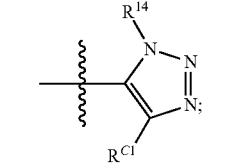
(5)

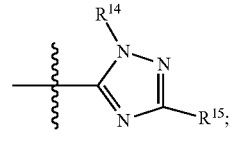
(6)

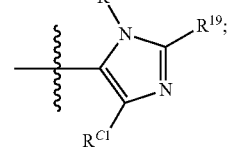
(7)

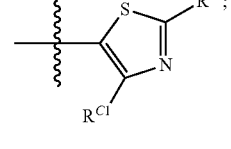
(8)

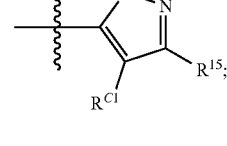
(9)

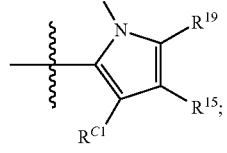
(10)

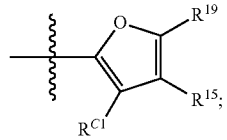
(11)

(12) 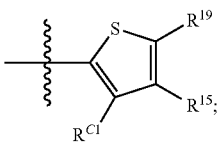

(13) 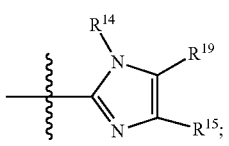

(14) 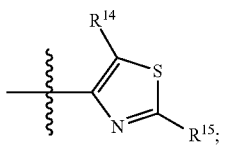

(15) 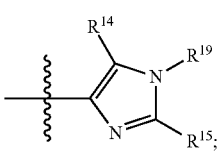

(16) 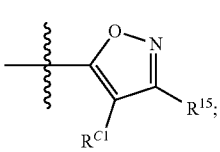

(17) 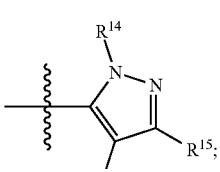

(18) 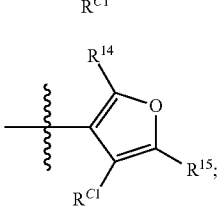

(19) 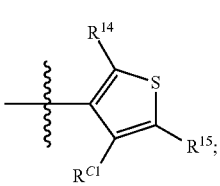

(20) 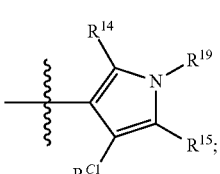

(21) 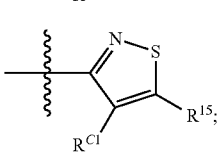

(22) 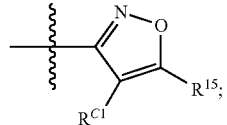

(23) 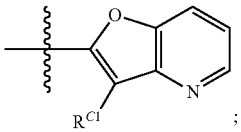

(24) 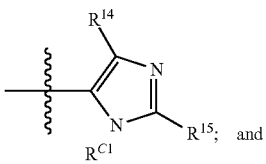; and

(25) 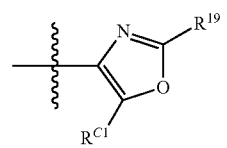

wherein:

$R^{15}$, $R^{19}$ and $R^{C1}$ are each independently H, $C_{1-4}$ alkyl, halogen or optionally substituted $C_{1-4}$ alkyl wherein said $C_{1-4}$ alkyl is optionally substituted $C_{1-4}$ alkyl is substituent with a halogen or —CO$_2$H.

In some embodiments, the $C_{1-4}$ alkyl is methyl or ethyl.

In some embodiments, the $C_{1-4}$ alkyl is methyl substituted with —COOH.

In some embodiments, in the compound of Formula (I'), (IA'), (III'), (IV'), (V'), (I-B'), (I-b'), (II-B'), (II-b'), (V-a), (V-b), (V-c), (V-d), (V-e), (V-e1), (V-e2), (V-f), (V-f1), (V-f2), (V-f3), (V-f4), (V-f5), (V-f6), (V-f7), (V-g), (V-g1), (V-g2), (V-g3), (V-g4), (V-g5), (V-g6), or (V-g7), Ring 2 is selected from any one of the following:

(1) 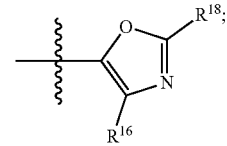

(2) 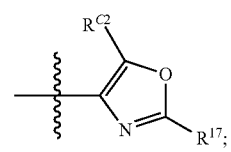

(3) 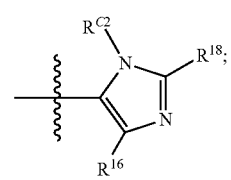

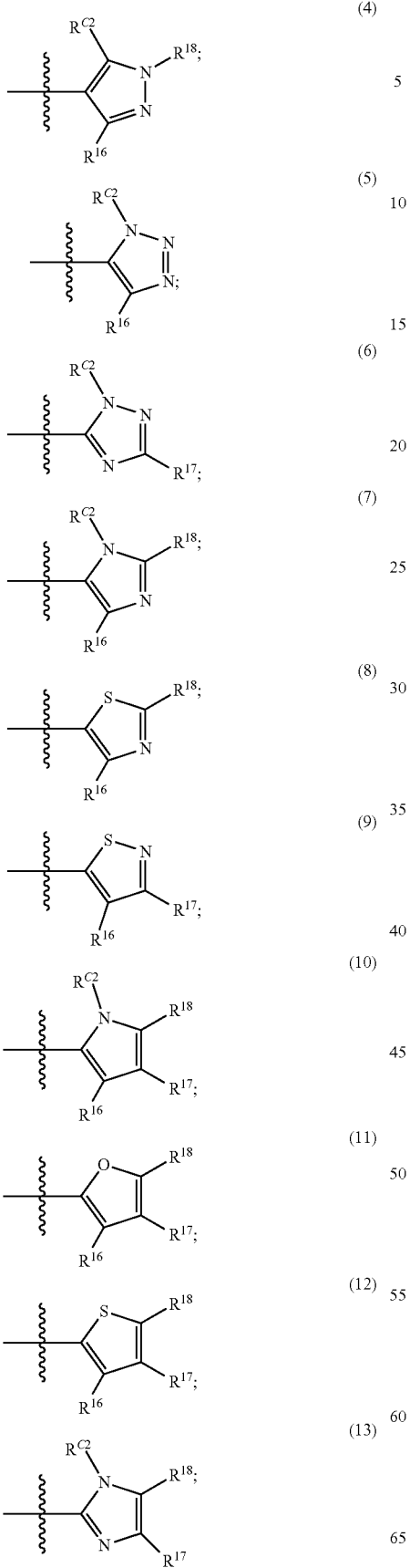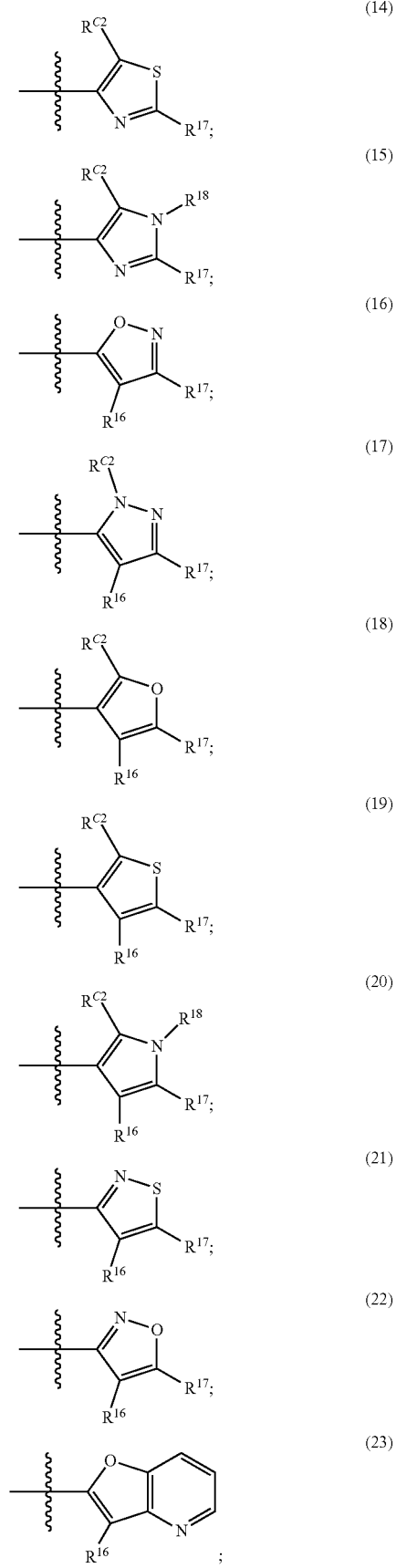

-continued

(24)
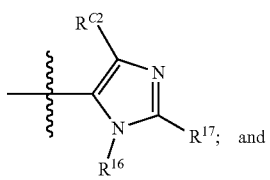

(25)
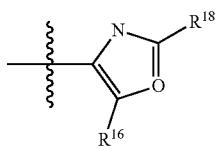

wherein:

R$^{16}$, R$^{17}$, R$^{18}$ and R$^{C2}$ are each independently H, C$_{1-4}$ alkyl, halogen or optionally substituted C$_{1-4}$ alkyl wherein said is optionally substituted C$_{1-4}$ alkyl is substituent with a halogen or —CO$_2$H.

In some embodiments, one or more of R$^{16}$, R$^{17}$, R$^{18}$ and R$^{C2}$ is methyl, ethyl, or methyl substituted with —COOH, provided that when r is 1, s is 0, Ring 1 is

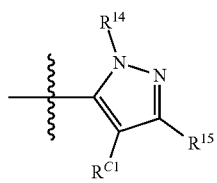

and Ring 2 is

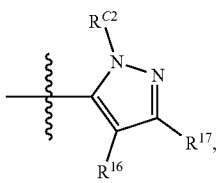

then at least one of X$_3$ and X$_4$ is S or at least one of X$_5$, X$_6$, and X$_9$ is N.

In some embodiments, one or more of R$^{16}$, R$^{17}$, R$^{18}$ and is methyl, ethyl, or methyl substituted with —COOH, provided that when r is 1, s is 0, Ring 1 is

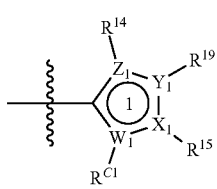

and Ring 2 is

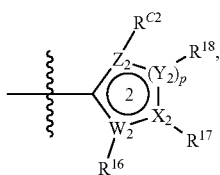

then at least one of X$_3$ and X$_4$ is S or at least one of X$_5$, X$_6$, and X$_9$ is N In some embodiments, Ring 1 and Ring 2 are each independently selected from any one of the following:

(1)
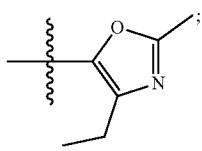

(2)
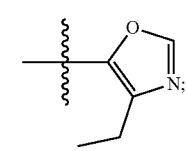

(3)
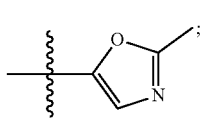

(4)
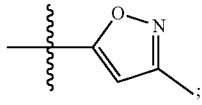

(5)
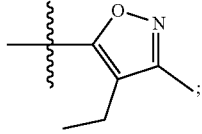

(6)
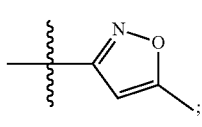

(7)
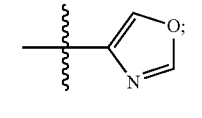

(8)
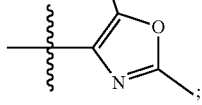

(9)
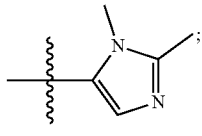

-continued
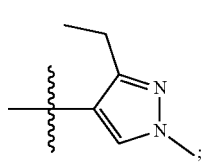 (10)
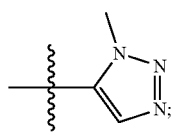 (11)
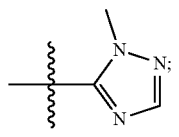 (12)
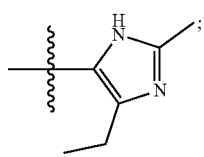 (13)
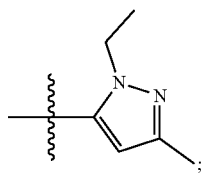 (14)
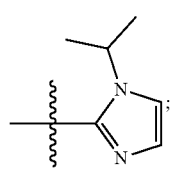 (15)
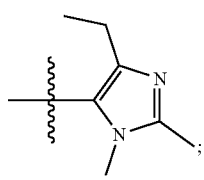 (16)
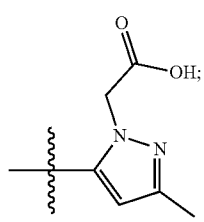 (17)
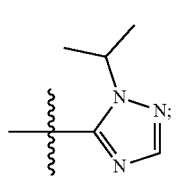 (18)
-continued
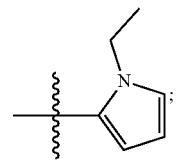 (19)
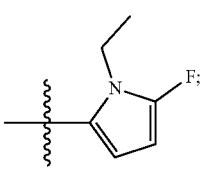 (20)
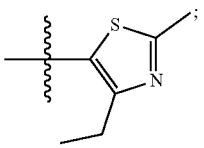 (21)
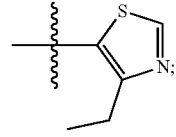 (22)
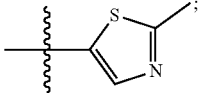 (23)
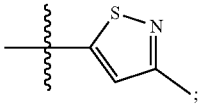 (24)
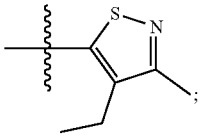 (25)
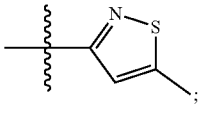 (26)
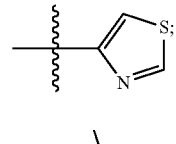 (27)
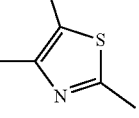 (28)
(29)

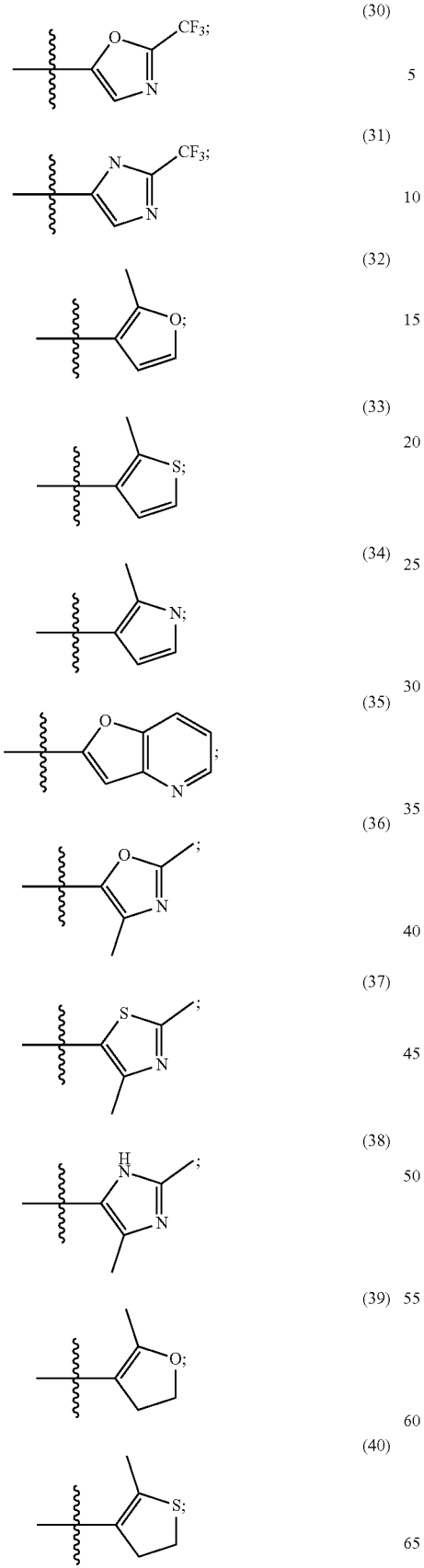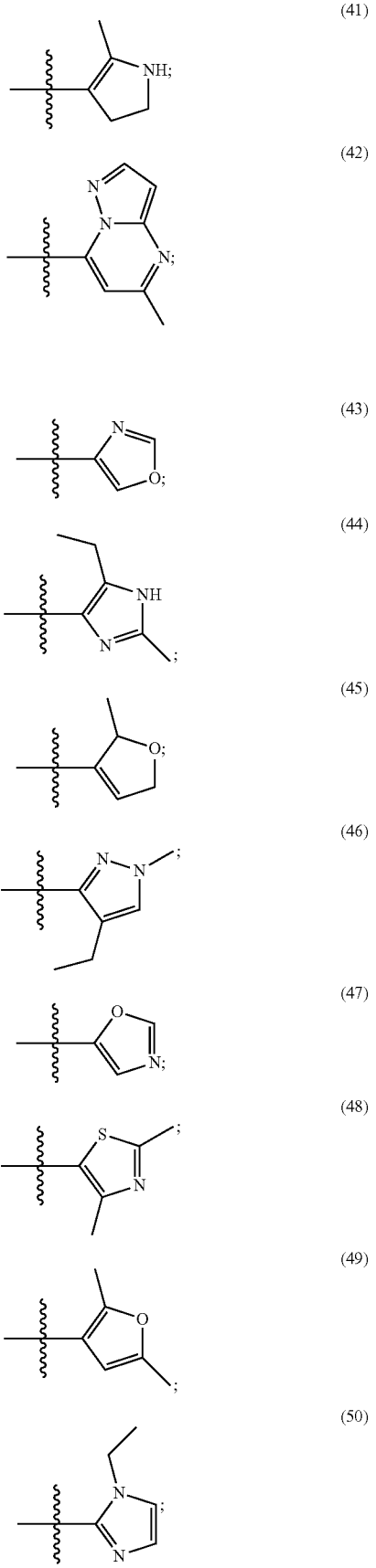

(51)
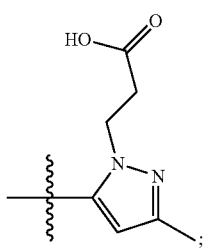
(52)
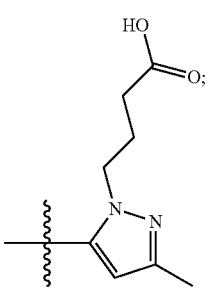
(53)
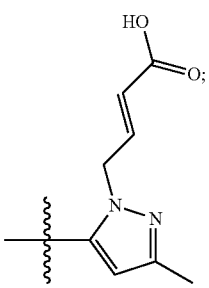
(54)
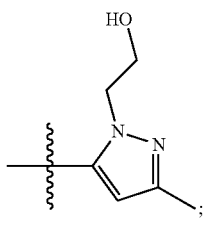
(55)
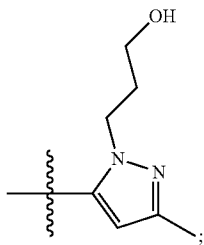
(56)
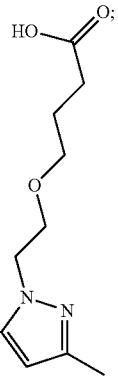
(57)
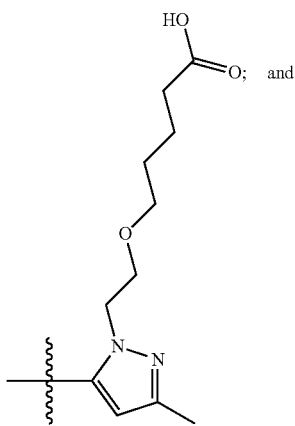
(58)
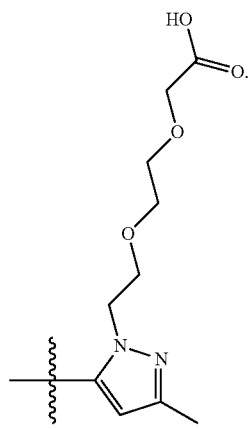
In some embodiments, the compounds of the disclosure are selected from the compounds listed in Table 1, or a tautomer thereof, or a prodrug thereof, or a salt thereof, particularly a pharmaceutically acceptable salt thereof.

TABLE 1
| Example No | Compound No. | Structure | LCMS (M + H)+ |
|---|---|---|---|
| 1 | 9 | 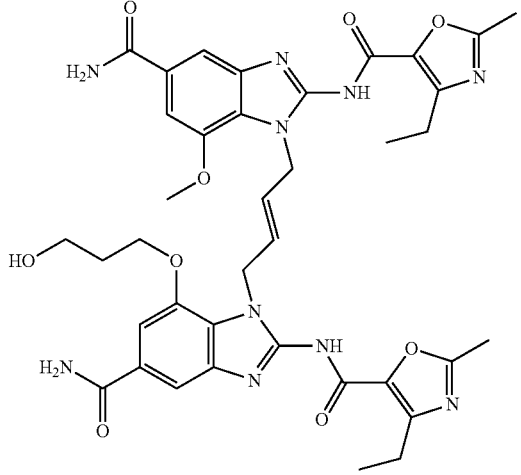 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCO)c21] | 783.30 |
| 2 | 10 | 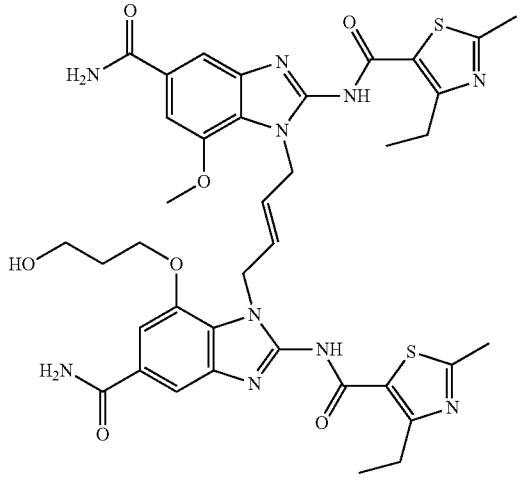 [SMILES: CCc1nc(C)sc1C(=O)Nc1nc2cc(C(N)=O)cc(OC)c2n1C/C=C/Cn1c(NC(=O)c2sc(C)nc2CC)nc2cc(C(N)=O)cc(OCCCO)c21] | 815.20 |
| 3 | 11 | 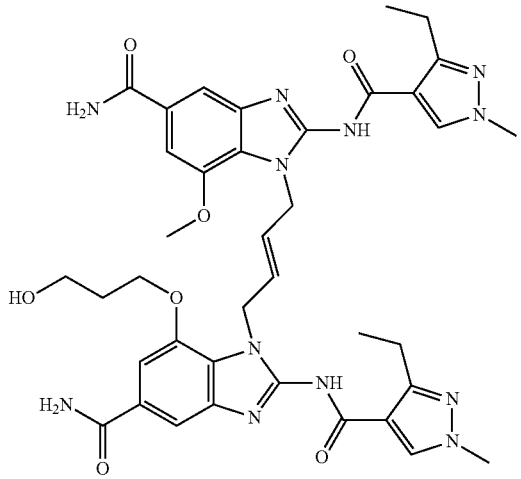 [SMILES: CCc1nn(C)cc1C(=O)Nc1nc2cc(C(N)=O)cc(OC)c2n1C/C=C/Cn1c(NC(=O)c2cn(C)nc2CC)nc2cc(C(N)=O)cc(OCCCO)c21] | 781.20 |

TABLE 1-continued

| Example No | Compound No. | Structure | LCMS (M + H)+ |
|---|---|---|---|
| 4 | 12 | 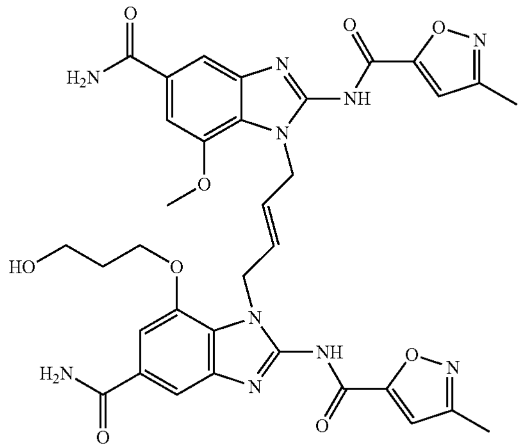 [SMILES: COc1cc(C(N)=O)cc2nc(NC(=O)c3cc(C)no3)n(C/C=C/Cn3c(NC(=O)c4cc(C)no4)nc4cc(C(N)=O)cc(OCCCO)c43)c12] | 727.30 |
| 5 | 13 | 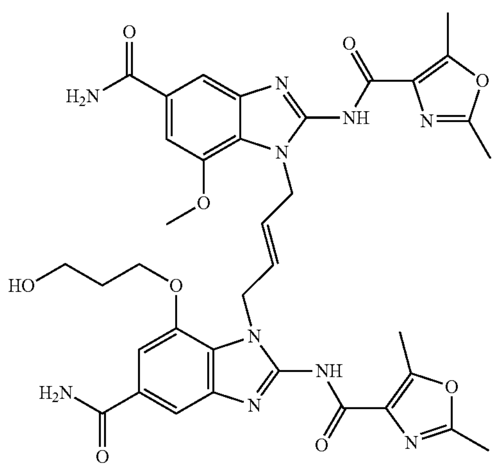 [SMILES: COc1cc(C(N)=O)cc2nc(NC(=O)c3nc(C)oc3C)n(C/C=C/Cn3c(NC(=O)c4nc(C)oc4C)nc4cc(C(N)=O)cc(OCCCO)c43)c12] | 755.10 |
| 6 | 14 | 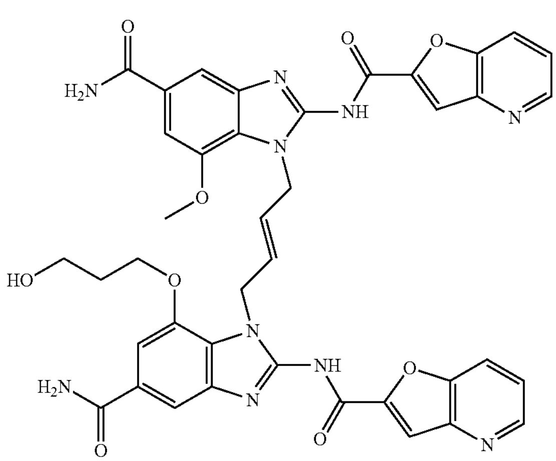 [SMILES: COc1cc(C(N)=O)cc2nc(NC(=O)c3cc4ncccc4o3)n(C/C=C/Cn3c(NC(=O)c4cc5ncccc5o4)nc4cc(C(N)=O)cc(OCCCO)c43)c12] | 799.20 |

TABLE 1-continued

| Example No | Compound No. | Structure | LCMS (M + H)+ |
|---|---|---|---|
| 7 | 15 | 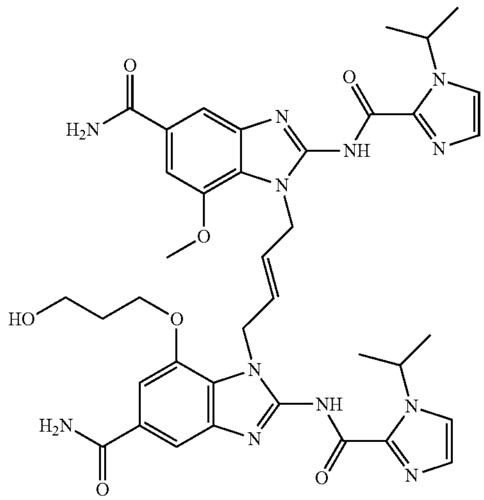 [SMILES: COc1cc(C(N)=O)cc2nc(NC(=O)c3nccn3C(C)C)n(C/C=C/Cn3c(NC(=O)c4nccn4C(C)C)nc4cc(C(N)=O)cc(OCCCO)c43)c12] | 781.40 |
| 8 | 16 | 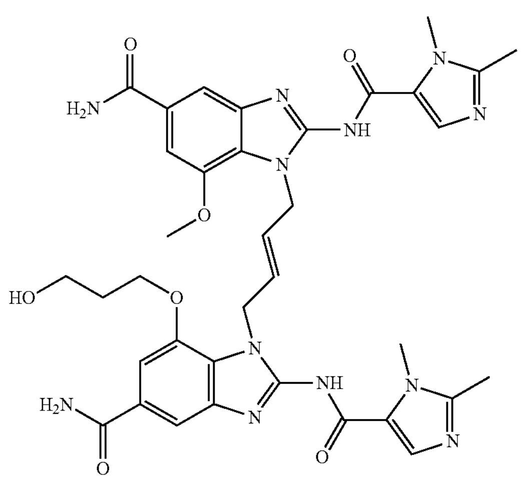 [SMILES: COc1cc(C(N)=O)cc2nc(NC(=O)c3cnc(C)n3C)n(C/C=C/Cn3c(NC(=O)c4cnc(C)n4C)nc4cc(C(N)=O)cc(OCCCO)c43)c12] | 753.15 |
| 9 | 17 | 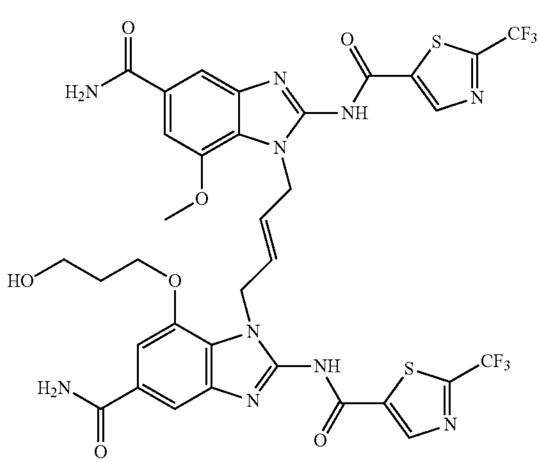 [SMILES: COc1cc(C(N)=O)cc2nc(NC(=O)c3cnc(C(F)(F)F)s3)n(C/C=C/Cn3c(NC(=O)c4cnc(C(F)(F)F)s4)nc4cc(C(N)=O)cc(OCCCO)c43)c12] | 867.05 |

TABLE 1-continued
| Example No | Compound No. | Structure | LCMS (M + H)+ |
|---|---|---|---|
| 10 | 18 | 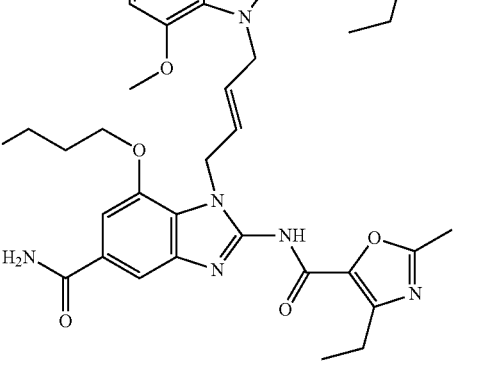 | 782.38 |
| 11 | 19 | 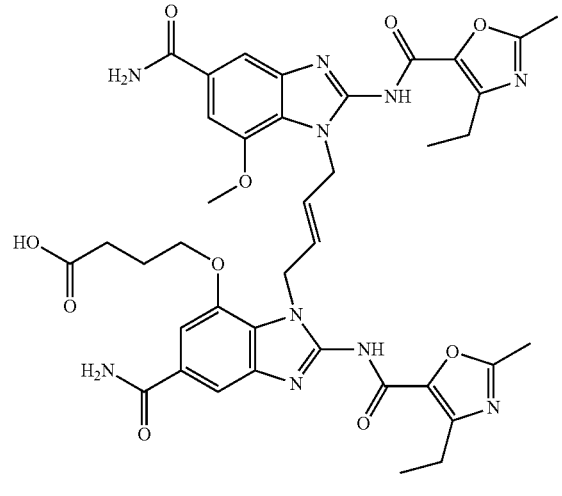 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCC(=O)O)c21] | 811.30 |
| 12 | 26 | 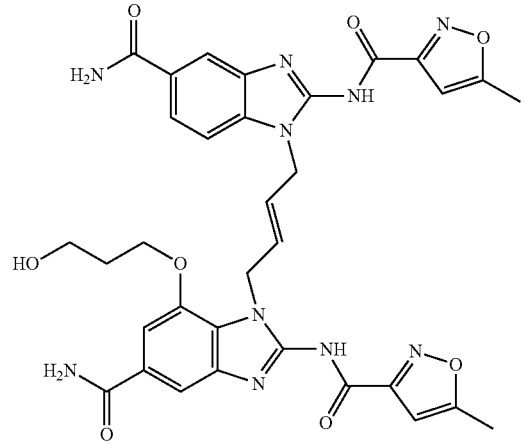 [SMILES: Cc1cc(C(=O)Nc2nc3cc(C(N)=O)ccc3n2C/C=C/Cn2c(NC(=O)c3cc(C)on3)nc3cc(C(N)=O)cc(OCCCO)c32)no1] | 697.26 |

TABLE 1-continued

| Example No | Compound No. | Structure | LCMS (M + H)+ |
|---|---|---|---|
| 13 | 27 | 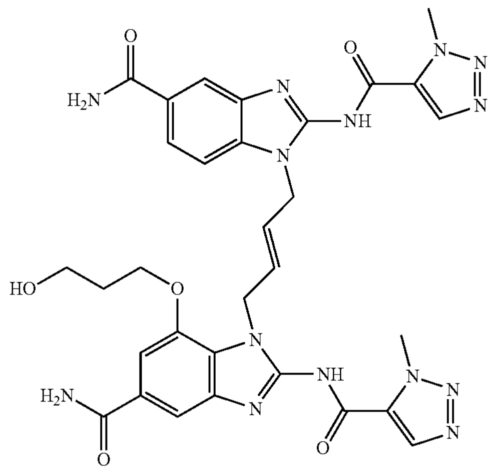 [SMILES: Cn1nncc1C(=O)Nc1nc2cc(C(N)=O)ccc2n1C/C=C/Cn1c(NC(=O)c2cnnn2C)nc2cc(C(N)=O)cc(OCCCO)c21] | 697.28 |
| 14 | 28 | 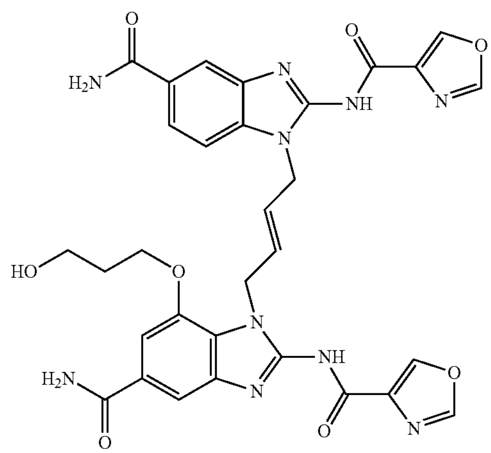 [SMILES: NC(=O)c1ccc2c(c1)nc(NC(=O)c1cocn1)n2C/C=C/Cn1c(NC(=O)c2cocn2)nc2cc(C(N)=O)cc(OCCCO)c21] | 669.22 |
| 15 | 36 | 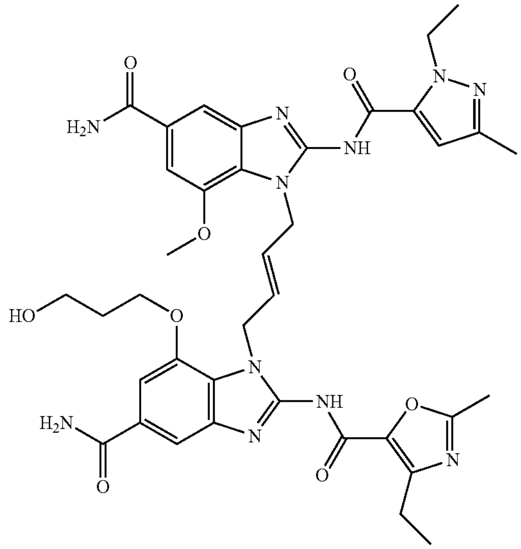 [SMILES: CCc1nc(C)oc1C(=O)Nc1nc2cc(C(N)=O)cc(OCCCO)c2n1C/C=C/Cn1c(NC(=O)c2cc(C)nn2CC)nc2cc(C(N)=O)cc(OC)c21] | 782.15 |

TABLE 1-continued

| Example No | Compound No. | Structure | LCMS (M + H)+ |
|---|---|---|---|
| 16 | 37 | 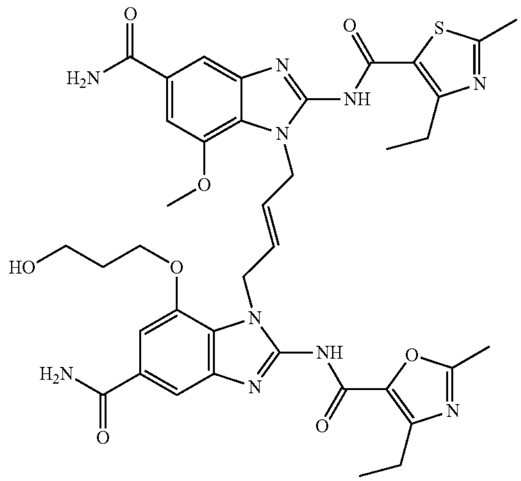 [SMILES: CCc1nc(C)oc1C(=O)Nc1nc2cc(C(N)=O)cc(OCCCO)c2n1C/C=C/Cn1c(NC(=O)c2sc(C)nc2CC)nc2cc(C(N)=O)cc(OC)c21] | 799.20 |
| 17 | 38 | 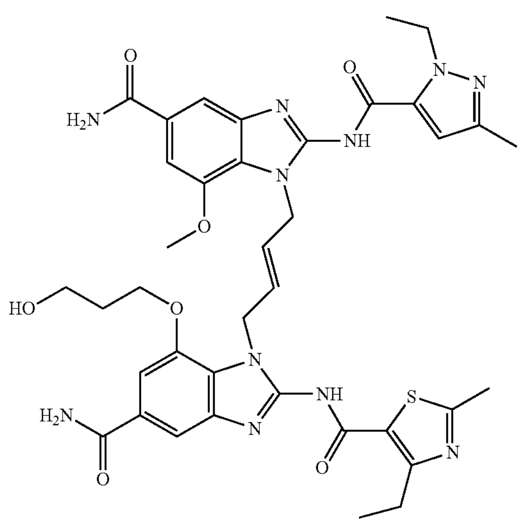 [SMILES: CCc1nc(C)sc1C(=O)Nc1nc2cc(C(N)=O)cc(OCCCO)c2n1C/C=C/Cn1c(NC(=O)c2cc(C)nn2CC)nc2cc(C(N)=O)cc(OC)c21] | 798.30 |
| 18 | 39 | 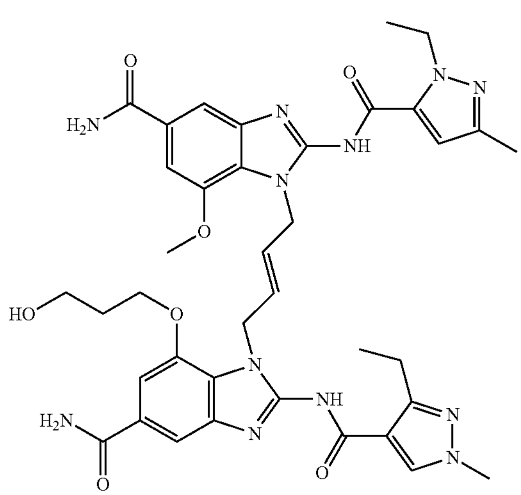 [SMILES: CCc1nn(C)cc1C(=O)Nc1nc2cc(C(N)=O)cc(OCCCO)c2n1C/C=C/Cn1c(NC(=O)c2cc(C)nn2CC)nc2cc(C(N)=O)cc(OC)c21] | 781.20 |

TABLE 1-continued

| Example No | Compound No. | Structure | LCMS (M + H)+ |
|---|---|---|---|
| 19 | 40 | 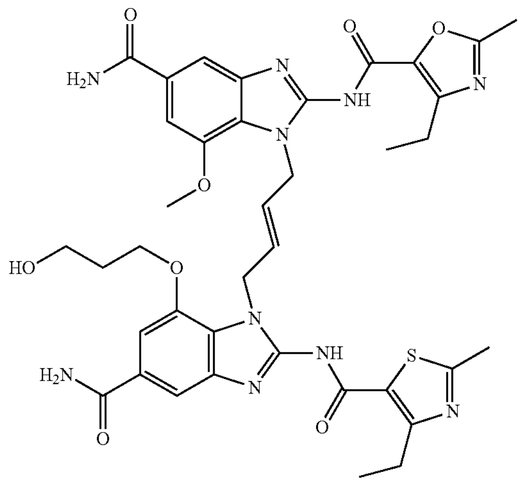 | 799.30 |
| 20 | 41 | 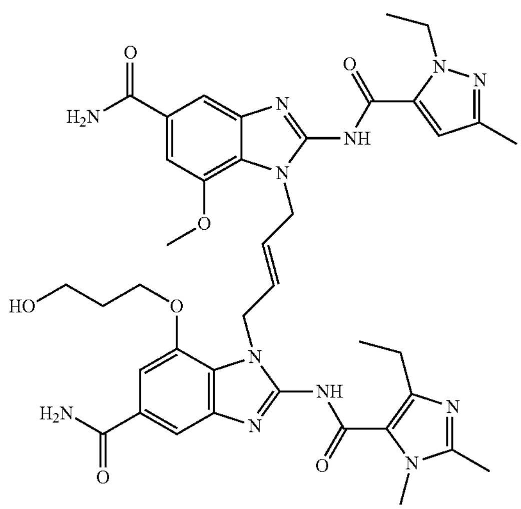 [SMILES: CCc1nc(C)n(C)c1C(=O)Nc1nc2cc(C(N)=O)cc(OCCCO)c2n1C/C=C/Cn1c(NC(=O)c2cc(C)nn2CC)nc2cc(C(N)=O)cc(OC)c21] | 795.30 |
| 21 | 42 | 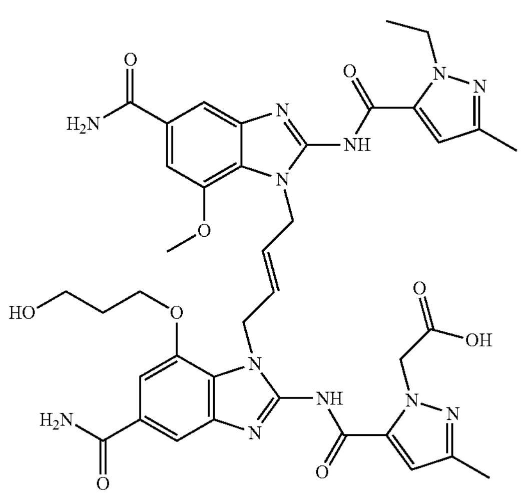 [SMILES: CCn1nc(C)cc1C(=O)Nc1nc2cc(C(N)=O)cc(OC)c2n1C/C=C/Cn1c(NC(=O)c2cc(C)nn2CC(=O)O)nc2cc(C(N)=O)cc(OCCCO)c21] | 811.30 |

TABLE 1-continued
| Example No | Compound No. | Structure | LCMS (M + H)+ |
|---|---|---|---|
| 22 | 43 | 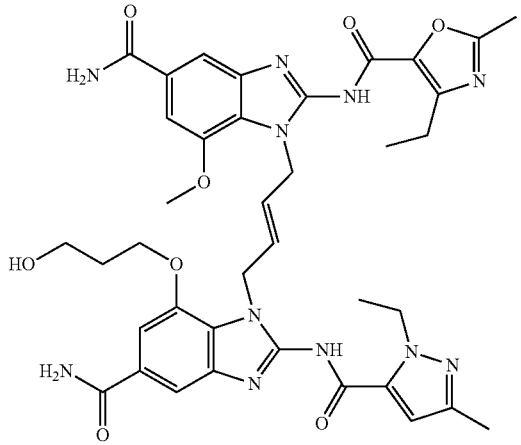 [SMILES: CCc1nc(C)oc1C(=O)Nc1nc2cc(C(N)=O)cc(OC)c2n1C/C=C/Cn1c(NC(=O)c2cc(C)nn2CC)nc2cc(C(N)=O)cc(OCCCO)c21] | 782.30 |
| 23 | 51 | 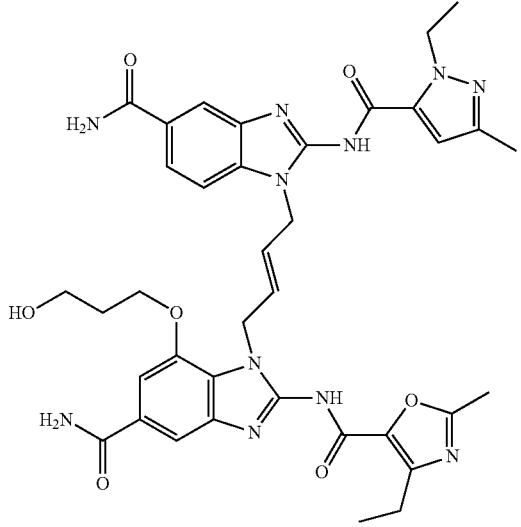 [SMILES: CCc1nc(C)oc1C(=O)Nc1nc2cc(C(N)=O)cc(OCCCO)c2n1C/C=C/Cn1c(NC(=O)c2cc(C)nn2CC)nc2cc(C(N)=O)ccc21] | 752.30 |
| 24 | 52 | 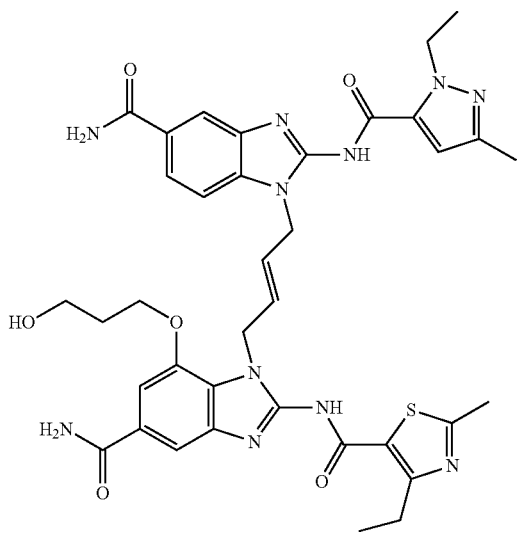 [SMILES: CCc1nc(C)sc1C(=O)Nc1nc2cc(C(N)=O)cc(OCCCO)c2n1C/C=C/Cn1c(NC(=O)c2cc(C)nn2CC)nc2cc(C(N)=O)ccc21] | 768.20 |

TABLE 1-continued

| Example No | Compound No. | Structure | LCMS (M + H)+ |
|---|---|---|---|
| 25 | 53 | 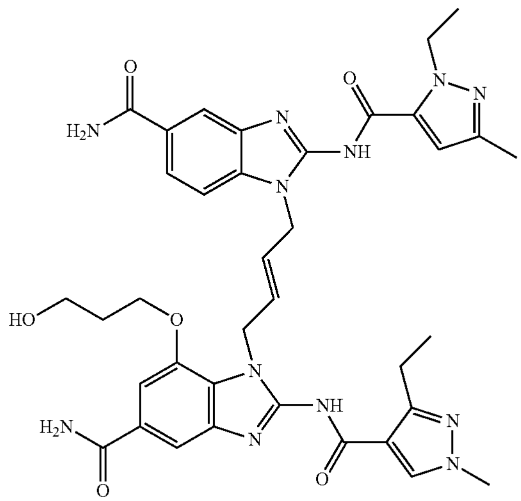 [SMILES: CCc1nn(C)cc1C(=O)Nc1nc2cc(C(N)=O)cc(OCCCO)c2n1C/C=C/Cn1c(NC(=O)c2cc(C)nn2CC)nc2cc(C(N)=O)ccc21] | 751.25 |
| 26 | 63 | 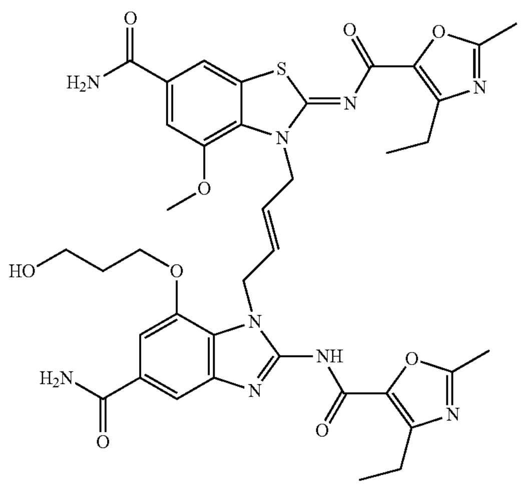 [SMILES: CCc1nc(C)oc1C(=O)/N=c1\sc2cc(C(N)=O)cc(OC)c2n1C/C=C/Cn1c(NC(=O)c2oc(C)nc2CC)nc2cc(C(N)=O)cc(OCCCO)c21] | 800.20 |
| 27 | 64 | 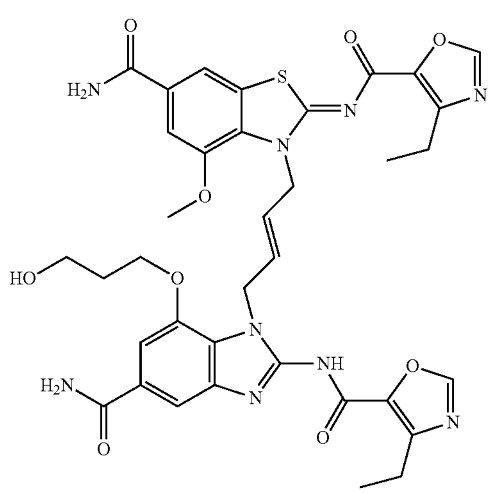 [SMILES: CCc1ncoc1C(=O)/N=c1\sc2cc(C(N)=O)cc(OC)c2n1C/C=C/Cn1c(NC(=O)c2ocnc2CC)nc2cc(C(N)=O)cc(OCCCO)c21] | 772.20 |

| Example No | Compound No. | Structure | LCMS (M + H)⁺ |
|---|---|---|---|
| 28 | 65 | 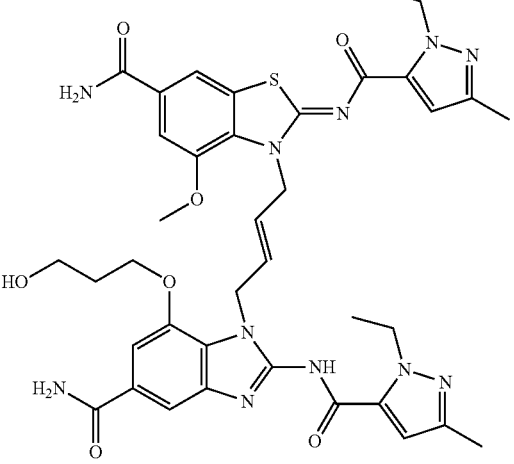 | 798.20 |
| 29 | 66 | 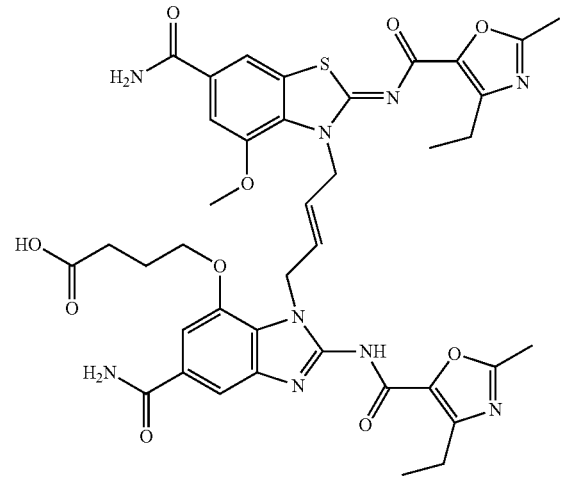 [SMILES: CCc1nc(C)oc1C(=O)/N=c1\sc2cc(C(N)=O)cc(OC)c2n1C/C=C/Cn1c(NC(=O)c2oc(C)nc2CC)nc2cc(C(N)=O)cc(OCCCC(=O)O)c21] | 828.20 |
| 30 | 67 | 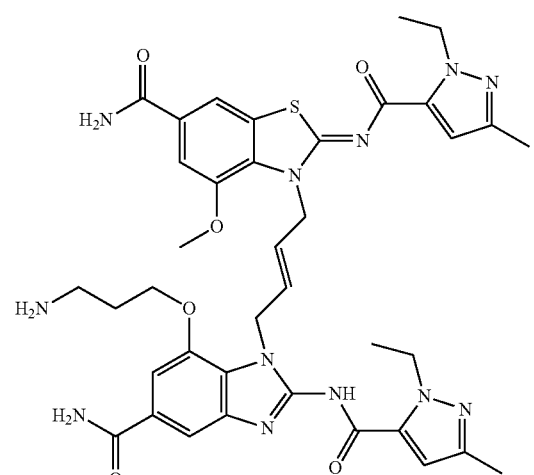 | 797.30 |

TABLE 1-continued
| Example No | Compound No. | Structure | LCMS (M + H)+ |
|---|---|---|---|
| 31 | 68 | 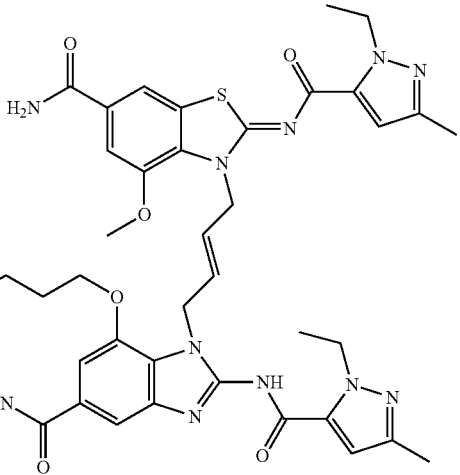 | 826.30 |
| 32 | 69 | 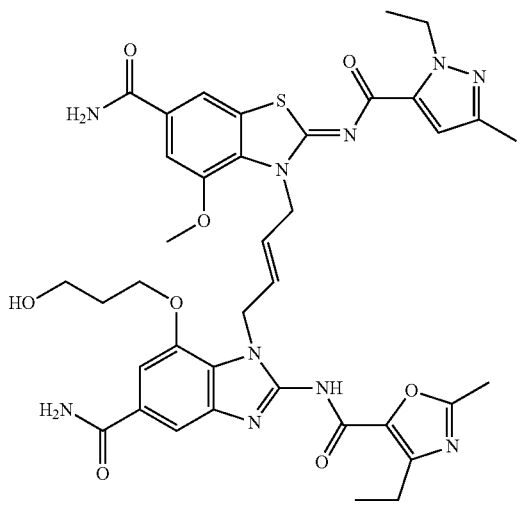 [SMILES: CCc1nc(C)oc1C(=O)Nc1nc2cc(C(N)=O)cc(OCCCO)c2n1C/C=C/Cn1/c(=N/C(=O)c2cc(C)nn2CC)sc2cc(C(N)=O)cc(OC)c21] | 799.30 |
| 33 | 70 | 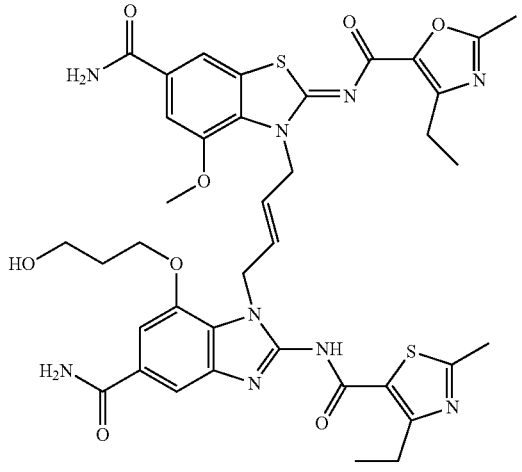 [SMILES: CCc1nc(C)oc1C(=O)/N=c1\sc2cc(C(N)=O)cc(OC)c2n1C/C=C/Cn1c(NC(=O)c2sc(C)nc2CC)nc2cc(C(N)=O)cc(OCCCO)c21] | 816.20 |

TABLE 1-continued

| Example No | Compound No. | Structure | LCMS (M + H)+ |
|---|---|---|---|
| 34 | 71 | 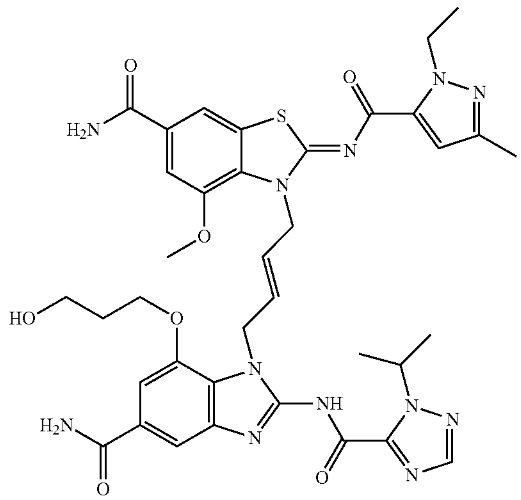 [SMILES: CCn1nc(C)cc1C(=O)/N=c1\sc2cc(C(N)=O)cc(OC)c2n1C/C=C/Cn1c(NC(=O)c2ncnn2C(C)C)nc2cc(C(N)=O)cc(OCCCO)c21] | 799.30 |
| 35 | 72 | 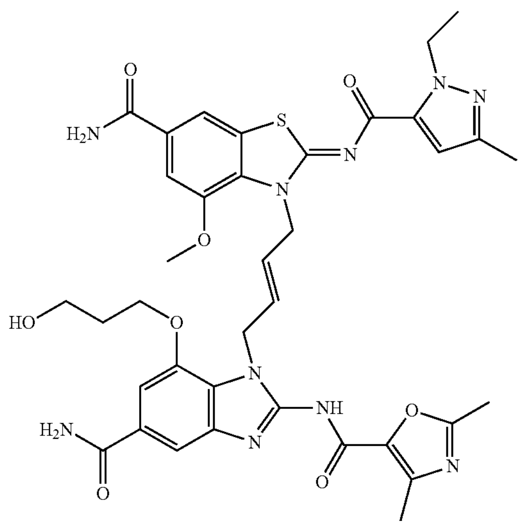 [SMILES: CCn1nc(C)cc1C(=O)/N=c1\sc2cc(C(N)=O)cc(OC)c2n1C/C=C/Cn1c(NC(=O)c2oc(C)nc2C)nc2cc(C(N)=O)cc(OCCCO)c21] | 785.20 |
| 36 | 73 | 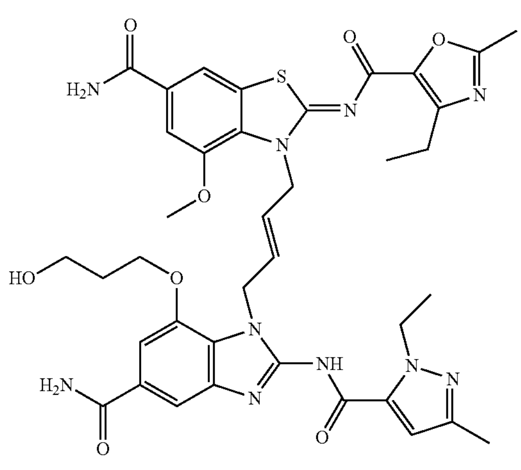 [SMILES: CCc1nc(C)oc1C(=O)/N=c1\sc2cc(C(N)=O)cc(OC)c2n1C/C=C/Cn1c(NC(=O)c2cc(C)nn2CC)nc2cc(C(N)=O)cc(OCCCO)c21] | 799.30 |

TABLE 1-continued
| Example No | Compound No. | Structure | LCMS (M + H)+ |
|---|---|---|---|
| 37 | 74 | 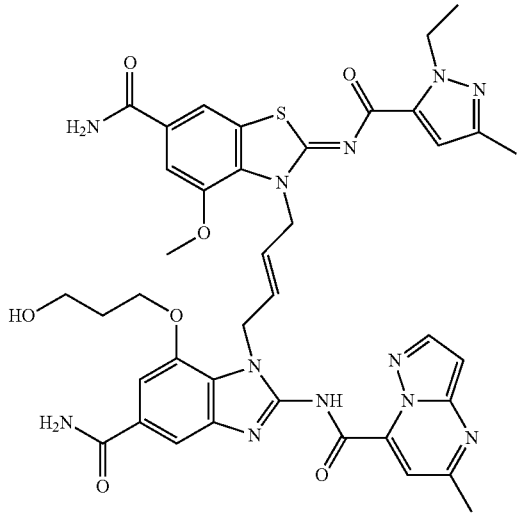 [SMILES: CCn1nc(C)cc1C(=O)/N=c1\sc2cc(C(N)=O)cc(OC)c2n1C/C=C/Cn1c(NC(=O)c2cc(C)nc3ccnn23)nc2cc(C(N)=O)cc(OCCCO)c21] | 822.25 |
| 38 | 75 | 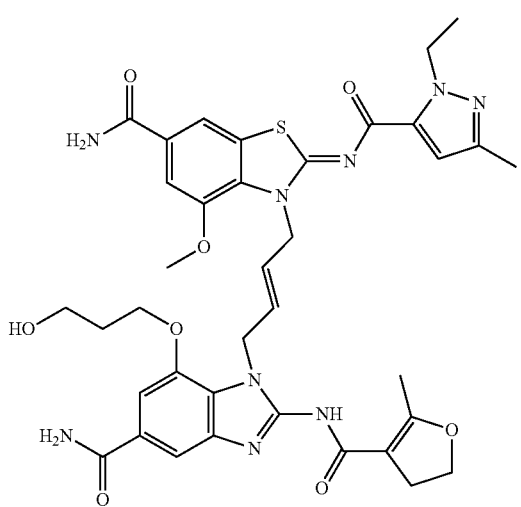 [SMILES: CCn1nc(C)cc1C(=O)/N=c1\sc2cc(C(N)=O)cc(OC)c2n1C/C=C/Cn1c(NC(=O)C2=C(C)OCC2)nc2cc(C(N)=O)cc(OCCCO)c21] | 772.30 |
| 39 | 76 | 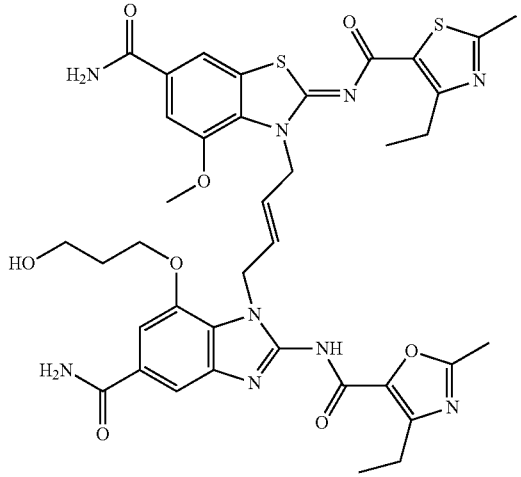 [SMILES: CCc1nc(C)oc1C(=O)Nc1nc2cc(C(N)=O)cc(OCCCO)c2n1C/C=C/Cn1/c(=N/C(=O)c2sc(C)nc2CC)sc2cc(C(N)=O)cc(OC)c21] | 816.20 |

TABLE 1-continued

| Example No | Compound No. | Structure | LCMS (M + H)+ |
|---|---|---|---|
| 40 | 84 | 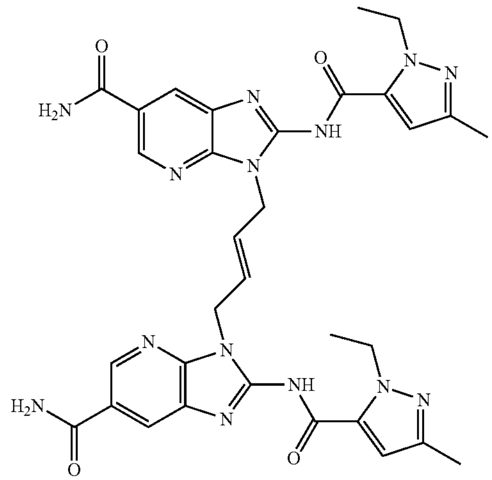 [SMILES: CCn1nc(C)cc1C(=O)Nc1nc2cc(C(N)=O)cnc2n1C/C=C/Cn1c(NC(=O)c2cc(C)nn2CC)nc2cc(C(N)=O)cnc21] | 679.20 |
| 41 | 85 | 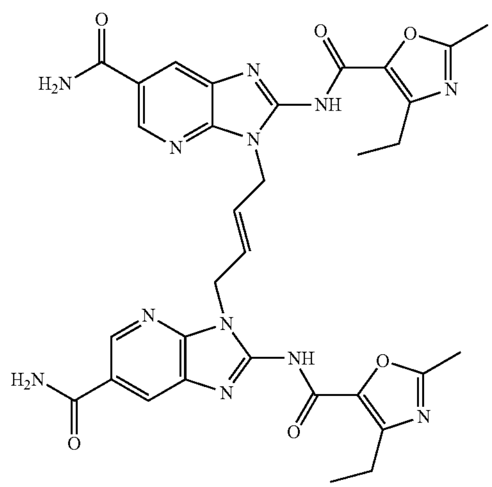 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cnc21] | 681.10 |
| 42 | 89 | 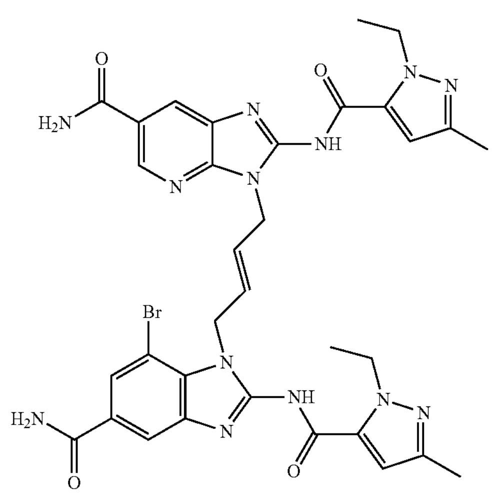 [SMILES: CCn1nc(C)cc1C(=O)Nc1nc2cc(C(N)=O)cnc2n1C/C=C/Cn1c(NC(=O)c2cc(C)nn2CC)nc2cc(C(N)=O)cc(Br)c21] | 757.20 |

TABLE 1-continued

| Example No | Compound No | Structure | LCMS (M + H)+ |
|---|---|---|---|
| 43 | 90 | 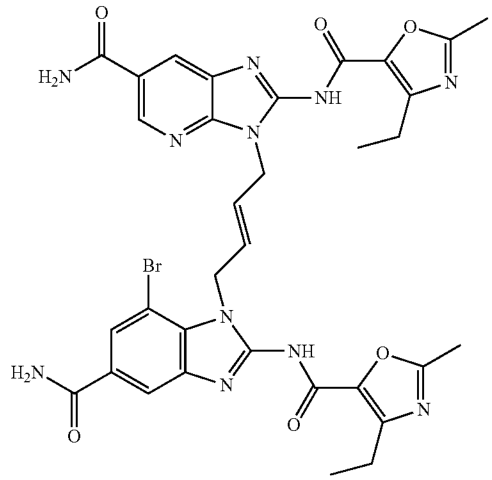 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cc(Br)c21] | 758.10 |
| 44 | 94 | 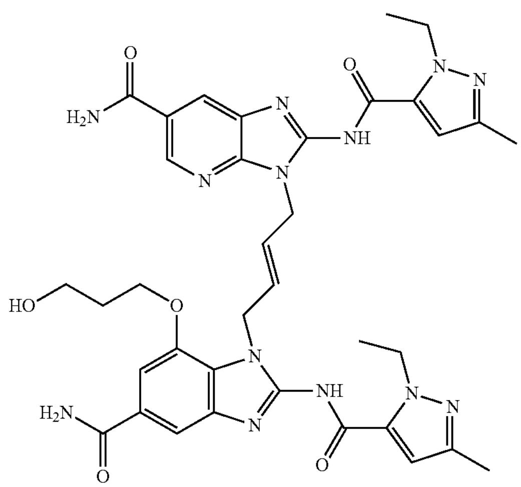 | 752.30 |
| 45 | 95 | 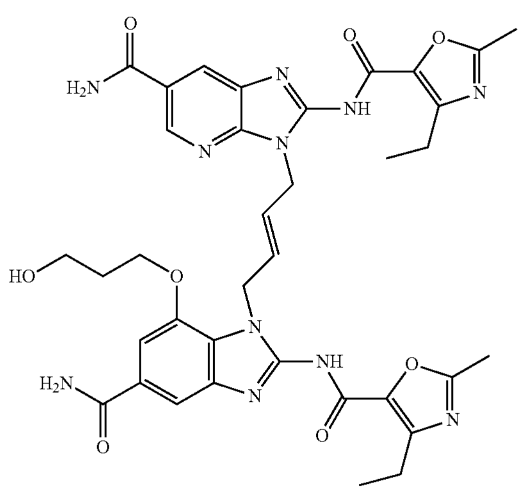 | 754.25 |

TABLE 1-continued

| Example No | Compound No. | Structure | LCMS (M + H)+ |
|---|---|---|---|
| 46 | 96 | 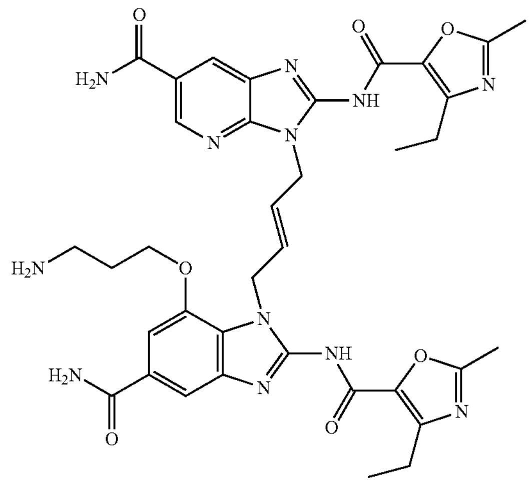 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cc(OCCCN)c21] | 753.30 |
| 47 | 97 | 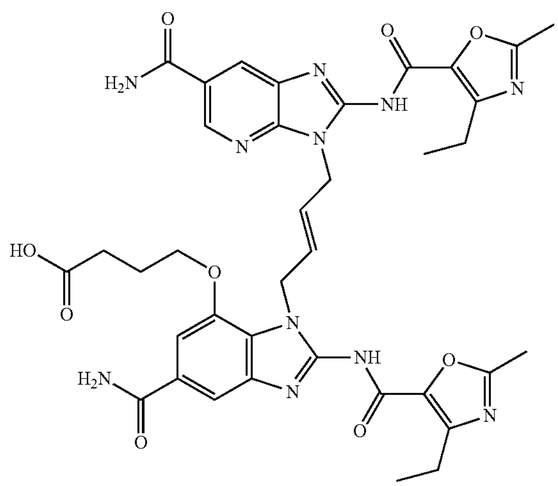 | 782.30 |
| 48 | 109 | 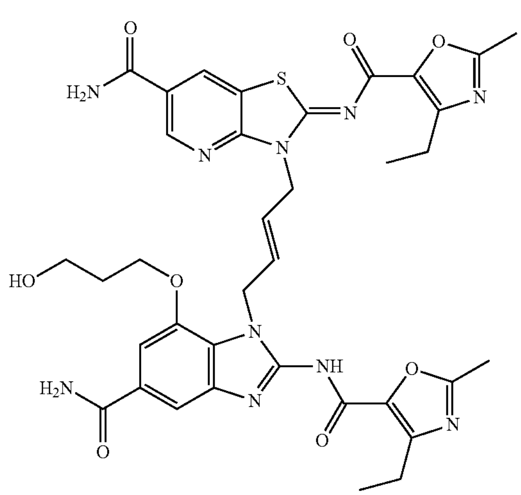 [SMILES: CCc1nc(C)oc1C(=O)/N=c1\sc2cc(C(N)=O)cnc2n1C/C=C/Cn1c(NC(=O)c2oc(C)nc2CC)nc2cc(C(N)=O)cc(OCCCO)c21] | 771.29 |

TABLE 1-continued

| Example No | Compound No. | Structure | LCMS (M + H)+ |
|---|---|---|---|
| 49 | 110 | 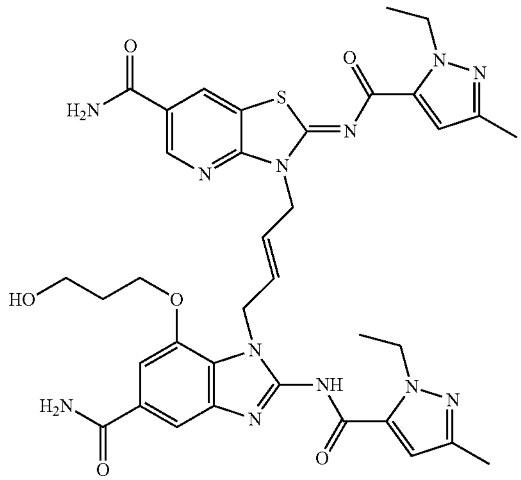 [SMILES: CCn1nc(C)cc1C(=O)/N=c1\sc2cc(C(N)=O)cnc2n1C/C=C/Cn1c(NC(=O)c2cc(C)nn2CC)nc2cc(C(N)=O)cc(OCCCO)c21] | 769.32 |
|  | 111 | | 753.34 |
|  | 112 | | 780.35 |

TABLE 1-continued

| Example No | Compound No. | Structure | LCMS (M + H)+ |
|---|---|---|---|
| | 113 | | 739.32 |
| | 114 | | 709.35 |
| | 115 | | 813.33 |

TABLE 1-continued
| Example No | Compound No. | Structure | LCMS (M + H)+ |
|---|---|---|---|
| | 116 | 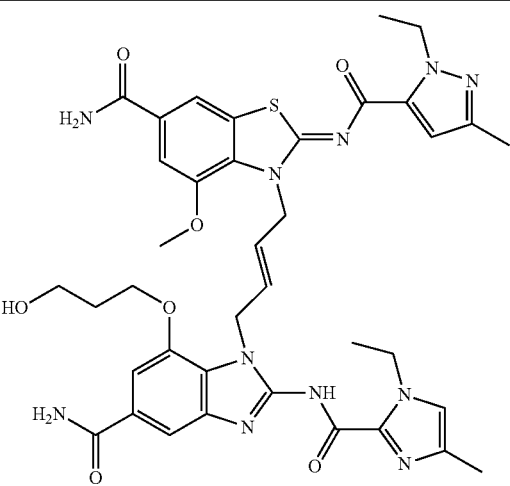 | 798.33 |
| | 117 | 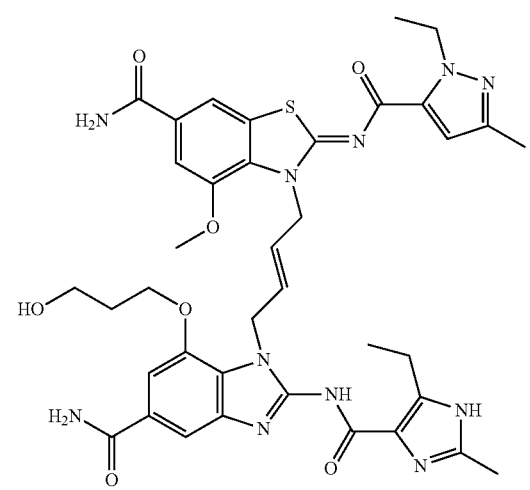 [SMILES: CCc1[nH]c(C)nc1C(=O)Nc1nc2cc(C(N)=O)cc(OCCCO)c2n1C/C=C/Cn1/c(=N/C(=O)c2cc(C)nn2CC)sc2cc(C(N)=O)cc(OC)c21] | 798.24 |
| | 118 | 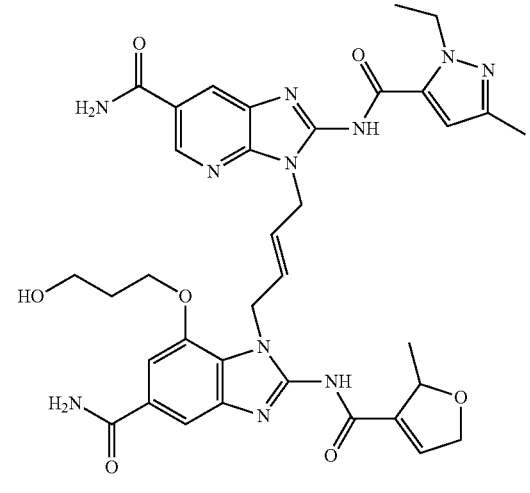 [SMILES: CCn1nc(C)cc1C(=O)Nc1nc2cc(C(N)=O)cnc2n1C/C=C/Cn1c(NC(=O)C2=CCOC2C)nc2cc(C(N)=O)cc(OCCCO)c21] | 726.31 |

TABLE 1-continued

| Example No | Compound No. | Structure | LCMS (M + H)+ |
|---|---|---|---|
| | 119 | | 775.32 |
| | 120 | | 825.38 |
| | 121 | | 753.34 |

TABLE 1-continued

| Example No | Compound No. | Structure | LCMS (M + H)+ |
|---|---|---|---|
| | 122 | | 738.29 |
| | 123 | | 767.34 |
| | 124 | | 752.34 |

TABLE 1-continued
| Example No | Compound No. | Structure | LCMS (M + H)+ |
|---|---|---|---|
| | 125 | 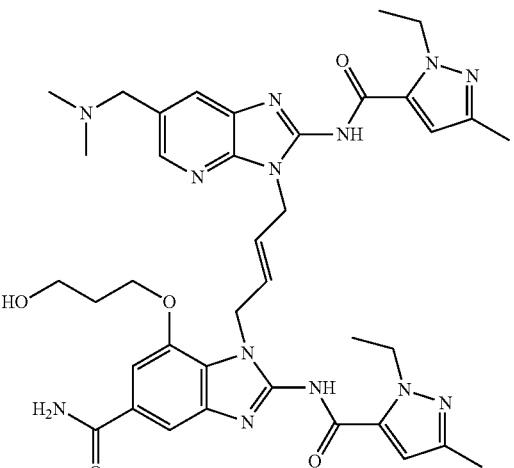 | 766.34 |
| | 126 | 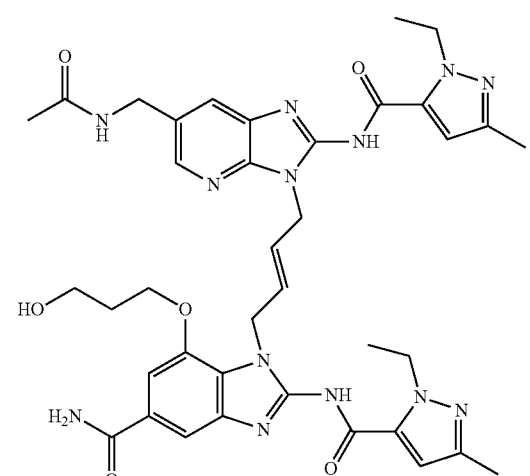 | 780.32 |
| | 127 | 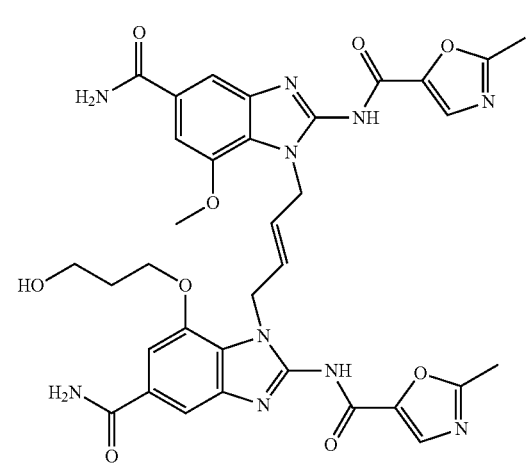 [SMILES: COc1cc(C(N)=O)cc2nc(NC(=O)c3cnc(C)o3)n(C/C=C/Cn3c(NC(=O)c4cnc(C)o4)nc4cc(C(N)=O)cc(OCCCO)c43)c12] | 727.21 |

TABLE 1-continued

| Example No | Compound No. | Structure | LCMS (M + H)+ |
|---|---|---|---|
| | 128 | | 769.28 |
| | 129 | | 694.28 |
| | 130 | | 811.28 |

TABLE 1-continued
| Example No | Compound No. | Structure | LCMS (M + H)+ |
|---|---|---|---|
| | 131 | 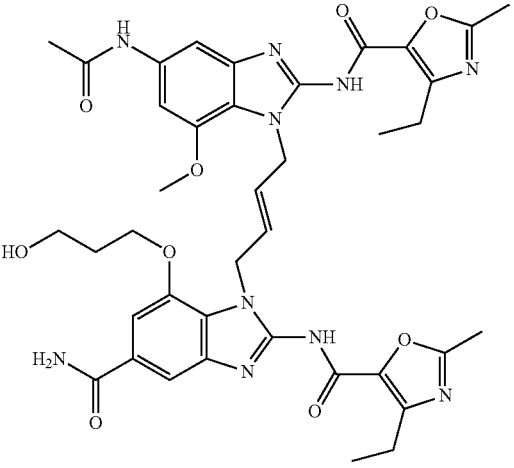 [SMILES: CCc1nc(C)oc1C(=O)Nc1nc2cc(NC(C)=O)cc(OC)c2n1C/C=C/Cn1c(NC(=O)c2oc(C)nc2CC)nc2cc(C(N)=O)cc(OCCCO)c21] | 797.27 |
| | 132 | 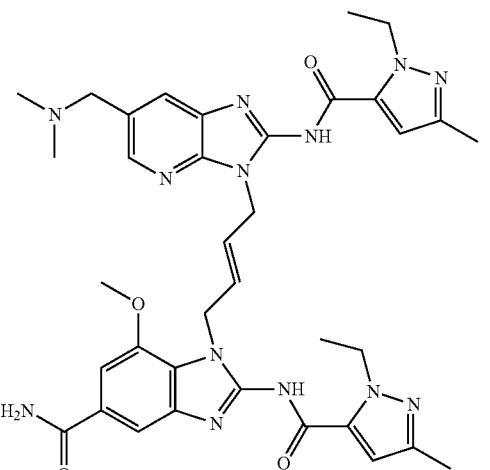 | 722.31 |
| | 133 | 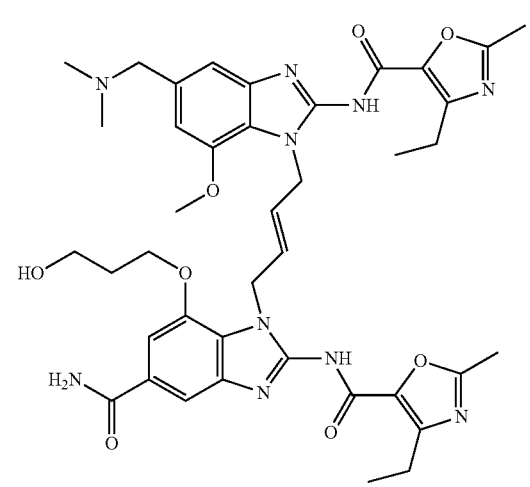 [SMILES: CCc1nc(C)oc1C(=O)Nc1nc2cc(CN(C)C)cc(OC)c2n1C/C=C/Cn1c(NC(=O)c2oc(C)nc2CC)nc2cc(C(N)=O)cc(OCCCO)c21] | 797.31 |

TABLE 1-continued
| Example No | Compound No. | Structure | LCMS (M + H)+ |
|---|---|---|---|
| | 134 | 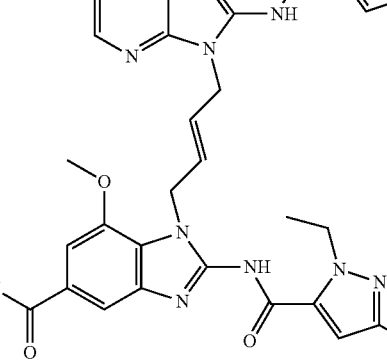 | 680.26 |
| | 135 | 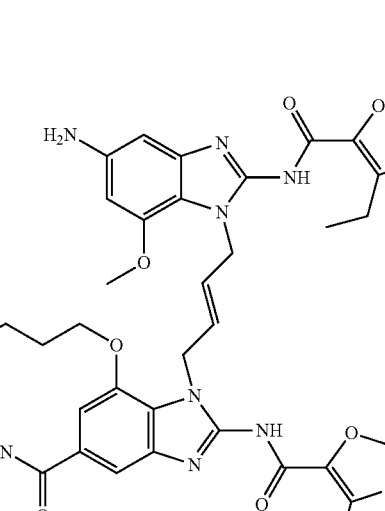 | 755.27 |
| | 136 | 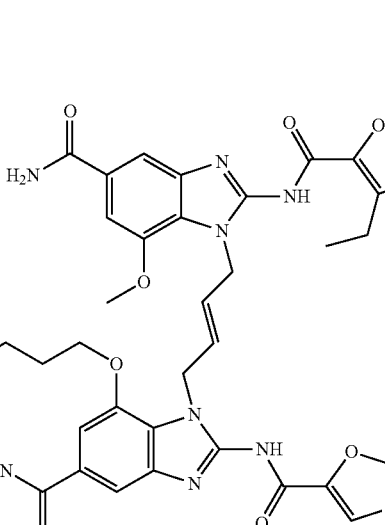 | 755.23 |

TABLE 1-continued
| Example No | Compound No. | Structure | LCMS (M + H)+ |
|---|---|---|---|
| | 137 | 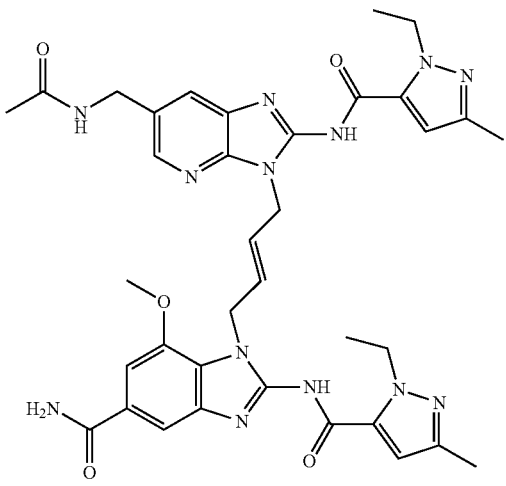 [SMILES: CCn1nc(C)cc1C(=O)Nc1nc2cc(CNC(C)=O)cnc2n1C/C=C/Cn1c(NC(=O)c2cc(C)nn2CC)nc2cc(C(N)=O)cc(OC)c21] | 736.28 |
| | 138 | 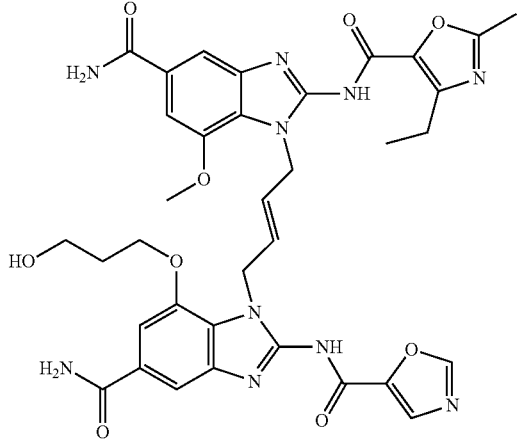 [SMILES: CCc1nc(C)oc1C(=O)Nc1nc2cc(C(N)=O)cc(OC)c2n1C/C=C/Cn1c(NC(=O)c2cnco2)nc2cc(C(N)=O)cc(OCCCO)c21] | 741.21 |
| | 139 | 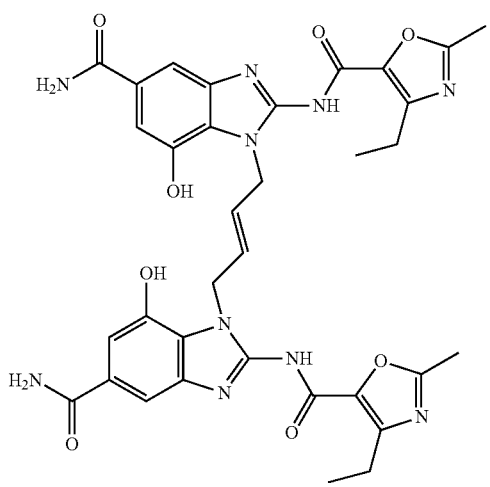 [SMILES: CCc1nc(C)oc1C(=O)Nc1nc2cc(C(N)=O)cc(O)c2n1C/C=C/Cn1c(NC(=O)c2oc(C)nc2CC)nc2cc(C(N)=O)cc(O)c21] | 711.12 |

TABLE 1-continued
| Example No | Compound No. | Structure | LCMS (M + H)+ |
|---|---|---|---|
| | 140 | 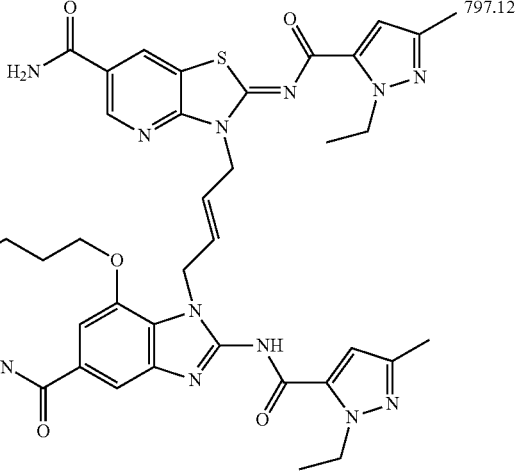 | 797.12 |
| | 141 | 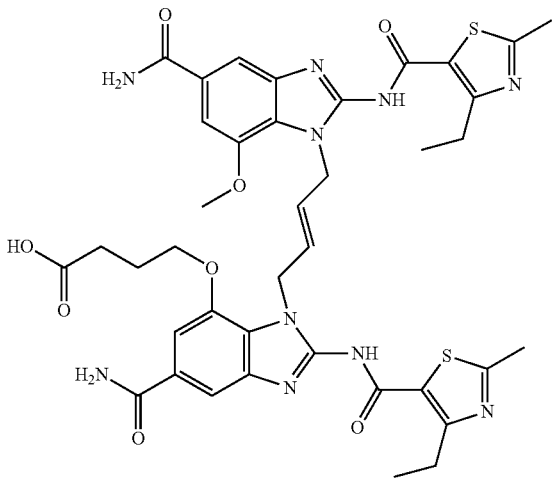 | 843.10 |
| | 142 | 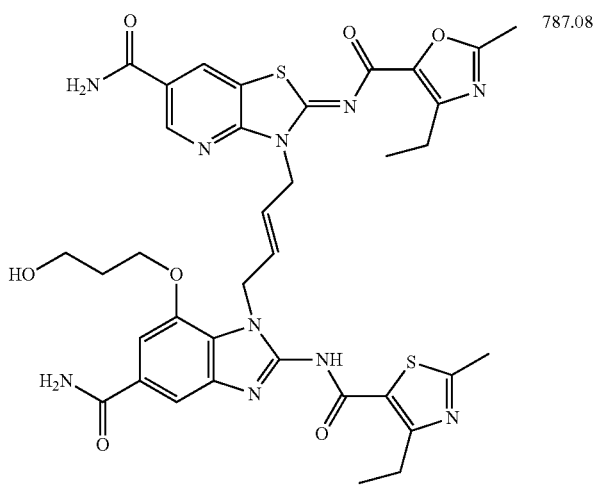 | 787.08 |

TABLE 1-continued

| Example No | Compound No | Structure | LCMS (M + H)⁺ |
|---|---|---|---|
| | 143 | | 770.13 |
| | 144 | | 786.10 |
| | 145 | | |

TABLE 1-continued

| Example No | Compound No. | Structure | LCMS (M + H)+ |
|---|---|---|---|
| 50 | 146 | 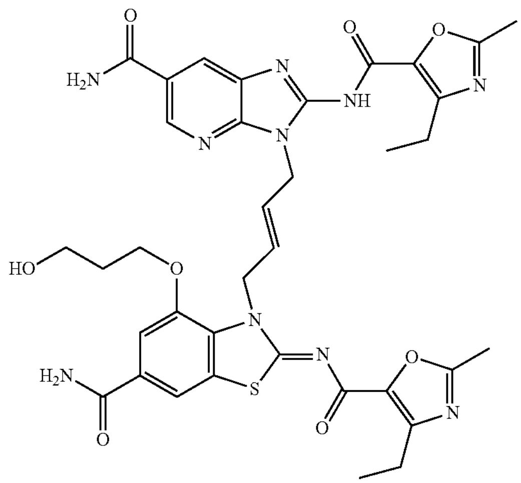 [SMILES: CCc1nc(C)oc1C(=O)/N=c1\sc2cc(C(N)=O)cc(OCCCO)c2n1C/C=C/Cn1c(NC(=O)c2oc(C)nc2CC)nc2cc(C(N)=O)cnc21] | 771.30 |
| | 147 | | 769.13 |
| 50a | 148 | 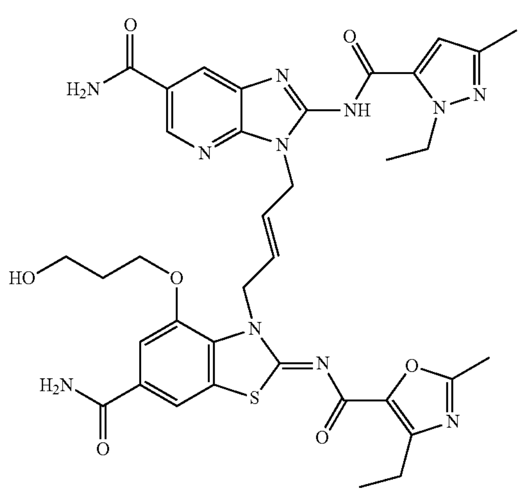 [SMILES: CCc1nc(C)oc1C(=O)/N=c1\sc2cc(C(N)=O)cc(OCCCO)c2n1C/C=C/Cn1c(NC(=O)c2cc(C)nn2CC)nc2cc(C(N)=O)cnc21] | 770.13 |

TABLE 1-continued
| Example No | Compound No. | Structure | LCMS (M + H)+ |
|---|---|---|---|
| | 149 | 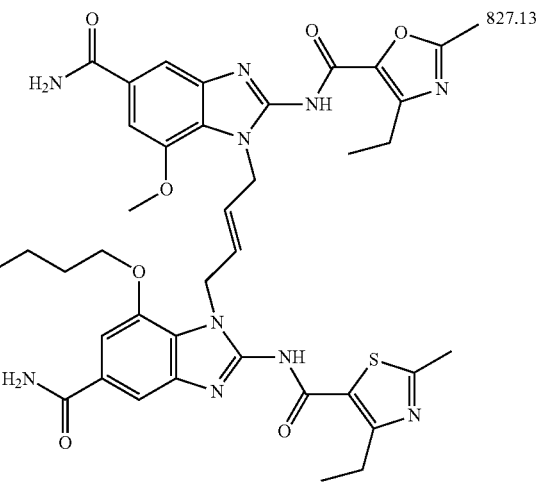 | 827.13 |
| | 150 | 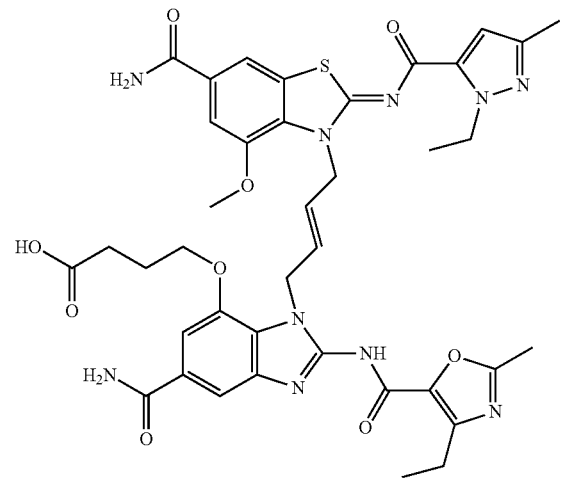 [SMILES: CCc1nc(C)oc1C(=O)Nc1nc2cc(C(N)=O)cc(OCCCC(=O)O)c2n1C/C=C/Cn1/c(=N/C(=O)c2cc(C)nn2CC)sc2cc(C(N)=O)cc(OC)c21] | 827.13 |
| | 151 | 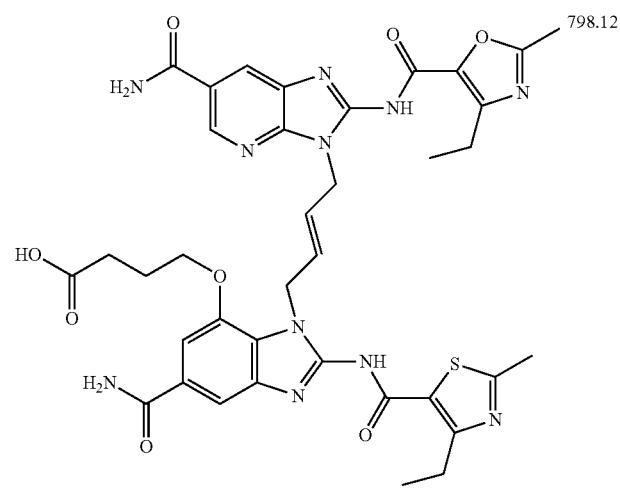 | 798.12 |

TABLE 1-continued

| Example No | Compound No. | Structure | LCMS (M + H)+ |
|---|---|---|---|
| | 152 | | |
| | 153 | | |
| | 154 | | |

TABLE 1-continued

| Example No | Compound No. | Structure | LCMS (M + H)+ |
|---|---|---|---|
| | 155 | | 799.11 |
| 51 | 167 | 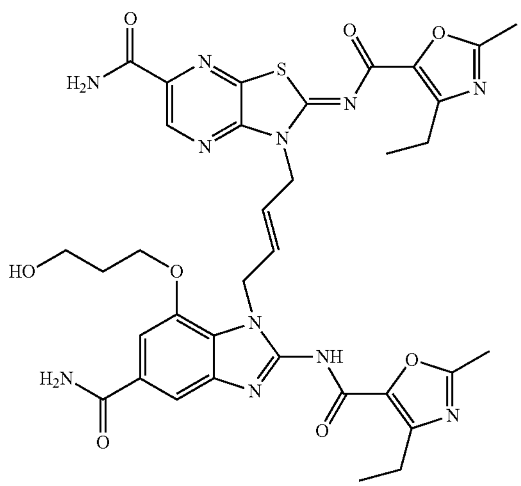 [SMILES: CCc1nc(C)oc1C(=O)/N=c1\sc2nc(C(N)=O)cnc2n1C/C=C/Cn1c(NC(=O)c2oc(C)nc2CC)nc2cc(C(N)=O)cc(OCCCO)c21] | 772.25 |
| 52 | 181 | 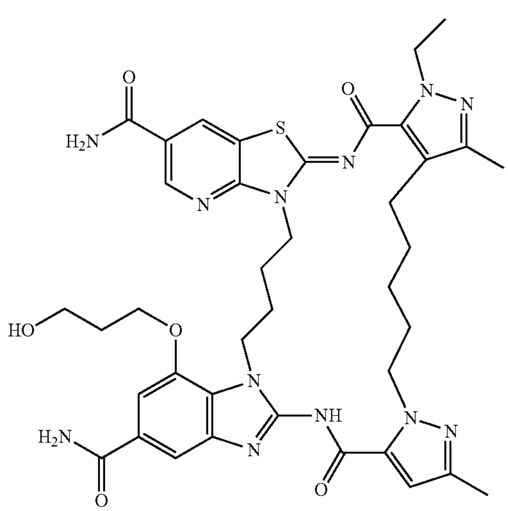 [SMILES: CCn1nc(C)c2c1C(=O)/N=C1\Sc3cc(C(N)=O)cnc3N1CCCCn1c(nc3cc(C(N)=O)cc(OCCCO)c31)NC(=O)c1cc(C)nn1CCCCC2] | 811.40 |

TABLE 1-continued
| Example No | Compound No. | Structure | LCMS (M + H)+ |
|---|---|---|---|
| | 182 | 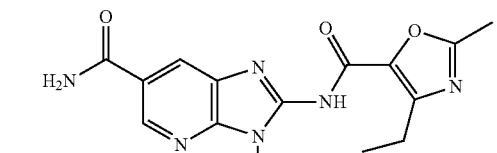 | |
In some embodiments, the compounds of the disclosure is compound:
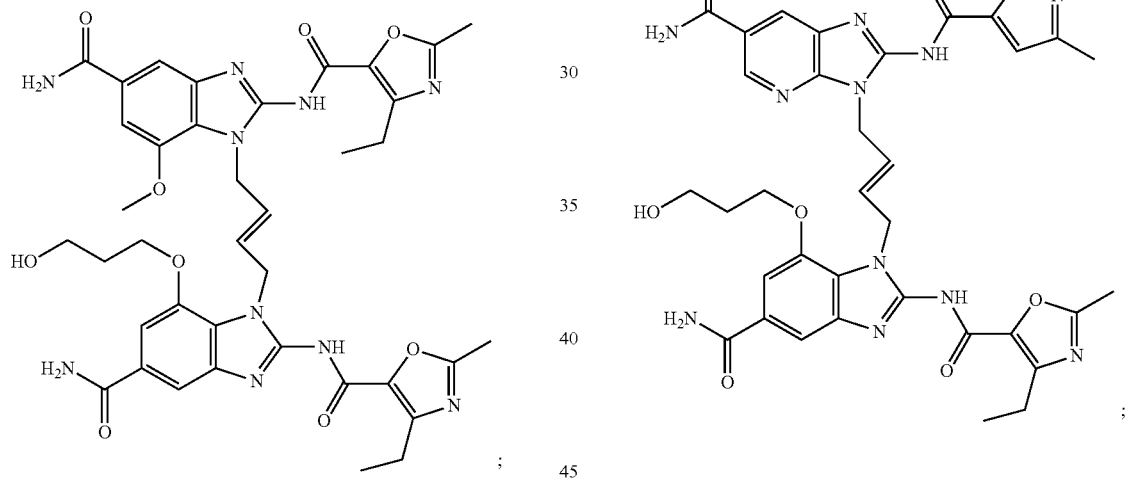
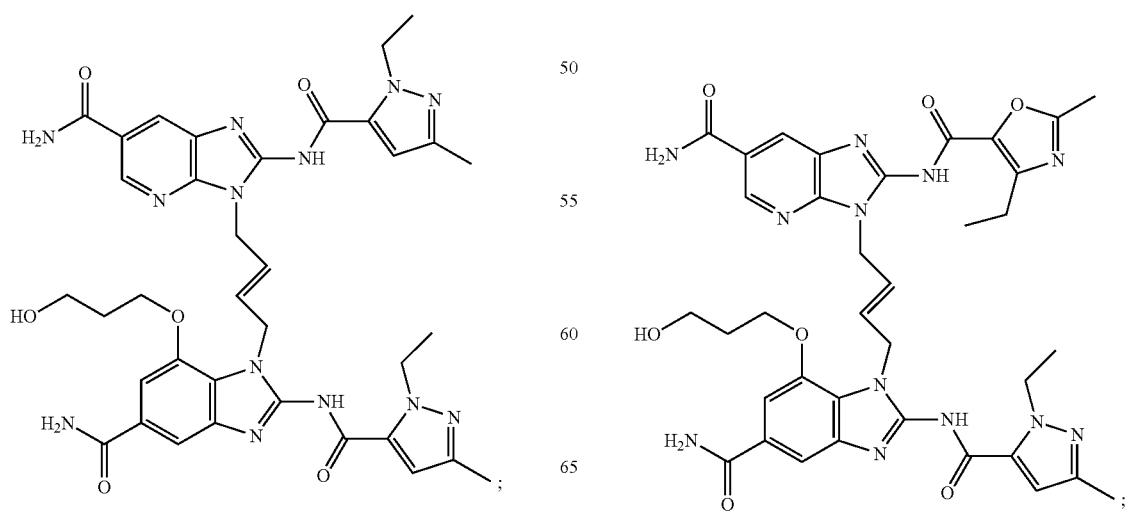

193
-continued
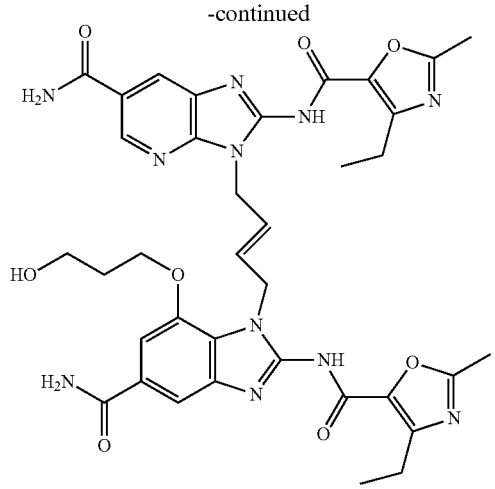
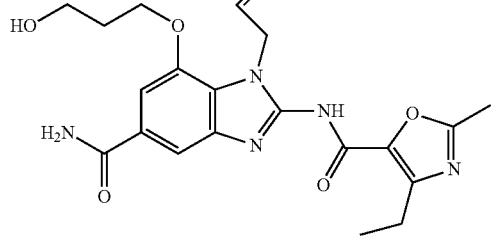
194
-continued
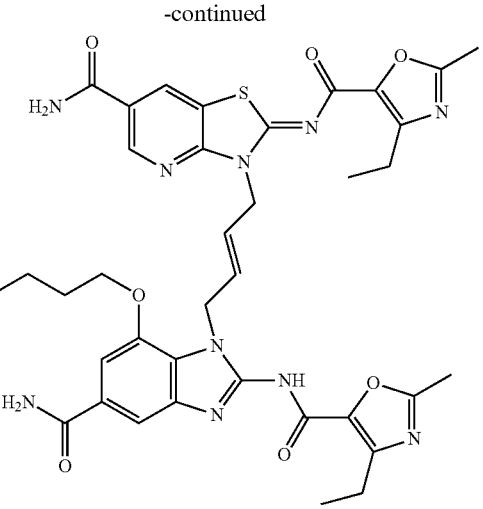
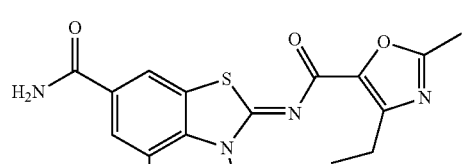
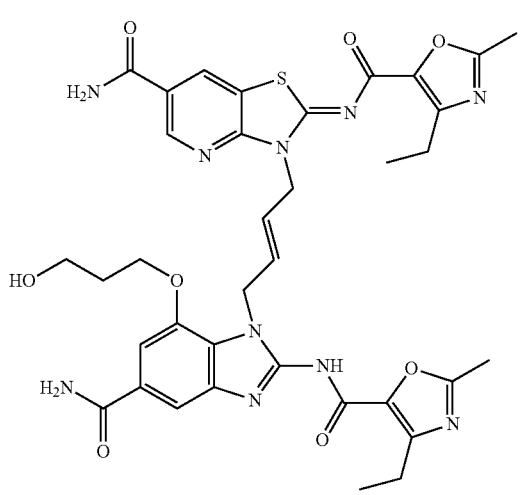
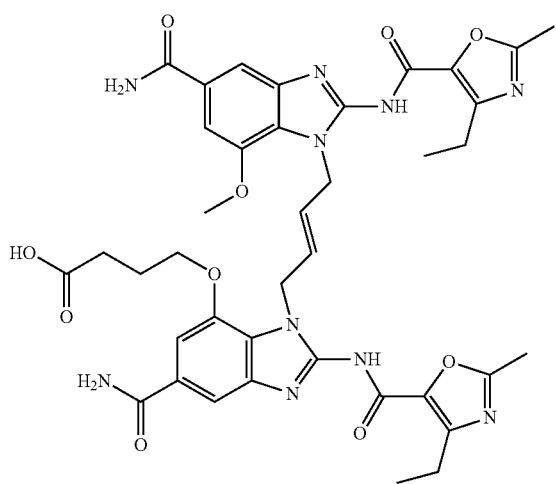
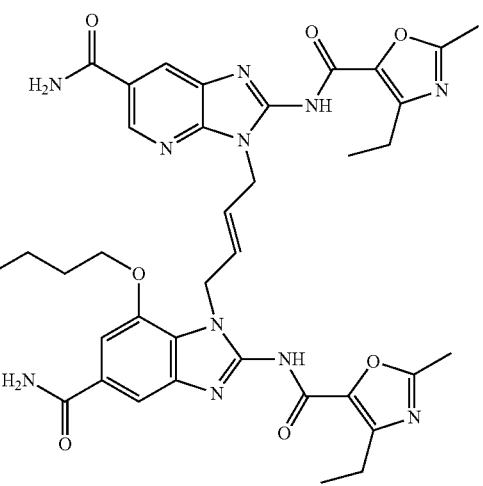

195
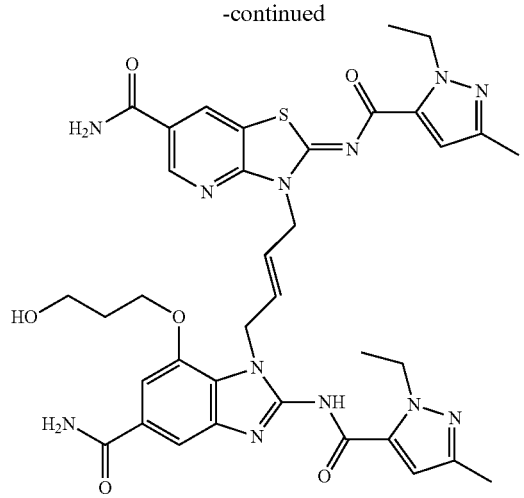
;
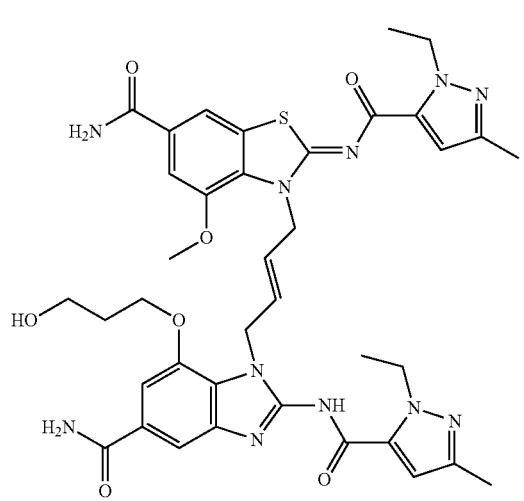
;
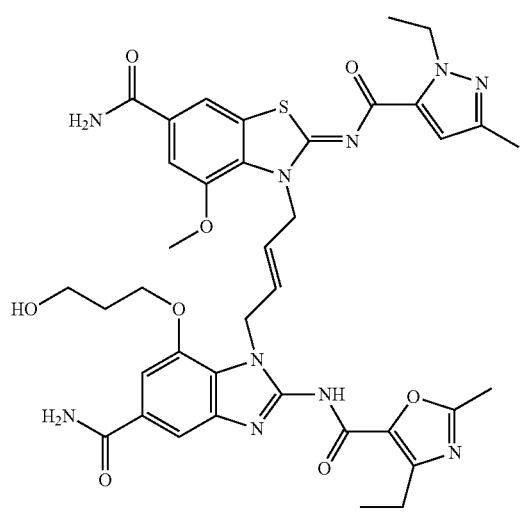
;
196
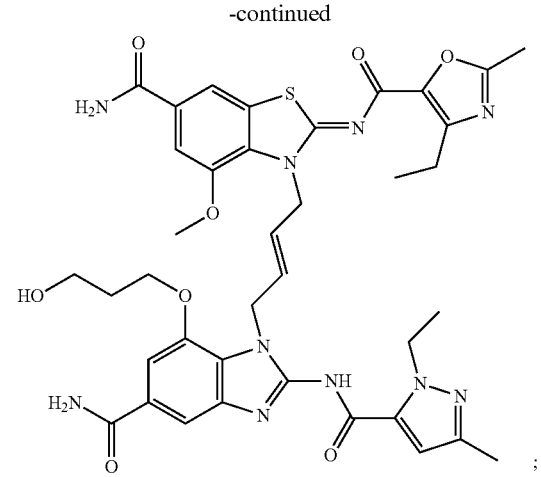
;
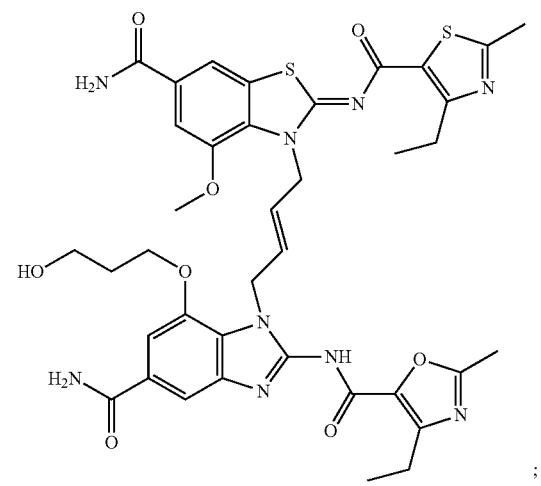 [SMILES: CCc1nc(C)oc1C(=O)/N=c1\sc2nc(C(N)=O)cnc2n1C/C=C/Cn1c(NC(=O)c2oc(C)nc2CC)nc2cc(C(N)=O)cc(OCCCO)c21]
;
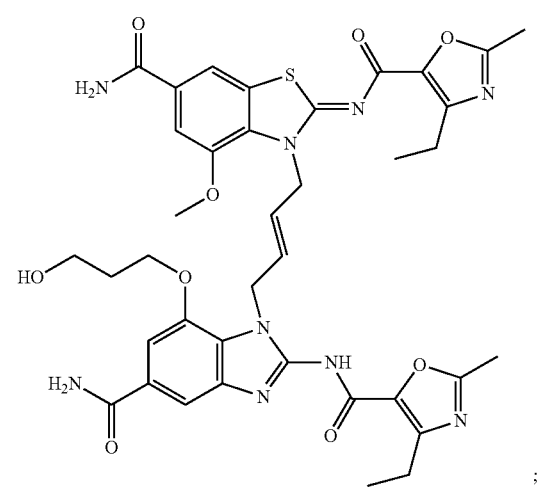
;

197
-continued
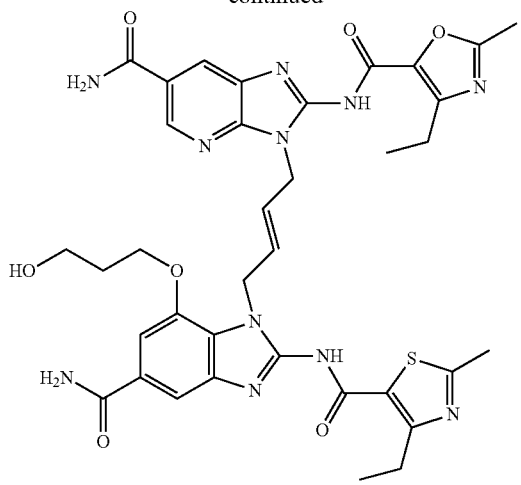
198
-continued
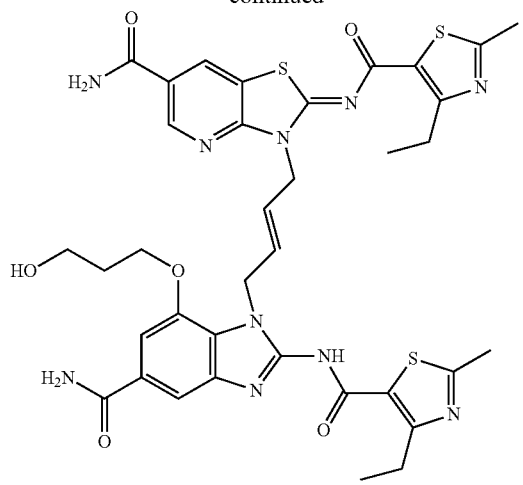
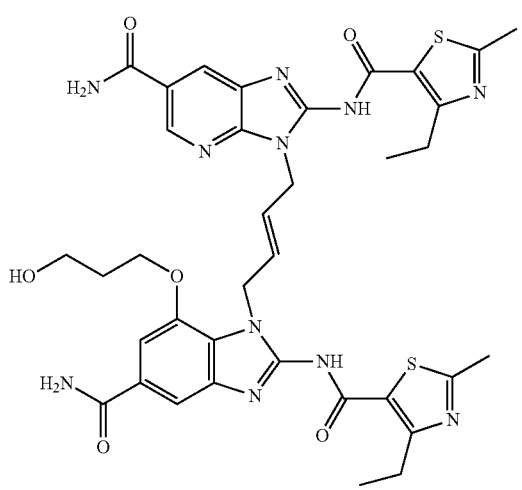
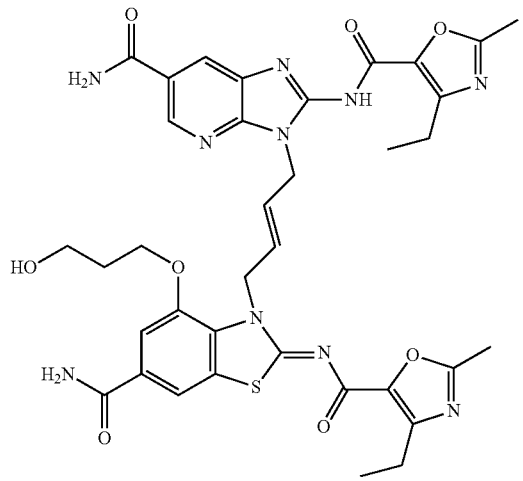
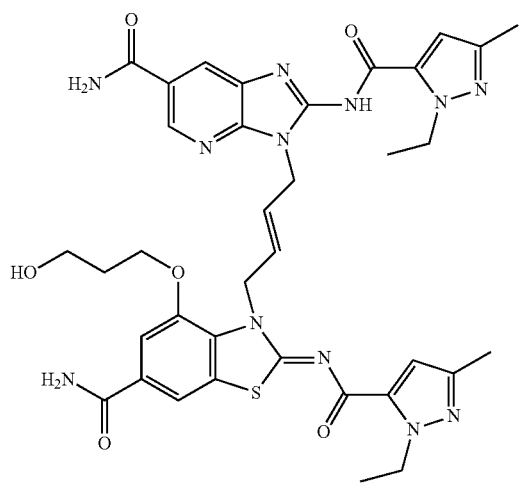

199
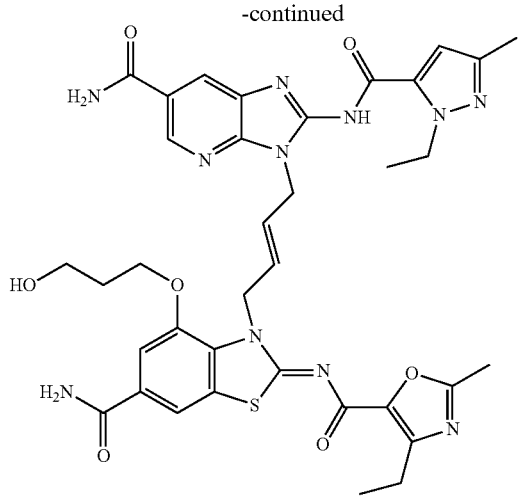
; or
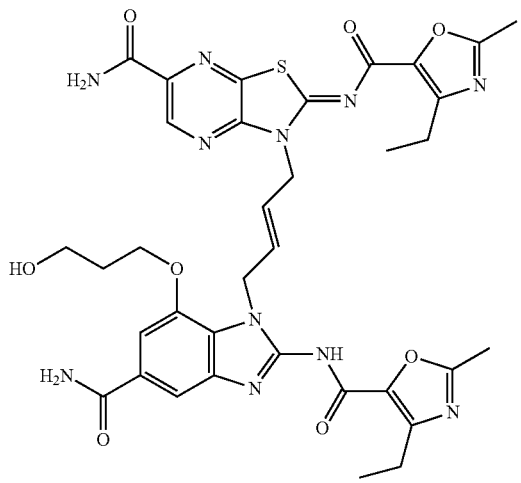
;
or a prodrug, solvate, pharmaceutically acceptable salt, or tautomer thereof.
In some embodiments, the compounds of the disclosure is compound:
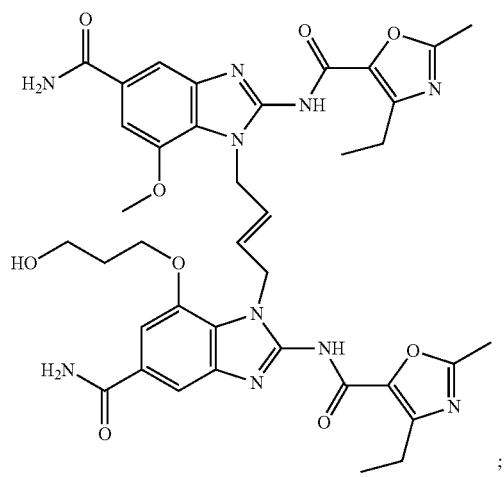
;
200
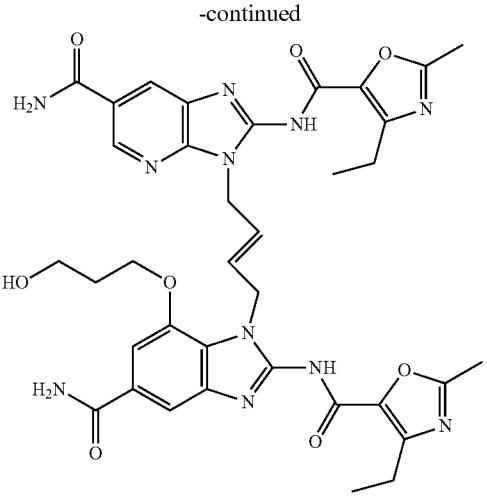
;
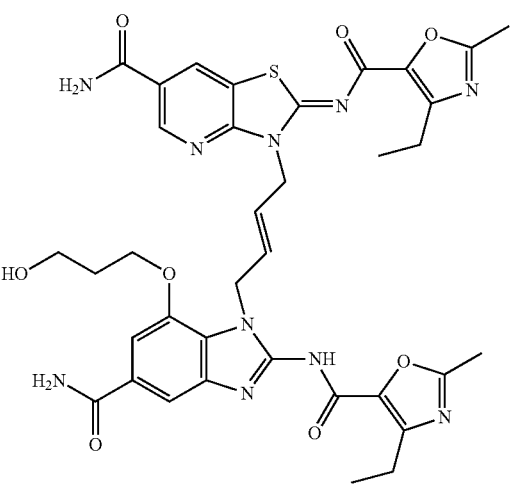
;
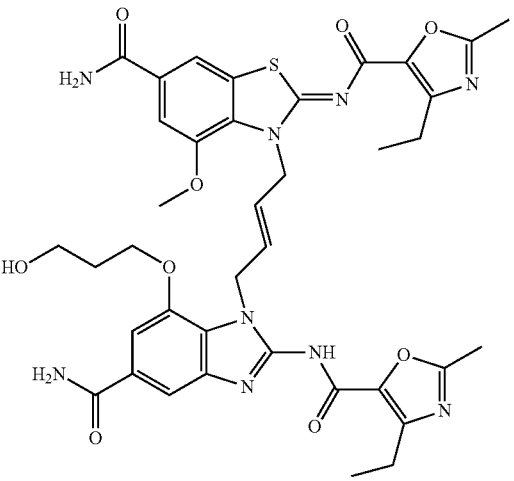
;

201
-continued
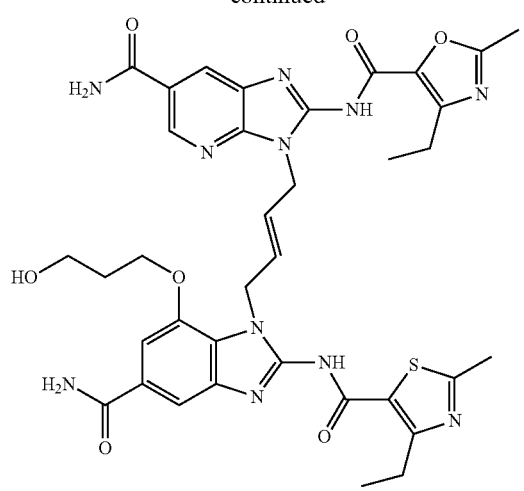
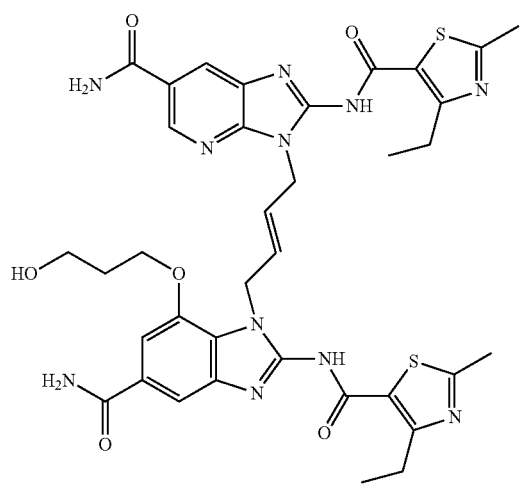
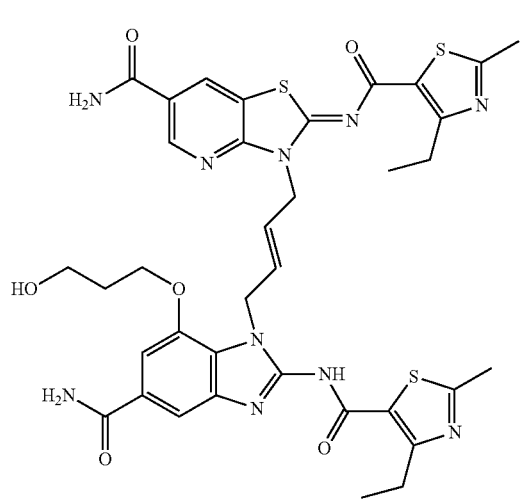
202
-continued
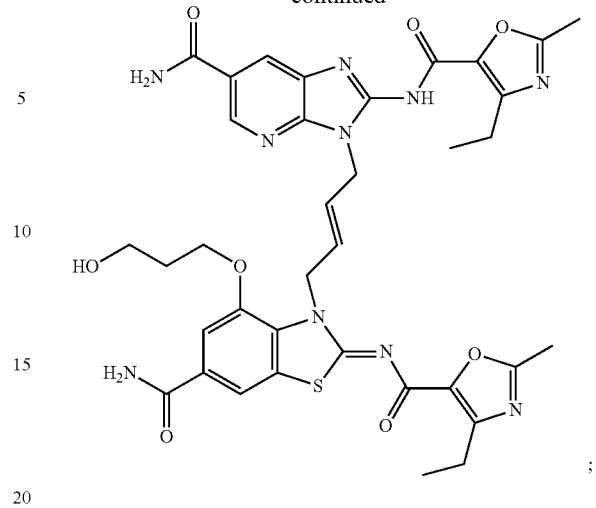
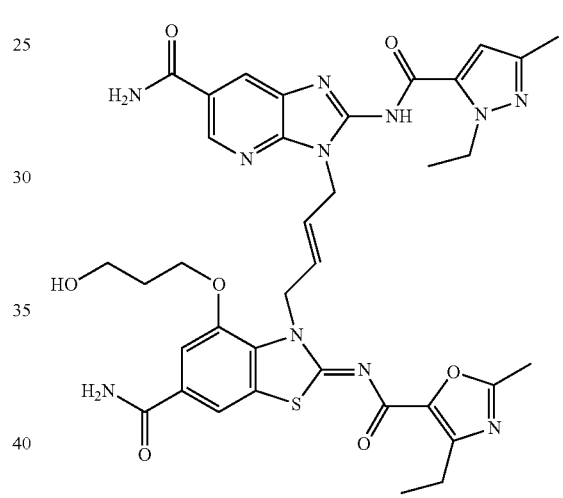
;  or
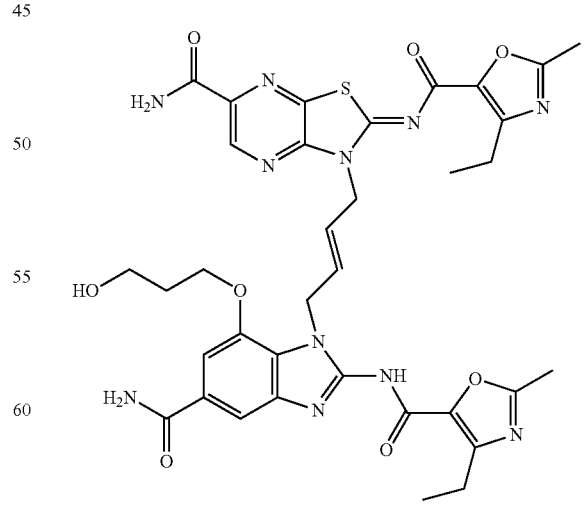
,
or a prodrug, solvate, pharmaceutically acceptable salt, or tautomer thereof.

In some embodiments, the compounds of the disclosure is compound:

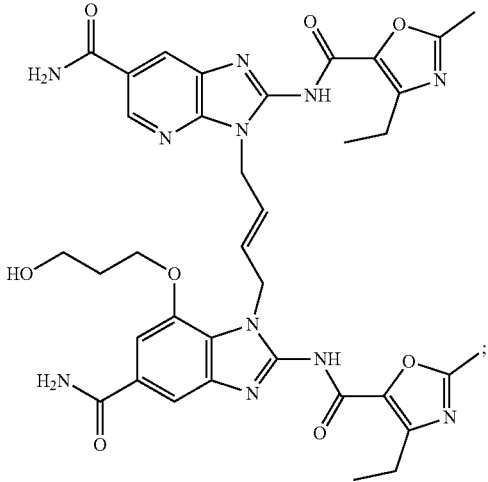

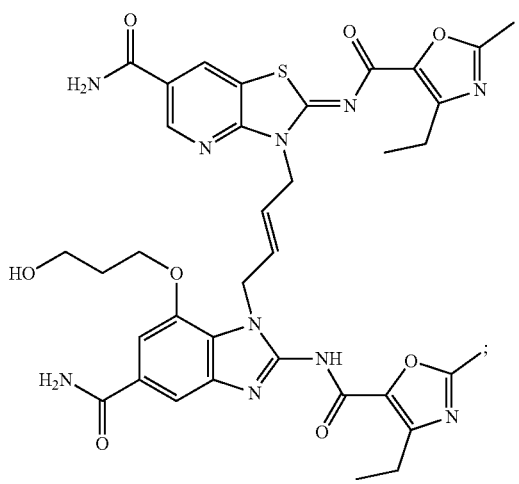

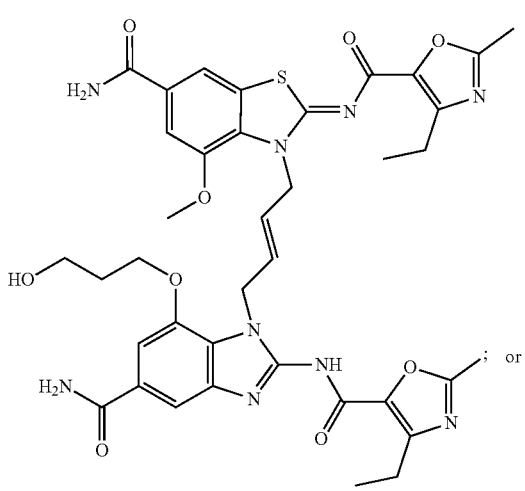

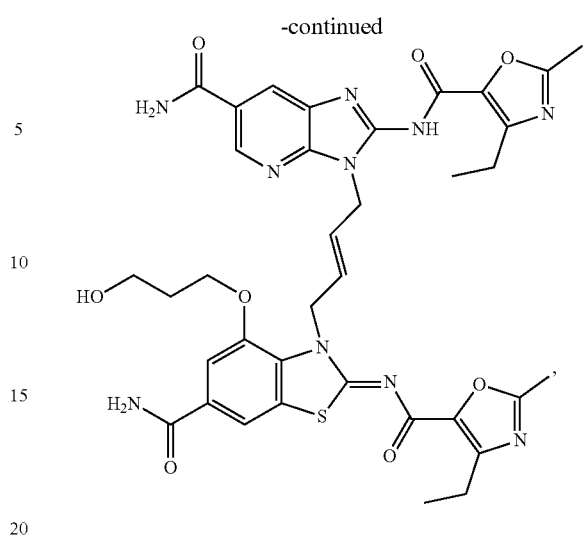

or a prodrug, solvate, pharmaceutically acceptable salt, or tautomer thereof.

In some embodiments, the compound of the disclosure is Example No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 38, 39, 40, 41, 42, 43, 44, 45, 46, 47, 48, 49, 50, 50a, 51, or 52 or Compound No. 111, 112, 113, 114, 115, 116, 117, 118, 120, 121, 122, 123, 124, 125, 126, 127, 128, 129, 130, 131, 132, 133, 134, 135, 136, 137, 138, 139, 140, 141, 142, 143, 144, 145, 147, 149, 150, 151, 152, 153, 154, 155, or 182. In some embodiments, the compound of the disclosure is Example No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, or 49, or Compound No. 111, 112, 113, 114, 115, 116, 117, 118, 120, 121, 122, 123, 124, 125, 126, 127, 128, 129, 130, 131, 132, 133, 134, 135, 136, 137, 138. In some embodiments, the compound of the disclosure is Compound No. 139, 140, 141, 142, 143, 144, 145, 146, 147, 148, 149, 150, 151, 152 or 153. In some embodiments, the compound of the disclosure is Compound No. 63, 95, 109, 135, 143, 144, 145, 146, or 148. In some embodiments, the compound of the disclosure is Compound No. 63, 95, 109, 135, 145, or 146. In some embodiments, the compound of the disclosure is Compound No. 143, 144, or 148.

In some embodiments, the compound of the disclosure is Example No. 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, 49, 50, 50a, 51, or 52 or Compound No. 111, 112, 113, 114, 115, 116, 117, 118, 120, 121, 122, 123, 124, 125, 126, 127, 128, 129, 130, 131, 132, 133, 134, 135, 136, 137, 138, 140, 141, 142, 143, 144, 145, 147, 149, 150, 151, 152, 153, 154, 155, or 182. In some embodiments, the compound of the disclosure is Example No. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, or 49, or Compound No. 111, 112, 113, 114, 115, 116, 117, 118, 120, 121, 122, 123, 124, 125, 126, 127, 128, 129, 130, 131, 132, 133, 134, 135, 136, 137, 138. In some embodiments, the compound of the disclosure is Compound No. 140, 141, 142, 143, 144, 145, 146, 147, 148, 149, 150, 151, 152 or 153.

In some embodiments, the compound of the disclosure is Example No. 37 (i.e., Compound No. 74) or Compound No. 119.

In some embodiments, the compound of the disclosure is Example No. 26 (i.e., Compound No. 63), Example No. 45 (i.e., Compound No. 95), Example No. 48 (i.e., Compound No. 109), or Example No. 50 (i.e., Compound No. 146).

In some embodiments, the compound of the disclosure is Example No. 45 (i.e., Compound No. 95) or Example No. 48 (i.e., Compound No. 109).

In some embodiments, the compound of the disclosure is Example No. 26 (i.e., Compound No. 63).

In some embodiments, the compound of the disclosure is Example No. 45 (i.e., Compound No. 95).

In some embodiments, the compound of the disclosure is Example No. 48 (i.e., Compound No. 109).

In some embodiments, the compound of the disclosure is Example No. 50 (i.e., Compound No. 146).

The compounds of this disclosure may contain one or more asymmetric centers (also referred to as a chiral center), such as a chiral carbon, or a chiral —SO— moiety. Compounds of this disclosure comprising one or more chiral centers may be present as racemic mixtures, diastereomeric mixtures, enantiomerically enriched mixtures, diastereomerically enriched mixtures, or as enantiomerically or diastereomerically pure individual stereoisomers.

The stereochemistry of the chiral center present in compounds of this disclosure are generally represented in the compound names and/or in the chemical structures illustrated herein. Where the stereochemistry of a chiral center present in a compound of this disclosure, or in any chemical structure illustrated herein, is not specified, the structure is intended to encompass any stereoisomer and all mixtures thereof. Accordingly, the present disclosure encompasses all isomers of the compounds of any one or more of Formula (I'), (IA'), (II'), (III'), (IV') or (V'), and salts thereof, whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Individual stereoisomers of a compound of this disclosure may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The disclosure also includes various deuterated forms of the compounds of this disclosure. Each available hydrogen atom attached to a carbon atom may be independently replaced with a deuterium atom. A person of ordinary skill in the art will know how to synthesize deuterated forms of the compounds of this disclosure. For example, α-deuterated α-amino acids are commercially available or may be prepared by conventional techniques (see for example: Elemes, Y. and Ragnarsson, U. J. Chem. Soc, Perkin Trans, 1, 1996, 6, 537-40). Employing such compounds may allow for the preparation of compounds in which the hydrogen atom at a chiral center is replaced with a deuterium atom. Other commercially available deuterated starting materials may be employed in the preparation of deuterated analogs of the compounds of this disclosure (see for example: methyl-$d_3$-amine available from Aldrich Chemical Co., Milwaukee, WI), or they may be synthesized using conventional techniques employing deuterated reagents (e.g. by reduction using lithium aluminum deuteride or sodium borodeuteride or by metal-halogen exchange followed by quenching with $D_2O$ or methanol-$d_3$)

Suitable pharmaceutically acceptable salts of the compounds of any one or more of Formula (I'), (IA'), (II'), (III'), (IV') or (V'), can include acid addition salts or base addition salts. For reviews of suitable pharmaceutically acceptable salts see Berge et al., J. Pharm. Sci., 66:1-19, (1977) and P. H. Stahl and C. G. Wermuth, Eds., Handbook of Pharmaceutical Salts: Properties, Selection and Use, Weinheim/Zurich:Wiley-VCH/VHCA (2002).

Salts of the compounds of any one or more of Formula (I'), (IA'), (II'), (III'), (IV') or (V'), comprising a basic amine or other basic functional group may be prepared by any suitable method known in the art, such as treatment of the free base with a suitable inorganic or organic acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecyl sulfate (estolate), ethane-1,2-di sulfonate (edisylate), ethane sulfonate (esylate), formate, fumarate (hemifumarate, etc.), galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride (dihydrochloride, etc.), hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate (diphosphate, etc.), proprionate, pyroglutamate, salicylate, sebacate, stearate, succinate, sulfate, tartrate, thiocyanate, p-toluenesulfonate (tosylate), undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate.

Salts of the disclosed compounds comprising a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N- bisdehydroabietylamine, glucamine, N-methylglucamine, collidine, choline, quinine, quinoline, and basic amino acids such as lysine and arginine.

The disclosure includes within its scope all possible stoichiometric and non-stoichiometric forms of the salts (e.g., hydrobromide, dihydrobromide, fumarte, hemifumarate, etc) of the compounds of any one or more of Formula (I'), (IA'), (II'), (III'), (IV') or (V').

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that the disclosure includes all polymorphs of any compound of this disclosure, e.g., all polymorphic forms of any compound named or depicted by structure herein, including any salts and/or solvates (particularly, hydrates) thereof.

Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the conditions used in crystallizing/recrystallizing the compound. Polymorphic forms may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The skilled artisan will appreciate that pharmaceutically acceptable solvates (particularly, hydrates) of a compound of any one or more of Formula (I'), (IA'), (II'), (III'), (IV') or (V'), including pharmaceutically acceptable solvates of a pharmaceutically acceptable salt of a compound of any one or more of Formula (I'), (IA'), (II'), (III'), (IV') or (V'), may be formed when solvent molecules are incorporated into the crystalline lattice during crystallization. Solvates may involve non-aqueous solvents such as ethanol, or they may involve water as the solvent that is incorporated into the crystalline lattice. Solvates wherein water is the solvent that is incorporated into the crystalline lattice are typically referred to as "hydrates."

The present disclosure includes within its scope all possible stoichiometric and non-stoichiometric salt and/or hydrate forms.

Salts and solvates (e.g. hydrates and hydrates of salts) of the compounds of the disclosure which are suitable for use in medicine are those wherein the counterion or associated solvent is pharmaceutically acceptable. Salts having non-pharmaceutically acceptable counterions are within the scope of the present disclosure, for example, for use as intermediates in the preparation of other compounds of the disclosure.

Typically, a pharmaceutically acceptable salt may be readily prepared by using a desired acid or base as appropriate. The resultant salt may crystallize or precipitate from solution, or form by trituration, and may be recovered by filtration, or by evaporation of the solvent.

Because the compounds of this disclosure are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the purer forms used in the pharmaceutical compositions.

The disclosure encompasses all prodrugs of the compounds of this disclosure, which upon administration to the recipient are capable of providing (directly or indirectly) a compound of this disclosure, or an active metabolite or residue thereof. Such derivatives are recognizable to those skilled in the art, without undue experimentation. Nevertheless, reference is made to the teaching of Burger's Medicinal Chemistry and Drug Discovery, $5^{th}$ Edition, Vol 1: Principles and Practice, which is incorporated herein by reference to the extent of teaching such derivatives.

It is to be further understood that the present disclosure includes within its scope all tautomeric or isomer forms of any free base form of the compounds of this disclosure as well as all possible stoichiometric and non-stoichiometric salt forms. The compounds of the disclosure are useful in the treatment or prevention of diseases and disorders in which modulation of STING is beneficial. Such STING mediated diseases and disorders include inflammation, allergic and autoimmune diseases, infectious diseases, cancer and precancerous syndromes. The compounds of the disclosure are also useful as an immunogenic composition or vaccine adjuvant. Accordingly, this disclosure is directed to a method of modulating STING comprising contacting a cell with a compound of the disclosure.

Methods of Use

In some embodiments, this disclosure provides a compound for use in an antibody-STING agonist candidate. In some embodiments, the antibody-STING agonist conjugate contains a linker. The disclosure further provides an antibody-STING agonist conjugate for use in therapy. The disclosure further provides the use of an antibody-STING agonist conjugate indicated above for the manufacture of a medicament. In some embodiments, the STING agonist has, or is modified to include, a group reactive with a conjugation point on an antibody.

One aspect of the disclosure provides methods of treatment or prevention of STING mediated diseases and disorders, in which agonizing STING is beneficial. Exemplary diseases/disorders include, but are not limited to, cancer, infectious disease (e.g., HIV, HBV, HCV, HPV, and influenza), vaccine adjuvant.

In some embodiments, the STING pathway may induce anti-tumor immunity by upregulating IFNβ and interferon (IFN)-stimulated genes (ISGs) in many cell types within tumors in response to agonistic, cytosolic nucleic acids.

In some embodiments, this disclosure provides a compound of the disclosure for use in therapy. This disclosure also provides a compound of any one or more of Formula (I'), (IA'), (II'), (III'), (IV'), or (V'), or a pharmaceutically acceptable salt thereof, for use in therapy. This disclosure particularly provides a compound of any one or more of Formula (I'), (IA'), (II'), (III'), (IV'), or (V'), or a pharmaceutically acceptable salt thereof, for use in the treatment of a STING-mediated disease or disorder.

This disclosure also provides a compound of any one or more of Formula (I'), (IA'), (II'), (III'), (IV'), or (V'), or a pharmaceutically acceptable salt thereof, for use as a vaccine adjuvant. There is also therefore provided an immunogenic composition or vaccine adjuvant comprising a compound of any one or more of Formula (I'), (IA'), (II'), (III'), (IV'), or (V'), or a pharmaceutically acceptable salt thereof.

In a further embodiment of the disclosure, there is provided a composition comprising a compound of any one or more of Formula (I'), (IA'), (II'), (III'), (IV'), or (V'), or a pharmaceutically acceptable salt thereof, and one or more immunostimulatory agents.

In some embodiments, this disclosure provides a compound of the disclosure for use in the treatment of a STING-mediated disease or disorder and/or for use as an immunogenic composition or a vaccine adjuvant. In some embodiments, this disclosure provides a compound of any one or more of Formula (I'), (IA'), (II'), (III'), (IV'), or (V'), or a pharmaceutically acceptable salt thereof, for use in the amelioration of organ injury or damage sustained as a result of a STING-mediated disease or disorder.

The disclosure further provides for the use of a compound of the disclosure in the manufacture of a medicament for treatment of a STING-mediated disease or disorder. The disclosure further provides for the use of a compound of any one or more of Formula (I'), (IA'), (II'), (III'), (IV'), or (V'), or a salt thereof, particularly a pharmaceutically acceptable salt thereof, in the manufacture of a medicament for treatment of a STING-mediated disease or disorder, for example the diseases and disorders recited herein.

The disclosure further provides for the use of a compound of any one or more of Formula (I'), (IA'), (II'), (III'), (IV'), or (V'), or a salt thereof, particularly a pharmaceutically acceptable salt thereof, in the manufacture of a vaccine. There is further provided the use of a compound of any one or more of Formula (I'), (IA'), (II'), (III'), (IV'), or (V'), or a pharmaceutically acceptable salt thereof, for the manufacture of an immunogenic composition or a vaccine composition comprising an antigen or antigenic composition, for the treatment or prevention of disease.

In some embodiments, the disclosure is directed to a method of treating a STING-mediated disease or disorder comprising administering a therapeutically effective amount of a compound of any one or more of Formula (I'), (IA'), (II'), (III'), (IV'), or (V'), or a salt, particularly a pharmaceutically acceptable salt thereof, to a human in need thereof.

In some embodiments, the disclosure is directed to a method of treating or preventing disease comprising the administration to a human subject suffering from or susceptible to disease, an immunogenic composition or a vaccine composition comprising an antigen or antigenic composition and a compound of any one or more of Formula (I'), (IA'), (II'), (III'), (IV'), or (V'), or a pharmaceutically acceptable salt thereof.

In some embodiments, this disclosure is directed to a compound of any one or more of Formula (I'), (IA'), (II'), (III'), (IV'), or (V'), or a pharmaceutically acceptable salt thereof for use in the treatment of inflammation, an autoimmune disease, an allergic disease, an infectious disease, an HIV infection, an AIDS infection, an HCV infection, influenza or a human papillomavirus (HPV) infection. In a further aspect there is provided a method of treating inflammation, an autoimmune disease, an allergic disease, an infectious disease, an HIV infection, an AIDS infection, an HCV infection, influenza or a human papillomavirus (HPV) infection comprising administering to a human in need thereof a therapeutically effective amount of a compound of any one or more of Formula (I'), (IA'), (II'), (III'), (IV'), or (V'), or a pharmaceutically acceptable salt thereof. In a further aspect there is provided a compound of any one or more of Formula (I'), (IA'), (II'), (III'), (IV'), or (V'), or a pharmaceutically acceptable salt thereof for use in the manufacture of a medicament for the treatment of inflammation, an autoimmune disease, an allergic disease, an infectious disease, an HIV infection, an AIDS infection, an HCV infection, influenza or human papillomavirus (HPV) infection.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MM), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblasts) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocyte (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polycythemia vera (PCV). Myeloid malignancies also include myelodysplasia (or myelodysplastic syndrome or MDS), which may be referred to as refractory anemia ($R^A$), refractory anemia with excess blasts (RAEB), and refractory anemia with excess blasts in transformation (RAEBT); as well as myelofibrosis (MFS) with or without angiogenic myeloid metaplasia.

Hematopoietic cancers also include lymphoid malignancies, which may affect the lymph nodes, spleens, bone marrow, peripheral blood, and/or extranidal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B-cell lymphomas include follicular lymphoma (FL); small lymphocytic lymphoma (SLL); marginal zone lymphoma (MZL) including nodal MZL, extranidal MZL, splenic MZL and splenic MZL with villous lymphocytes; lymphoplasmacytic lymphoma (LPL); and mucosa-associated-lymphoid tissue (MALT or extranidal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary, lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

In some embodiments, this disclosure is directed to a compound of any one or more of Formula (I'), (IA'), (II'), (III'), (IV') or (V'), or a pharmaceutically acceptable salt thereof for use in the treatment of cancer and pre-cancerous syndromes. In a further aspect there is provided a method of treating cancer and pre-cancerous syndromes comprising administering to a human in need thereof a therapeutically effective amount of a compound of any one or more of Formula (I'), (IA'), (II'), (III'), (IV') or (V'), or a pharmaceutically acceptable salt thereof. In a further aspect there is provided a compound of any one or more of Formula (I'), (IA'), (II'), (III'), (IV') or (V'), or a pharmaceutically acceptable salt thereof for use in the manufacture of a medicament for the treatment of cancer and pre-cancerous syndromes.

The compounds of this disclosure may be used to treat inflammation of any tissue and organs of the body, including musculoskeletal inflammation, vascular inflammation, neural inflammation, digestive system inflammation, ocular inflammation, inflammation of the reproductive system, and other inflammation.

Examples of cancer diseases and conditions in which compounds of this disclosure may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

Suitably the present disclosure relates to a method for treating or lessening the severity of cancers. In some embodiments, the compounds of the present disclosure may be used to treat sarcoma, breast cancer, colorectal cancer, gastroesophageal cancer, melanoma, non-small cell lung cancer (NSCLC), clear cell renal cell carcinoma (RCC), lymphomas, squamous cell carcinoma of the head and neck (SCCHN), hepatocellular carcinoma (HCC), and Non Hodgkin lymphoma (NHL). Suitably the present disclosure relates to a method for treating or lessening the severity of pre-cancerous syndromes in a mammal, including a human, In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In some embodiments, the human has a liquid tumor such as diffuse large B cell lymphoma (DLBCL), multiple myeloma, chronic lymphoblastic leukemia (CLL), follicular lymphoma, acute myeloid leukemia, and chronic myelogenous leukemia.

In some embodiments, the compounds of the present disclosure may be useful for treatment of skin cancers (e.g., non-melanoma skin cancer, squamous cell carcinoma, basal cell carcinoma) or actinic keratosis. In addition to a field effect for clearing superficial skin cancers, the compounds of the present disclosure may prevent the development of subsequent skin cancers and pre-malignant actinic keratosis in treated patients.

The compounds of the present disclosure may also be useful in the treatment of one or more diseases afflicting mammals which are characterized by cellular proliferation in the area of disorders associated with neo-vascularization and/or vascular permeability, fibrotic disorders, and metabolic disorders.

The compounds of this disclosure may be used to treat neurodegenerative diseases. Exemplary neurodegenerative diseases includes, but are not limited to, multiple sclerosis, Huntington's disease, Alzheimer's disease, Parkinson's disease, amyotrophic lateral sclerosis (ALS).

The compounds of this disclosure may be used to treat an infectious disease, which is any disease instigated by or coincident with an infection from a pathogen, derived from bacteria, derived from the DNA virus families, or RNA virus families.

The compounds of this disclosure may be employed alone or in combination with other therapeutic agents. As modulators of the immune response, the compounds of this disclosure may also be used in monotherapy or used in combination with another therapeutic agent in the treatment of diseases and conditions in which modulation of STING is beneficial. Combination therapies according to the present disclosure thus comprise the administration of a compound of any one or more of Formula (I'), (IA'), (II'), (III'), (IV'), or (V'), or a pharmaceutically acceptable salt thereof, and at least one other therapeutically active agent. In some embodiments, combination therapies according to the present disclosure comprise the administration of at least one compound of any one or more of Formula (I'), (IA'), (II'), (III'), (IV'), or (V'), or a pharmaceutically acceptable salt thereof, and at least one other therapeutic agent. The compound(s) of any one or more of Formula (I'), (IA'), (II'), (III'), (IV'), or (V'), and pharmaceutically acceptable salts thereof, and the other therapeutic agent(s) may be administered together in a single pharmaceutical composition or separately and, when administered separately this may occur simultaneously or sequentially in any order. The amounts of the compound(s) of any one or more of Formula (I'), (IA'), (II'), (III'), (IV'), or (V'), and pharmaceutically acceptable salts thereof, and the other therapeutic agent(s) and the relative timings of administration will be selected in order to achieve the desired combined therapeutic effect. Thus, in a further aspect, there is provided a combination comprising a compound of any one or more of Formula (I'), (IA'), (II'), (III'), (IV'), or (V'), or a pharmaceutically acceptable salt thereof, together with one or more other therapeutic agents.

The compounds of any one or more of Formula (I'), (IA'), (II'), (III'), (IV'), or (V'), and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators, methotrexate, leukotriene modulators, monoclonal antibody therapy, receptor therapies, or antigen non-specific immunotherapies.

The compounds of any one or more of Formula (I'), (IA'), (II'), (III'), (IV'), or (V'), and pharmaceutically acceptable salts thereof may be used in combination with radiotherapy and/or surgery and/or at least one other therapeutic agent which may be useful in the treatment of cancer and pre-cancerous syndromes. Any anti-neoplastic agent, anti-microtubule, anti-mitotic agent, hormone, hormonal analogues signal transduction pathway inhibitor, protein tyrosine kinase, or anti-angiogenic therapeutic agent, may be utilized in the combination.

Agents used in immunotherapeutic regimens, therapeutic agents used in proapoptotic regimens, or cell cycle signaling inhibitors may also be useful in combination with the compounds of any one or more of Formula (I'), (IA'), (II'), (III'), (IV') or (V').

In some embodiments, the combination of the present disclosure comprises a compound of any one or more of Formula (I'), (IA'), (II'), (III'), (IV'), or (V'), or a salt, particularly a pharmaceutically acceptable salt thereof, and at least one anti-neoplastic agent, anti-microtubule, anti-mitotic agent, hormone, hormonal analogues signal transduction pathway inhibitor, protein tyrosine kinase, or anti-angiogenic therapeutic agent, or a combination thereof, Additional examples of other therapeutic agents (e.g., anti-neoplastic agent) for use in combination or co-administered with a compound of any one or more of Formula (I'), (IA'), (II'), (III'), (IV'), or (V'), or a pharmaceutically acceptable salt thereof are immuno-modulators.

As used herein "immuno-modulators" refer to any substance including monoclonal antibodies that affects the immune system. Immuno-modulators can be used as antineoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, ICOS antibodies, OX-40 antibodies, PD-L1 antibodies, LAG3 antibodies, TIM-3 antibodies, 41BB antibodies and GITR antibodies.

Additional examples of other therapeutic agents (antineoplastic agent) for use in combination or co-administered with a compound of this disclosure are anti-PD-L1 agents (i.e. anti-PD-L1 antibodies) or PD-1 antagonists Thus, In some embodiments methods of treating a human in need thereof are provided comprising administering a compound of any one or more of Formula (I'), (IA'), (II'), (III'), (IV') or (V'), or a salt thereof and at least one immuno-modulator. In some embodiments, the immuno-modulator is selected from an ICOS agonist antibody, an OX-40 antibody, and a PD-1 antibody. In some embodiments, the human has cancer. Also provided herein is the use of a compound of any one or more of Formula (I'), (IA'), (II'), (III'), (IV') or (V'), or a salt thereof in combination with at least one immuno-modulator for the treatment of a human in need thereof.

Additional examples of other therapeutic agents for use in combination or co- administered with a compound of any one or more of Formula (I'), (IA'), (II'), (III'), (IV') or (V'), or a salt thereof are immunostimulatory agents.

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS. As used herein "immunostimulatory agent" refers to any agent that can stimulate the immune system. As used herein immunostimulatory agents include, but are not limited to, vaccine adjuvants.

The term "Toll-like receptor" (or "TLR") as used herein refers to a member of the Toll-like receptor family of proteins or a fragment thereof that senses a microbial product and/or initiates an adaptive immune response. In some embodiments, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity In some embodiments the immunostimulatory agent for use in combination with the compounds of the present disclosure is a TLR4 agonist. In some embodiments, the TLR4 agonist are referred to as CRX-601 and CRX-527. Additionally, another preferred embodiment employs the TLR4 agonist CRX 547. Still other embodiments include AGPs such as CRX 602 or CRX 526 providing increased stability to AGPs having shorter secondary acyl or alkyl chains.

Thus, In some embodiments, methods of treating a human in need thereof are provided comprising administering a compound of any one or more of Formula (I'), (IA'), (II'), (III'), (IV') or (V'), or a salt thereof and at least one immunostimulatory agent. In some embodiments, the immunostimulatory agent is a TLR4 agonist. In some embodiments, the immunostimulatory agent is an AGP. In yet another embodiment, the TLR4 agonist is selected from a compound having the formula CRX-601, CRX-527, CRX-547, CRX-602, or CRX-526. In some embodiments, the human has cancer. Also provided herein is the use a compound of any one or more of Formula (I'), (IA'), (II'), (III'), (IV') or (V'), or a salt thereof in combination with at least one immunostimulatory agent for the treatment of a human in need thereof.

In addition to the immunostimulatory agents described above, the compositions of the present disclosure may further comprise other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs).

Because of their adjuvant qualities, TLR agonists are preferably used in combinations with other vaccines, adjuvants and/or immune modulators, and may be combined in various combinations. Thus, in certain embodiments, the herein described compounds of any one or more of Formula (I'), (IA'), (II'), (III'), (IV'), or (V') that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Further active ingredients (antineoplastic agents) for use in combination or co-administered with the presently invented compounds of any one or more of Formula (I'), (IA'), (II'), (III'), (IV'), or (V') are IDO inhibitors.

Additional examples of other therapeutic agents (antineoplastic agent) for use in combination or co-administered with a compound of any one or more of Formula (I'), (IA'), (II'), (III'), (IV'), or (V') are CD73 inhibitors and A2a and A2b adenosine antagonists.

In some embodiments, the compound of the disclosure may be employed with other therapeutic methods of treating infectious disease. In particular, antiviral and antibacterial agents are envisaged.

The compounds of any one or more of Formula (I'), (IA'), (II'), (III'), (IV'), or (V'), and pharmaceutically acceptable salts thereof may be used in combination with at least one other therapeutic agent useful in the prevention or treatment of bacterial and viral infections. Examples of such agents include, without limitation: polymerase inhibitors; replication inhibitors; protease inhibitors; nucleoside and nucleotide reverse transcriptase inhibitors non-nucleoside reverse transcriptase inhibitors (including an agent having antioxidation activity such as immunocal, oltipraz etc.); chemokine receptor inhibitors; pharmacokinetic enhancers such as cobicistat; neuraminidase inhibitors; antiviral agents of undetermined mechanism of action.

The compounds of any one or more of Formula (I'), (IA'), (II'), (III'), (IV'), or (V'), and pharmaceutically acceptable salts thereof may also be used in combination with other therapeutic agents which may be useful in the treatment of Kaposi's sarcoma-associated herpesvirus infections (KSHV and KSHV- related)

In some embodiments of this disclosure, the at least one other therapeutic agent is an antimycobacterial agent or a bactericidal antibiotic. The compounds of any one or more of Formula (I'), (IA'), (II'), (III'), (IV'), or (V'), and pharmaceutically acceptable salts thereof may also be used in combination with at least one other therapeutic agent which may be useful in the treatment of TB infection *Mycobacterium tuberculosis*) and Tularemia *Francisella tularensis*) The compounds of any one or more of Formula (I'), (IA'), (II'), (III'), (IV'), or (V'), and pharmaceutically acceptable salts thereof may also be used in combination with an antimycobacterial agent.

The compounds of any one or more of Formula (I'), (IA'), (II'), (III'), (IV'), or (V'), and pharmaceutically acceptable salts thereof may also be used in combination with at least one other therapeutic agent which may be useful in the treatment of *Chlamydia, Plasmodium* infection, amyotrophic lateral sclerosis (ALS) or multiple sclerosis, .

The compounds of this disclosure may also be used as adjuvants to improve the immune response raised to any given antigen and/or reduce reactogenicity/toxicity in a patient, particularly a human, in need thereof. As such, a compound of this disclosure may be used in combination with vaccine compositions to modify, especially to enhance, the immune response for example by increasing the level or duration of protection and/or allowing a reduction in the antigenic dose.

The compounds of any one or more of Formula (I'), (IA'), (II'), (III'), (IV'), or (V'), and pharmaceutically acceptable salts thereof may be used in combination with one or more vaccines or immunogenic antigens useful in the prevention or treatment of viral infections.

Accordingly, this disclosure provides an immunogenic composition comprising an antigen or antigenic composition and a compound of any one or more of Formula (I'), (IA'), (II'), (III'), (IV'), or (V'), or a pharmaceutically acceptable salt thereof. There is further provided a vaccine composition comprising an antigen or antigenic composition and a compound of any one or more of Formula (I'), (IA'), (II'), (III'), (IV'), or (V'), or a pharmaceutically acceptable salt thereof.

The compounds of any one or more of Formula (I'), (IA'), (II'), (III'), (IV'), or (V'), and pharmaceutically acceptable salts thereof may also be used in combination with at least one other therapeutic agent which may be useful in the prevention or treatment of viral infections A compound that modulate STING, particularly a compound of any one or more of Formula (I'), (IA'), (II'), (III'), (IV'), or (V'), or a pharmaceutically acceptable salt thereof, may be administered in combination with other anti-inflammatory agents, For example, in the treatment of systemic lupus erythematosus and related lupus disorders, a compound that modulates STING, particularly a compound of any one or more of Formula (I'), (IA'), (II'), (III'), (IV'), or (V'), or a pharmaceutically acceptable salt thereof, may be administered in combination with at least one other therapeutic agent, including, a corticosteroid, an immunosuppressive agentan anti-BAFF antibody (immunoglobulin therapy anti-interferon-alpha therapy anti-cytokine therapies anti-interferon-gamma, immunomodulatory therapy and/or a platelet aggregation inhibitor (aspirin).

In treatment of vasculitis and disease with inflammation of small or medium size blood vessels, a compound that modulates STING, particularly a compound of any one or more of Formula (I'), (IA'), (II'), (III'), (IV'), or (V'), or a pharmaceutically acceptable salt thereof, may be administered in combination with alkylating agents and anti-TNF inhibitors In the treatment of psoriasis, a compound that modulates STING, particularly a compound of any one or more of Formula (I'), (IA'), (II'), (III'), (IV'), or (V'), or a pharmaceutically acceptable salt thereof, may be administered in combination with ixekizumab, tildrakizumab (MK-3222), or secukinumab (AIN457).

In some embodiments of this disclosure, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. For example, in the treatment of asthma, a compound that inhibits STING, particularly a compound of any one or more of Formula (I'), (IA'), (II'), (III'), (IV'), or (V'), or a pharmaceutically acceptable salt thereof, may be administered in combination with an inhaled corticosteroid, a long acting beta agonist ((LABA), a combination of an ICS and LABA a short acting beta agonist ((SABA) a leukotriene modifier (an anti-IgE a methylxanthine bronchodilator), a mast cell inhibitor, a long-acting muscarinic antagonist ((LAMA).

In some embodiments of this disclosure, the at least one other therapeutic agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid.

In some embodiments of this disclosure, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. For example, in the treatment of systemic scleroderma, a compound that modulates STING, particularly a compound of any one or more of Formula (I'), (IA'), (II'), (III'), (IV'), or (V'), or a pharmaceutically acceptable salt thereof, may be administered in combination with an oral corticosteroid an immunosuppressive agent a calcium channel blocker a topical emollient an ACE inhibitor a serotonin reuptake inhibitor an endothelin-1 receptor inhibitor an anti-fibrotic agent, a proton-pump Inhibitor In the treatment of Sjogren's syndrome, a compound that modulates STING, particularly a compound of any one or more of Formula (I'), (IA'), (II'), (III'), (IV'), or (V'), or a pharmaceutically acceptable salt thereof, may be administered in combination with anti-rheumatic agents.

In some embodiments of this disclosure, the at least one other therapeutic agent is a ciliary neurotrophic growth factor or a gene transfer agent. For example, in the treatment of retinitis pigmentosa, a compound that modulates STING, particularly a compound of any one or more of Formula (I'), (IA'), (II'), (III'), (IV'), or (V'), or a pharmaceutically acceptable salt thereof, may be administered in combination with a ciliary neurtotrophic growth factor (NT-501-CNTF) or gene transfer agent, UshStat®.

In some embodiments of this disclosure, the at least one other therapeutic agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, and inactivated influenza vaccine. For example, in the treatment of influenza, a compound that modulates STING, particularly a compound of any one or more of Formula (I'), (IA'), (II'), (III'), (IV'), or (V'), or a pharmaceutically acceptable salt thereof, may be administered in combination with a trivalent (IIV3) inactivated influenza vaccine, a quadrivalent (IIV4) inactivated influenza vaccine a trivalent recombinant influenza vaccine), a quadrivalent live attenuated influenza vaccine (an antiviral agent In the treatment of a *staphylococcus* infection, a compound that modulates STING, particularly a compound of any one or more of Formula (I'), (IA'), (II'), (III'), (IV'), or (V'), or a pharmaceutically acceptable salt thereof, may be administered in combination with an antibiotic In some embodiments of this disclosure, the at least one other therapeutic agent is selected from a topical immunomodulator or calcineurin inhibitor, a topical corticosteroid, an oral corticosteroid, an interferon gamma, an antihistamine, and an antibiotic.

The compounds of the disclosure may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity.

In a further aspect of the disclosure, there is provided a vaccine adjuvant comprising a compound of any one or more of Formula (I'), (IA'), (II'), (III'), (IV'), or (V'), or a pharmaceutically acceptable salt thereof. There is further provided a vaccine composition comprising a compound of any one or more of Formula (I'), (IA'), (II'), (III'), (IV'), or (V'), or a pharmaceutically acceptable salt thereof, and an antigen or antigen composition.

A therapeutically "effective amount" is intended to mean that amount of a compound that, when administered to a patient in need of such treatment, is sufficient to effective treat or prevent, as defined herein. Thus, e.g., a therapeutically effective amount of a compound of any one or more of Formula (I'), (IA'), (II'), (III'), (IV'), or (V'), or a pharmaceutically acceptable salt thereof, is a quantity of an inventive agent that, when administered to a human in need thereof, is sufficient to modulate the activity of STING such that a disease condition which is mediated by that activity is reduced, alleviated or prevented. The amount of a given compound that will correspond to such an amount will vary depending upon factors such as the particular compound (e.g., the potency (pICso), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this disclosure in any conventionally acceptable manner, for example for retardation, therapy or cure of a STING-mediated disease or disorder, as described hereinabove. In some embodiments, "treat" "treating" or "treatment" in reference to cancer refers to alleviating the cancer, eliminating or reducing one or more symptoms of the cancer, slowing or eliminating the progression of the cancer, and delaying the reoccurrence of the condition in a previously afflicted or diagnosed patient or subject.

"Prevent", "preventing" or "prevention" refers to the prophylactic administration of a drug to diminish the likelihood of the onset of or to delay the onset of a disease or biological manifestation thereof. Prophylactic therapy is appropriate, for example, when a subject is considered at high risk for developing cancer, such as when a subject has a strong family history of cancer or when a subject has been exposed to a carcinogen.

The compounds of the disclosure may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

In addition to the above described routes of administration suitable for treatment of oncology, the pharmaceutical compositions may be adapted for administration by intratumoral or peritumoral injection. The intratumorally or peritumoral injection of a compound of the present disclosure directly into or adjacent to a single solid tumor is expected to elicit an immune response that can attack and destroy cancer cells throughout the body, substantially reducing and in some cases permanently eliminating the tumor from the diseased subject. The activation of the immune system in this manner to kill tumors at a remote site is commonly known as the abscopal effect and has been demonstrated in animals with multiple therapeutic modalities. A further advantage of local or intratumoral or peritumoral administration is the ability to achieve equivalent efficacy at much lower doses, thus minimizing or eliminating adverse events that may be observed at much higher systemic doses The compounds of the disclosure may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the disclosure depend on the pharmacokinetic properties of that compound, such as absorption, distribution, and half-life, which can be determined by the skilled artisan. In addition, suitable dosing regimens, including the duration such regimens are administered, for a compound of the disclosure depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg, preferably, total daily dosages range from 1 mg to 250 mg.

For use in therapy, the compounds of the disclosure will be normally, but not necessarily, formulated into a pharmaceutical composition prior to administration to a patient. Accordingly, the disclosure also is directed to pharmaceutical compositions comprising a compound of the disclosure and at least one pharmaceutically acceptable excipient.

The pharmaceutical compositions of the disclosure may be prepared and packaged in bulk form or in unit dosage form. For oral application, for example, one or more tablets or capsules may be administered. A dose of the pharmaceutical composition contains at least a therapeutically effective amount of a compound of this disclosure (i.e., a compound of any one or more of Formula (I'), (IA'), (II'), (III'), (IV') or (V'), or a salt, particularly a pharmaceutically acceptable salt, thereof). When prepared in unit dosage form, the pharmaceutical compositions may contain from 1 mg to 1000 mg of a compound of this disclosure.

As provided herein, unit dosage forms (pharmaceutical compositions) comprising from 1 mg to 1000 mg of a compound of the disclosure may be administered one, two, three, or four times per day, preferably one, two, or three times per day, and more preferably, one or two times per day, to effect treatment of a STING-mediated disease or disorder.

The pharmaceutical compositions of the disclosure typically contain one compound of the disclosure. However, in certain embodiments, the pharmaceutical compositions of the disclosure contain more than one compound of the disclosure. In addition, the pharmaceutical compositions of the disclosure may optionally further comprise one or more additional therapeutic agents, (e.g., pharmaceutically active compounds).

As used herein, "pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the disclosure when administered to a patient and interactions which would result in pharmaceutical compositions that are not pharmaceutically acceptable are avoided. In addition, each excipient must of course be of sufficiently high purity to render it pharmaceutically acceptable.

The compounds of the disclosure and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the disclosure once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the disclosure. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In one aspect, the disclosure is directed to a solid oral dosage form such as a tablet or capsule comprising an effective amount of a compound of the disclosure and a diluent or filler. The oral solid dosage form may further comprise a disintegrant, or a lubricant.

It will be understood that the compounds of this disclosure may also be formulated with vaccines as adjuvants to modulate their activity. Such compositions may contain antibody (antibodies) or antibody fragment(s) or an antigenic component, optionally together with one or more other components with adjuvant activity.

Certain compounds of the disclosure may be potent immunomodulators and accordingly, care should be exercised in their handling.

The disclosure having been described, the following examples are offered by way of illustration and not limitation.

Examples

The following examples illustrate the disclosure. These examples are not intended to limit the scope of the present disclosure, but rather to provide guidance to the skilled artisan to prepare and use the Compounds, compositions, and methods of the present disclosure. While particular embodiments of the present disclosure are described, the skilled artisan will appreciate that various changes and modifications can be made without departing from the spirit and scope of the disclosure.

It will be understood that certain Compounds of the disclosure may be potent immunomodulators and accordingly, care should be exercised in their handling.

The reactions described herein are applicable for producing Compounds of the disclosure having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. Suitable protecting groups and the methods for protecting and de-protecting different substituents using such suitable protecting groups are well known to those skilled in the art; examples of which may be found in T. W. Greene 'Protective Groups in Organic Synthesis' (4th edition, J. Wiley and Sons, 2006). Unless otherwise noted, all starting materials were obtained from commercial suppliers and used without further purification.

ABBREVIATIONS

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

ACN Acetonitrile

DIPEA N,N-Diisopropylethylamine

DCM Dichloromethane

DMF Dimethylformamide

DMSO Dimethylsulfoxide

ESI Electrospray ionization

EtOAc Ethyl acetate

FBS Fetal bovine serum

HATU 2-(1H-7-Azabenzotriazol-1-yl)-1,1,3,3-tetramethyluronoium hexafluorphosphate HOBt Hydroxybenzotriazole HPLC High pressure liquid chromatography LiOH Lithium hydroxide MeOH Methanol $^1$H NMR Proton nuclear magnetic resonance spectroscopy TBAF Tetra-n-butylammonium fluoride TFA Trifluoroacetic acid THF Tetrahydrofuran PyBOP (Benzotriazole-1-yloxy)tripyrrolidinophosphonium hexafluorophosphate General procedure for synthesis of Compound Variant I, wherein $Z_1=Z_2$; $Y_1=Y_2$; $X_1=X_2$; $W_1=W_2$; $R^{14}=R^{C2}$; $R^{19}=R^{18}$; $R^{15}=R^{17}$ and $R^{C1}=R^{16}$ Variant I

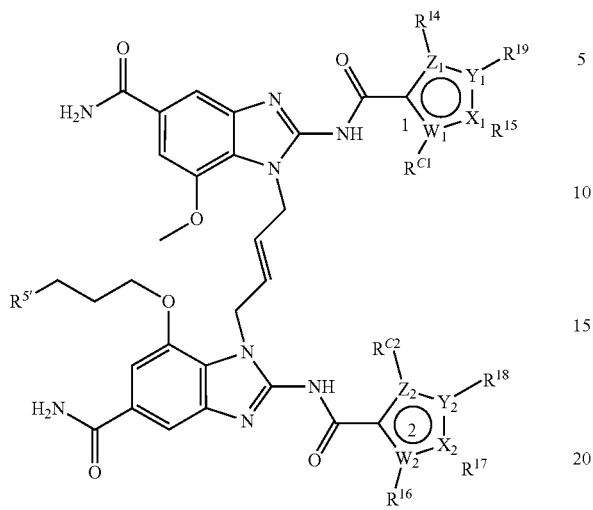

Scheme 1: The following scheme illustrates the exemplary synthesis of (E)-N-(5-carbamoyl-1-(4-(5-carbamoyl-2-(4-ethyl-2-methyloxazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide. The similar procedure may be generally used for the synthesis of Compound Variant I. As shown below, heterocyclic structures (Rings 1 and 2) can be introduced by using the corresponding carboxylic acid at Step I.

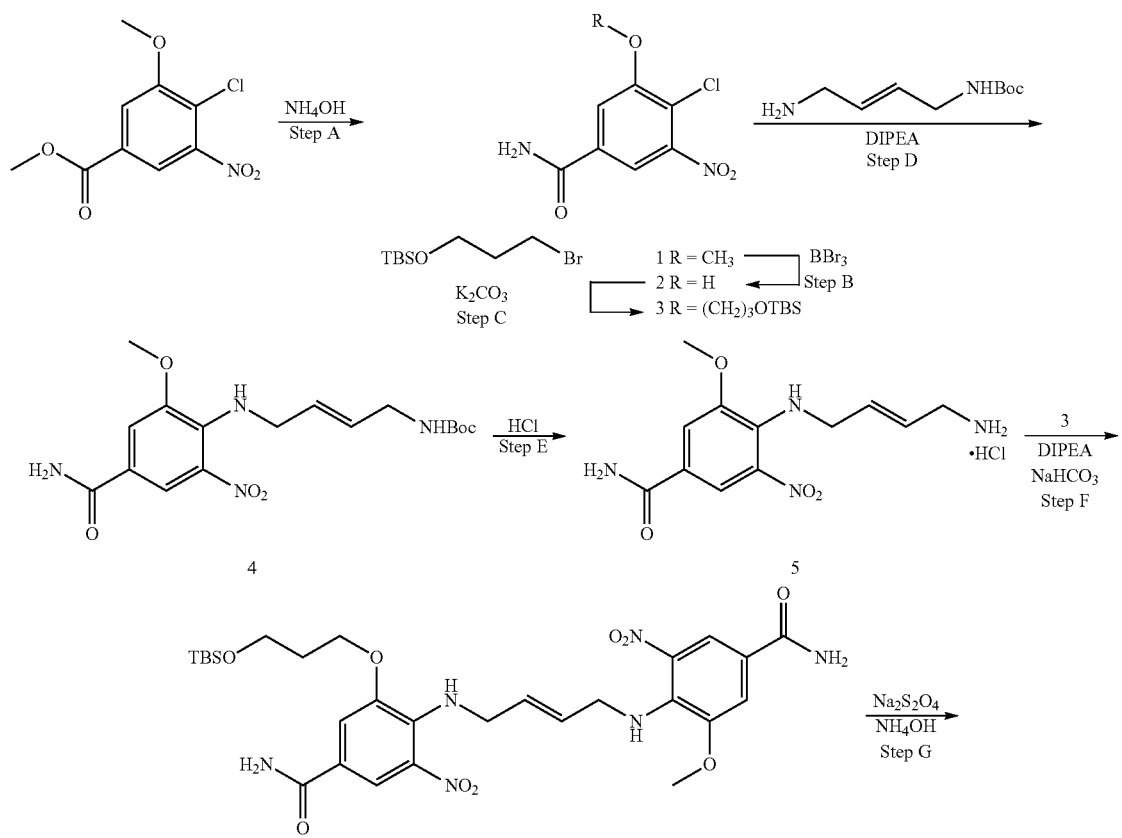

-continued

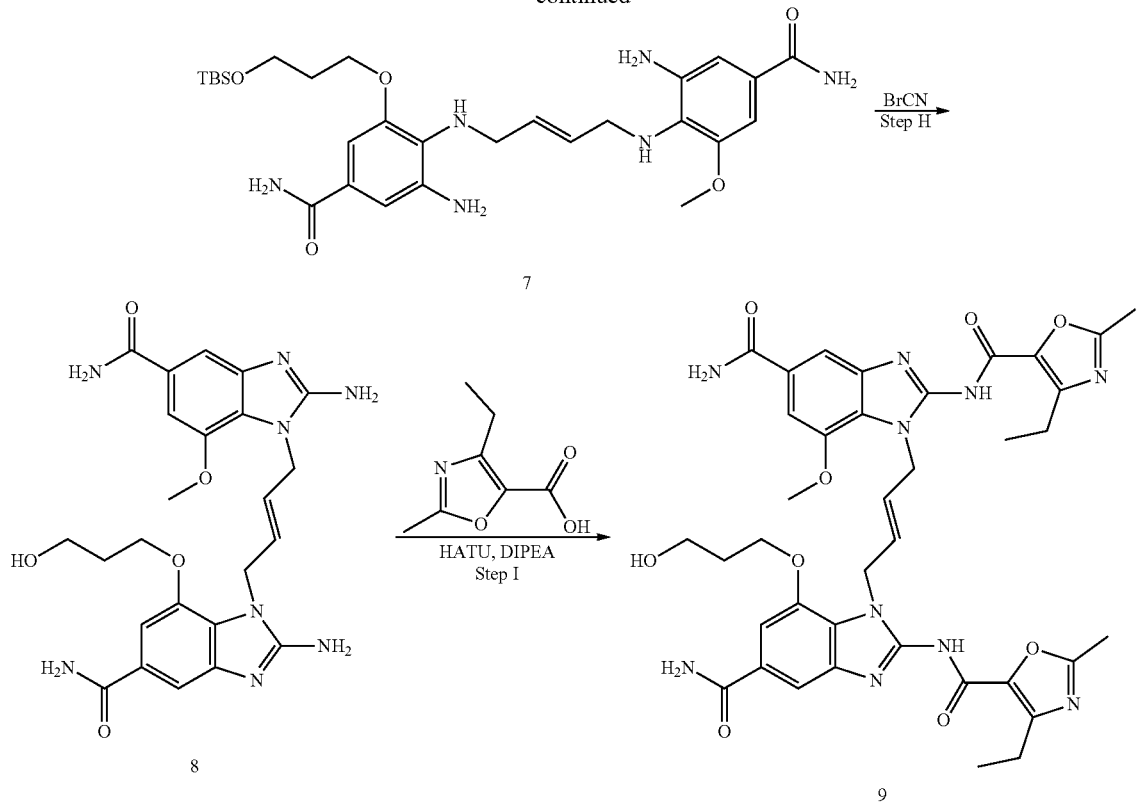

Example 1: (E)-N-(5-carbamoyl-1-(4-(5-carbamoyl-2-(4-ethyl-2-methyloxazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide, Compound 9

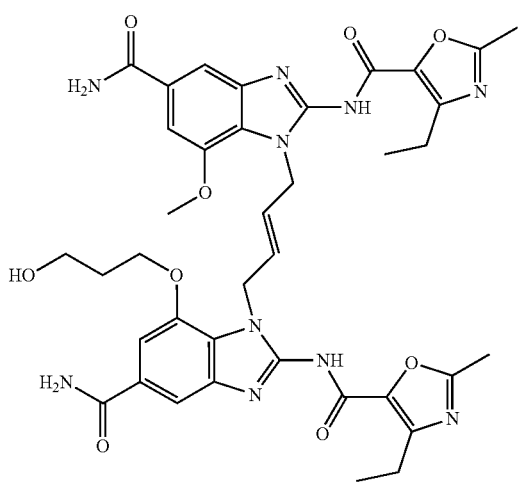

9

Step A: A mixture of methyl 4-chloro-3-methoxy-5-nitrobenzoate (15.0 g, 61.2 mmol) and NH₄OH (220 mL) under pressure was heated to 50° C. and stirred for 6 hours. The resulting solid was filtered and dried. The filtrate was distilled completely, and the resulting solid was combined with the filtered solid to afford 4-chloro-3-methoxy-5-nitrobenzamide, Compound 1 (12.0 g, 85% yield) as a yellow solid. $^1$H NMR (400 MHz, DMSO-d$_6$) δ 8.29 (s, 1H), 8.05 (d, J=1.8 Hz, 1H), 7.88 (d, J=1.9 Hz, 1H), 7.78 (s, 1H), 4.02 (s, 3H). ESI-MS: $C_8H_8C_1N_2O_4$ (M+H): calc. 231.01, found 231.00.

Step B: To a stirred solution of Compound 1, 4-chloro-3-methoxy-5-nitrobenzamide 1 (12.0 g, 52.1 mmol) in DCM (150 mL) under N$_2$ was added BBr$_3$ (1M in DCM, 208 mL, 208.7 mmol). The mixture was stirred at room temperature for 16 hours, then quenched with ice cold water (500 mL), and the resulting solid was filtered. The solid was washed with cold water and pentane to afford 4-chloro-3-hydroxy-5-nitrobenzamide, Compound 2 (10.0 g, 89% yield) as a light brown solid. $^1$H NMR (400 MHz, DMSO-d$_6$) δ 11.82-11.19 (m, 1H), 8.14 (s, 1H), 7.88 (d, J=1.9 Hz, 1H), 7.68 (d, J=2.0 Hz, 1H), 7.65-7.60 (m, 1H). ESI-MS: $C_7H_5C_1N_2O_4$ (M+H): calc. 217.00, found: 217.08.

Step C: To a stirred solution of 4-chloro-3-hydroxy-5-nitrobenzamide, Compound 2 (10 g, 46.3 mmol) in DMF (80 mL) was added (3-bromopropoxy)(tert-butyl)dimethylsilane (15.2 g, 60.2 mmol) and K$_2$CO$_3$ (12.8 g, 92.6 mmol). The mixture was heated to 100° C. and stirred for 2 hours. The mixture was cooled to room temperature and quenched with ice cold water (1 L). The resulting precipitate was filtered and dried. The solid was triturated in pentane, filtered, and dried to afford 3-(3-((tert-butyldimethylsilyl)oxy)propoxy)-4-chloro-5-nitrobenzamide, Compound 3 (13.0 g, 72% yield) as a yellow solid. $^1$H NMR (400 MHz, DMSO-d$_6$) δ

8.27 (s, 1H), 8.02 (d, J=1.8 Hz, 1H), 7.86 (d, J=1.9 Hz, 1H), 7.75 (s, 1H), 4.28 (t, J=6.0 Hz, 2H), 3.78 (t, J=6.1 Hz, 2H), 1.96 (q, J=5.9 Hz, 2H), 0.82 (s, 9H), 0.00 (s, 6H). ESI-MS: $C_{16}H_{26}ClN_2O_5Si$ (M+H): calc. 389.12, found: 389.27.

Step D: To a stirred solution of 4-chloro-3-methoxy-5-nitrobenzamide, Compound 1 (12.0 g, 52.2 mmol) in EtOH (250 mL) was added tert-butyl (E)-(4-aminobut-2-en-1-yl) carbamate HCl (13.9 g, 62.6 mmol) and DIPEA (27.3 mL, 156.5 mmol). The reaction mixture was heated to 120° C. and stirred for 16 hours, then cooled to 0° C., resulting in precipitate formation. The resulting precipitate was filtered and washed with cold EtOH to afford tert-butyl (E)-(4-((4-carbamoyl-2-methoxy-6-nitrophenyl)amino)but-2-en-1-yl) carbamate, Compound 4 (14.0 g, 70% yield) as an orange solid. $^1$H NMR (400 MHz, DMSO-$d_6$) δ 8.14 (d, J=2.0 Hz, 1H), 7.98 (s, 1H), 7.71 (t, J=6.2 Hz, 1H), 7.51 (d, J=2.0 Hz, 1H), 7.29 (s, 1H), 6.95-6.83 (m, 1H), 5.49 (t, J=2.6 Hz, 2H), 4.05 (d, J=5.7 Hz, 2H), 3.83 (s, 3H), 3.44 (q, J=4.4 Hz, 2H), 1.31 (s, 9H). ESI-MS: $C_{17}H_{25}N_4O_6$ (M+H): calc. 381.40, found: 381.30.

Step E; To a stirred solution of tert-butyl (E)-(4-((4-carbamoyl-2-methoxy-6-nitrophenyl)amino)but-2-en-1-yl) carbamate, Compound 4 (14.0 g, 36.8 mmol) in DCM (100 mL) was added HCl (4M in dioxane, 92.1 mL, 368.3 mmol). The mixture was stirred at room temperature for 2 hours. The resulting solid was filtered and washed with dioxane (75 mL) and pentane (100 mL) to afford (E)-4-((4-aminobut-2-en-1-yl)amino)-3-methoxy-5-nitrobenzamide-HCl, Compound 5 (10.5 g, 90% yield) as an orange solid. $^1$H NMR (400 MHz, DMSO-$d_6$) δ 8.17 (d, J=1.9 Hz, 1H), 8.03 (s, 1H), 7.90 (s, 3H), 7.55 (d, J=2.0 Hz, 1H), 7.32 (s, 1H), 5.87-5.78 (m, 1H), 5.63-5.53 (m, 1H), 4.14 (d, J=5.7 Hz, 2H), 3.85 (s, 3H), 3.36 (p, J=6.0 Hz, 2H). ESI-MS: $C_{12}H_{17}N_4O_4$ (M+H): calc. 281.12, found: 281.15.

Step F: To a stirred solution of (E)-4-((4-aminobut-2-en-1-yl)amino)-3-methoxy-5-nitrobenzamide-HCl, Compound 5 (10.0 g, 25.8 mmol) in n-butanol (120 mL) was added DIPEA (18.0 mL, 103.1 mmol), NaHCO$_3$ (4.328 g, 51.5 mmol) and 3-(3-((tert-butyldimethylsilyl)oxy)propoxy)-4-chloro-5-nitrobenzamide (12.2 g, 38.6 mmol). The mixture was heated under pressure to 120° C. and stirred for 24 hours. The mixture was cooled to 0° C., resulting in precipitate formation. The solid was filtered and washed with n-butanol (100 mL) and dried to afford (E)-3-(3-((tert-butyldimethylsilyl)oxy)propoxy)-4-((4-((4-carbamoyl-2-methoxy-6-nitrophenyl)amino)but-2-en-1-yl)amino)-5-nitrobenzamide, Compound 6 (9.0 g, 55% yield) as a dark red solid. $^1$H NMR (400 MHz, DMSO-$d_6$) δ 8.14 (d, J=2.2 Hz, 2H), 8.01 (d, J=8.3 Hz, 2H), 7.69 (p, J=7.2 Hz, 2H), 7.50 (s, 2H), 7.30 (s, 2H), 5.59 (d, J=4.5 Hz, 2H), 4.07 (dt, J=12.3, 5.9 Hz, 6H), 3.72 (q, J=6.4 Hz, 2H), 3.15 (d, J=4.8 Hz, 3H), 1.90 (p, J=6.5 Hz, 2H), 0.81 (s, 9H), −0.02 (s, 6H). ESI-MS: $C_{28}H_{41}N_6O_9Si$ (M+H): calc. 633.26, found: 633.45.

Step G: To a stirred solution of (E)-3-(3-((tert-butyldimethylsilyl)oxy)propoxy)-4-((4-((4-carbamoyl-2-methoxy-6-nitrophenyl)amino)but-2-en-1-yl)amino)-5-nitrobenzamide, Compound 6 (1 g, 1.58 mmol) at 0° C. was added Na$_2$S$_2$O$_4$ (2.74 g, 15.8 mmol) dissolved in water (10 mL). To this stirred mixture was added NH$_4$OH, and the mixture was warmed to room temperature and stirred for 45 minutes, then quenched with water and extracted with EtOAc (2×). The combined organic layers were washed with brine and dried over Na$_2$SO$_4$. The mixture was concentrated in vacuo to afford (E)-3-amino-4-((4-((2-amino-4-carbamoyl-6-methoxyphenyl)amino)but-2-en-1-yl)amino)-5-(3-((tert butyldimethylsilyl)oxy)propoxy)benzamide, Compound 7 (600 mg, 67% yield) as a light brown solid. $^1$H NMR (400 MHz, DMSO-$d_6$) δ 7.58 (s, 2H), 6.96 (d, J=19.7 Hz, 2H), 6.81 (dd, J=4.9, 1.9 Hz, 2H), 6.73 (dd, J=3.9, 1.9 Hz, 2H), 5.68-5.57 (m, 2H), 4.61 (s, 4H), 3.95 (t, J=6.1 Hz, 2H), 3.72 (d, J=1.7 Hz, 2H), 3.70 (s, 3H), 3.47 (s, 4H), 1.85 (p, J=6.1 Hz, 2H), 0.81 (s, 9H), −0.02 (s, 6H). ESI-MS: $C_{28}H_{45}N_6O_5Si$ (M+H): calc. 573.31, found: 573.20.

Step H: To a stirred solution of (E)-3-amino-4-((4-((2-amino-4-carbamoyl-6-methoxyphenyl)amino)but-2-en-1-yl)amino)-5-(3-((tert-butyldimethyl silyl)oxy)propoxy)benzamide, Compound 7 (600 mg, 1.05 mmol) in methanol (20 mL) under nitrogen was added cyanogen bromide (222 mg, 2.10 mmol). The mixture was stirred at room temperature for 1 hour. The resulting solid was filtered and washed with methanol (5 mL) to afford (E)-2-amino-1-(4-(2-amino-5-carbamoyl-7-(3-hydroxypropoxy)-1H-benzo[d]imidazol-1-yl)but-2-en-1-yl)-7-methoxy-1H-benzo[d]imidazole-5-carboxamide, Compound 8 (400 mg, 80% yield) as a white solid. $^1$H NMR (400 MHz, DMSO-$d_6$) δ 8.61 (s, 4H), 8.08 (s, 2H), 7.50 (d, J=3.4 Hz, 2H), 7.44 (d, J=8.7 Hz, 2H), 7.40 (s, 2H), 5.79 (q, J=4.4 Hz, 2H), 4.86 (dd, J=12.6, 4.0 Hz, 4H), 4.11 (t, J=6.3 Hz, 2H), 3.79 (s, 3H), 3.46 (s, 2H), 1.74 (p, J=6.4, 5.8 Hz, 2H). ESI-MS: $C_{24}H_{29}N_8O_5$ (M+H): calc. 509.22, found: 509.15.

Step I. To a stirred solution of (E)-2-amino-1-(4-(2-amino-5-carbamoyl-7-(3-hydroxypropoxy)-1H-benzo[d]imidazol-1-yl)but-2-en-1-yl)-7-methoxy-1H-benzo[d]imi-dazole-Compound 8 (200 mg, 0.32 mmol) in DMF (10 mL) was added 4-methyl-2-ethyloxazole-5-carboxlyic acid (124 mg, 0.80 mmol), HATU (305 mg, 0.80 mmol) and DIPEA (0.34 mL, 1.93 mmol). The mixture was stirred at room temperature for 16 hours, then concentrated in vacuo. The residue was purified over silica gel (EtOAc:MeOH 70:30 v/v) to afford (E)-N-(5-carbamoyl-1-(4-(5-carbamoyl-2-(4-ethyl-2-methyloxazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide, Compound 9 (60 mg, 24% yield) as a white solid. $^1$H NMR (400 MHz, DMSO-$d_6$) δ 12.67 (s, 2H), 7.92 (s, 2H), 7.59 (d, J=4.6 Hz, 2H), 7.29 (d, J=12.8 Hz, 4H), 5.75 (q, J=4.7 Hz, 2H), 4.91-4.80 (m, 4H), 4.03 (t, J=6.4 Hz, 2H), 3.73 (s, 3H), 3.43 (t, J=5.8 Hz, 2H), 2.75 (dt, J=12.6, 6.4 Hz, 4H), 2.35 (d, J=2.2 Hz, 6H), 1.69 (t, J=6.3 Hz, 2H), 0.96 (q, J=7.5 Hz, 6H). ESI-MS: $C_{38}H_{43}N_{10}O_9$ (M+H): calc. 783.31, found: 783.30.

Example 2: (E)-N-(5-carbamoyl-1-(4-(5-carbamoyl-2-(4-ethyl-2-methylthiazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methylthiazole-5-carboxamide, Compound 10

Example 3: (E)-1-(4-(5-carbamoyl-2-(3-ethyl-1-methyl-1H-pyrazole-4-carboxamido)-7-(3-hydroxypropoxy)-1H-benzo[d]imidazol-1-yl)but-2-en-1-yl)-2-(3-ethyl-1-methyl-1H-pyrazole-4-carboxamido)-7-methoxy-1H-benzo[d]imidazole-5-carboxamide, Compound 11

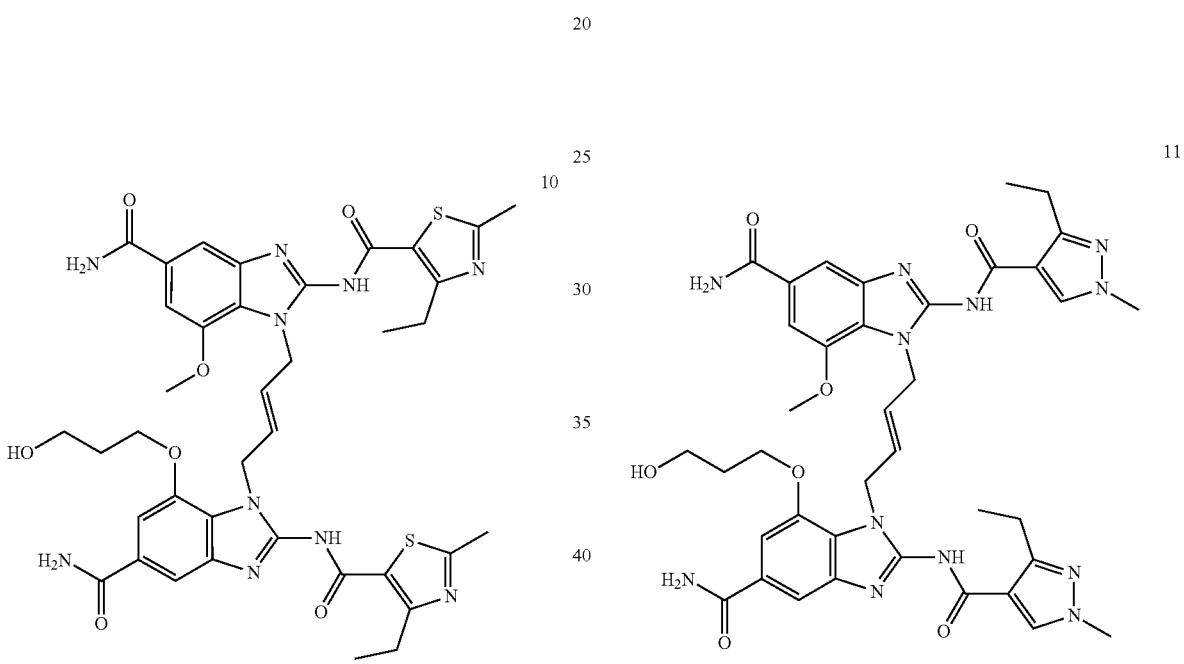

(E)-N-(5-carbamoyl-1-(4-(5-carbamoyl-2-(4-ethyl-2-methylthiazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methylthiazole-5-carboxamide was prepared as described in Example 1, except 4-ethyl-2-methylthiazole-5-carboxylic acid was used in Step I instead of 4-ethyl-2-methyloxazole-acid to afford (E)-N-(5-carbamoyl-1-(4-(5-carbamoyl-2-(4-ethyl-2-methylthiazole-1-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methylthiazole-5-carboxamide, Compound 10 (10 mg, 6% yield) as a white solid. $^1$H NMR (400 MHz, DMSO-$d_6$) δ 12.72 (s, 2H), 7.93 (s, 2H), 7.57 (dd, J=3.6, 1.3 Hz, 2H), 7.36-7.23 (m, 4H), 5.90-5.83 (m, 2H), 4.83 (s, 4H), 4.05 (t, J=6.4 Hz, 2H), 3.75 (s, 3H), 3.44 (d, J=5.3 Hz, 2H), 3.09-3.04 (m, 4H), 2.61 (s, 6H), 1.72 (t, J=6.3 Hz, 2H), 1.11 (dd, J=7.5, 1.2 Hz, 6H). ESI-MS: $C_{34}H_{43}N_{10}O_7S_2$ (M+H): calc. 815.27, found: 815.20.

(E)-1-(4-(5-carbamoyl-2-(3-ethyl-1-methyl-1H-pyrazole-4-carboxamido)-7-(3-hydroxypropoxy)-1H-benzo[d]imidazol-1-yl)but-2-en-1-yl)-2-(3-ethyl-1-methyl-1H-pyrazole-4-carboxamido)-7-methoxy-1H-benzo[d]imidazole-5-carboxamide was prepared as described in Example 1, except 3-ethyl-1-methyl-1H-pyrazole-4-carboxylic acid was used in Step I instead of 4-ethyl-2-methyloxazole-5-carboxylic acid to afford (E)-1-(4-(5-carbamoyl-2-(3-ethyl-1-methyl-1H-pyrazole-4-carboxamido)-7-(3-hydroxypropoxy)-1H-benzo[d]imidazol-1-yl)but-2-en-1-yl)-2-(3-ethyl-1-methyl-1H-pyrazole-4-carboxamido)-7-methoxy-1H-benzo[d]imidazole-5-carboxamide, Compound 11 (10 mg, 17% yield) as a white solid. $^1$H NMR (400 MHz, DMSO-$d_6$) δ 7.92 (d, J=15.8 Hz, 2H), 7.55 (d, J=4.1 Hz, 2H), 7.23 (s, 2H), 5.78 (m, 2H), 4.86 (d, J=7.2 Hz, 2H), 3.99 (s, 2H), 3.69 (d, J=14.7 Hz, 6H), 2.81 (s, 4H), 1.66 (s, 2H), 1.11-1.05 (m, 6H). ESI-MS: $C_{34}H_{45}N_{12}O_7$ (M+H): calc. 781.35, found: 781.20.

Example 4: (E)-N-(5-carbamoyl-1-(4-(5-carbamoyl-7-(3-hydroxypropoxy)-2-(3-methylisoxazole-5-carboxamido)-1H-benzo[d]imidazol-1-yl)but-2-en-1-yl)-7-methoxy-1H-benzo[d]imidazol-2-yl)-3-methylisoxazole-5-carboxamide, Compound 12

Example 5: (E)-N-(5-carbamoyl-1-(4-(5-carbamoyl-2-(2,5-dimethyloxazole-4-carboxamido)-7-(3-hydroxypropoxy)-1H-benzo[d]imidazol-1-yl)but-2-en-1-yl)-7-methoxy-1H-benzo[d]imidazol-2-yl)-2,5-dimethyloxazole-4-carboxamide, Compound 13

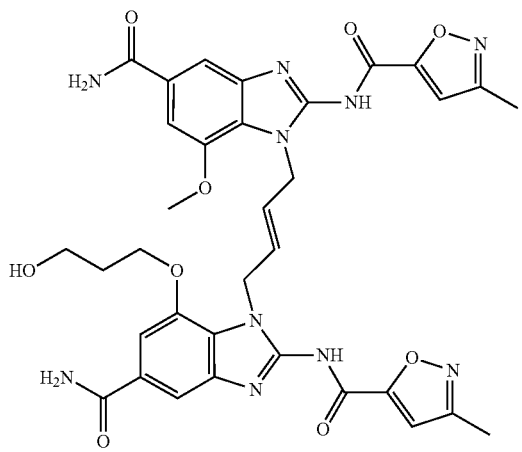

(E)-N-(5-carbamoyl-1-(4-(5-carbamoyl-7-(3-hydroxypropoxy)-2-(3-methylisoxazole-5-carboxamido)-1H-benzo[d]imidazol-1-yl)but-2-en-1-yl)-7-methoxy-1H-benzo[d]imidazol-2-yl)-3-methylisoxazole-5-carboxamide was prepared as described in Example 1, except 3-methylisoxazole-5-carboxylic acid was used in Step I instead of 4-ethyl-2-methyloxazole-5-carboxylic acid to afford (E)-N-(5-carbamoyl-1-(4-(5-carbamoyl-7-(3-hydroxypropoxy)-2-(3-methylisoxazole-5-carboxamido)-1H-benzo[d]imidazol-1-yl)but-2-en-1-yl)-7-methoxy-1H-benzo[d]imidazol-2-yl)-3-methylisoxazole-5-carboxamide, Compound 12 (15 mg, 10% yield) as a white solid. $^1$H NMR (400 MHz, DMSO-$d_6$) δ 12.87 (d, J=1.9 Hz, 2H), 7.96 (s, 2H), 7.62 (dd, J=3.0, 1.3 Hz, 2H), 7.33 (d, J=10.3 Hz, 2H), 7.28 (t, J=1.7 Hz, 2H), 6.69 (s, 2H), 5.83 (q, J=4.8 Hz, 2H), 4.89 (t, J=5.4 Hz, 4H), 4.00 (t, J=6.4 Hz, 2H), 3.68 (s, 3H), 3.39 (q, J=5.8 Hz, 2H), 2.18 (d, J=4.1 Hz, 6H), 1.64 (t, J=6.2 Hz, 2H). ESI-MS: $C_{34}H_{35}N_{10}O_9$ (M+H): calc. 727.25, found: 727.30.

(E)-N-(5-carbamoyl-1-(4-(5-carbamoyl-2-(2,5-dimethyloxazole-4-carboxamido)-7-(3-hydroxypropoxy)-1H-benzo[d]imidazol-1-yl)but-2-en-1-yl)-7-methoxy-1H-benzo[d]imidazol-2-yl)-2,5-dimethyloxazole-4-carboxamide was prepared as described in Example 1, except 2,5-dimethyloxazole-4-carboxylic acid was used in Step I instead of 4-ethyl-2-methyloxazole-5-carboxylic acid to afford (E)-N-(5-carbamoyl-1-(4-(5-carbamoyl-2-(2,5-dimethyloxazole-4-carboxamido)-7-(3-hydroxypropoxy)-1H-benzo[d]imidazol-1-yl)but-2-en-1-yl)-7-methoxy-1H-benzo[d]imidazol-2-yl)-2,5-dimethyloxazole-4-carboxamide, Compound 13 (20 mg, 13% yield) as a white solid. $^1$H NMR (400 MHz, DMSO-$d_6$) δ 12.65 (d, J=15.3 Hz, 1H), 7.92 (s, 2H), 7.59 (d, J=4.6 Hz, 2H), 7.28 (d, J=19.8 Hz, 4H), 5.79-5.57 (m, 2H), 4.85 (s, 4H), 4.04 (t, J=6.4 Hz, 2H), 3.74 (s, 3H), 3.44 (t, J=5.5 Hz, 2H), 2.61 (s, 2H), 2.42 (d, J=5.1 Hz, 6H), 2.31 (d, J=6.3 Hz, 6H). ESI-MS: $C_{36}H_{39}N_{10}O_9$ (M+H): calc. 755.28, found: 755.10.

Example 6: (E)-N-(5-carbamoyl-1-(4-(5-carbamoyl-2-(furo[3,2-13]pyridine-2-carboxamido)-7-(3-hydroxypropoxy)-1H-benzo[d]imidazol-1-yl)but-2-en-1-yl)-7-methoxy-1H-benzo[d]imidazol-2-yl)furo 13,2-13]pyridine-2-carboxamide, Compound 14

Example 7: (E)-1-(4-(5-carbamoyl-2-(1-isopropyl-1H-imidazole-2-carboxamido)-7-methoxy-1H-benzo[d]imidazol-1-yl)but-2-en-1-yl)-7-(3-hydroxypropoxy)-2-(1-isopropyl-1H-imidazole-2-carboxamido)-1H-benzo[d]imidazole-5-carboxamide, Compound 15

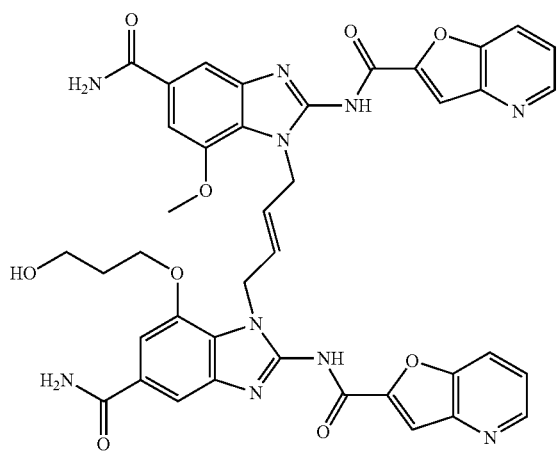

14

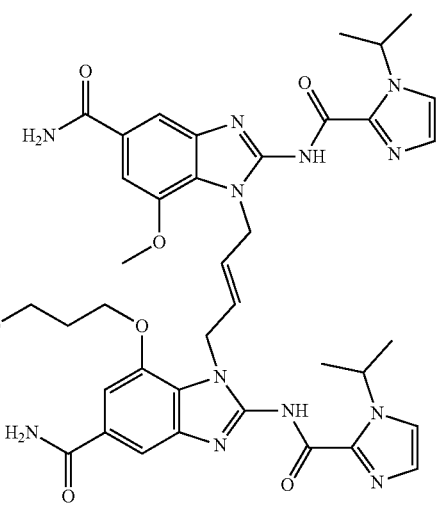

15

(E)-N-(5-carbamoyl-1-(4-(5-carbamoyl-2-(furo[3,2-b]pyridine-2-carboxamido)-7-(3-hydroxypropoxy)-1H-benzo[d]imidazol-1-yl)but-2-en-1-yl)-7-methoxy-1H-benzo[d]imidazol-2-yl)furo[3,2-b]pyridine-2-carboxamide was prepared as described in Example 1, except furo[3,2-b]pyridine-2-carboxylic acid was used in Step I instead of 4-ethyl-2-methyloxazole-5-carboxylic acid to afford (E)-N-(5-carbamoyl-1-(4-(5-carbamoyl-2-(furo[3,2-b]pyridine-2-carboxamido)-7-(3-hydroxypropoxy)-1H-benzo[d]imidazol-1-yl)but-2-en-1-yl)-7-methoxy-1H-benzo[d]imidazol-2-yl)furo[3,2-b]pyridine-2-carboxamide, Compound 14 (35 mg, 77% yield) as a white solid. $^1$H NMR (400 MHz, DMSO-$d_6$) δ 3.07 (d, J=4.7 Hz, 2H), 2.65 (d, J=8.4 Hz, 2H), 2.22-2.11 (m, 4H), 1.96 (dd, J=8.4, 4.8 Hz, 2H), 1.87 (dd, J=15.0, 6.3 Hz, 4H), 0.52 (q, J=4.3 Hz, 2H), -0.45 (t, J=4.4 Hz, 4H), -1.72 (s, 3H), -2.05 (t, J=6.0 Hz, 2H), -2.81 (dt, J=5.8, 2.9 Hz, 2H), -3.77 (t, J=6.2 Hz, 2H). ESI-MS: $C_{40}H_{35}N_{10}O_9$ (M+H): calc. 799.25, found: 799.20.

(E)-1-(4-(5-carbamoyl-2-(1-isopropyl-1H-imidazole-2-carboxamido)-7-methoxy-1H-benzo[d]imidazol-1-yl)but-2-en-1-yl)-7-(3-hydroxypropoxy)-2-(1-isopropyl-1H-imidazole-2-carboxamido)-1H-benzo[d]imidazole-5-carboxamide was prepared as described in Example 1, except 1-isopropyl-1H-imidazole-2-carboxylic acid was used in Step I instead of 4-ethyl-2-methyloxazole-5-carboxylic acid to afford (E)-1-(4-(5-carbamoyl-2-(1-isopropyl-1H-imidazole-2-carboxamido)-7-methoxy-1H-benzo[d]imidazol-1-yl)but-2-en-1-yl)-7-(3-hydroxypropoxy)-2-(1-isopropyl-1H-imidazole-2-carboxamido)-1H-benzo[d]imidazole-5-carboxamide, Compound (25 mg, 10% yield) as a white solid. $^1$H NMR (400 MHz, DMSO-$d_6$) δ 8.03 (d, J=18.1 Hz, 4H), 7.73 (s, 2H), 7.67 (dd, J=3.0, 1.2 Hz, 2H), 7.39 (d, J=10.2 Hz, 2H), 7.32 (t, J=1.8 Hz, 2H), 5.88 (d, J=14.4 Hz, 2H), 5.79 (dt, J=8.9, 4.9 Hz, 2H), 5.03 (s, 4H), 4.02 (t, J=6.4 Hz, 2H), 3.67 (s, 3H) 3.40 (d, J=6.1 Hz, 2H), 1.63 (p, J=6.2 Hz, 2H), 1.40 (dd, J=6.8, 2.3 Hz, 12H). ESI-MS: $C_{38}H_{45}N_{12}O_7$ (M+H): calc. 781.35, found: 781.40.

Example 8: (E)-1-(4-(5-carbamoyl-2-(1,2-dimethyl-1H-imidazole-5-carboxamido)-7-(3-hydroxy-propoxy)-1H-benzo[d]imidazol-1-yl)but-2-en-1-yl)-2-(1,2-dimethyl-1H-imidazole-Compound 16

Example 9: (E)-N-(5-carbamoyl-1-(4-(5-carbamoyl-7-(3-hydroxypropoxy)-2-(2-(trifluoro-methyl)thiazole-5-carboxamido)-1H-benzo[d]imidazol-1-yl)but-2-en-1-yl)-7-methoxy-1H-benzo[d]imidazol-2-yl)-2-(trifluoromethyl)thiazole-5-carboxamide, Compound 17

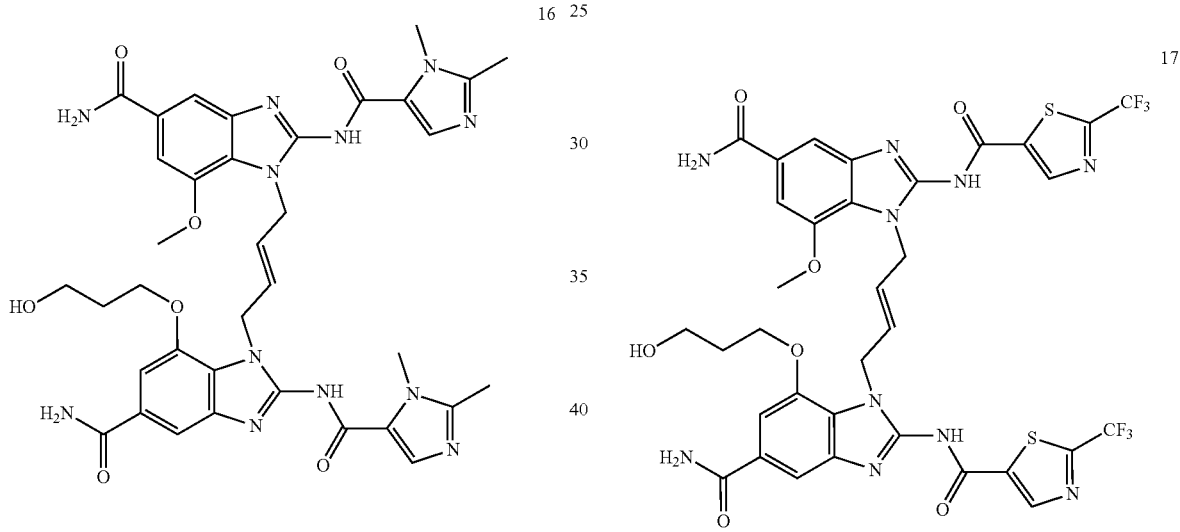

(E)-1-(4-(5-carb amoyl-2-(1,2-dimethyl-1H-imidazole-5-carboxamido)-7-(3-hydroxypropoxy)-1H-benzo[d]imidazol-1-yl)but-2-en-1-yl)-2-(1,2-dimethyl-1H-imidazole-5-carboxamido)-7-methoxy-1H-benzo[d]imidazole-5-carboxamide was prepared as described in Example 1, except 1,2-dimethyl-1H-imidazole-5-carboxylic acid was used in Step I instead of 4-ethyl-2-methyloxazole-5-carboxylic acid to afford (E)-1-(4-(5-carbamoyl-2-(1,2-dimethyl-1H-imidazole-5-carboxamido)-7-(3-hydroxypropoxy)-1H-benzo[d]imidazol-1-yl)but-2-en-1-yl)-2-(1,2-dimethyl-1H-imidazole-5-carboxamido)-7-methoxy-1H-benzo[d]imidazole-5-carboxamide, Compound 16 (40 mg, 13% yield) as a white solid. $^1$H NMR (400 MHz, DMSO-d$_6$) δ 7.89 (d, J=12.0 Hz, 2H), 7.59 (dd, J=7.0, 1.3 Hz, 2H), 7.29 (d, J=6.2 Hz, 2H), 5.80 (s, 2H), 4.95 (s, 4H), 3.95 (d, J=5.3 Hz, 6H), 3.47 (s, 2H), 1.70 (t, J=6.3 Hz, 2H). ESI-MS: $C_{36}H_{41}N_{12}O_7$ (M+H): calc. 753.31, found: 753.15.

(E)-N-(5-carbamoyl-1-(4-(5-carbamoyl-7-(3-hydroxypropoxy)-2-(2-(trifluoromethyl)thiazole-5-carboxamido)-1H-benzo[d]imidazol-1-yl)but-2-en-1-yl)-7-methoxy-1H-benzo[d]imidazol-2-yl)-2-(trifluoromethyl)thiazole-5-carboxamide was prepared as described in Example 1, except 2-(trifluoromethyl)thiazole-5-carboxylic acid was used in Step I instead of 4-ethyl-2-methyloxazole-5-carboxylic acid to afford (E)-N-(5-carbamoyl-1-(4-(5-carbamoyl-7-(3-hydroxypropoxy)-2-(2-(trifluoromethyl)thiazole-5-carboxamido)-1H-benzo[d]imidazol-1-yl)but-2-en-1-yl)-7-methoxy-1H-benzo[d]imidazol-2-yl)-2-(trifluoromethyl)thiazole-5-carboxamide, Compound 17 (10 mg, 5% yield) as a white solid. $^1$H NMR (400 MHz, DMSO-d$_6$) δ 12.91 (s, 2H), 8.41 (t, J=1.2 Hz, 2H), 7.99 (s, 2H), 7.66 (dd, J=3.4, 1.3 Hz, 2H), 7.36 (s, 3H), 7.21 (s, 1H), 7.08 (s, 1H), 6.95 (s, 1H), 5.95 (q, J=3.1, 2.1 Hz, 2H), 4.95 (s, 4H), 4.12 (t, J=6.4 Hz, 2H), 3.82 (s, 3H), 1.82-1.76 (m, 2H). ESI-MS: $C_{34}H_{29}F_6N_{10}O_7S_2$ (M+H): calc. 867.15, found: 867.05.

Example 10: (E)-N-(7-(3-aminopropoxy)-5-carbam-
oyl-1-(4-(5-carbamoyl-2-(4-ethyl-2-methyloxazole-
5-carboxamido)-7-methoxy-1H-benzo[d]imidazol-1-
yl)but-2-en-1-yl)-1H-benzo[d]imidazol-2-yl)-4-
ethyl-2-methyloxazole-5-carboxamide, Compound
18

Example 11: (E)-4-((5-carbamoyl-1-(4-(5-carbam-
oyl-2-(4-ethyl-2-methyloxazole-5-carboxamido)-7-
methoxy-1H-benzo[d]imidazol-1-yl)but-2-en-1-yl)-
2-(4-ethyl-2-methyloxazole-5-carboxamido)-1H-
benzo[d]imidazol-7-yl)oxy)butanoic acid,
Compound 19

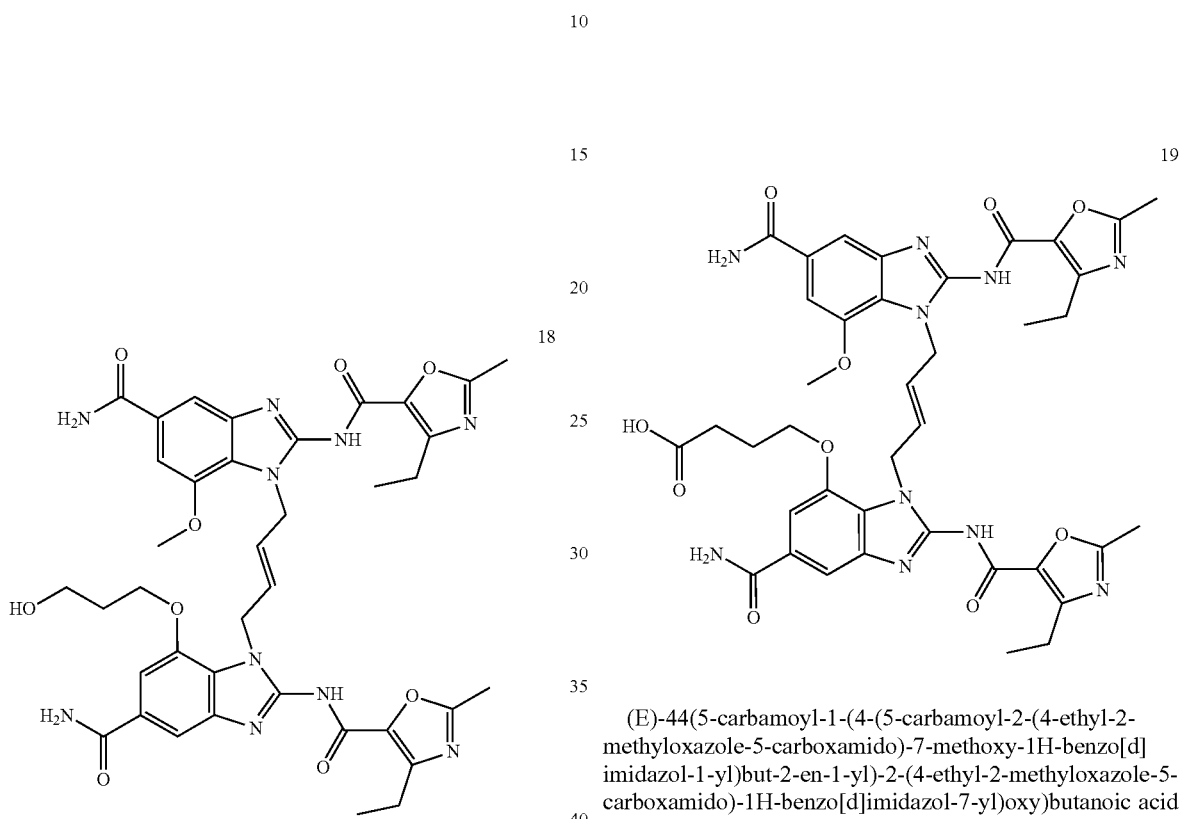

(E)-N-(7-(3-aminoprop oxy)-5-carbamoyl-1-(4-(5-car-
bamoyl-2-(4-ethyl-2-methyloxazole-yl)-4-ethyl-2-methyl-
oxazole-5-carboxamide was prepared as described in
Example 1, except tert-butyl (3-bromopropyl)carbamate
was used in Step C instead of (3-bromopropoxy)(tert-butyl)
dimethylsilane. Removal of the Boc group was accom-
plished by stirring the boc-protected amine of (E)-N-(7-(3-
aminoprop oxy)-5-carb amoyl-1-(4-(5-carbamoyl-2-(4-
ethyl-2-methyloxazol e-5-carboxamido)-7-methoxy-1H-
benzo[d]imidazol-1-yl)but-2-en-1-yl)-1H-benzo[d]
imidazol-2-yl)-4-ethyl-2-methyloxazole-5-carboxamide,
Compound 18 in dioxane (0.1 M) and HCl (4M in dioxane,
10 equivalents) for 1 hour. Removal of the solvent afforded
(E)-N-(7-(3-aminoprop oxy)-5-carbamoyl-1-(4-(5-carbam-
oyl-2-(4-ethyl-2-methyloxazole-5-carboxamido)-7-
methoxy-1H-benzo[d]imidazol-1-yl)but-2-en-1-yl)-1H-
benzo[d]imidazol-2-yl)-4-ethyl-2-methyloxazole-5-
carboxamide, Compound 18 (110 mg, 19% yield over 2
steps) as a white solid. $^1$H NMR (500 MHz, DMSO-$d_6$) δ
8.06 (s, 2H), 7.99 (s, 1H), 7.63 (dd, J=5.3, 1.3 Hz, 2H), 7.37
(d, J=1.3 Hz, 1H), 7.36-7.31 (m, 2H), 5.85-5.67 (m, 2H),
4.88 (dd, J=13.6, 5.2 Hz, 4H), 4.13 (t, J=6.2 Hz, 2H), 3.76
(s, 3H), 2.88 (d, J=6.2 Hz, 2H), 2.76 (qd, J=7.5, 4.7 Hz, 4H),
2.38 (d, J=3.6 Hz, 6H), 1.98-1.89 (m, 2H), 0.97 (t, J=7.5 Hz,
6H). ESI-MS: $C_{38}H_{44}N_{11}O_8$ (M+H): calc. 782.33, found:
782.38.

(E)-44(5-carbamoyl-1-(4-(5-carbamoyl-2-(4-ethyl-2-
methyloxazole-5-carboxamido)-7-methoxy-1H-benzo[d]
imidazol-1-yl)but-2-en-1-yl)-2-(4-ethyl-2-methyloxazole-5-
carboxamido)-1H-benzo[d]imidazol-7-yl)oxy)butanoic acid
was prepared as described in Example 1, except methyl
4-bromobutanoate was used in Step C instead of (3-bro-
mopropoxy)(tert-butyl)dimethylsilane. Hydrolysis of the
methyl ester was accomplished by stirring the ester of
(E)-4-((5-carbamoyl-1-(4-(5-carbamoyl-2-(4-ethyl-2-
methyl oxazol e-5-carboxamido)-7-m ethoxy-1H-benzo[d]
imidazol-1-yl)but-2-en-1-yl)-2-(4-ethyl-2-methyloxazole-5-
carboxamido)-1H-benzo[d]imidazol-7-yl)oxy)butanoic
acid, Compound 19 in a mixture of methanol:THF:$H_2O$
(1:1:0.25 v/v, 0.02 M) and LiOH·$H_2O$ (5 equivalents) for 16
hours. The resulting mixture was acidified with 1N HCl and
purified by HPLC to afford (E)-4-((5-carbamoyl-1-(4-(5-
carbamoyl-2-(4-ethyl-2-methyloxazole-5-carboxamido)-7-
methoxy-1H-benzo[d]imidazol-1-yl)but-2-en-1-yl)-2-(4-
ethyl-2-methyloxazole-5-carboxamido)-1H-benzo[d]
imidazol-7-yl)oxy)butanoic acid, Compound 19 (40 mg,
41% yield over 2 steps) as a white solid. $^1$H NMR (400
MHz, DMSO-$d_6$) δ 7.96 (s, 2H), 7.63 (t, J=1.6 Hz, 2H), 7.35
(s, 2H), 7.30 (d, J=1.4 Hz, 2H), 5.89-5.69 (m, 2H), 4.88 (dd,
J=12.9, 5.1 Hz, 4H), 4.03 (d, J=6.3 Hz, 2H), 2.77 (q, J=7.5
Hz, 4H), 2.38 (d, J=1.8 Hz, 6H), 1.86 (q, J=6.8 Hz, 2H), 0.97
(td, J=7.5, 3.3 Hz, 6H). ESI-MS: $C_{39}H_{43}N_{10}O_{10}$ (M+H):
calc. 811.31, found: 811.30.

General procedure for synthesis of Compound Variant II,
wherein $Z_1=Z_2$; $Y_1=Y_2$; $X_1=X_2$; $W_1=W_2$; $R^{14}=R^{C2}$;
$R^{19}=R^{18}$; $R^{15}=R^{17}$ and $R^{C1}=R^{16}$.

Variant II

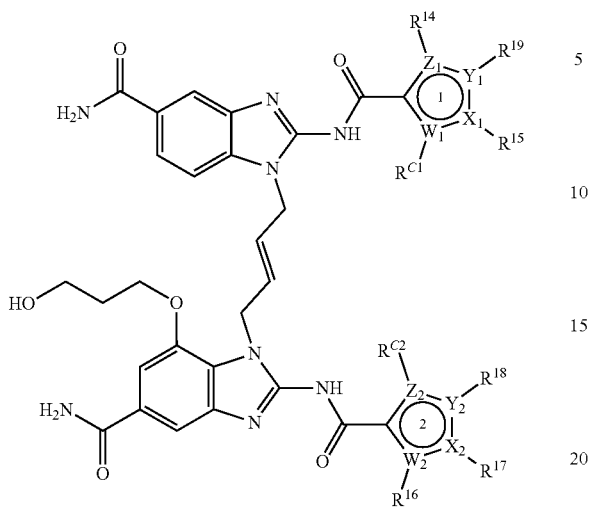

Scheme 2: The following scheme illustrates the exemplary synthesis of (E)-N-(5-carbamoyl-1-(4-(5-carb amoyl-2-(5-methylisoxazole-3-carboxamido)-1H-benzo[d]imidazol-1-yl)but-2-en-1-yl)-7-(3-hydroxypropoxy)-1H-benzo[d]imidazol-2-yl)-5-methylisoxazole-3-carboxamide. The similar procedure may be generally used for the synthesis of Compound Variant II. As shown below, heterocyclic structures (rings 1 and 2) can be introduced by using the corresponding carboxylic acid at Step G.

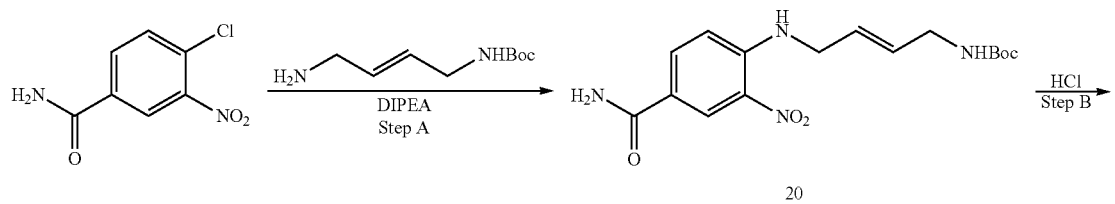

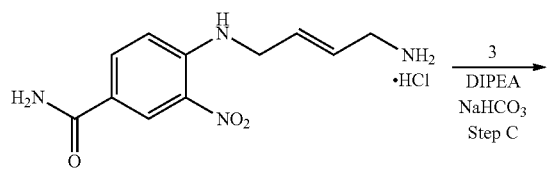

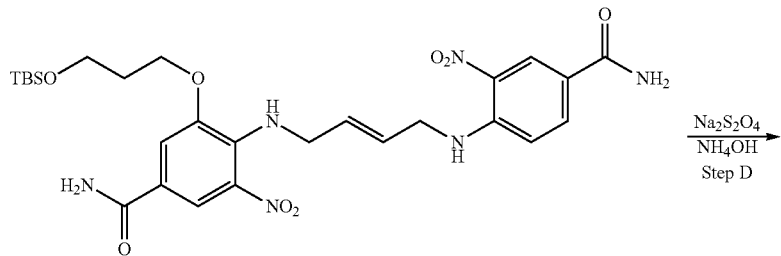

-continued
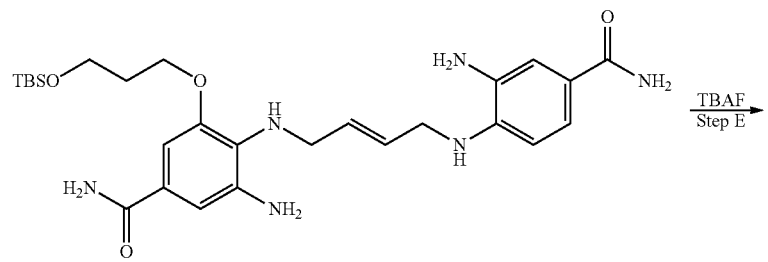
23
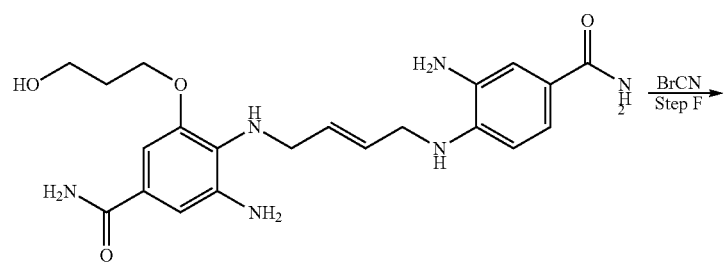
24
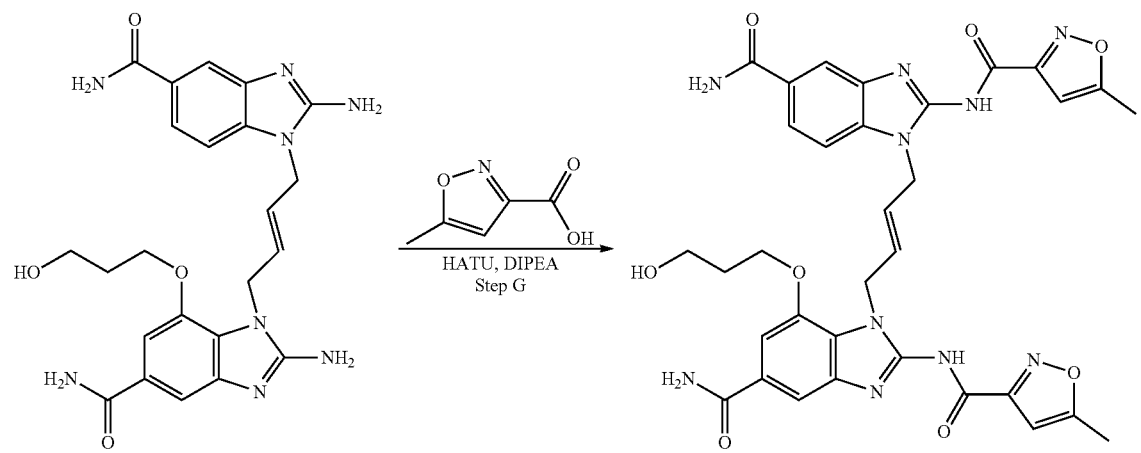
25 → 26

Example 12: (E)-N-(5-carbamoyl-1-(4-(5-carbamoyl-2-(5-methylisoxazole-3-carboxamido)-1H-benzo[d]imidazol-1-yl)but-2-en-1-yl)-7-(3-hydroxypropoxy)-1H-benzo[d]imidazol-2-yl)-Compound 26

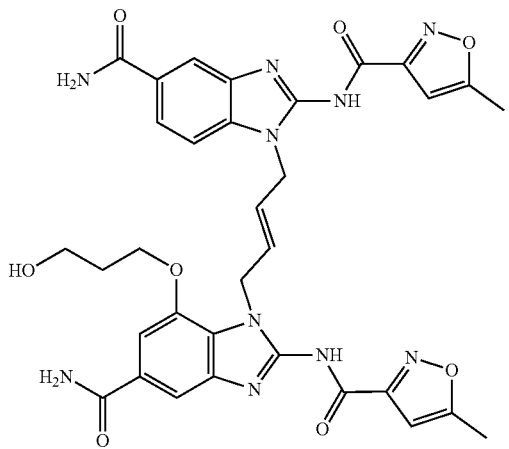

Step A: To a stirred solution of 4-chloro-5-nitrobenzamide (4 g, 19.9 mmol) in ethanol (80 mL) was added tert-butyl (E)-(4-aminobut-2-en-1-yl)carbamate (4.1 g, 21.9 mmol) and DIPEA (10.4 mL, 59.8 mmol). The mixture was heated to 120° C. and stirred for 12 hours, then cooled in an ice bath, and the resulting solid was filtered and washed with cold ethanol to afford tert-butyl (E)-(4-((4-carbamoyl-2-nitrophenyl)amino)but-2-en-1-yl)carbamate, Compound 20 (5.6 g, 80% yield) as a yellow solid. ESI-MS: $C_{16}H_{23}N_4O_5$ (M+H): calc. 351.16, found: 351.18.

Step B: To a stirred suspension of tert-butyl (E)-(4-((4-carbamoyl-2-nitrophenyl)amino)but-2-en-1-yl)carbamate (5.6 g, 16.0 mmol) in methanol (16 mL) was added HCl (4M in dioxane, 34.0 mL, 136 mmol). The mixture was stirred at room temperature for 1 hour. The resulting precipitate was filtered and washed with dioxane and dried to afford (E)-4-((4-aminobut-2-en-1-yl)amino)-3-nitrobenzamide-HCl, Compound 21 (4.58 g, 100% yield) as a yellow solid. ESI-MS: $C_{11}H_{15}N_4O_3$ (M+H): calc. 251.11, found: 251.12.

Step C: To a stirred solution of 3-(3-((tert-butyldimethylsilyl)oxy)propoxy)-4-chloro-5-nitrobenzamide, Compound 3 (prepared as described in Example 1, 3.8 g, 9.77 mmol) in n-butanol (33 mL) was added (E)-4-((4-aminobut-2-en-1-yl)amino)-3-nitrobenzamide-HCl (3.36 g, 11.7 mmol), DIPEA (6.81 mL, 39.1 mmol), and NaHCO₃ (1.64 g, 19.5 mmol). The mixture was heated to 120° C. and stirred for 12 hours. After cooling to room temperature, the mixture was concentrated in vacuo. Purification over silica gel (hexane:EtOAc 1:1 v/v) afforded (E)-3-(3-((tert-butyldimethylsilyl)oxy)propoxy)-4-((4-((4-carbamoyl-2-nitrophenyl)amino)but-2-en-1-yl)amino)-5-nitrobenzamide, Compound 22 (3.8 g, 65% yield) as an orange solid. ESI-MS: $C_{27}H_{39}N_6O_8Si$ (M+H): calc. 603.35, found: 603.29.

Step D: To a stirred solution of (E)-3-(3-((tert-butyldimethylsilyl)oxy)propoxy)-44(44(4-carbamoyl-2-nitrophenyl)amino)but-2-en-1-yl)amino)-5-nitrobenzamide, Compound 22 (4.0 g, 6.64 mmol) in methanol (95 mL) at 0° C. was added Na₂S₂O₄ (11.6 g, 66.4 mmol) in water (40 mL), followed immediately by NH₄OH (28% w/w in water, 23.1 mL, 166 mmol). The mixture was warmed to room temperature and stirred for 30 minutes. The mixture was diluted in water and extracted with EtOAc (3×). The combined organic layers were dried over MgSO₄ and concentrated in vacuo. Purification over silica gel (EtOAc:EtOH, 3:1 v/v) afforded (E)-3-amino-4-((4-((2-amino-4-carbamoylphenyl)amino)but-2-en-1-yl)amino)-5-(3-((tert-butyldimethylsilyl)oxy)propoxy)benzamide, Compound 23 (1.39 g, 39% yield) as an orange solid. ESI-MS: $C_{27}H_{43}N_6O_4Si$ (M+H): calc. 543.30, found: 543.34.

Step E: To a stirred solution of (E)-3-amino-4-((4-((2-amino-4-carbamoylphenyl)amino)but-2-en-1-yl)amino)-5-(3-((tert-butyldimethylsilyl)oxy)propoxy)benzamide, Compound 23 (1.4 g, 2.58 mmol) in THF (13 mL) under nitrogen was added TBAF (1M in THF, 5.2 mL, 5.2 mmol). The mixture was stirred at room temperature for 1 hour, then concentrated in vacuo. Purification over silica gel (EtOAc:EtOH 1:1 v/v) afforded (E)-3-amino-4-((4-((2-amino-4-carbamoylphenyl)amino)but-2-en-1-yl)amino)-5-(3-hydroxypropoxy)benzamide, Compound 24 (890 mg, 81% yield) as a yellow solid. ESI-MS: $C_{21}H_{29}N_6O_4$ (M+H): calc. 429.22, found: 429.25.

Step F: To a stirred solution of (E)-3-amino-4-((4-((2-amino-4-carbamoylphenyl)amino)but-2-en-1-yl)amino)-5-(3-hydroxypropoxy)benzamide, Compound 24 (890 mg, 2.1 mmol) in methanol (21 mL) under nitrogen was added BrCN (462 mg, 4.4 mmol). The mixture was stirred at room temperature for 12 hours. The resulting solid was filtered and washed with methanol (5 mL) to afford (E)-2-amino-1-(4-(2-amino-5-carbamoyl-1H-benzo[d]imidazol-1-yl)but-2-en-1-yl)-7-(3-hydroxypropoxy)-1H-benzo[d]imidazole-5-carboxamide, Compound 25 (1.1 g, 77% yield) as a white solid. ESI-MS: $C_{23}H_{27}N_8O_4$ (M+H): calc. 479.21, found: 479.25.

Step G: To a stirred solution of (E)-2-amino-1-(4-(2-amino-5-carbamoyl-1H-benzo[d]imidazol-1-yl)but-2-en-1-yl)-7-(3-hydroxypropoxy)-1H-benzo[d]imidazole-5-carboxamide, Compound 25 (150 mg, 0.23 mmol) in DMF (2.5 mL) was added 5-methylisoxazole-3-carboxylic acid (110 mg, 0.7 mmol), HATU (267 mg, 0.7 mmol) and DIPEA (0.25 mL, 1.4 mmol). The mixture was heated to 50° C. and stirred for 3 hours, then cooled to room temperature and methylamine (33% in EtOH w/w, 5.8 mL, 46.9 mmol) was added. The mixture was stirred at room temperature for 1 hour, then concentrated in vacuo. Purification over silica gel (DCM:MeOH 3:1 v/v) afforded (E)-N-(5-carbamoyl-1-(4-(5-carbamoyl-2-(5-methylisoxazole-3-carboxamido)-1H-benzo[d]imidazol-1-yl)but-2-en-1-yl)-7-(3-hydroxypropoxy)-1H-benzo[d]imidazol-2-yl)-5-methylisoxazole-3-carboxamide, Compound 26 (84 mg, 48% yield) as a white solid. ESI-MS: $C_{33}H_{33}N_{10}O_8$ (M+H): calc. 697.24, found: 697.26.

Example 13: (E)-1-(4-(5-carbamoyl-2-(1-methyl-1H-1,2,3-triazole-5-carboxamido)-1H-benzo[d]imidazol-1-yl)but-2-en-1-yl)-7-(3-hydroxypropoxy)-2-(1-methyl-1H-1,2,3-triazole-Compound 27

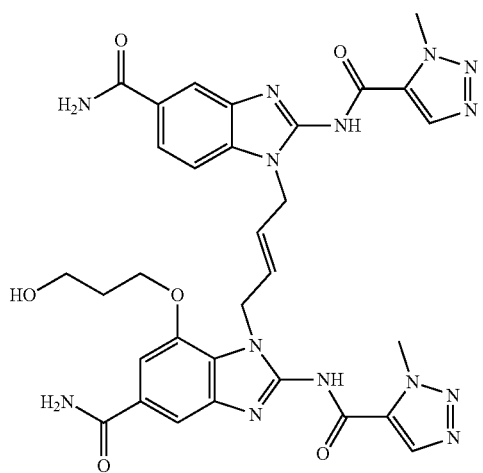

(E)-1-(4-(5-carbamoyl-2-(1-methyl-1H-1,2,3-triazole-5-carboxamido)-1H-benzo[d]imidazol-1-yl)but-2-en-1-yl)-7-(3-hydroxypropoxy)-2-(1-methyl-1H-1,2,3-triazole-5-carboxamido)-1H-benzo[d]imidazole-5-carboxamide was prepared as described in Example 12, except 1-methyl-1H-1,2,3-triazole-5-carboxylic acid was used in Step G instead of 4-ethyl-2-methyloxazole-5-carboxylic acid to afford (E)-1-(4-(5-carbamoyl-2-(1-methyl-1H-1,2,3-triazole-ox-amido)-1H-benzo[d]imidazol-1-yl)but-2-en-1-yl)-7-(3-hydroxypropoxy)-2-(1-methyl-1H-1,2,3-triazole-5-carboxamido)-1H-benzo[d]imidazole-5-carboxamide, Compound 27 (32 mg, 29% yield) as a white solid. ESI-MS: $C_{31}H_{33}N_{14}O_6$ (M+H): calc. 697.26, found: 697.28.

Example 14: (E)-N-(5-carbamoyl-1-(4-(5-carbamoyl-2-(oxazole-4-carboxamido)-1H-benzo[d]imidazol-1-yl)but-2-en-1-yl)-7-(3-hydroxypropoxy)-1H-benzo[d]imidazol-2-yl)oxazole-4-carboxamide, Compound 28

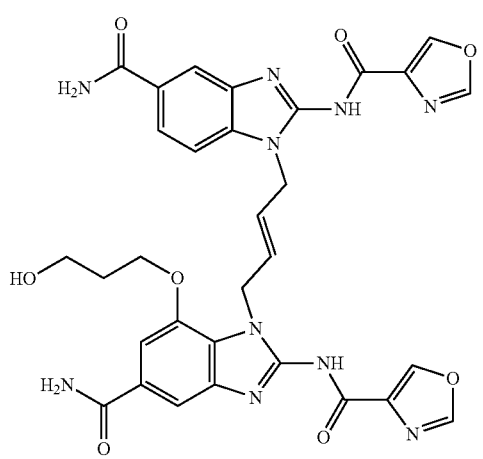

(E)-N-(5-carbamoyl-1-(4-(5-carbamoyl-2-(oxazole-4-carboxamido)-1H-benzo[d]imidazol-1-yl)but-2-en-1-yl)-7-(3-hydroxypropoxy)-1H-benzo[d]imidazol-2-yl)oxazole-4-carboxamide was prepared as described in Example 12, except oxazole-4-carboxylic acid was used in Step G instead of 4-ethyl-2-methyloxazole-5-carboxylic acid to afford (E)-N-(5-carbamoyl-1-(4-(5-carbamoyl-2-(oxazole-4-carboxamido)-1H-benzo[d]imidazol-1-yl)but-2-en-1-yl)-7-(3-hydroxypropoxy)-1H-benzo[d]imidazol-2-yl)oxazole-4-carboxamide, Compound 28 (27 mg, 26% yield) as a white solid. ESI-MS: $C_{31}H_{29}N_{10}O_8$ (M+H): calc. 669.21, found: 669.22.

General Procedure for Synthesis of Compound Variant III.

Variant III

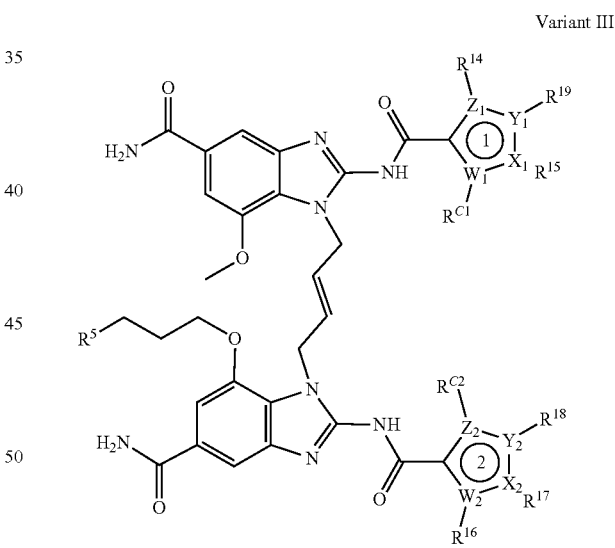

Scheme 3: The following scheme illustrates the exemplary synthesis of (E)-N-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide. The similar procedure may be generally used for the synthesis of Compound Variant III. As shown below, heterocyclic structures (rings 1 and 2) can be introduced by using the corresponding carboxylic acids at Step G and Step L, respectively.

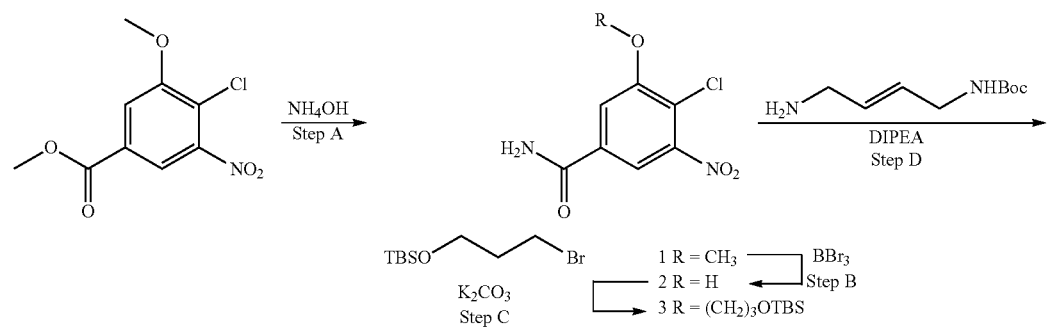
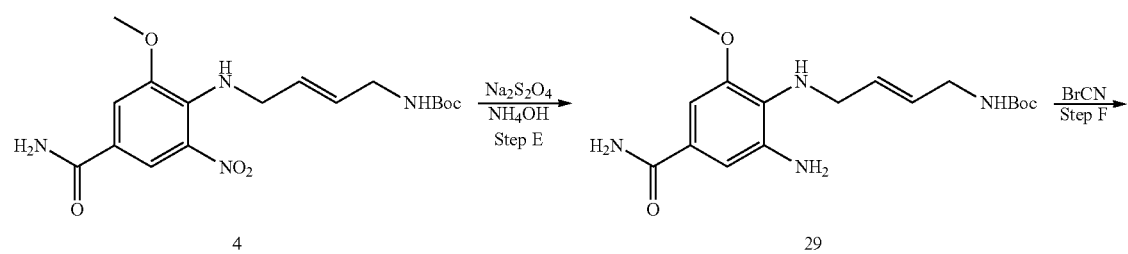
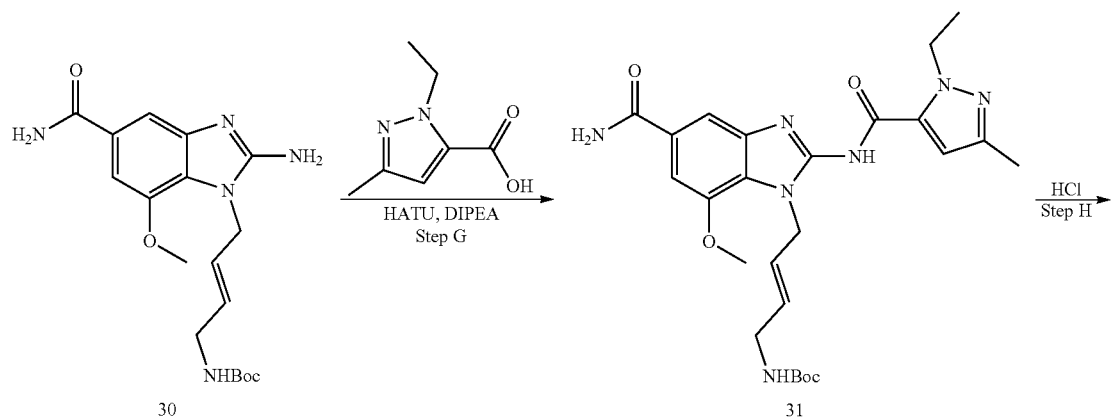
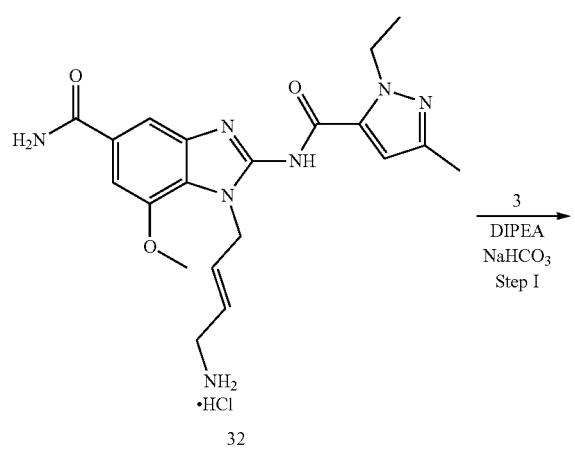

-continued
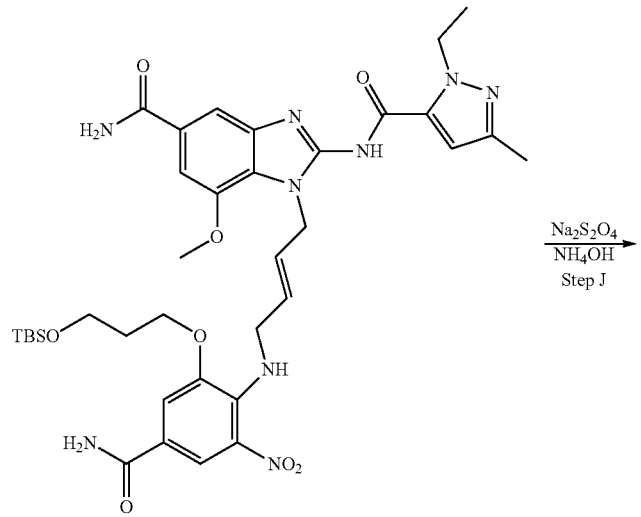
33
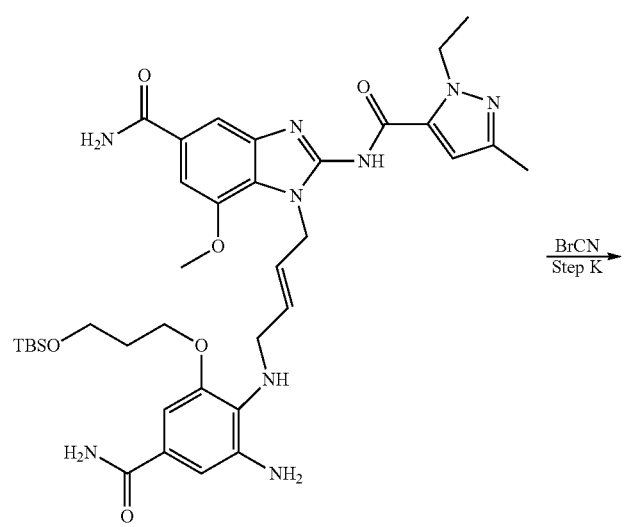
34
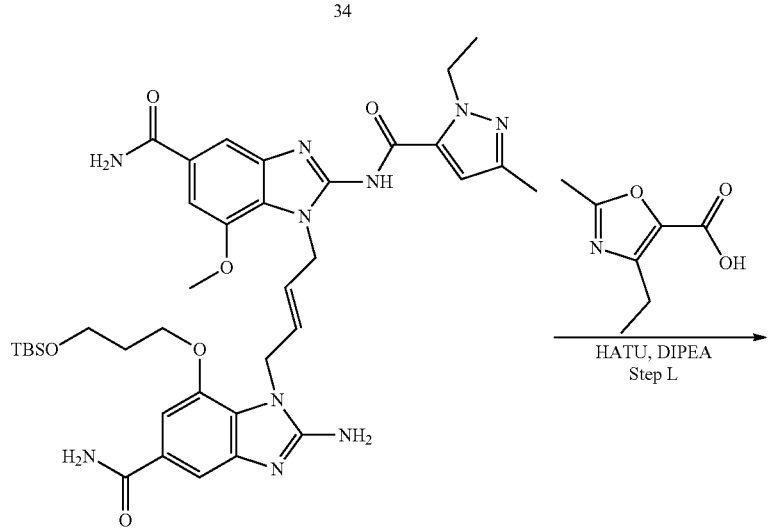
35

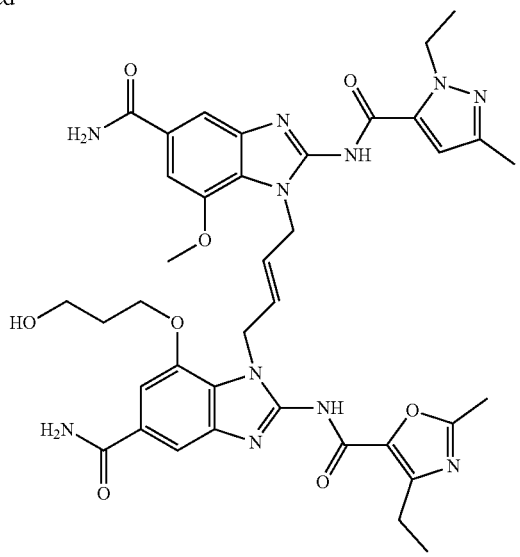

36

Example 15: (E)-N-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide, Compound 36

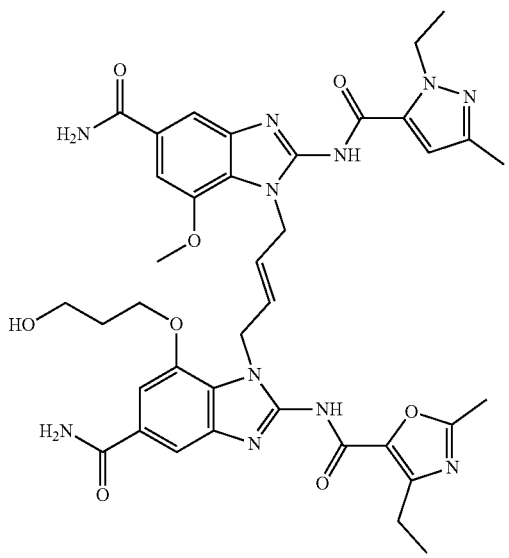

Steps A, B, C and D were conducted as described in Example 1.

Step E: To a stirred solution of tert-butyl (E)-(4-((4-carbamoyl-2-methoxy-6-nitrophenyl)amino)but-2-en-1-yl)carbamate, Compound 4 (prepared as described in Example 1, 2 g, 5.3 mmol) in methanol (70 mL) at 0° C. was added Na$_2$S$_2$O$_4$ (4.58 g, 26.3 mmol) dissolved in water (22 mL), followed immediately by the addition of NH$_4$OH (8 mL). The mixture was warmed to room temperature and stirred for 15 minutes, then diluted in water and extracted with EtOAc (3×). The combined organic layers were dried over MgSO$_4$ and concentrated to afford tert-butyl (E)-(4-((2-amino-4-carbamoyl-6-methoxyphenyl)amino)but-2-en-1-yl)carbamate, Compound 29 (1.80 g, 97% yield) as a brown solid. $^1$H NMR (400 MHz, DMSO-d$_6$) δ 7.58 (s, 1H), 6.98-6.85 (m, 2H), 6.82 (d, J=1.8 Hz, 1H), 6.74 (d, J=1.9 Hz, 1H), 5.62-5.43 (m, 2H), 4.63 (s, 2H), 3.71 (s, 3H), 3.52-3.41 (m, 4H), 1.32 (s, 9H). ESI-MS: C$_{17}$H$_{27}$N$_4$O$_4$ (M+H): calc. 351.20, found: 351.20.

Step F: To a stirred solution of tert-butyl (E)-(4-((2-amino-4-carbamoyl-6-methoxyphenyl)amino)but-2-en-1-yl)carbamate, Compound 29 (1.8 g, 5.14 mmol) in methanol (30 mL) under nitrogen at 0° C. was added cyanogen bromide (816 mg, 7.71 mmol). The mixture was stirred at room temperature for 16 hours, then concentrated in vacuo. The resulting residue was triturated in EtOAc and filtered to afford tert-butyl (E)-(4-(2-amino-5-carbamoyl-7-methoxy-1H-benzo[d]imidazol-1-yl)but-2-en-1-yl)carbamate, Compound 30 (1.8 g, 98% yield) as a white solid. $^1$H NMR (400 MHz, DMSO-d$_6$) δ 12.87 (s, 1H), 8.61 (s, 2H), 8.05 (s, 1H), 7.46 (d, J=1.3 Hz, 1H), 7.44-7.39 (m, 2H), 6.94 (t, J=5.9 Hz, 1H), 5.73-5.48 (m, 2H), 4.81 (d, J=4.5 Hz, 2H), 3.91 (s, 3H), 3.47 (t, J=5.0 Hz, 2H), 1.30 (s, 9H). ESI-MS: C$_{18}$H$_{26}$N$_5$O$_4$ (M+H): calc. 376.19, found: 376.20.

Step G: To a stirred solution of tert-butyl (E)-(4-(2-amino-5-carbamoyl-7-methoxy-1H-benzo[d]imidazol-1-yl)but-2-en-1-yl)carbamate, Compound 30 (1.8 g, 4.80 mmol) in DMF (12 mL) was added 1-ethyl-3-methyl-1H-pyrazole-5-carboxylic acid (1.1 g, 7.20 mmol), HATU (3.65 g, 9.59 mmol), and DIPEA (5.0 mL, 29.78 mmol). The mixture was heated to 60° C. and stirred for 3 hours, then cooled to room temperature and quenched with water. The mixture was extracted with EtOAc (2×200 mL) and the combined organic layers were dried over Na$_2$S$_2$O$_4$ and concentrated in vacuo. Purification over silica gel (DCM:MeOH 5:1) afforded tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate, Compound 31 (1.30 g, 53% yield) as a grey solid. $^1$H NMR (400 MHz, DMSO-d$_6$) δ 7.58 (s, 1H), 6.99-6.85 (m, 2H), 6.82 (d, J=1.8

Hz, 1H), 6.75 (d, J=1.9 Hz, 1H), 5.53 (tdt, J=15.5, 10.3, 5.0 Hz, 2H), 4.62 (s, 2H), 3.72 (s, 3H), 3.45 (t, J=5.7 Hz, 4H), 3.13 (q, J=5.2 Hz, 2H), 2.50 (s, 3H), 1.33 (s, 9H), 1.13 (t, J=7.1 Hz, 3H). ESI-MS: $C_{25}H_{34}N_7O_5$ (M+H): calc. 512.25, found: 512.30.

Step H: To a stirred solution of tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate, Compound 31 (1.30 g, 2.54 mmol) in DCM (15 mL) was added HCl (4M in dioxane, 6.36 mL, mmol). The mixture was stirred at room temperature for 2 hours. The resulting solid was filtered and washed with dioxane to afford (E)-1-(4-aminobut-2-en-1-yl)-2-(1-ethyl-3-methyl-1H-pyrazole-5-carboxamido)-7-methoxy-1H-benzo[d]imidazole-5-carboxamide-HCl, Compound 32 (1.10 g, 97% yield) as an orange solid. $^1$H NMR (400 MHz, DMSO-$d_6$) δ 7.91 (s, 2H), 7.63 (d, J=1.3 Hz, 1H), 7.42-7.31 (m, 2H), 6.64 (s, 1H), 5.99 (ddd, J=15.6, 6.5, 5.1 Hz, 1H), 5.62 (ddd, J=15.7, 7.0, 5.6 Hz, 1H), 4.94 (d, J=5.8 Hz, 2H), 4.59 (s, 2H), 3.95 (s, 3H), 3.43-3.35 (m, 2H), 2.14 (s, 3H), 1.31 (t, J=7.1 Hz, 3H). ESI-MS: $C_{20}H_{26}N_7O_3$ (M+H): calc. 412.47, found: 412.45.

Step I: To a stirred solution of 3-(3-((tert-butyldimethylsilyl)oxy)propoxy)-4-chloro-5-nitrobenzamide, Compound 3 (prepared as described in Example 1, 4.50 g, 11.59 mmol) in n-butanol (100 mL) was added (E)-1-(4-aminobut-2-en-1-yl)-2-(1-ethyl-3-methyl-1H-pyrazole-5-carboxamido)-7-methoxy-1H-benzo[d]imidazole-5-carboxamide-HCl, Compound 32 (7.77 g, 17.39 mmol), DIPEA (129 mL, 46.4 mmol), and NaHCO$_3$ (1.95 g, 23.19 mmol) The mixture was heated under pressure to 120° C. and stirred for 16 hours. The mixture was cooled to 0° C., and the resulting solid was filtered and washed with cold butanol and water. Purification over silica gel (DCM:MeOH 5:1 v/v) afforded (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-7-methoxy-1H-benzo[d]imidazole-5-carboxamide, Compound 33 (1.50 g, 17% yield) as a brown solid. (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-7-methoxy-1H-benzo[d]imidazole-5-carboxamide, Compound 33 without the TBS group was also isolated (2.50 g, 33% yield) as a brown solid. $^1$H NMR (400 MHz, DMSO-$d_6$) δ 12.89 (s, 1H), 8.19 (d, J=1.9 Hz, 1H), 8.05 (s, 1H), 7.79 (t, J=6.3 Hz, 1H), 7.71 (s, 1H), 7.59-7.52 (m, 1H), 7.39 (d, J=12.3 Hz, 3H), 6.65 (s, 1H), 5.79 (dtd, J=21.2, 15.4, 5.7 Hz, 2H), 4.95 (d, J=5.5 Hz, 2H), 4.64 (q, J=7.1 Hz, 2H), 4.19 (t, J=5.9 Hz, 2H), 4.05 (t, J=6.0 Hz, 2H), 3.92 (s, 3H), 3.69 (t, J=6.2 Hz, 2H), 2.21 (s, 3H), 1.87 (p, J=6.2 Hz, 2H), 1.38 (t, J=7.1 Hz, 3H), 0.85 (s, 9H) 0.01 (s, 6H). ESI-MS: $C_{36}H_{50}N_9O_8Si$ (M+H): calc. 764.35, found: 764.40.

Step J. To a stirred solution of (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-7-methoxy-1H-benzo[d]imidazole-5-carboxamide, Compound 33 (1.50 g, 1.97 mmol) in MeOH (50 mL) at 0° C. was added Na$_2$S$_2$O$_4$ (1.71 g, 9.83 mmol) dissolved in water (10 mL) immediately followed by NH$_4$OH (6.0 mL). The mixture was warmed to room temperature and stirred for 15 minutes. The mixture was diluted in water and extracted with EtOAc (2×200 mL). The combined organic layers were dried over Na$_2$SO$_4$ and concentrated in vacuo to afford (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-7-methoxy-1H-benzo[d]imidazole-Compound 34 (800 mg, 56% yield) as a brown solid. $^1$H NMR (400 MHz, DMSO-$d_6$) δ 8.68-8.59 (m, 1H), 8.42 (d, J=8.4 Hz, 1H), 7.95 (s, 2H), 7.63 (d, J=3.5 Hz, 2H), 7.41 (dd, J=8.5, 4.3 Hz, 1H), 7.35-7.27 (m, 3H), 6.86 (d, J=5.9 Hz, 1H), 6.50 (s, 2H), 5.94-5.73 (m, 2H), 5.00-4.84 (m, 4H), 4.52 (q, J=7.3 Hz, 4H), 3.99 (t, J=6.1 Hz, 2H), 3.72 (s, 3H), 3.38 (q, J=7.0 Hz, 2H), 3.17 (d, J=4.0 Hz, 3H), 1.32 (s, 9H), 1.09 (t, J=7.0 Hz, 3H). ESI-MS: $C_{36}H_{52}N_9O_6Si$ (M+H): calc. 734.37, found: 734.20.

Step K: To a stirred solution of (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-7-methoxy-1H-benzo[d]imidazole-5-carboxamide, Compound 34 (700 mg, 0.95 mmol) in MeOH (15 mL) was added cyanogen bromide (303 mg, 2.86 mmol). The mixture was stirred at room temperature for 2 hours. The mixture was concentrated in vacuo. The residue was triturated in EtOAc and filtered to afford (E)-2-amino-7-(3-((tert-butyldimethylsilyl)oxy)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-1H-benzo[d]imidazole-5-carboxamide, Compound 35 (500 mg, 69% yield) as a yellow solid. $^1$H NMR (400 MHz, DMSO-$d_6$) δ 12.85 (s, 2H), 8.54 (s, 2H), 8.06 (s, 1H), 7.98 (s, 1H), 7.66 (s, 1H), 7.47 (s, 1H), 7.43 (s, 1H), 7.41-7.30 (m, 3H), 6.50 (s, 1H), 5.94-5.81 (m, 1H), 5.81-5.70 (m, 1H), 4.88 (dd, J=26.8, 5.5 Hz, 4H), 4.53 (q, J=7.2 Hz, 2H), 4.07 (t, J=6.1 Hz, 2H), 3.76 (s, 3H), 3.62 (t, J=6.1 Hz, 2H), 3.17 (s, 3H), 1.75 (p, J=6.2 Hz, 2H), 1.28 (t, J=7.1 Hz, 3H), 0.81 (s, 9H). ESI-MS: $C_{37}H_{51}N_{10}O_6Si$ (M+H): calc. 759.37, found: 759.20.

Step L: To a stirred solution of (E)-2-amino-7-(3-((tert-butyldimethylsilyl)oxy)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-1H-benzo[d]imidazole-5-carboxamide, Compound 35 (100 mg, 0.12 mmol) in DMF (3 mL) was added 4-ethyl-2-methyloxazole-5-carboxylic acid (46 mg, mmol), HATU (113 mg, 0.30 mmol) and DIPEA (103 mL, 0.60 mmol). The mixture was heated to 70° C. and stirred for 16 hours. The mixture was cooled to room temperature and concentrated in vacuo. The residue was purified by HPLC (ACN:H$_2$O) to afford (E)-N-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide, Compound 36 (25 mg, 6% yield) as a brown solid. $^1$H NMR (400 MHz, Methanol-$d_4$) δ 7.63-7.56 (m, 2H), 7.30 (s, 2H), 5.84 (d, J=3.5 Hz, 2H), 5.03 (d, J=3.7 Hz, 4H), 4.57 (q, J=7.1 Hz, 2H), 4.09 (t, J=6.2 Hz, 2H), 3.79 (s, 3H), 3.63 (t, J=6.2 Hz, 2H), 2.87 (q, J=7.6 Hz, 2H), 2.46 (s, 3H), 2.20 (s, 3H), 1.84 (p, J=6.2 Hz, 2H), 1.33 (t, J=7.1 Hz, 3H), 1.12 (t, J=7.5 Hz, 3H). ESI-MS: $C_{38}H_{44}N_{11}O_8$ (M+H): calc. 782.33, found: 782.15.

255

Example 16: (E)-N-(5-carbamoyl-1-(4-(5-carbamoyl-2-(4-ethyl-2-methylthiazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide, Compound 37

256

Example 17: (E)-N-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methylthiazole-5-carboxamide, Compound 38

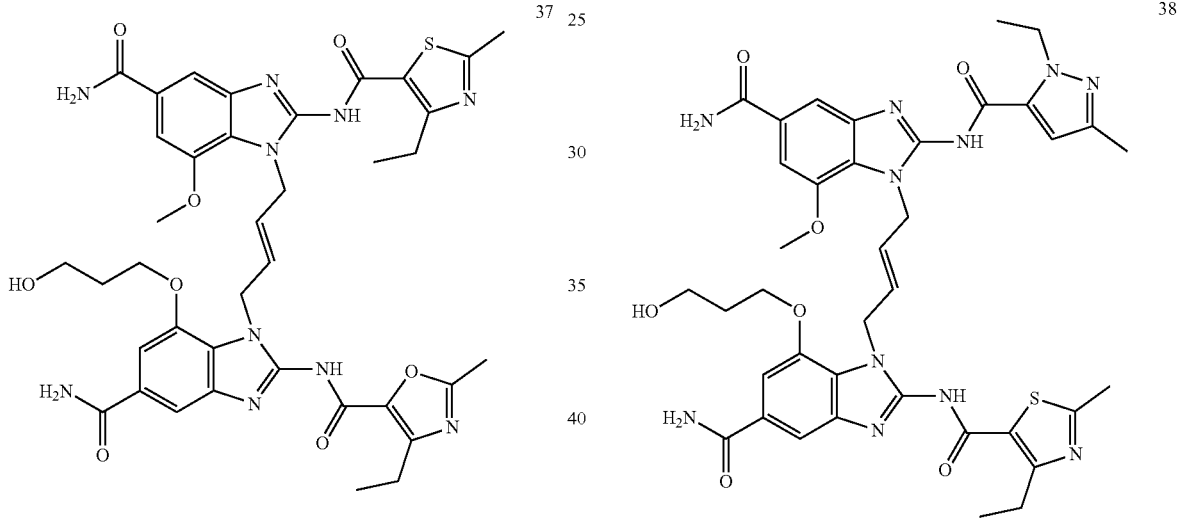

(E)-N-(5-carbamoyl-1-(4-(5-carbamoyl-2-(4-ethyl-2-methylthiazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide was prepared as described in Example 15, except 4-ethyl-2-methylthiazole-5-carboxylic acid was used in Step G instead of 1-ethyl-3-methyl-1H-pyrazole-5-carboxylic acid. Step L resulted in (E)-N-(5-carbamoyl-1-(4-(5-carbamoyl-2-(4-ethyl-2-methylthiazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide, Compound 37 (30 mg, 24% yield) as a white solid. $^1$H NMR (400 MHz, DMSO-$d_6$) δ 12.73 (d, J=21.2 Hz, 2H), 7.96 (s, 2H), 7.62 (d, J=6.5 Hz, 2H), 7.38-7.28 (m, 4H), 5.94-5.77 (m, 2H), 4.90 (d, J=5.3 Hz, 2H), 4.85 (d, J=5.6 Hz, 2H), 4.06 (d, J=6.5 Hz, 2H), 3.80 (s, 3H), 3.47 (t, J=6.1 Hz, 2H), 3.09 (q, J=7.5 Hz, 2H), 2.82 (q, J=7.5 Hz, 2H), 2.39 (s, 3H), 1.74 (p, J=6.2 Hz, 2H), 1.14 (t, J=7.5 Hz, 3H), 1.02 (t, J=7.5 Hz, 3H). ESI-MS: $C_{38}H_{43}N_{10}O_8S$ (M+H): calc. 799.29, found: 799.20.

(E)-N-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methylthiazole-5-carboxamide was prepared as described in Example 15, except 4-ethyl-2-methylthiazole-5-carboxylic acid was used in Step L instead of 4-ethyl-2-methyloxazole-5-carboxylic acid to afford (E)-N-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)-4-ethyl-2-methylthiazole-5-carboxamide, Compound 38 (35 mg, 21% yield) as a white solid. $^1$H NMR (400 MHz, Methanol-$d_4$) δ 7.53 (dd, J=4.8, 1.4 Hz, 2H), 7.31 (d, J=1.4 Hz, 1H), 7.25 (d, J=1.4 Hz, 1H), 6.53 (s, 1H), 5.93-5.77 (m, 2H), 4.99 (t, J=6.2 Hz, 4H), 4.55 (q, J=7.1 Hz, 2H), 4.14 (t, J=6.2 Hz, 2H), 3.74 (s, 3H), 3.65 (t, J=6.2 Hz, 2H), 3.15 (q, J=7.6 Hz, 2H), 2.65 (s, 3H), 2.16 (s, 3H), 1.89 (p, J=6.2 Hz, 2H), 1.31 (t, J=7.1 Hz, 3H), 1.22 (t, J=7.5 Hz, 3H). ESI-MS: $C_{38}H_{44}N_{11}O_7S$ (M+H): calc. 798.31, found: 798.30.

Example 18: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(3-ethyl-1-methyl-1H-pyrazole-4-carboxamido)-7-(3-hydroxypropoxy)-1H-benzo[d]imidazole-5-carboxamide, Compound 39

Example 19: (E)-N-(5-carbamoyl-1-(4-(5-carbamoyl-2-(4-ethyl-2-methylthiazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide, Compound 40

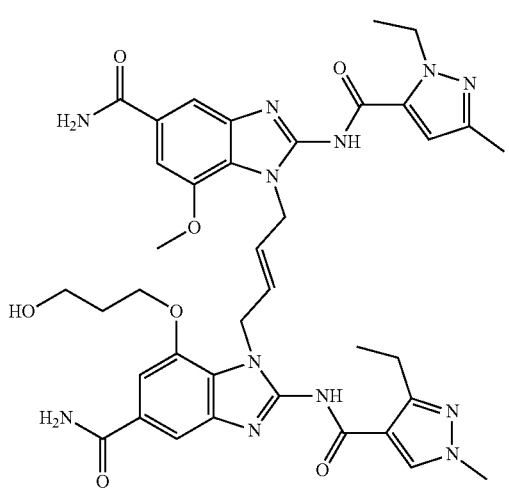

39

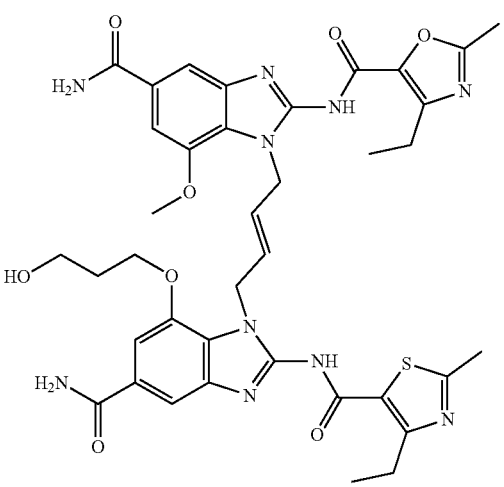

40

(E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(3-ethyl-1-methyl-1H-pyrazole-4-carboxamido)-7-(3-hydroxypropoxy)-1H-benzo[d]imidazole-5-carboxamide was prepared as described in Example except 3-ethyl-1-methyl-1H-pyrazole-4-carboxylic acid was used in Step L instead of 4-ethyl-2-methyloxazole-5-carboxylic acid to afford (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(3-ethyl-1-methyl-1H-pyrazole-4-carboxamido)-7-(3-hydroxypropoxy)-1H-benzo[d]imidazole-5-carboxamide, Compound 39 (20 mg, 19% yield) as a white solid. $^1$H NMR (400 MHz, Methanol-$d_4$) δ 7.89 (s, 1H), 7.52 (d, J=16.5 Hz, 2H), 7.31-7.22 (m, 2H), 6.54 (s, 1H), 5.81 (d, J=3.3 Hz, 2H), 4.99 (d, J=7.0 Hz, 4H), 4.58 (s, 3H), 4.01 (d, J=6.5 Hz, 2H), 3.77 (s, 3H), 3.74 (s, 2H), 3.59 (t, J=6.2 Hz, 2H), 2.90 (d, J=7.7 Hz, 2H), 2.16 (s, 3H), 1.84-1.74 (m, 2H), 1.27 (d, J=6.7 Hz, 3H), 1.16 (d, J=7.5 Hz, 3H). ESI-MS: $C_{38}H_{45}N_{12}O_7$ (M+H): calc. 781.35, found: 781.20.

(E)-N-(5-carbamoyl-1-(4-(5-carbamoyl-2-(4-ethyl-2-methylthiazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide was prepared as described in Example 15, except 4-ethyl-2-methyloxazole-5-carboxylic acid was used in Step G instead of 1-ethyl-3-methyl-1H-pyrazole-5-carboxylic acid and 4-ethyl-2-methylthiazole-5-carboxylic acid was used in Step L instead of 4-ethyl-2-methyloxazole-5-carboxylic acid resulting in (E)-N-(5-carbamoyl-1-(4-(5-carbamoyl-2-(4-ethyl-2-m ethylthiazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide, Compound 40 (40 mg, 25% yield) as a white solid. $^1$H NMR (400 MHz, DMSO-$d_6$) δ 12.73 (s, 2H), 7.95 (d, J=9.6 Hz, 2H), 7.62 (dd, J=14.9, 1.2 Hz, 2H), 7.40-7.20 (m, 4H), 5.84 (dt, J=9.9, 5.1 Hz, 2H), 4.87 (t, J=6.1 Hz, 4H), 4.09 (t, J=6.4 Hz, 2H), 3.77 (s, 3H), 3.47 (d, J=5.4 Hz, 2H), 3.09 (d, J=7.5 Hz, 2H), 2.81 (q, J=7.6 Hz, 2H), 2.38 (s, 3H), 1.74 (t, J=6.2 Hz, 2H), 1.14 (t, J=7.5 Hz, 3H), 1.00 (t, J=7.5 Hz, 3H). ESI-MS: $C_{38}H_{43}N_{10}O_8S$ (M+H): calc. 799.29, found: 799.30.

Example 20: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(4-ethyl-1,2-dimethyl-1H-imidazole-5-carboxamido)-7-(3-hydroxypropoxy)-1H-benzo[d]imidazole-5-carboxamide, Compound 41

Example 21: (E)-2-(5-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)carbamoyl)-3-methyl-1H-pyrazol-1-yl)acetic acid, Compound 42

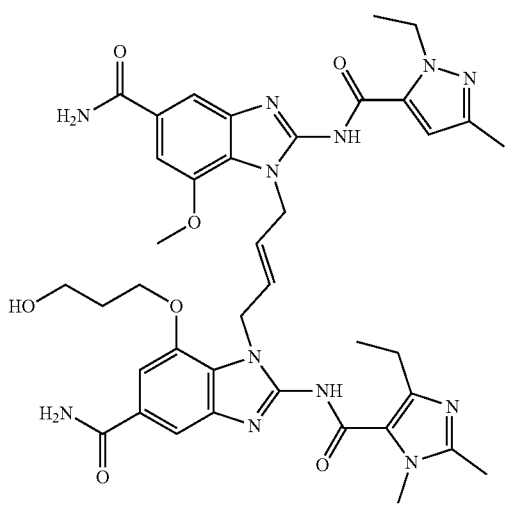

41

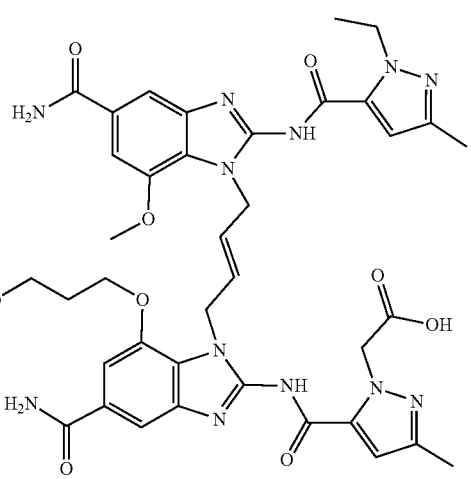

42

(E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(4-ethyl-1,2-dimethyl-1H-imidazole-5-carboxamido)-7-(3-hydroxypropoxy)-1H-benzo[d]imidazole-5-carboxamide was prepared as described in Example 15, except 4-ethyl-1,2-dimethyl-1H-imidazole-5-carboxylic acid was used in Step L instead of 4-ethyl-2-methyloxazole-5-carboxylic acid to afford (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(4-ethyl-1,2-dimethyl-1H-imidazole-5-carboxamido)-7-(3-hydroxypropoxy)-1H-benzo[d]imidazole-5-carboxamide, Compound 41 (26 mg, 20% yield) of a white solid. $^1$H NMR (400 MHz, Methanol-$d_4$) δ 7.64-7.49 (m, 2H), 7.43-7.18 (m, 2H), 6.53 (d, J=4.1 Hz, 1H), 5.98-5.65 (m, 2H), 5.02 (s, 3H), 4.14 (t, J=6.3 Hz, 2H), 3.97 (s, 3H), 3.81 (s, 3H), 2.99-2.91 (m, 2H), 2.56 (s, 3H), 2.17 (d, J=1.2 Hz, 3H), 1.90 (q, J=6.2 Hz, 2H), 1.29 (td, J=8.0, 7.5, 4.3 Hz, 6H), 1.14 (t, J=7.5 Hz, 4H). ESI-MS: $C_{39}H_{47}N_{12}O_7$ (M+H): calc. 795.36, found: 795.30.

(E)-2-(5-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)carbamoyl)-3-methyl-1H-pyrazol-1-yl)acetic acid was prepared as described in Example 15, except 1-(2-methoxy-2-oxoethyl)-3-methyl-1H-pyrazole-5-carboxylic acid in Step L instead of 4-ethyl-2-methyloxazole-5-carboxylic acid to afford (E)-2-(5-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-hydroxypropoxy)-1H-benzo[d]imidazol-2-yl)carbamoyl)-3-methyl-1H-pyrazol-1-yl)acetic acid, Compound 42 (20 mg, 40% yield) as a white solid. $^1$H NMR (400 MHz, DMSO-$d_6$) δ 7.94 (s, 2H), 7.60 (d, J=5.5 Hz, 2H), 7.26 (s, 4H), 6.51 (d, J=7.9 Hz, 2H), 5.80 (s, 2H), 4.87 (d, J=9.7 Hz, 4H), 4.49 (d, J=7.7 Hz, 2H), 3.99 (s, 2H), 3.68 (s, 3H), 3.38 (s, 2H), 2.07 (s, 6H), 1.63 (s, 2H), 1.23 (t, J=7.0 Hz, 3H). ESI-MS: $C_{38}H_{43}N_{12}O_9$ (M+H): calc. 811.32, found: 811.30.

Example 22: (E)-N-(5-carbamoyl-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide, Compound 43

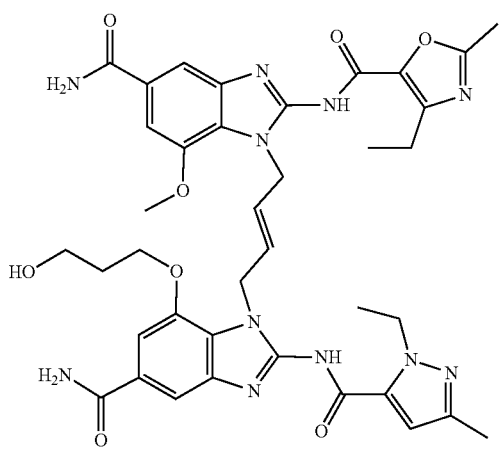

(E)-N-(5-carbamoyl-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide was prepared as described in Example 15, except 4-ethyl-2-methyloxazole-5-carboxylic acid was used in Step G instead of 1-ethyl-3-methyl-1H-pyrazole-5-carboxylic acid and 1-ethyl-3-methyl-1H-pyrazole-5-carboxylic acid was used in Step L instead of 4-ethyl-2-methyloxazole-5-carboxylic acid resulting in (E)-N-(5-carbamoyl-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-7-methoxy-1H-benzo[d]imidazol-2-yl)-4-ethyl-2-methyloxazole-5-carboxamide, Compound 43 (25 mg, 16% yield) as a white solid. $^1$H NMR (400 MHz, DMSO-$d_6$) δ 7.94 (s, 2H), 7.65-7.56 (m, 2H), 7.32-7.23 (m, 4H), 6.46 (s, 1H), 5.77 (d, J=3.4 Hz, 2H), 4.86 (d, J=16.8 Hz, 4H), 4.47 (d, J=7.2 Hz, 2H), 4.02 (t, J=6.4 Hz, 2H), 3.73 (s, 3H), 2.76 (t, J=7.5 Hz, 2H), 2.61 (s, 2H), 2.07 (s, 3H), 1.66 (t, J=6.2 Hz, 2H), 1.23 (d, J=7.0 Hz, 3H), 0.96 (t, J=7.5 Hz, 3H). ESI-MS: $C_{38}H_{44}N_{11}O_8$ (M+H): calc. 782.33, found: 782.30.

General Procedure for Synthesis of Compound Variant IV.

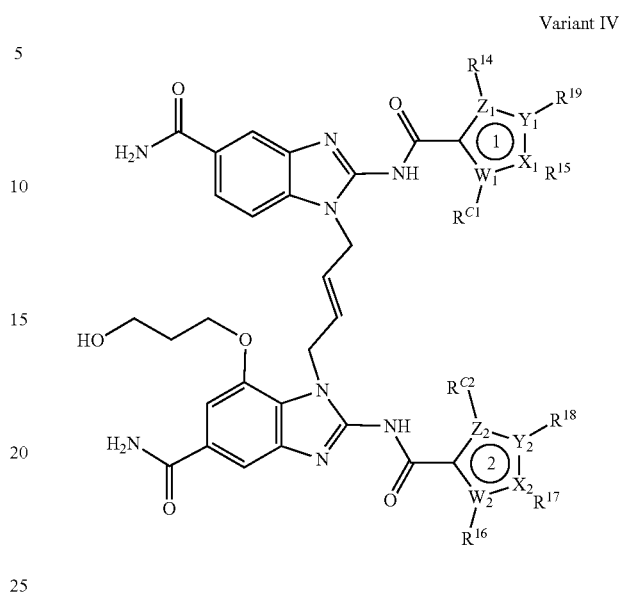

Scheme 4: The following scheme illustrates the exemplary synthesis of (E)-N-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide. The similar procedure may be generally used for the synthesis of Compound Variant IV. As shown below, heterocyclic structures (rings 1 and 2) can be introduced by using the corresponding carboxylic acids at Step D and Step I, respectively.

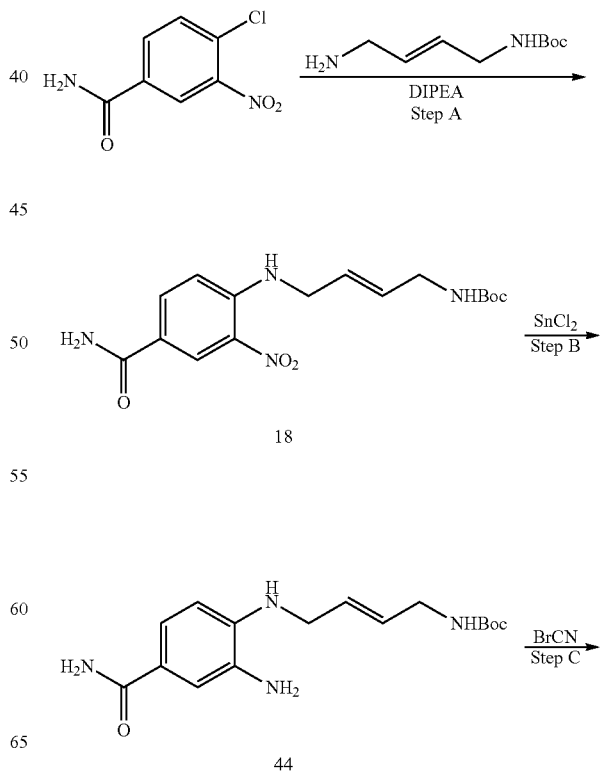

263
-continued
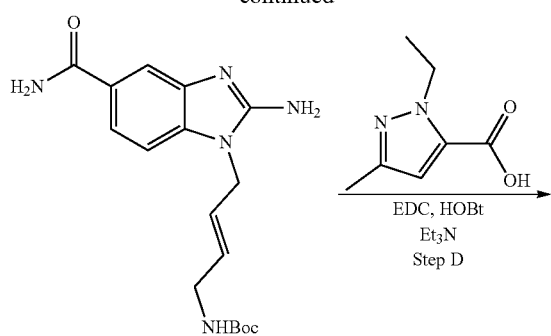
45
264
-continued
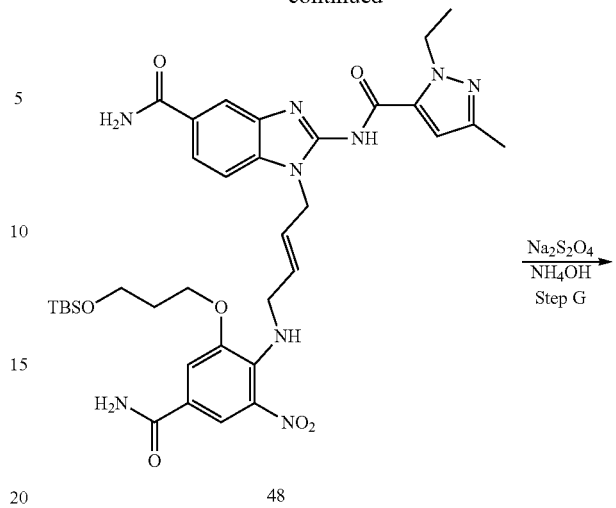
48
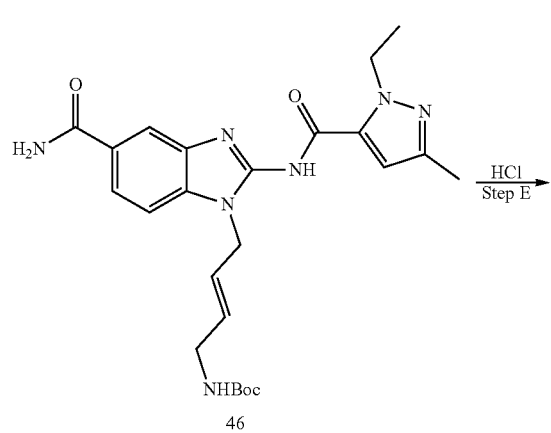
46
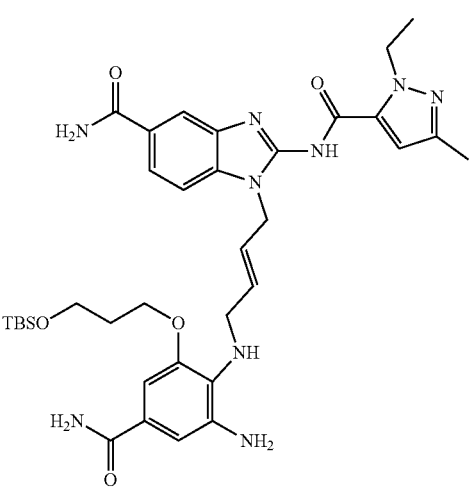
49
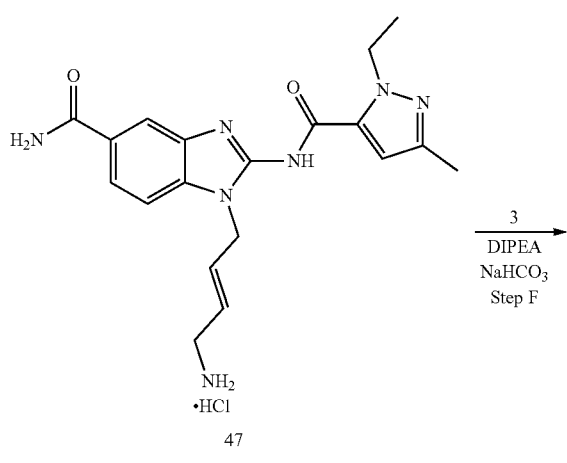
47
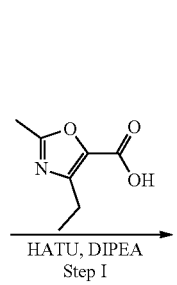
50

-continued

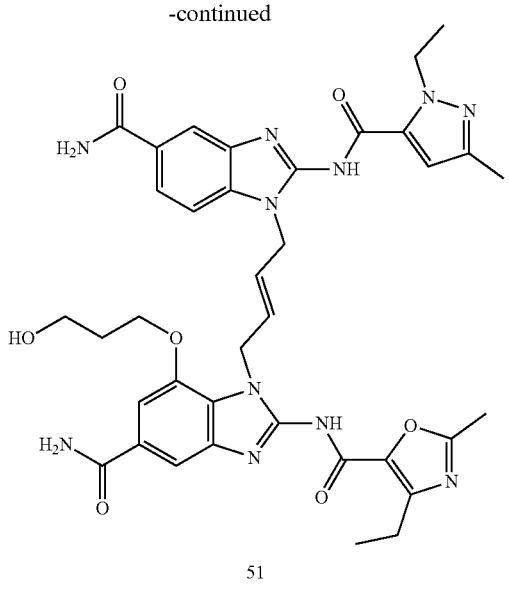

Example 23: (E)-N-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide, Compound 51

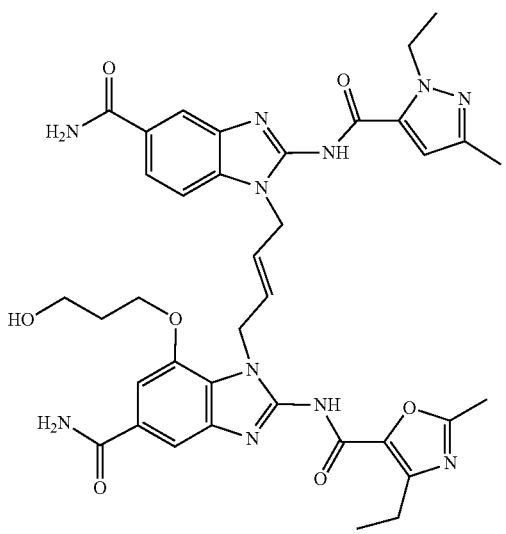

Steps A was conducted as described in Example 9.

Step B: To a stirred solution of tert-butyl (E)-(4-((4-carbamoyl-2-nitrophenyl)amino)but-2-en-1-yl)carbamate, Compound 18 (prepared as described in Example 9, 3.50 g, 10.0 mmol) in DMF (60 mL) under nitrogen was added $SnCl_2$ (15.15 g, 80.0 mmol). The mixture was stirred at room temperature for 24 hours, then quenched with aqueous $NaHCO_3$ and extracted with EtOAc (3×). The combined organic layers were dried over $Na_2SO_4$ and concentrated in vacuo to afford tert-butyl (E)-(4-((2-amino-4-carbamoylphenyl)amino)but-2-en-1-yl)carbamate, Compound 44 (3 g, 94% yield) as a brown oil. $^1$H NMR (400 MHz, DMSO-$d_6$) δ 7.95 (s, 1H), 7.08 (d, J=7.2 Hz, 2H), 6.95 (t, J=5.9 Hz, 1H), 6.35 (d, J=8.5 Hz, 1H), 5.61 (td, J=3.6, 2.3 Hz, 2H), 3.73 (d, J=Hz, 2H), 3.54 (t, J=4.8 Hz, 2H), 1.37 (s, 9H). ESI-MS: $C_{16}H_{25}N_4O_3$ (M+H): calc. 321.18, found: 321.10.

Step C: To a stirred solution of tert-butyl (E)-(4-((2-amino-4-carbamoylphenyl)amino)but-2-en-1-yl)carbamate, Compound 44 (3.0 g, 9.37 mmol) in MeOH (60 mL) was added cyanogen bromide (1.49 g, 14.05 mmol). The mixture was heated to 60° C. and stirred for 16 hours. The mixture was cooled to room temperature, quenched with aqueous $NaHCO_3$, and extracted with EtOAc (3×). The combined organic layers were dried over $Na_2SO_4$ and concentrated in vacuo to afford tert-butyl (E)-(4-(2-amino-5-carbamoyl-1H-benzo[d]imidazol-1-yl)but-2-en-1-yl)carbamate, Compound 45 (2.50 g, 77% yield) as a brown solid. $^1$H NMR (400 MHz, DMSO-$d_6$) δ 7.82-7.74 (m, 1H), 7.70 (d, J=1.6 Hz, 1H), 7.49 (dd, J=8.2, 1.6 Hz, 1H), 7.13 (d, J=8.2 Hz, 1H), 7.08-6.94 (m, 2H), 6.66 (s, 2H), 5.57 (t, J=2.8 Hz, 2H), 4.62 (s, 2H), 3.50 (d, J=5.6 Hz, 2H), 1.35 (s, 9H). ESI-MS: $C_{17}H_{24}N_5O_3$ (M+H): calc. 346.18, found: 346.15.

Step D: To a stirred solution of 1-ethyl-3-methyl-1H-pyrazole-5-carboxylic acid (1.67 g, mmol) in DCM (40 mL) was added EDC·HCl (3.75 g, 19.56 mmol) and HOBt (2.94 g, 21.73 mmol), and the mixture was stirred at room temperature for 15 minutes. Then, tert-butyl (E)-(4-(2-amino-5-carbamoyl-1H-benzo[d]imidazol-1-yl)but-2-en-1-yl)carbamate, Compound 45 (2.50 g, 7.24 mmol) dissolved in DMF (5 mL) was added, followed immediately by $Et_3N$ (5.05 mL, 36.21 mmol), and the mixture was stirred at room temperature for 3 days, then concentrated in vacuo. The resulting residue was diluted in water and extracted with EtOAc (3×). The combined organic layers were dried over $Na_2SO_4$ and concentrated in vacuo. Purification over silica gel (DCM:MeOH 20:1 v/v) afforded tert-butyl (E)-(4-(5-carbamoyl-2-(1-ethyl-3-methyl-1H-pyrazole-5-carboxamido)-1H-benzo[d]imidazol-1-yl)but-2-en-1-yl)carbamate, Compound 46 (2.50 g, 71% yield) as a white solid. $^1$H NMR (400 MHz, DMSO-$d_6$) δ 12.80 (s, 1H), 7.99-7.88 (m, 2H), 7.74 (dd, J=8.4, 1.7 Hz, 1H), 7.44 (d, J=8.4 Hz, 1H), 7.30 (s, 1H), 6.91 (t, J=6.0 Hz, 1H), 6.62 (s, 1H), 5.71-5.59 (m, 2H), 4.78 (d, J=4.9 Hz, 2H), 4.57 (q, J=7.1 Hz, 2H), 3.47 (t, J=5.2 Hz, 2H), 2.13 (s, 3H), 1.29 (d, J=13.2 Hz, 12H). ESI-MS: $C_{24}H_{32}N_7O_4$ (M+H): calc. 482.24, found: 482.30.

Step E: To a stirred solution of tert-butyl (E)-(4-(5-carbamoyl-2-(1-ethyl-3-methyl-1H-pyrazole-5-carboxamido)-1H-benzo[d]imidazol-1-yl)but-2-en-1-yl)carbamate, Compound 46 (2.0 g, 4.16 mmol) in dioxane (30 mL) was added HCl (4M in dioxane, 20 mL, 80 mmol). The mixture was stirred at room temperature for 16 hours, then concentrated in vacuo to afford (E)-1-(4-aminobut-2-en-1-yl)-2-(1-ethyl-3-methyl-1H-pyrazole-5-carboxamido)-1H-benzo[d]imidazole-Compound 47 (1.70 g, 98%) as a white solid. $^1$H NMR (400 MHz, DMSO-$d_6$) δ 8.04-7.92 (m, 4H), 7.81 (dd, J=8.4, 1.7 Hz, 1H), 7.49 (d, J=8.4 Hz, 1H), 7.36 (s, 1H), 6.69 (s, 1H), 6.01 (dt, J=15.6, 5.6 Hz, 1H), 5.71 (dt, J=15.6, 6.2 Hz, 1H), 4.91 (d, J=5.7 Hz, 2H), 4.61 (q, J=7.1 Hz, 2H), 3.43 (t, J=6.0 Hz, 2H), 2.18 (s, 3H), 1.36 (t, J=7.1 Hz, 3H). ESI-MS: $C_{19}H_{24}N_7O_2$ (M+H): calc. 382.19, found: 382.20.

Step F: To a stirred solution of 3-(3-((tert-butyldimethylsilyl)oxy)propoxy)-4-chloro-5-nitrobenzamide, Compound 3 (prepared as described in Example 1, 1 g, 2.58 mmol) in 1-butanol (10 mL) was added (E)-1-(4-aminobut-2-en-1-yl)-2-(1-ethyl-3-methyl-1H-pyrazole-5-carboxamido)-1H-benzo[d]imidazole-5-carboxamide-HCl, Compound 47 (1.18 g, 2.83 mmol), DIPEA (1.80 mL, 10.31 mmol), and NaHCO$_3$ (432 mg, 5.15 mmol). The mixture was heated to 120° C. under pressure for 16 hours, then cooled to 0° C. resulting in a red precipitate. The solid was filtered and washed with cold butanol (10 mL) and water (40 mL) to afford (E)-1-(4-(2-(3-((tert-butyldimethylsilyl)oxy) propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide, Compound 48 (600 mg, 32% yield) as a red solid. $^1$H NMR (400 MHz, DMSO-d$_6$) δ 12.78 (s, 1H), 8.11 (d, J=1.8 Hz, 1H), 8.02-7.89 (m, 3H), 7.72-7.64 (m, 2H), 7.46 (d, J=2.1 Hz, 1H), 7.39-7.27 (m, 3H), 6.57 (s, 1H), 5.72 (q, J=4.4 Hz, 2H), 4.76 (d, J=3.8 Hz, 2H), 4.54 (q, J=7.1 Hz, 2H), 4.09 (d, J=5.7 Hz, 2H), 3.97 (t, J=6.1 Hz, 2H), 3.59 (t, J=6.1 Hz, 2H), 2.12 (s, 3H), 1.77 (p, J=6.1 Hz, 2H), 1.28 (t, J=7.1 Hz, 3H), 0.74 (s, 9H), -0.11 (s, 6H). ESI-MS: C$_{35}$H$_{48}$N$_9$O$_7$Si (M+H): calc. 734.34, found: 734.40.

Step G: To a stirred solution of (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide, Compound 48 (600 mg, 0.82 mmol) in methanol (15 mL) at 0° C. was added Na$_2$S$_2$O$_4$ (1.42 g, 8.18 mmol) in water (7 mL) followed by NH$_3$ (25% v/v in water, 1.4 mL, 20.45 mmol). The mixture was warmed to room temperature and stirred for 10 minutes, then diluted in water and extracted with EtOAc (3×). The combined organic layers were dried over Na$_2$SO$_4$ and concentrated in vacuo to afford (E)-1-(4-((2-amino-6-(3-((tert-butyldimethylsilyl) oxy)propoxy)-4-carbamoylphenyl)amino)but-2-en-1-yl)-2-(1-ethyl-3-methyl-1H-pyrazole-5-carboxamido)-1H-benzo[d]imidazole-5-carboxamide, Compound 49 (400 mg, 70%) as a white solid. $^1$H NMR (400 MHz, DMSO-d$_6$) δ 12.82 (s, 1H), 8.02-7.91 (m, 2H), 7.80-7.72 (m, 1H), 7.60 (s, 1H), 7.33 (d, J=8.0 Hz, 2H), 6.97 (s, 1H), 6.83 (d, J=1.8 Hz, 1H), 6.73 (d, J=1.8 Hz, 1H), 6.65 (d, J=7.6 Hz, 1H), 5.91-5.80 (m, 1H), 5.80-5.69 (m, 1H), 4.80 (d, J=5.6 Hz, 2H), 4.69-4.52 (m, 4H), 3.91 (t, J=5.9 Hz, 2H), 3.68-3.52 (m, 4H), 2.17 (s, 3H), 1.76 (p, J=6.1 Hz, 2H), 1.34 (t, J=7.3 Hz, 3H), 0.78 (s, 9H), -0.06 (s, 6H). ESI-MS: C$_{35}$H$_{50}$N$_9$O$_5$Si (M+H): calc. 704.36, found: 704.40.

Step H: To a stirred solution of (E)-1-(4-((2-amino-6-(3-((tert-butyldimethylsilyl)oxy)propoxy)-4-carbamoylphenyl) amino)but-2-en-1-yl)-2-(1-ethyl-3-methyl-1H-pyrazole-5-carboxamido)-1H-benzo[d]imidazole-5-carboxamide, Compound 49 (400 mg, mmol) in methanol (15 mL) was added cyanogen bromide (241 mg, 2.27 mmol). The mixture was stirred at room temperature for 16 hours, then concentrated in vacuo to obtain (E)-2-amino-7-(3-((tert-butyl dim ethyl silyl)oxy)propoxy)-1-(4-(5-carbamoyl-2-(1-ethyl-3-methyl-1H-pyrazol e-carboxamide, Compound 50 (400 mg, 97%) as a white solid. $^1$H NMR (400 MHz, DMSO-d$_6$) δ 12.85 (s, 1H), 8.57 (s, 2H), 8.07 (s, 1H), 7.98 (d, J=11.2 Hz, 2H), 7.74 (dd, J=8.4, 1.8 Hz, 1H), 7.48-7.37 (m, 5H), 6.54 (d, J=4.4 Hz, 1H), 5.92 (d, J=15.6 Hz, 1H), 5.86-5.77 (m, 1H), 4.84 (dd, J=11.7, 5.4 Hz, 4H), 4.58-4.50 (m, 2H), 4.11 (q, J=6.3, 5.0 Hz, 2H), 3.62 (t, J=6.1 Hz, 2H), 2.14 (d, J=2.2 Hz, 3H), 1.77 (p, J=5.9 Hz, 2H), 1.29 (t, J=7.1 Hz, 3H), 0.81 (s, 9H). ESI-MS: C$_{36}$H$_{49}$N$_{10}$O$_5$Si (M+H): calc. 729.36, found: 729.40.

Step I: To a stirred solution of (E)-2-amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d] imidazol-1-yl)but-2-en-1-yl)-1H-benzo[d]imidazole-5-carboxamide, Compound 50 (150 mg, 0.21 mmol) in DMF (5 mL) was added 4-ethyl-2-methyloxazole-5-carboxylic acid (48 mg, 0.31 mmol), PyBOP (161 mg, 0.31 mmol) and DIPEA (0.11 mL, 0.62 mmol). The mixture was heated under pressure to 120° C. and stirred for 16 hours, then cooled to room temperature and concentrated in vacuo. The resulting residue was diluted with water, and the resulting solid was filtered and washed with water. Purification over silica gel (DCM:MeOH 4:1 v/v) afforded (E)-N-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-7-(3-hydroxypropoxy)-1H-benzo[d]imidazol-2-yl)-4-ethyl-2-methyloxazole-5-carboxamide, Compound 51 (13 mg, 8%) as a brown solid. $^1$H NMR (400 MHz, DMSO-d$_6$) δ 8.01-7.91 (m, 3H), 7.70 (dd, J=8.4, 1.7 Hz, 1H), 7.66-7.61 (m, 1H), 7.41 (d, J=8.5 Hz, 1H), 7.34 (s, 3H), 6.54 (s, 1H), 6.03-5.91 (m, 1H), 5.76-5.69 (m, 1H), 4.91 (d, J=5.4 Hz, 2H), 4.81 (d, J=5.6 Hz, 2H), 4.52 (d, J=7.1 Hz, 2H), 4.12 (d, J=6.6 Hz, 2H), 3.48 (t, J=6.0 Hz, 2H), 2.83 (q, J=7.5 Hz, 2H), 2.40 (s, 3H), 2.12 (s, 3H), 1.80-1.69 (m, 2H), 1.26 (t, J=7.1 Hz, 3H), 1.02 (td, J=7.5, 2.4 Hz, 3H). ESI-MS: C$_{37}$E$_{42}$N$_{11}$O$_7$ (M+H): calc. 752.32, found: 752.30.

Example 24: (E)-N-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-7-(3-hydroxypropoxy)-1H-benzo[d]imidazol-2-yl)-4-ethyl-2-methylthiazole-5-carboxamide, Compound 52

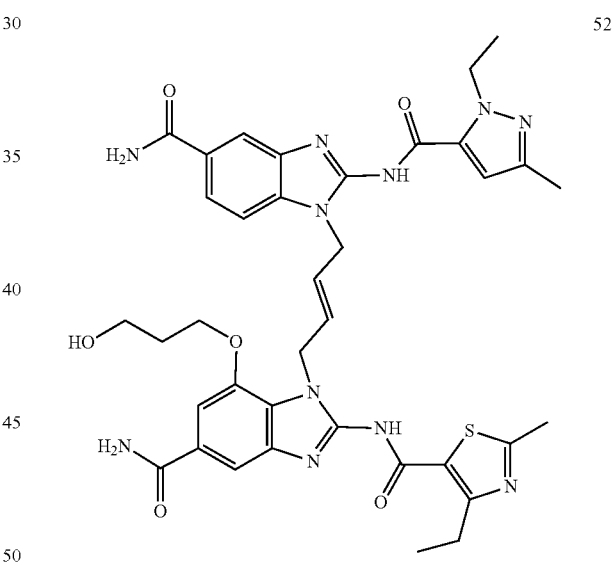

(E)-N-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-7-(3-hydroxypropoxy)-1H-benzo[d] imidazol-2-yl)-4-ethyl-2-methylthiazole-5-carboxamide was prepared as described in Example 23, except 4-ethyl-2-methylthiazole-5-carboxylic acid was used in Step I instead of 4-ethyl-2-methyloxazole-5-carboxylic acid to afford (E)-N-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-7-(3-hydroxypropoxy)-1H-benzo[d]imidazol-2-yl)-4-ethyl-2-methylthiazole-5-carboxamide, Compound 52 (18 mg, 29% yield) as a white solid. $^1$H NMR (400 MHz, DMSO-d$_6$) δ 8.76 (s, 3H), 8.54 (dd, J=8.4, 1.7 Hz, 1H), 8.44 (s, 1H), 8.24 (d, J=8.5 Hz, 1H), 8.16 (d, J=4.3 Hz, 3H), 7.37 (s, 1H), 6.89-6.54 (m, 2H), 5.68 (dd, J=24.8, 5.7 Hz, 4H), 5.36 (t, J=7.1 Hz, 2H), 4.33 (t, J=6.0 Hz, 2H), 3.93 (q, J=7.5 Hz, 2H), 2.93 (s, 3H), 2.61 (p, J=6.2 Hz, 2H), 2.09 (t, J=7.1 Hz, 3H), 1.97 (t, J=7.5 Hz, 3H). ESI-MS: $C_{37}E_{42}N_{11}O_6S$ (M+H): 768.30, found: 768.20.

Example 25: (E)-1-(4-(5-carbamoyl-2-(1-ethyl-3-methyl-1H-pyrazole-5-carboxamido)-1H-benzo[d]imidazol-1-yl)but-2-en-1-yl)-2-(3-ethyl-1-methyl-1H-pyrazole-4-carboxamido)-7-(3-hydroxypropoxy)-1H-benzo[d]imidazole-5-carboxamide, Compound 53

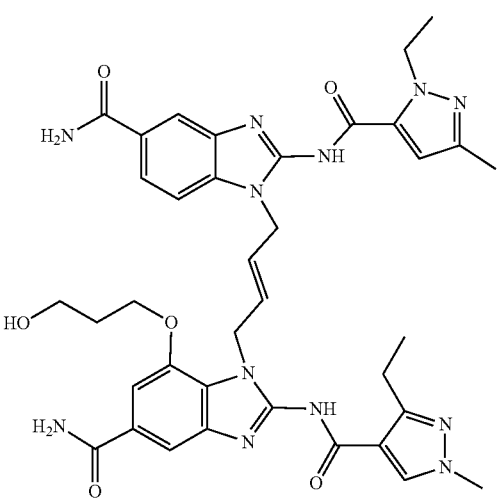

(E)-1-(4-(5-carbamoyl-2-(1-ethyl-3-methyl-1H-pyrazole-5-carboxamido)-1H-benzo[d]imidazol-1-yl)but-2-en-1-yl)-2-(3-ethyl-1-methyl-1H-pyrazole-4-carboxamido)-7-(3-hydroxypropoxy)-1H-benzo[d]imidazole-5-carboxamide was prepared as described in Example 23, except 3-ethyl-1-methyl-1H-pyrazole-4-carboxylic acid was used in Step I instead of 4-ethyl-2-methyloxazole-5-carboxylic acid to afford (E)-1-(4-(5-carbamoyl-2-(1-ethyl-3-methyl-1H-pyrazole-5-carboxamido)-1H-benzo[d]imidazol-1-yl)but-2-en-1-yl)-2-(3-ethyl-1-methyl-1H-pyrazole-4-carboxamido)-7-(3-hydroxypropoxy)-1H-benzo[d]imidazole-5-carboxamide, Compound 53 (18 mg, 29% yield) as a white solid. $^1$H NMR (400 MHz, DMSO-d$_6$) δ 8.01-7.91 (m, 4H), 7.70 (dd, J=8.4, 1.7 Hz, 1H), 7.63 (s, 1H), 7.40 (d, J=8.5 Hz, 1H), 7.32 (s, 3H), 6.54 (s, 1H), 5.97 (dt, J=15.9, 5.5 Hz, 1H), 5.76 (s, 1H), 4.94 (d, J=5.4 Hz, 2H), 4.81 (d, J=5.7 Hz, 2H), 4.51 (t, J=7.2 Hz, 2H), 4.11 (s, 5H), 3.48 (t, J=6.0 Hz, 2H), 2.84 (q, J=7.4 Hz, 2H), 2.11 (s, 3H), 1.74 (q, J=6.2 Hz, 2H), 1.26 (t, J=7.1 Hz, 3H), 1.12 (t, J=7.5 Hz, 3H). ESI-MS: $C_{37}E_{43}N_{12}O_6$ (M+H): calc. 751.34, found: 751.25.

General Procedure for Synthesis of Compound Variant V.

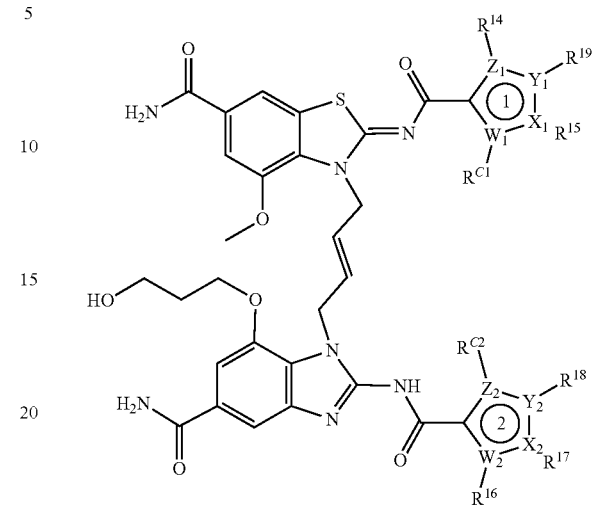

Variant V

Scheme 5: The following scheme illustrates the exemplary synthesis of N-(5-carbamoyl-1-((E)-4-((Z)-6-carbamoyl-2(4-ethyl-2-methyloxazole-5-carbonyl)imino)-4-methoxybenzo[d]thiazol-3 (2H)-yl)but-2-en-1-yl)-7-(3-hydroxypropoxy)-1H-benzo[d]imidazol-2-yl)-4-ethyl-2-methyloxazole-5-carboxamide. The similar procedure may be generally used for the synthesis of Compound Variant V. As shown below, heterocyclic structures (rings 1 and 2) can be introduced by using the corresponding carboxylic acids at Step E and Step J, respectively.

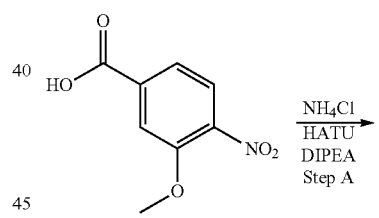

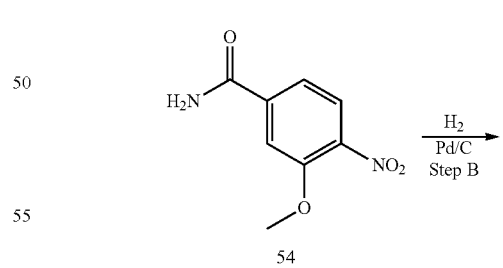

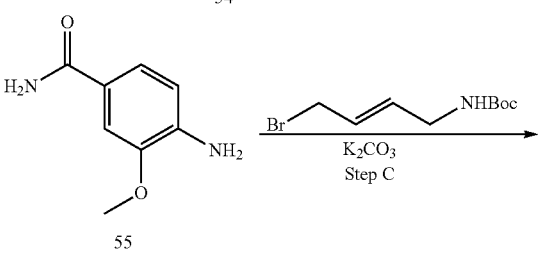

271
-continued
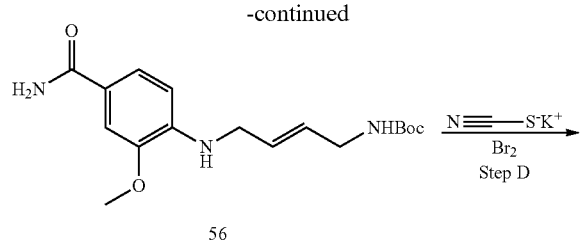
56
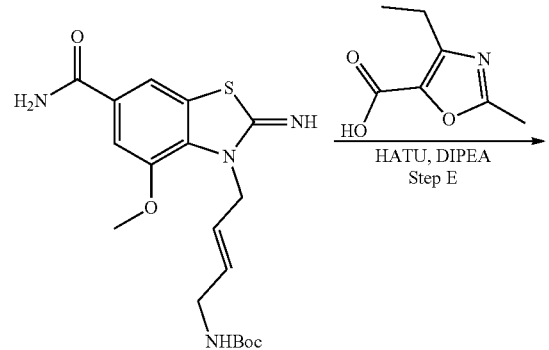
57
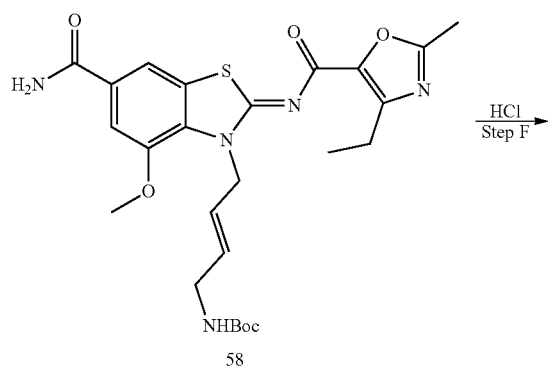
58
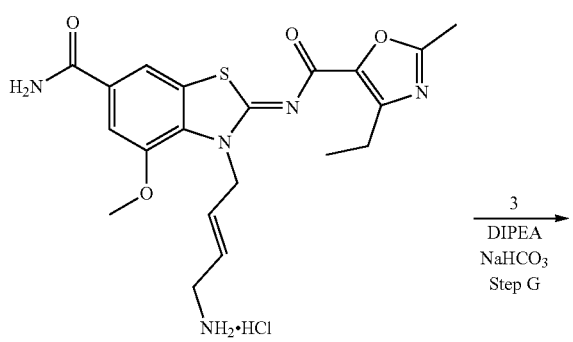
59
272
-continued
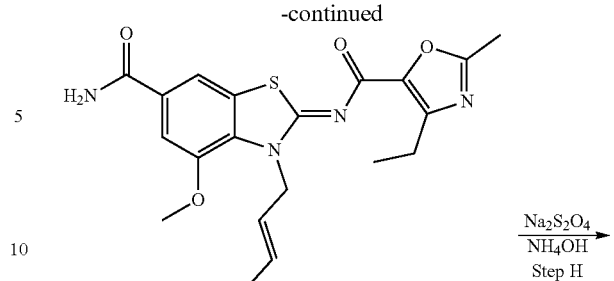
60
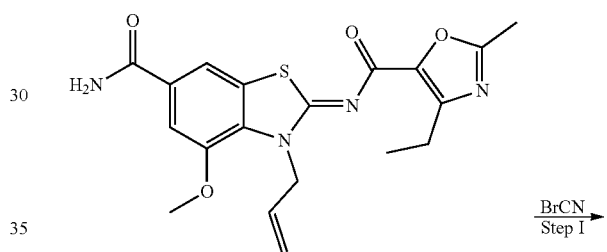
61
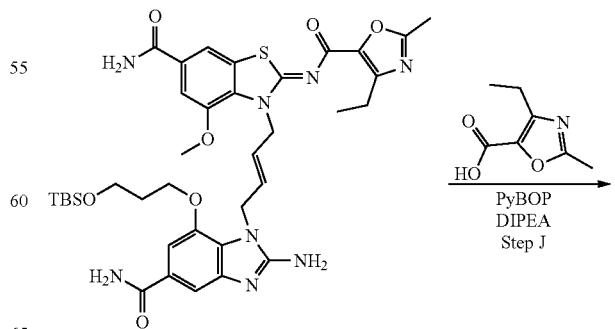
62

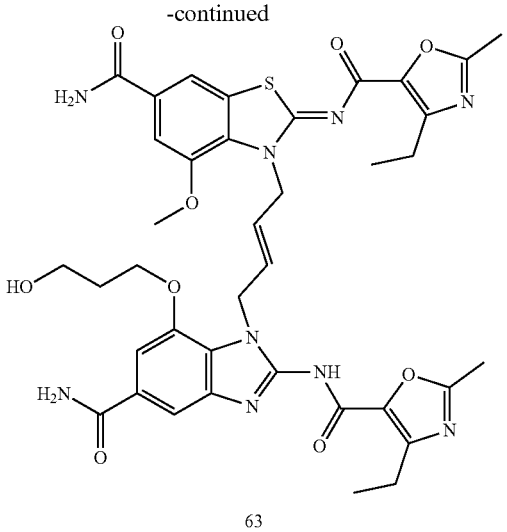

Example 26: N-(5-carbamoyl-14(E)-44(Z)-6-carbamoyl-2-((4-ethyl-2-methyloxazole-5-carbonyl)imino)-4-methoxybenzo[d]thiazol-3(211)-yl)but-2-en-1-yl)-7-(3-hydroxypropoxy)-1H-benzo[d]imidazol-2-yl)-4-ethyl-2-methyloxazole-5-carboxamide, Compound 63

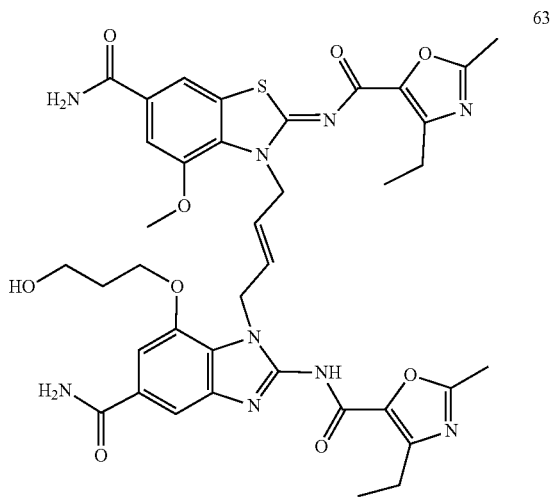 [SMILES: CCc1nc(C)oc1C(=O)/N=c1\sc2cc(C(N)=O)cc(OC)c2n1C/C=C/Cn1c(NC(=O)c2oc(C)nc2CC)nc2cc(C(N)=O)cc(OCCCO)c21]

Step A: To a stirred solution of 3-methoxy-4-nitrobenzoic acid (25.0 g, 126 mmol) in DMF (250 mL) was added NH$_4$Cl (20.0 g, 378 mmol), HATU (72.0 g, 190 mmol), and DIPEA (66 mL, 378 mmol). The mixture was stirred at room temperature for 3 hours, then diluted with water. The resulting precipitate was filtered to afford 3-methoxy-4-nitrobenzamide, Compound 54 (22.8 g, 92% yield) as a white solid. $^1$H NMR (400 MHz, DMSO-d$_6$) δ 8.24 (s, 1H), 7.95 (d, J=8.3 Hz, 1H), 7.73 (d, J=19.9 Hz, 2H), 7.58 (d, J=8.0 Hz, 1H), 3.98 (s, 3H). ESI-MS: C$_8$H$_9$N$_2$O$_4$ (M+H): calc. 197.05, found: 197.20.

Step B: To a stirred solution of 3-methoxy-4-nitrobenzamide, Compound 54 (16.0 g, 81.6 mmol) in methanol (350 mL) was added 10% Pd/C (3.0 g). The mixture was stirred at room temperature under a hydrogen atmosphere for 4 hours, then filtered over Celite and concentrated in vacuo to afford 4-amino-3-methoxybenzamide, Compound 55 (13.0 g, 96% yield) as a white solid. $^1$H NMR (400 MHz, DMSO-d$_6$) δ 7.59 (s, 1H), 7.35-7.27 (m, 2H), 6.89 (s, 1H), 6.59 (d, J=8.1 Hz, 1H), 3.79 (s, 3H). ESI-MS: C$_8$H$_{11}$N$_2$O$_2$ (M+H): calc. 167.07, found: 167.10.

Step C: To a stirred solution of 4-amino-3-methoxybenzamide, Compound 55 (7.0 g, 42.2 mmol) in DMF (35 mL) was added tert-butyl (E)-(4-bromobut-2-en-1-yl)carbamate (12.6 g, 50.6 mmol) and K$_2$CO$_3$ (8.74 g, 63.3 mmol). The mixture was heated to 100° C. and stirred for 16 hours, then it was diluted in water and extracted with EtOAc (3×). The combined organic layers were dried over Na$_2$SO$_4$ and concentrated in vacuo. Purification over silica gel (DCM:MeOH 10:1 v/v) afforded tert-butyl (E)-(4-((4-carbamoyl-2-methoxyphenyl)amino)but-2-en-1-yl)carbamate, Compound 56 (6.0 g, 42% yield) as a white solid. $^1$H NMR (400 MHz, DMSO-d$_6$) δ 7.61 (s, 1H), 7.37 (dd, J=8.2, 1.9 Hz, 1H), 7.32 (d, J=1.9 Hz, 1H), 6.99-6.87 (m, 2H), 6.45 (d, J=8.3 Hz, 1H), 5.60-5.45 (m, 3H), 3.81 (s, 3H), 3.74 (d, J=6.0 Hz, 2H), 3.56-3.45 (m, 2H), 1.36 (s, 9H). ESI-MS: C$_{17}$H$_{26}$N$_3$O$_4$ (M+H): calc. 336.18, found: 336.20.

Step D: To a stirred solution of tert-butyl (E)-(4-((4-carbamoyl-2-methoxyphenyl)amino)but-2-en-1-yl)carbamate, Compound 56 (6.7 g, 20.0 mmol) in acetic acid (12 mL) was added KSCN (7.77 g, 80.0 mmol), and the mixture was stirred at room temperature for 30 min. Then, Br$_2$ (1 mL, 20.0 mmol) dissolved in acetic acid (8 mL) was added dropwise, and the resulting mixture was stirred at room temperature for 16 hours. The mixture was quenched with water and the solids were filtered. The filtrate was adjusted to pH 9 with aqueous ammonia and extracted with EtOAc (3×). The combined organic layers were dried over Na$_2$SO$_4$ and concentrated in vacuo to afford tert-butyl (E)-(4-(6-carbamoyl-2-imino-4-methoxybenzo[d]thiazol-3(2H)-yl)but-2-en-1-yl)carbamate, Compound 57 (5.0 g, 63% yield) as a brown solid. $^1$H NMR (400 MHz, DMSO-d$_6$) δ 8.41 (s, 1H), 7.87 (s, 1H), 7.53 (d, J=1.6 Hz, 1H), 7.44-7.37 (m, 1H), 7.30 (d, J=12.6 Hz, 1H), 6.95 (t, J=5.9 Hz, 1H), 5.67-5.47 (m, 2H), 4.77 (d, J=5.3 Hz, 2H), 3.86 (s, 3H), 3.48 (t, J=5.3 Hz, 2H), 1.35 (d, J=7.5 Hz, 9H). ESI-MS: C$_{18}$H$_{25}$N$_4$O$_4$S (M+H): calc. 393.15, found: 393.50.

Step E: To a stirred solution of tert-butyl (E)-(4-(6-carbamoyl-2-imino-4-methoxybenzo[d]thiazol-3(2H)-yl)but-2-en-1-yl)carbamate, Compound 57 (2.0 g, 5.10 mmol) in DMF (20 mL) was added 4-ethyl-2-methyloxazole-5-carboxylic acid (948 mg, 6.12 mmol), HATU (2.91 g, 7.65 mmol), and DIPEA (4.44 mL, 25.50 mmol). The mixture was stirred for 16 hours, then quenched with water. The resulting solid was filtered and washed with water to afford tert-butyl ((E)-4-((Z)-6-carbamoyl-2-((4-ethyl-2-methyloxazole-5-carbonyl)imino)-4-methoxybenzo[d]thiazol-3(2H)-yl)but-2-en-1-yl)carbamate, Compound 58 (2.0 g, 74% yield) as a white solid. $^1$H NMR (400 MHz, DMSO-d$_6$) δ 8.08 (s, 1H), 7.97 (d, J=14.0 Hz, 1H), 7.61 (s, 1H), 7.49 (s, 1H), 6.92 (t, J=5.9 Hz, 1H), 5.81-5.60 (m, 2H), 5.31 (d, J=5.7 Hz, 2H), 3.99 (s, 3H), 3.51 (d, J=5.7 Hz, 2H), 2.99 (q, J=7.6 Hz, 2H), 2.47 (s, 3H), 1.31 (s, 9H), 1.05-0.95 (m, 3H). ESI-MS: C$_{25}$H$_{32}$N$_5$O$_6$S (M+H): calc. 530.20, found: 530.30.

Step F: tert-butyl ((E)-4-((Z)-6-carbamoyl-2-((4-ethyl-2-methyloxazole-5-carbonyl)imino)-4-methoxybenzo[d]thiazol-3(2H)-yl)but-2-en-1-yl)carbamate, Compound 58 (2.0 g, 3.78 mmol) was stirred in HCl (4M in dioxane, 100 mL) for 6 hours. The mixture was concentrated in vacuo to afford N-((Z)-3-((E)-4-aminobut-2-en-1-yl)-6-carbamoyl-4-methoxybenzo[d]thiazol-2(3H)-ylidene)-4-ethyl-2-methyloxazole-5-carboxamide-HCl, Compound 59 (2.0 g, 100% yield) as a white solid. $^1$H NMR (400 MHz, DMSO-d$_6$) δ 8.16 (s, 1H), 8.06 (s, 2H), 8.03 (d, J=1.5 Hz, 1H), 7.66 (d, J=1.5 Hz, 1H), 7.51 (s, 1H), 6.07 (dt, J=15.7, 5.7 Hz, 1H), 5.69 (dt, J=15.6, 6.3 Hz, 1H), 5.37 (d, J=5.6 Hz, 2H), 3.98 (s, 3H), 3.42 (p, J=6.0 Hz, 2H), 3.00 (q, J=7.6 Hz, 2H), 2.48 (s, 3H), 1.22 (t, J=7.5 Hz, 3H). ESI-MS: C$_{20}$H$_{24}$N$_5$O$_4$S (M+H): calc. 430.15, found: 430.25.

Step G: To a stirred solution of 3-(3-((tert-butyldimethylsilyl)oxy)propoxy)-4-chloro-5-nitrobenzamide, Compound 3 (prepared as described in Example 1, 800 mg, 2.15 mmol) in DMSO (2.5 mL) was added N$_4$Z)-3-((E)-4-aminobut-2-en-1-yl)-6-carbamoyl-4-methoxybenzo[d]thiazol-2 (3H)-ylidene)-4-ethyl-2-methyloxazole-5-carboxamide-HCl, Compound 59 (1.2 g, 2.58 mmol) and Et$_3$N (1.5 mL, 10.75 mmol). The mixture was stirred at room temperature for 5 hours, then quenched with water. The resulting solid was filtered and washed with water to afford N-((Z)-3-((E)-4-((2-(3-((tert-butyldimethylsilyl)oxy)propoxy)-4-carbamoyl-6-nitrophenyl)amino)but-2-en-1-yl)-6-carbamoyl-4-methoxybenzo[d]thiazol-2(3H)-ylidene)-4-ethyl-2-methyloxazole-5-carboxamide, Compound 60 (800 mg, 47% yield) as a yellow solid. $^1$H NMR (400 MHz, DMSO-d$_6$) δ 8.13-8.05 (m, 2H), 8.02-7.93 (m, 2H), 7.67 (t, J=6.3 Hz, 1H), 7.57 (d, J=1.5 Hz, 1H), 7.51-7.42 (m, 2H), 7.28 (s, 1H), 5.80 (dt, J=15.7, 5.6 Hz, 1H), 5.67 (dt, J=15.6, 5.6 Hz, 1H), 5.27 (d, J=5.6 Hz, 2H), 4.12 (t, J=5.9 Hz, 2H), 3.96 (t, J=6.1 Hz, 2H), 3.89 (s, 3H), 3.61 (t, J=6.2 Hz, 2H), 2.90 (q, J=7.5 Hz, 2H), 1.78 (p, J=6.1 Hz, 2H), 1.13 (t, J=7.5 Hz, 3H), 0.78 (s, 9H), −0.07 (s, 6H). ESI-MS: C$_{36}$H$_{48}$N$_7$O$_9$SSi (M+H): calc. 782.29, found: 782.30.

Step H: To a stirred solution of N-((Z)-3-((E)-4-((2-(3-((tert-butyldimethylsilyl)oxy)propoxy)-4-carbamoyl-6-nitrophenyl)amino)but-2-en-1-yl)-6-carbamoyl-4-methoxybenzo[d]thiazol-2(3H)-ylidene)-4-ethyl-2-methyloxazole-5-carboxamide, Compound (1.30 g, 1.66 mmol) in MeOH (30 mL) at 0° C. was added Na$_2$S$_2$O$_4$ (5.79 g, 33.28 mmol) dissolved in water (7.5 mL), followed immediately by aqueous NH$_4$OH (6.0 mL, 41.58 mmol). The mixture was allowed to warm to room temperature and stirred for 4 hours, then it was diluted with water and extracted with EtOAc (2×). The combined organic layers were dried over Na$_2$SO$_4$ and concentrated in vacuo. Purification over silica gel (DCM:MeOH 9:1 v/v) afforded N-((Z)-3-((E)-4-((2-amino-6-(3-((tert-butyldimethylsilyl)oxy)propoxy)-4-carbamoylphenyl)amino)but-2-en-1-yl)-6-carbamoyl-4-methoxybenzo[d]thiazol-2(3H)-ylidene)-4-ethyl-2-methyloxazole-5-carboxamide, Compound 61 (700 mg, 56% yield) as a yellow solid. $^1$H NMR (400 MHz, DMSO-d$_6$) δ 8.07 (s, 1H), 7.98 (dd, J=5.5, 1.5 Hz, 1H), 7.59 (d, J=1.5 Hz, 2H), 7.51-7.42 (m, 1H), 6.96-6.91 (m, 1H), 6.81 (d, J=1.8 Hz, 1H), 6.70 (d, J=1.8 Hz, 1H), 5.87-5.67 (m, 2H), 5.29 (d, J=5.6 Hz, 2H), 4.62 (s, 2H), 3.90 (s, 3H), 3.87 (q, J=5.9, 4.4 Hz, 2H), 3.60 (t, J=6.1 Hz, 2H), 2.97 (p, J=7.7 Hz, 2H), 1.72 (p, J=6.2 Hz, 2H), 1.17 (t, J=7.5 Hz, 3H), 0.76 (d, J=12.7 Hz, 9H), −0.08 (s, 6H). ESI-MS: C$_{36}$H$_{50}$N$_7$O$_7$SSi (M+H): calc. 752.32, found: 752.15.

Step I: To a stirred solution of N-((Z)-3-((E)-4-((2-amino-6-(3-((tert-butyldimethylsilyl)oxy)propoxy)-4-carbamoylphenyl)amino)but-2-en-1-yl)-6-carbamoyl-4-methoxybenzo[d]thiazol-2(3H)-ylidene)-4-ethyl-2-methyloxazole-5-carboxamide, Compound 61 (70 mg, 0.09 mmol) in methanol (5 mL) was added cyanogen bromide (19 mg, 0.19 mmol). The mixture was stirred at room temperature for 16 hours, then concentrated in vacuo. The residue was triturated in pentane and filtered to afford N-((Z)-3-((E)-4-(2-amino-7-(3-(((tert-butyldimethylsilyl)oxy)propoxy)-5-carbamoyl-1H-benzo[d]imidazol-1-yl)but-2-en-1-yl)-6-carbamoyl-4-methoxybenzo[d]thiazol-2(3H)-ylidene)-4-ethyl-2-methyloxazole-5-carboxamide, Compound 62 (70 mg, 88% yield) as a grey solid. $^1$H NMR (400 MHz, DMSO-d$_6$) δ 8.46 (s, 2H), 8.05 (d, J=12.4 Hz, 2H), 8.00-7.95 (m, 1H), 7.57 (s, 1H), 7.46 (t, J=19.2 Hz, 3H), 7.34 (s, 1H), (dt, J=15.8, 5.5 Hz, 1H), 5.78-5.69 (m, 1H), 5.29 (d, J=5.4 Hz, 2H), 4.84 (d, J=5.5 Hz, 2H), 4.05 (t, J=6.2 Hz, 2H), 3.81 (s, 3H), 3.60 (t, J=6.2 Hz, 2H), 2.80 (q, J=7.5 Hz, 2H), 2.43 (s, 3H), 1.72 (p, J=6.3 Hz, 2H), 1.04 (t, J=7.5 Hz, 3H), 0.80 (s, 9H), -0.11 (s, 6H). ESI-MS: C$_{37}$H$_{49}$N$_8$O$_7$SSi (M+H): calc. 777.31, found: 777.30.

Step J. To a stirred solution of N-((Z)-3-((E)-4-(2-amino-7-(3-(((tert-butyldimethylsilyl)oxy)propoxy)-5-carbamoyl-1H-benzo[d]imidazol-1-yl)but-2-en-1-yl)-6-carbamoyl-4-methoxybenzo[d]thiazol-2(3H)-ylidene)-4-ethyl-2-methyloxazole-5-carboxamide, Compound 62 (220 mg, 0.26 mmol) in DMF (2 mL) was added 4-ethyl-2-methyloxazole-5-carboxylic acid (59 mg, 0.38 mmol), PyBOP (199 mg, 0.38 mmol), and DIPEA (0.22 mL, 1.28 mmol). The mixture was stirred at 125° C. for 16 hours, then it was concentrated in vacuo. The resulting residue was triturated in cold water and filtered. The solid was purified by HPLC (ACN:H$_2$O) to afford N-(5-carbamoyl-1-((E)-4-((Z)-6-carbamoyl-2-((4-ethyl-2-methyloxazole-5-carbonyl)imino)-4-methoxybenzo[d]thiazol-3(2H)-yl)but-2-en-1-yl)-7-(3-hydroxypropoxy)-1H-benzo[d]imidazol-2-yl)-4-ethyl-2-methyloxazole-5-carboxamide, Compound 63 (130 mg, 63%) as a white solid. $^1$H NMR (400 MHz, DMSO-d$_6$) δ 8.05 (s, 1H), 7.97 (s, 2H), 7.62 (s, 1H), 7.54 (s, 1H), 7.49 (s, 1H), 7.31 (s, 2H), 5.82 (d, J=4.0 Hz, 2H), 5.28 (s, 2H), 4.90 (s, 2H), 4.06 (t, J=6.3 Hz, 2H), 3.80 (s, 3H), 3.45 (q, J=5.8 Hz, 2H), 2.85-2.73 (m, 4H), 1.71 (t, J=6.3 Hz, 2H), 1.00 (t, J=7.5 Hz, 6H). ESI-MS: C$_{38}$H$_{42}$N$_9$O$_9$S (M+H): calc. 800.27, found: 800.20.

Example 27: N-(5-carbamoyl-14(E)-4-((Z)-6-carbamoyl-2-((4-ethyloxazole-5-carbonyl)-imino)-4-methoxybenzo[d]thiazol-3(211)-yl)but-2-en-1-yl)-7-(3-hydroxypropoxy)-1H-benzo-[d]imidazol-2-yl)-4-ethyloxazole-5-carboxamide, Compound 64

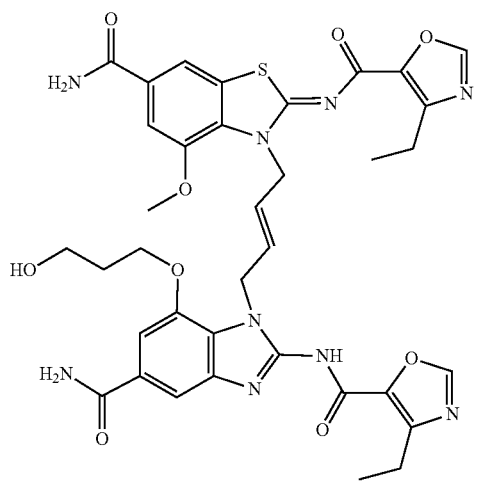

N-(5-carb amoyl-1-((E)-44(Z)-6-carb amoyl-2-((4-ethyloxazole-5-carb onyl)imino)-4-methoxybenzo[d]thiazol-3 (2H)-yl)but-2-en-1-yl)-7-(3-hydroxypropoxy)-1H-benzo[d]

imidazol-2-yl)-4-ethyloxazole-5-carboxamide was prepared as described in Example 26, except 4-ethyloxazole-5-carboxylic acid was used in Steps E and J instead of 4-ethyl-2-methyloxazole-5-carboxylic acid. Step J resulted in N-(5-carbamoyl-1-((E)-4-((Z)-6-carbamoyl-2-((4-ethyloxazole-1H-benzo[d]imidazol-2-yl)-4-ethyloxazole-5-carboxamide, Compound 64 (18 mg, 29% yield) as a white solid. $^1$H NMR (400 MHz, DMSO-d$_6$) δ 8.38 (s, 1H), 8.26 (s, 1H), 8.06 (s, 1H), 7.99 (s, 2H), 7.59 (d, J=31.1 Hz, 2H), 7.32 (s, 2H), 6.53 (s, 1H), 5.82 (d, J=3.0 Hz, 2H), 5.31 (s, 2H), 4.92 (s, 2H), 4.06 (t, J=6.5 Hz, 2H), 3.79 (s, 3H), 3.43 (d, J=5.7 Hz, 2H), 2.85 (dt, J=10.0, 5.0 Hz, 4H), 1.69 (t, J=6.2 Hz, 2H), 1.02 (t, J=7.5 Hz, 6H). ESI-MS: $C_{36}H_{38}N_9O_9S$ (M+H): calc. 772.24, found: 772.20.

Example 28: (Z)-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide, Compound 65

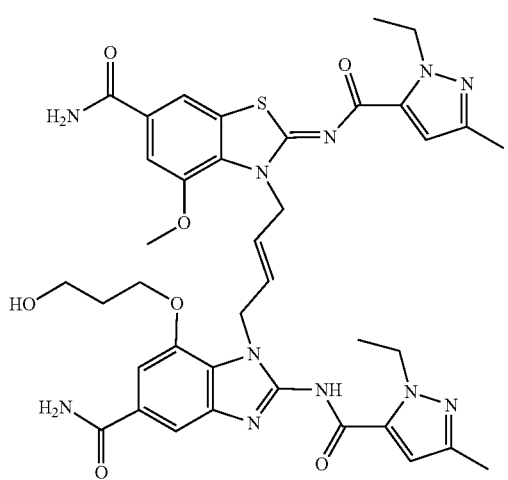

(Z)-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide was prepared as described in Example 26, except 4-ethyloxazole-5-carboxylic acid was used in Steps E and J instead of 4-ethyl-2-methyloxazole-5-carboxylic acid. Step J resulted in (Z)-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide, Compound 65 (30 mg, 29% yield) as a white solid. $^1$H NMR (400 MHz, DMSO-d$_6$) δ 8.08 (s, 1H), 7.98 (d, J=1.5 Hz, 2H), 7.66-7.47 (m, 3H), 7.38-7.27 (m, 2H), 6.62 (s, 1H), 6.49 (s, 1H), 5.87 (q, J=4.5 Hz, 2H), 5.31 (s, 2H), 4.93 (s, 2H), 4.59-4.50 (m, 4H), 4.04 (t, J=6.4 Hz, 2H), 3.77 (s, 3H), 3.46-3.41 (m, 2H), 2.09 (d, J=3.7 Hz, 6H), 1.67 (t, J=6.2 Hz, 2H), 1.27 (dt, J=7.1, 3.5 Hz, 6H). ESI-MS: $C_{38}H_{44}N_{11}O_7S$ (M+H): calc. 798.31, found: 798.20.

Example 29: 4-45-carbamoyl-14(E)-4-((Z)-6-carbamoyl-2-((4-ethyl-2-methyloxazole-5-carbonyl)imino)-4-methoxybenzo[d]thiazol-3(2H)-yl)but-2-en-1-yl)-2-(4-ethyl-2-methyloxazole-5-carboxamido)-1H-benzo[d]imidazol-7-yl)oxy)butanoic acid, Compound 66

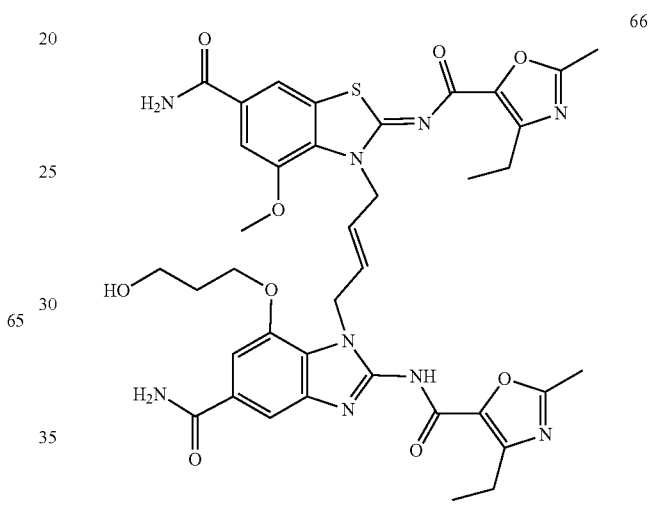

4-((5-carbamoyl-14(E)-4-((Z)-6-carbamoyl-2-((4-ethyl-2-methyloxazole-5-carbonyl)imino)-4-methoxybenzo[d]thiazol-3(2H)-yl)but-2-en-1-yl)-2-(4-ethyl-2-methyloxazole-acid was prepared as described in Example 26, except methyl 4-(5-carbamoyl-2-chloro-3-nitrophenoxy)butanoate was used in Step G instead of 3-(3-((tert-butyldimethylsilyl)oxy)propoxy)-4-chloro-5-nitrobenzamide, Compound 3. The hydrolysis of the methyl ester of 4-((5-carbamoyl-1-((E)-4-((Z)-6-carbamoyl-2-((4-ethyl-2-methyloxazole-5-carbonyl)imino)-4-methoxybenzo[d]thiazol-3(2H)-yl)but-2-en-1-yl)-2-(4-ethyl-2-methyloxazole-5-carboxamido)-1H-benzo[d]imidazol-7-yl)oxy)butanoic acid, Compound 66 was carried out as described in Example 11 to afford 4-(5-carbamoyl-14(E)-4-((Z)-6-carbamoyl-2-((4-ethyl-2-methyloxazole-5-carbonyl)imino)-4-methoxybenzo[d]thiazol-3 (2H)-yl)but-2-en-1-yl)-2-(4-ethyl-2-methyloxazole-5-carboxamido)-1H-benzo[d]imidazol-7-yl)oxy)butanoic acid, Compound 66 (120 mg, 76% yield) as a white solid. $^1$H NMR (400 MHz, DMSO-d$_6$) δ 12.70 (s, 1H), 12.16 (s, 1H), 8.00 (d, J=34.0 Hz, 3H), 7.63 (s, 1H), 7.51 (d, J=18.6 Hz, 2H), 7.31 (d, J=15.5 Hz, 2H), 5.81 (q, J=17.4, 16.6 Hz, 2H), 5.27 (s, 2H), 4.90 (s, 2H), 3.99 (d, J=6.8 Hz, 2H), 3.79 (s, 3H), 2.77 (q, J=7.6 Hz, 4H), 2.29 (t, J=7.3 Hz, 2H), 1.90-1.74 (m, 2H), 1.12-0.85 (m, 6H). ESI-MS: $C_{39}H_{42}N_9O_{10}S$ (M+H): calc. 828.27, found: 828.20.

Example 30: (Z)-3-((E)-4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-41-ethyl-3-methyl-1H-pyrazole-5-carbonyl)imino)-4-methoxy-2,3-dihydrobenzo[d]thiazole-6-carboxamide, Compound 67

Example 31: 4-((5-carbamoyl-1-((E)-4-((Z)-6-carbamoyl-2-((1-ethyl-3-methyl-1H-pyrazole-[d]thiazol-3(2H)-yl)but-2-en-1-yl)-2-(1-ethyl-3-methyl-1H-pyrazole-5-carboxamido)-1H-benzo[d]imidazol-7-yl)oxy)butanoic acid, Compound 68

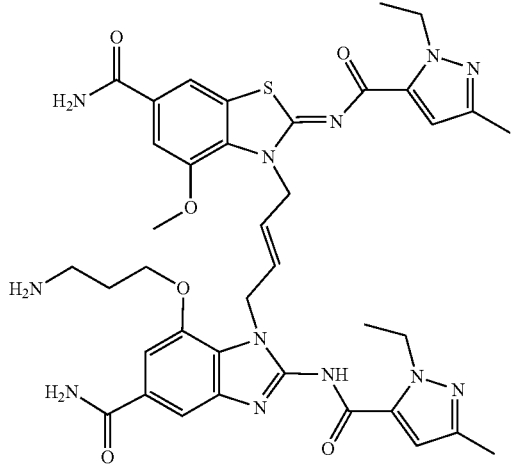

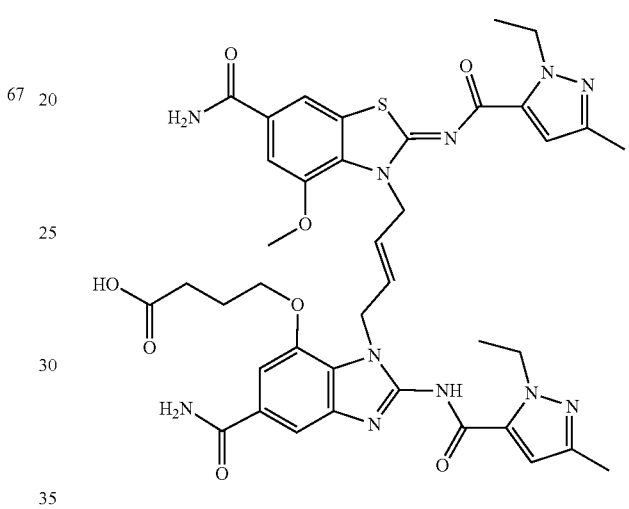

(Z)-3-((E)-4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-24(1-ethyl-3-methyl-1H-pyrazole-5-carbonyl)imino)-4-methoxy-2,3-dihydrobenzo[d]thiazole-6-carboxamide was prepared as described in Example 26, except tert-butyl (3-(5-carbamoyl-2-chloro-3-nitrophenoxy)propyl)carbamate was used in Step G instead of 3-(3-((tert-butyldimethylsilyl)oxy)propoxy)-4-chloro-5-nitrobenzamide, Compound 3 and 1-ethyl-3-methyl-1H-pyrazole-5-carboxylic acid was used in Steps E and J instead of 4-ethyl-2-methyloxazole-5-carboxylic acid. The removal of the Boc group of boc-protected Compound 67 was carried out as described in Example 10 to afford (Z)-3-((E)-4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide, Compound 67 (30 mg, 88% yield) as a white solid. $^1$H NMR (400 MHz, DMSO-$d_6$) δ 8.04 (s, 1H), 7.94 (d, J=1.4 Hz, 2H), 7.64 (s, 2H), 7.53-7.47 (m, 2H), 7.37-7.27 (m, 2H), 6.58 (s, 1H), 5.87-5.72 (m, 1H), 5.27 (d, J=4.5 Hz, 2H), 4.89 (d, J=4.4 Hz, 2H), 4.47 (q, J=7.0 Hz, 4H), 4.02 (t, J=5.9 Hz, 2H), 3.69 (s, 3H), 2.83 (q, J=6.5 Hz, 2H), 1.81 (t, J=6.8 Hz, 2H), 1.26-1.21 (m, 6H). ESI-MS: $C_{38}H_{45}N_{12}O_6S$ (M+H): calc. 797.32, found: 797.30.

4-((5-carbamoyl-14(E)-4-((Z)-6-carbamoyl-2-((1-ethyl-3-methyl-1H-pyrazole-5-carbonyl)imino)-4-methoxybenzo[d]thiazol-3 (2H)-yl)but-2-en-1-yl)-2-(1-ethyl-3-methyl-1H-pyrazole-5-carboxamido)-1H-benzo[d]imidazol-7-yl)oxy)butanoic acid was prepared as described in Example 26, except methyl 4-(5-carbamoyl-2-chloro-3-nitrophenoxy)butanoate was used in Step G instead of 3-(3-((tert-butyldimethylsilyl)oxy)propoxy)-4-chloro-5-nitrobenzamide, Compound 3 and 1-ethyl-3-methyl-1H-pyrazole-5-carboxylic acid was used in Steps E and J instead of 4-ethyl-2-methyloxazole-5-carboxylic acid. The hydrolysis of the methyl ester of Compound 68 was carried out as described in Example 11 to afford 4-((5-carbamoyl-14(E)-4-((Z)-6-carbamoyl-2-((1-ethyl-3-methyl-1H-pyrazole-5-carbonyl)imino)-4-methoxybenzo[d]thiazol-3(2H)-yl)but-2-en-1-yl)-2-(1-ethyl-3-methyl-1H-pyrazole-5-carboxamido)-1H-benzo[d]imidazol-7-yl)oxy)butanoic acid, Compound 68 (70 mg, 49% yield) as a white solid. $^1$H NMR (400 MHz, DMSO-$d_6$) δ 8.06 (s, 1H), 7.96 (d, J=5.1 Hz, 2H), 7.64 (s, 1H), 7.53 (s, 1H), 7.48 (s, 1H), 7.31 (d, J=14.1 Hz, 2H), 6.60 (s, 1H), 6.49 (s, 1H), 5.87 (tdd, J=10.2, 5.2 Hz, 2H), 5.31 (d, J=5.3 Hz, 2H), 4.93 (d, J=5.1 Hz, 2H), 4.50 (dd, J=7.4, 4.9 Hz, 4H), 3.98 (t, J=6.5 Hz, 2H), 3.76 (s, 3H), 2.26 (t, J=7.2 Hz, 2H), 2.09 (d, J=2.8 Hz, 6H), 1.79 (p, J=7.0 Hz, 2H), 1.26 (q, J=6.7 Hz, 6H). ESI-MS: $C_{39}H_{44}N_{11}O_8S$ (M+H): calc. 826.30, found: 826.30.

Example 32: N-(5-carbamoyl-1-((E)-4-((Z)-6-carbamoyl-2-((l-ethyl-3-methyl-1H-pyrazole-hydroxypropoxy)-1H-benzo[d]imidazol-2-yl)-4-ethyl-2-methyloxazole-5-carboxamide, Compound 69

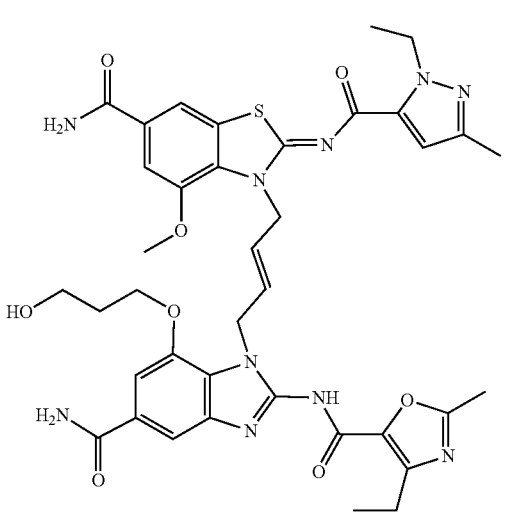

N-(5-carbamoyl-1-((E)-4-((Z)-6-carbamoyl-24(1-ethyl-3-methyl-1H-pyrazole-5-carb onyl)imino)-4-methoxybenzo[d]thiazol-3 (2H)-yl)but-2-en-1-yl)-7-(3-hydroxypropoxy)-1H-benzo[d]imidazol-2-yl)-4-ethyl-2-methyloxazole-5-carboxamide was prepared as described in Example 26, except 1-ethyl-3-methyl-1H-pyrazole-5-carboxylic acid was used in Step E instead of 4-ethyl-2-methyloxazole-5-carboxylic acid. Step J resulted in N-(5-carbamoyl-14(E)-4-((Z)-6-carbamoyl-2-((1-ethyl-3-methyl-1H-pyrazole-5-carbonyl)imino)-4-methoxybenzo[d]thiazol-3 (2H)-yl)but-2-en-1-yl)-7-(3-hydroxypropoxy)-1H-benzo[d]imidazol-2-yl)-4-ethyl-2-methyl oxazol e-5-carboxamide, Compound 69 (30 mg, 26% yield) as a white solid. $^1$H NMR (400 MHz, DMSO-$d_6$) δ 8.04 (s, 1H), 7.94 (d, J=1.5 Hz, 2H), 7.59 (d, J=1.3 Hz, 1H), 7.50 (d, J=1.5 Hz, 1H), 7.46 (s, 1H), 7.31-7.26 (m, 2H), 6.56 (s, 1H), 5.91-5.74 (m, 2H), 5.27 (d, J=4.4 Hz, 2H), 4.87 (s, 2H), 4.47 (t, J=7.1 Hz, 2H), 4.02 (d, J=6.3 Hz, 2H), 3.75 (s, 3H), 3.41 (d, J=6.0 Hz, 2H), 2.76 (q, J=7.5 Hz, 2H), 2.35 (s, 3H), 2.07 (s, 3H), 1.67 (t, J=6.2 Hz, 2H), 1.24 (t, J=7.1 Hz, 3H), 0.96 (t, J=7.6 Hz, 3H). ESI-MS: $C_{38}H_{43}N_{10}O_8S$ (M+H): calc. 799.29, found: 799.30.

Example 33: N-((Z)-6-carbamoyl-3-((E)-4-(5-carbamoyl-2-(4-ethyl-2-methylthiazole-5-carboxamido)-7-(3-hydroxypropoxy)-1H-benzo[d]imidazol-1-yl)but-2-en-1-yl)-4-methoxybenzo[d]thiazol-2(3H)-ylidene)-4-ethyl-2-methyloxazole-5-carboxamide, Compound 70

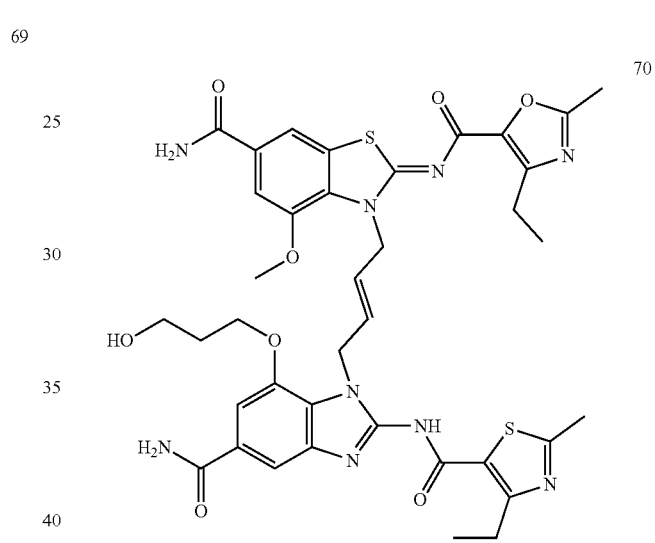

N-((Z)-6-carbamoyl-34(E)-4-(5-carbamoyl-2-(4-ethyl-2-methylthiazole-5-carboxamido)-7-(3-hydroxypropoxy)-1H-benzo[d]imidazol-1-yl)but-2-en-1-yl)-4-methoxybenzo[d]thiazol-2(3H)-ylidene)-4-ethyl-2-methyloxazole-5-carboxamide was prepared as described in Example 26, except 4-ethyl-2-methylthiazole-5-carboxylic acid was used in Step J instead of 4-ethyl-2-methyloxazole-5-carboxylic acid to afford N-((Z)-6-carbamoyl-3-((E)-4-(5-carbamoyl-2-(4-ethyl-2-methylthiazole-5-carboxamido)-7-(3-hydroxypropoxy)-1H-benzo[d]imidazol-1-yl)but-2-en-1-yl)-4-methoxybenzo[d]thiazol-2(3H)-ylidene)-4-ethyl-2-methyloxazole-5-carboxamide, Compound 70 (20 mg, 19% yield) as a white solid. $^1$H NMR (400 MHz, DMSO-$d_6$) δ 8.02 (s, 1H), 7.93 (q, J=5.6, 3.8 Hz, 2H), 7.53 (dd, J=22.5, 1.4 Hz, 2H), 7.47 (s, 1H), 7.29 (d, J=7.3 Hz, 2H), 5.91-5.76 (m, 2H), 5.25 (d, J=4.8 Hz, 2H), 4.83 (d, J=5.0 Hz, 2H), 4.06 (t, J=6.4 Hz, 2H), 3.77 (s, 3H), 3.03 (t, J=7.5 Hz, 2H), 2.74 (t, J=7.5 Hz, 2H), 2.37 (s, 3H), 1.71 (q, J=6.2 Hz, 2H), 1.09 (d, J=7.6 Hz, 3H), 0.96 (d, J=7.5 Hz, 3H). ESI-MS: $C_{38}N_{42}N_9O_8S_2$ (M+H): calc. 816.25, found: 816.20.

Example 34: (Z)-3-((E)-4-(5-carbamoyl-7-(3-hydroxypropoxy)-2-(1-isopropyl-1H-1,2,4-triazole-5-carboxamido)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide, Compound 71

Example 35: N-(5-carbamoyl-14(E)-44(Z)-6-carbamoyl-2-((1-ethyl-3-methyl-1H-pyrazole-hydroxypropoxy)-1H-benzo[d]imidazol-2-yl)-2,4-dimethyloxazole-5-carboxamide, Compound 72

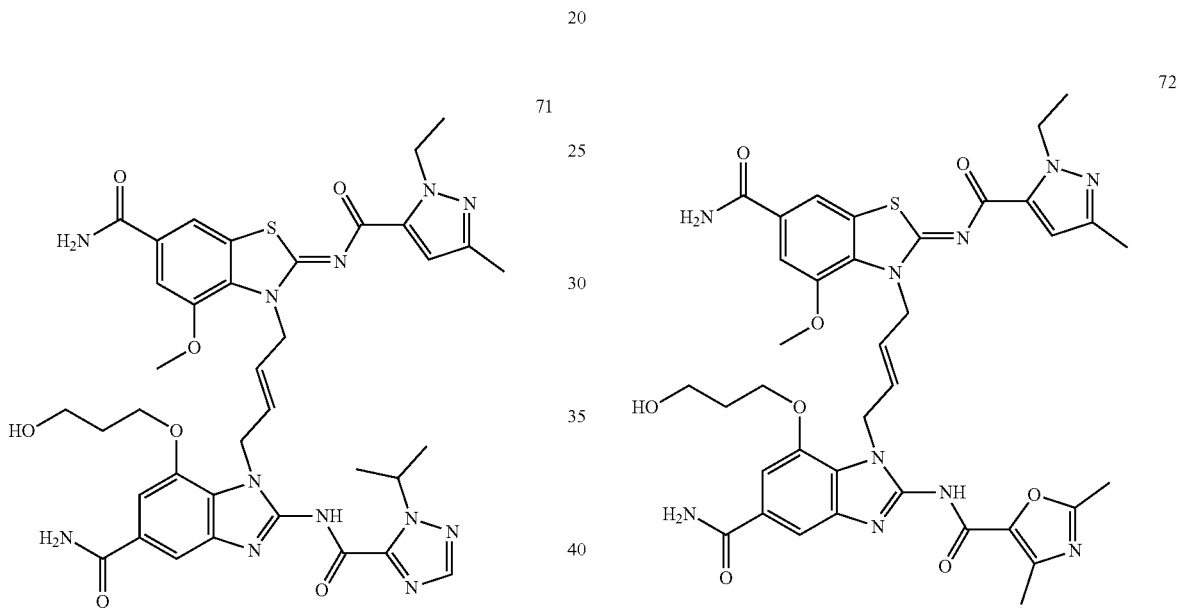

(Z)-3-((E)-4-(5-carbamoyl-7-(3-hydroxypropoxy)-2-(1-isopropyl-1H-1,2,4-triazole-5-carboxamido)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide was prepared as described in Example 26, except 1-ethyl-3-methyl-1H-pyrazole-5-carboxylic acid was used in Step E and 1-isopropyl-1H-1,2,4-triazole-5-carboxylic acid was used in Step J instead of 4-ethyl-2-methyloxazole-5-carboxylic acid to afford (Z)-3-((E)-4-(5-carbamoyl-7-(3-hydroxypropoxy)-2-(1-isopropyl-1H-1,2,4-triazole-5-carboxamido)-1H-benzo[d]imidazol-1-yl)but-2-en-1-yl)-2-((1-ethyl-3-methyl-1H-pyrazole-5-carbonyl)imino)-4-m ethoxy-2,3-dihydrobenzo[d]thiazole-6-carboxamide, Compound 71 (25 mg, 23% yield) as a white solid. $^1$H NMR (400 MHz, DMSO-d$_6$) δ 8.12-7.89 (m, 4H), 7.68 (s, 1H), 7.56-7.46 (m, 2H), 7.35 (d, J=12.6 Hz, 2H), 6.59 (s, 1H), (q, J=16.0 Hz, 2H), 5.64 (s, 1H), 5.30 (d, J=5.3 Hz, 2H), 4.95 (s, 2H), 4.49 (q, J=7.1 Hz, 2H), 4.02 (t, J=6.4 Hz, 2H), 3.74 (s, 3H), 2.10 (s, 3H), 1.65 (t, J=6.2 Hz, 2H), 1.34 (d, J=6.6 Hz, 6H), 1.28-1.22 (m, 5H). ESI-MS: C$_{37}$H$_{43}$N$_{12}$O$_7$S (M+H): calc. 799.30, found: 799.30.

N-(5-carbamoyl-1-((E)-4-((Z)-6-carbamoyl-24(1-ethyl-3-methyl-1H-pyrazole-5-carbonyl)imino)-4-methoxybenzo[d]thiazol-3(2H)-yl)but-2-en-1-yl)-7-(3-hydroxypropoxy)-1H-benzo[d]imidazol-2-yl)-2,4-dimethyloxazole-5-carboxamide was prepared as described in Example 26, except 1-ethyl-3-methyl-1H-pyrazole-5-carboxylic acid was used in Step E and 2,4-dimethyloxazole-5-carboxylic acid was used in Step J instead of 4-ethyl-2-methyloxazole-5-carboxylic acid to afford N-(5-carbamoyl-1-((E)-4-((Z)-6-carbamoyl-2-((l-ethyl-3-methyl-1H-pyrazole-5-carbonyl)imino)-4-methoxybenzo[d]thiazol-3(2H)-yl)but-2-en-1-yl)-7-(3-hydroxypropoxy)-1H-benzo[d]imidazol-2-yl)-2,4-dimethyloxazole-5-carboxamide, Compound 72 (30 mg, 26% yield) as a white solid. $^1$H NMR (400 MHz, DMSO-d$_6$) δ 8.04 (s, 1H), 7.94 (d, J=1.6 Hz, 2H), 7.60 (d, J=1.2 Hz, 1H), 7.50 (d, J=1.6 Hz, 1H), 7.46 (s, 1H), 7.28 (d, J=4.5 Hz, 2H), 6.57 (s, 1H), 5.90-5.75 (m, 2H), 5.27 (d, J=4.5 Hz, 2H), 4.88 (s, 2H), 4.47 (t, J=7.0 Hz, 2H), 4.02 (s, 2H), 3.40 (t, J=6.1 Hz, 2H), 2.34 (s, 3H), 2.25 (s, 3H), 2.07 (s, 3H), 1.71-1.61 (m, 2H), 1.24 (t, J=7.1 Hz, 3H). ESI-MS: C$_{37}$H$_{41}$N$_{10}$O$_8$S (M+H): calc. 785.28, found: 785.20.

Example 36: N-((Z)-6-carbamoyl-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-4-methoxybenzo[d]thiazol-2(3H)-ylidene)-4-ethyl-2-methyloxazole-5-carboxamide, Compound 73

Example 37: N-((Z)-6-carbamoyl-3-((E)-4-(5-carbamoyl-7-(3-hydroxypropoxy)-2-(5-methylpyrazolo[1,5-a]pyrimidine-7-carboxamido)-1H-benzo[d]imidazol-1-yl)but-2-en-1-yl)-4-methoxybenzo[d]thiazol-2(3H)-ylidene)-4-ethyl-2-methyloxazole-5-carboxamide, Compound 74

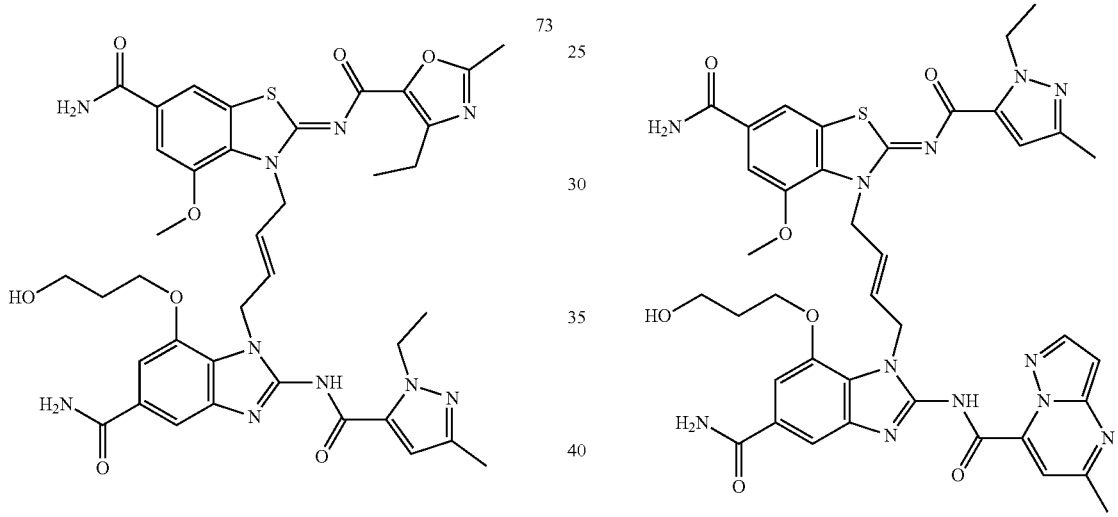

N-((Z)-6-carbamoyl-34(E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-4-methoxybenzo[d]thiazol-2(3H)-ylidene)-4-ethyl-2-methyloxazole-5-carboxamide was prepared as described in Example 26, except 1-ethyl-3-methyl-1H-pyrazole-5-carboxylic acid was used in Step J instead of 4-ethyl-2-methyloxazole-5-carboxylic acid to afford N-((Z)-6-carbamoyl-3-((E)-4-(5-carbamoyl-2-(1-ethyl-3-methyl-1H-pyrazole-5-c arb oxamido)-7-(3-hydroxypropoxy)-1H-benzo[d]imidazol-1-yl)but-2-en-1-yl)-4-methoxybenzo[d]thiazol-2(3H)-ylidene)-4-ethyl-2-methyloxazole-5-carboxamide, Compound 73 (29 mg, 31% yield) as a white solid. $^1$H NMR (400 MHz, DMSO-d$_6$) δ 8.02-7.95 (m, 2H), 7.62 (d, J=1.2 Hz, 1H), 7.57-7.49 (m, 2H), 7.37-7.30 (m, 2H), 6.48 (s, 1H), 5.83 (td, J=3.9, 2.5 Hz, 2H), 5.28 (d, J=3.5 Hz, 2H), 4.92 (d, J=3.5 Hz, 2H), 4.54-4.50 (m, 2H), 4.05 (t, J=6.4 Hz, 2H), 3.79 (s, 3H), 3.42 (t, J=6.0 Hz, 2H), 2.78 (q, J=7.5 Hz, 2H), 2.41 (s, 3H), 2.10 (s, 3H), 1.67 (p, J=6.3 Hz, 2H), 1.26 (t, J=7.1 Hz, 3H), 1.00 (t, J=7.5 Hz, 3H). ESI-MS: $C_{38}H_{43}N_{10}O_8S$ (M+H): calc. 799.29, found: 799.30.

N-((Z)-6-carbamoyl-34(E)-4-(5-carbamoyl-7-(3-hydroxypropoxy)-2-(5-methylpyrazolo[1,5-a]pyrimidine-7-carboxamido)-1H-benzo[d]imidazol-1-yl)but-2-en-1-yl)-4-methoxybenzo[d]thiazol-2(3H)-ylidene)-4-ethyl-2-methyloxazole-5-carboxamide was prepared as described in Example 26, except 5-methylpyrazolo[1,5-a]pyrimidine-7-carboxylic acid was used in Step J instead of 4-ethyl-2-methyloxazole-5-carboxylic acid to afford N-((Z)-6-carbamoyl-3-((E)-4-(5-carb amoyl-7-(3-hydroxypropoxy)-2-(5-methylpyrazolo[1,5-a]pyrimidine-7-carboxamido)-1H-benzo[d]imidazol-1-yl)but-2-en-1-yl)-4-methoxybenzo[d]thiazol-2(3H)-ylidene)-4-ethyl-2-methyloxazole-5-carboxamide, Compound 74 (40 mg, 47% yield) as a white solid. $^1$H NMR (400 MHz, DMSO-d$_6$) δ 8.03 (d, J=2.3 Hz, 1H), 7.90 (s, 1H), 7.65 (s, 1H), 7.44 (s, 1H), 7.28 (s, 1H), 6.95 (s, 1H), 6.60-6.50 (m, 2H), 5.79 (d, J=3.4 Hz, 2H), 5.24 (s, 2H), 4.89 (s, 2H), 4.42 (d, J=7.4 Hz, 2H), 3.97 (d, J=7.6 Hz, 3H), 3.36 (d, J=6.2 Hz, 2H), 2.04 (s, 3H), 1.70-1.57 (m, 2H), 1.20 (t, J=7.2 Hz, 5H). ESI-MS: $C_{39}H_{40}N_{11}O_8S$ (M+H): calc. 822.27, found: 822.25.

Example 38: (Z)-3-((E)-4-(5-carbamoyl-7-(3-hydroxypropoxy)-2-(2-methyl-4,5-dihydrofuran-3-carboxamido)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide, Compound 75

Example 39: N-(5-carbamoyl-H(E)-4-((Z)-6-carbamoyl-2-((4-ethyl-2-methylthiazole-5-carbonyl)imino)-4-methoxybenzo[d]thiazol-3(2H)-yl)but-2-en-1-yl)-7-(3-hydroxypropoxy)-1H-benzo[d]imidazol-2-yl)-4-ethyl-2-methyloxazole-5-carboxamide, Compound 76

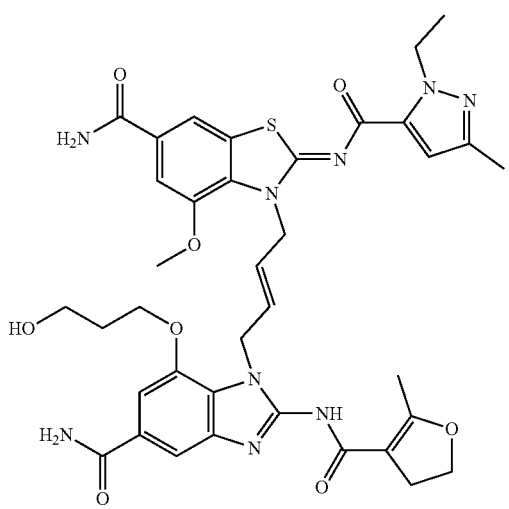

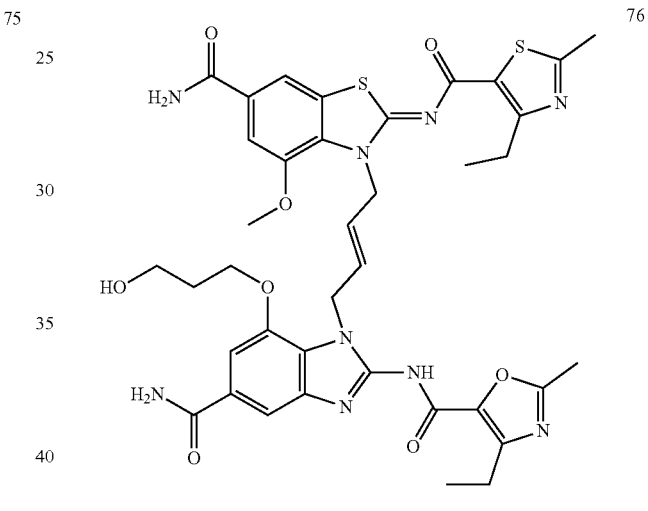

(Z)-3-((E)-4-(5-carbamoyl-7-(3-hydroxypropoxy)-2-(2-methyl-4, 5-dihydrofuran-3-carboxamido)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide was prepared as described in Example 26, except 1-ethyl-3-methyl-1H-pyrazole-5-carboxylic acid was used in Step E and 2-methyl-4,5-dihydrofuran-3-carboxylic acid was used in Step J instead of 4-ethyl-2-methyloxazole-5-carboxylic acid to afford (Z)-3-((E)-4-(5-carbamoyl-7-(3-hydroxypropoxy)-2-(2-methyl-4, 5-dihydrofuran-3-carboxamido)-1H-benzo[d]imidazol-1-yl)but-2-en-1-yl)-2-((1-ethyl-3-methyl-1H-pyrazole-5-carbonyl)imino)-4-methoxy-2,3-dihydrobenzo[d]thiazole-6-carboxamide, Compound 75 (15 mg, 18% yield) as a white solid. $^1$H NMR (400 MHz, DMSO-$d_6$) δ 8.62 (d, J=1.4 Hz, 1H), 7.98 (d, J=1.5 Hz, 1H), 7.53 (dd, J=3.5, 1.5 Hz, 2H), 6.56 (s, 1H), –5.74 (m, 2H), 5.30 (d, J=5.1 Hz, 2H), 4.98 (d, J=4.9 Hz, 2H), 4.48 (q, J=7.1 Hz, 2H), 4.02 (t, J=6.3 Hz, 2H), 3.79 (s, 3H), 3.50 (s, 2H), 3.40 (t, J=6.1 Hz, 2H), 2.72 (d, J=7.1 Hz, 2H), 2.30 (s, 3H), 2.10 (s, 3H), 1.65 (p, J=6.3 Hz, 2H), 1.27 (t, J=7.1 Hz, 3H). ESI-MS: $C_{37}H_{42}N_9O_8S$ (M+H): calc. 772.28, found: 772.30.

N-(5-carbamoyl-1-((E)-4-((Z)-6-carbamoyl-24(4-ethyl-2-methylthiazole-5-carb onyl)imino)-4-methoxybenzo[d]thiazol-3 (2H)-yl)but-2-en-1-yl)-7-(3-hydroxypropoxy)-1H-benzo[d]imidazol-2-yl)-4-ethyl-2-methyloxazole-5-carboxamide was prepared as described in Example 26, except 4-ethyl-2-methylthiazole-5-carboxylic acid was used in Step E instead of 4-ethyl-2-methyloxazole-5-carboxylic acid. Step J resulted in N-(5-carbamoyl-1-((E)-4-((Z)-6-carbamoyl-2-(4-ethyl-2-methylthiazole-5-carbonyl)imino)-4-methoxybenzo[d]thiazol-3(2H)-yl)but-2-en-1-yl)-7-(3-hydroxypropoxy)-1H-benzo[d]imidazol-2-yl)-4-ethyl-2-methyloxazole-5-carboxamide, Compound 76 (35 mg, 18% yield) as a white solid. $^1$H NMR (400 MHz, DMSO-$d_6$) δ 8.04 (s, 1H), 7.95-7.91 (m, 2H), 7.59 (d, J=1.3 Hz, 1H), 7.52 (d, J=1.5 Hz, 1H), 7.46 (s, 1H), 7.31-7.25 (m, 2H), 5.92 (dt, J=15.7, 5.4 Hz, 1H), 5.85-5.74 (m, 1H), 5.20 (d, J=5.8 Hz, 2H), 4.87 (d, J=5.5 Hz, 2H), 4.01 (t, J=6.5 Hz, 2H), 3.81 (s, 3H), 3.03 (q, J=7.5 Hz, 2H), 2.76 (q, J=7.5 Hz, 2H), 2.35 (s, 3H), 1.68 (t, J=6.2 Hz, 2H), 1.11 (t, J=7.5 Hz, 3H), 0.96 (t, J=7.5 Hz, 3H). ESI-MS: $C_{38}H_{42}N_9O_8S_2$ (M+H): calc. 816.25, found: 816.20.

General procedure for synthesis of Compound Variant VI, wherein $Z_1=Z_2$; $Y_1=Y_2$; $X_1=X_2$; $W_1=W_2$; $R^{14}=R^{C2}$; $R^{19}=R^{18}$; $R^{15}=R^{17}$ and $R^{C1}=R^{16}$.

Variant VI

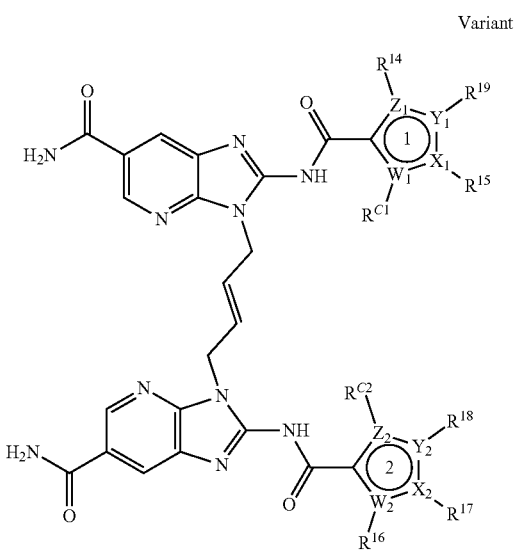

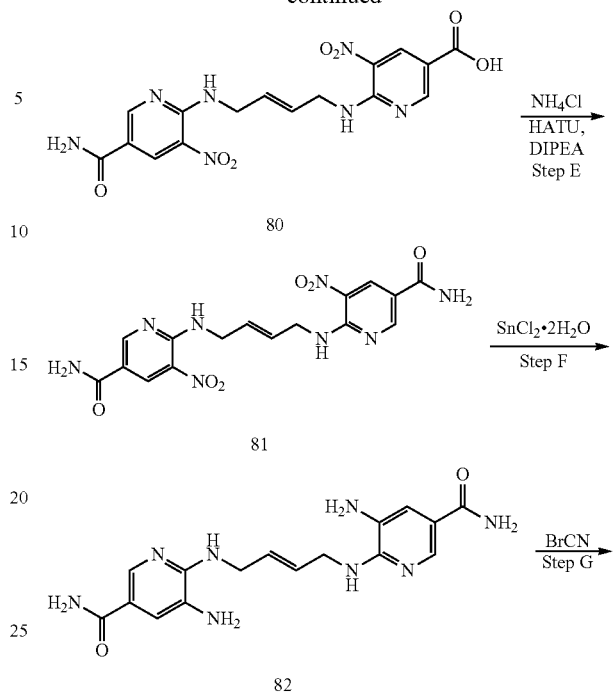

Scheme 6: The following scheme illustrates the exemplary synthesis of (E)-3,3'-(but-2-ene-1,4-diyl)bis(2-(1-ethyl-3-methyl-1H-pyrazole-5-carboxamido)-3H-imidazo[4,5-b]pyridine-6-carboxamide). The similar procedure may be generally used for the synthesis of Compound Variant VI. As shown below, heterocyclic structures (rings 1 and 2) can be introduced by using the corresponding carboxylic acid at Step H.

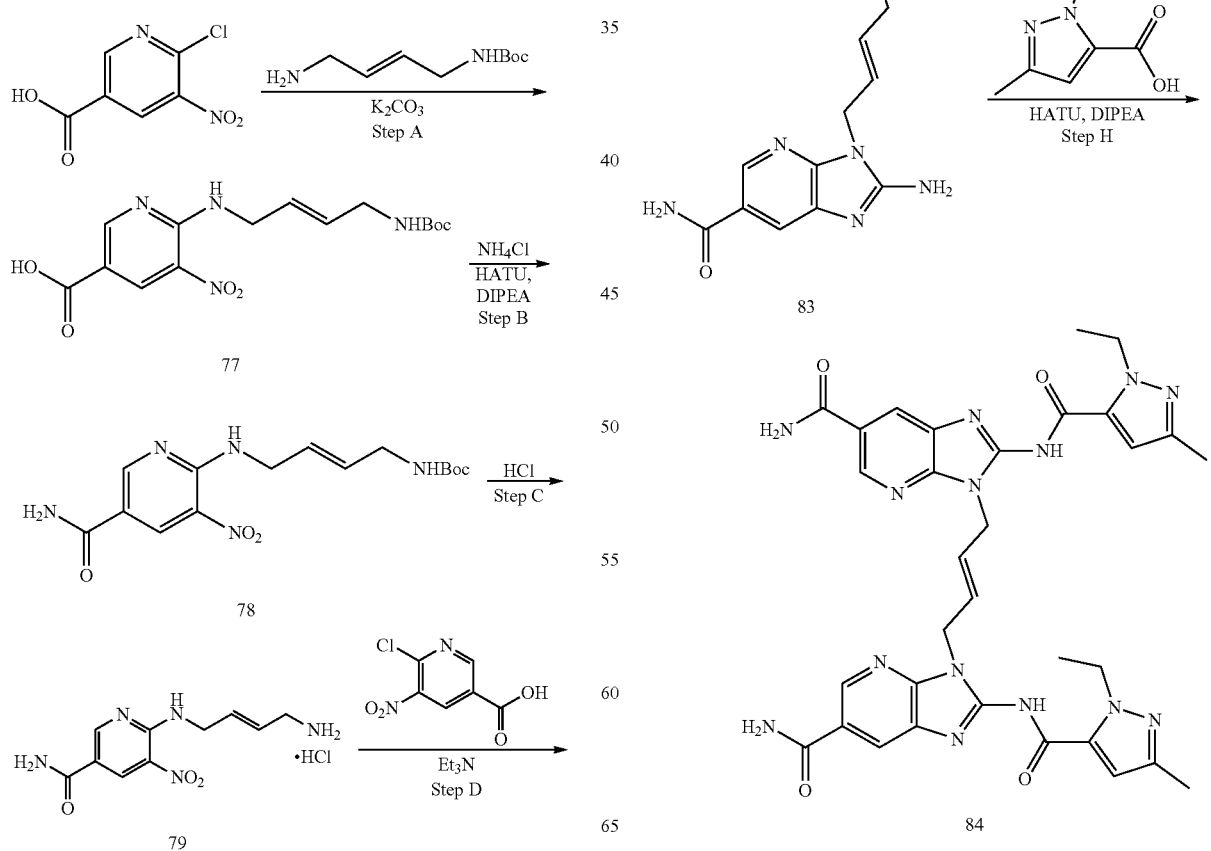

Example 40: (E)-3,3'-(but-2-ene-1,4-diyl)bis(2-(1-ethyl-3-methyl-1H-pyrazole-5-carboxamido)-3H-imidazo[4,5-b]pyridine-6-carboxamide), Compound 84

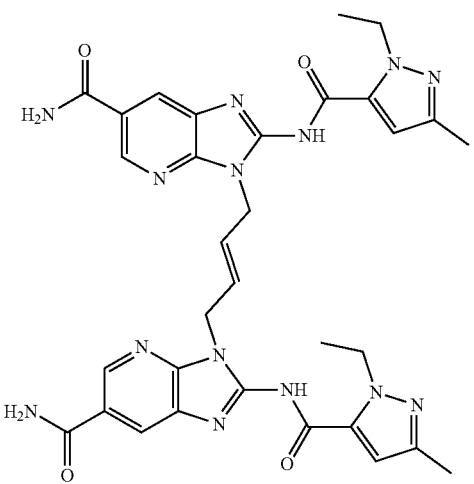

Step A: To a stirred solution of 6-chloro-5-nitronicotinic acid (500 mg, 2.5 mmol) and DMSO (10 mL) was added tert-butyl N-(4-aminobut-2-en-1-yl)carbamate (600 mg, 2.7 mmol) and K$_2$CO$_3$ (1.0 g, 7.2 mmol). The reaction mixture was stirred at room temperature for 16 hours. The mixture was cooled to 0° C., diluted in water, neutralized to pH 7.0 with 1M HCl and then extracted with EtOAc (2x, 100 mL). The combined organic layers were dried over MgSO$_4$ and concentrated in vacuo to afford (E)-6-((4-((tert-butoxycarbonyl)amino)but-2-en-1-yl)amino)-5-nitronicotinic acid, Compound 77 (700 mg, 80% yield) as a yellow solid. $^1$H NMR (400 MHz, DMSO-d$_6$) δ 13.18 (s, 1H), 8.97 (t, J=5.8 Hz, 1H), 8.86 (d, J=2.2 Hz, 1H), 8.71 (d, J=2.2 Hz, 1H), 6.93 (t, J=5.9 Hz, 1H), 5.60 (qt, J=15.5, 5.1 Hz, 2H), 4.20 (t, J=5.5 Hz, 2H), 3.50 (t, J=5.5 Hz, 2H), 1.33 (s, 9H). ESI-MS: C$_{15}$H$_{21}$N$_4$O$_6$ (M+H) calc. 353.14, found 353.20.

Step B: To a stirred solution of (E)-6-((4-((tert-butoxycarbonyl)amino)but-2-en-1-yl)amino)-5-nitronicotinic acid, Compound 77 (700 mg, 1.9 mmol) and DMF (10 mL) under N$_2$ was added NH$_4$Cl (530 mg, 9.9 mmol) and HATU (1.0 g, 4.0 mmol). The mixture was stirred at room temperature for 5 minutes, then DIPEA (1.75 mL, 9.9 mmol) was added. After 16 hours the reaction was quenched with ice cold water (30 mL) and stirred for 1 hour, resulting in the formation of a white precipitate. The solid was filtered and dried under vacuum to afford tert-butyl (E)-(4-((5-carbamoyl-3-nitropyridin-2-yl)amino)but-2-en-1-yl)carbamate, Compound 78 (440 mg, 63% yield) as a white solid. $^1$H NMR (400 MHz, DMSO-d$_6$) δ 8.94-8.83 (m, 4H), 8.10 (s, 1H), 7.47 (s, 1H), 6.97 (d, J=6.4 Hz, 1H), 5.66 (dt, J=15.7, 5.1 Hz, 1H), 5.58 (dt, J=15.6, 5.0 Hz, 1H), 4.21 (t, J=5.7 Hz, 2H), 3.51 (q, J=8.1, 6.8 Hz, 2H), 1.35 (s, 9H). ESI-MS: C$_{15}$H$_{22}$N$_5$O$_5$ (M+H) calc. 352.15, found 352.15.

Step C: A solution of tert-butyl (E)-(4-((5-carbamoyl-3-nitropyridin-2-yl)amino)but-2-en-1-yl)carbamate, Compound 78 (2 g, 5.7 mmol) in dioxane (10 mL) under N$_2$ was cooled to 0° C., and HCl (4M in dioxane, 20 mL, 80 mmol) was added. The reaction mixture was warmed to room temperature and stirred for 1 hour. The mixture was concentrated in vacuo to afford (E)-6-((4-aminobut-2-en-1-yl)amino)-5-nitronicotinamide-HCl, Compound 79 (2 g, 100% yield) as a white solid. $^1$H NMR (400 MHz, DMSO-d$_6$) δ 8.96-8.83 (m, 3H), 8.12 (s, 1H), 7.93 (s, 2H), 7.46 (s, 1H), 5.98-5.87 (m, 1H), 5.67-5.55 (m, 1H), 4.27-4.19 (m, 2H), 3.43-3.32 (m, 2H). ESI-MS: C$_{10}$H$_{14}$N$_5$O$_3$ (M+H) calc. 252.10, found 252.10.

Step D: To a stirred solution of (E)-6-((4-aminobut-2-en-1-yl)amino)-5-nitronicotinamide-HCl, Compound 79 (200 mg, 0.79 mmol) and DMF (5 mL) was added 6-chloro-5-nitronicotinamide (194 mg, 0.956 mmol) and Et$_3$N (0.22 mL, 1.58 mmol). The mixture was stirred at room temperature for 16 hours, then quenched with ice water and neutralized to pH 7.0 with 1M HCl. The resulting precipitate was filtered and dried to afford (E)-6-((4-((5-carbamoyl-3-nitropyridin-2-yl)amino)but-2-en-1-yl)amino)-5-nitronicotinic acid, Compound 80 (170 mg, 59% yield) as a yellow solid. $^1$H NMR (400 MHz, DMSO-d$_6$) δ 13.17 (s, 1H), 8.98 (t, J=5.8 Hz, 1H), 8.88-8.80 (m, 4H), 8.68 (d, J=2.0 Hz, 1H), 8.06 (s, 1H), 7.43 (s, 1H), 5.81-5.63 (m, 2H), 4.20 (dt, J=8.1, 3.7 Hz, 4H). ESI-MS: C$_{16}$H$_{16}$N$_7$O$_7$ (M+H): calc. 418.10, found: 418.00.

Step E: To a stirred solution of (E)-6-((4-((5-carbamoyl-3-nitropyridin-2-yl)amino)but-2-en-1-yl)amino)-5-nitronicotinic acid, Compound 80 (170 mg, 0.41 mmol) and DMF (5 mL) was added HATU (186 mg, 0.49 mmol), DIPEA (0.15 mL, 0.81 mmol) and ammonium chloride (40 mg, 0.81 mmol). The mixture was stirred at room temperature for 16 hours, then quenched with ice water. The resulting solid was filtered and dried to afford (E)-6,6'-(but-2-ene-1,4-diylbis(azanediyl))bis(5-nitronicotinamide), Compound 81 (150 mg, 88% yield) as a dark brown solid. $^1$H NMR (400 MHz, DMSO-d$_6$) δ 8.88 (ddd, J=13.4, 10.1, 4.0 Hz, 6H), 8.09 (s, 2H), 7.45 (s, 2H), 5.79 (t, J=2.9 Hz, 2H), 4.23 (d, J=5.4 Hz, 4H). ESI-MS: C$_{16}$H$_{17}$N$_8$O$_6$ (M+H): calc. 417.12, found: 417.10.

Step F: To a stirred solution of (E)-6,6'-(but-2-ene-1,4-diylbis(azanediyl))bis(5-nitronicotinamide), Compound 81 (200 mg, 0.48 mmol) in concentrated HCl (20 mL) was added anhydrous SnCl$_2$ (546 mg, 2.88 mmol). The mixture was stirred at room temperature for 1 hour, then cooled to 0° C. and quenched by adjusting the pH to pH 10 with 6M NaOH. The resulting solid was filtered and dried to afford (E)-6,6'-(but-2-ene-1,4-diylbis(azanediyl))bis(5-aminonicotinamide), Compound 82 (120 mg, 70% yield) as a light brown solid. $^1$H NMR (400 MHz, DMSO-d$_6$) δ 8.23 (s, 6H), 5.84 (tt, J=3.4, 1.5 Hz, 2H), 3.48-3.37 (m, 4H). ESI-MS: C$_{16}$H$_{21}$N$_8$O$_2$ (M+H): calc. 357.17, found: 357.52.

Step G: To a stirred solution of (E)-6,6'-(but-2-ene-1,4-diylbis(azanediyl))bis(5-aminonicotinamide), Compound 82 (60 mg, 0.17 mmol) in MeOH (7.5 mL) and DMSO (1.5 mL) under N$_2$ was added cyanogen bromide (71 mg, 0.67 mmol). The mixture was stirred at room temperature for 16 hours, then concentrated in vacuo. The resulting residue was suspended in EtOAc (15 mL) and stirred for 15 minutes. The solid was filtered, then suspended in water (30 mL) and stirred an additional 30 minutes. The solids were filtered and discarded. The filtrate was basified with aqueous NaHCO$_3$, stirred for 10 minutes, then filtered and dried to afford (E)-3,3'-(but-2-ene-1,4-diyl)bis(2-amino-3H-imidazo[4,5-b]pyridine-6-carboxamide), Compound 83 (35 mg, 51% yield) as a grey solid. $^1$H NMR (400 MHz, DMSO-d$_6$) δ 8.36 (d, J=2.0 Hz, 2H), 7.87 (s, 2H), 7.80 (d, J=1.9 Hz, 2H), 7.22 (s, 2H), 6.89 (d, J=14.1 Hz, 4H), 5.63 (d, J=3.1 Hz, 2H), 4.66-4.56 (m, 4H). ESI-MS: C$_{18}$H$_{19}$N$_{10}$O$_2$ (M+H): calc. 407.41, found: 407.60.

Step H: A mixture of (E)-3,3'-(but-2-ene-1,4-diyl)bis(2-amino-3H-imidazo[4,5-b]pyridine-6-carboxamide), Compound 83 (50 mg, 0.12 mmol), 1-ethyl-3-methyl-1H-pyrazole-5-carboxylic acid (57 mg, 0.37 mmol), HATU (140 mg, 0.37 mmol), DIPEA (0.17 mL, 0.98 mmol) and DMF (5 mL) under pressure was heated to 60° C. and stirred for 16 hours, then concentrated in vacuo. The resulting residue was suspended in water and stirred for 30 minutes. The solid was filtered and then suspended in EtOH (3 mL) and stirred for 30 minutes. The solid was filtered and washed with EtOH (2 mL) to afford (E)-3,3'-(but-2-ene-1,4-diyl)bis(2-(1-ethyl-3-methyl-1H-pyrazole-5-carboxamido)-3H-imidazo[4,5-b]pyridine-6-carboxamide), Compound 84 (35 mg, 42% yield) as a brown solid. $^1$H NMR (400 MHz, DMSO-$d_6$) δ 12.82 (s, 2H), 8.66 (d, J=1.9 Hz, 2H), 8.14-8.01 (m, 4H), 7.49 (s, 2H), 6.49 (s, 2H), 5.89 (t, J=2.9 Hz, 2H), 4.83-4.67 (m, 4H), 4.48 (q, J=7.1 Hz, 4H), 2.06 (s, 6H), 1.23 (t, J=7.1 Hz, 6H). ESI-MS: $C_{32}H_{35}N_{14}O_4$ (M+H): calc. 679.29, found: 679.20.

Example 41: (E)-N,N'-(but-2-ene-1,4-diylbis(6-carbamoyl-311-imidazo[4,5-13]pyridine-3,2-diyl))bis(4-ethyl-2-methyloxazole-5-carboxamide), Compound 85

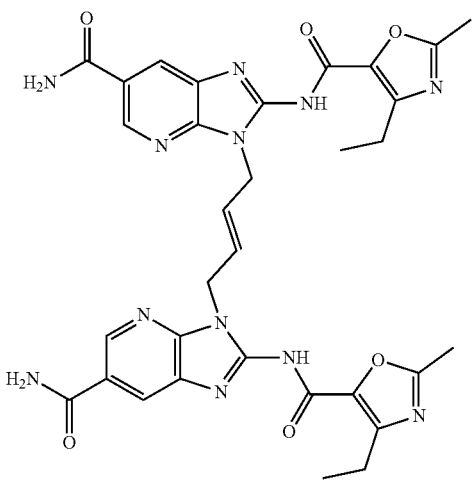

(E)-N,N'-(but-2-ene-1,4-diylbis(6-carbamoyl-3H-imidazo[4,5-b]pyridine-3,2-diyl))bis(4-ethyl-2-methyloxazole-5-carboxamide) was prepared as described in Example 40, except ethyl-2-methyloxazole-5-carboxlyic acid was used in Step H instead of 1-ethyl-3-methyl-1h-pyrazole-5-carboxylic acid to afford (E)-N,N'-(but-2-ene-1,4-diylbis(6-carbamoyl-3H-imidazo[4,5-b]pyridine-3,2-diyl))bis(4-ethyl-2-methyloxazole-5-carboxamide), Compound 85 (12 mg, 16% yield) as a light brown solid. $^1$H NMR (400 MHz, DMSO-$d_6$) δ 12.82 (s, 2H), 8.66 (d, J=1.9 Hz, 2H), 8.10 (s, 2H), 7.49 (s, 2H), 6.49 (s, 2H), 5.89 (t, J=2.9 Hz, 2H), 4.78-4.68 (m, 4H), 4.48 (q, J=7.1 Hz, 4H), 2.06 (s, 6H), 1.23 (t, J=7.1 Hz, 6H). ESI-MS: $C_{32}H_{33}N_{12}O_6$ (M+H): calc. 681.26, found: 681.10.

General procedure for synthesis of Compound Variant VII, wherein $Z_1=Z_2$; $Y_1=Y_2$; $X_1=X_2$; $W_1=W_2$; $R^{14}=R^{C2}$; $R^{19}=R^{18}$; $R^{15}=R^{17}$ and $R^{C1}=R^{16}$.

Variant VII

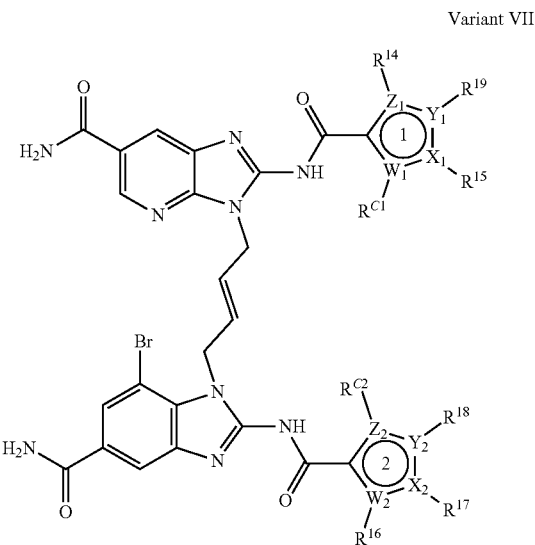

Scheme 7: The following scheme illustrates the exemplary synthesis of (E)-3-(4-(7-bromo-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxamide. The similar procedure may be generally used for the synthesis of Compound Variant VII. As shown below, heterocyclic structures (rings 1 and 2) can be introduced by using the corresponding carboxylic acid at Step G.

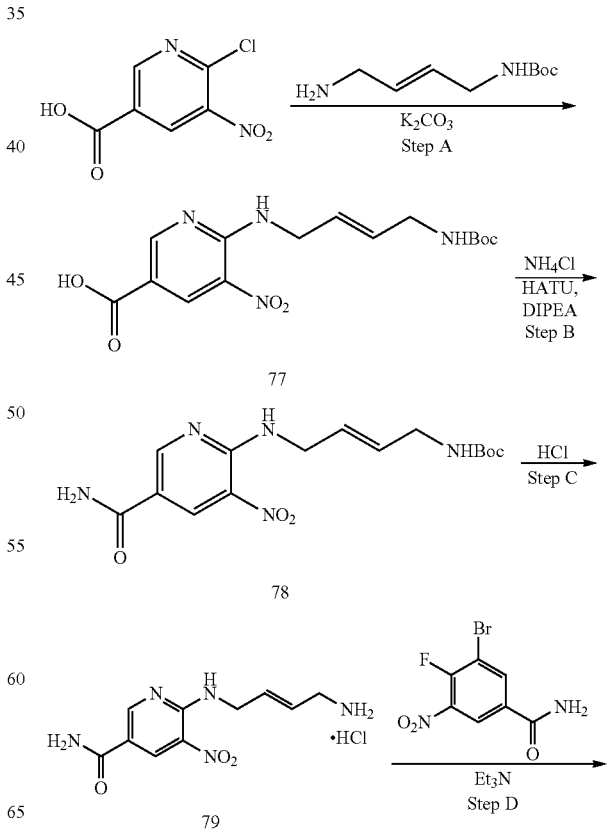

-continued

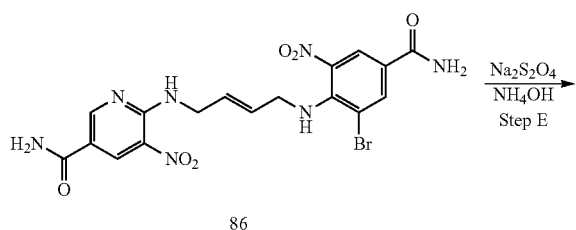

86

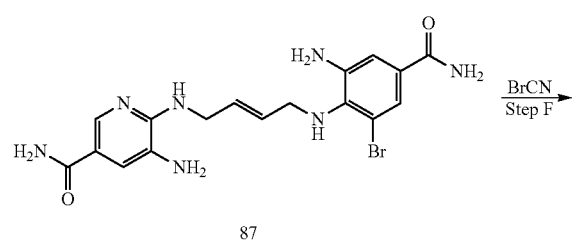

87

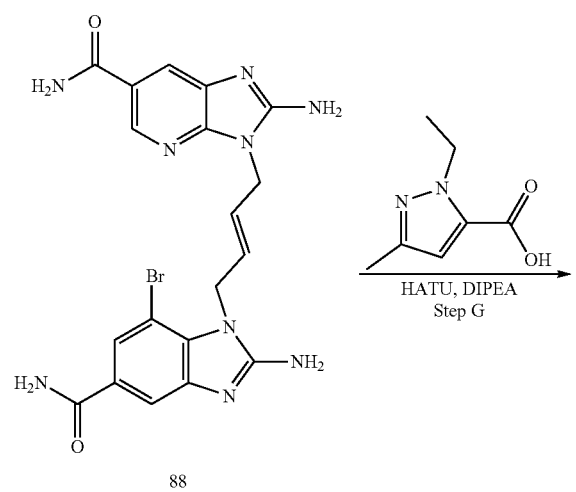

88

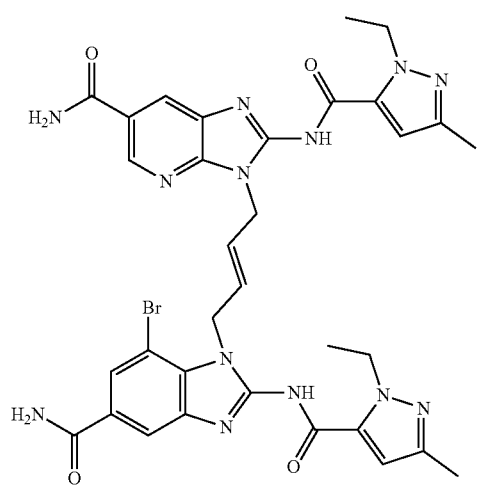

89

Example 42: (E)-3-(4-(7-bromo-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxamide, Compound 89

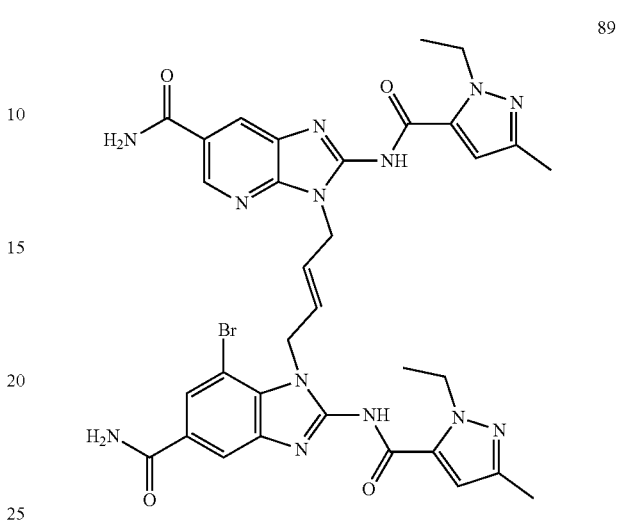

Steps A, B, and C were conducted as described in Example 40.

Step D: To a stirred solution of 3-bromo-4-fluoro-5-nitrobenzamide (700 mg, 2.7 mmol) and DMF (20 mL) under $N_2$ was added (E)-6-((4-aminobut-2-en-1-yl)amino)-5-nitronicotinamide-HCl, Compound 79 (prepared as described in example 40, 700 mg, 2.8 mmol) and triethylamine (1.85 mL, 18.3 mmol). The mixture was stirred at room temperature for 16 hours, then quenched with cold water (200 mL) and stirred for 1 hour, resulting in the formation of a yellow precipitate. The solid was filtered and washed with diethyl ether and dried to afford (E)-6-((4-((2-bromo-4-carbamoyl-6-nitrophenyl)amino)but-2-en-1-yl)amino)-5-nitronicotinamide, Compound 86 (1.2 g, 91% yield) as a yellow solid. $^1$H NMR (400 MHz, DMSO-$d_6$) δ 8.83 (s, 2H), 8.76 (t, J=5.8 Hz, 1H), 8.24 (q, J=2.2 Hz, 2H), 8.05 (s, 1H), 8.00 (s, 1H), 7.42 (d, J=7.7 Hz, 2H), 6.61 (t, J=6.0 Hz, 1H), 5.64 (dt, J=15.6, 5.5 Hz, 1H), 5.51 (dt, J=15.7, 6.0 Hz, 1H), 4.10 (t, J=5.5 Hz, 2H), 3.77 (t, J=5.9 Hz, 2H). ESI-MS: $C_{17}H_{17}BrN_7O_6$ (M+H) calc. 495.26, found 495.90.

Step E: To a stirred solution of (E)-6-((4-((2-bromo-4-carbamoyl-6-nitrophenyl)amino)but-2-en-1-yl)amino)-5-nitronicotinamide, Compound 86 (1.2 g, 2.4 mmol) and methanol (20 mL) under $N_2$ at 0° C. was added $Na_2S_2O_4$ (4.2 g, 24.0 mmol) dissolved in water (8 mL) followed immediately by the addition of $NH_4OH$ (3.6 mL, 212 mmol). The mixture was warmed to room temperature and stirred for 20 minutes, then diluted with water (30 mL) and extracted EtOAc (2×). The combined organic layers were dried over $Na_2SO_4$ and concentrated in vacuo to afford crude (E)-5-amino-6-((4-((2-amino-6-bromo-4-carbamoylphenyl)amino)but-2-en-1-yl)amino)nicotinamide, Compound 87 (260 mg, 25% yield) as a light yellow solid. $^1$H NMR (400 MHz, DMSO-$d_6$) δ 7.94 (d, J=2.1 Hz, 1H), 7.72 (s, 1H), 7.53 (s, 1H), 7.31-7.26 (m, 2H), 7.12 (dd, J=12.8, 2.0 Hz, 3H), 6.88 (s, 1H), 6.16 (d, J=5.7 Hz, 1H), 5.77 (d, J=4.2 Hz, 2H), (s, 2H), 4.82 (s, 2H), 4.08-3.89 (m, 2H), 3.56 (d, J=7.0 Hz, 2H). ESI-MS: $C_{17}H_{21}BrN_7O_2$ (M+H) calc. 435.30, found 435.90.

Step F: To a stirred solution of (E)-5-amino-6-((4-((2-amino-6-bromo-4-carbamoylphenyl)amino)but-2-en-1-yl)amino)nicotinamide, Compound 87 (260 mg, 0.6 mmol) and methanol (10 mL) under N$_2$ was added cyanogen bromide (380 mg, 3.6 mmol), and the mixture was stirred at room temperature for 16 hours. The mixture was concentrated in vacuo, and the resulting residue was stirred in aqueous NaHCO$_3$ (10 mL) for 1 hour. The solid was filtered, washed with water, and dried to afford crude (E)-2-amino-3-(4-(2-amino-7-bromo-5-carbamoyl-1H-benzo[d]imidazol-1-yl)but-2-en-1-yl)-3H-imidazo[4,5-b]pyridine-6-carboxamide, Compound 88 (220 mg, 76% yield) as a white solid. $^1$H NMR (400 MHz, DMSO-d$_6$) δ 8.35 (d, J=1.9 Hz, 1H), 7.87 (d, J=8.4 Hz, 2H), 7.79 (d, J=2.0 Hz, 1H), 7.65-7.61 (m, 1H), 7.54 (dd, J=8.9, 1.6 Hz, 1H), 7.19 (d, J=20.1 Hz, 2H), 6.84 (s, 2H), 6.69 (s, 2H), 5.73-5.65 (m, 1H), 5.49 (dd, J=5.6 Hz, 1H), 4.85 (d, J=4.8 Hz, 2H), 4.61 (d, J=5.6 Hz, 2H). ESI-MS: C$_{19}$H$_{91}$BrN$_9$O$_2$ (M-H) calc. 483.32, found 483.85.

Step G: A mixture of (E)-2-amino-3-(4-(2-amino-7-bromo-5-carbamoyl-1H-benzo[d]imidazol-1-yl)but-2-en-1-yl)-3H-imidazo[4,5-b]pyridine-6-carboxamide, Compound 88 (130 mg, 0.26 mmol), 1-ethyl-3-methyl-1 h-pyrazole-5-carboxylic acid (124 mg, 0.8 mmol), HATU (305 mg, 0.8 mmol), DIPEA (0.29 mL, 2.2 mmol) and DMF (5 mL), under pressure was heated to 50° C., and stirred for 16 hours. The reaction mixture was cooled to room temperature, quenched with water (50 mL) and stirred for 30 minutes, resulting in a brown precipitate. The solid was filtered, washed with diethyl ether, and dried to afford (E)-3-(4-(7-bromo-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxamide, Compound 89 (25 mg, 13% yield) as a light brown solid. $^1$H NMR (400 MHz, DMSO-d$_6$) δ 12.94 (d, J=70.1 Hz, 2H), 8.70 (d, J=1.9 Hz, 1H), 8.12 (d, J=5.8 Hz, 2H), 8.04 (s, 1H), 7.99 (s, 1H), 7.93-7.88 (m, 1H), 7.48 (d, J=33.2 Hz, 2H), 6.53 (d, J=7.8 Hz, 2H), 6.06-5.88 (m, 1H), 5.76 (d, J=15.5 Hz, 1H), 5.09 (d, J=5.1 Hz, 2H), 4.78 (d, J=5.6 Hz, 2H), 4.50 (q, J=7.1 Hz, 4H), 2.10 (d, J=6.5 Hz, 6H), 1.26 (td, J=7.1, 2.5 Hz, 6H). ESI-MS: C$_{33}$H$_{35}$BrN$_{13}$O$_4$ (M+H) calc. 757.20, found 757.2.

Example 43: (E)-N-(7-bromo-5-carbamoyl-1-(4-(6-carbamoyl-2-(4-ethyl-2-methyloxazole-5-carboxamido)-3H-imidazo[4,5-b]pyridin-3-yl)but-2-en-1-yl)-1H-benzo[d]imidazol-2-yl)-4-ethyl-2-methyloxazole-5-carboxamide, Compound 90

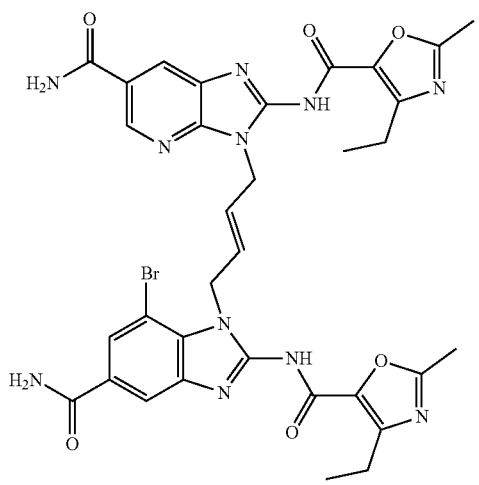

(E)-N-(7-bromo-5-carbamoyl-1-(4-(6-carbamoyl-2-(4-ethyl-2-methyloxazole-5-carboxamido)-3H-imidazo[4,5-b]pyridin-3-yl)but-2-en-1-yl)-1H-benzo[d]imidazol-2-yl)-4-ethyl-2-methyloxazole-5-carboxamide was prepared as described in Example 42, except ethyl-2-methyloxazole-5-carboxlyic acid (55 mg, 0.35 mmol) was used in Step G instead of 1-ethyl-3-methyl-1h-pyrazole-5-carboxylic acid to afford (E)-N-(7-bromo-5-carbamoyl-1-(4-(6-carbamoyl-2-(4-ethyl-2-methyloxazole-5-carboxamido)-3H-imidazo[4,5-b]pyridin-3-yl)but-2-en-1-yl)-1H-benzo[d]imidazol-2-yl)-4-ethyl-2-methyloxazole-5-carboxamide, Compound 90 (3.0 mg, 2.1% yield) as a light brown solid. $^1$H NMR (400 MHz, DMSO-d$_6$) δ 8.69 (s, 1H), 8.18-7.90 (m, 6H), 7.50 (d, J=32.9 Hz, 2H), 5.90 (s, 1H), 5.73 (s, 1H), 5.06 (s, 2H), 4.75 (d, J=5.3 Hz, 2H), 3.17 (s, 6H), 1.25 (d, J=9.6 Hz, 4H), 0.98 (q, J=7.2 Hz, 6H). ESI-MS: C$_{33}$H$_{33}$BrN$_{11}$O$_6$ (M+H): calc. 758.17, found: 758.10.

General procedure for synthesis of Compound Variant VIII, wherein Z$_1$=Z$_2$; Y$_1$=Y$_2$; X$_1$=X$_2$; W$_1$=W$_2$, R$^{14}$=R$^{C2}$; R$^{19}$=R$^{18}$; R$^{15}$=R$^{17}$ and R$^{C1}$=R$^{16}$.

Variant VIII

Scheme 8: The following scheme illustrates the exemplary synthesis of (E)-3-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxamide. The similar procedure may be generally used for the synthesis of Compound Variant VIII. As shown below, heterocyclic structures (rings 1 and 2) can be introduced by using the corresponding carboxylic acid at Step G.

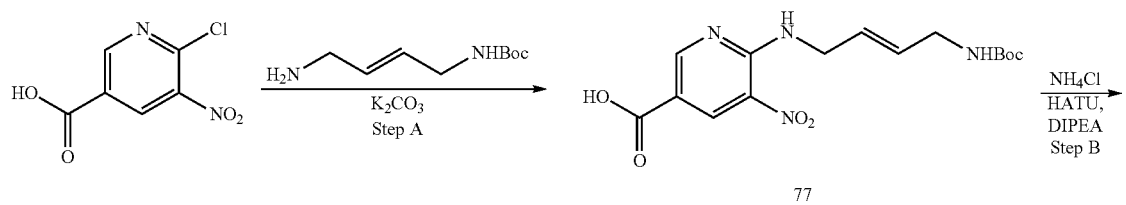
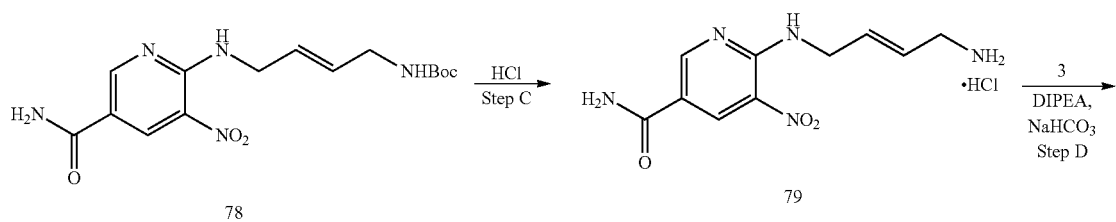
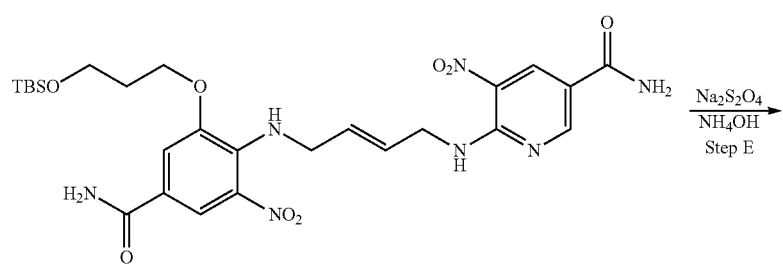
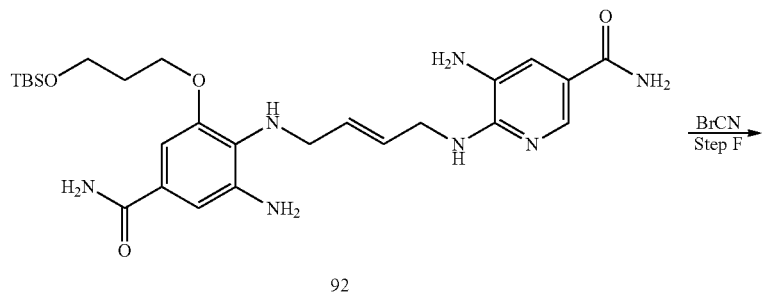
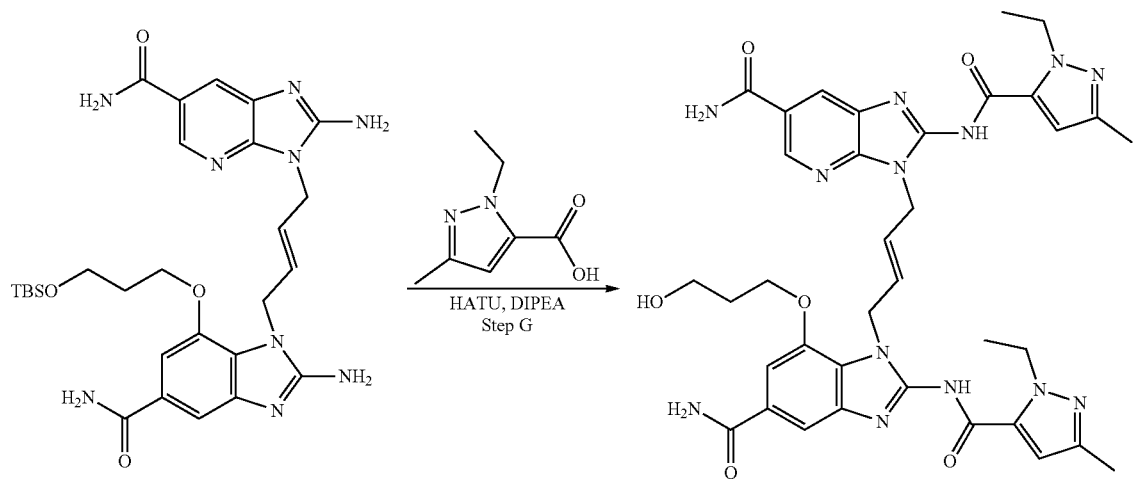

Example 44: (E)-3-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxamide, Compound 94

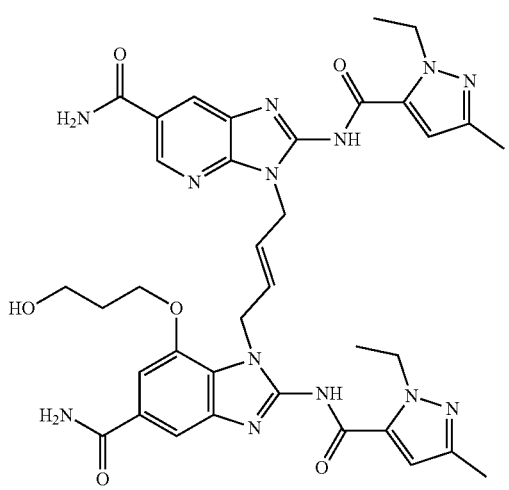

Steps A, B and C were conducted as described in Example 40.

Step D: To a stirred solution of 3-(3-((tert-butyldimethylsilyl)oxy)propoxy)-4-chloro-5-nitrobenzamide, Compound 3 (prepared as described in Example 1, 1.0 g, 2.67 mmol) in 1-butanol (25 mL) was added NaHCO$_3$ (435 mg, 5.17 mmol) and DIPEA (1.86 mL, 14.39 mmol), and the mixture was stirred at room temperature for 10 minutes. Then, (E)-6-((4-aminobut-2-en-1-yl)amino)-5-nitronicotinamide·HCl, Compound 79 (prepared as described in Example 42, 1.2 g, 4.78 mmol) was added, and the mixture was heated to 120° C. under pressure and stirred for 16 hours, then the mixture was cooled to room temperature and concentrated in vacuo. Purification over silica gel (DCM:MeOH 10:1 v/v) afforded (E)-6-((4-((2-(3-((tert-butyldimethylsilyl)oxy)propoxy)-4-carbamoyl-6-nitrophenyl)amino)but-2-en-1-yl)amino)-5-nitronicotinamide, Compound 91 (600 mg, 37% yield) as a red solid. $^1$H NMR (400 MHz, DMSO-d$_6$) δ 8.88 (s, 2H), 8.86-8.81 (m, 1H), 8.16 (d, J=1.9 Hz, 1H), 8.09 (s, 1H), 8.01 (s, 1H), 7.71 (t, J=6.1 Hz, 1H), 7.53 (d, J=2.0 Hz, 1H), 7.46 (s, 1H), 7.31 (s, 1H), 5.79-5.64 (m, 2H), 4.19 (t, J=5.2 Hz, 2H), 4.14 (d, J=5.3 Hz, 2H), 4.09 (t, J=6.0 Hz, 2H), 3.72 (t, J=6.2 Hz, 2H), 1.92 (p, J=6.2 Hz, 2H), 0.82 (s, 9H), −0.01 (s, 6H). ESI-MS: C$_{26}$H$_{38}$N$_7$O$_8$Si (M+H): calc. 604.25, found: 604.10.

Step E: To a stirred solution of (E)-6-((4-((2-(3-((tert-butyldimethylsilyl)oxy)propoxy)-4-carbamoyl-6-nitrophenyl)amino)but-2-en-1-yl)amino)-5-nitronicotinamide, Compound 91 (600 mg, 0.99 mmol) in methanol (10 mL) at 0° C. was added Na$_2$S$_2$O$_4$ (1.73 g, 9.93 mmol) dissolved in water (5 mL), followed by aqueous ammonia (25% v/v, 2.1 mL, 123.5 mmol). The mixture was allowed to warm to room temperature and stirred for 20 minutes, then it was diluted in water and extracted with EtOAc (2×). The combined organic layers were dried over Na$_2$SO$_4$ and concentrated in vacuo to afford (E)-5-amino-6-((4-((2-amino-6-(3-((tert-butyldimethylsilyl)oxy)propoxy)-4-carbamoylphenyl)amino)but-2-en-1-yl)amino)nicotinamide, Compound 92 (380 mg, 70% yield) as a yellow solid. $^1$H NMR (400 MHz, DMSO-d$_6$) δ 8.15 (d, J=2.2 Hz, 1H), 7.94 (d, J=2.0 Hz, 1H), 7.60 (s, 1H), 7.51 (s, 1H), 7.11-7.04 (m, 1H), 6.99-6.74 (m, 5H), 5.74 (d, J=3.6 Hz, 2H), 4.67 (s, 2H), 4.00 (d, J=3.9 Hz, 2H), 3.75 (q, J=6.5 Hz, 2H), 3.55 (s, 2H), 1.94-1.82 (m, 2H), (d, J=3.7 Hz, 9H), 0.01 (s, 6H). ESI-MS: C$_{26}$H$_{42}$N$_7$O$_4$Si (M+H): calc. 544.30, found: 544.30.

Step F: To a stirred solution of (E)-5-amino-6-((4-((2-amino-6-(3-((tert-butyldimethylsilyl)oxy)propoxy)-4-carbamoylphenyl)amino)but-2-en-1-yl)amino)nicotinamide, Compound 92 (380 mg, 0.70 mmol) in methanol (15 mL) was added cyanogen bromide (444 mg, 4.19 mmol), and the mixture was stirred at room temperature for 16 hours. The mixture was concentrated in vacuo, and the resulting residue was triturated in aqueous NaHCO$_3$ and filtered to afford (E)-2-amino-3-(4-(2-amino-7-(3-((tert-butyl dim ethyl silyl)oxy)prop oxy)-5-carb amoyl-1H-benzo[d]imidazol-1-yl)but-2-en-1-yl)-3H-imidazo[4,5-b]pyridine-6-carboxamide, Compound 93 (200 mg, 48% yield) as a brown solid. $^1$H NMR (400 MHz, DMSO-d$_6$) δ 8.39 (d, J=1.9 Hz, 1H), 7.97-7.71 (m, 4H), 7.39 (s, 1H), 7.26 (s, 1H), 7.15-7.04 (m, 3H), 6.89 (d, J=5.3 Hz, 2H), 5.70 (dt, J=14.6, 5.2 Hz, 2H), 4.74 (d, J=4.9 Hz, 2H), 4.64 (s, 2H), 4.05 (q, J=6.4 Hz, 2H), 3.50 (d, J=5.7 Hz, 2H), 1.77 (d, J=6.6 Hz, 2H), 0.84 (d, J=7.8 Hz, 9H). ESI-MS: C$_{28}$H$_{40}$N9O$_4$Si (M+H): calc. 594.29, found: 594.30.

Step G: To a stirred solution of (E)-2-amino-3-(4-(2-amino-7-(3-((tert-butyldimethylsilyl)oxy)propoxy)-5-carb amoyl-1H-benzo[d]imidazol-1-yl)but-2-en-1-yl)-3H-imidazo[4,5-b]pyridine-6-carboxamide, Compound 93 (320 mg, 0.44 mmol) in DMF (10 mL) was added 1-ethyl-3-methyl-1H-pyrazole-5-carboxylic acid (81 mg, 0.53 mmol), HATU (250 mg, 0.66 mmol), and DIPEA (0.24 mL, 1.83 mmol). The mixture was heated to 70° C. and stirred for 16 hours, then concentrated in vacuo. The salts were removed by trituration in water before purification by HPLC (1% v/v TFA in ACN:H$_2$O:THF) to afford (E)-3-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxamide, Compound 94 (90 mg, 27% yield) as a white solid. $^1$H NMR (400 MHz, DMSO-d$_6$) δ 8.74-8.67 (m, 1H), 8.12 (s, 2H), 7.96 (s, 1H), 7.63 (s, 1H), 7.52 (s, 1H), 7.32 (d, J=8.1 Hz, 2H), 6.52 (d, J=12.9 Hz, 2H), 5.97-5.79 (m, 2H), 4.92 (d, J=5.1 Hz, 2H), 4.78 (d, J=5.2 Hz, 2H), 4.50 (h, J=7.1 Hz, 4H), 4.11 (t, J=6.4 Hz, 2H), 3.46 (d, J=6.0 Hz, 2H), 2.10 (s, 6H), 1.75 (t, J=6.2 Hz, 2H), 1.26 (td, J=7.1, 2.2 Hz, 6H). ESI-MS: C$_{36}$H$_{42}$N$_{13}$O$_6$ (M+H): calc. 752.33, found: 752.30.

Example 45: (E)-N-(5-carbamoyl-1-(4-(6-carbamoyl-2-(4-ethyl-2-methyloxazole-5-carboxamido)-3H-imidazo[4,5-b]pyridin-3-yl)but-2-en-1-yl)-7-(3-hydroxypropoxy)-1H-benzo[d]imidazol-2-yl)-4-ethyl-2-methyloxazole-5-carboxamide, Compound 95

Example 46: (E)-N-(7-(3-aminopropoxy)-5-carbamoyl-1-(4-(6-carbamoyl-2-(4-ethyl-2-methyloxazole-5-carboxamido)-3H-imidazo[4,5-b]pyridin-3-yl)but-2-en-1-yl)-1H-benzo[d]imidazol-2-yl)-4-ethyl-2-methyloxazole-5-carboxamide, Compound 96

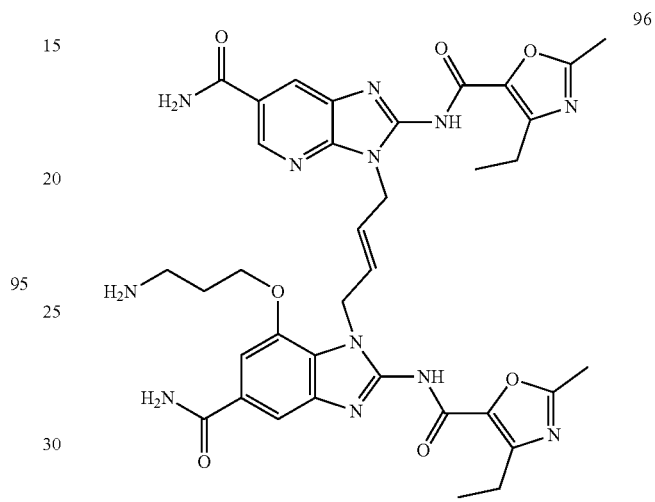

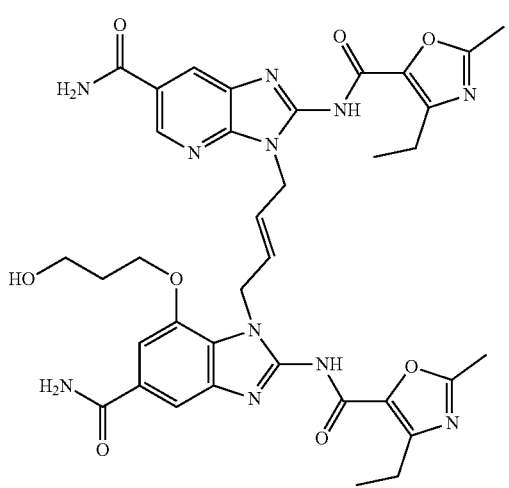

(E)-N-(5-carbamoyl-1-(4-(6-carbamoyl-2-(4-ethyl-2-methyloxazole-5-carboxamido)-3H-imidazo[4,5-b]pyridin-3-yl)but-2-en-1-yl)-7-(3-hydroxypropoxy)-1H-benzo[d]imidazol-2-yl)-4-ethyl-2-methyloxazole-5-carboxamide was prepared as described in Example 44, except ethyl-2-methyloxazole-5-carboxlyic acid was used in Step G instead of 1-ethyl-3-methyl-1h-pyrazole-5-carboxylic acid to afford (E)-N-(5-carbamoyl-1-(4-(6-carbamoyl-2-(4-ethyl-2-methyloxazole-5-carboxamido)-3H-imidazo[4,5-b]pyridin-3-yl)but-2-en-1-yl)-7-(3-hydroxypropoxy)-1H-benzo[d]imidazol-2-yl)-4-ethyl-2-methyloxazole-5-carboxamide, Compound 95 (30 mg, 15% yield) as a light brown solid. $^1$H NMR (400 MHz, DMSO-$d_6$) δ 8.69 (d, J=1.9 Hz, 1H), 8.17-8.09 (m, 2H), 7.95 (s, 1H), 7.62 (s, 1H), 7.52 (s, 1H), 7.32 (s, 2H), 5.90-5.77 (m, 2H), 4.89 (d, J=5.1 Hz, 2H), 4.75 (d, J=5.0 Hz, 2H), 4.12 (t, J=6.4 Hz, 2H), 2.79 (p, J=7.5 Hz, 4H), 2.40 (d, J=3.7 Hz, 6H), 1.75 (t, J=6.2 Hz, 2H), 0.98 (td, J=7.6, 3.0 Hz, 6H). ESI-MS: $C_{36}H_{40}N_{11}O_8$ (M+H): calc. 754.30, found: 754.25.

(E)-N-(7-(3-aminoprop oxy)-5-carbamoyl-1-(4-(6-carbamoyl-2-(4-ethyl-2-methyloxazole-ethyl-2-methyloxazole-5-carboxamide was prepared as described in Example 44, except tert-butyl (3-bromopropyl)carbamate was used for the synthesis of 3-(3-((tert-butyldimethylsilyl)oxy)propoxy)-4-chloro-5-nitrobenzamide, Compound 3 and ethyl-2-methyloxazole-5-carboxlyic acid was used in Step G instead of 1-ethyl-3-methyl-1h-pyrazole-5-carboxylic acid. The removal of the Boc group of boc-protected (E)-N-(7-(3-aminopropoxy)-5-carbamoyl-1-(4-(6-carbamoyl-2-(4-ethyl-2-methyloxazole-5-carboxamido)-3H-imidazo[4,5-b]pyridin-3-yl)but-2-en-1-yl)-1H-benzo[d]imidazol-2-yl)-4-ethyl-2-methyloxazole-5-carboxamide, Compound 96 was carried out as described in Example 10 to afford (E)-N-(7-(3-aminoprop oxy)-5-carbamoyl-1-(4-(6-carbamoyl-2-(4-ethyl-2-methyl oxazol e-5-c arb oxamido)-3H-imidazo[4,5-b]pyridin-3-yl)but-2-en-1-yl)-1H-benzo[d]imidazol-2-yl)-4-ethyl-2-methyloxazole-5-carboxamide, Compound 96 (16 mg, 69% yield) as a light brown solid. $^1$H NMR (400 MHz, DMSO-$d_6$) δ 8.69 (d, J=1.9 Hz, 1H), 8.13-8.10 (m, 1H), 7.94 (s, 1H), 7.72 (s, 2H), 7.64 (d, J=1.2 Hz, 1H), 7.54 (s, 1H), 7.34 (d, J=1.4 Hz, 1H), 5.93-5.85 (m, 1H), 5.73 (d, J=15.6 Hz, 1H), 4.90 (d, J=5.1 Hz, 2H), 4.75 (d, J=5.3 Hz, 2H), 4.17 (t, J=6.0 Hz, 2H), 2.95 (d, J=6.4 Hz, 2H), 2.77 (q, J=7.3 Hz, 4H), 2.40 (d, J=8.3 Hz, 6H), 1.97 (t, J=7.0 Hz, 2H), 0.95 (dt, J=9.6, 7.6 Hz, 6H). ESI-MS: $C_{36}H_{41}N_{12}O_7$ (M+H): calc. 753.31, found: 753.30.

Example 47: (E)-4-05-carbamoyl-1-(4-(6-carbamoyl-2-(4-ethyl-2-methyloxazole-5-carboxamido)-3H-imidazo[4,5-b]pyridin-3-yl)but-2-en-1-yl)-2-(4-ethyl-2-methyloxazole-5-carboxamido)-1H-benzo[d]imidazol-7-yl)oxy)butanoic acid, Compound 97

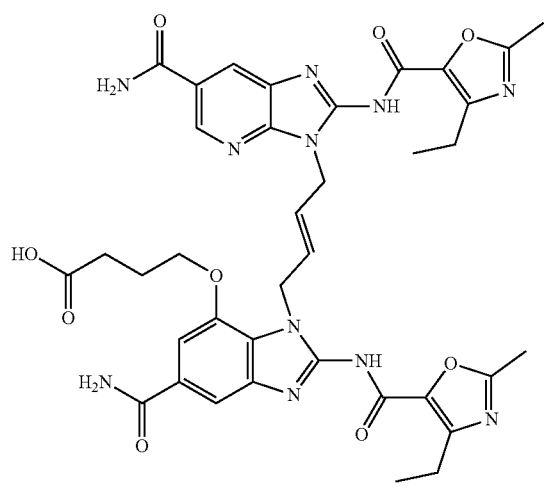

(E)-4-((5-carbamoyl-1-(4-(6-carbamoyl-2-(4-ethyl-2-methyloxazole-5-carboxamido)-3H-imidazo[4,5-b]pyridin-3-yl)but-2-en-1-yl)-2-(4-ethyl-2-methyloxazole-5-carboxamido)-1H-benzo[d]imidazol-7-yl)oxy)butanoic acid was prepared as described in Example 44, except methyl 4-bromobutanoate was used for the synthesis of 3-(3-((tert-butyldimethylsilyl)oxy)propoxy)-4-chloro-5-nitrobenzamide, Compound 3 and ethyl-2-methyloxazole-5-carboxlyic acid was used in Step G instead of 1-ethyl-3-methyl-1 h-pyrazole-5-carboxylic acid. The hydrolysis of the methyl ester of (E)-4-((5-carbamoyl-1-(4-(6-carbamoyl-2-(4-ethyl-2-methyloxazole-5-carboxamido)-3H-imidazo[4,5-b]pyridin-3-yl)but-2-en-1-yl)-2-(4-ethyl-2-methyloxazole-5-carboxamido)-1H-benzo[d]imidazol-7-yl)oxy)butanoic acid, Compound 97 was carried out as described in Example 11 to afford (E)-4-((5-carbamoyl-1-(4-(6-carbamoyl-2-(4-ethyl-2-methyloxazole-5-carboxamido)-3H-imidazo[4,5-b]pyridin-3-yl)but-2-en-1-yl)-2-(4-ethyl-2-methyloxazole-5-carboxamido)-1H-benzo[d]imidazol-7-yl)oxy)butanoic acid, Compound 97 (15 mg, 65% yield) as a light brown solid. $^1$H NMR (400 MHz, DMSO-$d_6$) δ 8.68 (d, J=1.9 Hz, 1H), 8.14-8.09 (m, 2H), 7.96 (s, 1H), 7.63 (d, J=1.3 Hz, 1H), 7.54 (s, 1H), 7.35 (t, J=3.1 Hz, 1H), 7.31 (d, J=1.4 Hz, 1H), 5.87 (dt, J=15.7, 5.2 Hz, 1H), 5.81-5.70 (m, 1H), 4.90 (d, J=5.1 Hz, 2H), 4.74 (d, J=5.3 Hz, 2H), 4.07 (t, J=6.4 Hz, 2H), 2.77 (qd, J=7.5, 3.5 Hz, 4H), 2.65 (s, 2H), 2.40 (d, J=3.6 Hz, 6H), 1.88 (p, J=6.7 Hz, 2H), 0.96 (td, J=7.5, 1.7 Hz, 6H). ESI-MS: $C_{37}H_{40}N_{11}O_9$(M+H): calc 782.29, found: 782.30.

General Procedure for Synthesis of Compound Variant IX

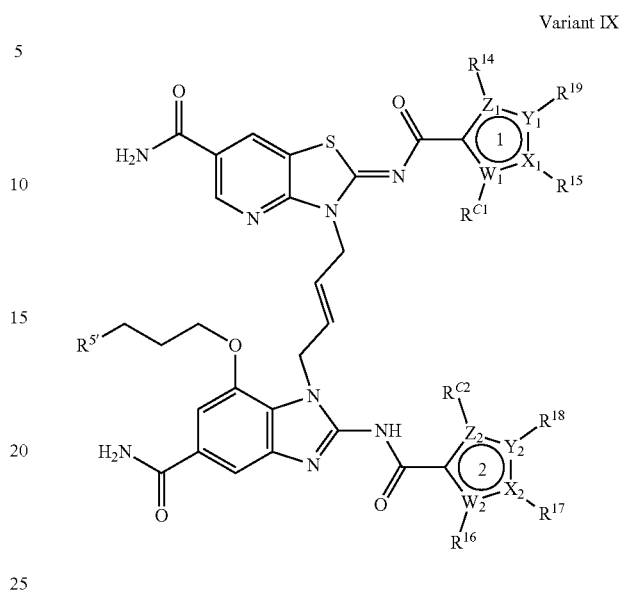

Scheme 9: The following scheme illustrates the exemplary synthesis of N-(5-carbamoyl-1-((E)-4-((Z)-6-carbamoyl-2-((4-ethyl-2-methyloxazole-5-carbonyl)imino)thiazolo[4,5-b]pyridin-3(2H)-yl)but-2-en-1-yl)-7-(3-hydroxypropoxy)-1H-benzo[d]imidazol-2-yl)-4-ethyl-2-methyloxazole-5-carboxamide. The similar procedure may be generally used for the synthesis of Compound Variant IX. As shown below, heterocyclic structures (Rings 1 and 2) can be introduced by using the corresponding carboxylic acid at Steps E and L.

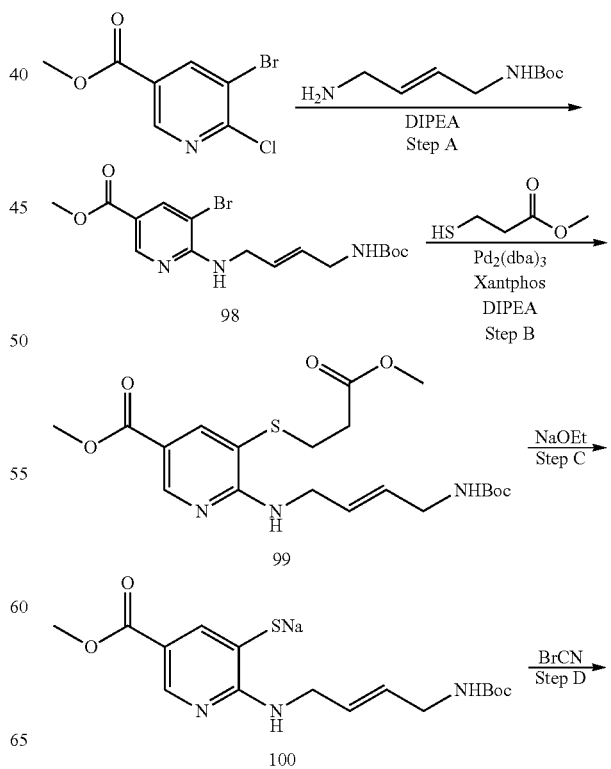

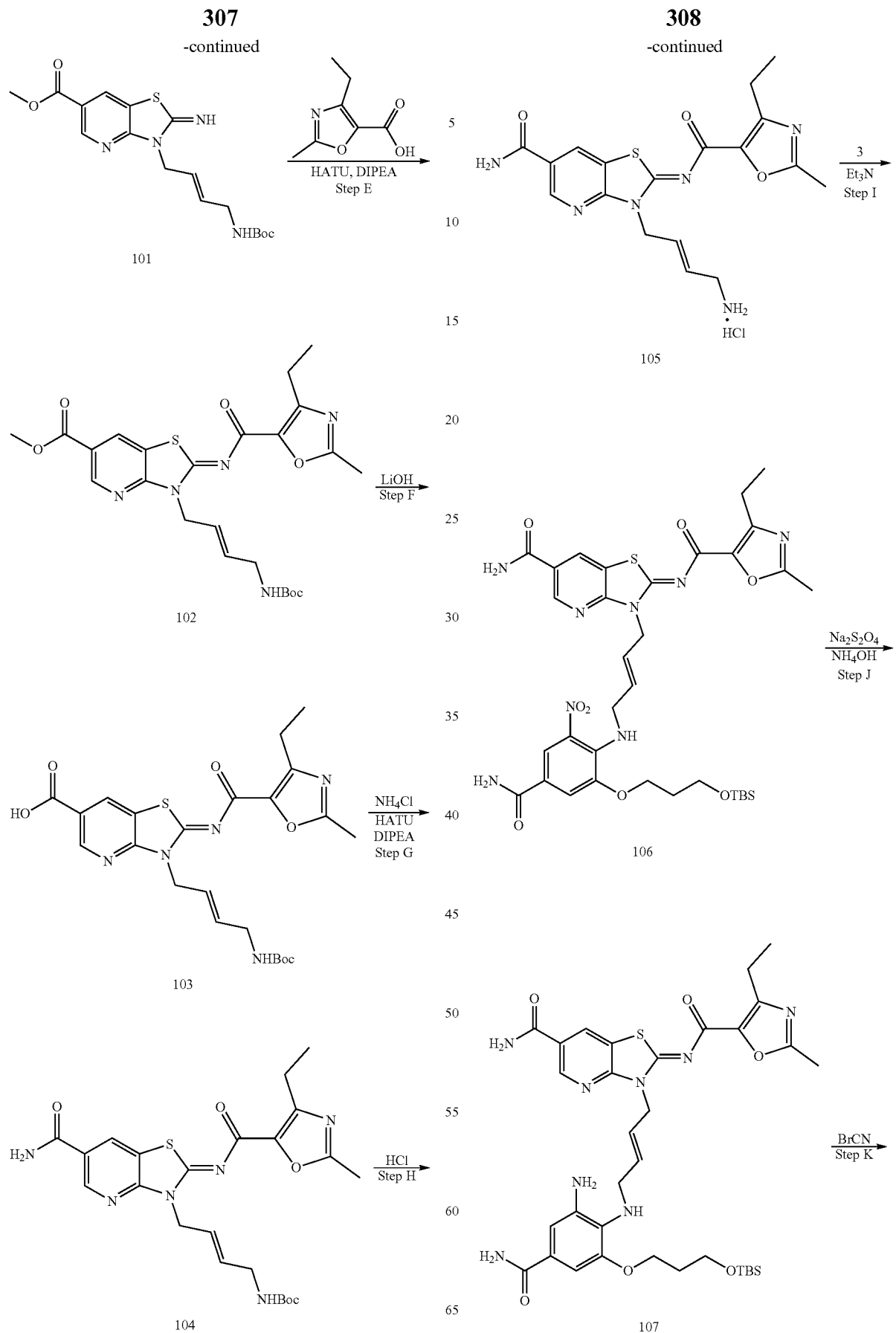

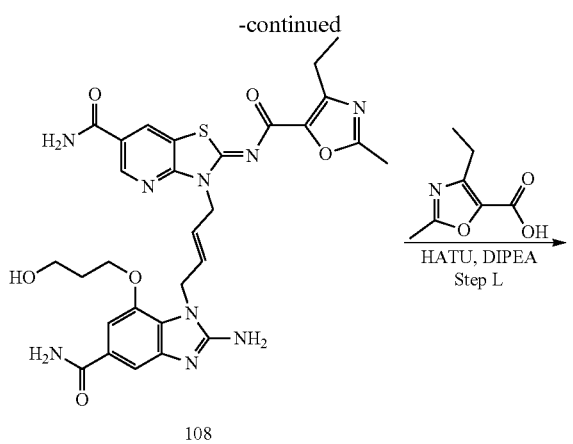

108

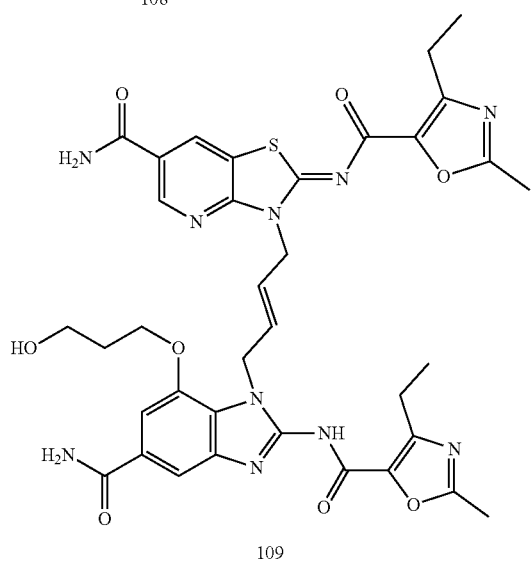

109

Example 48: N-(5-carbamoyl-1-((E)-4-((Z)-6-carbamoyl-2-((4-ethyl-2-methyloxazole-5-carbonyl)imino)thiazolo[4,5-13]pyridin-3(2H)-yl)but-2-en-1-yl)-7-(3-hydroxypropoxy)-1H-benzo[d]imidazol-2-yl)-4-ethyl-2-methyloxazole-5-carboxamide, Compound 109

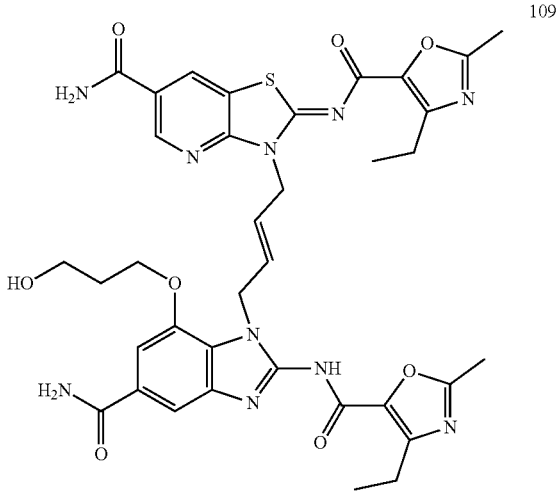 [SMILES: CCc1nc(C)oc1C(=O)/N=c1\sc2cc(C(N)=O)cnc2n1C/C=C/Cn1c(NC(=O)c2oc(C)nc2CC)nc2cc(C(N)=O)cc(OCCCO)c21]

109

Step A: To a stirred solution of methyl 5-bromo-6-chloronicotinate (10 g, 39.92 mmol) in DMSO (150 mL) was added tert-butyl (E)-(4-aminobut-2-en-1-yl)carbamate (10.66 g, 47.86 mmol) and DIPEA (20.8 mL, 160.04 mmol) at 0° C. The mixture was allowed to warm to room temperature and stirred for 48 hours. The mixture was quenched with ice water and stirred for 10 minutes, then extracted with EtOAc. The combined organic layers were dried over $Na_2SO_4$ and concentrated in vacuo. The residue was purified over silica gel (hexane:EtOAc 70:30 v/v) to afford methyl (E)-5-bromo-6-((4-((tert-butoxycarbonyl)amino)but-2-en-1-yl)amino)nicotinate, Compound 98 (6.0 g, 38% yield) as a yellow oil. $^1$H NMR (400 MHz, DMSO-$d_6$) δ 8.56 (d, J=2.0 Hz, 1H), 8.09 (d, J=2.0 Hz, 1H), 7.32 (t, J=5.9 Hz, 1H), 6.92 (s, 1H), 5.65-5.45 (m, 2H), 4.01 (d, J=7.1 Hz, 2H), 3.78 (s, 3H), 3.49 (d, J=5.8 Hz, 2H), 1.35 (s, 9H). ESI-MS: $C_{16}H_{23}BrN_3O_4$ (M+H): calc. 400.08, found: 400.10.

Step B: To a stirred solution of methyl (E)-5-bromo-6-((4-((tert-butoxycarbonyl)amino)but-2-en-1-yl)amino)nicotinate, Compound 98 (3.2 g, 7.99 mmol), methyl 3-mercaptopropanoate (2.67 mL, 23.98 mmol) and DIPEA (2.79 mL) in dioxane (40 mL) was added Xantphos (462 mg, 0.80 mmol) followed by tris(dibenzylideneacetone)dipalladium (O) $Pd_2(dba)_3$ (366 mg, 0.40 mmol). The mixture was heated to 110° C. and stirred for 16 hours, then quenched with water and extracted with EtOAc. The combined organic layers were dried over $Na_2SO_4$ and concentrated in vacuo. The residue was purified over silica gel (hexane:EtOAc 1:1 v/v) to afford methyl (E)-6-((4-((tert-butoxycarbonyl)amino)but-2-en-1-yl)amino)-5-((3-methoxy-3-oxopropyl)thio)nicotinate, Compound 99 (3.0 g, 85% yield) as an orange oil. $^1$H NMR (400 MHz, DMSO-$d_6$) δ 8.51 (d, J=2.2 Hz, 1H), 7.90 (d, J=2.2 Hz, 1H), 7.28 (t, J=5.9 Hz, 1H), 6.90 (t, J=5.9 Hz, 1H), 5.63-5.40 (m, 2H), 4.05-3.96 (m, 2H), 3.74 (s, 3H), 3.53 (s, 3H), 3.46 (t, J=5.7 Hz, 2H), 2.93 (t, J=6.9 Hz, 2H), 2.53 (t, J=6.9 Hz, 2H), 1.31 (s, 9H). ESI-MS: $C_{20}H_{30}N_3O_6S$ (M+H): calc. 440.18, found: 440.20.

Step C: To a stirred solution of methyl (E)-6-((4-((tert-butoxycarbonyl)amino)but-2-en-1-yl)amino)-5-((3-methoxy-3-oxopropyl)thio)nicotinate, Compound 99 (3.0 g, 6.83 mmol) in THF (40 mL) was added NaOEt (21% in EtOH, 2.4 mL, 7.51 mmol), and the mixture was stirred at room temperature for 1 hour. The mixture was diluted in DCM, and the resulting solid was filtered and washed with DCM to afford sodium (E)-2-((4-((tert-butoxycarbonyl)amino)but-2-en-1-yl)amino)-5-(methoxycarbonyl)pyridine-3-thiolate, Compound 100 (1.9 g, 74% yield) as a white solid. $^1$H NMR (400 MHz, DMSO-$d_6$) δ 7.93 (d, J=2.2 Hz, 1H), 7.54 (d, J=2.2 Hz, 1H), 7.38 (t, J=6.0 Hz, 1H), 6.98 (t, J=5.8 Hz, 1H), 5.60 (qt, J=15.5, 5.3 Hz, 2H), 4.01-3.93 (m, 2H), 3.53 (t, J=5.8 Hz, 2H), 1.37 (s, 9H). ESI-MS: $C_{16}H_{22}N_3O^4S$ (M-H): 352.14, found: 352.10.

Step D: To a stirred solution of sodium (E)-2-((4-((tert-butoxycarbonyl)amino)but-2-en-1-yl)amino)-5-(methoxycarbonyl)pyridine-3-thiolate, Compound 100 (1.9 g, 5.06 mmol) in MeOH (50 mL) at 0° C. was added BrCN (0.91 g, 8.60 mmol). The mixture was warmed to room temperature and stirred for 16 hours. The resulting solid was filtered and washed with MeOH to afford methyl (E)-3-(4-((tert-butoxycarbonyl)amino)but-2-en-1-yl)-2-imino-2,3-dihydrothiazolo[4,5-b]pyridine-6-carboxylate, Compound 101 (1.6 g, 84% yield) as a yellow solid. $^1$H NMR (400 MHz, DMSO-$d_6$) δ 10.65 (s, 1H), 8.95-8.78 (m, 2H), 6.91 (q, J=6.1 Hz, 1H), 5.72-5.53 (m, 2H), 4.83 (d, J=5.3 Hz, 2H), 3.85 (d, J=11.7 Hz, 3H), 3.52-3.42 (m, 2H), 1.29 (s, 9H). ESI-MS: $C_{17}H_{23}N_4O_4S$ (M+H): calc. 379.14, found: 379.10.

Step E: To a stirred solution of methyl (E)-3-(4-((tert-butoxycarbonyl)amino)but-2-en-1-yl)-2-imino-2,3-dihydrothiazolo[4,5-b]pyridine-6-carboxylate, Compound 101 (1.60 g, 4.23 mmol) and 4-ethyl-2-methyloxazole-5-carboxylic acid (0.98 g, 6.34 mmol) in DMF (20 mL) was added DIPEA (3.69 mL, 21.14 mmol) followed by HATU (3.21 g, 8.46 mmol). The mixture was stirred at room temperature for 6 hours, then it was diluted in water and stirred for 5 minutes. The resulting solid was filtered and dried to afford methyl (Z)-3-((E)-4-((tert-butoxycarbonyl)amino)but-2-en-1-yl)-24(4-ethyl-2-methyloxazole-5-carbonyl)imino)-2,3-dihydrothiazolo[4,5-b]pyridine-6-carboxylate, Compound 102 (560 mg, 25% yield) as a white solid. $^1$H NMR (400 MHz, DMSO-$d_6$) δ 9.01-8.79 (m, 2H), 6.89 (t, J=6.0 Hz, 1H), 5.68 (qt, J=16.1, 5.4 Hz, 2H), 5.01 (d, J=5.5 Hz, 2H), 3.87 (s, 3H), 3.46 (t, J=5.5 Hz, 2H), 3.31 (s, 3H), 2.98 (q, J=7.5 Hz, 2H), 1.26 (s, 8H), 1.18 (t, J=7.5 Hz, 3H). ESI-MS: $C_{24}H_{30}N_5O_6S$ (M+H): calc. 516.18, found: 516.20.

Step F: To a stirred solution of methyl (Z)-34(E)-4-((tert-butoxycarbonyl)amino)but-2-en-1-yl)-2-((4-ethyl-2-methyloxazole-5-carbonyl)imino)-2,3-dihydrothiazolo[4,5-b]pyridine-6-carboxylate, Compound 102 (560 mg, 1.09 mmol) in MeOH:THF:Water (2:2:1 v/v/v, 50 mL) was added LiOH·H$_2$O (91 mg, 2.17 mmol). The mixture was stirred at room temperature for 4 hours, then concentrated to remove the organic solvents. The residue was neutralized to pH<7 with aqueous HCl, and the resulting solid was filtered and dried to afford (Z)-34E)-4-((tert-butoxycarbonyl)amino)but-2-en-1-yl)-2-((4-ethyl-2-methyloxazole-5-carbonyl)imino)-2,3-dihydrothiazolo[4,5-b]pyridine-6-carboxylic acid, Compound 103 (450 mg, 82% yield) as a white solid. $^1$H NMR (400 MHz, DMSO-$d_6$) δ 8.99 (d, J=1.9 Hz, 1H), 8.88 (d, J=1.9 Hz, 1H), 6.92 (t, J=5.9 Hz, 1H), 5.70 (pt, J=19.9, 5.0 Hz, 2H), 5.06 (d, J=5.5 Hz, 2H), 3.50 (t, J=5.5 Hz, 2H), 3.03 (q, J=7.5 Hz, 2H), 2.34 (s, 3H), 1.30 (s, 9H), 1.23 (t, J=7.5 Hz, 3H). ESI-MS: $C_{23}H_{28}N_5O_6S$ (M+H): calc. 502.17, found: 502.20.

Step G: To a stirred solution of (Z)-3-((E)-4-((tert-butoxycarbonyl)amino)but-2-en-1-yl)-2-((4-ethyl-2-methyloxazole-5-carbonyl)imino)-2,3-dihydrothiazolo[4,5-b]pyridine-6-carboxylic acid, Compound 103 (450 mg, 0.90 mmol) in DMF (10 mL) was added DIPEA (0.39 mL, 2.24 mmol), HATU (614 mg, 1.61 mmol), and NH$_4$Cl (145 mg, 2.69 mmol). The mixture was stirred at room temperature for 6 hours, then diluted in water and stirred for 10 minutes. The resulting solid was filtered and dried to afford tert-butyl ((E)-4-((Z)-6-carbamoyl-2-((4-ethyl-2-methyloxazole-5-carbonyl)imino)thiazolo[4,5-b]pyridin-3(2H)-yl)but-2-en-1-yl)carbamate, Compound 104 (390 mg, 87% yield) as a white solid. $^1$H NMR (400 MHz, DMSO-$d_6$) δ 8.92 (d, J=2.0 Hz, 1H), 8.73 (d, J=2.0 Hz, 1H), 8.16 (s, 1H), 7.62 (s, 1H), 6.89 (t, J=5.8 Hz, 1H), 5.79-5.57 (m, 2H), 5.01 (d, J=5.5 Hz, 2H), 3.46 (t, J=5.3 Hz, 2H), 2.99 (q, J=7.5 Hz, 2H), 2.45 (s, 3H), 1.26 (s, 9H), 1.19 (t, J=7.5 Hz, 3H). ESI-MS: $C_{23}H_{29}N_6O_5S$ (M+H): calc. 501.18, found: 501.20.

Step H: A mixture of afford tert-butyl ((E)-4-((Z)-6-carbamoyl-2-((4-ethyl-2-methyloxazole-5-carbonyl)imino)thiazolo[4,5-b]pyridin-3(2H)-yl)but-2-en-1-yl)carbamate, Compound 104 (390 mg, 0.86 mmol) and HCl (4M in dioxane, 6 mL, 6 mmol) was stirred at room temperature for 6 hours. The mixture was concentrated in vacuo to afford (E)-4-((Z)-6-carbamoyl-244-ethyl-2-methyl oxazol e-5-carb onyl)imino)thiazolo[4, 5-b]pyri din-3 (2H)-yl)but-2-en-1-aminium chloride, Compound 105 (390 mg, 100% yield) as a brown solid. $^1$H NMR (400 MHz, DMSO-$d_6$) δ 9.00 (d, J=2.1 Hz, 1H), 8.82 (d, J=1.9 Hz, 1H), 8.29 (s, 1H), 8.04 (s, 2H), 7.66 (s, 1H), 6.12-6.06 (m, 1H), 5.74-5.69 (m, 1H), 5.11 (d, J=5.6 Hz, 2H), 3.41 (dd, J=10.5, 4.9 Hz, 2H), 3.02 (t, J=7.5 Hz, 2H), 1.24 (t, J=7.5 Hz, 3H). ESI-MS: $C_{18}H_{21}N_6O_3S$ (M+H): calc. 401.13, found: 401.20.

Step I: To a stirred solution of (E)-4-((Z)-6-carbamoyl-2-((4-ethyl-2-methyloxazole-5-carbonyl)imino)thiazolo[4,5-b]pyridin-3(2H)-yl)but-2-en-1-aminium chloride, Compound 105 (390 mg, 0.89 mmol) in DMF (10 mL) was added Et$_3$N (0.63 mL, 4.46 mmol), and the mixture was stirred for 5 minutes. 3-(3-((tert-butyldimethylsilyl)oxy)propoxy)-4-chloro-5-nitrobenzamide, Compound 3 (prepared as described in Example 1, 432 mg, 1.16 mmol) was added, and the mixture was stirred at room temperature for 16 hours, then poured over water and stirred for 5 minutes. The resulting solid was filtered and purified over silica gel (DCM:MeOH 20:1 v/v) to afford N-((Z)-3-((E)-4-((2-(3-((tert-butyl dim ethyl silyl)oxy)prop oxy)-4-carbamoyl-6-nitrophenyl)amino)but-2-en-1-yl)-6-carbamoylthiazolo[4,5-b]pyridin-2(3H)-ylidene)-4-ethyl-2-methyloxazole-5-carboxamide, Compound 106 (350 mg, 52% yield) as a yellow solid. $^1$H NMR (400 MHz, DMSO-$d_6$) δ 8.89 (d, J=2.0 Hz, 1H), 8.71 (d, J=2.0 Hz, 1H), 8.14 (s, 1H), 8.01 (d, J=1.9 Hz, 1H), 7.90 (s, 1H), 7.63 (dd, J=12.3, 6.0 Hz, 2H), 7.39 (d, J=2.0 Hz, 1H), 7.25 (s, 1H), −5.66 (m, 2H), 4.98 (d, J=4.8 Hz, 2H), 4.07 (dt, J=5.2, 2.3 Hz, 2H), 3.93 (t, J=6.0 Hz, 2H), 3.58 (t, J=6.1 Hz, 2H), 2.87 (q, J=7.5 Hz, 2H), 2.43 (s, 3H), 1.76 (q, J=6.1 Hz, 2H), 1.10 (t, J=7.6 Hz, 3H), 0.75 (s, 9H), −0.09 (s, 6H). ESI-MS: $C_{34}H_{45}N_8O_8SSi$ (M+H): calc. 753.28, found: 753.20.

Step J: To a stirred solution of N-((Z)-3-((E)-4-((2-(3-((tert-butyldimethyl silyl)oxy)propoxy)-4-carb amoyl-6-nitrophenyl)amino)but-2-en-1-yl)-6-carbamoylthiazolo[4,5-b]pyridin-2(3H)-ylidene)-4-ethyl-2-methyloxazole-5-carboxamide, Compound 106 (350 mg, 0.46 mmol) in MeOH (20 mL) at 0° C. was added Na$_2$S$_2$O$_4$ (960 mg, 4.65 mmol) in water (10 mL) followed by NH$_4$OH (25% aqueous solution, 1.64 mL, 11.62 mmol). The mixture was stirred at room temperature for 4 hours, then diluted in water and extracted with EtOAc. The combined organic layers were dried over Na$_2$SO$_4$ and concentrated in vacuo to afford N-((Z)-3-((E)-4-((2-amino-6-(3-((tert-butyl dim ethyl silyl)oxy)prop oxy)-4-carb amoylphenyl)amino)but-2-en-1-yl)-6-carbamoylthiazolo[4, 5-b]pyridin-2(3H)-ylidene)-4-ethyl-2-methyloxazole-5-carboxamide, Compound107 (220 mg, 65% yield) as a brown solid. $^1$H NMR (400 MHz, DMSO-$d_6$) δ 8.94 (d, J=2.0 Hz, 1H), 8.76 (d, J=2.0 Hz, 1H), 8.18 (s, 1H), 7.60 (d, J=29.8 Hz, 2H), 6.94 (s, 1H), 6.80 (d, J=1.8 Hz, 1H), 6.70 (d, J=1.9 Hz, 1H), 5.92-5.77 (m, 2H), 5.04 (d, J=5.0 Hz, 2H), 4.62 (s, 2H), 3.89 (t, J=6.0 Hz, 2H), 3.62 (t, J=6.2 Hz, 2H), 2.99 (q, J=7.6 Hz, 2H), 2.48 (s, 3H), 1.75 (q, J=6.0, 4.2 Hz, 2H), 1.18 (d, J=7.7 Hz, 3H), 0.78 (s, 9H), −0.07 (s, 6H). ESI-MS: $C_{34}H_{47}N_8O_6SSi$ (M+H): calc. 723.30, found: 723.20.

Step K: To a stirred solution of N-((Z)-3-((E)-4-((2-amino-6-(3-((tert-butyldimethyl silyl)oxy)propoxy)-4-carbamoylphenyl)amino)but-2-en-1-yl)-6-carbamoylthiazolo[4,5-b]pyridin-2(3H)-ylidene)-4-ethyl-2-methyloxazole-5-carboxamide, Compound107 (220 mg, 0.30 mmol) in MeOH (8 mL) was added BrCN (55 mg, 0.52 mmol). The mixture was stirred at room temperature for 20 hours, then concentrated in vacuo to afford N-((Z)-3-((E)-4-(2-amino-5-carbamoyl-7-(3-hydroxypropoxy)-1H-benzo[d]imidazol-1-yl)but-2-en-1-yl)-6-carbamoylthiazolo[4,5-b]pyridin-2(3H)-ylidene)-4-ethyl-2-methyloxazole-5-carboxamide, Compound 108 (200 mg, 91% yield) as a white solid. $^1$H NMR (400 MHz, DMSO-$d_6$) δ 8.94 (d, J=2.0 Hz, 1H), 8.78 (d, J=2.0 Hz, 1H), 8.58 (s, 2H), 8.19 (s, 1H), 8.04 (s, 1H), 7.66 (s, 1H), 7.49-7.33 (m, 3H), 5.85 (qt, J=15.7, 5.1 Hz, 2H), 5.05 (d, J=5.1 Hz, 2H), 4.83 (d, J=5.1 Hz, 2H), 4.07 (t, J=6.4 Hz, 2H), 3.39 (d, J=6.0 Hz, 2H), 2.77 (q, J=7.5 Hz, 2H), 2.45 (s, 3H), 1.67 (p, J=6.5 Hz, 2H), 1.02 (t, J=7.5 Hz, 3H). ESI-MS: $C_{29}H_{32}N_9O_6S$ (M+H): calc. 634.21, found: 634.15.

Step L: To a stirred solution of N-((Z)-3-((E)-4-(2-amino-5-carbamoyl-7-(3-hydroxypropoxy)-1H-benzo[d]imidazol-1-yl)but-2-en-1-yl)-6-carbamoylthiazolo[4,5-b]pyridin-2(3H)-ylidene)-4-ethyl-2-methyloxazole-5-carboxamide, Compound 108 (200 mg, 0.28 mmol) and 4-ethyl-2-methyloxazole-5-carboxylic acid (65 mg, 0.42 mmol) in DMF was added $Et_3N$ (0.2 mL, 1.04 mmol) and benzotriazole-1-yl-oxy-tris-pyrrolidino-phosphonium hexafluorophosphate (PyBOP) (220 mg, 0.42 mmol). The mixture was stirred at room temperature for 16 hours, then poured over water and stirred for 5 minutes. The resulting solid was filtered and dried, and then stirred in $MeNH_2$ (33% in EtOH, 1 mL) to hydrolyze the undesired ester. The mixture was concentrated in vacuo, and the residue was purified by HPLC (ACN: water) to afford N-(5-carbamoyl-1-((E)-4-((Z)-6-carbamoyl-2-((4-ethyl-2-methyloxazole-5-carbonyl)imino)thiazolo[4,5-b]pyridin-3 (2H)-yl)but-2-en-1-yl)-7-(3-hydroxypropoxy)-1H-benzo[d]imidazol-2-yl)-4-ethyl-2-methyloxazole-5-carboxamide, Compound109 (45 mg, 18% yield) as a white solid. $^1H$ NMR (400 MHz, DMSO-$d_6$) δ 8.88 (d, J=2.0 Hz, 1H), 8.71 (d, J=2.0 Hz, 1H), 8.14 (s, 1H), 7.92 (s, 1H), 7.59 (d, J=12.5 Hz, 2H), 7.27 (s, 2H), 6.49 (s, 1H), 5.82 (dd, J=21.6, 16.6 Hz, 2H), 4.99 (s, 2H), 4.86 (s, 2H), 4.05 (d, J=6.7 Hz, 1H), 2.81-2.71 (m, 6H), 1.74-1.64 (m, 2H), 0.94 (td, J=7.6, 3.6 Hz, 6H). ESI-MS: $C_{36}H_{39}N_{10}O_8S$ (M+H): calc. 771.26, found: 771.29.

Example 49: (Z)-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-((1-ethyl-3-methyl-1H-pyrazole-5-carbonyl)imino)-2,3-dihydrothiazolo[4,5-b]pyridine-6-carboxamide, Compound 110

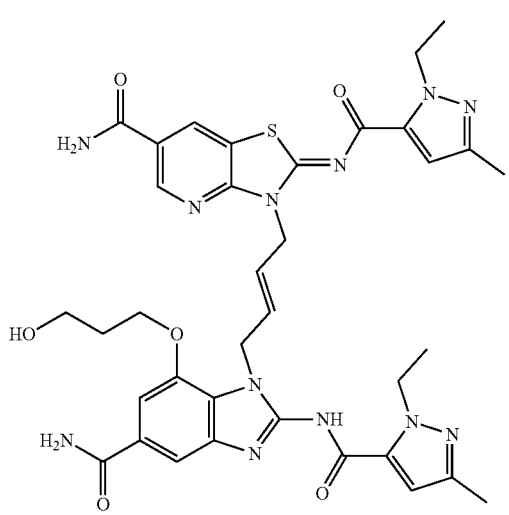

(Z)-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-((1-ethyl-3-methyl-1H-pyrazole-5-carbonyl)imino)-2,3-dihydrothiazolo[4,5-b]pyridine-6-carboxamide, Compound 110 was prepared as described in Example 48, except 1-ethyl-3-methyl-1H-pyrazole-5-carboxylic acid was used in steps E and L instead of 4-ethyl-2-methyloxazole-5-carboxylic acid to afford (Z)-3-((E)-4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-((1-ethyl-3-methyl-1H-pyrazole-5-carbonyl)imino)-2,3-dihydrothiazolo[4,5-b]pyridine-6-carboxamide, Compound 110 (13 mg, 5% yield) as a white solid. $^1H$ NMR (400 MHz, DMSO-$d_6$) δ 8.92 (s, 1H), 8.75 (s, 1H), 8.17 (s, 1H), 7.96 (s, 1H), 7.62 (d, J=8.2 Hz, 2H), 7.31 (s, 2H), 6.62 (s, 1H), 6.48 (s, 1H), 5.98 (dt, J=15.8, 5.6 Hz, 1H), 5.91-5.79 (m, 1H), 5.07 (d, J=5.6 Hz, 2H), 4.92 (d, J=5.4 Hz, 2H), 4.49 (dt, J=14.2, 7.1 Hz, 4H), 4.08 (t, J=6.3 Hz, 2H), 2.10 (d, J=5.8 Hz, 6H), 1.72 (p, J=6.3 Hz, 2H), 1.33-1.23 (m, 6H). ESI-MS: $C_{36}H_{41}N_{12}O_6S$ (M+H): calc. 769.29, found: 769.32.

General Procedure for Synthesis of Compound Variant X

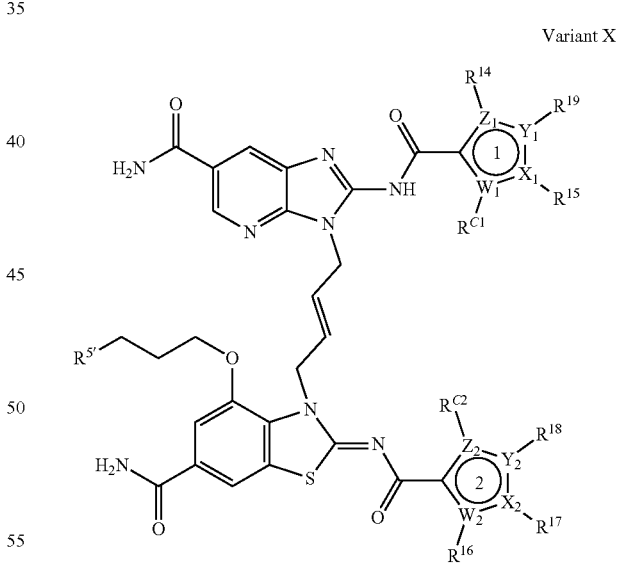

Variant X

Scheme 10: The following scheme illustrates the exemplary synthesis of N-(6-carbamoyl-3-((E)-4-((Z)-6-carbamoyl-2-((4-ethyl-2-methyloxazole-5-carbonyl)imino)-4-(3-hydroxypropoxy)benzo[d]thiazol-3 (2H)-yl)but-2-en-1-yl)-3H-imidazo[4,5-b]pyridin-2-yl)-4-ethyl-2-methyloxazole-5-carboxamide The similar procedure may be generally used for the synthesis of Compound Variant X. As shown below, heterocyclic structures (rings 1 and 2) can be introduced by using the corresponding carboxylic acid at Step G and the corresponding isothiocyanate at Step L.

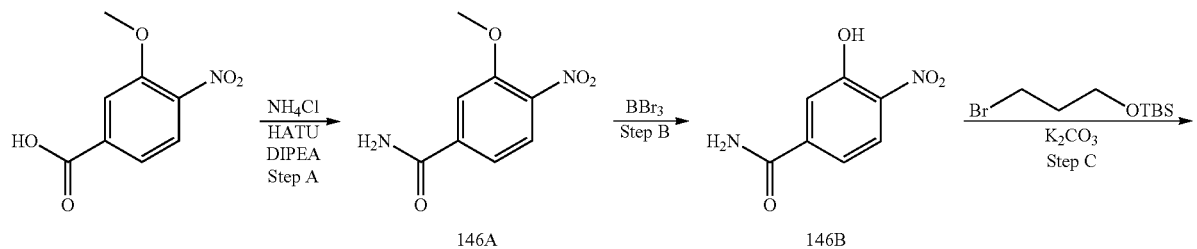
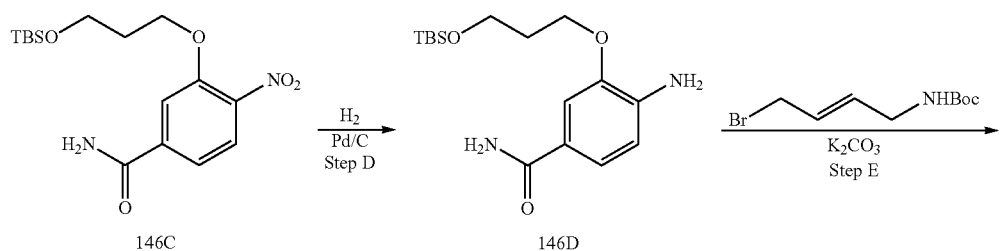
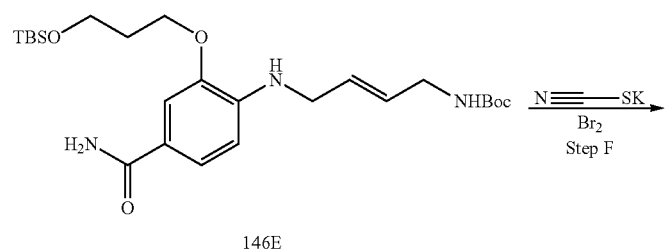
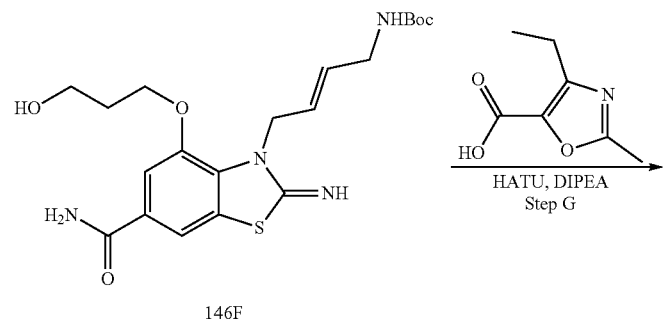
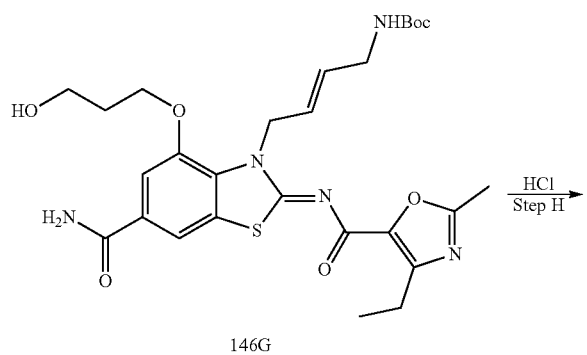

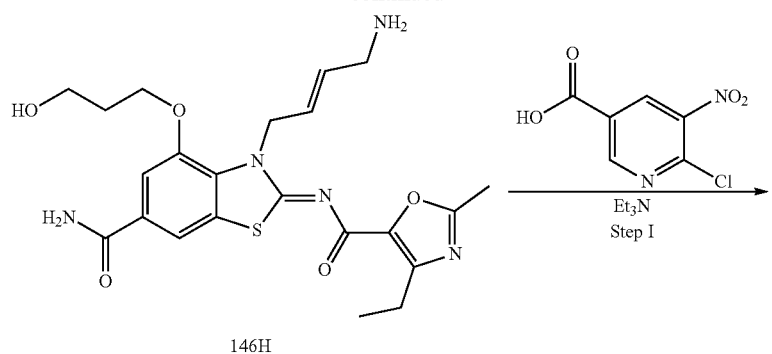
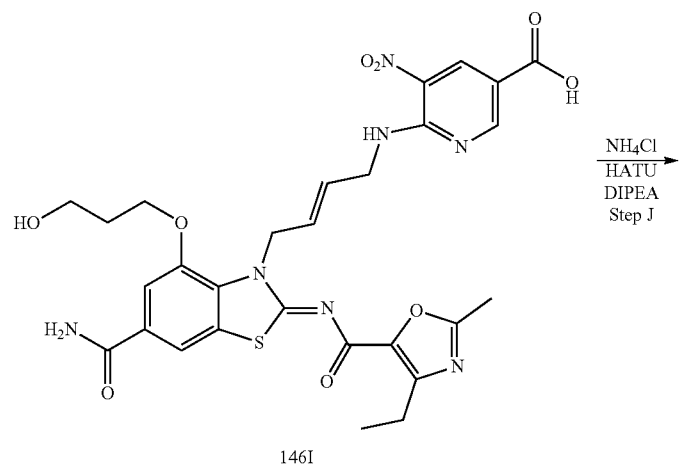
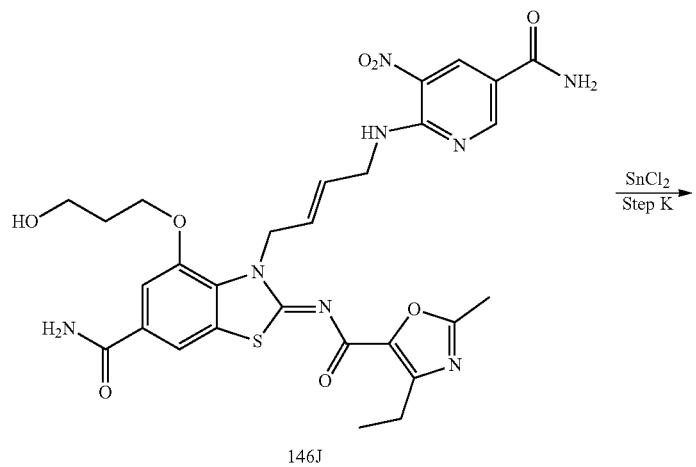

-continued
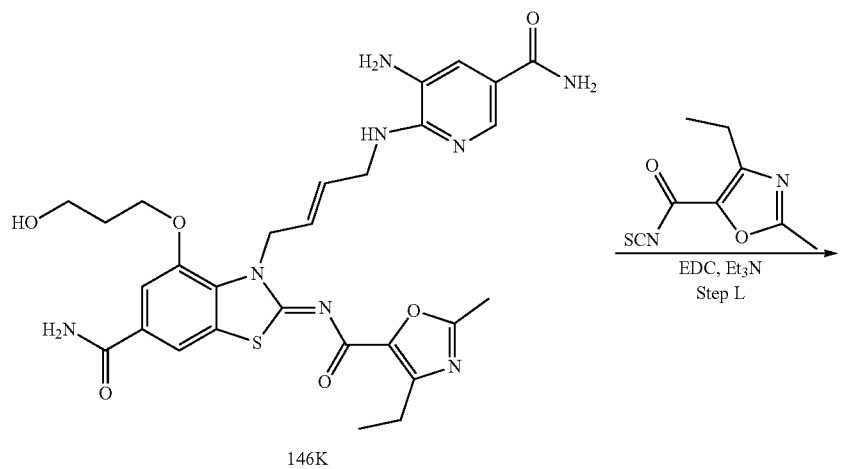
146K
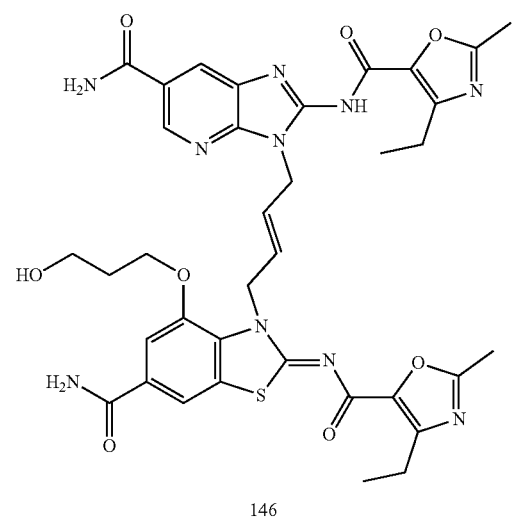
146

Example 50: N-(6-carbamoyl-3-((E)-4-((Z)-6-carbamoyl-2-((4-ethyl-2-methyloxazole-5-carbonyl)imino)-4-(3-hydroxypropoxy)benzo[d]thiazol-3(2H)-yl)but-2-en-1-yl)-3H-imidazo[4,5-b]pyridin-2-yl)-4-ethyl-2-methyloxazole-5-carboxamide, Compound 146

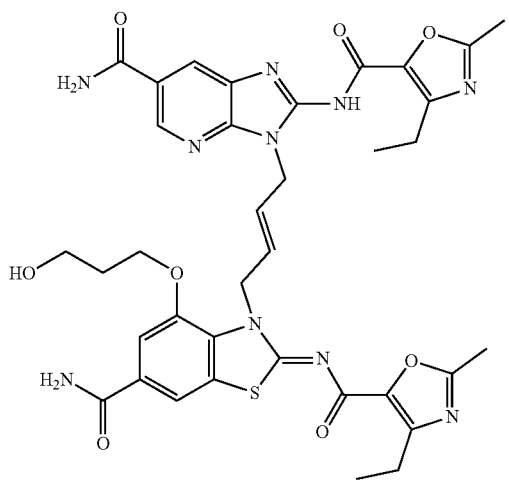

Step A: To a stirred solution of 3-methoxy-4-nitrobenzoic acid (30 g, 152.3 mmol) in DMF (300 mL) at 0° C. was added HATU (86.8 g, 228.4 mmol) and DIPEA (80 mL, 456.8 mmol), and the mixture was stirred for 10 minutes. Then, NH$_4$Cl (24.4 g, 456.8 mmol) was added, and the mixture was warmed to room temperature and stirred for 3 hours. The mixture was poured over ice water, and the resulting precipitate was filtered and dried to afford 3-methoxy-4-nitrobenzamide, Compound 146A (25.0 g, 83% yield) as a white solid. $^1$H NMR (400 MHz, DMSO-d$_6$) δ 8.23 (s, 1H), 7.94 (d, J=8.3 Hz, 1H), 7.75 (d, J=1.7 Hz, 1H), 7.70 (s, 1H), 7.57 (dd, J=8.4, 1.7 Hz, 1H), 3.98 (s, 3H). ESI-MS: C$_8$H$_9$N$_2$O$_4$(M+H): calc. 197.05, found: 197.05. ESI-MS: C$_8$H$_9$N$_2$O$_4$(M+H): calc. 197.05, found: 197.05.

Step B: To a stirred solution of 3-methoxy-4-nitrobenzamide, Compound 146A (15 g, 75.6 mmol) in DCM (150 mL) under nitrogen at 0° C. was added BBr$_3$ (1M in DCM, 383 mL, 382.6 mmol), and the mixture was allowed to warm to room temperature and stirred for 16 hours. The mixture was then poured over ice water, and the resulting precipitate was filtered and dried to afford 3-hydroxy-4-nitrobenzamide, Compound 146B (8 g, 56% yield) as a yellow solid. $^1$H NMR (400 MHz, DMSO-d$_6$) δ 11.16 (s, 1H), 8.11 (s, 1H), 7.89 (d, J=8.6 Hz, 1H), 7.59 (s, 1H), 7.52 (d, J=1.7 Hz, 1H), 7.36 (dd, J=8.5, 1.8 Hz, 1H). ESI-MS: C$_7$H$_7$N$_2$O$_4$ (M+H): calc. 183.03, found: 183.05.

Step C: To a stirred solution of 3-hydroxy-4-nitrobenzamide, Compound146B (8 g, 43.9 mmol) in DMF (120 ml) was added potassium carbonate (12.14 g, 87.9 mmol) and (3-bromopropoxy)(tert-butyl)dimethylsilane (14.45 g, 57.1 mmol), and the mixture was heated to 100° C. and stirred for 2 hours. The mixture was cooled to room temperature and poured over ice water, and the resulting precipitate was filtered and dried to afford 3-(3-((tert-butyldimethylsilyl)oxy)propoxy)-4-nitrobenzamide, Compound 146C (9 g, 57% yield) as a brown solid. $^1$H NMR (400 MHz, DMSO-d$_6$) δ 8.83 (s, 1H), 8.52 (d, J=8.4 Hz, 1H), 8.31 (d, J=18.8 Hz, 2H), 8.15 (d, J=8.4 Hz, 1H), 4.85 (t, J=5.8 Hz, 2H), 4.33 (t, J=6.1 Hz, 2H), 3.93 (s, 2H), 1.42 (s, 9H), 0.58 (s, 6H). ESI-MS: C$_{16}$H$_{27}$N$_2$O$_5$Si (M+H): calc. 355.16.

Step D: To a stirred solution of 3-(3-((tert-butyldimethylsilyl)oxy)propoxy)-4-nitrobenzamide, Compound 146C (9 g, 25.4 mmol) in MeOH (100 mL) was added Pd/C (1.8 g, 20% w/w), and the mixture was stirred for 16 hours under a hydrogen atmosphere. The mixture was filtered over Celite and concentrated in vacuo to afford 4-amino-3-(3-((tert-butyldimethylsilyl)oxy)propoxy)benzamide, Compound 146D (7.5 g, 91% yield) as a yellow solid. $^1$H NMR (400 MHz, DMSO-d$_6$) δ 7.57 (s, 1H), 7.35-7.24 (m, 2H), 6.96-6.79 (m, 1H), 6.59 (d, J=8.1 Hz, 1H), 5.20 (s, 2H), 4.03 (t, J=6.1 Hz, 2H), 3.79 (t, J=6.1 Hz, 2H), 1.92 (p, J=6.2 Hz, 2H), 0.86 (s, 9H). ESI-MS: C$_{16}$H$_{29}$N$_2$O$_3$Si (M+H): calc. 325.19, found: 325.20.

Step E: To a stirred solution of 4-amino-3-(3-((tert-butyldimethylsilyl)oxy)propoxy)benzamide, Compound 146D (7.5 g, 23.1 mmol) in DMF (110 mL) was added potassium carbonate (7.79 g, 34.7 mmol) and tert-butyl (E)-(4-bromobut-2-en-1-yl)carbamate (6.36 g, 25.4 mmol), and the mixture was heated to 100° C. and stirred for 16 hours. The mixture was cooled to room temperature and poured over ice water, and the resulting precipitate was filtered and dried. Purification over silica gel (DCM:MeOH 20:1 v/v) afforded tert-butyl (E)-(4-((2-(3-((tert-butyldimethylsilyl)oxy)propoxy)-4-carbamoylphenyl)amino)but-2-en-1-yl)carbamate, Compound 146E (7 g, 61% yield) as a white solid. $^1$H NMR (400 MHz, DMSO-d$_6$) δ 5.56-5.38 (m, 2H), 3.99 (dt, J=9.5, 6.0 Hz, 2H), 3.76 (t, J=6.0 Hz, 2H), 3.47 (d, J=6.1 Hz, 1H), 1.89 (h, J=6.2 Hz, 2H), 1.36-1.31 (m, 6H), 1.26-1.15 (m, 2H), 0.81 (d, J=1.6 Hz, 9H). ESI-MS: C$_{25}$H$_{44}$N$_3$O$_5$Si (M+H): calc. 494.30, found: 494.30.

Step F: To a stirred solution of tert-butyl (E)-(4-((2-(3-((tert-butyldimethylsilyl)oxy)propoxy)-4-carbamoylphenyl)amino)but-2-en-1-yl)carbamate, Compound 146E (7 g, 14.2 mmol) in acetic acid (70 mL) at 0° C. was added potassium thiocyanate (5.51 g, 56.8 mmol), and the mixture was stirred for 20 minutes. Then, Br$_2$ (2.49 g, 15.6 mmol) dissolved in acetic acid (25 mL) was added dropwise, and the mixture was allowed to warm to room temperature and stirred for 16 hours. The mixture was poured over ice water and solids removed by filtration. The filtrate was extracted with EtOAc and the organic layer discarded. The aqueous layer was basified with aqueous ammonia and extracted with EtOAc, and the combined organic layers were dried over Na$_2$SO$_4$ and concentrated in vacuo to afford tert-butyl (E)-(4-(6-carbamoyl-4-(3-hydroxypropoxy)-2-iminobenzo[d]thiazol-3(2H)-yl)but-2-en-1-yl)carbamate, Compound 146F (3 g, 29% yield) as a white solid. $^1$H NMR (400 MHz, DMSO-d$_6$) δ 7.83 (s, 1H), 7.49 (d, J=1.5 Hz, 1H), 7.37 (d, J=1.6 Hz, 1H), 7.23 (s, 1H), 6.89 (t, J=6.0 Hz, 1H), 5.65-5.53 (m, 1H), 5.44 (ddt, J=15.7, 10.7, 5.4 Hz, 1H), 4.76 (d, J=5.4 Hz, 2H), 4.13-4.06 (m, 3H), 3.55 (dd, J=6.5, 4.9 Hz, 2H), 3.44 (t, J=5.4 Hz, 2H), 1.91-1.84 (m, 2H), 1.30 (s, 9H). ESI-MS: C$_{20}$H$_{29}$N$_4$O$_5$S (M+H): calc. 437.18, found: 437.10.

Step G: To a stirred solution of tert-butyl (E)-(4-(6-carbamoyl-4-(3-hydroxypropoxy)-2-iminobenzo[d]thiazol-3(2H)-yl)but-2-en-1-yl)carbamate, Compound 146F (6 g, 13.8 mmol) and 4-ethyl-2-methyloxazole-5-carboxylic acid (2.56 g, 16.5 mmol) in DMF (60 mL) was added DIPEA (12 mL, 68.8 mmol) and HATU (7.84 g, 20.6 mmol) and the mixture was stirred at room temperature for 3 hours. The mixture was poured over ice water, and the resulting solid was filtered and dried. Purification over silica gel (DCM: MeOH 20:1 v/v) afforded tert-butyl ((E)-4-((Z)-6-carbamoyl-2-((4-ethyl-2-methyloxazole-5-carbonyl)imino)-4-(3-hydroxypropoxy)benzo[d]thiazol-3(2H)-yl)but-2-en-1-yl)carbamate, Compound 146G (4 g, 50% yield) as a white solid. $^1$H NMR (400 MHz, DMSO-$d_6$) δ 8.10 (s, 1H), 7.99 (s, 1H), 7.61 (s, 1H), 7.49 (s, 1H), 6.92 (t, J=5.9 Hz, 1H), 5.78 (dt, J=15.7, 5.8 Hz, 1H), 5.57 (dt, J=15.7, 5.4 Hz, 1H), 5.34 (d, J=5.6 Hz, 2H), 4.27 (t, J=6.3 Hz, 2H), 3.63 (q, J=5.8 Hz, 2H), 3.50 (d, J=11.4 Hz, 2H), 3.00 (q, J=7.5 Hz, 2H), 2.47 (s, 4H), 2.00 (p, J=6.2 Hz, 2H), 1.31 (s, 9H), 1.21 (t, J=7.5 Hz, 4H). ESI-MS: $C_{27}H_{36}N_5O_7S$ (M+H): calc. 574.23, found: 574.25.

Step H: tert-butyl ((E)-4-((Z)-6-carbamoyl-2-((4-ethyl-2-methyloxazole-5-carbonyl)imino)-4-(3-hydroxypropoxy)benzo[d]thiazol-3(2H)-yl)but-2-en-1-yl)carbamate, Compound 146G (350 mg, 0.610 mmol) was stirred in HCl (4M in dioxane, 10 mL) at 30° C. for 1 hour. The mixture was concentrated in vacuo to afford N-((Z)-3-((E)-4-aminobut-2-en-1-yl)-6-carbamoyl-4-(3-hydroxypropoxy)benzo[d]thiazol-2(3H)-ylidene)-4-ethyl-2-methyloxazole-5-carboxamide, Compound 146H (311 mg, 100% yield) as a white solid. $^1$H NMR (400 MHz, DMSO-$d_6$) δ 8.12 (s, 1H), 8.06-7.91 (m, 3H), 7.67-7.59 (m, 1H), 7.46 (s, 1H), 6.06 (dt, J=5.3 Hz, 1H), 5.56 (dd, J=14.5, 7.3 Hz, 1H), 5.36 (d, J=5.3 Hz, 2H), 4.25 (t, J=6.4 Hz, 2H), 3.59 (t, J=6.1 Hz, 2H), 3.43-3.31 (m, 2H), 2.96 (q, J=7.6 Hz, 2H), 2.44 (s, 3H), 1.98 (p, J=6.4 Hz, 2H), 1.18 (t, J=7.4 Hz, 3H). ESI-MS: $C_{22}H_{28}N_5O_5S$ (M+H): calc. 474.17, found: 474.20.

Step I: To a stirred solution of 6-chloro-5-nitronicotinic acid (115 mg, 0.569 mmol) in ACN (10 mL) was added N-((Z)-3-((E)-4-aminobut-2-en-1-yl)-6-carbamoyl-4-(3-hydroxypropoxy)benzo[d]thiazol-2(3H)-ylidene)-4-ethyl-2-methyloxazole-5-carboxamide, Compound 146H (347 mg, 0.682 mmol) and Et$_3$N (0.40 mL, 2.85 mmol), and the mixture was heated to 100° C. and stirred for 16 hours. The mixture was cooled to room temperature, and the resulting solid was filtered and washed with ACN to afford 6-(((E)-4-((Z)-6-carbamoyl-2-((4-ethyl-2-methyloxazole-5-carbonyl)imino)-4-(3-hydroxypropoxy)benzo[d]thiazol-3 (2H)-yl)but-2-en-1-yl)amino)-5-nitronicotinic acid, Compound 146I (200 mg, 54% yield) as a yellow solid. $^1$H NMR (400 MHz, DMSO-$d_6$) δ 8.89-8.75 (m, 2H), 8.68 (s, 1H), 8.09 (s, 1H), 7.97 (s, 1H), 7.59 (s, 1H), 7.45 (s, 1H), 5.89 (dt, J=15.8, 5.4 Hz, 1H), 5.73 (dt, J=15.7, 5.3 Hz, 1H), 5.34 (d, J=Hz, 2H), 4.21 (d, J=6.6 Hz, 2H), 3.53 (t, J=6.1 Hz, 2H), 2.92 (q, J=7.5 Hz, 2H), 2.84-2.77 (m, 2H), 1.87 (p, J=6.4 Hz, 2H), 1.09 (q, J=7.4 Hz, 6H). ESI-MS: $C_{28}H_{30}N_7O_9S$ (M+H): calc. 640.17, found: 640.20.

Step J. To a stirred solution of 6-(((E)-4-((Z)-6-carbamoyl-2-((4-ethyl-2-methyloxazole-5-carbonyl)imino)-4-(3-hydroxypropoxy)benzo[d]thiazol-3(2H)-yl)but-2-en-1-yl) amino)-5-nitronicotinic acid, Compound 146I (200 mg, 0.312 mmol) in DMF (10 mL) was added NH$_4$Cl (33 mg, 0.624 mmol), HATU (177 mg, 0.468 mmol) and DIPEA (0.27 mL, 1.56 mmol), and the mixture heated to 30° C. and stirred for 16 hours. The mixture was cooled to room temperature and poured over ice water, and the resulting precipitate was filtered and dried to afford N-((Z)-6-carbamoyl-3-((E)-4-((5-carbamoyl-3-nitropyridin-2-yl)amino)but-2-en-1-yl)-4-(3-hydroxypropoxy)benzo[d]thiazol-2(3H)-ylidene)-4-ethyl-2-methyloxazole-5-carboxamide, Compound 146J (200 mg, 99% yield) as a yellow solid. $^1$H NMR (400 MHz, DMSO-$d_6$) δ 8.85 (d, J=8.1 Hz, 3H), 8.07 (s, 2H), 7.97 (d, J=10.9 Hz, 1H), 7.60 (s, 1H), 7.46 (s, 2H), 5.90 (dt, J=15.9, 5.3 Hz, 1H), 5.75 (dd, J=13.0, 7.7 Hz, 1H), 5.34 (d, J=5.3 Hz, 2H), 4.21 (q, J=6.2 Hz, 4H), 3.54 (q, J=5.7 Hz, 2H), 2.90 (d, J=3.8 Hz, 2H), 2.45 (s, 3H), 1.87 (p, J=6.3 Hz, 2H), 1.10 (t, J=7.5 Hz, 3H). ESI-MS: $C_{28}H_{31}N_8O_8S$ (M+H): calc. 639.19, found: 639.20.

Step K: To a stirred solution of N-((Z)-6-carbamoyl-3-((E)-4-((5-carbamoyl-3-nitropyridin-2-yl)amino)but-2-en-1-yl)-4-(3-hydroxypropoxy)benzo[d]thiazol-2(3H)-ylidene)-4-ethyl-2-methyloxazole-5-carboxamide, Compound 146J (200 mg, 0.313 mmol) in concentrated HCl (10 mL) at 0° C. was added SnCl$_2$ (272 mg, 1.57 mmol), and the mixture was stirred for 1 hour. The mixture was quenched with 6N NaOH, and the resulting precipitate was filtered to afford N-((Z)-34(E)-4-((3-amino-5-carbamoylpyridin-2-yl)amino)but-2-en-1-yl)-6-carbamoyl-4-(3-hydroxypropoxy)benzo[d]thiazol-2(3H)-ylidene)-4-ethyl-2-methyloxazole-5-carboxamide, Compound 146K (120 mg, 63% yield) as a white solid. $^1$H NMR (400 MHz, DMSO-$d_6$) δ 8.07 (s, 1H), 7.92 (d, J=26.0 Hz, 2H), 7.51 (d, J=47.5 Hz, 3H), 7.06 (s, 1H), 6.86 (s, 1H), 6.15 (s, 1H), −5.71 (m, 2H), 5.31 (s, 2H), 4.72 (s, 2H), 4.20 (t, J=6.4 Hz, 2H), 3.97 (s, 2H), 3.53 (s, 2H), 2.90 (q, J=7.6 Hz, 3H), 1.91-1.78 (m, 2H), 1.09 (t, J=7.7 Hz, 3H). ESI-MS: $C_{28}H_{33}N_8O_6S$ (M+H): calc. 609.22, found: 609.20.

Step L: To a stirred solution of N-((Z)-3-((E)-44(3-amino-5-carbamoylpyridin-2-yl)amino)but-2-en-1-yl)-6-carbamoyl-4-(3-hydroxypropoxy)benzo[d]thiazol-2(3H)-ylidene)-4-ethyl-2-methyloxazole-5-carboxamide, Compound 146K (120 mg, 0.197 mmol) in DMF (5 mL) at 0° C. was added 4-ethyl-2-methyloxazole-5-carbonyl isothiocyanate (1.48 mL, 0.591 mmol), and the mixture was stirred for 10 minutes. Then, EDC.HCl (94 mg, 0.492 mmol) and Et$_3$N (0.14 mL, 0.985 mmol) were added, and the mixture was allowed to warm to room temperature and was stirred for 16 hours. The mixture was concentrated in vacuo, the residue was diluted in EtOAc and washed with water. The organic layer was dried over Na$_2$SO$_4$ and concentrated in vacuo. Purification by reverse phase HPLC (ACN:water) afforded N-(6-carbamoyl-3-((E)-4-((Z)-6-carbamoyl-2-((4-ethyl-2-methyloxazole-5-carbonyl)imino)-4-(3-hydroxypropoxy) benzo[d]thiazol-3 (2H)-yl)but-2-en-1-yl)-3H-imidazo[4,5-b]pyridin-2-yl)-4-ethyl-2-methyloxazole-5-carboxamide, Compound 146 (80 mg, 53% yield) as a white solid. $^1$H NMR (400 MHz, DMSO-$d_6$) δ 12.71 (s, 1H), 8.65 (d, J=1.9 Hz, 1H), 8.14-8.05 (m, 2H), 8.02 (s, 1H), 7.92 (d, J=1.4 Hz, 1H), 7.53-7.45 (m, 2H), 7.43 (s, 1H), 5.84 (dt, J=15.7, 5.1 Hz, 1H), (dt, J=15.6, 5.4 Hz, 1H), 5.26 (d, J=5.0 Hz, 2H), 4.70 (d, J=5.3 Hz, 2H), 4.09 (t, J=6.4 Hz, 2H), 3.42 (s, 2H), 2.82-2.70 (m, 4H), 2.37 (d, J=9.8 Hz, 6H), 1.72 (p, J=6.2 Hz, 2H), 0.94 (dt, J=17.7, 7.5 Hz, 6H). ESI-MS: $C_{36}H_{39}N_{10}O_8S$ (M+H): calc. 771.26, found: 771.30.

Example 50a: Synthesis of Compound 148: N-((Z)-6-carbamoyl-3-((E)-4-(6-carbamoyl-2-(1-ethyl-3-methyl-1H-pyrazole-5-carboxamido)-3H-imidazo[4,5-b]pyridin-3-yl)but-2-en-1-yl)-4-(3-hydroxypropoxy)benzo[d]thiazol-2(3H)-ylidene)-4-ethyl-2-methyloxazole-5-carboxamide, Compound 148

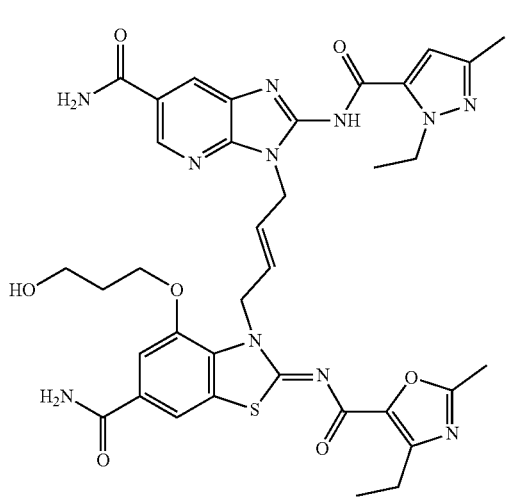

148

The title compound was prepared as described in Example 50, except 1-ethyl-5-isothiocyanato-3-methyl-1H-pyrazole was used in step L instead of 4-ethyl-2-methyloxazole-5-carbonyl isothiocyanate to afford N-((Z)-6-carbamoyl-3-((E)-4-(6-carbamoyl-2-(1-ethyl-3-methyl-1H-pyrazole-5-carboxamido)-3H-imidazo[4,5-b]pyridin-3-yl)but-2-en-1-yl)-4-(3-hydroxypropoxy)benzo[d]thiazol-2(3H)-ylidene)-4-ethyl-2-methyloxazole-5-carboxamide, compound 148 (265 mg, 70% yield) as a light brown solid. $^1$H NMR (400 MHz, DMSO-$d_6$) δ 8.66 (d, J=1.9 Hz, 1H), 8.20-7.99 (m, 3H), 7.91 (s, 1H), 7.47 (d, J=28.9 Hz, 3H), 6.45 (s, 1H), 5.82 (ddt, J=50.9, 15.7, 5.5 Hz, 2H), 5.25 (d, J=5.1 Hz, 2H), 4.72 (d, J=5.5 Hz, 2H), 4.45 (q, J=7.1 Hz, 2H), 4.08 (t, J=6.5 Hz, 2H), 2.77 (t, J=7.5 Hz, 2H), 2.37 (s, 3H), 2.06 (s, 3H), 1.72 (p, J=6.2 Hz, 2H), 1.22 (t, J=7.1 Hz, 3H), 0.96 (t, J=7.6 Hz, 3H). ESI-MS: $C_{36}H_{40}N_{11}O_7S$ (M+H): calc. 770.28, found: 770.20.

General procedure for synthesis of Compound Variant XI wherein $Z_1=Z_2$; $Y_1=Y_2$; $X_1=X_2$; $W_1=W_2$; $R^{14}=R^{C2}$; $R^{19}=R^{18}$; $R^{15}=R^{17}$ and $R^{C1}=R^{16}$.

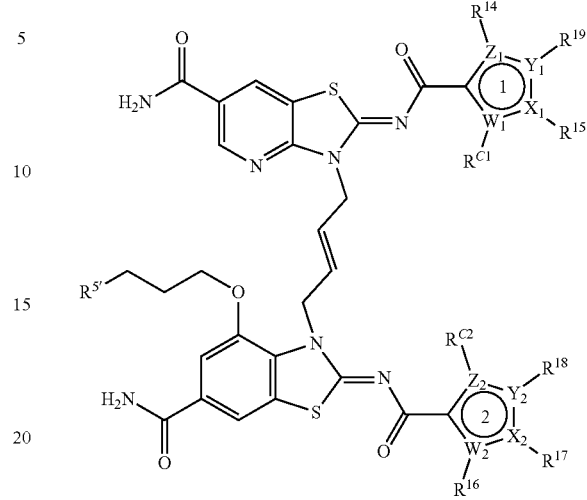

Variant XI

Scheme 11: The following scheme illustrates the exemplary synthesis of (N-(5-carbamoyl-1-((E)-4-((Z)-6-carbamoyl-2-((4-ethyl-2-methyloxazole-5-carbonyl)imino)thiazolo[4,5-b]pyrazin-3(2H)-yl)but-2-en-1-yl)-7-(3-hydroxypropoxy)-1H-benzo[d]imidazol-2-yl)-4-ethyl-2-methyloxazole-5-carboxamide. The similar procedure may be generally used for the synthesis of Compound Variant XI.

Scheme 11

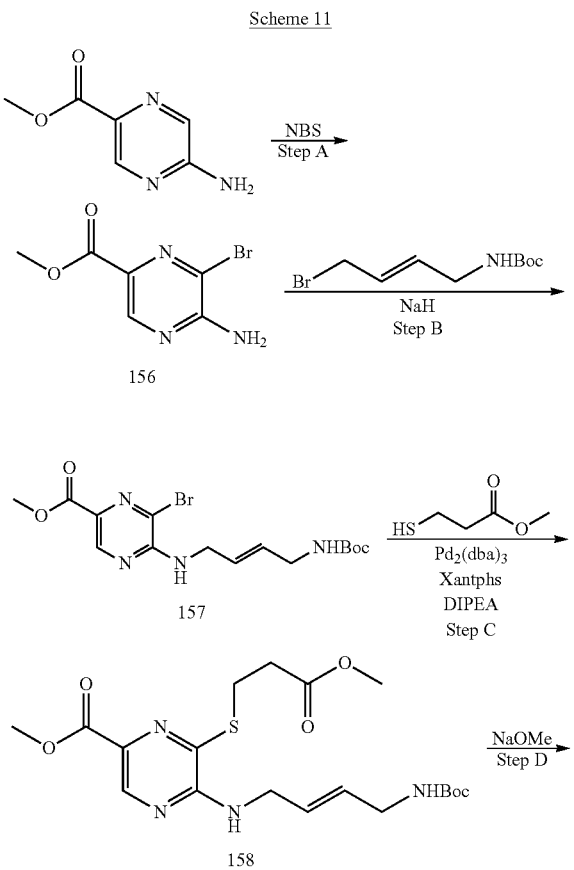

327
-continued
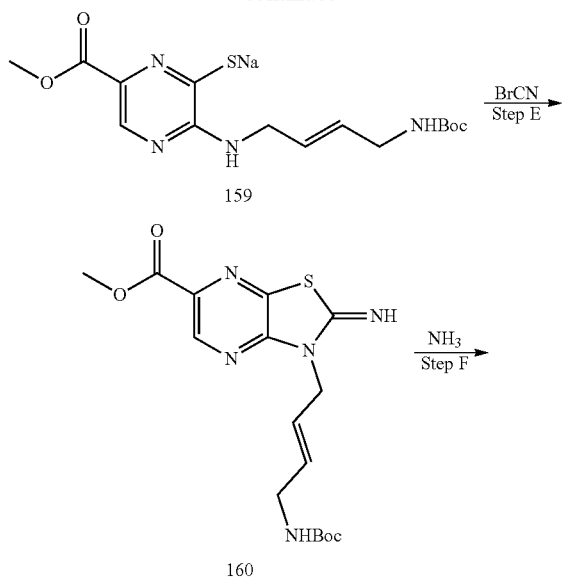
328
-continued
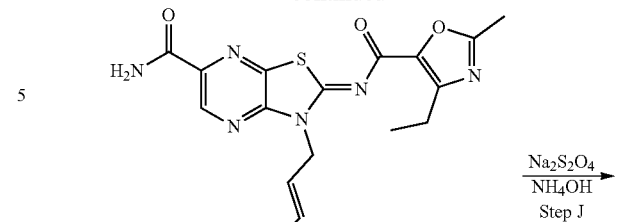
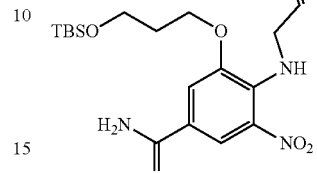
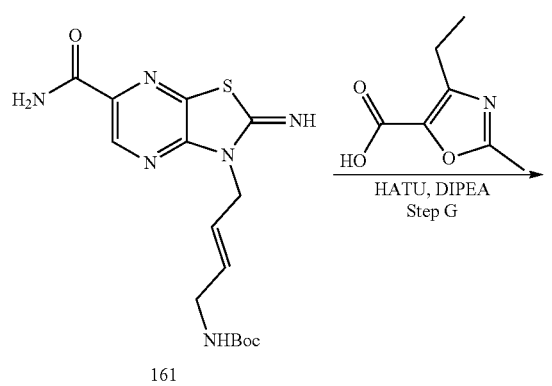
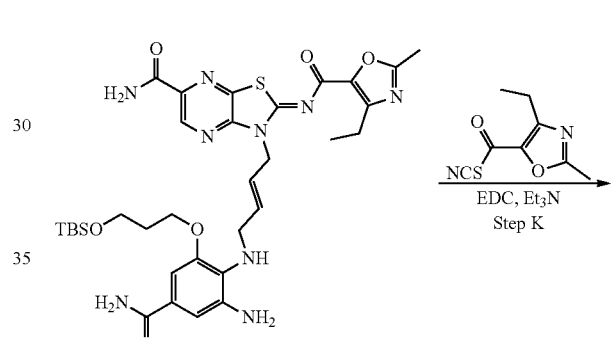
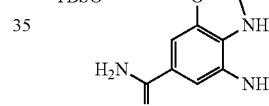
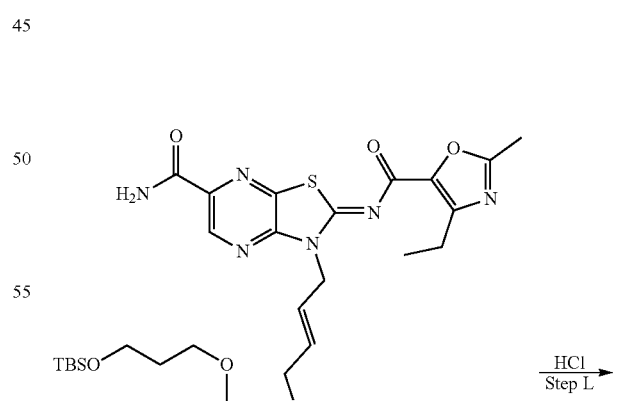
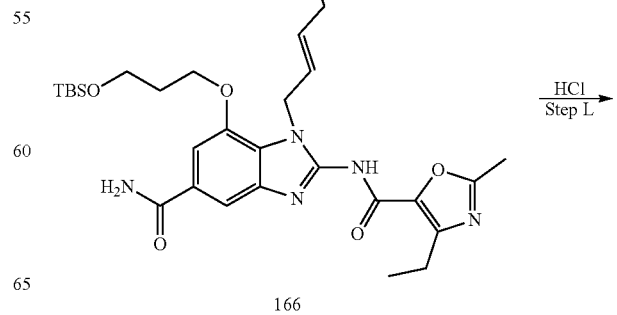
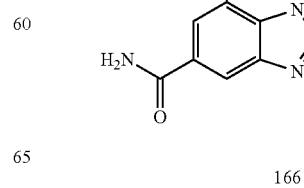

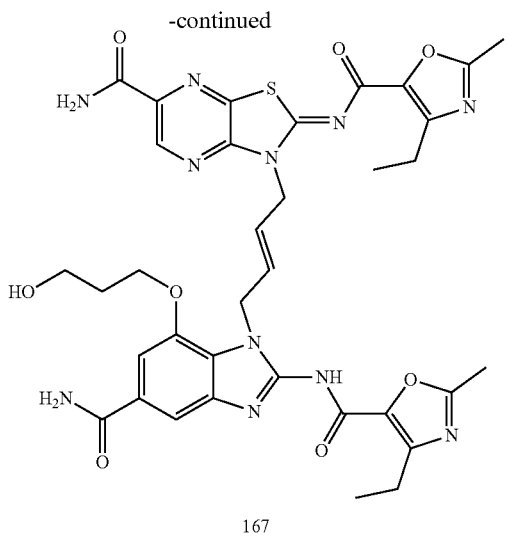

Example 51: N-(5-carbamoyl-1-((E)-4-((Z)-6-carbamoyl-2-((4-ethyl-2-methyloxazole-5-carbonyl)imino)thiazolo[4,5-13]pyrazin-3(2H)-yl)but-2-en-1-yl)-7-(3-hydroxypropoxy)-1H-benzo[d]imidazol-2-yl)-4-ethyl-2-methyloxazole-5-carboxamide, Compound 167

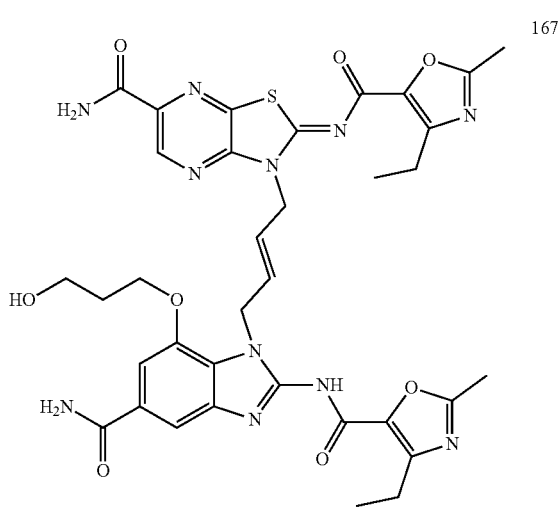 [SMILES: CCc1nc(C)oc1C(=O)/N=c1\sc2nc(C(N)=O)cnc2n1C/C=C/Cn1c(NC(=O)c2oc(C)nc2CC)nc2cc(C(N)=O)cc(OCCCO)c21]

Step A: To a stirred solution of methyl 5-aminopyrazine-2-carboxylate (10.0 g, 65.4 mmol) in ACN (100 mL) was added N-bromosuccinimide (11.6 g, 65.4 mmol), and the mixture was stirred at room temperature for 6 hours. The reaction was quenched with water and extracted with EtOAc, and the combined organic layers were dried over $Na_2SO_4$ and concentrated to afford methyl 5-amino-6-bromopyrazine-2-carboxylate, Compound 156 (7.5 g, 50% yield) as a solid.

Step B: To a stirred solution of NaH (60% in mineral oil, 700 mg, 17.4 mmol) in THF (20 mL) at 0° C. was added methyl 5-amino-6-bromopyrazine-2-carboxylate, Compound 156 (4.0 g, 17.4 mmol), and the mixture was stirred for 20 minutes. Tert-butyl (E)-(4-bromobut-2-en-1-yl)carbamate (4.3 g, 17.4 mmol) was added, and the mixture was warmed to room temperature and stirred for 16 hours. The reaction was quenched with water and extracted with EtOAc, and the combined organic layers were dried over $Na_2SO_4$ and concentrated in vacuo. Purification over silica gel (hexane:EtOAc 30:70) afforded methyl (E)-6-bromo-5-((4-((tert-butoxycarbonyl)amino)but-2-en-1-yl)amino)pyrazine-2-carboxylate, Compound 157 (3.0 g, 43% yield) as a yellow solid. $^1$H NMR (400 MHz, Chloroform-d) δ 8.72 (d, J=3.9 Hz, 1H), 5.77-5.69 (m, 2H), 4.17 (ddt, J=4.0, 2.6, 1.3 Hz, 2H), 3.95 (d, J=4.6 Hz, 3H), 3.82-3.70 (m, 2H), 1.44 (d, J=1.5 Hz, 9H). ESI-MS: $C_{15}H_{22}BrN_4O_4$ (M+H): calc. 401.07, found: 401.10.

Step C: To a stirred solution of methyl (E)-6-bromo-5-((4-((tert-butoxycarbonyl)amino)but-2-en-1-yl)amino)pyrazine-2-carboxylate, Compound 157 (2.0 g, 4.99 mmol) and methyl 3-mercaptopropanoate (0.65 mL, 5.99 mmol) in toluene (20 mL) was added DIPEA (1.78 mL, 9.98 mmol), $Pd_2(dba)_3$ (230 mg, 0.25 mmol) and Xantphos (300 mg, 0.499 mmol) in a sealed tube, and the mixture was heated to 110° C. and stirred for 16 hours. The mixture was filtered, and the filtrate was concentrated in vacuo. Purification over silica gel (hexane:EtOAc afforded methyl (E)-5-((4-((tert-butoxycarbonyl)amino)but-2-en-1-yl)amino)-64(3-methoxy-3-oxopropyl)thio)pyrazine-2-carboxylate, Compound 158 (1.5 g, 69% yield) as a white solid. $^1$H NMR (400 MHz, Chloroform-d) δ 8.53 (d, J=12.0 Hz, 1H), 5.80-5.61 (m, 2H), 4.17-4.12 (m, 2H), 3.92 (d, J=4.4 Hz, 3H), 3.75 (d, J=5.7 Hz, 2H), 3.72 (d, J=1.0 Hz, 3H), 3.57 (td, J=6.7, 2.2 Hz, 2H), 2.86 (td, J=6.7, 3.5 Hz, 2H), 1.44 (d, J=1.0 Hz, 9H). ESI-MS: $C_{19}H_{29}N_4O_6S$ (M+H): calc. 441.17, found: 441.20.

Step D: To a stirred solution of methyl (E)-5-((4-((tert-butoxycarbonyl)amino)but-2-en-1-yl)amino)-6-((3-methoxy-3-oxopropyl)thio)pyrazine-2-carboxylate, Compound 158 (1.3 g, 2.95 mmol) in THF (20 mL) was added NaOMe (25% in MeOH, 0.7 mL, 3.25 mmol), and the mixture was stirred at room temperature for 1 hour. The mixture was concentrated in vacuo and triturated in pentane to afford sodium (E)-3-((4-((tert-butoxycarbonyl)amino)but-2-en-1-yl)amino)-6-(methoxycarbonyl)pyrazine-2-thiolate, Compound 159 (1 g, 90% yield) as a light yellow solid. ESI-MS: $C_{15}H_{23}N_4O_4S$ (M+H): calc. 355.14, found: 355.10.

Step E: To a stirred solution of (E)-3-((4-((tert-butoxycarbonyl)amino)but-2-en-1-yl)amino)-6-(methoxycarbonyl)pyrazine-2-thiolate, Compound 159 (1 g, 2.66 mmol) in methanol (10 mL) was added cyanogen bromide (420 mg, 3.99 mmol), and the mixture was stirred at room temperature for 2 hours. The mixture was concentrated in vacuo, and the residue was purified over silica gel (hexane:EtOAc 1:1) to afford methyl (E)-3-(4-((tert-butoxycarbonyl)amino)but-2-en-1-yl)-2-imino-2,3-dihydrothiazolo[4,5-b]pyrazine-6-carboxylate, Compound 160 (800 mg, 80% yield) as a yellow solid. $^1$H NMR (400 MHz, Chloroform-d) δ 8.78 (s, 1H), 5.76 (q, J=4.7 Hz, 2H), 4.72-4.67 (m, 2H), 3.99 (s, 3H), 3.73 (s, 2H). ESI-MS: $C_{16}H_{22}N_5O_4S$ (M+H): calc. 380.13, found: 380.05.

Step F: To a stirred solution of (E)-3-(4-((tert-butoxycarbonyl)amino)but-2-en-1-yl)-2-imino-2,3-dihydrothiazolo[4,5-b]pyrazine-6-carboxylate, Compound 160 (400 mg, 1.06 mmol) in methanol (10 mL) was added aqueous ammonia (25% v/v, 5 mL), and the mixture was stirred at room temperature for 16 hours. The mixture was concentrated in vacuo to afford tert-butyl (E)-(4-(6-carbamoyl-2-iminothiazolo[4, 5-b]pyrazin-3 (2H)-yl)but-2-en-1-yl)carbamate, Compound 161 (350 mg, 91% yield) as a yellow solid. $^1$H NMR (400 MHz, DMSO-$d_6$) δ 9.50 (s, 1H), 8.62 (s, 1H), 8.01 (s, 1H), 7.58 (s, 1H), 6.92 (t, J=5.8 Hz, 1H), 5.61 (q, J=3.5 Hz, 2H), 4.56 (d, J=4.1 Hz, 2H), 1.35 (s, 9H). ESI-MS: $C_{15}H_{21}N_6O_3S$ (M+H): calc. 364.13, found: 364.10.

Step G: To a stirred solution of tert-butyl (E)-(4-(6-carbamoyl-2-iminothiazolo[4,5-b]pyrazin-3(2H)-yl)but-2-en-1-yl)carbamate, Compound 161 (350 mg, 0.96 mmol) in DMF (20 mL) was added 4-ethyl-2-methyloxazole-5-carboxylic acid (225 mg, 1.44 mmol), HATU (730 mg, 1.92 mmol), and DIPEA (0.52 mL, 2.88 mmol), and the mixture was stirred at room temperature for 16 hours. The mixture was poured over ice water, and the resulting solid was filtered and dried to afford tert-butyl ((E)-4-((Z)-6-carbamoyl-2-((4-ethyl-2-methyloxazole-5-carbonyl)imino)thiazolo[4,5-b]pyrazin-3(2H)-yl)but-2-en-1-yl)carbamate, Compound 162 (280 mg, 58%) as a white solid. $^1$H NMR (400 MHz, DMSO-$d_6$) δ 9.04 (s, 1H), 8.34 (s, 1H), 7.82 (s, 1H), 6.91 (t, J=5.9 Hz, 1H), 5.74 (q, J=4.8 Hz, 2H), 5.02 (d, J=4.5 Hz, 2H), 3.51 (t, J=4.9 Hz, 2H), 3.02 (q, J=7.5 Hz, 2H), 1.31 (s, 9H), 1.24 (d, J=7.5 Hz, 3H). ESI-MS: $C_{22}H_{28}N_7O_5S$ (M+H): calc. 502.18, found: 502.30.

Step H: To a stirred solution of tert-butyl ((E)-4-((Z)-6-carbamoyl-2-((4-ethyl-2-methyloxazole-5-carb onyl)imino)thiazolo[4,5-b]pyrazin-3 (2H)-yl)but-2-en-1-yl)carbamate, Compound 162 (280 mg, 0.56 mmol) in dioxane (10 mL) was added HCl (4M in dioxane, 2 mL, 20% v/v), and the mixture was stirred at room temperature for 3 hours. The mixture was concentrated in vacuo to afford N-((Z)-3-((E)-4-aminobut-2-en-1-yl)-6-carbamoylthiazolo[4, 5-b]pyrazin-2(3H)-ylidene)-4-ethyl-2-methyloxazole-5-carboxamide, Compound 163 (250 mg, 97%) as a white solid. $^1$H NMR (400 MHz, DMSO-$d_6$) δ 9.05 (d, J=6.4 Hz, 1H), 8.36 (d, J=9.3 Hz, 1H), 7.96 (s, 1H), 7.84 (d, J=13.0 Hz, 1H), 5.75 (d, J=6.8 Hz, 2H), 5.05 (dd, J=25.5, 5.0 Hz, 2H), 3.42 (p, J=5.9 Hz, 2H), 3.03 (q, J=7.5 Hz, 2H), 1.24 (td, J=7.5, 5.2 Hz, 3H). ESI-MS: $C_{17}H_{20}N_7O_3S$ (M+H): calc. 402.13, found: 402.10.

Step I: To a stirred solution of N-((Z)-3-((E)-4-aminobut-2-en-1-yl)-6-carbamoylthiazolo[4,5-b]pyrazin-2(3H)-ylidene)-4-ethyl-2-methyloxazole-5-carboxamide, Compound 163 (250 mg, 0.62 mmol) in DMSO (10 mL) was added 3-(3-((tert-butyldimethylsilyl)oxy)propoxy)-4-fluoro-5-nitrobenzamide, Compound 3 (230 mg, 0.62 mmol) and Et$_3$N (0.26 mL, 1.87 mmol), and the mixture was stirred at room temperature for 16 hours. The mixture was quenched with ice water, and the resulting solid was filtered and purified over silica gel (EtOAc) to afford N-((Z)-34(E)-4-((2-(3-((tert-butyldimethylsilyl)oxy)propoxy)-4-carbamoyl-6-nitrophenyl)amino)but-2-en-1-yl)-6-carbamoylthiazolo[4,5-b]pyrazin-2(3H)-ylidene)-4-ethyl-2-methyloxazole-5-carboxamide, Compound 164 (200 mg, 42% yield) as a yellow solid. $^1$H NMR (400 MHz, DMSO-$d_6$) δ 8.99 (s, 1H), 8.32 (s, 1H), 8.02 (d, J=1.8 Hz, 1H), 7.91 (s, 1H), 7.82 (s, 1H), 7.62 (t, J=6.4 Hz, 1H), 7.43 (d, J=2.0 Hz, 1H), 7.26 (s, 1H), 5.87-5.71 (m, 2H), 4.97 (d, J=4.6 Hz, 2H), 4.11 (t, J=5.4 Hz, 2H), 3.99 (t, J=6.1 Hz, 2H), 3.65 (t, J=6.2 Hz, 2H), 2.91 (q, J=7.5 Hz, 2H), 1.82 (q, J=6.2 Hz, 2H), 1.15 (t, J=7.5 Hz, 3H), 0.80 (s, 9H). ESI-MS: C33H44N9O8Ssi (M+H): calc. 754.27, found: 754.30.

Step J: To a stirred solution of N-((Z)-3-((E)-4-((2-(3-((tert-butyldimethylsilyl)oxy)propoxy)-4-carbamoyl-6-nitrophenyl)amino)but-2-en-1-yl)-6-carbamoylthiazolo[4,5-b]pyrazin-2(3H)-ylidene)-4-ethyl-2-methyloxazole-5-carboxamide, Compound 164 (200 mg, 0.27 mmol) in methanol (20 mL) was added Na$_2$S$_2$O$_4$ (230 mg, 1.33 mmol) in water (4 mL) and NH$_4$OH (5 mL) at 0° C., and the mixture was warmed to room temperature and stirred for 15 minutes. The mixture was poured over ice water and extracted with DCM:MeOH 10:1, and the combined organic layers were concentrated in vacuo. The residues was triturated in ether to afford N-((Z)-3-((E)-4-((2-amino-6-(3-((tert-butyldimethylsilyl)oxy)propoxy)-4-carbamoylphenyl)amino)but-2-en-1-yl)-6-carbamoylthiazolo[4,5-b]pyrazin-2(3H)-ylidene)-4-ethyl-2-methyloxazole-5-carboxamide, Compound 165 (150 mg, 78% yield) as a white solid. ESI-MS: $C_{33}H_{46}N_9O_6Ssi$ (M+H): calc. 724.30, found: 724.30.

Step K: To a stirred solution of N-((Z)-3-((E)-4-((2-amino-6-(3-((tert-butyldimethylsilyl)oxy)propoxy)-4-carbamoylphenyl)amino)but-2-en-1-yl)-6-carbamoylthiazolo[4,5-b]pyrazin-2(3H)-ylidene)-4-ethyl-2-methyloxazole-5-carboxamide, Compound 165 (150 mg, 0.21 mmol) in DMF (10 mL) was added cyanic 4-ethyl-2-methyloxazole-thioanhydride (0.4M in dioxane, 1 mL, 0.41 mmol), EDCI-HCl (81 mg, 0.41 mmol), and Et$_3$N (0.15 mL, 1.03 mmol), and the mixture was stirred at room temperature for 4 hours. The reaction was quenched with water, and the resulting solid was filtered and washed with water and pentane to afford N-(7-(3-((tert-butyldimethylsilyl)oxy)prop oxy)-5-carbamoyl-1-((E)-4-((Z)-6-carbamoyl-2-((4-ethyl-2-methyl oxazole-5-carb onyl)imino)thiazolo [4,5-b]pyrazin-3 (2H)-yl)but-2-en-1-yl)-1H-benzo[d]imidazol-2-yl)-4-ethyl-2-methyloxazole-5-carboxamide, Compound 166 (100 mg, 55% yield) as a white solid. $^1$H NMR (400 MHz, DMSO-$d_6$) δ 12.69 (s, 1H), 8.94 (s, 1H), 8.31 (s, 1H), 7.92 (s, 1H), 7.79 (s, 1H), 7.58 (d, J=1.3 Hz, 1H), 7.32-7.23 (m, 2H), 5.99-5.58 (m, 2H), 5.02-4.81 (m, 4H), 4.07 (t, J=6.1 Hz, 2H), 3.62 (t, J=6.2 Hz, 2H), 2.75 (dq, J=7.5 Hz, 4H), 2.38 (d, J=18.5 Hz, 6H), 1.76 (p, J=6.0 Hz, 2H), 0.97 (td, J=7.5, 6.2 Hz, 6H), 0.77 (s, 9H), −0.06 (s, 6H). ESI-MS: $C_{41}H_{52}N_{11}O_8Ssi$ (M+H): calc. 886.34, found: 886.40.

Step L: To a stirred solution of N-(7-(3-((tert-butyldimethylsilyl)oxy)propoxy)-5-carbamoyl-1-((E)-4-((Z)-6-carbamoyl-2-((4-ethyl-2-methyloxazole-5-carbonyl)imino)thiazolo[4,5-b]pyrazin-3(2H)-yl)but-2-en-1-yl)-1H-benzo[d]imidazol-2-yl)-4-ethyl-2-methyloxazole-5-carboxamide, Compound 166 (50 mg, 0.056 mmol) in methanol (1 mL) was added HCl (4M in dioxane, 2 mL, 1:2 v/v), and the mixture was stirred at room temperature for 3 hours. The mixture was concentrated in vacuo, and the residue was triturated in dioxane to afford N-(5-carbamoyl-1-((E)-4-((Z)-6-carbamoyl-2-((4-ethyl-2-methyloxazole-5-carbonyl)imino)thiazolo[4,5-b]pyrazin-3(2H)-yl)but-2-en-1-yl)-7-(3-hydroxypropoxy)-1H-benzo[d]imidazol-2-yl)-4-ethyl-2-methyloxazole-5-carboxamide, Compound 167 (28 mg, 32% yield) as a white solid. $^1$H NMR (400 MHz, DMSO-$d_6$) δ 12.57 (s, 1H), 8.99 (s, 1H), 8.33 (s, 1H), 7.93 (s, 1H), 7.81 (s, 1H), 7.61 (s, 1H), 7.30 (s, 2H), 6.02-5.90 (m, 1H), 5.74 (d, J=15.6 Hz, 1H), 4.99 (d, J=5.5 Hz, 2H), 4.90 (d, J=5.3 Hz, 2H), 4.10 (t, J=6.3 Hz, 2H), 3.44 (q, J=5.8 Hz, 2H), 2.79 (dq, J=15.0, 7.5 Hz, 4H), 2.42 (d, J=20.6 Hz, 6H), 1.76 (q, J=6.2 Hz, 2H), 1.01 (q, J=7.5 Hz, 6H). ESI-MS: $C_{35}H_{38}N_{11}O_8S$ (M+H): calc. 772.25, found: 772.30.

General procedure for synthesis of Compound Variant XII, wherein $Z_1=Z_2$; $Y_1=Y_2$; $X_1=X_2$; $W_1=W_2$; \R$^{19}$=R$^{18}$ and R$^{15}$=R$^{17}$.

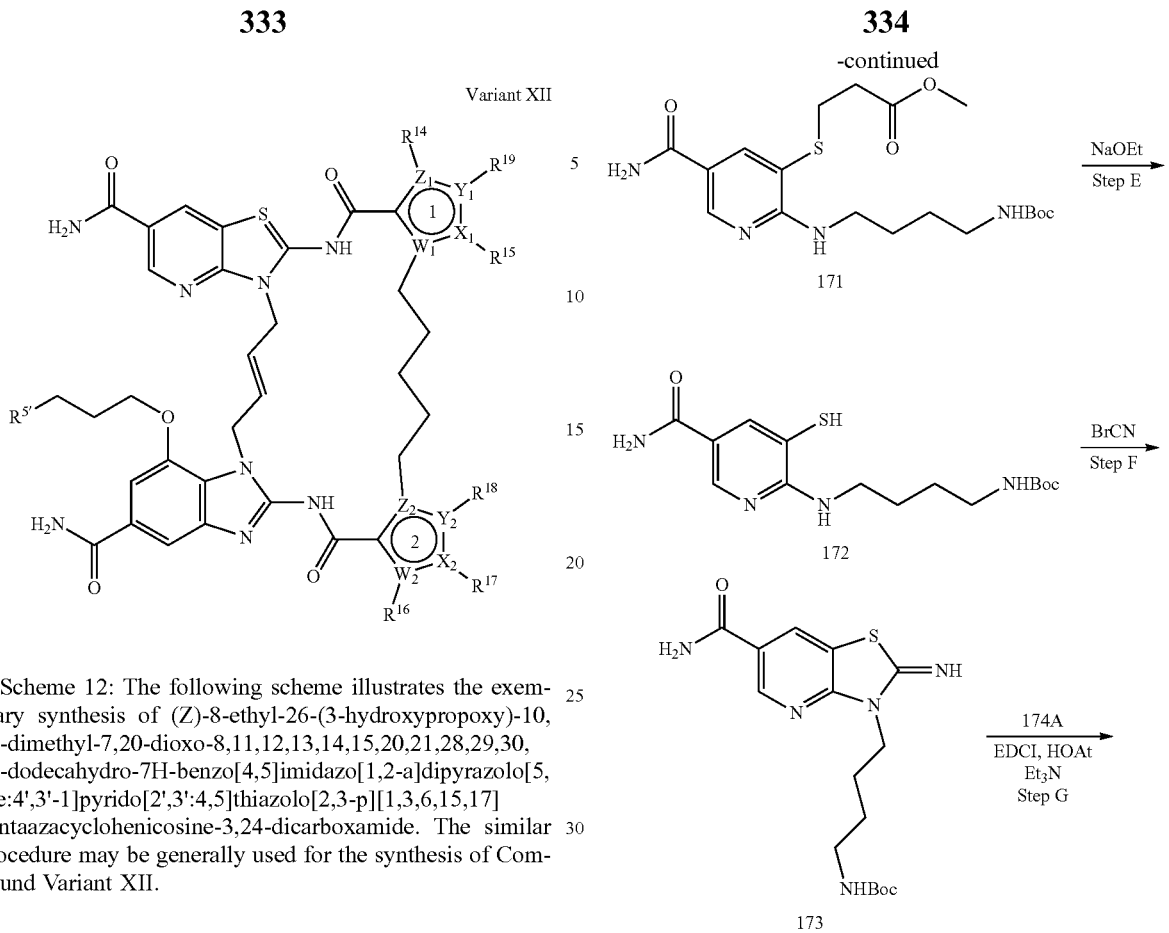
Scheme 12: The following scheme illustrates the exemplary synthesis of (Z)-8-ethyl-26-(3-hydroxypropoxy)-10,18-dimethyl-7,20-dioxo-8,11,12,13,14,15,20,21,28,29,30,31-dodecahydro-7H-benzo[4,5]imidazo[1,2-a]dipyrazolo[5,1-e:4',3'-1]pyrido[2',3':4,5]thiazolo[2,3-p][1,3,6,15,17]pentaazacyclohenicosine-3,24-dicarboxamide. The similar procedure may be generally used for the synthesis of Compound Variant XII.
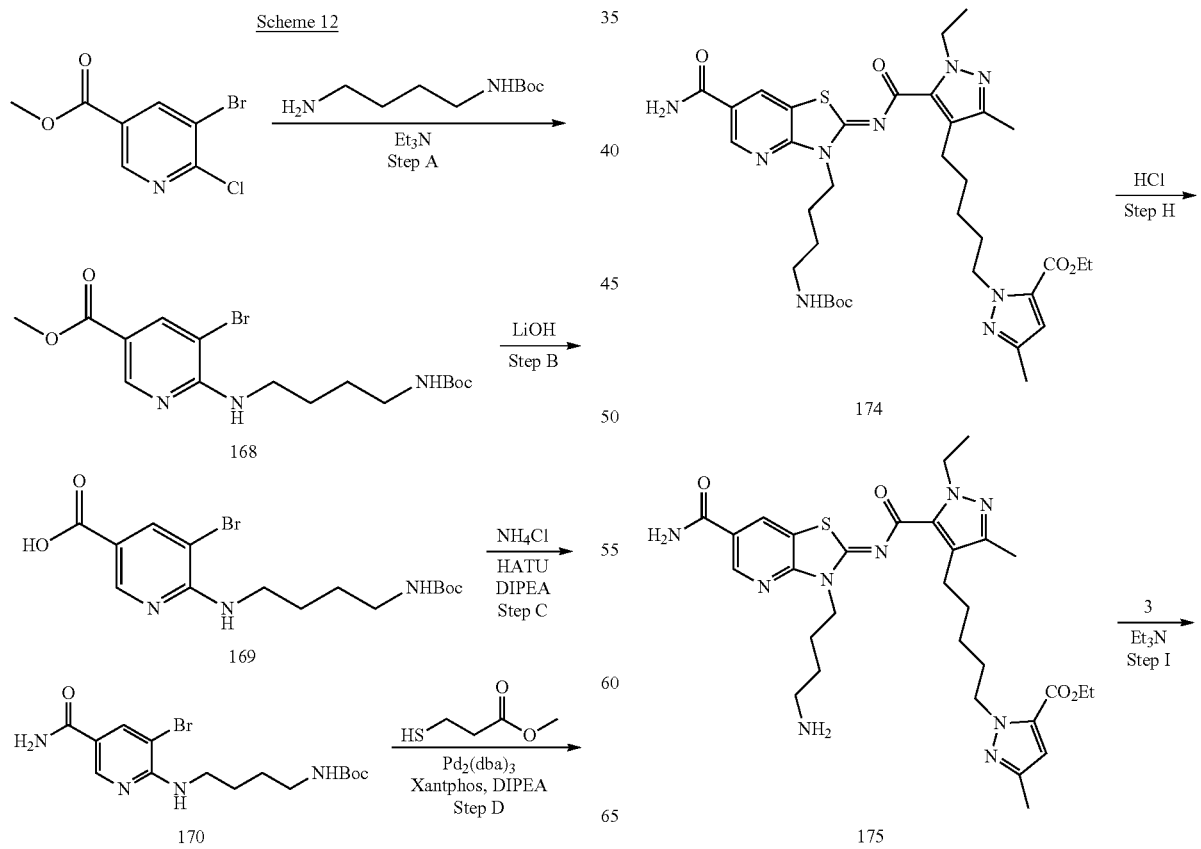

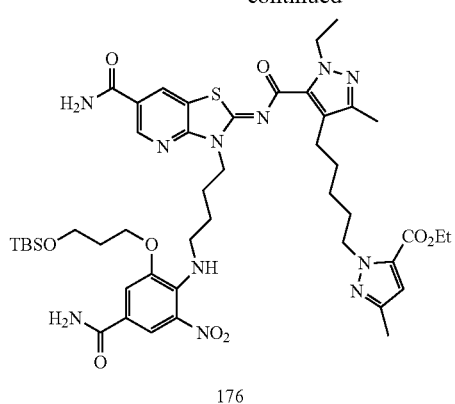
176
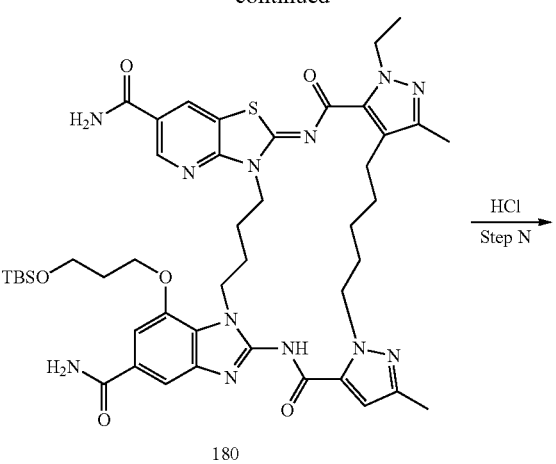
180
Na₂S₂O₄
NH₄OH
Step J
HCl
Step N
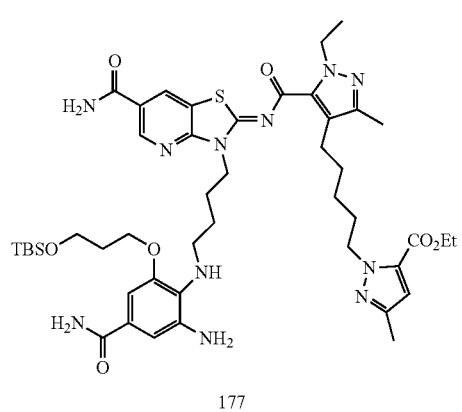
177
BrCN
Step K
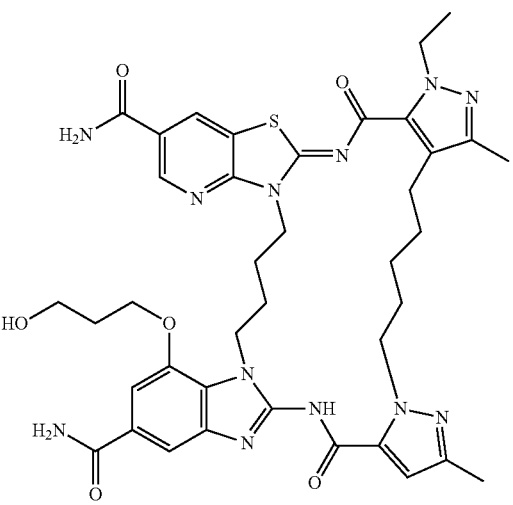
181
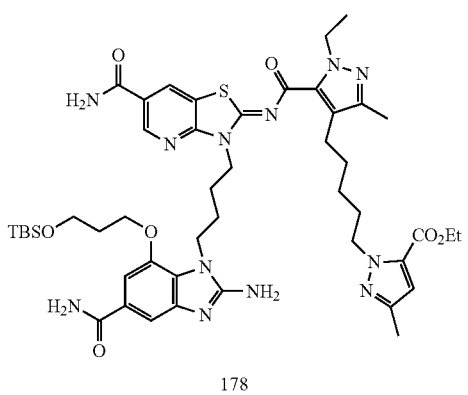
178
LiOH
Step L
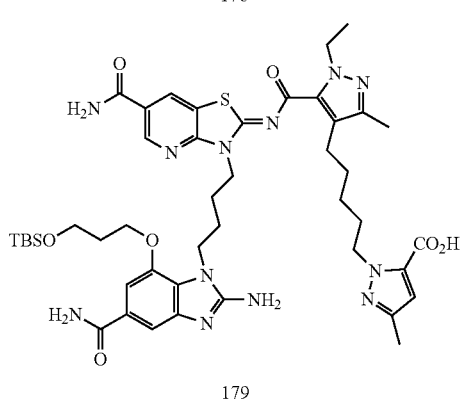
179
HATU
DIPEA
DMAP
Step M
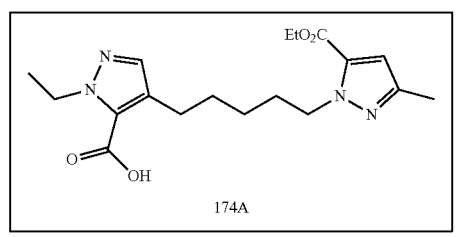 [SMILES: CCOC(=O)c1cc(C)nn1CCCCCc1cnn(CC)c1C(=O)O]
174A Example 52: (Z)-8-ethyl-26-(3-hydroxypropoxy)-10,18-dimethyl-7,20-dioxo-8,11,12,13,14,15,20,21,28,29,30,31-dodecahydro-7H-benzo[4,5]imidazo[1,2-a]dipyrazolo[5,1-e:4',3'-1]pyrido[2',3':4,5]thiazolo[2,3-p][1,3,6,15,17]pentaazacyclohenicosine-3,24-dicarboxamide, Compound 181

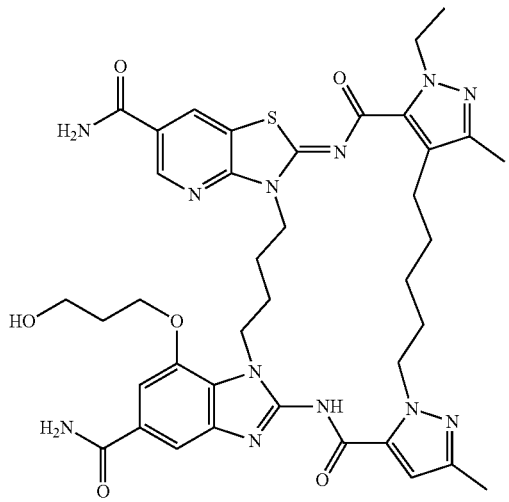

Step A: To a stirred solution of methyl 5-bromo-6-chloronicotinate (2.0 g, 8.03 mmol) and tert-butyl (4-aminobutyl)carbamate (1.8 g, 9.64 mmol) in DMSO (10 mL) was added Et$_3$N (1.7 mL, 12.05 mmol), and the mixture was stirred at room temperature for 16 hours. The reaction was quenched with water and extracted with EtOAc, and the combined organic layers were dried over Na$_2$SO$_4$ and concentrated in vacuo. The residue was purified over silica gel (EtOAc:hexane 30:70 v/v) to afford methyl 5-bromo-6-((4-((tert-butoxycarbonyl)amino)butyl)amino)nicotinate, compound 168 (2.0 g, 62% yield) as a yellow oil. $^1$H NMR (400 MHz, DMSO-d$_6$) δ 8.57 (d, J=2.0 Hz, 1H), 8.07 (d, J=2.1 Hz, 1H), 7.16 (d, J=6.2 Hz, 1H), 6.78 (s, 1H), 3.78 (s, 3H), 3.41 (q, J=6.7 Hz, 2H), 2.92 (q, J=6.6 Hz, 2H), 1.53 (dq, J=15.1, 7.7, 7.0 Hz, 2H), 1.36 (s, 11H). ESI-MS: C$_{16}$H$_{25}$BrN$_3$O$_4$ (M+H): calc. 402.10, found: 402.06.

Step B: To a stirred solution of methyl 5-bromo-6-((4-((tert-butoxycarbonyl)amino)butyl)amino)nicotinate, compound 168 (2.0 g, 4.99 mmol) in MeOH (25 mL) and THF (15 mL) was added LiOH·H$_2$O (628 mg, 14.96 mmol) dissolved in water (15 mL), and the mixture was stirred at room temperature for 16 hours. The solvent was removed, and the residue was diluted in water and acidified with 1N HCl. The aqueous layer was extracted with EtOAc, and the combined organic layers were dried over Na$_2$SO$_4$ and concentrated in vacuo to afford 5-bromo-6((4-((tert-butoxycarbonyl)amino)butyl)amino)nicotinic acid, compound 169 (1.6 g, 82%) as a white solid. $^1$H NMR (400 MHz, DMSO-d$_6$) δ 8.49 (d, J=2.0 Hz, 1H), 8.00 (d, J=1.9 Hz, 1H), 7.00 (d, J=6.3 Hz, 1H), 6.76 (t, J=5.8 Hz, 1H), 3.36 (d, J=6.5 Hz, 2H), 2.88 (q, J=6.6 Hz, 2H), 1.48 (p, J=7.1 Hz, 2H), 1.32 (m, 11H). ESI-MS: C$_{15}$H$_{23}$BrN$_3$O$_4$ (M+H): calc. 388.08, found: 388.10.

Step C: To a stirred solution of 5-bromo-6-((4-((tert-butoxycarbonyl)amino)butyl)amino)nicotinic acid, compound 169 (1.6 g, 4.13 mmol) and NH$_4$Cl (1.1 g, 20.67 mmol) in DMF (15 mL) was added HATU (2.3 g, 6.20 mmol) and DIPEA (2.1 mL, 12.40 mmol), and the mixture was stirred at room temperature for 16 hours. The reaction was quenched with water and extracted with EtOAc, and the combined organic layers were dried over Na$_2$SO$_4$ and concentrated in vacuo. The residue was purified over silica gel (EtOAc:hexane 80:20 v/v) to afford tert-butyl (4-((3-bromo-5-carbamoylpyridin-2-yl)amino)butyl)carbamate, compound 170 (1.20 g, 75% yield) as a white solid. $^1$H NMR (400 MHz, DMSO-d$_6$) δ 8.53 (d, J=2.1 Hz, 1H), 8.14 (d, J=2.1 Hz, 1H), 7.75 (s, 1H), 7.17 (s, 1H), 6.78 (dt, J=11.8, 5.6 Hz, 2H), 3.39 (q, J=6.6 Hz, 2H), 2.92 (q, J=7.8, 7.2 Hz, 2H), 1.52 (t, J=7.6 Hz, 2H), 1.36 (s, 11H). ESI-MS: C$_{15}$H$_{24}$BrN$_4$O$_3$ (M+H): calc. 387.10, found: 387.10.

Step D: To a degassed solution of tert-butyl (4-((3-bromo-5-carbamoylpyridin-2-yl)amino)butyl)carbamate, compound 170 (500 mg, 1.30 mmol) and DIPEA (0.67 mL, 3.89 mmol) in dioxane (15 mL) was added Pd$_2$(dba)$_3$ (59 mg, 0.06 mmol), Xanthphos (75 mg, 0.13 mmol) and methyl 3-mercaptopropanoate (0.3 mL, 2.59 mmol), and the mixture was heated to 95° C. and stirred for 16 hours. The mixture was cooled to room temperature and diluted in EtOAc, then extracted with water and brine. The combined organic layers were dried over Na$_2$SO$_4$ and concentrated in vacuo. The residue was purified over silica gel (EtOAc: hexane 80:20 v/v) to afford methyl 3-((2-((4-((tert-butoxy carb onyl)amino)butyl)amino)-5-carbamoylpyridin-3-yl) thio)propanoate, compound 171 (400 mg, 72% yield) as a yellow solid. $^1$H NMR (400 MHz, DMSO-d$_6$) δ 8.47 (d, J=2.3 Hz, 1H), 7.95 (d, J=2.2 Hz, 1H), 7.39-7.31 (m, 1H), 7.27-7.21 (m, 1H), 6.82-6.71 (m, 2H), 3.58 (s, 3H), 3.36 (q, J=6.4 Hz, 2H), 2.93-2.86 (m, 4H), 2.52 (t, J=6.9 Hz, 2H), 1.47 (q, J=7.6, 7.0 Hz, 2H), 1.32 (m, 11H). ESI-MS: C$_{19}$H$_{31}$BrN$_4$O$_5$S (M+H): calc. 427.19, found: 427.20.

Step E: To a stirred solution of methyl 34(2-(4-((tert-butoxycarbonyl)amino)butyl)amino)-5-carbamoylpyridin-3-yl)thio)propanoate, compound 171 (200 mg, 0.47 mmol) in THF (5 mL) was added NaOEt (21% in EtOH, 0.16 mL, 0.52 mmol), and the reaction was stirred under nitrogen for 1 hour. The mixture was concentrated in vacuo to afford sodium 2-((4-((tert-butoxy carb onyl)amino)butyl)amino)-5-carbamoylpyridine-3-thiolate, compound 172 (180 mg, 100% yield) as a red oil. $^1$H NMR (400 MHz, DMSO-d$_6$) δ 12.56 (s, 1H), 8.62-8.34 (m, 1H), 7.92 (d, J=14.5 Hz, 1H), 7.60 (s, 1H), 7.28 (s, 1H), 6.93-6.70 (m, 1H), 3.41 (s, 2H), 2.95 (p, J=7.0, 6.5 Hz, 2H), 1.52 (d, J=52.4 Hz, 4H), 1.37 (d, J=3.8 Hz, 9H). ESI-MS: C$_{15}$H$_{25}$N$_4$O$_3$S (M+H): calc. 341.16, found: 341.10.

Step F: To a stirred solution of sodium 2-(4-((tert-butoxycarbonyl)amino)butyl)amino)-5-carbamoylpyridine-3-thiolate, compound 172 (180 mg, 0.50 mmol) in MeOH (5 mL) was added BrCN (79 mg, 0.75 mmol), and the mixture was stirred under nitrogen for 2 hours. The mixture was evaporated in vacuo, and the residue was triturated in EtOAc and the solids collected to afford tert-butyl (4-(6-carbamoyl-2-iminothiazolo[4,5-b]pyridin-3(2H)-yl)butyl)carbamate, compound 173 (50 mg, 27%) as a white solid. $^1$H NMR (400 MHz, DMSO-d$_6$) δ 10.79 (s, 1H), 8.95 (d, J=2.0 Hz, 1H), 8.84 (d, J=1.9 Hz, 1H), 8.25 (s, 1H), 7.71 (s, 1H), 6.82 (s, 1H), 4.30 (t, J=7.4 Hz, 2H), 2.94 (d, J=6.6 Hz, 2H), 1.75-1.62 (m, 2H), 1.45 (q, J=7.4 Hz, 2H), 1.36 (d, J=1.6 Hz, 9H). ESI-MS: C$_{16}$H$_{23}$N$_5$O$_3$S (M+Na): calc. 387.15, found: 387.10.

Step G: To a stirred solution of tert-butyl (4-(6-carbamoyl-2-iminothiazolo[4,5-b]pyridin-3(2H)-yl)butyl)carbamate, compound 173 (50 mg, 0.14 mmol) and 4-(5-(5-(ethoxycarbonyl)-3-methyl-1H-pyrazol-1-yl)pentyl)-1-ethyl-1H-pyrazole-5-carboxylic acid, compound 174A (51 mg, mmol) in DMF (2 mL) was added EDC.HCl (34 mg, 0.18 mmol), HOBt (31 mg, 0.20 mmol) and Et$_3$N (0.06 mL, 0.41 mmol), and the mixture was stirred at room temperature for 16 hours. The reaction was quenched with water and extracted with EtOAc, and the combined organic layers were dried over Na$_2$SO$_4$ and concentrated in vacuo. The residue was purified over silica gel (EtOAc: hexane 80:20 v/v) to afford ethyl (Z)-1-(5-(5-(3-(4-((tert-butoxycarbonyl)amino)butyl)-6-carbamoylthiazolo[4,5-b]pyridin-2(3H)-ylidene)carbamoyl)-1-ethyl-1H-pyrazol-4-yl)pentyl)-3-methyl-1H-pyrazole-5-carboxylate, compound 174 (40 mg, 41% yield) as a white solid. $^1$H NMR (400 MHz, DMSO-d$_6$) δ 8.99 (d, J=2.0 Hz, 1H), 8.77 (d, J=2.0 Hz, 1H), 8.20 (s, 1H), 7.64 (s, 1H), 6.76 (s, 1H), 6.56 (s, 1H), 4.55 (q, J=7.1 Hz, 2H), 4.44 (t, J=7.1 Hz, 2H), 4.38 (t, J=7.0 Hz, 2H), 4.22 (q, J=7.1 Hz, 2H), 2.92 (d, J=6.5 Hz, 2H), 2.80 (t, J=7.6 Hz, 2H), 2.13 (d, J=3.5 Hz, 6H), 1.83-1.69 (m, 4H), 1.52 (t, J=7.9 Hz, 2H), 1.41 (t, J=8.0 Hz, 2H), 1.35 (d, J=5.3 Hz, 2H), 1.31 (s, 9H), 1.25. ESI-MS: C$_{39}$H$_{50}$N$_9$O$_6$S (M+H): calc. 724.35, found: 724.50.

Step H: To a stirred solution of ethyl (Z)-1-(5-(5-((3-(4-((tert-butoxycarbonyl)amino)butyl)-6-carbamoylthiazolo[4,5-b]pyridin-2(3H)-ylidene)carbamoyl)-1-ethyl-1H-pyrazol-4-yl)pentyl)-3-methyl-1H-pyrazole-5-carboxylate, compound 174 (200 mg, mmol) in DCM (5 mL) was added HCl (4M in dioxane, 0.5 mL, 10% v/v), and the mixture was stirred at room temperature for 30 minutes. The mixture was concentrated in vacuo to afford ethyl (Z)-1-(5-(5-((3-(4-aminobutyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 175 (180 mg, 100% yield) as a light brown oil. $^1$H NMR (400 MHz, DMSO-d$_6$) δ 9.02 (d, J=2.0 Hz, 1H), 8.81 (d, J=1.9 Hz, 1H), 8.28 (s, 1H), 7.87 (s, 2H), 7.66 (s, 1H), 6.57 (s, 1H), 4.56 (q, J=7.1 Hz, 2H), 4.49 (t, J=6.8 Hz, 2H), 4.38 (t, J=7.0 Hz, 2H), 4.23 (q, J=7.1 Hz, 2H), 2.79 (q, J=8.9, 8.2 Hz, 4H), 2.14 (d, J=3.5 Hz, 6H), 1.89 (p, J=7.2 Hz, 2H), 1.74 (p, J=7.4 Hz, 2H), 1.61-1.46 (m, 4H), 1.35 (t, J=7.1 Hz, 3H), 1.25 (t, J=7.1 Hz, ESI-MS: C$_{30}$H$_{42}$N$_9$O$_4$S (M+H): calc. 624.30, found: 624.30.

Step I: To a stirred solution of ethyl (Z)-1-(5-(5-((3-(4-aminobutyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 175 (180 mg, 0.27 mmol) in DMSO (10 mL) was added Et$_3$N (0.19 mL, 1.37 mmol), and the mixture was stirred at room temperature for 15 minutes. Then, 3-(3-((tert-butyldimethylsilyl)oxy)propoxy)-4-fluoro-5-nitrobenzamide, compound 3 (101 mg, 0.27 mmol) was added, and the mixture was stirred an additional 4 hours. The reaction was quenched with water and extracted with EtOAc, and the combined organic layers were dried over Na$_2$SO$_4$ and concentrated in vacuo. The residue was purified over silica gel (DCM: MeOH 95:5 v/v) to afford ethyl (Z)-1-(5-(5-((3-(4-((2-(3-((tert-butyldimethylsilyl)oxy)propoxy)-4-carbamoyl-6-nitrophenyl)amino)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 176 (180 mg, 68% yield) as a yellow solid. 12% of the TBS deprotected product was also present. ESI-MS: C$_{46}$H$_{66}$N$_{11}$O$_9$SSi (M+H): calc. 976.45, found: 976.30.

Step J: To a stirred solution of ethyl (Z)-1-(5-(5-((3-(4-((2-(3-((tert-butyldimethylsilyl)oxy)propoxy)-4-carbamoyl-6-nitrophenyl)amino)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 176 (180 mg, 0.18 mmol) in MeOH (10 mL) and DCM (1 mL) was added NH$_4$OH (25% v/v solution, 0.65 mL, 4.6 mmol) at 0° C., followed by Na$_2$S$_2$O$_4$ (160 mg, 0.92 mmol) dissolved in water (0.9 mL), and the mixture was stirred at 0° C. for 5 minutes. The reaction was diluted in water and extracted with DCM, and the combined organic layers were dried over Na$_2$SO$_4$ and concentrated in vacuo to afford ethyl (Z)-1-(5-(5-((3-(4-((2-amino-6-(3-((tert-butyldimethylsilyl)oxy)propoxy)-4-carbamoylphenyl)amino)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 177 (170 mg, 98% yield) as a light brown solid. 13% of the TBS deprotected product was also present. ESI-MS: C$_{46}$H$_{68}$N$_{11}$O$_7$SSi (M+H): calc. 946.47, found: 946.40.

Step K: To a stirred solution of ethyl (Z)-1-(5-(5-((3-(4-((2-amino-6-(3-((tert-butyldimethylsilyl)oxy)propoxy)-4-carbamoylphenyl)amino)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 177 (1 g, 1.06 mmol) in MeOH (10 mL) was added BrCN (123 mg, 1.16 mmol), and the mixture was stirred at room temperature for 2 hours. The mixture was concentrated in vacuo to afford ethyl (Z)-1-(5-(5-((3-(4-(2-amino-7-(3-((tert-butyldimethylsilyl)oxy)propoxy)-5-carbamoyl-1H-benzo[d]imidazol-1-yl)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 178 (1.1 g, 100% yield) as a light brown solid. 8% of the TBS deprotected product was also present. ESI-MS: C47H$_{67}$N$_{12}$O$_7$SSi (M+H): calc. 971.47, found: 971.50.

Step L: To a stirred solution of ethyl (Z)-1-(5-(5-((3-(4-(2-amino-7-(3-((tert-butyldimethylsilyl)oxy)propoxy)-5-carbamoyl-1H-benzo[d]imidazol-1-yl)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylate, compound 178 (1.1 g, 1.05 mmol) in MeOH (6 mL) and THF (6 mL) was added LiOH·H$_2$O (132 mg, 3.14 mmol) dissolved in water (3 mL), and the mixture was stirred at room temperature for 4 hours. The solvent was removed, and the residue was diluted in water and washed with EtOAc. The aqueous layer was acidified with 0.5 N HCl, and the resulting precipitate was filtered and dried to afford (Z)-1-(5-(5-(3-(4-(2-amino-7-(3-((tert-butyldimethylsilyl)oxy)propoxy)-5-carbamoyl-1H-benzo[d]imidazol-1-yl)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylic acid, compound 179 (0.90 g, 91% yield) as a white solid. 30% of the TBS deprotected product was also present. ESI-MS: C$_{45}$H$_{63}$N$_{12}$O$_7$SSi (M+H): calc. 943.44, found: 943.50.

Step M: To a stirred solution of afford (Z)-1-(5-(5-((3-(4-(2-amino-7-(3-((tert-butyldimethylsilyl)oxy)propoxy)-5-carbamoyl-1H-benzo[d]imidazol-1-yl)butyl)-6-carbamoylthiazolo[4,5-b]pyridin-2(3H)-ylidene)carbamoyl)-1-ethyl-3-methyl-1H-pyrazol-4-yl)pentyl)-3-methyl-1H-pyrazole-5-carboxylic acid, compound 179 (900 mg, 0.95 mmol) in DMF (10 mL) was added HATU (522 mg, 1.36 mmol), DIPEA (1.6 mL, 9.54 mmol) and DMAP (90 mg, cat), and the mixture was heated to 60° C. and stirred under nitrogen for 24 hours. The mixture was concentrated in vacuo, and the residue was stirred in water for 15 minutes. The resulting solids were suspended in EtOH and heated to 80° C. for 30 minutes, then immediately filtered and dried to afford (Z)-26-(3-((tert-butyldimethylsilyl)oxy)propoxy)-8-ethyl-10,18-dimethyl-7,20-dioxo-8,11,12,13,14,15,20,21,28,29,30,31-dodecahydro-7H-benzo[4,5]imidazo[1,2-a]

dipyrazolo[5,1-e:4',3'-1]pyrido[2',3':4,5]thiazolo[2,3-p][1,3,6,15,17]pentaazacyclohenicosine-3,24-dicarboxamide, compound 180 (600 mg, 68% yield). ESI-MS: $C_{45}H_{61}N_{12}O_6SSi$ (M+H): calc. 925.42, found: 925.40.

Step N: To a suspension of (Z)-26-(3-((tert-butyldimethylsilyl)oxy)propoxy)-8-ethyl-benzo[4,5]imidazo[1,2-a]dipyrazolo[5,1-e:4',3'-1]pyrido[2',3':4,5]thiazolo[2,3-p][1,3,6,15,17]pentaazacyclohenicosine-3,24-dicarboxamide, compound 180 (50 mg, 0.054 mmol) in MeOH (5 mL) was added HCl (4M in dioxane, 0.2 mL), and the mixture was stirred at room temperature for 1 hour. The resulting solid was filtered and washed with MeOH to afford (Z)-8-ethyl-26-(3-hydroxypropoxy)-10,18-dimethyl-7,20-dioxo-8,11,12,13,14,15,20,21,28,29,30,31-dodecahydro-7H-benzo[4,5]imidazo[1,2-a]dipyrazolo[5,1-e:4',3'-1]pyrido[2',3':4,5]thiazolo[2,3-p][1,3,6,15,17]pentaazacyclohenicosine-3,24-dicarboxamide, compound 181 (10 mg, 23%) as a white solid. ESI-MS: $C_{39}H_{47}N_{12}O_6S$ (M+H): calc. 811.34, found: 811.40.

Example 53: Activation of Human STING Signaling in THP1 Cells

THP1-Dual™ Human Monocytes cells with the homozygous HAQ allele, known to be a natural variant allele of STING occurring in ~20% of the human population (Invivogen) have been engineered with two independent gene reporter systems: a secreted embryonic alkaline phosphatase (SEAP) reporter gene for NFkB activity, and secreted luciferase reporter for interferon response gene 3 (IRF3) activity were used. $4 \times 10^5$ THP1-Dual™ cells were incubated with test Compounds in a 5-fold titration steps from 1 to 0.0128 µM in RPMI media with 10% FBS, for 24 hours at 37° C. with 5% $CO_2$. Cell culture supernatants (20 µl) from each incubated sample was added to resuspended QUANTI-Blue™ Solution (Invivogen, 180 IA) in each well of a flat-bottom 96-well plate, then incubated for 2 h. NFkB levels were evaluated using a spectrophotometer at 620-655 nm.

To evaluate IRF3 reporter levels, cell culture supernatant (20 µl) from each incubated sample was added to QUANTI-Luc™ assay solution (Invivogen, 50 µl), and the luminescence was measured with a SpectraMax M3 spectrophotometer (Molecular Devices).

NFkB and IRF3 reporter levels were also determined for THP1-Dual™ KI-hSTING-H232 Cells and THP1-Dual™ KI-hSTING-R232 Cells. THP1-Dual™ KI-hSTING-H232 Cells (R232H Haplotype) were generated from THP1-Dual™ KO-STING cells by knockin of the intronless coding sequence (from the ATG to TGA) of the R232H human STING variant (Invivogen). R232H has been identified as a natural variant allele of STING occurring in ~14% of the human population. THP1-Dual™ KI-hSTING-R232 Cells (R232 Haplotype) were generated from THP1-Dual™ KO-STING cells by knockin of the intronless coding sequence (from the ATG to the TGA) of the R232 hSTING variant. Genomic studies indicate that this variant, which contains an arginine at position 232 (R232), is the most prevalent variant with an occurrence (homozygous allele) of ~45-58% in the human population.

The EC50 value was determined from the dose response curve based on reference Compounds. Table 2a provides the results for IRF3 reporter induction THP1-Dual™ Human Monocytes cells and Table 2b provides the results for IRF3 reporter induction in THP1-Dual™ KI-hSTING-H232 Cells and THP1-Dual™ KI-hSTING-R232 Cells ("A" means <30 nM; "B" means ≥30 nM and <100 nM; "C" means ≥100 nM).

TABLE 2a

| Example No. | Compound No. | $EC_{50}$ |
|---|---|---|
| 1 | 9 | B |
| 22 | 43 | A |
| 25 | 53 | C |
| 10 | 18 | B |
| 26 | 63 | C |
| 28 | 65 | A |
| 29 | 66 | C |
| 32 | 69 | C |
| 45 | 95 | B |
| 47 | 97 | C |
| 48 | 109 | B |
| 50 | 146 | C |
| 50a | 148 | C |
| 51 | 167 | C |

TABLE 2b

| Example No. | Compound No. | $EC_{50}$ (THP1-Dual ™ KI-hSTING-H232 Cells) | $EC_{50}$ (THP1-Dual ™ KI-hSTING-R232 Cells) |
|---|---|---|---|
| 1 | 9 | A | A |
| 26 | 63 | A | A |
| 29 | 66 | C | A |
| 32 | 69 | A | A |
| 45 | 95 | A | A |
| 48 | 109 | A | A |
| 50 | 146 | A | A |
| 50a | 148 | A | A |
| 51 | 167 | B | B |

Example 54: Activation of Human STING Signaling in Permeabilized THP1 Cells $4 \times 10^5$ THP1-Dual™ cells (NFκB-SEAP and IRF-Lucia luciferase Reporter Monocytes, Invivogen) were incubated with test Compounds in a 5-fold titration steps from 1 to 12.8 nM in permeabilized buffer (50 mM HEPES pH 7.0, 100 mM KCl, 3 mM $MgCl_2$, 85 mM sucrose, 0.2% BSA, 1 mM ATP, 0.1 mM GTP, 0.1 mM TTP, 1 µg/ml digitonin) for 30 minutes on ice. Cells were then washed and incubated in a fresh RPMI media with 10% FBS at 37° C. with 5% $CO_2$ for 24 h. Cell culture supernatants from each sample were collected and NFkB and IRF3 were evaluated as above. Table 3 provides the results for IRF3 induction ("A" means <1 µM; "B" means ≥1 µM and <50 µM; "C" means ≥50 µM).

TABLE 3

| Example No. | Compound No. | IRF3 $EC_{50}$ |
|---|---|---|
| 1 | 9 | A |
| 2 | 10 | A |
| 3 | 11 | B |
| 4 | 12 | B |
| 5 | 13 | C |
| 6 | 14 | C |
| 7 | 15 | C |
| 8 | 16 | C |
| 9 | 17 | C |
| 10 | 18 | A |
| 11 | 19 | A |

TABLE 3-continued

| Example No. | Compound No. | IRF3 EC$_{50}$ |
|---|---|---|
| 12 | 26 | A |
| 13 | 27 | C |
| 14 | 28 | C |
| 15 | 36 | A |
| 16 | 37 | A |
| 17 | 38 | A |
| 18 | 39 | A |
| 19 | 40 | A |
| 20 | 41 | C |
| 22 | 43 | A |
| 23 | 51 | A |
| 24 | 52 | A |
| 25 | 53 | A |
| 26 | 63 | A |
| 27 | 64 | C |
| 28 | 65 | A |
| 29 | 66 | A |
| 30 | 67 | A |
| 33 | 70 | C |
| 34 | 71 | B |
| 38 | 75 | C |
| 39 | 76 | A |
| 40 | 84 | A |
| 41 | 85 | B |
| 42 | 89 | A |
| 43 | 90 | A |
| 44 | 94 | A |
| 45 | 95 | A |
| 46 | 96 | A |
| 47 | 97 | A |
| 48 | 109 | A |
| 49 | 110 | A |
|  | 111 | A |
|  | 112 | A |
|  | 113 | B |
|  | 114 | B |
|  | 115 | A |
|  | 122 | A |
|  | 123 | A |
|  | 125 | A |
|  | 126 | A |
|  | 128 | A |
|  | 129 | B |
|  | 130 | B |
|  | 131 | B |
|  | 132 | B |
|  | 133 | B |
|  | 134 | A |
|  | 135 | B |
|  | 136 | C |
|  | 137 | C |
|  | 138 | C |
|  | 139 | C |
|  | 140 | A |
|  | 141 | B |
|  | 142 | A |
|  | 143 | A |
|  | 144 | C |
|  | 145 | C |
| 50 | 146 | A |
|  | 147 | B |
| 50a | 148 | A |
|  | 149 | A |
|  | 150 | A |
|  | 151 | A |
|  | 155 | A |

EQUIVALENTS

The details of one or more embodiments of the invention are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A method of treating a STING mediated disease or disorder in a subject in need thereof, comprising administering to the subject a pharmaceutically effective amount of the compound of Formula (V-f1), Formula (V-f2), Formula (V-f3), Formula (V-f4), Formula (V-f5), Formula (V-f6), Formula (V-f7), Formula (V-h1), Formula (V-h2), Formula (V-h3), Formula (V-h4), Formula (V-h5), Formula (V-h6), or Formula (V-h7):

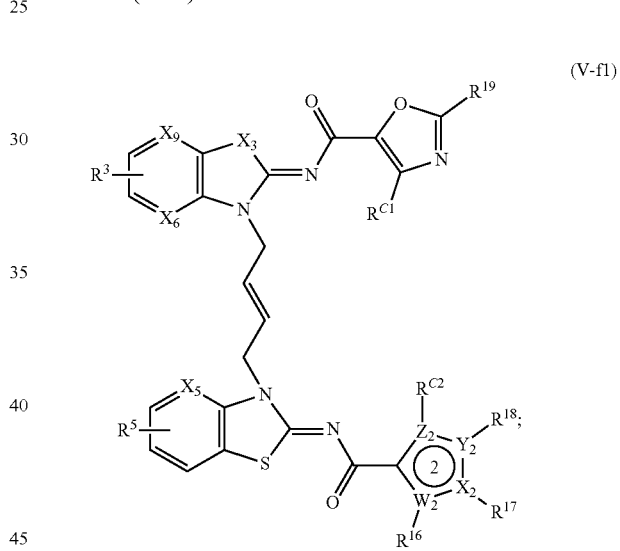

(V-f1)

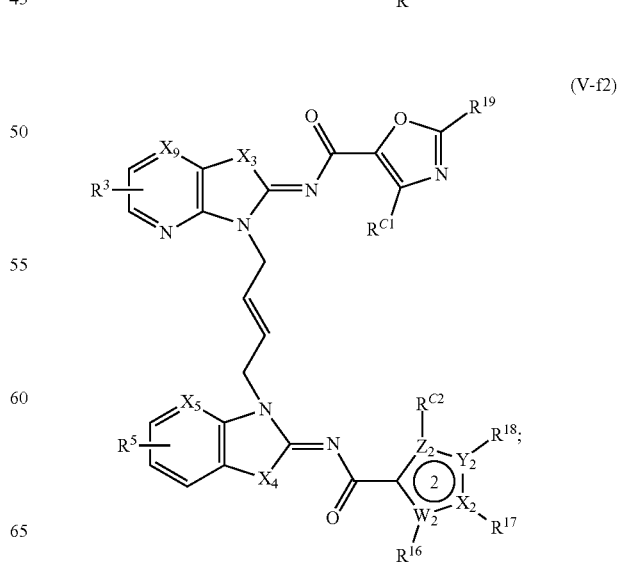

(V-f2)

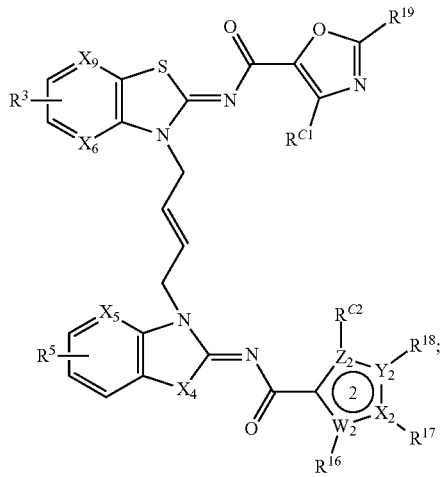
(V-f3)
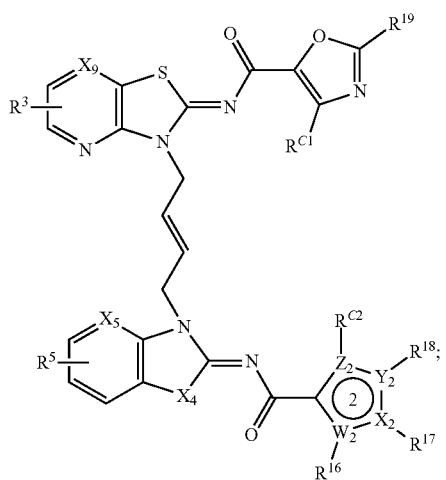
(V-f4)
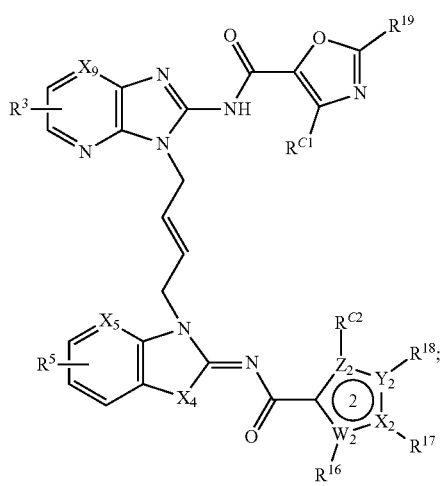
(V-f5)
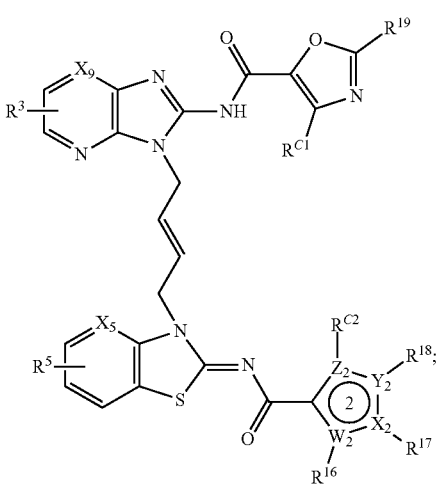
(V-f6)
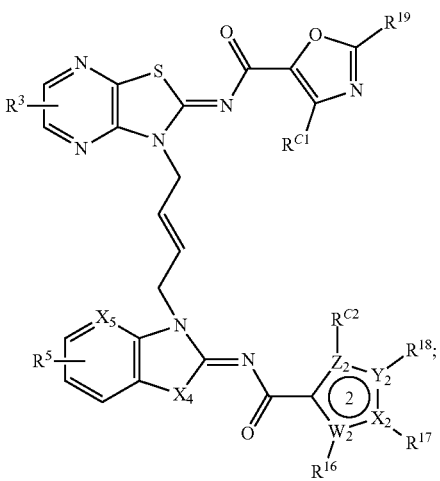
(V-f7)
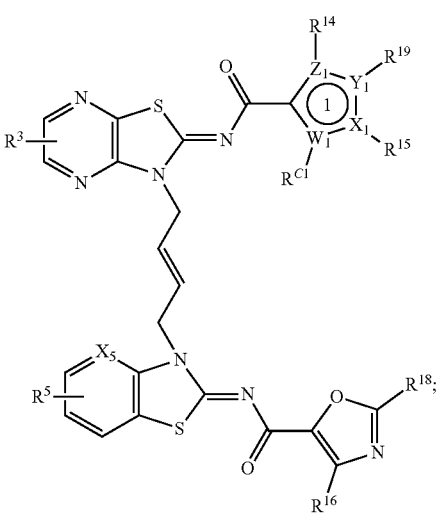
(V-h1)

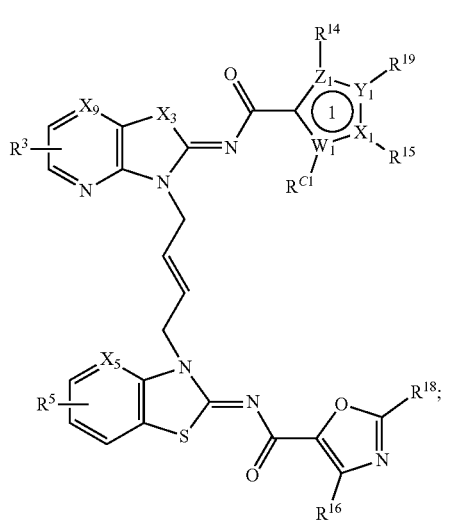
(V-h2)
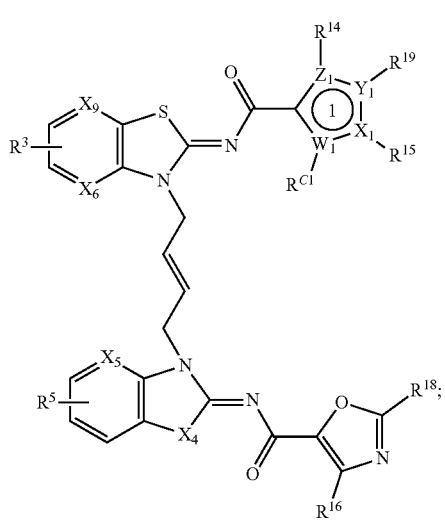
(V-h4)
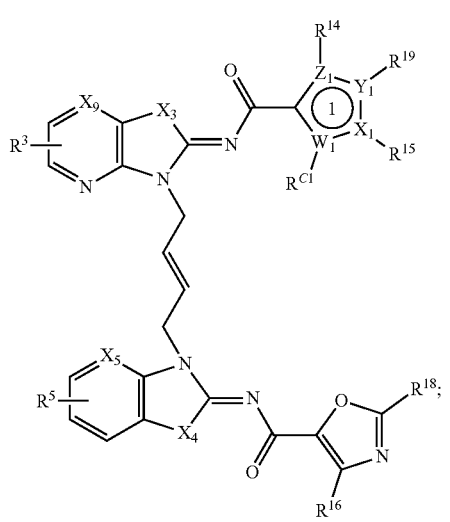
(V-h3)
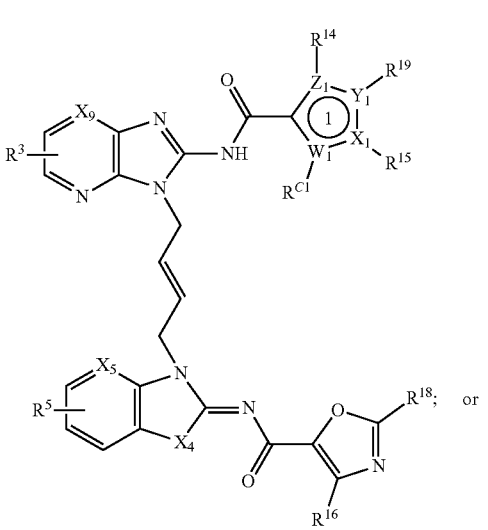
(V-h5)
(V-h6)
or -continued (V-h7)

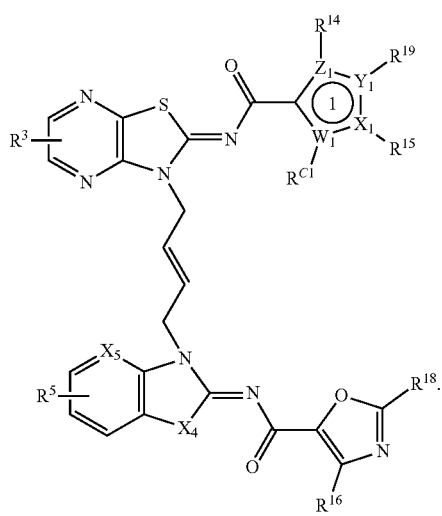

or a prodrug, solvate, pharmaceutically acceptable salt, or tautomer thereof, wherein:
$Y_1$, $Z_1$, $Y_2$, and $Z_2$ are each independently O, S, or N;
$X_1$, $W_1$, $X_2$, and $W_2$ are each independently C or N;
$X_3$ and $X_4$, when present, are each independently S or NW;
$X_5$ is N or CR A2;
$X_6$, when present, is N or $CR^{41}$;
$X_9$, when present, is N or CH;
$R^3$ and $R^5$ are each independently —CON($R^d$)($R^f$), —CH$_2$N($R^d$)($R^f$), —N($R^d$)($R^f$), —N($R^d$)CO($R^f$), —CH$_2$N($R^d$)CO($R^f$) or one of $R^3$ and $R^5$ is —CON($R^d$)($R^f$), —CH$_2$N($R^d$)($R^f$), —N($R^d$)($R^f$), —N($R^d$)CO($R^f$) or —CH$_2$N($R^d$)CO($R^f$), and the other of $R^3$ and $R^5$ is H, —COOH, or —CO$_2R^c$;
$R^c$ is $C_{1-4}$ alkyl;
$R^{42}$ and $R^{41}$, when present, are each independently halogen, hydroxyl, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-,
wherein $C_{1-6}$ alkyl of said optionally substituted ($C_{1-6}$ alkyl) or substituted ($C_{1-6}$ alkyl)oxy- is optionally substituted with 1-4 substituents each independently selected from the group comprising hydroxyl, $C_{1-4}$ alkoxyl, —N($R^e$)($R^f$), —CO$_2$($R^f$), —CON($R^e$)($R^f$), and —COOH;
each $R^d$ is independently H, hydroxy, or $C_{1-4}$ alkyl;
each $R^e$ is independently selected from H, ($C_{1-4}$ alkyl), —CO($C_{1-4}$ alkyl), —OCO($C_{1-4}$ alkyl), and —CO$_2$($C_{1-4}$ alkyl);
each $R^f$ is independently H, hydroxy, or ($C_{1-4}$ alkyl);
$R^{C2}$ and $R^{14}$ are each independently absent or $C_{1-4}$ alkyl, wherein $C_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;
$R^{16}$ and $R_{C1}$ are each independently absent, H or $C_{1-4}$ alkyl; and
$R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$.

2. The method of claim 1, wherein the compound is Formula (V-i1), Formula (V-i2), Formula (V-i3), Formula (V-i4), Formula (V-i5), Formula (V-i6), or Formula (V-i7):

(V-i1)

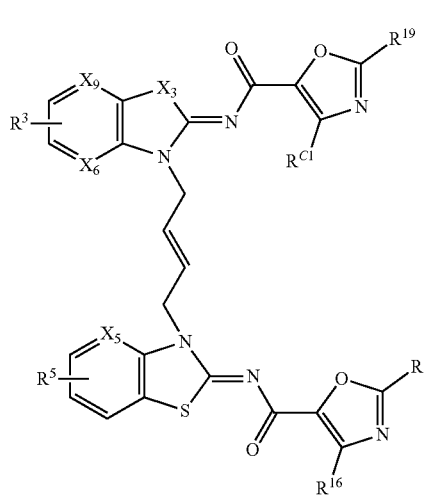

(V-i2)

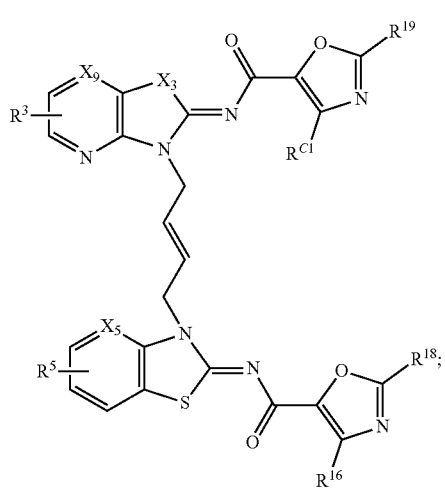

(V-i3)

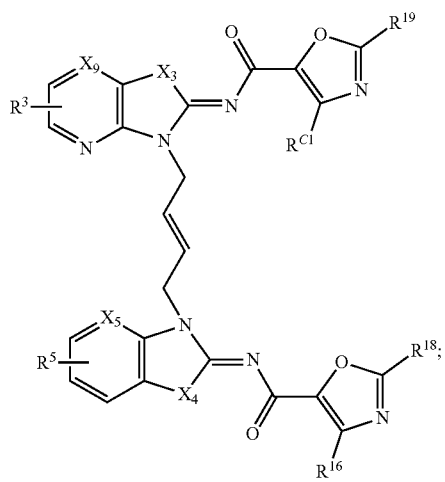

(V-i4)
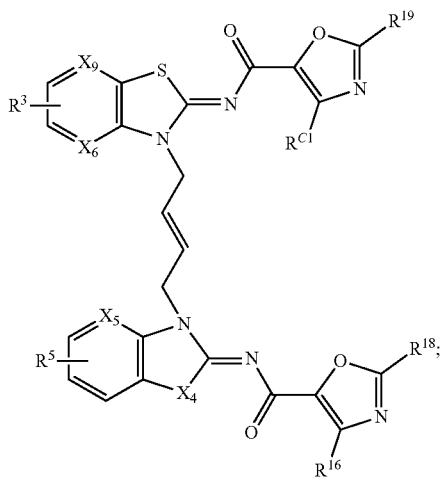
(V-i5)
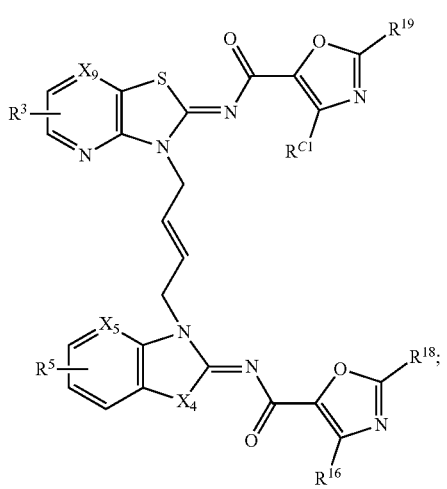
(V-i6)
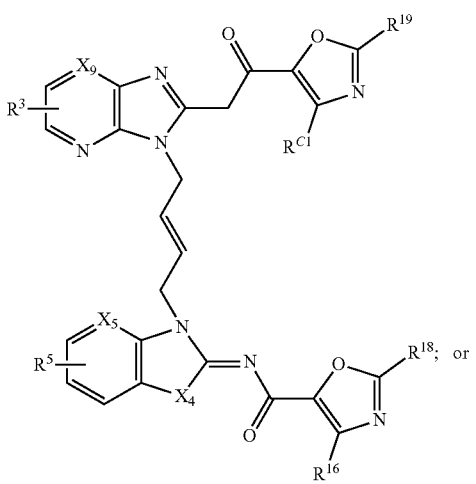
(V-i7)
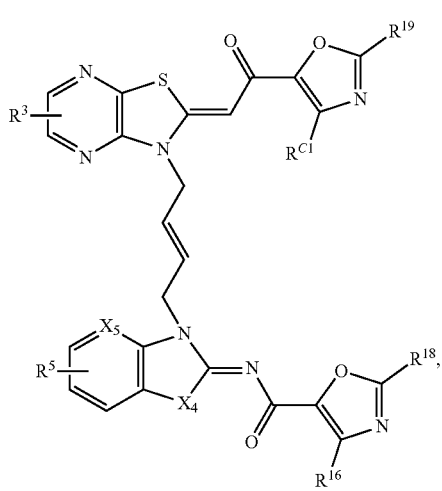
or a prodrug, solvate, pharmaceutically acceptable salt, or tautomer thereof.
3. The method of claim 1, wherein Ring 2 is selected from:
(1)
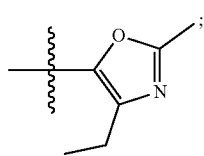
(2)
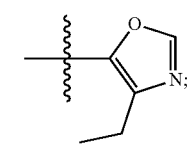
(3)
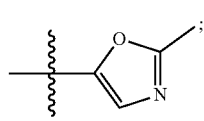
(4)
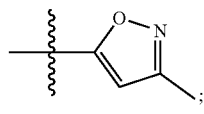
(5)
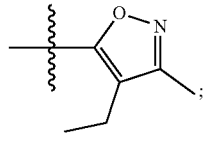
(6)
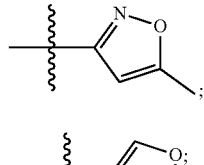
(7)
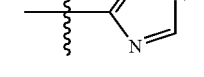

-continued
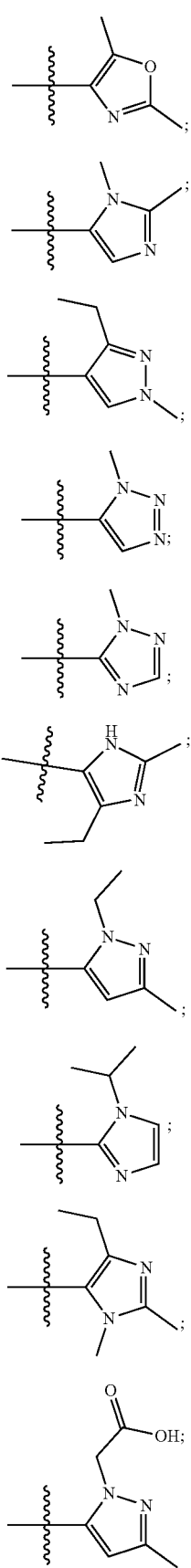
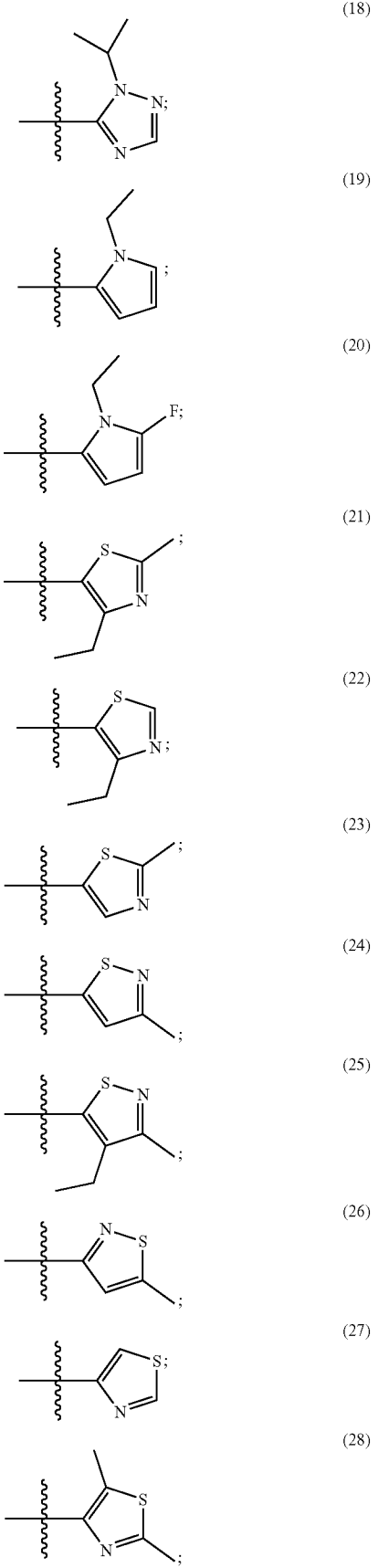

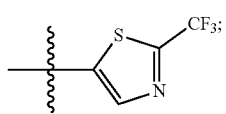 (29)
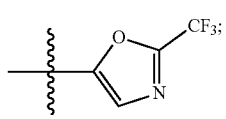 (30)
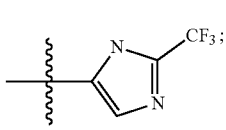 (31)
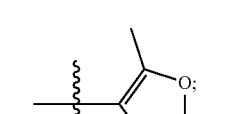 (32)
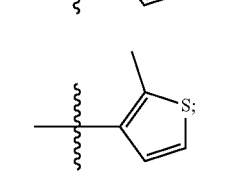 (33)
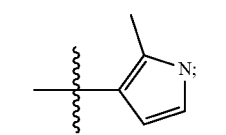 (34)
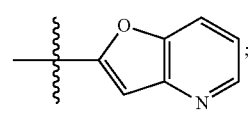 (35)
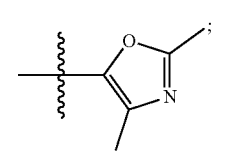 (36)
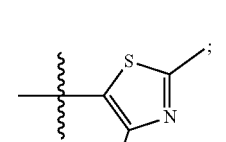 (37)
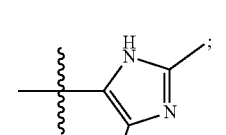 (38)
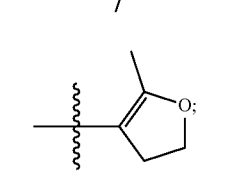 (39)
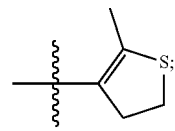 (40)
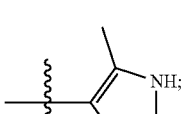 (41)
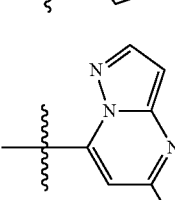 (42)
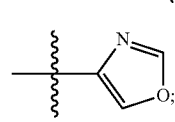 (43)
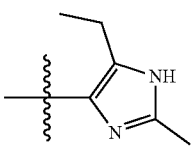 (44)
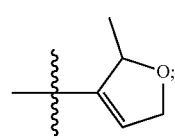 (45)
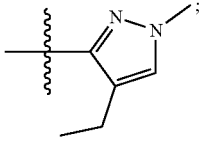 (46)
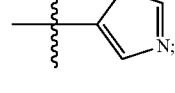 (47)
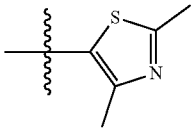 (48)
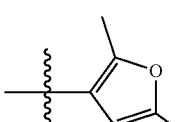 (49)
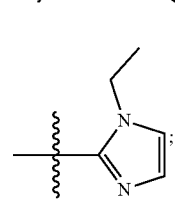 (50)

(51)
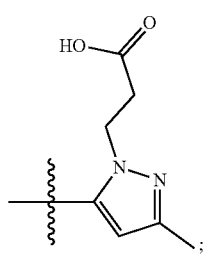
(52)
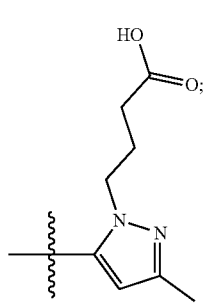
(53)
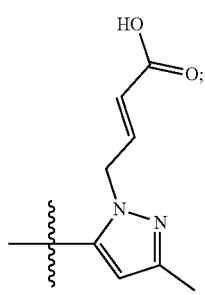
(54)
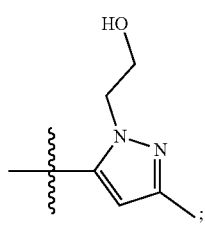
(55)
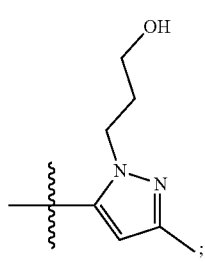
(56)
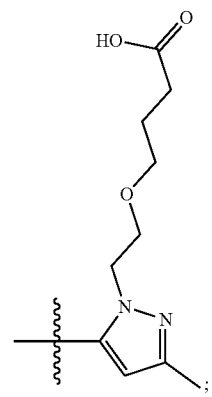
(57)
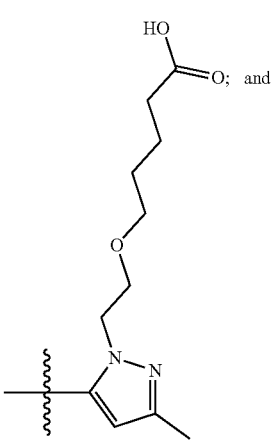
(58)
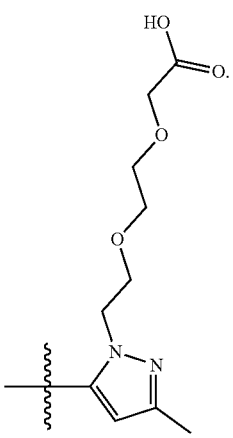
4. The method of claim 1, wherein Ring 1 is selected from:
(1)
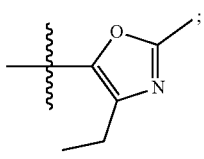

(2) 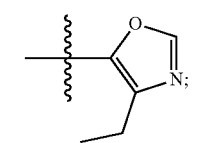
(3) 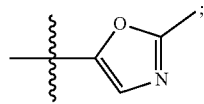
(4) 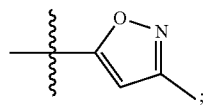
(5) 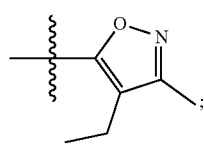
(6) 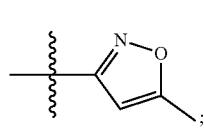
(7) 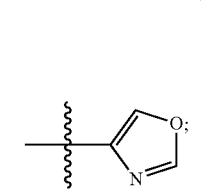
(8) 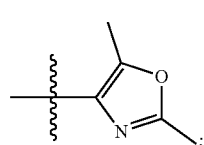
(9) 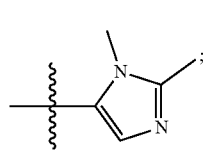
(10) 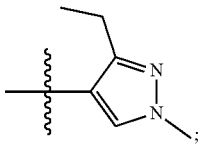
(11) 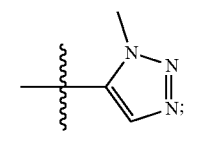
(12) 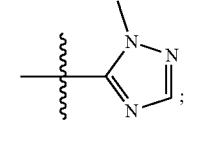
(13) 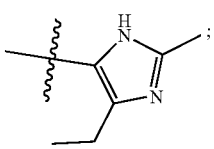
(14) 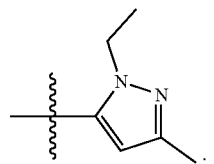
(15) 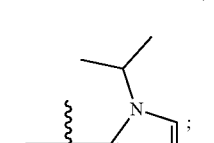
(16) 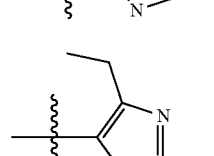
(17) 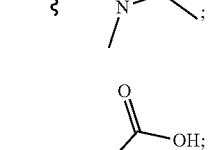
(18) 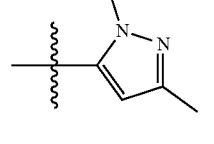
(19) 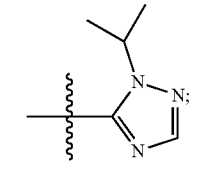
(20) 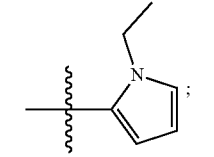
(21) 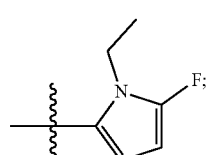
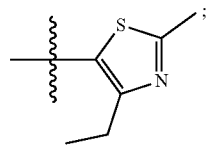

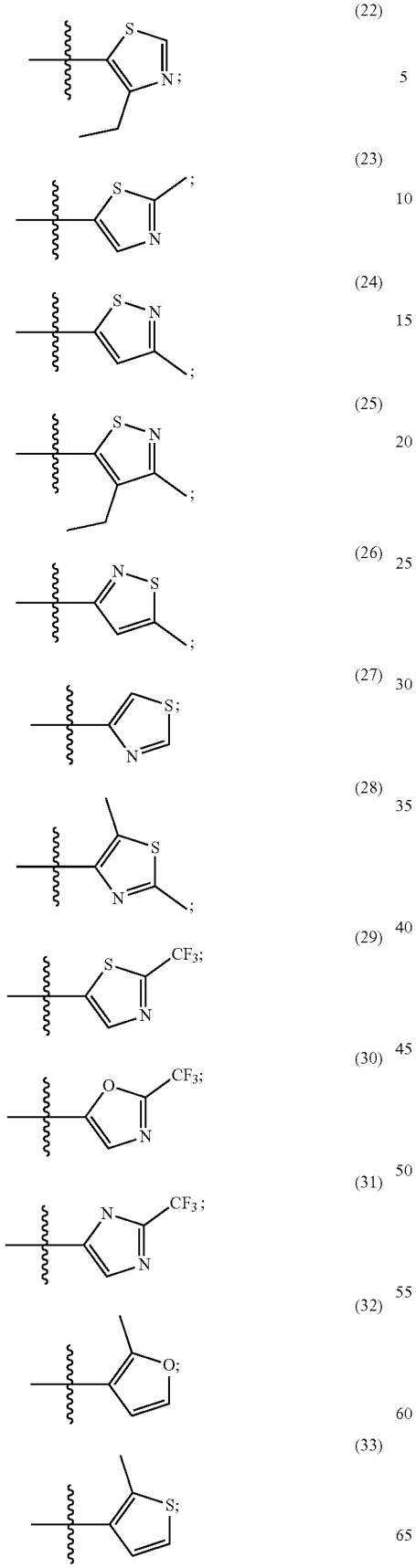
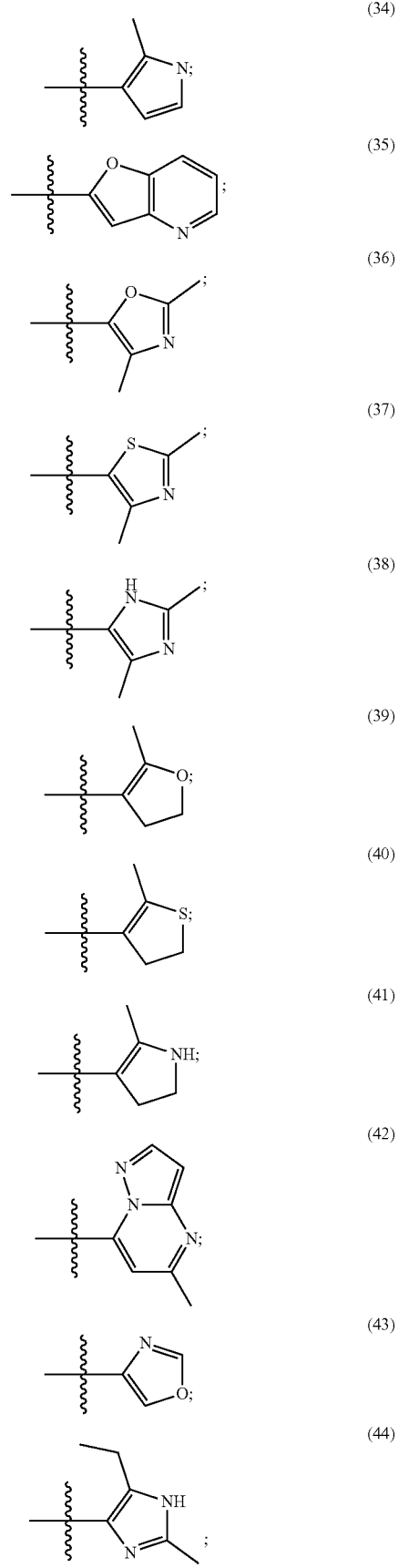

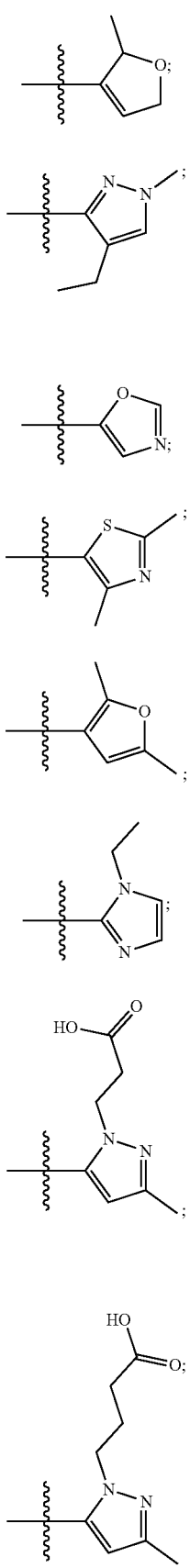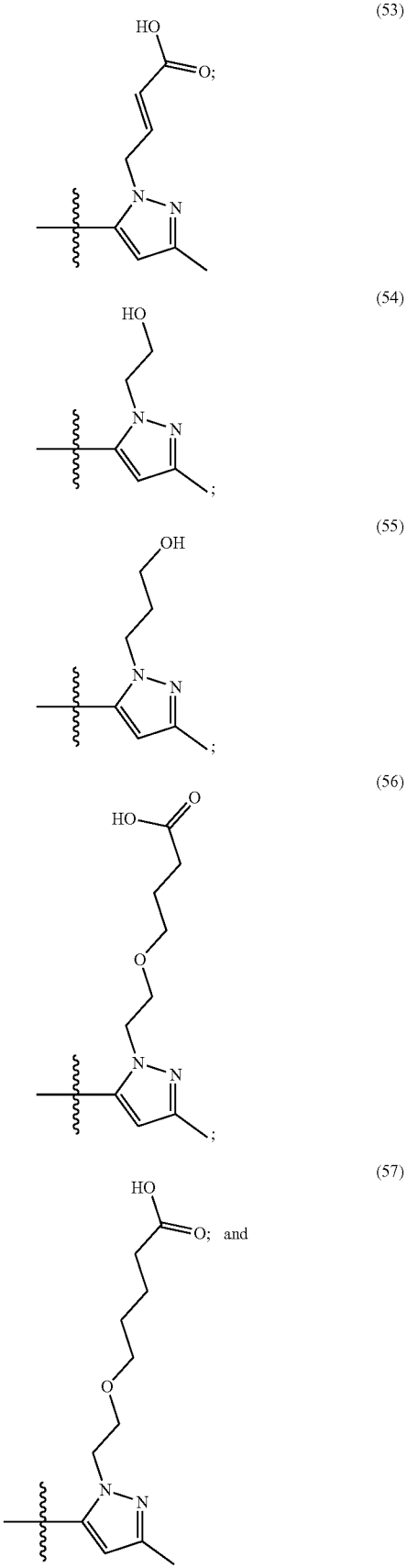

-continued (58)

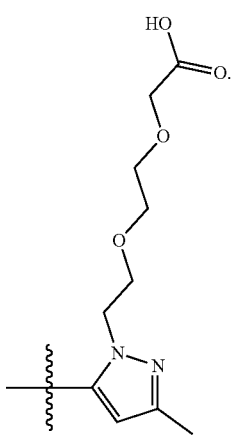

5. The method of claim 1, wherein the compound is Example No. 26, 27, 29, 32, 33, 35, 36, 39, 41, 43, 45, 46, 47, 48, 50, 50a, or 51 or Compound No. 111, 113, 120, 142, 143, 150, 151, 153, 155, 167, or 182, or a prodrug, solvate, pharmaceutically acceptable salt, or tautomer thereof.

6. The method of claim 1, wherein the compound is:

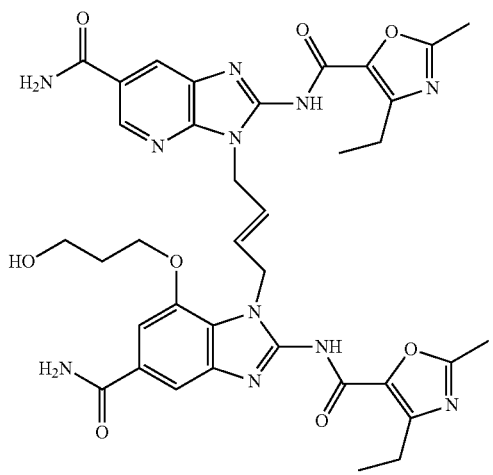 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cc(OCCCO)c21]

or a prodrug, solvate, pharmaceutically acceptable salt, or tautomer thereof.

7. The method of claim 1, wherein the compound is:

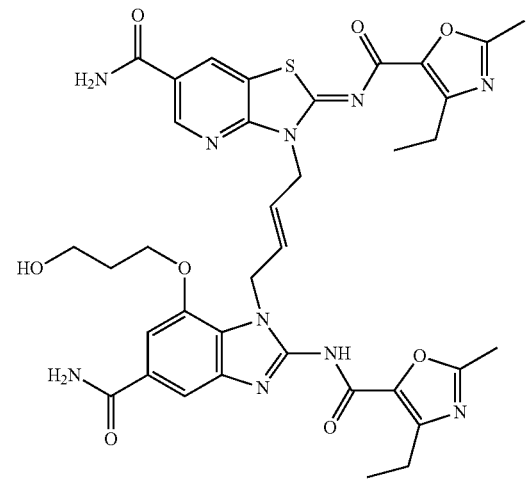

or a prodrug, solvate, pharmaceutically acceptable salt, or tautomer thereof.

8. The method of claim 1, wherein $R^{14}$ is absent or $C_{1-4}$ alkyl.

9. The method of claim 1, wherein the compound is administered in combination with at least one immunomodulator.

10. The method of claim 1, wherein the STING mediated disease or disorder is a cancer.

11. The method of claim 10, wherein the cancer is breast cancer, head and neck cancer, gastric cancer, melanoma, renal cell carcinoma (RCC), esophageal cancer, non-small cell lung carcinoma, prostate cancer, colorectal cancer, ovarian cancer, or pancreatic cancer.

* * * * *

UNITED STATES PATENT AND TRADEMARK OFFICE
CERTIFICATE OF CORRECTION

PATENT NO. : 11,939,343 B2
APPLICATION NO. : 17/469983
DATED : March 26, 2024
INVENTOR(S) : Jeremy R. Duvall et al.

It is certified that error appears in the above-identified patent and that said Letters Patent is hereby corrected as shown below:

In the Specification

At Column 100, Line number 47 to 67:

"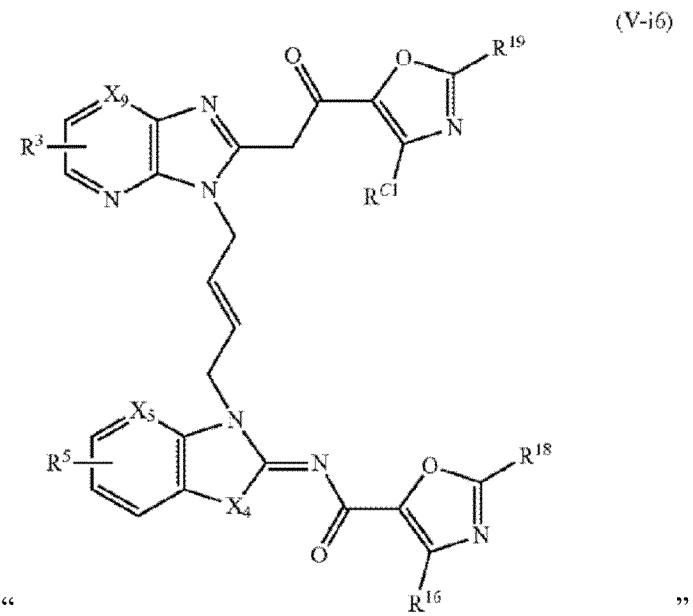"

Should read:

Signed and Sealed this
Sixth Day of August, 2024

Katherine Kelly Vidal
*Director of the United States Patent and Trademark Office*

CERTIFICATE OF CORRECTION (continued)  Page 2 of 6
U.S. Pat. No. 11,939,343 B2

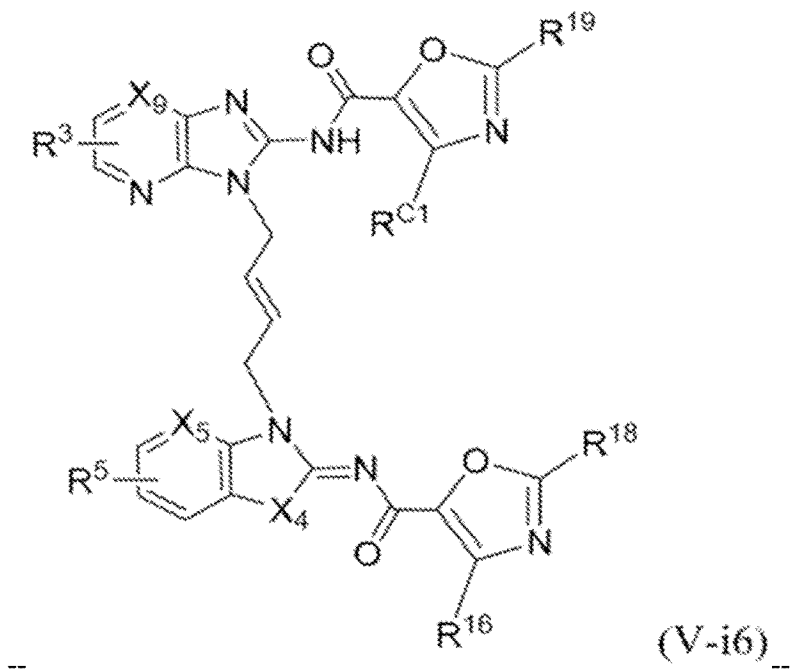

--                                                              (V-i6) --

At Column 101, Line numbers 4 to 24:

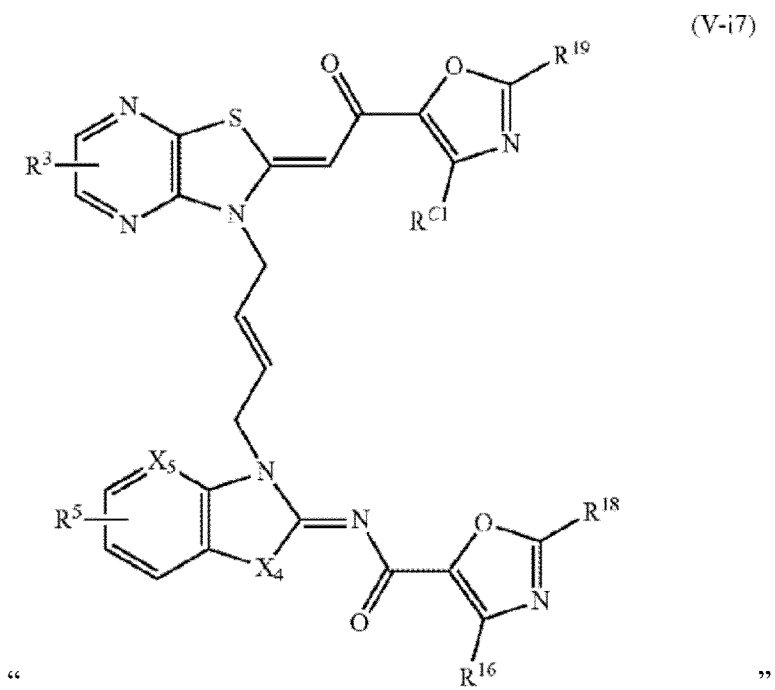

"                                                              (V-i7)

Should read:

CERTIFICATE OF CORRECTION (continued)
U.S. Pat. No. 11,939,343 B2

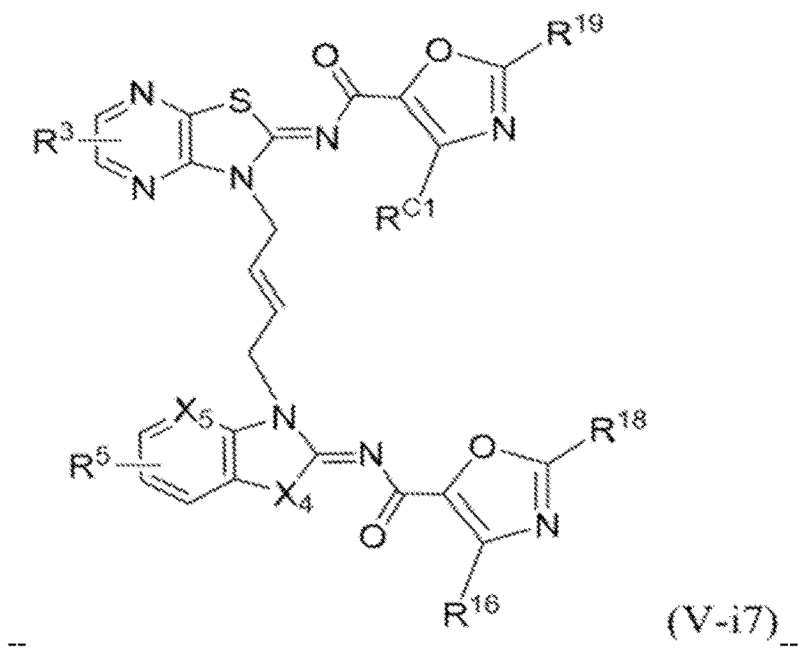

-- (V-i7) --

In the Claims

At Column 346, Claim number 1, Line numbers 45-65:

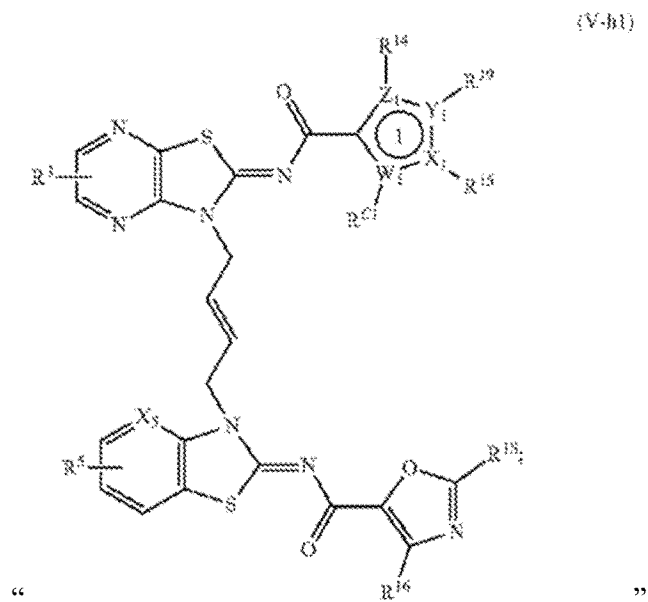

"  (V-h1)  "

Should read:

CERTIFICATE OF CORRECTION (continued)
U.S. Pat. No. 11,939,343 B2

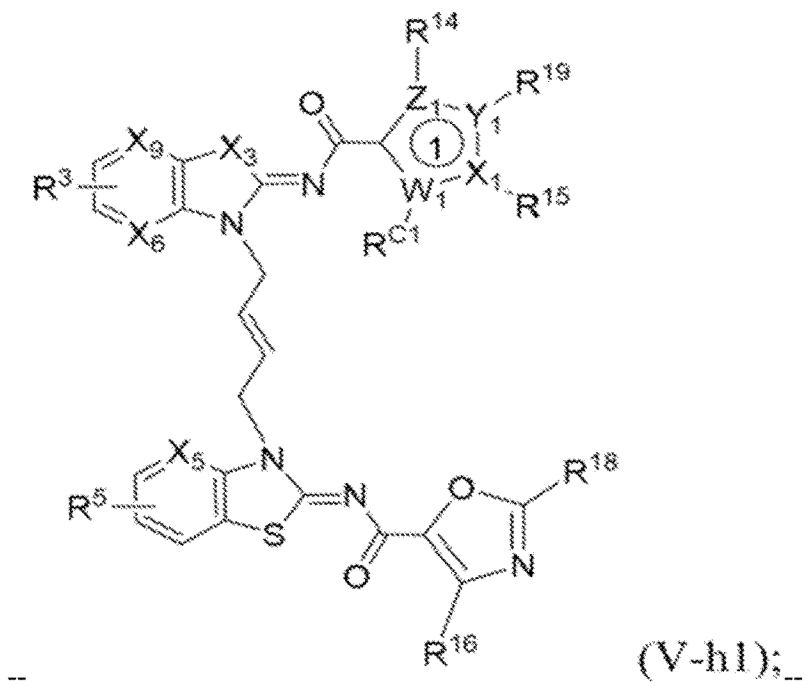

(V-h1);

At Column 349, Claim number 1, Line number 25:
"$Y_1$, $Z_1$, $Y_2$, and $Z_2$ are each independently O, S, or N;"
Should read:
--$Y_1$, $Z_1$, $Y_2$, and $Z_2$ are each independently O, S, C, or N;--

At Column 349, Claim number 1, Line number 28:
"NW;"
Should read:
--$NR^f$;--

At Column 349, Claim number 1, Line number 29:
"$X_5$ is N or CR A2;"
Should read:
--$X_5$ is N or $CR^{A2}$;--

At Column 349, Claim number 1, Line number 35:
"-$CH_2N(R^d)CO(R^f)$"
Should read:
-- -$CH_2N(R^d)CO(R^f)$,--

CERTIFICATE OF CORRECTION (continued)
U.S. Pat. No. 11,939,343 B2

At Column 351, Claim number 2, Line numbers 50-65:

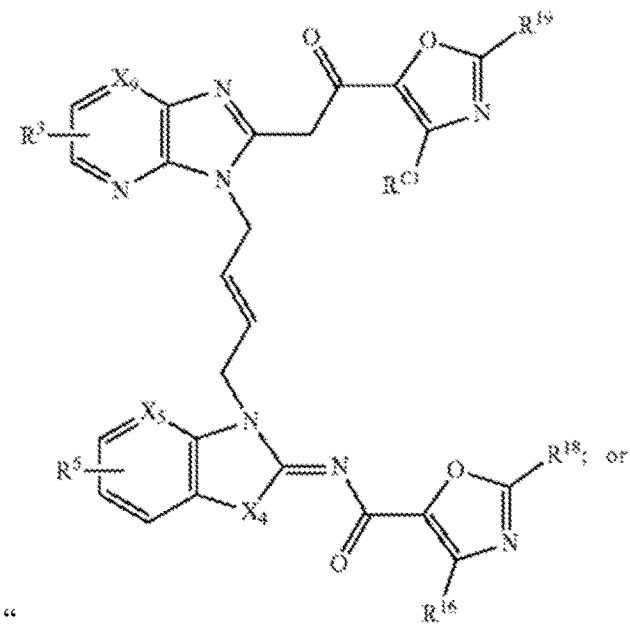

" "

Should read:

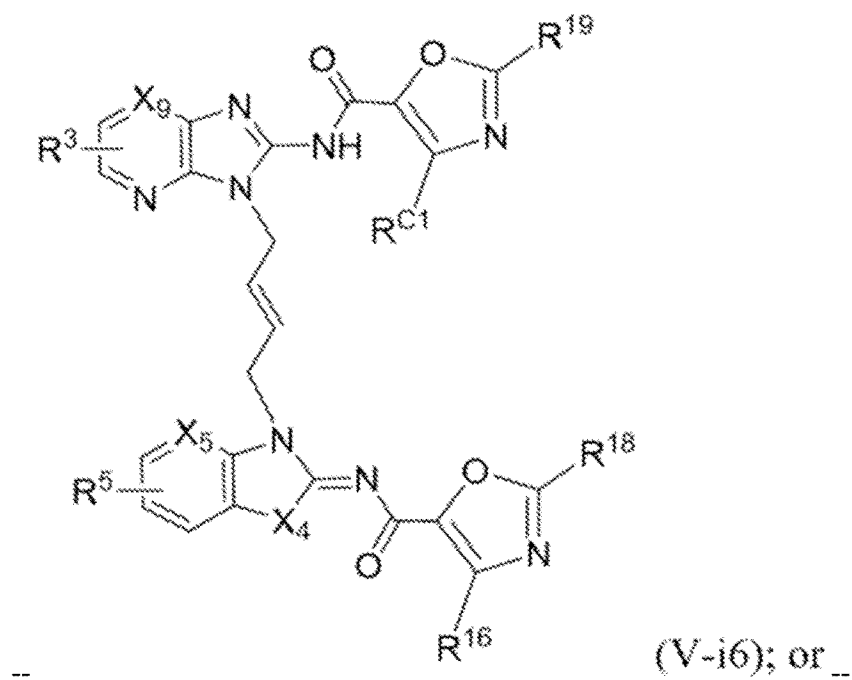

--  (V-i6); or --

At Column 352, Claim number 2, Line numbers 1-20:

CERTIFICATE OF CORRECTION (continued)
U.S. Pat. No. 11,939,343 B2

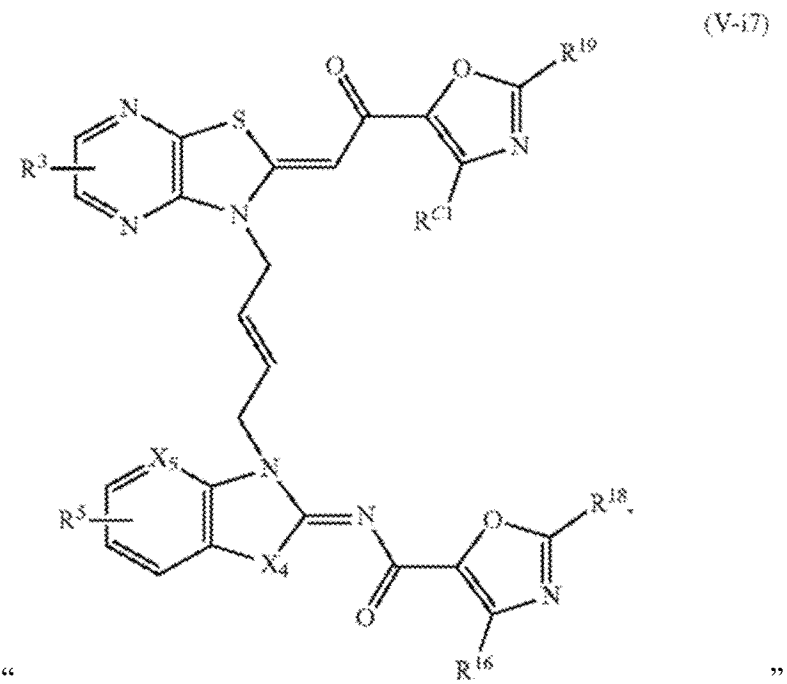

" "

Should read:

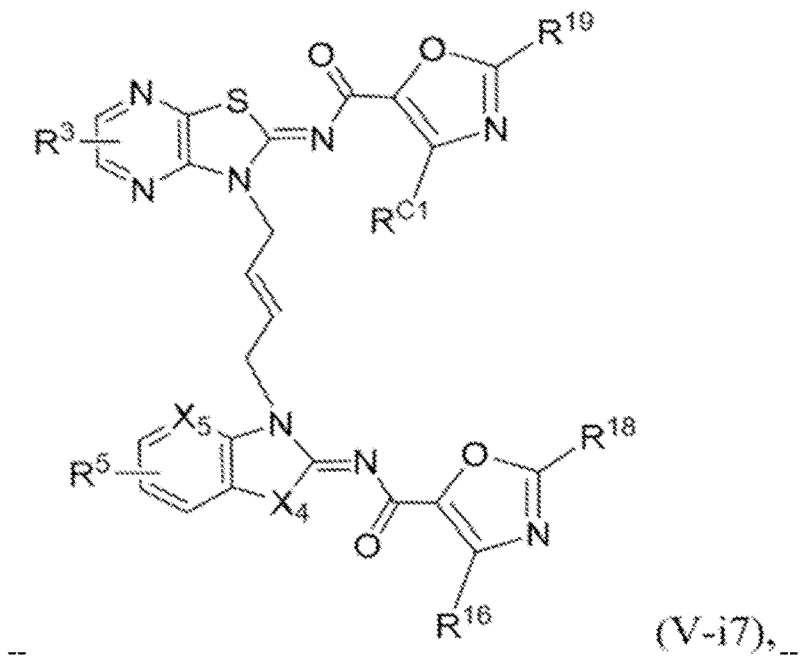

--